(12) United States Patent
Hettmann et al.

(10) Patent No.: US 11,298,359 B2
(45) Date of Patent: Apr. 12, 2022

(54) ANTI-HER3 ANTIBODY-DRUG CONJUGATE

(71) Applicants: DAIICHI SANKYO COMPANY, LIMITED, Tokyo (JP); DAIICHI SANKYO EUROPE GMBH, Munich (DE)

(72) Inventors: Thore Hettmann, Martinsried (DE); Reimar Abraham, Martinsried (DE); Sabine Blum, Martinsried (DE); Suguru Ueno, Tokyo (JP)

(73) Assignees: DAIICHI SANKYO COMPANY, LIMITED, Tokyo (JP); DAIICHI SANKYO EUROPE GMBH, Munich (DE)

( * ) Notice: Subject to any disclaimer, the term of this patent is extended or adjusted under 35 U.S.C. 154(b) by 0 days.

(21) Appl. No.: 16/264,395

(22) Filed: Jan. 31, 2019

(65) Prior Publication Data

US 2019/0151328 A1    May 23, 2019

Related U.S. Application Data

(63) Continuation of application No. 15/285,156, filed on Oct. 4, 2016, now Pat. No. 10,383,878, which is a continuation of application No. PCT/JP2015/002020, filed on Apr. 10, 2015.

(30) Foreign Application Priority Data

Apr. 10, 2014   (JP) ................. 2014-081454

(51) Int. Cl.
| | | |
|---|---|---|
| *A61K 39/00* | (2006.01) | |
| *A61K 31/5377* | (2006.01) | |
| *A61K 47/68* | (2017.01) | |
| *A61K 39/395* | (2006.01) | |
| *C07K 16/30* | (2006.01) | |

(Continued)

(52) U.S. Cl.
CPC .... *A61K 31/5377* (2013.01); *A61K 39/39558* (2013.01); *A61K 47/6803* (2017.08); *A61K 47/6851* (2017.08); *A61K 47/6855* (2017.08); *A61K 47/6857* (2017.08); *A61K 47/6861* (2017.08); *A61K 47/6863* (2017.08); *A61K 47/6869* (2017.08); *C07K 16/2863* (2013.01); *C07K 16/3015* (2013.01); *C07K 16/3023* (2013.01); *C07K 16/32* (2013.01); *A61K 2039/505* (2013.01); *C07K 2317/21* (2013.01); *C07K 2317/24* (2013.01); *C07K 2317/565* (2013.01); *C07K 2317/76* (2013.01); *C07K 2317/77* (2013.01)

(58) Field of Classification Search
CPC ............ A61K 47/6851; A61K 47/6857; A61K 47/6869; A61K 39/39558; A61K 47/6803; A61K 47/6855; A61K 2039/505; A61K 47/6889; C07K 16/3015; A61P 35/00
See application file for complete search history.

(56) References Cited

U.S. PATENT DOCUMENTS

| | | |
|---|---|---|
| 5,480,968 A | 1/1996 | Kraus et al. |
| 5,834,476 A | 11/1998 | Terasawa et al. |
| 5,837,673 A | 11/1998 | Tsujihara et al. |

(Continued)

FOREIGN PATENT DOCUMENTS

| | | |
|---|---|---|
| CA | 2927832 A1 | 11/2011 |
| CA | 2815154 A1 | 2/2012 |

(Continued)

OTHER PUBLICATIONS

Kang et al, Engineering multivalent antibodies to target heregulin-induced HER3 signaling in breast cancer cells, mAbs, 2013, vol. 64, No. 1, pp. 15-29.

Russian Office Action dated Mar. 5, 2019 in corresponding application No. 2016143351.

Sievers et al, Antibody-Drug Conjugates in Cancer Therapy, Annual Review of Medicine, 2013, vol. 64, No. 1, pp. 15-29.

(Continued)

*Primary Examiner* — Sheela J. Huff
(74) *Attorney, Agent, or Firm* — Foley & Lardner LLP

(57) ABSTRACT

To provide an antitumor drug having excellent therapeutic effect, which is excellent in terms of antitumor effect and safety. Provided is an antibody-drug conjugate in which an antitumor compound represented by the following formula is conjugated to an anti-HER3 antibody via a linker having a structure represented by the formula: -$L^1$-$L^2$-$L^P$-NH—$(CH_2)n^1$-$L^a$-$(CH_2)n^2$-C(=O)— or -$L^1$-$L^2$-$L^P$- (the anti-HER3 antibody is connected to the terminal of $L^1$, the antitumor compound is connected to the carbonyl group of —$(CH_2)n^2$-C(=O)— moiety or the C terminal of $L^P$, with the nitrogen atom of the amino group at position 1 as a connecting position).

[Chem. 1]

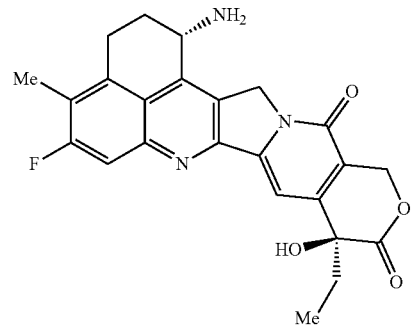

17 Claims, 30 Drawing Sheets

Specification includes a Sequence Listing.

(51) Int. Cl.
*C07K 16/28* (2006.01)
*C07K 16/32* (2006.01)

(56) References Cited

U.S. PATENT DOCUMENTS

| | | | |
|---|---|---|---|
| 5,892,043 | A | 4/1999 | Tsujihara et al. |
| 5,968,511 | A | 10/1999 | Akita et al. |
| 6,214,345 | B1 | 4/2001 | Firestone et al. |
| 6,291,671 | B1 | 9/2001 | Inoue et al. |
| 6,835,807 | B1 | 12/2004 | Susaki et al. |
| 7,585,491 | B2 | 9/2009 | Govindan |
| 7,837,980 | B2 | 11/2010 | Alley et al. |
| 2003/0148931 | A1 | 8/2003 | Takahashi et al. |
| 2003/0166513 | A1 | 9/2003 | Imura et al. |
| 2004/0185053 | A1 | 9/2004 | Govindan |
| 2005/0123536 | A1 | 6/2005 | Law et al. |
| 2005/0271671 | A1 | 12/2005 | Griffiths |
| 2005/0276812 | A1 | 12/2005 | Ebens et al. |
| 2006/0193865 | A1 | 8/2006 | Govindan |
| 2007/0071764 | A1 | 3/2007 | Sullivan et al. |
| 2008/0050310 | A1 | 2/2008 | Ebens, Jr. et al. |
| 2008/0131363 | A1 | 6/2008 | Govindan et al. |
| 2008/0161245 | A1 | 7/2008 | Kratz et al. |
| 2008/0305044 | A1 | 12/2008 | McDonagh et al. |
| 2009/0274713 | A1 | 11/2009 | Chari et al. |
| 2011/0070248 | A1 | 3/2011 | Ichikawa et al. |
| 2011/0229406 | A1 | 9/2011 | Hettmann et al. |
| 2011/0293513 | A1 | 12/2011 | Govindan et al. |
| 2012/0121615 | A1 | 5/2012 | Flygare et al. |
| 2012/0201809 | A1 | 8/2012 | Bhat et al. |
| 2013/0123178 | A1 | 5/2013 | Dimarchi et al. |
| 2015/0297748 | A1 | 10/2015 | Masuda et al. |
| 2015/0352224 | A1 | 12/2015 | Naito et al. |
| 2016/0287722 | A1 | 10/2016 | Govindan |
| 2017/0021031 | A1 | 1/2017 | Hettmann et al. |
| 2019/0151328 | A1 | 5/2019 | Hettmann et al. |

FOREIGN PATENT DOCUMENTS

| | | | |
|---|---|---|---|
| CA | 2859255 A1 | 6/2013 | |
| CN | 1227499 A | 9/1999 | |
| CN | 1764478 A | 4/2006 | |
| CN | 101490087 A | 7/2009 | |
| EP | 0 495 432 A1 | 7/1992 | |
| EP | 0 737 686 A1 | 10/1996 | |
| EP | 0 916 348 A1 | 5/1999 | |
| EP | 1 155 702 A1 | 11/2001 | |
| EP | 2 907 824 A1 | 8/2015 | |
| JP | H05-059061 A | 3/1993 | |
| JP | H08-337584 A | 12/1996 | |
| JP | H10-095802 A | 4/1998 | |
| JP | H1171280 A | 3/1999 | |
| JP | H11-092405 A | 4/1999 | |
| JP | 2002-060351 A | 2/2002 | |
| JP | 2005-511627 A | 4/2005 | |
| JP | 2006-511526 A | 4/2006 | |
| JP | 2008-521828 A | 6/2008 | |
| JP | 2009-538629 A | 11/2009 | |
| JP | 2012-100671 A | 5/2012 | |
| JP | 2012-225887 A | 10/2012 | |
| JP | 2013-534535 A | 9/2013 | |
| JP | 2013-534906 A | 9/2013 | |
| JP | 2017-503784 A | 2/2017 | |
| KR | 1020010052385 A | 6/2001 | |
| KR | 1020110044808 A | 4/2011 | |
| RU | 2404810 C2 | 7/2008 | |
| TW | I232930 | 5/2005 | |
| TW | 200817434 A | 4/2008 | |
| WO | WO-97/46260 A1 | 12/1997 | |
| WO | WO-00/25825 A1 | 5/2000 | |
| WO | WO-02/00734 A1 | 1/2002 | |
| WO | WO-03/013602 A1 | 2/2003 | |
| WO | WO 03/043583 A2 | 5/2003 | |
| WO | WO-2005/112919 A2 | 12/2005 | |
| WO | WO 2006/065533 A2 | 6/2006 | |
| WO | WO-2006/065533 A2 | 6/2006 | |
| WO | WO 2006/092230 A2 | 9/2006 | |
| WO | WO-2007/077028 A2 | 7/2007 | |
| WO | WO-2007/100385 A2 | 9/2007 | |
| WO | WO-2008/100624 A2 | 8/2008 | |
| WO | WO-2011/011474 A1 | 1/2011 | |
| WO | WO-2011/068845 A1 | 6/2011 | |
| WO | WO-2012/019024 A2 | 2/2012 | |
| WO | WO-2012/064733 A2 | 5/2012 | |
| WO | WO 2013/163229 A1 | 10/2013 | |
| WO | WO 2013/188740 A1 | 12/2013 | |
| WO | WO-2014/057687 A1 | 4/2014 | |
| WO | WO-2014/061277 A1 | 4/2014 | |
| WO | WO-2014/107024 A1 | 7/2014 | |
| WO | WO-2015/155998 A1 | 10/2015 | |

OTHER PUBLICATIONS

United States Office Action dated Apr. 5, 2019 in U.S. Appl. No. 15/821,697.
Alimandi et al., "Cooperative signaling of ErbB3 and ErbB2 in neoplastic transformation and human mammary carcinomas," Oncogene 10:1813-1821 (1995).
Alley et al., "Antibody-drug conjugates: targeted drug delivery for cancer," Current Opinion in Chemical Biology 14:529-537 (2010).
Barginear et al., "Trastuzumab-DM1: A Review of the Novel Immuno-Conjugate for HER2-Overexpressing Breast Cancer," The Open Breast Cancer Journal 1:25-30 (2009).
Beck, Alain, "The Next Generation of Antibody-drug Conjugates Comes of Age," Discovery Medicine 10(53):329-339 (Oct. 16, 2010).
Damle, Nitin K., "Tumour-targeted chemotherapy with immunoconjugates of calicheamicin," Expert Opin. Biol. Ther. 4(9):1445-1452 (2004).
De Jager et al., "DX-8951f: Summary of Phase I Clinical Trials," Ann. N.Y. Acad. Sci. 922:260-273 (2000).
Defazio et al., "Expression of c-erbB Receptors, Heregulin and Oestrogen Receptor in Human Breast Cell Lines," Int. J. Cancer 87:487-498 (2000).
Ducry et al., "Antibody-Drug Conjugates: Linking Cytotoxic Payloads to Monoclonal Antibodies," Bioconjugate Chem. 21:5-13 (2010).
Inoue et al., "CM-Dextran-Polyalcohol-Camptothecin Conjugate: DE-310 with a Novel Carrier System and Its Preclinical Data," Polymer Drugs in the Clinical Stage, 145-153 (2003).
Joto et al., "DX-8951F, A Water-Soluble Camptothecin Analog, Exhibits Potent Antitumor Activity Against a Human Lung Cancer Cell Line and its SN-38-Resistant Variant," Int. J. Cancer 72:680-686 (1997).
Kraus et al., "Demonstration of ligand-dependent signaling by the erbB-3 tyrosine kinase and its constitutive activation in human breast tumor cells," Proc. Natl. Acad. Sci. USA 90:2900-2904 (Apr. 1993).
Kraus et al., "Isolation and characterization of ERBB3, a third member of the ERBB/epidermal growth factor receptor family: Evidence for overexpression in a subset of human mammary tumors," Proc. Natl. Acad. Sci. USA 86:9193-9197 (Dec. 1989).
Kumazawa et al., "Antitumor activity of DX-8951f: a new camptothecin derivative," Exp. Opin. Invest. Drugs 7(4):625-632 (1998).
Kumazawa et al., "DE-310, a novel macromolecular carrier system for the camptothecin analog DX-8951f: Potent antitumor activities in various murine tumor models," Cancer Sci. 95(2):168-175 (Feb. 2004).
Kumazawa et al., "Potent and broad antitumor effects of DX-8951f, a water-soluble camptothecin derivative, against various human tumors xenografted in nude mice," Cancer Chemother. Pharmacol. 42:210-220 (1998).
Mitsui et al., "A New Water-soluble Camptothecin Derivative, DX-8951f, Exhibits Potent Antitumor Activity against Human Tumors in vitro and in vivo," Jpn. J. Cancer Res. 86:776-782 (Aug. 1995).
Naidu et al., "Expression of c-erbB3 protein in primary breast carcinomas," British Journal of Cancer 78(10): 1385-1390 (1998).

(56) References Cited

OTHER PUBLICATIONS

Nakada et al., "Novel antibody drug conjugates containing exatecan derivative-based cytotoxic payloads," Bioorganic & Medical Chemistry Letters 26(6):1542-1545 (2016).
Plowman et al., "Molecular cloning and expression of an additional epidermal growth factor receptor-related gene," Proc. Natl. Acad. Sci. USA 87:4905-4909 (Jul. 1990).
Senter et al., "The discovery and development of brentuximab vedotin for use in relapsed Hodgkin lymphoma and systemic anaplastic large cell lymphoma," Nature Biotechnology 30(7):631-637 (Jul. 2012).
Soepenberg et al., "Phase I and Pharmacokinetic Study of DE-310 in Patients with Advanced Solid Tumors," Clin. Cancer Res. 11:703-711 (Jan. 15, 2005).
Takiguchi et al., "Antitumor Effect of DX-8951, a Novel Camptothecin Analog, on Human Pancreatic Tumor Cells and Their CPT-11-resistant Variants Cultured in vitro and Xeografted in Nude Mice," Jpn. J. Cancer Res. 88:760-769 (Aug. 1997).
Wente et al., "DE-310, a macromolecular prodrug of the topoisomerase-I-inhibitor exatecan (DX-8951), in patients with operable solid tumors," Investigational New Drugs 23:339-347 (2005).
English-language translation of International Search Report issued in International Patent Application No. PCT/JP2015/002020 dated Jul. 20, 2015.
Burke P J et al. (2009), "Design, Synthesis, and Biological Evaluation of Antibody-Drug Conjugates Comprised of Potent Camptothecin Analogues", Bioconjugate Chemistry, vol. 20, No. 6, pp. 1242-1250.
Extended European Search Report issued in European Patent Application No. 15743738.5 dated Aug. 9, 2017.
Extended European Search Report issued in European Patent Application No. 15776810.2 dated Aug. 11, 2017.
Canadian Office Action dated Apr. 13, 2018 in corresponding application No. 2939802.
European Search Report issued in corresponding application No. 14874745 dated May 10, 2017.
N. Masucuchi, "Pharmacokinetics of DE-310, a novel macromolecular carrier system for the camptothecin analog DX-8951f, in tumor-bearing mice," Pharmazie 59: 374-377 (2004).
Office Action issued in Canada Application No. 2885800 dated Mar. 28, 2017.
Office Action issued in Colombia Application No. NC2016/0000187 dated May 9, 2017.
Otto Soepenberg, "Liquid chromatographic assays for DE-310, a novel camptothecin analog, and two major enzymatic products in human matrices," Journal of Chromatography B, 799, 15-22 (2004).
Thomas M. Cardillo, "Humanized Anti-Trop-2 IgG-SN-38 Conjugate for Effective Treatment of Diverse Epithelial Cancers: Preclinical Studies in Human Cancer Xenograft Models and Monkeys," Clinical Cancer Research vol. 17, No. 10, Mar. 3, 2011, pp. 3157-3169.
Yoshinobu Shiose, "Systematic Research of Peptide Spacers Controlling Drug Release from Macromolecular Prodrug System, Carboxymethyldextran Polyalcohol-Peptide-Drug Conjugates," Bioconjugate Chem. 20, 60-70 (2009).
Yusuke Ochi, "A possible mechanism for the long-lasting antitumor effect of the macromolecular conjugate DE-310: mediation by cellular uptake and drug release of its active camptothecin analog DX-8951," Cancer Chemother Pharmacol (2005) 55: 323-332.
Office Action issued in U.S. Appl. No. 15/187,179 dated Oct. 21, 2016.
Taiwanese Office Action dated Jul. 30, 2018 in corresponding application No. 104111534.
Chinese Office Action dated Nov. 1, 2016 in corresponding application No. 201380053256.2.
Conjugation site modulates the in vivo stability and therapeutic activity of antibody-drug conjugates, Shen et al, Nature Biotechnology, 2012, vol. 30, pp. 184-189, Abstract only.

Japanese Notice of Allowance dated Oct. 18, 2016 in corresponding application No. 2016-166850.
Japanese Office Action dated Dec. 6, 2016 in corresponding application No. 2016-540705.
Korean Office Action dated May 1, 2018 in corresponding application No. 10-2016-7015961.
Methods for site-specific drug conjugation to antibodies, Behrens et al., mAbs, 2014, vol. 6, No. 1, pp. 46-53.
Russian Office Action dated Oct. 11, 2018 in corresponding application No. 2016123597.
Barok et al, Trastuzumab-DM1 is highly effective in preclinical models of HER2-positive gastric cancer, Cancer Letters, 2011, vol. 306, No. 2, pp. 172-179.
Oguma et al, Validation study of a method for assaying DE-310, a macromolecular carrier conjugate containing an anti-tumor camptothecin derivative, and the free drug in tumor tissue by high performance liquid chromatography/atmospheric pressure chemical ionization tandem mass spectrometry, Biomedical Chromatography, 2005, vol. 19, No. 1, pp. 19-26.
Acchione et al, Impact of linker and conjugation chemistry on antigen binding, Fc receptor binding and thermal stability of model antibody-drug conjugates, mAbs, 2012, pp. 362-372.
Colombian Reconsideration Petition dated Mar. 15, 2018 in corresponding application No. NC2016/0000187.
Rowinsky, Preclinical and Clinical Development of Exatecan(DX-8951f), Camptothecins in Cancer Therapy, 2005, pp. 317-318.
Kang et al, Engineering multivalent antibodies to target heregulin-induced HER3 signaling in breast cancer cells, mAbs, Mar./Apr. 2014, vol. 6, No. 2, pp. 340-353.
Howard A., et al.,"Phase II Study of the Antibody Drug Conjugate Trastuzumab-DM1 for the Treatment of Human Epidermal Growth Factor Receptor 2 (HER2)-Positive Breast Cancer After Prior HER2-Directed Therapy", Journal of Clinical Oncology, vol. 29, pp. 398-405, 2011 (8 pages).
I. Sullivan, et al. "Osimertinib in the treatment of patients with epidermal growth factor receptor T790M mutation-positive metastatic non-small cell lung cancer: clinical trial evidence and experience", Therapeutic Advances in Respiratory Disease, vol. 10(6), pp. 549-565, 2016 (17 pages).
International Search Report and Written Opinion for correspondence Application No. PCT/JP2018/007152 dated Apr. 24, 2018.
K. Yonesaka, et al., "Anti-HER3 monoclonal antibody patritumab sensitizes refractory non-small cell lung cancer to the epidermal growth factor receptor inhibitor erlotinib",Oncogene vol. 35, pp. 878-886, 2016 (10 pages.
Kawakami et al.—"The anti-HER3 antibody patritumab abrogates cetuximab resistance mediated by heregulin in colorectal cancer cells", Oncotarget, vol. 5, No. 23, Dec.-May 2014, 11847-11856—10 pages.
Kimio Yonesaka, "Anti-HER3 Antibody Patritumab Overcomes Resistance to EGFR Inhibitor in Non-small Cell Lung Cancer", The Japan Lung Cancer Society, vol. 55, pp. 948-955, 2015 (8 pages).
N.V. Sergina, et al. "Escape from HER-family tyrosine kinase inhibitor therapy by the kinase-inactive HER3", Nature, vol. 445, pp. 437-441, 2007 (6 pages).
P. Janne, et al., "Phase 1 study of the Anti-HER3 Antibody Drug Conjugate U3-1402 in Metastic or Unresectable EGFR-mutant NSCLC.", Journal of Thoracic Oncology, vol. 12, No. 11, Supp. Supplement 2, pp. S2290, abstract No. P3.04-013, Nov. 2017 (3 pages).
Office Action dated Aug. 20, 2019 issued in a corresponding Chinese Patent Application No. 201480071134.0, (13 pages).
Office Action dated May 11, 2017 issued in a corresponding Taiwanese Patent Application No. 102136742, (9 pages).
Office Action dated Nov. 29, 2021 issued in a corresponding Indian Patent Application No. 202018030127, (7 pages).
Tian, et al., "A general approach to site-specific antibody drug conjugates", Proceedings of the National Academy of Sciences 111(5):1766-1771 (2014).

FIG.1

Full-length amino acid sequence of heavy chain of anti-HER3 human antibody U1-59 (SEQ ID NO: 583)

Full-length amino acid sequence of light chain of anti-HER3 human antibody U1-59 (SEQ ID NO: 584)

```
D I E M T Q S P D S L A V S L G E R A T I N C R S S Q S V L Y S S S N R
N Y L A W Y Q Q N P G Q P P K L L I Y W A S T R E S G V P D R F S G S G
S G T D F T L T I S S L Q A E D V A V Y Y C Q Q Y Y S T P R T F G Q G T
K V E I K R T V A A P S V F I F P P S D E Q L K S G T A S V V C L L N N
F Y P R E A K V Q W K V D N A L Q S G N S Q E S V T E Q D S K D S T Y S
L S S T L T L S K A D Y E K H K V Y A C E V T H Q G L S S P V T K S F N
R G E C
```

FIG.11
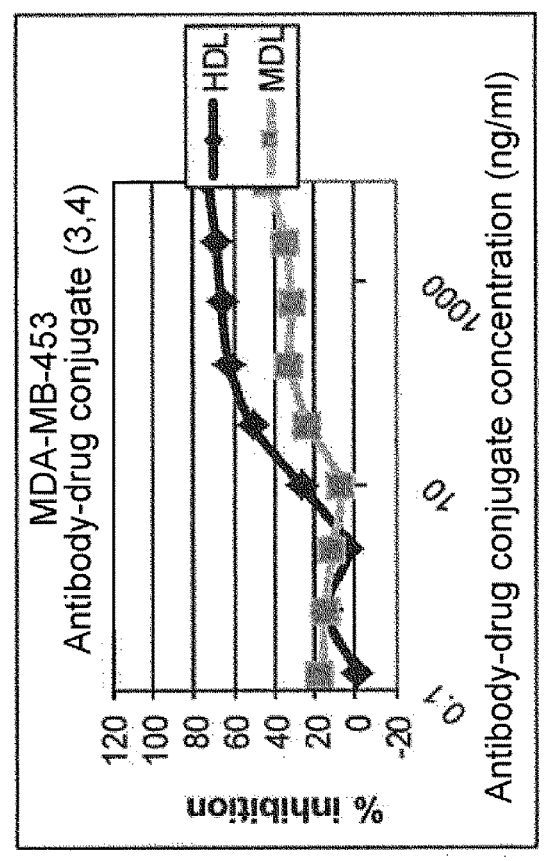
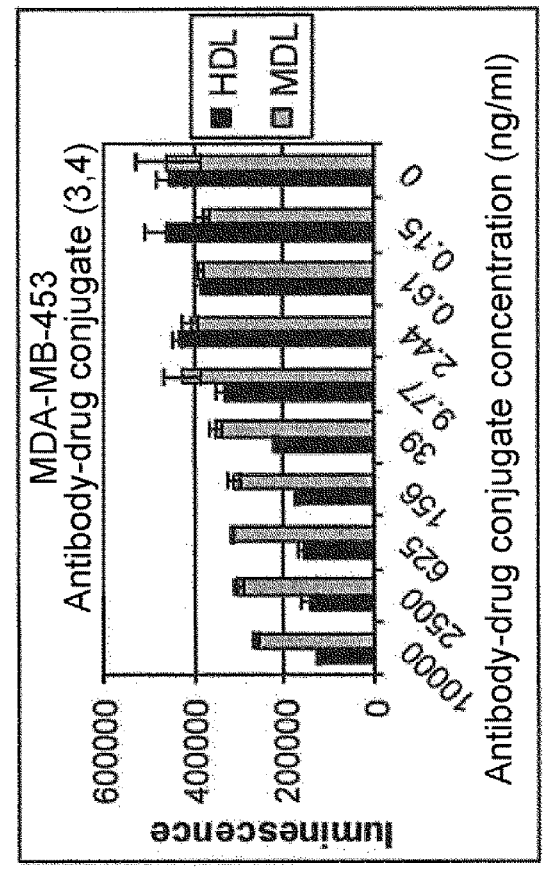

SEQUENCE LISTING

```
<160> NUMBER OF SEQ ID NOS: 594

<210> SEQ ID NO 1
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 1
gaggtgcagc tggtggagtc tggaggaggc ttgatccagc ctggggggtc cctgagactc      60
tcctgtgcag cctctgggtt caccgtcagt agcaactaca tgagctgggt ccgccaggct     120
ccagggaagg ggctggattg ggtctcagtt atttatagcg gtggtagcac atactacgca     180
gactccgtga aggccgatt caccatctcc agagacaatt ccaagaacac gctgtatctt     240
caaatgaaca gcctgagagc cgaggacacg gccgtgtatt actgtgcgag agggcagtgg     300
ctggacgtct ggggccaagg gaccacggtc accgtctcct ca                       342

<210> SEQ ID NO 2
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 2

Glu Val Gln Leu Val Glu Ser Gly Gly Gly Leu Ile Gln Pro Gly Gly
1               5                  10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Asp Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gln Trp Leu Asp Val Trp Gly Gln Gly Thr Thr Val Thr Val
```

Ser Ser

<210> SEQ ID NO 3
<211> LENGTH: 336
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Antibody

<400> SEQUENCE: 3

```
gatattgtga tgactcagtc tccactctcc ctgcccgtca cccctggaga gccggcctcc      60
atctcctgca ggtcaagtca gagcctcctg catagtaatg gatacaacta tttggattgg    120
tacctgcaga ggccagggca gtctccacaa ctcctgttct atttgggttt tcatcgggcc    180 tccgggcc ctgacaggtt cagtggcagt ggatcaggca cagattttac actgaaaatc       240
agcagagtgg aggctgagga tgttggggtt tattactgca ggcaagctct acaaactccg    300
ctcactttcg gcggagggac caaggtggag atcaaa                              336
```

<210> SEQ ID NO 4
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Antibody

<400> SEQUENCE: 4

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Arg Pro Gly Gln Ser
        35                  40                  45

Pro Gln Leu Leu Phe Tyr Leu Gly Phe His Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Arg Gln Ala
                85                  90                  95

Leu Gln Thr Pro Leu Thr Phe Gly Gly Gly Thr Lys Val Glu Ile Lys
            100                 105                 110

<210> SEQ ID NO 5
<211> LENGTH: 374
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Antibody

<400> SEQUENCE: 5

```
caggtgcagc tgcaggagtc gggcccagga ctggtgaagc cttcacagac cctgtccctc      60
acctgtactg tctctggtgg ctccatcagc agtggtggtt actactggag ctggatccgc    120
```

```
cagcacccag ggaagggcct ggagtggatt gggtacatct attccagtgg gagcacctac    180
tacaacccgt ccctcaagag tcgagttacc atatcagtag acacgtctaa gaaccagttc    240
tccctgaagc tgagctctgt gactgccgcg gacacggccg tgtattactg tgcgagagat    300
agggaactgg aactttacta ctactactac ggtatggacg tctggggcca agggaccacg    360
gtcaccgtct cctc                                                      374
```

<210> SEQ ID NO 6
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 6

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Ser Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Glu Leu Glu Leu Tyr Tyr Tyr Tyr Gly Met
            100                 105                 110

Asp Val Trp Gly Gln Gly Thr Thr Val Thr Val Ser
        115                 120
```

<210> SEQ ID NO 7
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 7

```
gatattgtga tgactcagtc tccactctcc ctgcccgtca cccctggaga gccggcctcc     60
atctcctgca ggtctagtca gagcctcctg tatagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagatttac actgaaaatc     240 agcagagtgg aggctgagga tgttgggatt tattactgca tgcaagctct acaaactccg    300
ctcactttcg gcggagggac caaggtggag atcaaa                              336
```

<210> SEQ ID NO 8
<211> LENGTH: 112
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<223> OTHER INFORMATION: Antibody

<400> SEQUENCE: 8

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 9
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 9
cagatcacct tgaaggagtc tggtcctacg ctggtgaaac ccacacagac cctcacgctg      60
acctgcacct tctctgggtt ctcactcagc actagtggag tgggtgtggg ctggatccgt     120
cagcccccag gaaaggccct ggactggctt gcactcattt attggaatga tgataagcgc     180
tacagcccat ctctgaagag caggctcacc atcaccaagg acacctccaa aaaccaggtg     240
gtccttacaa tgaccaacat ggatcttgtg gacacagcca catattactg tgtacacaga     300
gacgaagttc gagggtttga ctactggggc cagggaaccc tggtcaccgt ctcctca       357

<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 10

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Asp
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val

```
                65                  70                  75                  80
Val Leu Thr Met Thr Asn Met Asp Leu Val Asp Thr Ala Thr Tyr Tyr
                        85                  90                  95

Cys Val His Arg Asp Glu Val Arg Gly Phe Asp Tyr Trp Gly Gln Gly
                100                 105                 110

Thr Leu Val Thr Val Ser Ser
            115

<210> SEQ ID NO 11
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 11
gatgttgtga tgactcagtc tccactctcc ctgcccgtca cccttggaca gccggcctcc      60
atctcctgca ggtctagtca aagcctcgta tacagtgatg gatacaccta cttgcattgg     120
tttcagcaga ggccaggcca atctccaagg cgcctaattt ataaggtttc taactgggac     180
tctggggtcc cagacagatt cagcggcagt gggtcaggca ctgatttcac actgaaaatc     240
agcagggtgg aggctgagga tgttggggtt tattactgca tgcaaggtgc acactggccg     300
atcaccttcg gccaagggac acgactggag attaaa                               336

<210> SEQ ID NO 12
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 12

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Tyr Thr Tyr Leu His Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ala His Trp Pro Ile Thr Phe Gly Gln Gly Thr Arg Leu Glu Ile Lys
            100                 105                 110

<210> SEQ ID NO 13
<211> LENGTH: 374
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

<223> OTHER INFORMATION: Antibody

<400> SEQUENCE: 13

```
caggtgcagc tgcaggagtc gggcccagga ctggtgaagc cttcacagac cctgtccctc      60
acctgcactg tctctggtgg ctccatcagc agtggtgggt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtatttctg tgcgagagat     300
cgggaacttg agggttactc caactactac ggtgtggacg tctggggcca agggaccacg     360
gtcaccgtct cctc                                                        374
```

<210> SEQ ID NO 14
<211> LENGTH: 124
<212> TYPE: PRT
<213> ORGANISM: Artificial Sequence
<220> FEATURE:
<223> OTHER INFORMATION: Description of Artificial Sequence: Synthetic
   polypeptide
<220> FEATURE:
<223> OTHER INFORMATION: Antibody

<400> SEQUENCE: 14

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg Asp Arg Glu Leu Glu Gly Tyr Ser Asn Tyr Tyr Gly Val
            100                 105                 110

Asp Val Trp Gly Gln Gly Thr Thr Val Thr Val Ser
        115                 120
```

<210> SEQ ID NO 15
<211> LENGTH: 321
<212> TYPE: DNA
<213> ORGANISM: Artificial Sequence
<220> FEATURE:
<223> OTHER INFORMATION: Description of Artificial Sequence: Synthetic
   polynucleotide
<220> FEATURE:
<223> OTHER INFORMATION: Antibody

<400> SEQUENCE: 15

```
gacatccaga tgacccagtc tccatcctcc ctgtctgcat ctgtaggaga cagagtcacc      60
atcacttgcc gggcaagtca ggccattagc aactatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag cctgcagcct     240
gaagattttg caacttatta ctgtcaacag aataatagtc tccgatcac cttcggccaa     300
gggacacgac tggagattaa a                                                321
```

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Asn Ser Leu Pro Ile
                85                  90                  95

Thr Phe Gly Gln Gly Thr Arg Leu Glu Ile Lys
            100                 105

<210> SEQ ID NO 17
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 17
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcag caccgcctac      240 ctgcagtgga gcagcctgaa ggcctcggac accgccatgt attactgtgc gagacatgaa     300
aactacggtg actacaacta ctggggccag ggaaccctgg tcaccgtctc ctca           354

<210> SEQ ID NO 18
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 18

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

```
Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg His Glu Asn Tyr Gly Asp Tyr Asn Tyr Trp Gly Gln Gly Thr
            100                 105                 110

Leu Val Thr Val Ser Ser
            115
```

```
<210> SEQ ID NO 19
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 19
gacatccaga tgacccagtc tccatcctcc ctgtctgcat ctgtcggaga cagagtcacc      60
atcacttgcc gggcaagtca gagcattcgc agctatttaa attggtatca gcagaaacca     120
gggaaagccc ctaagctcct gatctatgct gcttccagtt tgcaaagtgg ggtcccatca     180
aggttcagtg gcagtggatc tgggacagat ttcactctca ccatcagcag tctgcaacct     240
gaagattttg cactttactg ctgtcaacag agtaacggtt ccccgctcac tttcggcgga     300
gggaccaagg tggagatcaa a                                                321
```

```
<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 20

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Arg Ser Tyr
             20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Leu Tyr Cys Cys Gln Gln Ser Asn Gly Ser Pro Leu
                 85                  90                  95

Thr Phe Gly Gly Gly Thr Lys Val Glu Ile Lys
            100                 105
```

```
<210> SEQ ID NO 21
```

<211> LENGTH: 380
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody

<400> SEQUENCE: 21

```
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag gaagggcct ggagtggatt gggtacatct attacagtgg agcacctac       180
tacaacccgt ccctcaggag tcgagttacc atatcagtag acacgtctaa gaaccagttc     240
tccctgaagc tgagctctgt gactgccgcg gacacggccg tgtattactg tgcgagagat     300
agagagagag agtgggatga ttacggtgac ccccaaggta tggacgtctg gggccaaggg    360
accacggtca ccgtctcctc                                                380
```

<210> SEQ ID NO 22
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Antibody

<400> SEQUENCE: 22

```
Gln Val Gln Leu Gln Glu Ser Gly Pro Gly Leu Val Lys Pro Ser Gln
1               5                   10                  15
Thr Leu Ser Leu Thr Cys Thr Val Ser Gly Gly Ser Ile Ser Ser Gly
            20                  25                  30
Gly Tyr Tyr Trp Ser Trp Ile Arg Gln His Pro Gly Lys Gly Leu Glu
        35                  40                  45
Trp Ile Gly Tyr Ile Tyr Tyr Ser Gly Ser Thr Tyr Tyr Asn Pro Ser
    50                  55                  60
Leu Arg Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Asp Arg Glu Arg Glu Trp Asp Asp Tyr Gly Asp Pro Gln
            100                 105                 110
Gly Met Asp Val Trp Gly Gln Gly Thr Thr Val Thr Val Ser
        115                 120                 125
```

<210> SEQ ID NO 23
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody

<400> SEQUENCE: 23

```
gacatccaga tgacccagtc tccatcctcc ctgtctgcat ctgtaggaga cagagtcacc      60
atcacttgcc gggcaagtca gagcattagc agctatttac attggtatca gcagaaacca    120
```

| gggaaagccc | ctaagctcct | gatccatgct | gcatccagtt | tacaaagtgg | ggtcccatca | 180 |
| aggttcagtg | gcagtggatc | tgggacagat | ttcactctca | ccatcagtag | tctgcaacct | 240 |
| gaagattttg | caacttacta | ctgtcaacag | agttacagta | acccgctcac | tttcggcgga | 300 |
| gggaccaagg | tggagatcca | a | | | | 321 |

```
<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 24
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu His Trp Tyr Gln Gln Lys Pro Gly Lys Ala Pro Lys Leu Leu Ile
        35                  40                  45

His Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Leu
                85                  90                  95

Thr Phe Gly Gly Gly Thr Lys Val Glu Ile Gln
            100                 105

```
<210> SEQ ID NO 25
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 25
```

| gaggtgcagc | tggtgcagtc | tggagcagag | gtgaaaaagc | ccggggagtc | tctgaagatc | 60 |
| tcctgtaagg | gttctggata | cagctttacc | agctactgga | tcggctgggt | gcgccagatg | 120 |
| cccgggaaag | gcctggagtg | gatggggatc | atctggcctg | gtgactctga | taccatatac | 180 |
| agcccgtcct | tccaaggcca | ggtcaccatc | tcagccgaca | agtccatcag | caccgcctac | 240 |
| ctgcagtgga | gcagcctgaa | ggcctcggac | accgccatgt | attactgtgc | gagacatgaa | 300 |
| aactacggtg | actacaacta | ctggggccag | ggaaccctgg | tcaccgtctc | ctca | 354 |

```
<210> SEQ ID NO 26
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 26
```

```
Glu Val Gln Leu Val Gln Ser Gly Ala Glu Val Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Trp Pro Gly Asp Ser Asp Thr Ile Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Glu Asn Tyr Gly Asp Tyr Asn Tyr Trp Gly Gln Gly Thr
            100                 105                 110

Leu Val Thr Val Ser Ser
        115
```

<210> SEQ ID NO 27
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody

<400> SEQUENCE: 27

```
gacatccaga tgacccagtc tccatcctcc ctgtctgcat ctgtgggaga cagagtcacc      60
atcacttgcc gggcaagtca gagcattcga agttatttaa attggtatca gcagaaaccg     120
gggaatgccc ctaaactcct gatctatgct gcatccagtt tgcaaagtgg ggtcccatca     180
aggttcagtg gcagtggatc tgggacagat ttcactctca ccatcagcag tctgcaacct     240
gaagattttg cactttacta ctgtcaacag agtatcagtt ccccgctcac tttcggcgga     300
gggaccaagg tggagatcaa a                                               321
```

<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Antibody

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Tyr
            20                  25                  30

Leu Asn Trp Tyr Gln Gln Lys Pro Gly Asn Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Leu Tyr Tyr Cys Gln Gln Ser Ile Ser Ser Pro Leu
```

Thr Phe Gly Gly Gly Thr Lys Val Glu Ile Lys
            100                 105

<210> SEQ ID NO 29
<211> LENGTH: 374
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 29
caggtgcagc tggtgcagtc tggggctgag gtgaagaagc ctggggcctc agtgaaggtc      60
tcctgcaagg cttctggata caccttcacc agttatgata tcaactgggt gcgacaggcc     120
actggacaag gcttgagtg gatgggatgg atgaaccta acagtggtga cactggctat      180
gcacaggtgt tccagggcag agtcaccatg acctggaaca cctccataag cacagcctac     240
atggaactga gcagcctgag atctgaggac acggccgtgt attactgtgc gagatttggg     300
gatctcccgt atgactacag ttactacgaa tggttcgacc cctggggcca gggaaccctg     360
gtcaccgtct cctc                                                      374

<210> SEQ ID NO 30
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asp Thr Gly Tyr Ala Gln Val Phe
    50                  55                  60

Gln Gly Arg Val Thr Met Thr Trp Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Gly Asp Leu Pro Tyr Asp Tyr Ser Tyr Tyr Glu Trp Phe
            100                 105                 110

Asp Pro Trp Gly Gln Gly Thr Leu Val Thr Val Ser
        115                 120

<210> SEQ ID NO 31
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 31

```
gacatccaga tgacccagtc tccatcctcc ctgtctgcat ctgtaggaga cagagtcacc      60
atcacttgcc gggcaagcca gagcattagc agctatttaa attggtatca gcagagacca     120
gggaaagccc ctaagctcct gatctatgca gcatccagtt tgcaaagtgg ggtcccatca     180
aggttcagtg gcagtggatc tgggacagat ttcactctca ccatcagcag tctgcaacct    240
gaagattttg caacttacta ctgtcaacag agttacagta ccccgctcac tttcggcgga    300
gggaccaagg tggagatcaa a                                              321
```

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Antibody

<400> SEQUENCE: 32

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Ser Ile Ser Ser Tyr
            20                  25                  30
Leu Asn Trp Tyr Gln Gln Arg Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Leu
                85                  90                  95
Thr Phe Gly Gly Gly Thr Lys Val Glu Ile Lys
            100                 105
```

<210> SEQ ID NO 33
<211> LENGTH: 386
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody

<400> SEQUENCE: 33

```
caggtacagc tgcagcagtc aggtccagga ctggtgaagc cctcgcagac cctctcactc      60
acctgtgcca tctccgggga cagtgtctct agcaacagtg ctgcttggaa ctggatcagg    120
cagtccccat cgagaggcct tgagtggctg ggaaggacat actacaggtc caagtggtat    180
aatgattatg cagtatctgt gaaaagtcga ataaccatca acccagacac atccaagaac    240
cagttctccc tgcagctgaa ctctgtgact cccgaggaca cggctgtgta ttactgtgca    300
agagatctct acgattttg gagtggttat ccctactact acggtatgga cgtctggggc     360
caagggacca cggtcaccgt ctcctc                                          386
```

<210> SEQ ID NO 34
<211> LENGTH: 128

<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 34

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Leu Tyr Asp Phe Trp Ser Gly Tyr Pro Tyr
            100                 105                 110

Tyr Tyr Gly Met Asp Val Trp Gly Gln Gly Thr Thr Val Thr Val Ser
        115                 120                 125

<210> SEQ ID NO 35
<211> LENGTH: 383
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 35
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaaggacat actacaggtc caagtggtat     180
aatgattatg cagtatctgt gaaaagtcga ataaccatca cccagacac atccaagaac      240 cagttctccc tgcagctgaa ctctgtgact cccgaggaca cggctgtgta ttactgtgca     300
agagattact atggttcggg gagtttctac tactactacg gtatggacgt ctggggccaa     360
gggaccacgg tcaccgtctc ctc                                              383

<210> SEQ ID NO 36
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 36

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Tyr Tyr Gly Ser Gly Ser Phe Tyr Tyr Tyr
            100                 105                 110

Tyr Gly Met Asp Val Trp Gly Gln Gly Thr Thr Val Thr Val Ser
        115                 120                 125

<210> SEQ ID NO 37
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 37
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaaggtcct gatctatgct gcatccaatt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctcggac gttcggccaa    300
gggaccaagg tggaaatcaa a                                              321

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Val Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Glu Ile Lys
            100                 105

```
<210> SEQ ID NO 39
<211> LENGTH: 371
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 39
caggtgcagc tgcaggagtc gggcccagga ctggtgaagc cttcggagac cctgtccctc      60
acctgcactg tctctggtgg ctccatcagt agttactact ggagctggat ccggcagccc     120
gccgggaagg gactggagtg gattgggcat atctatacca gtgggagcac caactacaac     180
ccctccctca gagtcgagt caccatgtca gtagacacgt ccaagaacca gttctccctg      240
aagctgagct ctgtgaccgc cgcggacacg gccgtgtatt actgtgcgag agaagcgatt     300
tttggagtgg ccccctacta ctactacggt atggacgtct ggggccaagg gaccacggtc     360
accgtctcct c                                                         371

<210> SEQ ID NO 40
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly His Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ala Ile Phe Gly Val Ala Pro Tyr Tyr Tyr Gly Met Asp
            100                 105                 110

Val Trp Gly Gln Gly Thr Thr Val Thr Val Ser
        115                 120

<210> SEQ ID NO 41
<211> LENGTH: 377
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 41
caggtgcagc tggtgcagtc tggggctgag gtgaagaagc ctggggcctc agtgaaggtc      60
tcctgcaagg cttctggata caccttcacc ggctactata tgcactgggt gcgacaggcc    120
```

```
cctggacaag ggcttgagtg gatgggatgg atcaaccata atattggtgg cacaaactgt    180
gcacagaagt tcagggcag ggtcaccatg accaggaca cgtccatcag cacagcctac     240
atggagctga gcaggctgag atctgacgac acggccgtgt attactgtgc gagaggggga    300
cggtatagca gcagctggtc ctactactac tacggtatgg acgtctgggg ccaagggacc    360
acggtcaccg tctcctc                                                   377
```

```
<210> SEQ ID NO 42
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ile Gly Gly Thr Asn Cys Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Arg Tyr Ser Ser Ser Trp Ser Tyr Tyr Tyr Tyr Gly
            100                 105                 110

Met Asp Val Trp Gly Gln Gly Thr Thr Val Thr Val Ser
        115                 120                 125
```

```
<210> SEQ ID NO 43
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 43
gatattctga tgacccagac tccactctct ctgtccgtca cccctggaca gccggcctcc    60
atctcctgca gtctagtca gagcctcctg cttagtgatg gagggaccta tttgtattgg    120
tacctgcaga agccaggcca gcctccacag ctcctgatct atgaagtttc caaccggttc    180
tctggagtgc cagataggtt cagtggcagc gggtcaggga cagatttcac actgaaaatc    240
agccgggtgg aggctgagga tgttggggtt tattactgca tgcaaagtat gcagcttccg    300 atcacctcg gccaagggac acgactggaa attaaa                               336
```

```
<210> SEQ ID NO 44
<211> LENGTH: 112
<212> TYPE: PRT
<213> ORGANISM: Artificial Sequence
<220> FEATURE:
```

<223> OTHER INFORMATION: Description of Artificial Sequence: Synthetic
polypeptide
<220> FEATURE:
<223> OTHER INFORMATION: Antibody

<400> SEQUENCE: 44

Asp Ile Leu Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Leu Ser
            20                  25                  30

Asp Gly Gly Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Met Gln Leu Pro Ile Thr Phe Gly Gln Gly Thr Arg Leu Glu Ile Lys
            100                 105                 110

<210> SEQ ID NO 45
<211> LENGTH: 380
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Antibody

<400> SEQUENCE: 45
caggtgcagc tgcaggagtc gggcccagga ctggtgaagc cttcggagac cctgtccctc      60
acctgcactg tctctggtgg ctccgtcagc agtggtggtt actactggag ctggatccgg     120
cagcccccag ggaagggact ggagtggatt gggtatatct attacagtgg gagcaccaac     180
tacaacccct ccctcaagag tcgagtcacc atatcagtag acacgtccaa gaaccagttc     240
tccctgaagc tgagctctgt gaccgctgcg gacacggccg tgtattactg tgcgagaggg     300
ggggacagta actacgagga ttactactac tactacggta tggacgtctg gggccaaggg     360
accacggtca ccgtctcctc                                                 380

<210> SEQ ID NO 46
<211> LENGTH: 126
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Antibody

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gly Asp Ser Asn Tyr Glu Asp Tyr Tyr Tyr Tyr Tyr
            100                 105                 110

Gly Met Asp Val Trp Gly Gln Gly Thr Thr Val Thr Val Ser
        115                 120                 125

<210> SEQ ID NO 47
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 47
gacatccaga tgacccagtc tccatcctcc ctgtctgcat ctgtaggaga cagagtcacc      60
atcacttgcc gggcaagtca gagcattagc atctatttac attggtatca gcagaaacca     120
gggaaagccc ctaagctctt gatctctgct gcatccagtt tgcaaagtgg ggtcccgtca     180
aggttcagtg gcagtggatc tgggacagat ttcactctca ccatcagaag tctgcaacct     240
gaagattttg caacttacta ctgtcaacag agttacactt ccccgatcac cttcggccaa     300
gggacacgac tggagattaa a                                                321

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ile Tyr
            20                  25                  30

Leu His Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Arg Ser Leu Gln Pro
65                  70                  75                  80

Glu Asp Phe Ala Thr Tyr Tyr Cys Gln Gln Ser Tyr Thr Ser Pro Ile
                85                  90                  95

Thr Phe Gly Gln Gly Thr Arg Leu Glu Ile Lys
            100                 105

<210> SEQ ID NO 49
<211> LENGTH: 380
<212> TYPE: DNA
<213> ORGANISM: Artificial Sequence
<220> FEATURE:
<223> OTHER INFORMATION: Description of Artificial Sequence: Synthetic

```
polynucleotide
<220> FEATURE:
<223> OTHER INFORMATION: Antibody

<400> SEQUENCE: 49
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactggagtg gattgggtat atctattaca gtgggagcac caactacaac   180
ccctccctca agagtcgagt caccatatca gtagacacgt ccaagcacca gttctccctg   240
aagctgagct ctgtgaccgc tgcggacacg gccgtgtatt actgtgcgag agattcgagt   300
tactatgata gtagtggtta ttacttatac tactacgcta tggacgtctg gggccaaggg   360
accacggtca ccgtctcctc                                               380

<210> SEQ ID NO 50
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 50

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys His Gln Phe Ser Leu
65                  70                  75                  80

Lys Leu Ser Ser Val Thr Ala Ala Asp Thr Ala Val Tyr Tyr Cys Ala
                85                  90                  95

Arg Asp Ser Ser Tyr Tyr Asp Ser Ser Gly Tyr Tyr Leu Tyr Tyr Tyr
            100                 105                 110

Ala Met Asp Val Trp Gly Gln Gly Thr Thr Val Thr Val Ser
        115                 120                 125

<210> SEQ ID NO 51
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 51
gacatcgtga tgacccagtc tccagactcc ctggctgtgt ctctgggcga gagggccacc    60
atcaactgca agtccagcca gagtgtttta tacagctcca acaataagaa ctacttagct   120
tggtaccagc agaaaccagg acagcctcct aagctgctca tttcctgggc atctacccgg   180
gaatccgggg tccctgaccg attcagtggc agcgggtctg ggacagattt cactctcacc   240
atcagcagcc tgcaggctga agatgtggca gtttattact gtcagcaata ttatactact   300
```

```
cctctcactt tcggccctgg gaccaaagtg gatatcaaa                              339
```

```
<210> SEQ ID NO 52
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 52
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Leu Thr Phe Gly Pro Gly Thr Lys Val Asp Ile
            100                 105                 110

Lys

```
<210> SEQ ID NO 53
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 53
gaggtgcaac tggtggagtc tgggggaggc ttggtacagc ctggggggtc cctgagactc        60
tcctgtgcag cctctggatt caccttcagt atctatagca tgaactgggt ccgccaggct       120
ccagggaagg ggctggagtg ggtttcatac attagtagta gtagtagtac catatactac       180
gcagactctg tgaagggccg attcaccatc tccagagaca atgccaagaa ctcactgtat       240
ctgcaaatga acagcctgag agacgaggac acggctgtgt attactgtgc gagagatagg       300
ggtgacttcg atgcttttga tatctgggcc aagggacaa tggtcaccgt ctcttca          357
```

```
<210> SEQ ID NO 54
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 54
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                85                  90                  95

Ala Arg Asp Arg Gly Asp Phe Asp Phe Asp Ile Trp Gly Gln Gly
            100                 105                 110

Thr Met Val Thr Val Ser Ser
        115

<210> SEQ ID NO 55
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 55
gacatccaga tgacccagtc tccatcctcc ctgtctgcat ctgtaggaga cagagtcacc      60
atcacttgcc aggcgagtca ggacattacc aactatttga attggtatca gcagaaacca     120
gggaaagccc ctaagctcct gatctacgat gcatccaatt tggaaacagg gtcccatca     180 aggttcagtg gaagtggatc tgggacagat tttactttca ccatcagcag cctgcagcct     240
gaagatattg caacatataa ctgtcaacag tgtgaaaatt tcccgatcac cttcggccaa     300
gggacacgac tggagattaa a                                               321

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 56

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Asn Cys Gln Gln Cys Glu Asn Phe Pro Ile
                85                  90                  95

Thr Phe Gly Gln Gly Thr Arg Leu Glu Ile Lys

<210> SEQ ID NO 57
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 57

```
gatattgtga tgactcagtc tccactctcc ctgcccgtca cccctggaga gccggcctcc    60
atctcctgca ggtctagtca gagcctcctg tatagtaatg gatacaagta tttggattgg   120
tacctgcaga agccagggca gtctccacag ctcctgatct atttgggttc taatcgggcc   180
tccggggtcc ctgacaggtt cagtggcagt ggatcaggca cagatttcac actgaaaatc   240
agcagagtgg aggctgagga tgttggggtt tattattgca tgcaggctct acaaactccg   300
atcaccttcg gccaagggac acgactggag attaaa                            336
```

<210> SEQ ID NO 58
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 58

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Lys Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110

<210> SEQ ID NO 59
<211> LENGTH: 374
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 59

```
caggtgcagc tgcaggagtc gggcccagga ctggtgaagc cttcggagac cctgtccctc    60
acctgcactg tctctggtgg ctccgtcagc agtggtggtt actactggaa ctggatccgg   120
cagcccccag ggaagggact ggagtggatt gggtatatca attacagtgg gagcaccaac   180
```

```
tacaacccct ccctcaagag tcgagtcacc atatcagtag acacgtccaa gaaccagttc    240
tccctgaagc tgagctctgt gaccgctgcg gacacggccg tgtattactg tgcgagagat    300
cgagaactgg aactttacta ctactactac ggtatggacg tctggggcca agggaccacg    360
gtcaccgtct cctc                                                      374
```

<210> SEQ ID NO 60
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 60

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Asn Trp Ile Arg Gln Pro Pro Gly Lys Gly Leu Glu
        35                  40                  45

Trp Ile Gly Tyr Ile Asn Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Glu Leu Glu Leu Tyr Tyr Tyr Tyr Gly Met
            100                 105                 110

Asp Val Trp Gly Gln Gly Thr Thr Val Thr Val Ser
        115                 120
```

<210> SEQ ID NO 61
<211> LENGTH: 374
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 61

```
caggtgcagc tgcaggagtc gggcccagga ctggtgaagc cttctgagac cctgtccctc    60
acctgcactg tctctggtgg ctccgtcagc agtggtggtt actactggaa ctggatccgg    120
cagcccccag ggaagggact ggagtggatt gggtatatca attacagtgg gagcaccaac    180
tacaacccct ccctcaagag tcgagtcacc atatcagtag acacgtccaa gaaccagttc    240
tccctgaagc tgagctctgt gaccgctgcg gacacggccg tgtattactg tgcgagagat    300
cgagaactgg aactttacta ctactactac ggtatggacg tctggggcca agggaccacg    360
gtcaccgtct cctc                                                      374
```

<210> SEQ ID NO 62
<211> LENGTH: 120
<212> TYPE: PRT
<213> ORGANISM: Artificial Sequence
<220> FEATURE:

<223> OTHER INFORMATION: Description of Artificial Sequence: Synthetic
    polypeptide
<220> FEATURE:
<223> OTHER INFORMATION: Antibody

<400> SEQUENCE: 62

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Asn Trp Ile Arg Gln Pro Pro Gly Lys Gly Leu Glu
        35                  40                  45

Trp Ile Gly Tyr Ile Asn Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Arg Glu Leu Glu Leu Tyr Tyr Tyr Tyr Gly Met
            100                 105                 110

Asp Val Trp Gly Gln Gly Thr Thr
        115                 120

<210> SEQ ID NO 63
<211> LENGTH: 336
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Antibody

<400> SEQUENCE: 63
gatattgtga tgactcagtc tccactctcc ctgcccgtca cccctggaga gccggcctcc      60
atctcctgca ggtctagtca gagcctcctg tatagtaatg gatacaagta tttggattgg     120
tacctgcaga agccagggca gtctccacag ctcatgatct atttgggttc taatcgggcc     180
tccggggtcc ctgacaggtt cagtggcagt ggatcaggca cagattttac actgaaaatc     240
agcagagtgg aggctgagga tgttggggtt tattattgca tgcaggctct acaaactccg     300
atcaccttcg gccaagggac acgactggag attaaa                               336

<210> SEQ ID NO 64
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Antibody

<400> SEQUENCE: 64

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Lys Tyr Leu Asp Trp Tyr Leu Gln Lys Pro Gly Gln Ser
        35                  40                  45

Pro Gln Leu Met Ile Tyr Leu Gly Ser Asn Arg Ala Ser Gly Val Pro

```
                  50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                     85                  90                  95

Leu Gln Thr Pro Ile Thr Phe Gly Gln Gly Thr Arg Leu Glu Ile Lys
                100                 105                 110

<210> SEQ ID NO 65
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 65
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagcagct     300
cgccttgact actactacgg tatggacgtc tggggccaag ggaccacggt caccgtctcc     360
tca                                                                  363

<210> SEQ ID NO 66
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 66

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Ala Arg Leu Asp Tyr Tyr Tyr Gly Met Asp Val Trp Gly
            100                 105                 110

Gln Gly Thr Thr Val Thr Val Ser Ser
            115                 120

<210> SEQ ID NO 67
<211> LENGTH: 321
<212> TYPE: DNA
```

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 67

```
gacatccaga tgacccagtc tccatcctcc ctgtctgcat ctgtaggaga cagagtctcc    60
atcacttgcc gggcaagtca gagcattaac agctatttaa attggtttca gcagaagcca   120
gggaaagccc ctcagctcct gatctttggt gcatccggtt tgcaaagtgg ggtcccatca   180
aggttcagtg gcagtggatc tgggacagat ttcactctca ccatcaacag tctgcaacct   240
gaagattttg caacttacta ctgtcaacag agttacagtt ccccgctcac cttcggccaa   300
gggacacgac tggagattaa a                                             321
```

<210> SEQ ID NO 68
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 68

Asp Ile Gln Met Thr Gln Ser Pro Ser Ser Leu Ser Ala Ser Val Gly
1               5                   10                  15

Asp Arg Val Ser Ile Thr Cys Arg Ala Ser Gln Ser Ile Asn Ser Tyr
            20                  25                  30

Leu Asn Trp Phe Gln Gln Lys Pro Gly Lys Ala Pro Gln Leu Leu Ile
        35                  40                  45

Phe Gly Ala Ser Gly Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Ser Pro Leu
                85                  90                  95

Thr Phe Gly Gln Gly Thr Arg Leu Glu Ile Lys
            100                 105

<210> SEQ ID NO 69
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 69

```
caggtgcagc tacagcagtg gggcgcagga ctgttgaagc cttcggagac cctgtccctc    60
acctgcgctg tctatggtgg gtccttcagt ggttactact ggagctggat ccgccagccc   120
ccagggaagg ggctggagtg gattggggaa atcaatcata gtggaagcac caactacaac   180
ccgtccctca agagtcgagt caccatatca gtagaaacgt ccaagaacca gttctccctg   240
aagctgagct ctgtgaccgc cgcggacacg gctgtgtatt actgtgcgag agataagtgg   300
acctggtact tcgatctctg ggccgtggc accctggtca ctgtctcctc a             351
```

<210> SEQ ID NO 70
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 70

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Glu Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Trp Thr Trp Tyr Phe Asp Leu Trp Gly Arg Gly Thr Leu
            100                 105                 110

Val Thr Val Ser Ser
        115

<210> SEQ ID NO 71
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 71
gacatcgaga tgacccagtc tccagactcc ctggctgtgt ctctgggcga gagggccacc      60
atcaactgca ggtccagcca gagtgtttta tacagctcca gcaataggaa ctacttagct     120
tggtaccagc agaacccagg acagcctcct aagctgctca tttactgggc ttctacccgg     180
gaatccgggg tccctgaccg attcagtggc agcgggtctg ggacagattt cactctcacc     240
atcagcagcc tgcaggctga agatgtggca gtttattact gtcagcaata ttatagtact     300
cctcggacgt tcggccaagg gaccaaggtg gaaatcaaa                            339

<210> SEQ ID NO 72
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 72

Asp Ile Glu Met Thr Gln Ser Pro Asp Ser Leu Ala Val Ser Leu Gly
1               5                   10                  15

```
Glu Arg Ala Thr Ile Asn Cys Arg Ser Ser Gln Ser Val Leu Tyr Ser
                20                  25                  30

Ser Ser Asn Arg Asn Tyr Leu Ala Trp Tyr Gln Gln Asn Pro Gly Gln
            35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys

<210> SEQ ID NO 73
<211> LENGTH: 374
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 73
caggtgcagc tgcaggagtc gggcccagga ctggtgaagc cttcacagac cctgtccctc    60
acctgcactg tctctggtgg ctccatcagc agtggtggtt actactggag ctggatccgc   120
cagcacccag ggaagggcct ggagtggatg ggaacatct  attacagtgg gagcacctac   180
tacaacccgt ccctcaagag tcgagttacc atatcagtag acacgtctga gaaccagttc   240
tccctgaagc tgaactctgt gactgccgcg gacacggccg tatattactg tgcgagaggg   300
ggaactggaa ccaattacta ctactactac ggtatggacg tctggggcca agggaccacg   360
gtcaccgtct cctc                                                     374

<210> SEQ ID NO 74
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 74

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Gly Tyr Tyr Trp Ser Trp Ile Arg Gln His Pro Gly Lys Gly Leu Glu
            35                  40                  45

Trp Met Gly Asn Ile Tyr Tyr Ser Gly Ser Thr Tyr Tyr Asn Pro Ser
50                  55                  60

Leu Lys Ser Arg Val Thr Ile Ser Val Asp Thr Ser Glu Asn Gln Phe
65                  70                  75                  80

Ser Leu Lys Leu Asn Ser Val Thr Ala Ala Asp Thr Ala Val Tyr Tyr
                85                  90                  95

Cys Ala Arg Gly Gly Thr Gly Thr Asn Tyr Tyr Tyr Tyr Gly Met
```

100                 105                 110
Asp Val Trp Gly Gln Gly Thr Thr Val Thr Val Ser
        115                 120

<210> SEQ ID NO 75
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 75
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gctgggccac tggcatccca    180
aacaggttca gtggcagtgg gtctgggaca gacttcactc tcaccatcag cagactggag    240
cctgaagatt ttgcagtgta ttactgtcag cagtatggta gctcaccgct cactttcggc    300
ggagggacca aggtggagat caaa                                           324

<210> SEQ ID NO 76
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 76

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Trp Ala Thr Gly Ile Pro Asn Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 77
<211> LENGTH: 377
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 77
caggtgcagc tgcaggagtc gggcccagga ctggtgaagc cttcacagac cctgtccctc     60

```
acctgcactg tctctggtgt ctccatcagc agtggtggtt actactggag ctggatccgc    120
cagcacccag ggatgggcct ggagtggatt gggtacatct attacagtgg agcacctac     180 tacaacccgt ccctcaagag tcgagtcacc atatcagaag acacgtctaa gaaccagttc    240
tccctgaagc tgagctctgt gactgccgcg gacacggccg tgtattactg tgcgagagat    300
tccgagtccg agtatagcag ctcgtcgaac tacggtatgg acgtctgggg ccaagggacc    360
acggtcaccg tctcctc                                                   377
```

```
<210> SEQ ID NO 78
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 78
```

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Ile Ser Ser Gly
            20                  25                  30

Gly Tyr Tyr Trp Ser Trp Ile Arg Gln His Pro Gly Met Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Glu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Glu Ser Glu Tyr Ser Ser Ser Ser Asn Tyr Gly
            100                 105                 110

Met Asp Val Trp Gly Gln Gly Thr Thr Val Thr Val Ser
        115                 120                 125
```

```
<210> SEQ ID NO 79
<211> LENGTH: 377
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 79
caggtgcagc tgcaggagtc gggcccagga ctggtgaagc cttcacagac cctgtccctc     60
acctgcactg tctctggtgt ctccatcagc agtggtggtt actactggag ctggatccgc    120
cagcacccag ggatgggcct ggagtggatt gggtacatct attacagtgg agcacctac     180 tacaacccgt ccctcaagag tcgagtcacc atatcagaag acacgtctaa gaaccagttc    240
tccctgaagc tgagctctgt gactgccgcg gacacggccg tgtattactg tgcgagagat    300
tccgagtccg agtatagcag ctcgtcgaac tacggtatgg acgtctgggg ccaagggacc    360
acggtcaccg tctcctc                                                   377
```

```
<210> SEQ ID NO 80
<211> LENGTH: 125
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 80

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Ile Ser Ser Gly
            20                  25                  30

Gly Tyr Tyr Trp Ser Trp Ile Arg Gln His Pro Gly Met Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Glu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Glu Ser Glu Tyr Ser Ser Ser Ser Asn Tyr Gly
            100                 105                 110

Met Asp Val Trp Gly Gln Gly Thr Thr Val Thr Val Ser
        115                 120                 125

<210> SEQ ID NO 81
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 81
gacatccaga tgacccagtc tccatcctcc ctgtctgcat ctgtaggaga cagaatcacc    60
atcacttgcc gggcaagtca gaccattagc agctatttaa attggtatca gcagaaacca   120
gggaaagccc ctaagctcct gatctatgct gcatccagtt tgcaaggtgg ggtcccatca   180
aggttcagtg gcagtgtatc tgggacagat ttcaccctca ccgtcagcag tctgcaacct   240
gaagattttg caacttacta ctgtcaacag agttacagta accgctcac tttcggcgga   300 gggaccaagg tggagatcaa a                                             321

<210> SEQ ID NO 82
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 82

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Thr Ile Ser Ser Tyr
            20                  25                  30

Leu Asn Trp Tyr Gln Gln Lys Pro Gly Lys Ala Pro Lys Leu Leu Ile
```

```
                35                  40                  45
Tyr Ala Ala Ser Ser Leu Gln Gly Gly Val Pro Ser Arg Phe Ser Gly
             50                  55                  60

Ser Val Ser Gly Thr Asp Phe Thr Leu Thr Val Ser Ser Leu Gln Pro
 65                  70                  75                  80

Glu Asp Phe Ala Thr Tyr Tyr Cys Gln Gln Ser Tyr Ser Asn Pro Leu
                 85                  90                  95

Thr Phe Gly Gly Gly Thr Lys Val Glu Ile Lys
            100                 105
```

<210> SEQ ID NO 83
<211> LENGTH: 371
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody

<400> SEQUENCE: 83

```
gaggtgcagc tggtgcagtc tggagcagag gtgaaaaagc ccggggagtc tctgaagatc    60
tcctgtaagg gttctggata cagttttacc agctactgga tcggctgggt gcgccagatg   120
cccgggaaag gcctggagtg gatggggatc atctatcctg gtgactctga taccagatac   180
agcccgtcct tccaaggcca ggtcaccatg tcagccgaca gtccatcag taccgcctac   240 ctgcagctga gcagccatga aggcctcgga caccgccatg tattactgtg cgagacagat   300
ggctggaaac tacgtacatc acgggtgatc gagacgtcct ggggccaagg gaccacggtc   360
accgtctcct c                                                        371
```

<210> SEQ ID NO 84
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Antibody

<400> SEQUENCE: 84

```
Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
     50                  55                  60

Gln Gly Gln Val Thr Met Ser Ala Asp Lys Ser Ile Ser Thr Ala Tyr
 65                  70                  75                  80

Leu Gln Leu Ser Ser His Glu Gly Leu Gly His Arg His Val Leu Leu
                 85                  90                  95

Cys Glu Thr Asp Gly Trp Lys Leu Arg Thr Ser Arg Val Ile Glu Thr
            100                 105                 110

Ser Trp Gly Gln Gly Thr Thr Val Thr Val Ser
        115                 120
```

```
<210> SEQ ID NO 85
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 85
gaaattgtgt tgacgcagtc tccaggcacc ctgtctttgt ctccagggga agagccacc     60 ctctcctgca gggccagtca gagtgttatc agcatctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccgtg cagttttggc   300
caggggacca aactggagat caaa                                          324

<210> SEQ ID NO 86
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 86

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ile Ser Ile
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Ser Phe Gly Gln Gly Thr Lys Leu Glu Ile Lys
            100                 105

<210> SEQ ID NO 87
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 87
caggtgcagc tgcaggagtc gggcccagga ctggtgaagc cttcacagac cctgtccctc     60
acctgcactg tctctggtgg ctccatcagc agtggtgatt actactggag ctggatccgc   120
cagcacccag ggaagggcct ggagtggatt gggtacatct attacagtgg gagcacctac   180
tacaacccgt ccctcaggag tcgagttacc atatcagtag acacgtctaa gaaccagttc   240
```

```
tccctgaagc tgagctctgt gactgccgcg gacacggccg tgtattactg tgcgagagcg    300
gattacgatt tttggagtgg ttattttgac tactggggcc agggaaccct ggtcaccgtc    360
tcctca                                                                366
```

<210> SEQ ID NO 88
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 88

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120
```

<210> SEQ ID NO 89
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 89

```
gacatccaga tgacccagtc tccatcctcc ctgtctgcat ctgtaggaga cagagtcacc    60
atcacttgcc gggcaagtca gggcattaga aatgatttag gctggtatca gcagatacct    120
gggaaagccc ctaagcgcct gatctatgct gcatccagtt tgcaaagtgg ggtcccatca    180
aggttcagcg gcagtggatc tgggacagaa ttcactctca caatcaacag cctgcagcct    240
gaagattttg caacttatta ctgtctacag cataatggtt acccgtggac gttcggccaa    300
gggaccaagg tggaaatcaa ac                                              322
```

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody -continued

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Ile Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Asn Ser Leu Gln Pro
65                  70                  75                  80

Glu Asp Phe Ala Thr Tyr Tyr Cys Leu Gln His Asn Gly Tyr Pro Trp
                85                  90                  95

Thr Phe Gly Gln Gly Thr Lys Val Glu Ile Lys
            100                 105

<210> SEQ ID NO 91
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 91
caggtgcagc tgcaggagtc gggcccagga ctggtgaagc cttcacagac cctgtccctc      60
acctgcactg tctctggtgg ctccatcagc agtggtgatt actactggag ctggatccgc     120
cagcacccag ggaagggcct ggagtggatt ggatacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagcg     300
gattacgatt tttggagtgg ttattttgac tactggggcc agggaaccct ggtcaccgtc     360
tcctca                                                                366

<210> SEQ ID NO 92
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 92

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr

```
                    85                  90                  95
Cys Ala Arg Ala Asp Tyr Asp Phe Trp Ser Gly Tyr Phe Asp Tyr Trp
                100                 105                 110

Gly Gln Gly Thr Leu Val Thr Val Ser Ser
        115                 120

<210> SEQ ID NO 93
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 93
gacttccaga tgacccagtc tccatcctcc ctgtctgcat ctgtaggaga cagagtcacc    60
atcacttgcc gggcaagtca ggacattcga aatgatttag ctggtatcg gcagaaacct   120 gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccgtggac gttcggccaa   300
gggaccaagg tggaaatcaa ac                                            322

<210> SEQ ID NO 94
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 94

Asp Phe Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Arg Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
                100                 105

<210> SEQ ID NO 95
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 95
```

```
caggtgcagc tgcaggagtc gggcccagga ctggtgaagc cttcacagac cctgtccctc        60
acctgcactg tctctggtgg ctccatcagc agtggtgatt actactggag ctggatccgc       120
cagcacccag ggaagggcct ggagtggatt ggatacatct attacagtgg gagcacctac       180
tacaacccgt ccctcaagag tcgagttacc atatcaatag acacgtctaa gaaccagttc       240
tccctgaagc tgagctctgt gactgccgcg gacacggccg tgtattactg cgagagcg        300 gattacgatt tttggaatgg ttattttgac tactggggcc agggaaccct ggtcaccgtc       360
tcctca                                                                  366
```

<210> SEQ ID NO 96
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 96

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Asn Gly Tyr Phe Asp Tyr Trp
            100                 105                 110

Gly Gln Gly Thr Leu Val Thr Val Ser Ser
        115                 120
```

<210> SEQ ID NO 97
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 97

```
gacatccaga tgacccagtc tccatcctcc ctgtctgcat ctgtaggaga cagagtcacc        60
atcacttgcc gggcaagtca ggacattaga aatgatttag ctggtatcg cagaaacct       120 gggaaagccc ctaagcgcct gatctatgct gcatccagtt tgcaaagtgg ggtcccatca       180
aggttcagcg gcagtggatc tgggacagaa ttcactctca caatcagcag cctgcagcct       240
gaagattttg caacttatta ctgtctacag cataatagtt acccgtggac gttcggccaa       300
gggaccaagg tggaaatcaa a                                                 321
```

<210> SEQ ID NO 98

<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Antibody

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Arg Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 99
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody

<400> SEQUENCE: 99
caggtgcagc tgcaggagtc gggcccagga ctggtgaagc ctacacagac cctgtccctc     60
acctgcactg tctctggtgg ctccatcagc agtggtgatt actactggag ctggatccgc    120
cagcacccag ggaagggcct ggagtggatt gggtacatct attacagtgg gagcacctac    180
tacaacccgt ccctcaagag tcgacttacc atatcagtag acacgtctaa gaaccagttc    240
tccctgaagc tgagctctgt gactgccgcg gacacggccg tgtattactg tgcgagagca    300
gattacgatt tttggagtgg ttactttgac tactggggcc agggaaccct ggtcaccgtc    360
tcctca                                                              366

<210> SEQ ID NO 100
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Antibody

<400> SEQUENCE: 100

Gln Val Gln Leu Gln Glu Ser Gly Pro Gly Leu Val Lys Pro Thr Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu

```
                35                  40                  45
Trp Ile Gly Tyr Ile Tyr Tyr Ser Gly Ser Thr Tyr Tyr Asn Pro Ser
     50                  55                  60

Leu Lys Ser Arg Leu Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 101
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 101
gacatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataataatt acccgtggac gttcggccaa    300
gggaccaagg tggaaatcaa a                                              321

<210> SEQ ID NO 102
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 102

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Asn Tyr Pro Trp
                 85                  90                  95

Thr Phe Gly Gln Gly Thr Lys Val Glu Ile Lys
            100                 105

<210> SEQ ID NO 103
<211> LENGTH: 366
```

<212> TYPE: DNA
<213> ORGANISM: Artificial Sequence
<220> FEATURE:
<223> OTHER INFORMATION: Description of Artificial Sequence: Synthetic
 polynucleotide
<220> FEATURE:
<223> OTHER INFORMATION: Antibody

<400> SEQUENCE: 103
caggtgcagc tgcaggagtc gggcccagga ctggtgaagc cttcacagac cctgtccctc      60
acctgcactg tctctggtgg ctccatcagt agtggtgatt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagt tgagctctgt gactgccgcg gacacggccg tgtattactg tgcgagagcc     300
gattacgatt tttggagtgg ttattttgac tactggggcc agggaaccct ggtcaccgtc     360
tcctca                                                                366

<210> SEQ ID NO 104
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 104

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 105
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 105
gacatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagcgcct gatctatgct gcatccagtt tgcaaagtgg ggtcccatca     180

```
aggttcagcg gcagtggatc tgggacagaa ttcactctca caatcagcag cctgcagcct    240
gaagattttg caacttatta ctgtctacag cataataatt acccgtggac gttcggccaa    300
gggaccaagg tggaaatcaa a                                              321
```

<210> SEQ ID NO 106
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 106

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Trp
                85                  90                  95

Thr Phe Gly Gln Gly Thr Lys Val Glu Ile Lys
            100                 105
```

<210> SEQ ID NO 107
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 107

```
caggtgcagc tgcaggagtc gggcccagga ctggtgaagc cttcacagac cctgtccctc    60
acctgcactg tctctggtgg ctccatcagc agtggtggtt actactggag ctggatccgc    120
cagcacccag ggaagggcct ggagtggatt gggtacatct attacagtgg gagcacctac    180
tacaacccgt ccctcaagag tcgagttacc atatcagtag acacgtctaa gaaccagttc    240
tccctgaagc tgagctctgt gactgccgcg gacacggccg tgtattactg tgcgagagag    300
gacgacggta tggacgtctg ggccaaggga accacggtca ccgtctcctc a             351
```

<210> SEQ ID NO 108
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 108

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Glu Asp Asp Gly Met Asp Val Trp Gly Gln Gly Thr Thr
            100                 105                 110

Val Thr Val Ser Ser
        115

<210> SEQ ID NO 109
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 109
gatattgtga tgactcagtc tccactctcc ctgcccgtca cccctggaga gccggcctcc      60
atttcctgca ggtctagtca gagcctcctg catagtaatg gatacaacta tttggaatgg     120
tacctgcaga agccagggca gtccccacag ttcatgattt atttgggtc taatcgggcc      180 tccggggtcc ctgacaggtt cagtggcagt ggatcaggca cagattttac actgaaaatc     240
agcagagtgg aggctgagga tgttggggtt tattactgca tgcaagctct acaaactccg     300
atcaccttcg gccaagggac acgactggag attaaa                                336

<210> SEQ ID NO 110
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 110

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Glu Trp Tyr Leu Gln Lys Pro Gly Gln Ser
        35                  40                  45

Pro Gln Phe Met Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Leu Gln Thr Pro Ile Thr Phe Gly Gln Gly Thr Arg Leu Glu Ile Lys
            100                 105                 110

<210> SEQ ID NO 111
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 111
caggtgcagc tgcaggagtc gggcccagga ctggtgaagc cttcacagac cctgtccctc      60
acctgcactg tctctggtgg ctccatcagc agtggtgatt actactggag ctggatccgc     120
cagtacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgaggtctgt gactgccgcg gacacggccg tgtattactg tgcgagagcg     300
gattacgatt tttggagtgg ttattttgac tactggggcc agggaaccct ggtcaccgtc     360
tcctca                                                               366

<210> SEQ ID NO 112
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 112

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Tyr Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 113
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody -continued

<400> SEQUENCE: 113

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatactt acccgtggac gttcggccaa   300
gggaccaagg tggaaatcaa ac                                            322
```

<210> SEQ ID NO 114
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Trp
                85                  90                  95

Thr Phe Gly Gln Gly Thr Lys Val Glu Ile Lys
            100                 105

<210> SEQ ID NO 115
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 115

```
caggtgcagc tgcaggagtc gggcccagga ctggtgaagc cttcggagac cctgtccctc    60
acctgcactg tctctggtgg ctccgtcagc agtggtggtt actactggag ctggatccgg   120
cagcccccag ggaagggact ggagtggatt gggtatatct attacagtgg gagcaccaac   180
tacaacccct ccctcaagag tcgagtcacc atatcagtag acacgtccaa gaaccagttc   240
tccctgaagc tgagctctgt gaccgctgcg gacacggccg tgtattactg tgcgagagat   300
ggggacgtgg atacagctat ggtcgatgct tttgatatct ggggccaagg acaatggtc   360
accgtctcct ca                                                      372
```

<210> SEQ ID NO 116
<211> LENGTH: 124
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 116

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Asp Val Asp Thr Ala Met Val Asp Ala Phe Asp
            100                 105                 110

Ile Trp Gly Gln Gly Thr Met Val Thr Val Ser Ser
        115                 120
```

<210> SEQ ID NO 117
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 117

```
gaaattgtat tgacgcagtc tccaggcacc ctgtctttgt ctccagggga aagagccacc      60
ctctcctgca gggccagtca gagtttaagc ggcaactact tagcctggta ccagcagaag     120
cctggccagg ctcccaggct catcatctgt ggtgcatcca gcagggccac tggcatccca     180
gacaggttca gtggcagtgg gtctgggaca gacttcactc tcaccatcac aagactggag     240
cctgaagatt ttgcagtgta ttactgtcag cagtatgata ggtcaccgct cactttcggc     300
ggagggacca aggtggagat caaa                                            324
```

<210> SEQ ID NO 118
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 118

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Ser Gly Asn
            20                  25                  30

Tyr Leu Ala Trp Tyr Gln Gln Lys Pro Gly Gln Ala Pro Arg Leu Ile
        35                  40                  45
```

Ile Cys Gly Ala Ser Ser Arg Ala Thr Gly Ile Pro Asp Arg Phe Ser
            50                  55                  60

Gly Ser Gly Ser Gly Thr Asp Phe Thr Leu Thr Ile Thr Arg Leu Glu
 65                  70                  75                  80

Pro Glu Asp Phe Ala Val Tyr Tyr Cys Gln Gln Tyr Asp Arg Ser Pro
                85                  90                  95

Leu Thr Phe Gly Gly Gly Thr Lys Val Glu Ile Lys
            100                 105

<210> SEQ ID NO 119
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 119
caggtgcagc tgcaggagtc gggcccagga ctggtgaagc cttcacagac cctgtccctc      60
acctgcactg tctctggtgg ctccatcagc agtggtgatt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg cgagagga      300 gattacgatt tttggagtgg agagtttgac tactggggcc agggaaccct ggtcaccgtc     360
tcctca                                                               366

<210> SEQ ID NO 120
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 120

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Gly Asp Tyr Asp Phe Trp Ser Gly Glu Phe Asp Tyr Trp
            100                 105                 110

Gly Gln Gly Thr Leu Val Thr Val Ser Ser
        115                 120

<210> SEQ ID NO 121

<211> LENGTH: 386
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Antibody

<400> SEQUENCE: 121

```
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt gggtacatct atgacagtgg gagcacctac     180
tacaacccgt ccctcaagag tcgagttacc atatcagtag acacgtctaa gaaccagttc     240
tccctgaagc tgaggtctgt gactgccgcg gacacggccg tgtattactg tgcgagagat     300
caggggcagg acggatacag ctatggttac ggctactact acggtatgga cgtctggggc     360
caagggacca cggtcaccgt ctcctc                                          386
```

<210> SEQ ID NO 122
<211> LENGTH: 128
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Antibody

<400> SEQUENCE: 122

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Asp Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg Asp Gln Gly Gln Asp Gly Tyr Ser Tyr Gly Tyr Gly Tyr
            100                 105                 110

Tyr Tyr Gly Met Asp Val Trp Gly Gln Gly Thr Thr Val Thr Val Ser
        115                 120                 125
```

<210> SEQ ID NO 123
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Antibody

<400> SEQUENCE: 123

```
gacatccaga tgacccagtc tccatcctcc ctgtctgcat ctgtaggaga cagagtcacc      60
atcacttgcc aggcgagtca ggacattagc aattatttaa attggtatca gcagaaacca     120
```

```
gggaaagccc ctaaactcct gatctacgtt gcatccaatt tggaaacagg ggtcccatca      180
aggttcagtg gaagtggatc tgggacagat tttactttca ccatcagcag cctgcagcct      240
gaagatattg caacatatta ctgtcaacag tgtgataatc tccctctcac tttcggcgga      300
gggaccaagg tggagatcaa a                                                321
```

<210> SEQ ID NO 124
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 124

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Val Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Cys Asp Asn Leu Pro Leu
                85                  90                  95

Thr Phe Gly Gly Gly Thr Lys Val Glu Ile Lys
            100                 105
```

<210> SEQ ID NO 125
<211> LENGTH: 365
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 125

```
caggtgcagc tgcaggagtc gggcccagga ctggtgaagc cttcacagac cctgtccctc       60
acctgcactg tctctggtgg ctccatcagc agtggtgatt actactggag ctggatccgc      120
cagcacccag ggaagggcct ggagtggatt ggatacatct attacagtgg gagcacctac      180
tacaacccgt ccctcaagag tcgagttacc atatcagtag acacgtctaa gaaccagttc      240
tccctgaagc tgagctctgt gactgccgcg gacacggccg tgtattactg cgagagcg        300 gattacgatt tttggagtgg ttattttgac tactggggcc agggaaccct ggtcaccgtc      360
tcctc                                                                  365
```

<210> SEQ ID NO 126
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 126

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser
        115                 120

<210> SEQ ID NO 127
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 127
gacatccaga tgacccagtc tccatcctcc ctgtctgcat ctgtaggaga cagagtcacc      60
atcacttgcc gggcaagtca ggacattaga aatgatttag ctggtatcg cagaaaacct     120 gggaaagccc ctaagcgcct gatctatgct gcatcccgtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccgtggac gttcggccaa    300
gggaccaagg tggaaatcaa ac                                             322

<210> SEQ ID NO 128
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Arg Gln Lys Pro Gly Lys Ala Pro Lys Arg Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
            85                  90                  95

Thr Phe Gly Gln Gly Thr Lys Val Glu Ile Lys
            100                 105

<210> SEQ ID NO 129
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 129
caggtgcagc tgcaggagtc gggcccagga ctggtgaagc cttcacagac cctgtccctc      60
acctgcactg tctctggtgg ctccatcagc agtggtgatt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagcc     300
gattacgatt tttggagtgg ttattttgac tactggggcc agggaaccct ggtcaccgtc     360
tcctca                                                                366

<210> SEQ ID NO 130
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 130

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
            115                 120

<210> SEQ ID NO 131
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide <220> FEATURE:
<223> OTHER INFORMATION: Antibody

<400> SEQUENCE: 131

```
gacatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctatgct gcatccagtt tgcaaaatgg ggtcccatca     180
aggttcagcg gcagtggatc tgggacagaa ttcactctca caatcagcag cctgcagcct     240
gaagattttg caacttatta ctgtctacag cataatagtt acccgtggac gttcggccaa     300
gggaccaagg tggaaatcaa ac                                              322
```

<210> SEQ ID NO 132
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 132

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Lys Pro Gly Lys Ala Pro Lys Arg Leu Ile
        35                  40                  45
Tyr Ala Ala Ser Ser Leu Gln Asn Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Tyr Pro Trp
                85                  90                  95
Thr Phe Gly Gln Gly Thr Lys Val Glu Ile Lys
            100                 105
```

<210> SEQ ID NO 133
<211> LENGTH: 365
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 133

```
caggtgcagc tgcaggagtc gggcccagga ctggtgaagc cttcacagac cctgtccctc      60
acctgcactg tctctggtgg ctccatcagc agtggtgatt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagcg     300
gattacgatt tttggagtgg ttattttgac tactggggcc agggaatcct ggtcaccgtc     360
tcctc                                                                 365
```

```
<210> SEQ ID NO 134
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 134

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Ile Leu Val Thr Val Ser
        115                 120

<210> SEQ ID NO 135
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 135
gacatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagcgcct gatttatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccgtggac gttcggccaa    300
gggaccaagg tggaaatcaa ac                                             322

<210> SEQ ID NO 136
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30
```

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 137
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 137
caggtgcagc tgcaggagtc gggcccagga ctggtgaagc cttcacagac cctgtccctc    60
acctgcactg tctctggtgg ctccatcagt agtggtgatt actactggag ctggatccgc   120
cagcacccag ggaagggcct ggagtggatt gggtacatct attacagtgg gagcacctac   180
tacaacccgt ccctcaagag tcgagttacc atatcagtag acacgtctaa gaaccagttc   240
tccctgaagt tgagctctgt gactgccgcg gacacggccg tgtattactg tgcgagagcc   300
gattacgatt tttggaatgg ttattttgac tactggggcc agggaaccct ggtcaccgtc   360
tcctca                                                             366

<210> SEQ ID NO 138
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 138

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Asn Gly Tyr Phe Asp Tyr Trp
            100                 105                 110

Gly Gln Gly Thr Leu Val Thr Val Ser Ser
        115                 120

<210> SEQ ID NO 139
<211> LENGTH: 321
<212> TYPE: DNA
<213> ORGANISM: Artificial Sequence
<220> FEATURE:
<223> OTHER INFORMATION: Description of Artificial Sequence: Synthetic
     polynucleotide
<220> FEATURE:
<223> OTHER INFORMATION: Antibody

<400> SEQUENCE: 139

```
gacatccaga tgacccagtc tccatcctcc ctgtctgcat ctgtaggaga cagagtcacc        60
atcacttgcc gggcaagtca gggcattaga aatgatttag gctggtatca gcagaaacca       120
gggaaagccc ctaagcgcct gatctatgct gcatccagtt tgcaaagtgg ggtcccatca       180
aggttcagcg gcagtggatc tgggacagaa ttcactctca caatcagcag cctgcagcct       240
gaagattttg caacttatta ctgtctacag cataataatt acccgtggac gttcggccaa       300
gggaccaagg tggaaatcaa a                                                 321
```

<210> SEQ ID NO 140
<211> LENGTH: 107
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: Antibody

<400> SEQUENCE: 140

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Trp
                85                  90                  95

Thr Phe Gly Gln Gly Thr Lys Val Glu Ile Lys
            100                 105
```

<210> SEQ ID NO 141
<211> LENGTH: 366
<212> TYPE: DNA
<213> ORGANISM: Artificial Sequence
<220> FEATURE:
<223> OTHER INFORMATION: Description of Artificial Sequence: Synthetic
     polynucleotide
<220> FEATURE:
<223> OTHER INFORMATION: Antibody

<400> SEQUENCE: 141

```
caggtgcagc tgcaggagtc gggcccagga ctggtgaagc cttcacagac cctgtccctc        60
acctgcactg tctctggtgg ctccatcagc agtggtgatt actactggag ctggatccgc       120
cagcacccag ggaagggcct ggagtggatt gggtacatct attacagtgg gagcacctac       180
```

```
tacaacccgt ccctcaagag tcgagttacc atatcagtag acacgtctaa gaaccagttc    240
tccctgaagc tgagctctgt gactgccgcg gacacggccg tgtattactg tgcgagagcc    300
gattacgatt tttggagtgg ttattttgac tactggggcc agggaaccct ggtcaccgtc    360
tcctca                                                               366

<210> SEQ ID NO 142
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 142

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 143
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 143
gacatccagc tgacccagtc tccatcctcc ctgtctgcat ctgtaggaga cagagtcacc    60
atcacttgcc gggcaagtca gggcattaga aatgatttag ctggtatca gcagaaacca    120 gggaaagccc ctaagcgcct gatctatgct gcatccagtt tgcaaaatgg ggtcccatca    180
aggttcagcg gcagtggatc tgggacagaa ttcactctca caatcagcag cctgcagcct    240
gaagattttg caactattta ctgtctacag cataatagtt acccgtggac gttcggccaa    300
gggaccaagg tggaaatcaa ac                                            322

<210> SEQ ID NO 144
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: Antibody

<400> SEQUENCE: 144

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Asn Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 145
<211> LENGTH: 365
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 145
caggtgcagc tgcaggagtc gggcccagga ctggtgaagc cttcacagac cctgtccctc      60
acctgcactg tctctggtgg ctccatcagc agtggtgatt actactggag ctggatccgc     120
cagtacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgggctctgt gactgccgcg gacacggccg tgtatttctg tgcgagagcc     300
gattacgatt tttggagtgg ttattttgac ttctggggcc agggaaccct ggtcaccgtc     360
tcctc                                                                365

<210> SEQ ID NO 146
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 146

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Tyr Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Gly Ser Val Thr Ala Ala Asp Thr Ala Val Tyr Phe
                85                  90                  95

Cys Ala Arg Ala Asp Tyr Asp Phe Trp Ser Gly Tyr Phe Asp Phe Trp
            100                 105                 110

Gly Gln Gly Thr Leu Val Thr Val Ser
        115                 120

<210> SEQ ID NO 147
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 147
gacatccaga tgacccagtc tccatcctcc ctgtctgcat ctgtaggaga cagagtcacc      60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatggtt acccgtggac gttcggccaa    300
gggaccaagg tggaaatcaa ac                                              322

<210> SEQ ID NO 148
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Gly Tyr Pro Trp
                85                  90                  95

Thr Phe Gly Gln Gly Thr Lys Val Glu Ile Lys
            100                 105

<210> SEQ ID NO 149
<211> LENGTH: 365
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 149

```
caggtgcagc tgcaggagtc gggcccagga ctggtgaagc cttcacagac cctgtccctc    60
acctgcactg tctctggtgg ctccatcagc agtggtgatt actactggag ctggatccgc   120
cagtacccag ggaagggcct ggagtggatt gggtacatct attacagtgg gagcacctac   180
tacaacccgt ccctcaagag tcgagttacc atatcagtag acacgtctaa gaaccagttc   240
tccctgaagc tgggctctgt gactgccgcg gacacggccg tgtatttctg tgcgagagcc   300
gattacgatt tttggagtgg ttatttttgac ttctggggcc agggaaccct ggtcaccgtc   360
tcctc                                                                365
```

<210> SEQ ID NO 150
<211> LENGTH: 121
<212> TYPE: PRT
<213> ORGANISM: Artificial Sequence
<220> FEATURE:
<223> OTHER INFORMATION: Description of Artificial Sequence: Synthetic
  polypeptide
<220> FEATURE:
<223> OTHER INFORMATION: Antibody

<400> SEQUENCE: 150

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Tyr Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Gly Ser Val Thr Ala Ala Asp Thr Ala Val Tyr Phe
                85                  90                  95

Cys Ala Arg Ala Asp Tyr Asp Phe Trp Ser Gly Tyr Phe Asp Phe Trp
            100                 105                 110

Gly Gln Gly Thr Leu Val Thr Val Ser
        115                 120
```

<210> SEQ ID NO 151
<211> LENGTH: 322
<212> TYPE: DNA
<213> ORGANISM: Artificial Sequence
<220> FEATURE:
<223> OTHER INFORMATION: Description of Artificial Sequence: Synthetic
  polynucleotide
<220> FEATURE:
<223> OTHER INFORMATION: Antibody

<400> SEQUENCE: 151

```
gacatccaga tgacccagtc tccatcctcc ctgtctgcat ctgtaggaga cagagtcacc    60
atcacttgcc gggcaagtca gggcattaga aatgatttag ctggtatcag cagaaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatggtt acccgtggac gttcggccaa   300
gggaccaagg tggaaatcaa ac                                             322
```

<210> SEQ ID NO 152
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 152

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Gly Tyr Pro Trp
                85                  90                  95

Thr Phe Gly Gln Gly Thr Lys Val Glu Ile Lys
            100                 105

<210> SEQ ID NO 153
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 153
caggtgcagc tgcaggagtc gggcccagga ctggtgaagc cttcacagac cctgtccctc      60
acctgcactg tctctggtgg ctccatcagt agtggtgatt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagcg     300
gattacgatt tttggagtgg ttattttgac tcctggggcc agggaaccct ggtcaccgtc     360
tcctca                                                                366

<210> SEQ ID NO 154
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 154

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

```
Asp Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ala Asp Tyr Asp Phe Trp Ser Gly Tyr Phe Asp Ser Trp
                100                 105                 110

Gly Gln Gly Thr Leu Val Thr Val Ser Ser
            115                 120
```

<210> SEQ ID NO 155
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody

<400> SEQUENCE: 155

```
gacatccaga tgacccagtc tccatcctcc ctgtctgcat ctgtaggaga cagagtcacc      60
atcacttgcc gggcaagtca gggcattaga aatgatttag gctggtatca gcagatacct     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatggtt acccgtggac gttcggccaa     300
gggaccaagg tggaaatcaa a                                               321
```

<210> SEQ ID NO 156
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Antibody

<400> SEQUENCE: 156

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Gln Ile Pro Gly Lys Ala Pro Lys Arg Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Gly Tyr Pro Trp
                 85                  90                  95

Thr Phe Gly Gln Gly Thr Lys Val Glu Ile Lys
            100                 105
```

```
<210> SEQ ID NO 157
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 157
caggttcagc tggtgcagtc tggagctgag gtgaagaagc ctggggcctc agtgaaggtc      60
tcctgcaagg cttctggtta cacctttacc aactatggta tcagctgggt gcggcaggcc     120
cctggacaag gcttgagtg gatgggatgg atcagcgctt acgatggtta cagaaactat      180
gcacagaagc tccagggcag agtcaccatg accacagaca catccacgac cactgcctac     240
atggagctga ggagcctgag atctgacgac acggccgtgt attactgtgc gagagatgtt     300
caagactacg gtgactacga ctactttgac tactggggcc agggaaccct ggtcaccgtc     360
tcctca                                                                 366

<210> SEQ ID NO 158
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 158

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asp Gly Tyr Arg Asn Tyr Ala Gln Lys Leu
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Val Gln Asp Tyr Gly Asp Tyr Asp Tyr Phe Asp Tyr Trp
            100                 105                 110

Gly Gln Gly Thr Leu Val Thr Val Ser Ser
        115                 120

<210> SEQ ID NO 159
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 159
gacatccaga tgacccagtc tccatcctcc ctgtctgcat ctgtaggaga cagagtcacc      60
atcacttgcc gggcaagtca gagcattagc agttatttaa attggtatca gcagaaacca     120
```

```
gggaaagccc ctaacctcct gatctatgct gcatccagtt tgcaaagtgg ggtcccatca    180
agattcaggg gcagtggatc tgggacagat ttcactctca ccatcagcag tctgcaacct    240
gaagattttg caacttacta ctgtcaacag agttacagta ccccatcac cttcggccaa     300 gggacacgac tggagattaa a                                              321
```

<210> SEQ ID NO 160
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 160

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105
```

<210> SEQ ID NO 161
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 161

```
caggtgcagc tgcaggagtc gggcccagga ctggtgaagc ctttacagac cctgtccctc    60
acctgcactg tctctggtgg ctccatcagc agtggtgatt actactggag ctggatccgc    120
cagcacccag ggaagggcct ggagtggatt gggtacatct attacagtgg gaccacctac    180
tacaacccgt ccctcaagag tcgagttacc atatcagtag acacgtctaa gaaccagttc    240
gccctgaagc tgaactctgt gactgccgcg gacacggccg tgtattactg tgcgagagcc    300
gattacgatt tttggagtgg ttattttgac tactggggcc agggaaccct ggtcaccgtc    360
tcctca                                                               366
```

<210> SEQ ID NO 162
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: Antibody

<400> SEQUENCE: 162

Gln Val Gln Leu Gln Glu Ser Gly Pro Gly Leu Val Lys Pro Leu Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Thr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ala Leu Lys Leu Asn Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 163
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 163
gacatccaga tgacccagtc tccatcctcc ctgtctgcat ctgtaggaga cagagtcacc        60
atcacttgcc gggcaggtca gggcattaga aatgatttag ctggtatca gcagaaacca       120 gggaaagccc ctcagcgcct gatctatgct gcatccagtt tgcaaagtgg ggtcccatca      180
aggttcagcg gcagtggatc tgggacagaa ttctctctca caatctccag cctgcagcct      240
gaagattttg caacttatta ctgtctacag cataatagtt acccgtggac gttcggccaa      300
gggaccaagg tggaaatcaa ac                                               322

<210> SEQ ID NO 164
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Arg Ala Gly Gln Gly Ile Arg Asn Asp
            20                  25                  30

Leu Gly Trp Tyr Gln Gln Lys Pro Gly Lys Ala Pro Gln Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Ser Leu Thr Ile Ser Ser Leu Gln Pro

```
                65                  70                  75                  80
Glu Asp Phe Ala Thr Tyr Tyr Cys Leu Gln His Asn Ser Tyr Pro Trp
                    85                  90                  95

Thr Phe Gly Gln Gly Thr Lys Val Glu Ile Lys
            100                 105
```

<210> SEQ ID NO 165
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 165
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatat attagtagta gtggtaataa catataccac     180
gcagactctg tgaagggccg attcaccatc tccagggaca acgccaagaa ctcactgtat     240
ctgcaaatga acagcctgag agccgaggac acggccgtgt attactgtgc gagagagaga     300
tatagtggct acgacgaccc tgatggtttt gatatctggg gccaagggac aatggtcacc     360
gtctcttca                                                             369

<210> SEQ ID NO 166
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 166

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Asn Asn Ile Tyr His Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Ser Gly Tyr Asp Asp Pro Asp Gly Phe Asp Ile
            100                 105                 110

Trp Gly Gln Gly Thr Met Val Thr Val Ser Ser
        115                 120
```

<210> SEQ ID NO 167
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody

<400> SEQUENCE: 167
gacatccaga tgacccagtc tccatcctcc ctgtctgcat ctgtaggaga cagagtcacc    60
atcacttgcc aggcgagtca ggacattagc aactatttaa gttggtttca gcagaaacca   120
gggaaagccc ctaagctcct gatccacgat gcatccaatt tggaaacagg ggtcccttca   180
aggttcagtg gaagtggatc tgggacagat tttactttca ccatcagcag cctgcagcct   240
gaagatattg caacatatta ctgtcaacag tatgataatc ccccgtgcag ttttggccag   300
gggaccaagc tggagatcaa a                                             321

<210> SEQ ID NO 168
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Ser Trp Phe Gln Gln Lys Pro Gly Lys Ala Pro Lys Leu Leu Ile
        35                  40                  45

His Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Pro Pro Cys
                85                  90                  95

Ser Phe Gly Gln Gly Thr Lys Leu Glu Ile Lys
            100                 105

<210> SEQ ID NO 169
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 169
caggtgcagc tgcaggagtc gggcccagga ctggtgaagc cttcacagac cctgtccctc    60
acctgcactg tctctggtgg ctccatcagc agtggttatt actactggag ctggatccgc   120
cagcacccag gaagggcct ggagtggatt gggtacatct attacagtgg gaccacctac   180
tacaatccgt ccttcaagag tcgagttacc atatcagtag acacgtctaa gaaccagttc   240
tccctgaaac tgagctctgt gactgccgcg gacacggccg tgtattactg cgagagcc    300 gattacgatt tttggagtgg tcactttgac tactgggggcc agggaaccct ggtcaccgtc   360
tcctca                                                              366

<210> SEQ ID NO 170
<211> LENGTH: 122
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Antibody

<400> SEQUENCE: 170

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Tyr Tyr Tyr Trp Ser Trp Ile Arg Gln His Pro Gly Lys Gly Leu Glu
        35                  40                  45

Trp Ile Gly Tyr Ile Tyr Tyr Ser Gly Thr Thr Tyr Tyr Asn Pro Ser
    50                  55                  60

Phe Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly His Phe Asp Tyr Trp
            100                 105                 110

Gly Gln Gly Thr Leu Val Thr Val Ser Ser
        115                 120

<210> SEQ ID NO 171
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 171
gacatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccgtggac gttcggccaa    300
gggaccaagg tggaaatcaa a                                              321

<210> SEQ ID NO 172
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp

```
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
                100                 105

<210> SEQ ID NO 173
<211> LENGTH: 365
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 173
caggttcagc tggtgcagtc tggagctgag gtgaagaagc ctggggcctc agtgaaggtc      60
tcctgcaagg cttctggtta cacctttacc agctatggta tcagctgggt gcgacaggcc    120
cctggacaag gacttgagtg gatgggatgg atcagcgctt acgatggtca cacaaactat    180
gcacagaagc tccagggcag agtcaccatg accacagaca catccacgaa cacagcctac    240
atggagctga ggagcctgag atctgacgac acggccgttt attactgtgc gagagacccc    300
catgactaca gtaactacga ggcttttgac ttctggggcc agggaaccct ggtcaccgtc    360
tcctc                                                               365

<210> SEQ ID NO 174
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 174

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asp Gly His Thr Asn Tyr Ala Gln Lys Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Pro His Asp Tyr Ser Asn Tyr Glu Ala Phe Asp Phe Trp
                100                 105                 110

Gly Gln Gly Thr Leu Val Thr Val Ser
```

<210> SEQ ID NO 175
<211> LENGTH: 519
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody

<400> SEQUENCE: 175

```
atgaggtccc ctgctcagct cctggggctc ctgctactct ggctccgagg tgccagatgt    60
gacatccaga tgacccagtc tccatcctcc ctgtctgcat ctgtaggaga cagagtcacc   120
atcacttgcc gggcaagtca gagcattagc agttatttaa attggtatca gcagaaacca   180
gggaaagccc ctaacctcct gatctatgct gcatccagtt tgcaaagtgg ggtcccatca   240
agattcagtg gcagtggatc tgggacagat ttcactctca ccatcagcag tctgcaacct   300
gaagattttg caacttacta ctgtcaacag agttacagta ccccatcac cttcggccaa   360
gggacacgac tggagattaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgcc                          519
```

<210> SEQ ID NO 176
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Antibody

<400> SEQUENCE: 176

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Asn Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Ile
                85                  90                  95
Thr Phe Gly Gln Gly Thr Arg Leu Glu Ile Lys
            100                 105

<210> SEQ ID NO 177
<211> LENGTH: 534
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody

<400> SEQUENCE: 177

```
accatggact ggacctggag ggtccttttc ttggtggcag cagcaacagg tgcccactcc      60
caggttcagc tggtgcagtc tggagctgag gtgaagaagc tggggcctc agtgaaggtc      120 tcctgcaagg cttctggtta cacctttacc aactatggta tcagctgggt gcggcaggcc    180
cctggacaag gcttgagtg gatgggatgg atcagcgctt acgatggtta cagaaactat    240
gcacagaagc tccagggcag agtcaccatg accacagaca catccacgac cactgcctac    300
atggagctga ggagcctgag atctgacgac acggccgtgt attactgtgc gagagatgtt    360
caagactacg gtgactacga ctactttgac tactggggcc agggaaccct ggtcaccgtc    420
tcctcagctt ccaccaaggg cccatccgtc ttccccctgg tgccctgctc caggagcacc    480
tccgagagca cagccgccct gggctgcctg gtcaaggact acttccccga accg            534
```

```
<210> SEQ ID NO 178
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 178
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asp Gly Tyr Arg Asn Tyr Ala Gln Lys Leu
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Val Gln Asp Tyr Gly Asp Tyr Asp Tyr Phe Asp Tyr Trp
            100                 105                 110

Gly Gln Gly Thr Leu Val Thr Val Ser Ser
        115                 120

```
<210> SEQ ID NO 179
<211> LENGTH: 504
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 179
cagctcctgg ggctcctgct actctggctc cgaggtgcca gatgtgacat ccagatgacc      60
cagtctccat cctccctgtc tgcatctgta ggagacagag tcaccatcac ttgccgggca    120
agtcagagca ttagcagtta tttaaattgg tatcagcaga accagggaa agcccctaac     180 ctcctgatct atgctgcatc cagtttgcaa agtggggtcc catcaagatt cagtggcagt    240
ggatctggga cagatttcac tctcaccatc agcagtctgc aacctgaaga ttttgcaact    300
```

```
tactactgtc aacagagtta cagtacccccc atcaccttcg gccaagggac acgactggag    360
attaaacgaa ctgtggctgc accatctgtc ttcatcttcc cgccatctga tgagcagttg    420
aaatctggaa ctgcctctgt tgtgtgcctg ctgaataact tctatcccag agaggccaaa    480
gtacagtgga aggtggataa cgcc                                            504
```

<210> SEQ ID NO 180
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 180

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105
```

<210> SEQ ID NO 181
<211> LENGTH: 493
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 181

```
catctgtggt tcttcctcct gctggtggca gctcccagat gggtcctgtc ccaggtgcag    60
ctgcaggagt cgggcccagg actggtgaag ccttcacaga ccctgtccct cacctgcact    120
gtctctggtg gctccatcaa cagtggtgat tactactgga gctggatccg ccagcaccca    180
gggaagggcc tggagtggat tgggtacatc tattacagtg ggagcaccta ctacaacccg    240
tccctcaaga gtcgagttac catatcagta gacacgtcta agaaccagtt ctccctgaag    300
ctgagctctg tgactgccgc ggacacggcc gtgtattact gtgcgagagc agattacgat    360
ttttggagtg gttactttga ctactggggc cagggaaccc tggtcaccgt ctcctcagcc    420
tccaccaagg gcccatcggt cttccccctg gcaccctcct ccaagagcac ctctgggggc    480
acaacggccc tgg                                                        493
```

<210> SEQ ID NO 182
<211> LENGTH: 122
<212> TYPE: PRT
<213> ORGANISM: Artificial Sequence
<220> FEATURE:

<223> OTHER INFORMATION: Description of Artificial Sequence: Synthetic
polypeptide
<220> FEATURE:
<223> OTHER INFORMATION: Antibody

<400> SEQUENCE: 182

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 183
<211> LENGTH: 518
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Antibody

<400> SEQUENCE: 183
atgagggtcc ctgctcagct cctggggctc ctgctgctct ggttcccagg tgccaggtgt     60
gacatccaga tgacccagtc tccatcctcc ctgtctgcat ctgtaggaga cagagtcacc    120
atcacttgcc gggcaagtca gggcattaga aatgatttag ctggtatca gcagaaacca    180 gggaaagccc ctaagcgcct gatctatgct gcatccagtt tgcaaagtgg ggtcccatca    240
aggttcagcg gcagtggatc tgggacagaa ttcactctca caatcagcag cctgcagcct    300
gaagattttg caacttatta ctgtctacag cataatagtt acccgtggac gttcggccaa    360
gggaccaagg tggaaatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgc                            518

<210> SEQ ID NO 184
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Antibody

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp

```
            20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105
```

<210> SEQ ID NO 185
<211> LENGTH: 436
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 185

```
tggttcttcc ttctgctggt ggcagctccc agatgggtcc tgtcccaggt gcagctgcag    60
gagtcgggcc caggactggt gaagccttca cagaccctgt ccctcacctg cactgtctct   120
ggtggctcca tcagcagtgg tggttactac tggagctgga tccgccagca cccagggaag   180
ggcctggagt ggattgggta catctattac agtgggagca cctactacaa cccgtccctc   240
aagagtcgag ttaccatatc agtagacacg tctaagaacc agttctccct gaagctgagc   300
tctgtgactg ccgcggacac ggccgtgtat tactgtgcga gagatggcta tgatagtagt   360
ggttattacc acggctactt tgactactgg ggccagggaa ccctggtcac cgtctcctca   420
gcctccacca agggcc                                                   436
```

<210> SEQ ID NO 186
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 186

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Tyr Asp Ser Ser Gly Tyr Tyr His Gly Tyr Phe
            100                 105                 110
```

Asp Tyr Trp Gly Gln Gly Thr Leu Val Thr Val Ser Ser
            115                 120                 125

<210> SEQ ID NO 187
<211> LENGTH: 521
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 187
caggtcttca tttctctgtt gctctggatc tctggtgcct acggggacat cgtgatgacc      60
cagtctccag actccctggc tgtgtctctg ggcgagaggg ccaccatcaa ctgcaagtcc     120
agccagagtg tttatacag ctccaacaat aagaactact agcttggta ccagcagaaa      180 ccaggacagc ctcctaagct gctcatttac tgggcatcta cccgggaatc cggggtccct     240
gaccgattca gtggcagcgg gtctgggaca gatttcactc tcaccatcag cagcctgcag     300
gctgaagatg tggcagttta ttactgtcag caatattata gtactccgct cactttcggc     360
ggagggacca aggtggagat caaacgaact gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg c                        521

<210> SEQ ID NO 188
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 188

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys

<210> SEQ ID NO 189
<211> LENGTH: 455
<212> TYPE: DNA
<213> ORGANISM: Artificial Sequence
<220> FEATURE:
<223> OTHER INFORMATION: Description of Artificial Sequence: Synthetic
      polynucleotide <220> FEATURE:
<223> OTHER INFORMATION: Antibody

<400> SEQUENCE: 189

| | |
|---|---|
| ctgtggttct tcctcctgct ggtggcagct cccagatggg tcctgtccca ggtgcagctg | 60 |
| caggagtcgg gcccaggact ggtgaagcct tcacagaccc tgtccctcac ctgcactgtc | 120 |
| tctggtggct ccatcagtag tggtgattac tactggagct ggatccgcca gcacccaggg | 180 |
| aagggcctgg agtggattgg gtacatctat acagtggga gcacctacta caacccgtcc | 240 |
| ctcaagagtc gagttaccat atcagtagac acgtctaaga accagttctc cctgaagttg | 300 |
| agctctgtga ctgccgcgga cacggccgtg tattactgtg cgagagccga ttacgatttt | 360 |
| tggagtggtt attttgacta ctggggccag ggaaccctgg tcaccgtctc ctcagcctcc | 420 |
| accaagggcc catcggtctt ccccctggca ccctc | 455 |

<210> SEQ ID NO 190
<211> LENGTH: 122
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Antibody

<400> SEQUENCE: 190

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120
```

<210> SEQ ID NO 191
<211> LENGTH: 442
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Antibody

<400> SEQUENCE: 191

| | |
|---|---|
| gtgcccgctc agcgcctggg gctcctgctg ctctggttcc caggtgccag gtgtgacatc | 60 |
| cagatgaccc agtctccatc ctccctgtct gcatctgtag agacagagt caccatcact | 120 |
| tgccgggcaa gtcagggcat tagaaatgat ttaggctggt atcagcagaa accagggaaa | 180 |
| gcccctaagc gcctgatcta tgctgcatcc agtttgcaaa gtggggtccc atcaaggttc | 240 |

```
agcggcagtg gatctgggac agaattcact ctcacaatca gcagcctgca gcctgaagat    300
tttgcaactt attactgtct acagcataat aattacccgt ggacgttcgg ccaagggacc    360
aaggtggaaa tcaaacgaac tgtggctgca ccatctgtct tcatcttccc gccatctgat    420
gagcagttga aatctggaac tg                                            442
```

<210> SEQ ID NO 192
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 192

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Trp
                85                  90                  95

Thr Phe Gly Gln Gly Thr Lys Val Glu Ile Lys
            100                 105
```

<210> SEQ ID NO 193
<211> LENGTH: 427
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 193

```
tggttcttcc ttctgctggt ggcagctccc agatgggtcc tgtcccaggt gcagctgcag    60
gagtcgggcc caggactggt gaagccttca cagaccctgt ccctcacctg cactgtctct    120
ggtggctcca tcagcagtgg tgattactac tggagctgga tccgccagca cccagggaag    180
ggcctggagt ggattgggta catctattac agtgggagca cctactacaa cccgtccctc    240
aagagtcgag ttaccatatc agtagacacg tctaagaacc agttctccct gaagctgagc    300
tctgtgactg ccgcggacac ggccgtgtat ttctgtgcga gagccgatta cgattttgg     360 agtggttatt ttgactactg gggccaggga accctggtca ccgtctcctc agcctccacc    420
aagggcc                                                             427
```

<210> SEQ ID NO 194
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide <220> FEATURE:
<223> OTHER INFORMATION: Antibody

<400> SEQUENCE: 194

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 195
<211> LENGTH: 518
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 195
atgagggtcc ccgctcagct cctggggctc ctgctgctct ggttcccagg tgccaggtgt      60
gacatccaga tgacccagtc tccatcctcc ctgtctgcat ctgtaggaga cagagtcacc     120
atcacttgcc gggcaagtca gggcattaga aatgatttag ctggtatca gcagaaacca     180 gggaaagccc ctaagcgcct gatctatgct gcatccagtt tgcaaagtgg ggtcccatca     240
aggttcagcg gcagtggatc tgggacagaa ttcactctca caatcagcag cctgcagcct     300
gaagattttg caacttatta ctgtctacag cataatactt acccgtggac gttcggccaa     360
gggaccaagg tggaaatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgc                             518

<210> SEQ ID NO 196
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 196

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
              35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Thr Tyr Pro Trp
                 85                  90                  95

Thr Phe Gly Gln Gly Thr Lys Val Glu Ile Lys
                100                 105

<210> SEQ ID NO 197
<211> LENGTH: 428
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 197
tggttcttcc ttctgctggt ggcagctccc agatgggtcc tgtcccaggt gcagctgcag     60
gagtcgggcc caggactggt gaagccttca cagaccctgt ccctcacctg cactgtctct    120
ggtggctcca tcagcagtgg tgattactac tggagctgga tccgccagca cccagggaag    180
ggcctggagt ggattgggta catctattac agtgggagca cctactacaa cccgtccctc    240
aagagtcgag ttaccatatc agtagacacg tctaagaacc agttctccct gaagctgagc    300
tctgtgactg ccgcggacac ggccgtgtat ttctgtgcga gagccgatta cgattttggg    360
aatggttatt ttgactactg gggccaggga accctggtca ccgtctcctc agcctccacc    420
aagggccc                                                             428

<210> SEQ ID NO 198
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 198

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                 20                  25                  30

Asp Tyr Tyr Trp Ser Trp Ile Arg Gln His Pro Gly Lys Gly Leu Glu
              35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Phe
                 85                  90                  95

Cys Ala Arg Ala Asp Tyr Asp Phe Trp Asn Gly Tyr Phe Asp Tyr Trp
                100                 105                 110

Gly Gln Gly Thr Leu Val Thr Val Ser Ser

<210> SEQ ID NO 199
<211> LENGTH: 519
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody

<400> SEQUENCE: 199

```
atgagggtcc ccgctcagct cctggggctc ctgctgctct ggttcccagg tgccaggtgt      60
gacatccaga tgacccagtc tccatcctcc ctgtctgcat ctgtaggaga cagagtcacc     120
atcacttgcc gggcaagtca gggcattaga aatgatttag ctggtatca gcagaaacca     180
gggaaagccc ctaagcgcct gatctatgct gcttccagtt tgcaaagtgg ggtcccatca     240
aggttcagcg gcagtggatc tgggacagaa ttcactctca caatcagcag cctgcagcct     300
gaagattttg caacttatta ctgtctacag cataatactt acccgtggac gttcggccaa     360
gggaccaagg tggaaatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgcc                           519
```

<210> SEQ ID NO 200
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Antibody

<400> SEQUENCE: 200

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Thr Tyr Pro Trp
                85                  90                  95
Thr Phe Gly Gln Gly Thr Lys Val Glu Ile Lys
            100                 105
```

<210> SEQ ID NO 201
<211> LENGTH: 398
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody

<400> SEQUENCE: 201

```
ttggtggcag cagctacagg cacccacgcc caggtccagc tggtacagtc tggggctgag      60
gtgaagaagc ctggggcctc agtgaaggtc tcctgcaagg tttccggata caccctcact     120
gaattatcca tgtactgggt gcgacaggct cctggaaaag gcttgagtg atgggaggt       180 tttgatcctg aagatggtga acaatctac gcacagaagt tccagggcag agtcaccatg     240
accgaggaca catctacaga cacagcctac atggagctga gcagcctgag atctgaggac     300
acggccgtgt attactgtgc aactgggtgg aactacgtct ttgactactg gggccaggga    360
accctggtca ccgtctcctc agcctccacc aagggccc                            398
```

<210> SEQ ID NO 202
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Antibody

<400> SEQUENCE: 202

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met Tyr Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Trp Asn Tyr Val Phe Asp Tyr Trp Gly Gln Gly Thr Leu
            100                 105                 110

Val Thr Val Ser Ser
        115
```

<210> SEQ ID NO 203
<211> LENGTH: 388
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody

<400> SEQUENCE: 203

```
ggatccagtg gggatattgt gatgactcag tctccactct ccctgcccgt cacccctgga      60
gagccggcct ccatctcctg caggtccagt cagagcctcc tgcatagtaa tggatacaac     120
tatttggatt ggtacctgca gaagccaggg cagtctccac agctcctgat ctatttggat     180
tctcatcggg cctccggggt ccctgacagg ttcagtggca gtggatcagg cacagatttt     240
acactgaaaa tcagcagagt ggaggctgag gatgttgggg tttattactg catgcaagct     300
ctacaaactc cgctcacttt cggcggaggg accaaggtgg agatcaaacg aactgtggct     360
gcaccatctg tcttcatctt cccgccat                                        388
```

<210> SEQ ID NO 204
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Antibody

<400> SEQUENCE: 204

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Asp Ser His Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 205
<211> LENGTH: 446
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Antibody

<400> SEQUENCE: 205
tggttcttcc ttctgctggt ggcagctccc agatgggtcc tgtcccaggt gcagctgcag      60
gagtcgggcc caggactggt gaagccttca cagaccctgt ccctcacctg cactgtctct     120
ggtggctcca tcagcagtgg tgattactac tggagctgga tccgccagca cccagggaag     180 gcctggagt ggattgggta catctattac agtgggagca cctactacaa cccgtccctc      240
aagagtcgag ttaccatatc agtagacacg tctaagaacc agttctccct gaagctgagc     300
tctgtgactg ccgcggacac ggccgtgtat ttctgtgcga gagccgatta cgattttgg      360 agtggttatt ttgactactg gggccaggga accctggtca ccgtctcctc agcctccacc     420
aagggcccat cgagtcttcc ccctgg                                          446

<210> SEQ ID NO 206
<211> LENGTH: 122
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Antibody

<400> SEQUENCE: 206

Gln Val Gln Leu Gln Glu Ser Gly Pro Gly Leu Val Lys Pro Ser Gln
1               5                   10                  15

```
Thr Leu Ser Leu Thr Cys Thr Val Ser Gly Gly Ser Ile Ser Ser Gly
             20                  25                  30

Asp Tyr Tyr Trp Ser Trp Ile Arg Gln His Pro Gly Lys Gly Leu Glu
         35                  40                  45

Trp Ile Gly Tyr Ile Tyr Tyr Ser Gly Ser Thr Tyr Tyr Asn Pro Ser
     50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Phe
                 85                  90                  95

Cys Ala Arg Ala Asp Tyr Asp Phe Trp Ser Gly Tyr Phe Asp Tyr Trp
             100                 105                 110

Gly Gln Gly Thr Leu Val Thr Val Ser Ser
         115                 120
```

<210> SEQ ID NO 207
<211> LENGTH: 519
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody

<400> SEQUENCE: 207

```
atgagggtcc ccgctcagct cctggggctc ctgctgctct ggttcccagg tgccaggtgt    60
gacatccaga tgacccagtc tccatcctcc ctgtctgcat ctgtaggaga cagagtcacc   120
atcacttgcc gggcaagtca gggcattaga aatgatttag ctggtatca gcagaaacca   180
gggaaagccc ctaagcgcct gatctatgct gcatccagtt tgcaaagtgg ggtcccatca   240
aggttcagcg gcagtggatc tgggacaaaa ttcactctca ctatcagcag cctgcagcct   300
gaagattttg caacttatta ctgtctacag cataatactt acccgtggac gttcggccaa   360
gggaccaagg tggaaatcag acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgcc                          519
```

<210> SEQ ID NO 208
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Antibody

<400> SEQUENCE: 208

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Lys Phe Thr Leu Thr Ile Ser Ser Leu Gln Pro
65                  70                  75                  80
```

```
Glu Asp Phe Ala Thr Tyr Tyr Cys Leu Gln His Asn Thr Tyr Pro Trp
                85                  90                  95

Thr Phe Gly Gln Gly Thr Lys Val Glu Ile Arg
            100                 105
```

<210> SEQ ID NO 209
<211> LENGTH: 564
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 209

```
accatgaaac atctgtggtt cttcctcctg ctggtggcag ctcccagatg ggtcctgtcc    60
caggtgcagc tgcaggagtc gggcccagga ctggtgaagc cttcacagac cctgtccctc   120
acctgcactg tctctggtgg ctccatcagc agtggtgatt actactggag ctggatccgc   180
cagcacccag ggaagggcct ggagtggatt gggtacatct attacagtgg gagcacctac   240
tacaacccgt ccctcaagag tcgagttacc atatcagtag acacgtctaa gaaccagttc   300
tccctgaagc tgagctctgt gactgccgcg gacacggccg tgtattactg tgcgagagcg   360
gattacgatt tttggagtgg ttattttgac tactggggcc agggaatcct ggtcaccgtc   420
tcctcagcct ccaccaaggg cccatcggtc ttccccctgg cacctcctc caagaacacc    480
tctggggca cagcggccct gggctgcctg gtcaaggact acttccccga accggtgacg   540
gtgtcctgga actcaggcgc cctg                                         564
```

<210> SEQ ID NO 210
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 210

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Ile Leu Val Thr Val Ser Ser
        115                 120
```

<210> SEQ ID NO 211

<211> LENGTH: 519
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody

<400> SEQUENCE: 211

| | |
|---|---|
| atgagggtcc ccgctcagct cctggggctc ctgctgctct ggttcccagg tgccaggtgt | 60 |
| gacatccaga tgacccagtc tccatcctcc ctgtctgcat ctgtaggaga cagagtcacc | 120 |
| atcacttgcc gggcaagtca gggcattaga aatgatttag ctggtatca gcagaaacca | 180 |
| gggaaagccc ctaagcgcct gatctatgct gcatccagtt tgcaaagtgg ggtcccatca | 240 |
| aggttcagcg gcagtggatc tgggacagaa ttcactctca caatcagcag cctgcagcct | 300 |
| gaagattttg caacttatta ctgtctacag cataatagtt acccgtggac gttcggccaa | 360 |
| gggaccaagg tggaaatcaa acgaactgtg gctgcaccat ctgtcttcat cttcccgcca | 420 |
| tctgatgagc agttgaaatc tggaactgcc tctgttgtgt gcctgctgaa taacttctat | 480 |
| cccagagagg ccaaagtaca gtggaaggtg gataacgcc | 519 |

<210> SEQ ID NO 212
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Antibody

<400> SEQUENCE: 212

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 213
<211> LENGTH: 432
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody

<400> SEQUENCE: 213

| | |
|---|---|
| tggttcttcc ttctgctggt ggcagctccc agatgggtcc tgtcccaggt gcagctgcag | 60 |
| gagtcgggcc caggactggt gaagccttca gaccctgt ccctcacctg cactgtctct | 120 |

```
ggtggctcca tcagcagtgg tgattactac tggagctgga tccgccagca cccagggaag    180
ggcctggagt ggattggata catctattac agtgggagca cctactacaa ttcgtccctc    240
aagagtcgag ttaccatatc agtagacacg tctaagaacc agttctccct gaagctgagc    300
tctgtgactg ccgcggacac ggccgtgtat tactgtgcga gagcggatta cgattttggg    360
agtggttatt ttgactactg gggccaggga accctggtca ccgtctcctc agcctccacc    420
aagggcccat cg                                                         432
```

<210> SEQ ID NO 214
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 214

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Ser Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Gly Ser Gly Tyr Phe Asp Tyr Trp
            100                 105                 110

Gly Gln Gly Thr Leu Val Thr Val Ser Ser
        115                 120
```

<210> SEQ ID NO 215
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 215

```
ggtgccaggt gtgacatcca gatgacccag tctccatcct ccctgtctgc atctgtagga     60
gacagagtca ccatcacttg ccgggcaagt cagggcatta gaaatgattt aggctggtat    120
cagcagaaac ctgggaaagc ccctaagcgc ctgatctatg ctgcatccag tttgcaaagt    180
ggggtcccat caaggttcag cggcagtgga tctgggacag aattcactct cacaatcagc    240
agcctgcagc ctgaagattt tgcaacttat tactgtctac agcacaatag ttacccgtgg    300
acgttcggcc aagggaccaa ggtggaaatc aaacgaactg tggctgcacc atctgtcttc    360
atcttcccgc ca                                                        372
```

<210> SEQ ID NO 216

<210> SEQ ID NO 216
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Antibody

<400> SEQUENCE: 216

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105
```

<210> SEQ ID NO 217
<211> LENGTH: 548
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody

<400> SEQUENCE: 217

```
aggttcttcc ttctgctggt ggcagctccc agatgggtcc tgtcccaggt gcagctgcag      60
gagtcgggcc caggactggt gaagccttca cagaccctgt ccctcacctg cactgtctct     120
ggtggctcca tcagcagtgg tgattactac tggagctgga tccgcagca cccagggaag     180
ggcctggagt ggattggata catctattac agtgggagca cctactacaa cccgtccctc     240
aagagtcgag ttaccatatc agtagacacg tctaagaacc agttctccct gaagctgagc     300
tctgtgactg ccgcggacac ggccgtgtat tactgtgcga gagccgatta cgattttttgg    360
agtggttatt ttgactactg gggccaggga accctggtca ccgtctcctc agcctccacc     420
aagggcccat cggtcttccc cctggcaccc tcctccaaga gcacctctgg gggcacagcg    480
gccctgggct gcctggtcaa ggactacttc cccgaaccgg tgacggtgtc gtggaactca     540
ggcgccct                                                              548
```

<210> SEQ ID NO 218
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Antibody

<400> SEQUENCE: 218

Gln Val Gln Leu Gln Glu Ser Gly Pro Gly Leu Val Lys Pro Ser Gln

```
                1               5                  10                      15
            Thr Leu Ser Leu Thr Cys Thr Val Ser Gly Gly Ser Ile Ser Ser Gly
                            20                  25                  30

Asp Tyr Tyr Trp Ser Trp Ile Arg Gln His Pro Gly Lys Gly Leu Glu
                        35                  40                  45

Trp Ile Gly Tyr Ile Tyr Tyr Ser Gly Ser Thr Tyr Tyr Asn Pro Ser
                50                  55                  60

Leu Lys Ser Arg Val Thr Ile Ser Val Asp Thr Ser Lys Asn Gln Phe
            65                  70                  75                  80

Ser Leu Lys Leu Ser Ser Val Thr Ala Ala Asp Thr Ala Val Tyr Tyr
                            85                  90                  95

Cys Ala Arg Ala Asp Tyr Asp Phe Trp Ser Gly Tyr Phe Asp Tyr Trp
                            100                 105                 110

Gly Gln Gly Thr Leu Val Thr Val Ser Ser
                        115                 120

<210> SEQ ID NO 219
<211> LENGTH: 517
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 219
atgagggtcc ccgctcagct cctggggctc ctgctgctct ggttcccagg tgccaggtgt       60
gacatccaga tgacccagtc tccatcctcc ctgtctgcat ctgtaggaga cagagtcacc      120
atcacttgcc gggcaagtca gggcattaga aatgatttag ctggtatca gcagaaacca      180 gggaaagccc ctaagcgcct gatctatgct gcatccagtt tgcaaagtgg ggtcccatca      240
aggttcagcg gcagtggatc tgggacagaa ttcactctca caatcagcag cctgcagcct      300
gaagattttg caacttatta ctgtctacag cataatagtt acccgtggac gttcggccaa      360
gggaccaagg tggaaatcaa acgaactgtg gctgcaccat ctgtcttcat cttcccgcca      420
tctgatgagc agttgaaatc tggaactgcc tctgttgtgt gcctgctgaa taacttctat      480
cccagagagg ccaaagtaca gtggaaggtg gataacg                              517

<210> SEQ ID NO 220
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 220

Asp Ile Gln Met Thr Gln Ser Pro Ser Ser Leu Ser Ala Ser Val Gly
            1               5                   10                  15

Asp Arg Val Thr Ile Thr Cys Arg Ala Ser Gln Gly Ile Arg Asn Asp
                            20                  25                  30

Leu Gly Trp Tyr Gln Gln Lys Pro Gly Lys Ala Pro Lys Arg Leu Ile
                        35                  40                  45

Tyr Ala Ala Ser Ser Leu Gln Ser Gly Val Pro Ser Arg Phe Ser Gly
                50                  55                  60
```

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
            100                 105

<210> SEQ ID NO 221
<211> LENGTH: 446
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 221
ctgtggttct tccttctgct ggtggcagct cccagatggg tcctgtccca ggtgcagctg    60
caggagtcgg gcccaggact ggtgaagcct tcacagaccc tgtccctcac ctgcactgtc   120
tctggtggct ccatcagcag tggtgattac tactggagct ggatccgcca gcacccaggg   180
aagggcctgg agtggattgg gtacatctat acagtggga gcacctacta caacccgtcc    240
ctcaagagtc gagttaccat gtcagtagac acgtctaaga accagttctc cctgaagctg   300
agctctgtga ctgccgcgga cacggccgtg tattactgtg cgagagccga ttacgatttt   360
tggagtggtc actttgactg ctggggccag ggaaccctgg tcaccgtctc ctcagcttcc   420
accaagggcc catccgtctt ccccc                                         446

<210> SEQ ID NO 222
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 222

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Met Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ala Asp Tyr Asp Phe Trp Ser Gly His Phe Asp Cys Trp
            100                 105                 110

Gly Gln Gly Thr Leu Val Thr Val Ser Ser
        115                 120

<210> SEQ ID NO 223
<211> LENGTH: 419
<212> TYPE: DNA

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 223

```
atgagggtcc ccgctcagct cctggggctc ctgctgctct ggttcccagg tgccaggtgt     60
gacatccaga tgacccagtc tccatcctcc ctgtctgcat ctgtaggaga cagagtcacc    120
atcacttgcc gggcaagtca gggcattaga gatgatttag gctggtatca gcagaaacca    180
gggaaagccc ctaagcgcct gatctatgct gaatccagtt tgcaaagtgg ggtcccatca    240
aggttcagcg gcagtggatc tgggacagaa ttcactctca caatcagcag cctgcagcct    300
gaagattttg caacttatta ctgtctacag catcatagtt acccgtggac gttcggccaa    360
gggaccaagg tggaaatcaa acgaactgtg gctgcaccat ctgtcttcat cttcccgcc    419
```

<210> SEQ ID NO 224
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 224

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asp Asp
            20                  25                  30

Leu Gly Trp Tyr Gln Gln Lys Pro Gly Lys Ala Pro Lys Arg Leu Ile
        35                  40                  45

Tyr Ala Glu Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His His Ser Tyr Pro Trp
                85                  90                  95

Thr Phe Gly Gln Gly Thr Lys Val Glu Ile Lys
            100                 105

<210> SEQ ID NO 225
<211> LENGTH: 504
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 225

```
tggctgagct gggttttcct cgttgctctt ttaagaggtg tccagtgtca ggtgcagctg     60
gtggagtctg ggggaggcgt ggtccagcct gggaggtccc tgagactctc ctgtgcagcg    120
tctggattca ccttcaatag ctatgacatg cactgggtcc gccaggctcc aggcaagggg    180
ctggagtggg tggcagttat atggtatgat ggaagtaata atactatgc agactccgtg    240 aagggccgat tcaccatctc tagagacaat tccaagaaca cgctgtatct gcaaatgaac    300
```

```
agcctgagag ccgaggacac ggctgtgtat tactgtgcga gagaccgctt gtgtactaat    360
ggtgtatgct atgaagacta cggtatggac gtctggggcc aagggaccac ggtcaccgtc    420
tcctcagctt ccaccaaggg cccatccgtc ttccccctgg cgcctgctc caggagcacc     480 tccgagagca cagccgccct gggc                                            504
```

```
<210> SEQ ID NO 226
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 226

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Ser Tyr
            20                  25                  30

Asp Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Leu Cys Thr Asn Gly Val Cys Tyr Glu Asp Tyr Gly
            100                 105                 110

Met Asp Val Trp Gly Gln Gly Thr Thr Val Thr Val Ser Ser
        115                 120                 125
```

```
<210> SEQ ID NO 227
<211> LENGTH: 504
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 227
atgagggtcc ctgctcagct cctggggctc ctgctgctct ggctctcagg tgccagatgt    60
gacatccaga tgacccagtc tccatcctcc ctgtctgcat ctgtaggaga cagagtcacc    120
atcacttgcc aggcgagtca ggacattagc aactatttaa attggtatca gcagaaacca    180
gggaaagccc ctaaggtcct gatctacgat gcatccaatt tggaaacagg ggtcccatca    240
aggttcagtg gaagtggatc tgggacagat tttactttca ccatcagcag cctgcagcct    300
gaagatgttg caacatatta ctgtcaaaca tatgatactc tcccgctcac tttcggcgga    360
gggaccaagg tggagatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtgg                                            504
```

```
<210> SEQ ID NO 228
```

<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 228

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Val Ala Thr Tyr Tyr Cys Gln His Tyr Asp Thr Leu Pro Leu
                85                  90                  95

Thr Phe Gly Gly Gly Thr Lys Val Glu Ile Lys
            100                 105

<210> SEQ ID NO 229
<211> LENGTH: 472
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 229
ggactgtgca agaacatgaa acacctgtgg ttcttcctcc tgctggtggc agctcccaga      60
tgggtcctgt cccaggtgca gctgcaggag tcgggcccag gactggtgaa gcctttacag     120
accctgtccc tcacctgcac tgtctctggt ggctccatca gcagtggtga ttactactgg     180
agctggatcc gccagcaccc agggaagggc ctggagtgga ttgggtacat ctattacagt     240
gggaccacct actacaaccc gtccctcaag agtcgagtta ccatatcagt agacacgtct     300
aagaaccagt tcgccctgaa gctgaactct gtgactgccg cggacacggc cgtgtattac     360
tgtgcgagag ccgattacga tttttggagt ggttattttg actactgggg ccagggaacc     420
ctggtcaccg tctcctcagc ttccaccaag ggcccatccg tcttccccct gg             472

<210> SEQ ID NO 230
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 230

Gln Val Gln Leu Gln Glu Ser Gly Pro Gly Leu Val Lys Pro Leu Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
          35                  40                  45

Trp Ile Gly Tyr Ile Tyr Tyr Ser Gly Thr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ala Leu Lys Leu Asn Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 231
<211> LENGTH: 531
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody

<400> SEQUENCE: 231
atgagggtcc ctgctcagct cctggggctc ctgctgctct ggttcccagg tgccaggtgt    60
gacatccaga tgacccagtc tccatcctcc ctgtctgcat ctgtaggaga cagagtcacc   120
atcacttgcc gggcaggtca gggcattaga aatgatttag ctggtatca gcagaaacca   180 gggaaagccc ctcagcgcct gatctatgct gcatccagtt tgcaaagtgg ggtcccatca   240
aggttcagcg gcagtggatc tgggacagaa ttctctctca aatctccag cctgcagcct   300 gaagattttg caacttatta ctgtctacag cataatagtt acccgtggac gttcggccaa   360
gggaccaagg tggaaatcaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc ttccaatcgg g             531

<210> SEQ ID NO 232
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 232

Asp Ile Gln Met Thr Gln Ser Pro Ser Ser Leu Ser Ala Ser Val Gly
1               5                   10                  15

Asp Arg Val Thr Ile Thr Cys Arg Ala Gly Gln Gly Ile Arg Asn Asp
            20                  25                  30

Leu Gly Trp Tyr Gln Gln Lys Pro Gly Lys Ala Pro Gln Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Glu Asp Phe Ala Thr Tyr Tyr Cys Leu Gln His Asn Ser Tyr Pro Trp

```
                    85                  90                  95
Thr Phe Gly Gln Gly Thr Lys Val Glu Ile Lys
            100                 105

<210> SEQ ID NO 233
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: prim_transcript
<222> LOCATION: (1)..(26)

<400> SEQUENCE: 233
cgggatccat gtcctagcct aggggc                                          26

<210> SEQ ID NO 234
<211> LENGTH: 39
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: prim_transcript
<222> LOCATION: (1)..(39)

<400> SEQUENCE: 234
gctctagatt aatgatgatg atgatgatgt tgtcctaaa                            39

<210> SEQ ID NO 235
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-1 CDR-1-h

<400> SEQUENCE: 235

Gly Gly Ser Ile Asn Ser Gly Asp Tyr Tyr Trp Ser
1               5                   10

<210> SEQ ID NO 236
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-1 CDR-2-h

<400> SEQUENCE: 236

Tyr Ile Tyr Tyr Ser Gly Ser Thr Tyr Tyr Asn Pro Ser Leu Lys Ser
1               5                   10                  15

<210> SEQ ID NO 237
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-1 CDR-3-h
```

```
<400> SEQUENCE: 237

Ala Asp Tyr Asp Phe Trp Ser Gly Tyr Phe Asp Tyr
1               5                   10

<210> SEQ ID NO 238
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-1 CDR-1-l

<400> SEQUENCE: 238

Arg Ala Ser Gln Gly Ile Arg Asn Asp Leu Gly
1               5                   10

<210> SEQ ID NO 239
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-1 CDR-2-l

<400> SEQUENCE: 239

Ala Ala Ser Ser Leu Gln Ser
1               5

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-1 CDR-3-l

<400> SEQUENCE: 240

Leu Gln His Asn Ser Tyr Pro Trp Thr
1               5

<210> SEQ ID NO 241
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 2-CDR-1h

<400> SEQUENCE: 241

Gly Gly Ser Ile Ser Ser Gly Asp Tyr Tyr Trp Ser
1               5                   10

<210> SEQ ID NO 242
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: U 1 - 2-CDR-2h

<400> SEQUENCE: 242

Tyr Ile Tyr Tyr Ser Gly Ser Thr Tyr Tyr Asn Pro Ser Leu Arg Ser
1               5                   10                  15

<210> SEQ ID NO 243
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 2-CDR-3h

<400> SEQUENCE: 243

Ala Asp Tyr Asp Phe Trp Ser Gly Tyr Phe Asp Tyr
1               5                   10

<210> SEQ ID NO 244
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 2-CDR-1l

<400> SEQUENCE: 244

Arg Ala Ser Gln Gly Ile Arg Asn Asp Leu Gly
1               5                   10

<210> SEQ ID NO 245
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 2-CDR-2l

<400> SEQUENCE: 245

Ala Ala Ser Ser Leu Gln Ser
1               5

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 2-CDR-3l

<400> SEQUENCE: 246

Leu Gln His Asn Gly Tyr Pro Trp Thr
1               5

<210> SEQ ID NO 247
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: U 1 - 3-CDR-1-h

<400> SEQUENCE: 247

Gly Gly Ser Ile Ser Ser Gly Gly Tyr Tyr Trp Ser
1               5                   10

<210> SEQ ID NO 248
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 3-CDR-2h

<400> SEQUENCE: 248

Tyr Ile Tyr Tyr Ser Gly Ser Thr Tyr Tyr Asn Pro Ser Leu Lys Ser
1               5                   10                  15

<210> SEQ ID NO 249
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 3-CDR-3h

<400> SEQUENCE: 249

Asp Gly Tyr Asp Ser Ser Gly Tyr Tyr His Gly Tyr Phe Asp Tyr
1               5                   10                  15

<210> SEQ ID NO 250
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 3-CDR-1l

<400> SEQUENCE: 250

Lys Ser Ser Gln Ser Val Leu Tyr Ser Ser Asn Asn Lys Asn Tyr Leu
1               5                   10                  15

Ala

<210> SEQ ID NO 251
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 3-CDR-2l

<400> SEQUENCE: 251

Trp Ala Ser Thr Arg Glu Ser
1               5

<210> SEQ ID NO 252
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: U 1 - 3-CDR-3l

<400> SEQUENCE: 252

Gln Gln Tyr Tyr Ser Thr Pro Leu Thr
1               5

<210> SEQ ID NO 253
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 4-CDR-1h

<400> SEQUENCE: 253

Gly Gly Ser Ile Ser Ser Gly Asp Tyr Tyr Trp Ser
1               5                   10

<210> SEQ ID NO 254
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 4-CDR-2h

<400> SEQUENCE: 254

Tyr Ile Tyr Tyr Ser Gly Ser Thr Tyr Tyr Asn Pro Ser Leu Lys Ser
1               5                   10                  15

<210> SEQ ID NO 255
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 4-CDR-3h

<400> SEQUENCE: 255

Ala Asp Tyr Asp Phe Trp Ser Gly Tyr Phe Asp Tyr
1               5                   10

<210> SEQ ID NO 256
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 4-CDR-1l

<400> SEQUENCE: 256

Arg Ala Ser Gln Gly Ile Arg Asn Asp Leu Gly
1               5                   10

<210> SEQ ID NO 257
<211> LENGTH: 7
<212> TYPE: PRT
```

<210> SEQ ID NO 257
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 4-CDR-2l

<400> SEQUENCE: 257

Ala Ala Ser Ser Leu Gln Ser
1               5

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 4-CDR-3l

<400> SEQUENCE: 258

Leu Gln His Asn Asn Tyr Pro Trp Thr
1               5

<210> SEQ ID NO 259
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 5-CDR-1h

<400> SEQUENCE: 259

Gly Gly Ser Ile Ser Ser Gly Asp Tyr Tyr Trp Ser
1               5                   10

<210> SEQ ID NO 260
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 5-CDR-2h

<400> SEQUENCE: 260

Tyr Ile Tyr Tyr Ser Gly Ser Thr Tyr Tyr Asn Pro Ser Leu Lys Ser
1               5                   10                  15

<210> SEQ ID NO 261
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 5-CDR-3h

<400> SEQUENCE: 261

Ala Asp Tyr Asp Phe Trp Ser Gly Tyr Phe Asp Tyr
1               5                   10

<210> SEQ ID NO 262
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 5-CDR-1l

<400> SEQUENCE: 262

Arg Ala Ser Gln Gly Ile Arg Asn Asp Leu Gly
1               5                   10

<210> SEQ ID NO 263
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 5-CDR-2l

<400> SEQUENCE: 263

Ala Ala Ser Ser Leu Gln Ser
1               5

<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 5-CDR-3l

<400> SEQUENCE: 264

Leu Gln His Asn Thr Tyr Pro Trp Thr
1               5

<210> SEQ ID NO 265
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-6-CDR-1h

<400> SEQUENCE: 265

Gly Gly Ser Ile Ser Ser Gly Asp Tyr Tyr Trp Ser
1               5                   10

<210> SEQ ID NO 266
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-6-CDR-2h

<400> SEQUENCE: 266

Tyr Ile Tyr Tyr Ser Gly Ser Thr Tyr Tyr Asn Pro Ser Leu Lys Ser
1               5                   10                  15

<210> SEQ ID NO 267
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-6-CDR-3h

<400> SEQUENCE: 267

Ala Asp Tyr Asp Phe Trp Asn Gly Tyr Phe Asp Tyr
1               5                   10

<210> SEQ ID NO 268
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-6-CDR-1l

<400> SEQUENCE: 268

Arg Ala Ser Gln Gly Ile Arg Asn Asp Leu Gly
1               5                   10

<210> SEQ ID NO 269
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-6-CDR-2l

<400> SEQUENCE: 269

Ala Ala Ser Ser Leu Gln Ser
1               5

<210> SEQ ID NO 270
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-6-CDR-3l

<400> SEQUENCE: 270

Leu Gln His Asn Thr Tyr Pro Trp Thr
1               5

<210> SEQ ID NO 271
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 7-CDR-1h

<400> SEQUENCE: 271

Gly Gly Ser Ile Ser Ser Gly Asp Tyr Tyr Trp Ser
1               5                   10
```

```
<210> SEQ ID NO 272
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 7-CDR-2h

<400> SEQUENCE: 272

Tyr Ile Tyr Tyr Ser Gly Ser Thr Tyr Tyr Asn Pro Ser Leu Lys Ser
1               5                   10                  15

<210> SEQ ID NO 273
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 7-CDR-3h

<400> SEQUENCE: 273

Ala Asp Tyr Asp Phe Trp Ser Gly Tyr Phe Asp Tyr
1               5                   10

<210> SEQ ID NO 274
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 7-CDR-1l

<400> SEQUENCE: 274

Arg Ala Ser Gln Asp Ile Arg Asn Asp Leu Gly
1               5                   10

<210> SEQ ID NO 275
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 7-CDR-2l

<400> SEQUENCE: 275

Ala Ala Ser Ser Leu Gln Ser
1               5

<210> SEQ ID NO 276
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 7-CDR-3l

<400> SEQUENCE: 276

Leu Gln His Asn Ser Tyr Pro Trp Thr
1               5
```

<210> SEQ ID NO 277
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 8-CDR-1h

<400> SEQUENCE: 277

Gly Tyr Thr Leu Thr Glu Leu Ser Met Tyr
1               5                   10

<210> SEQ ID NO 278
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 8-CDR-2h

<400> SEQUENCE: 278

Gly Phe Asp Pro Glu Asp Gly Glu Thr Ile Tyr Ala Gln Lys Phe Gln
1               5                   10                  15

Gly

<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 8-CDR-3h

<400> SEQUENCE: 279

Gly Trp Asn Tyr Val Phe Asp Tyr
1               5

<210> SEQ ID NO 280
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 8-CDR-1l

<400> SEQUENCE: 280

Arg Ser Ser Gln Ser Leu Leu His Ser Asn Gly Tyr Asn Tyr Leu Asp
1               5                   10                  15

<210> SEQ ID NO 281
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 8-CDR-2l

<400> SEQUENCE: 281

```
Leu Asp Ser His Arg Ala Ser
1               5

<210> SEQ ID NO 282
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 8-CDR-3l

<400> SEQUENCE: 282

Met Gln Ala Leu Gln Thr Pro Leu Thr
1               5

<210> SEQ ID NO 283
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 9-CDR-1h

<400> SEQUENCE: 283

Gly Gly Ser Ile Ser Ser Gly Asp Tyr Tyr Trp Ser
1               5                   10

<210> SEQ ID NO 284
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 9-CDR-2h

<400> SEQUENCE: 284

Tyr Ile Tyr Tyr Ser Gly Ser Thr Tyr Tyr Asn Pro Ser Leu Lys Ser
1               5                   10                  15

<210> SEQ ID NO 285
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 9-CDR-3h

<400> SEQUENCE: 285

Ala Asp Tyr Asp Phe Trp Asn Gly Tyr Phe Asp Tyr
1               5                   10

<210> SEQ ID NO 286
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 9-CDR-1l

<400> SEQUENCE: 286
```

Arg Ala Ser Gln Asp Ile Arg Asn Asp Leu Gly
1               5                   10

<210> SEQ ID NO 287
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 9-CDR-2l

<400> SEQUENCE: 287

Ala Ala Ser Ser Leu Gln Ser
1               5

<210> SEQ ID NO 288
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 9-CDR-3l

<400> SEQUENCE: 288

Leu Gln His Asn Ser Tyr Pro Trp Thr
1               5

<210> SEQ ID NO 289
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-10-CDR-1h

<400> SEQUENCE: 289

Gly Gly Ser Ile Ser Ser Gly Asp Tyr Tyr Trp Ser
1               5                   10

<210> SEQ ID NO 290
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-10-CDR-2h

<400> SEQUENCE: 290

Tyr Ile Tyr Tyr Ser Gly Ser Thr Tyr Tyr Asn Pro Ser Leu Lys Ser
1               5                   10                  15

<210> SEQ ID NO 291
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-10-CDR-3h

<400> SEQUENCE: 291

Ala Asp Tyr Asp Phe Trp Ser Gly Tyr Phe Asp Tyr
1               5                   10

<210> SEQ ID NO 292
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-10-CDR-1l

<400> SEQUENCE: 292

Arg Ala Ser Gln Gly Ile Arg Asn Asp Leu Gly
1               5                   10

<210> SEQ ID NO 293
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-10-CDR-2l

<400> SEQUENCE: 293

Ala Ala Ser Ser Leu Gln Ser
1               5

<210> SEQ ID NO 294
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-10-CDR-3l

<400> SEQUENCE: 294

Leu Gln His Asn Asn Tyr Pro Trp Thr
1               5

<210> SEQ ID NO 295
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 -11-CDR-1h

<400> SEQUENCE: 295

Gly Gly Ser Ile Ser Ser Gly Asp Tyr Tyr Trp Ser
1               5                   10

<210> SEQ ID NO 296
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 -11-CDR-2h

```
<400> SEQUENCE: 296

Tyr Ile Tyr Tyr Ser Gly Ser Thr Tyr Tyr Asn Pro Ser Leu Lys Ser
1               5                   10                  15

<210> SEQ ID NO 297
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 -11-CDR-3h

<400> SEQUENCE: 297

Ala Asp Tyr Asp Phe Trp Ser Gly Tyr Phe Asp Tyr
1               5                   10

<210> SEQ ID NO 298
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 -11-CDR-1l

<400> SEQUENCE: 298

Arg Ala Ser Gln Gly Ile Arg Asn Asp Leu Gly
1               5                   10

<210> SEQ ID NO 299
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 -11-CDR-2l

<400> SEQUENCE: 299

Ala Ala Ser Ser Leu Gln Ser
1               5

<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 -11-CDR-3l

<400> SEQUENCE: 300

Leu Gln His Asn Thr Tyr Pro Trp Thr
1               5

<210> SEQ ID NO 301
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: U 1 - 12-CDR-1h

<400> SEQUENCE: 301

Gly Gly Ser Ile Ser Ser Gly Asp Tyr Tyr Trp Ser
1               5                   10

<210> SEQ ID NO 302
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 - 12-CDR-2h

<400> SEQUENCE: 302

Tyr Ile Tyr Tyr Ser Gly Ser Thr Tyr Tyr Asn Pro Ser Leu Lys Ser
1               5                   10                  15

<210> SEQ ID NO 303
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-12-CDR-3h

<400> SEQUENCE: 303

Ala Asp Tyr Asp Phe Trp Ser Gly Tyr Phe Asp Tyr
1               5                   10

<210> SEQ ID NO 304
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-12-CDR-1l

<400> SEQUENCE: 304

Arg Ala Ser Gln Gly Ile Arg Asn Asp Leu Gly
1               5                   10

<210> SEQ ID NO 305
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-12-CDR-2l

<400> SEQUENCE: 305

Ala Ala Ser Ser Leu Gln Ser
1               5

<210> SEQ ID NO 306
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide <220> FEATURE:
<223> OTHER INFORMATION: U1-12-CDR-3l

<400> SEQUENCE: 306

Leu Gln His Asn Asn Tyr Pro Trp Thr
1               5

<210> SEQ ID NO 307
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 -13-CDR-1h

<400> SEQUENCE: 307

Gly Gly Ser Ile Ser Ser Gly Gly Tyr Tyr Trp Ser
1               5                   10

<210> SEQ ID NO 308
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 -13-CDR-2h

<400> SEQUENCE: 308

Tyr Ile Tyr Tyr Ser Gly Ser Thr Tyr Tyr Asn Pro Ser Leu Lys Ser
1               5                   10                  15

<210> SEQ ID NO 309
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 -13-CDR-3h

<400> SEQUENCE: 309

Glu Asp Asp Gly Met Asp Val
1               5

<210> SEQ ID NO 310
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 -13-CDR-1l

<400> SEQUENCE: 310

Arg Ser Ser Gln Ser Leu Leu His Ser Asn Gly Tyr Asn Tyr Leu Glu
1               5                   10                  15

<210> SEQ ID NO 311
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: U 1 -13-CDR-2l

<400> SEQUENCE: 311

Leu Gly Ser Asn Arg Ala Ser
1               5

<210> SEQ ID NO 312
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U 1 -13-CDR-3l

<400> SEQUENCE: 312

Met Gln Ala Leu Gln Thr Pro Ile Thr
1               5

<210> SEQ ID NO 313
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-14-CDR-1h

<400> SEQUENCE: 313

Gly Gly Ser Ile Ser Ser Gly Asp Tyr Tyr Trp Ser
1               5                   10

<210> SEQ ID NO 314
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-14-CDR-2h

<400> SEQUENCE: 314

Tyr Ile Tyr Tyr Ser Gly Ser Thr Tyr Tyr Asn Pro Ser Leu Lys Ser
1               5                   10                  15

<210> SEQ ID NO 315
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-14-CDR-3h

<400> SEQUENCE: 315

Ala Asp Tyr Asp Phe Trp Ser Gly Tyr Phe Asp Tyr
1               5                   10

<210> SEQ ID NO 316
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<223> OTHER INFORMATION: U1-14-CDR-1l

<400> SEQUENCE: 316

Arg Ala Ser Gln Gly Ile Arg Asn Asp Leu Gly
1               5                   10

<210> SEQ ID NO 317
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-14-CDR-2l

<400> SEQUENCE: 317

Ala Ala Ser Ser Leu Gln Ser
1               5

<210> SEQ ID NO 318
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-14-CDR-3l

<400> SEQUENCE: 318

Leu Gln His Asn Thr Tyr Pro Trp Thr
1               5

<210> SEQ ID NO 319
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-15-CDR-1h

<400> SEQUENCE: 319

Gly Gly Ser Val Ser Ser Gly Gly Tyr Tyr Trp Ser
1               5                   10

<210> SEQ ID NO 320
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-15-CDR-2h

<400> SEQUENCE: 320

Tyr Ile Tyr Tyr Ser Gly Ser Thr Asn Tyr Asn Pro Ser Leu Lys Ser
1               5                   10                  15

<210> SEQ ID NO 321
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-15-CDR-3h

<400> SEQUENCE: 321

Asp Gly Asp Val Asp Thr Ala Met Val Asp Ala Phe Asp Ile
1               5                   10

<210> SEQ ID NO 322
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-15-CDR-1l

<400> SEQUENCE: 322

Arg Ala Ser Gln Ser Leu Ser Gly Asn Tyr Leu Ala
1               5                   10

<210> SEQ ID NO 323
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-15-CDR-2l

<400> SEQUENCE: 323

Gly Ala Ser Ser Arg Ala Thr
1               5

<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-15-CDR-3l

<400> SEQUENCE: 324

Gln Gln Tyr Asp Arg Ser Pro Leu Thr
1               5

<210> SEQ ID NO 325
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-16-CDR-1h

<400> SEQUENCE: 325

Gly Gly Ser Ile Ser Ser Gly Asp Tyr Tyr Trp Ser
1               5                   10

<210> SEQ ID NO 326
<211> LENGTH: 16
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-16-CDR-2h

<400> SEQUENCE: 326

Tyr Ile Tyr Tyr Ser Gly Ser Thr Tyr Tyr Asn Pro Ser Leu Lys Ser
1               5                   10                  15

<210> SEQ ID NO 327
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-16-CDR-3h

<400> SEQUENCE: 327

Ala Asp Tyr Asp Phe Trp Ser Gly Tyr Phe Asp Tyr
1               5                   10

<210> SEQ ID NO 328
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-16-CDR-1l

<400> SEQUENCE: 328

Arg Ala Ser Gln Gly Ile Arg Asn Asp Leu Gly
1               5                   10

<210> SEQ ID NO 329
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-16-CDR-2l

<400> SEQUENCE: 329

Ala Ala Ser Ser Leu Gln Ser
1               5

<210> SEQ ID NO 330
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-16-CDR-3l

<400> SEQUENCE: 330

Leu Gln His Asn Ser Tyr Pro Trp Thr
1               5

<210> SEQ ID NO 331
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-17-CDR-1h

<400> SEQUENCE: 331

Gly Gly Ser Ile Ser Ser Gly Asp Tyr Tyr Trp Ser
1               5                   10

<210> SEQ ID NO 332
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-17-CDR-2h

<400> SEQUENCE: 332

Tyr Ile Tyr Tyr Ser Gly Ser Thr Tyr Tyr Asn Ser Ser Leu Lys Ser
1               5                   10                  15

<210> SEQ ID NO 333
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-17-CDR-3h

<400> SEQUENCE: 333

Ala Asp Tyr Asp Phe Trp Ser Gly Tyr Phe Asp Tyr
1               5                   10

<210> SEQ ID NO 334
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-17-CDR-1l

<400> SEQUENCE: 334

Arg Ala Ser Gln Gly Ile Arg Asn Asp Leu Gly
1               5                   10

<210> SEQ ID NO 335
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-17-CDR-2l

<400> SEQUENCE: 335

Ala Ala Ser Ser Leu Gln Ser
1               5

<210> SEQ ID NO 336
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-17-CDR-3l

<400> SEQUENCE: 336

Leu Gln His Asn Ser Tyr Pro Trp Thr
1               5

<210> SEQ ID NO 337
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-18-CDR-1h

<400> SEQUENCE: 337

Gly Gly Ser Ile Ser Ser Gly Asp Tyr Tyr Trp Ser
1               5                   10

<210> SEQ ID NO 338
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-18-CDR-2h

<400> SEQUENCE: 338

Tyr Ile Tyr Tyr Ser Gly Ser Thr Tyr Tyr Asn Pro Ser Leu Lys Ser
1               5                   10                  15

<210> SEQ ID NO 339
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-18-CDR-3h

<400> SEQUENCE: 339

Ala Asp Tyr Asp Phe Trp Ser Gly Tyr Phe Asp Tyr
1               5                   10

<210> SEQ ID NO 340
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-18-CDR-1l

<400> SEQUENCE: 340

Arg Ala Ser Gln Gly Ile Arg Asn Asp Leu Gly
1               5                   10
```

```
<210> SEQ ID NO 341
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-18-CDR-2l

<400> SEQUENCE: 341

Ala Ala Ser Ser Leu Gln Ser
1               5

<210> SEQ ID NO 342
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-18-CDR-3l

<400> SEQUENCE: 342

Leu Gln His Asn Ser Tyr Pro Trp Thr
1               5

<210> SEQ ID NO 343
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-19-CDR-1h

<400> SEQUENCE: 343

Gly Gly Ser Ile Ser Ser Gly Asp Tyr Tyr Trp Ser
1               5                   10

<210> SEQ ID NO 344
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-19-CDR-2h

<400> SEQUENCE: 344

Tyr Ile Tyr Tyr Ser Gly Ser Thr Tyr Tyr Asn Pro Ser Leu Lys Ser
1               5                   10                  15

<210> SEQ ID NO 345
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-19-CDR-3h

<400> SEQUENCE: 345

Gly Asp Tyr Asp Phe Trp Ser Gly Glu Phe Asp Tyr
1               5                   10
```

<210> SEQ ID NO 346
<211> LENGTH: 12
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: U1-20-CDR-1h

<400> SEQUENCE: 346

Gly Gly Ser Ile Ser Ser Gly Gly Tyr Tyr Trp Ser
1               5                   10

<210> SEQ ID NO 347
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: U1-20-CDR-2h

<400> SEQUENCE: 347

Tyr Ile Tyr Asp Ser Gly Ser Thr Tyr Tyr Asn Pro Ser Leu Lys Ser
1               5                   10                  15

<210> SEQ ID NO 348
<211> LENGTH: 19
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: U1-20-CDR-3h

<400> SEQUENCE: 348

Asp Gln Gly Gln Asp Gly Tyr Ser Tyr Gly Tyr Gly Tyr Tyr Tyr Gly
1               5                   10                  15

Met Asp Val

<210> SEQ ID NO 349
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: U1-20-CDR-1l

<400> SEQUENCE: 349

Gln Ala Ser Gln Asp Ile Ser Asn Tyr Leu Asn
1               5                   10

<210> SEQ ID NO 350
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: U1-20-CDR-2l

<400> SEQUENCE: 350

Val Ala Ser Asn Leu Glu Thr
1               5

<210> SEQ ID NO 351
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-20-CDR-3l

<400> SEQUENCE: 351

Gln Gln Cys Asp Asn Leu Pro Leu Thr
1               5

<210> SEQ ID NO 352
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-21-CDR-1h

<400> SEQUENCE: 352

Gly Gly Ser Ile Ser Ser Gly Asp Tyr Tyr Trp Ser
1               5                   10

<210> SEQ ID NO 353
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-21-CDR-2h

<400> SEQUENCE: 353

Tyr Ile Tyr Tyr Ser Gly Ser Thr Tyr Tyr Asn Pro Ser Leu Lys Ser
1               5                   10                  15

<210> SEQ ID NO 354
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-21-CDR-3h

<400> SEQUENCE: 354

Ala Asp Tyr Asp Phe Trp Ser Gly Tyr Phe Asp Tyr
1               5                   10

<210> SEQ ID NO 355
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-21-CDR-1l

<400> SEQUENCE: 355

-continued

Arg Ala Ser Gln Asp Ile Arg Asn Asp Leu Gly
1               5                   10

<210> SEQ ID NO 356
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-21-CDR-2l

<400> SEQUENCE: 356

Ala Ala Ser Arg Leu Gln Ser
1               5

<210> SEQ ID NO 357
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-21-CDR-3l

<400> SEQUENCE: 357

Leu Gln His Asn Ser Tyr Pro Trp Thr
1               5

<210> SEQ ID NO 358
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-22-CDR-1h

<400> SEQUENCE: 358

Gly Gly Ser Ile Ser Ser Gly Asp Tyr Tyr Trp Ser
1               5                   10

<210> SEQ ID NO 359
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-22-CDR-2h

<400> SEQUENCE: 359

Tyr Ile Tyr Tyr Ser Gly Ser Thr Tyr Tyr Asn Pro Ser Leu Lys Ser
1               5                   10                  15

<210> SEQ ID NO 360
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-22-CDR-3h

```
<400> SEQUENCE: 360

Ala Asp Tyr Asp Phe Trp Ser Gly Tyr Phe Asp Tyr
1               5                   10

<210> SEQ ID NO 361
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-22-CDR-1l

<400> SEQUENCE: 361

Arg Ala Ser Gln Gly Ile Arg Asn Asp Leu Gly
1               5                   10

<210> SEQ ID NO 362
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-22-CDR-2l

<400> SEQUENCE: 362

Ala Ala Ser Ser Leu Gln Asn
1               5

<210> SEQ ID NO 363
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-22-CDR-3l

<400> SEQUENCE: 363

Leu Gln His Asn Ser Tyr Pro Trp Thr
1               5

<210> SEQ ID NO 364
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-23-CDR-1h

<400> SEQUENCE: 364

Gly Gly Ser Ile Ser Ser Gly Asp Tyr Tyr Trp Ser
1               5                   10

<210> SEQ ID NO 365
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-23-CDR-2h
```

<400> SEQUENCE: 365

Tyr Ile Tyr Tyr Ser Gly Ser Thr Tyr Tyr Asn Pro Ser Leu Lys Ser
1               5                   10                  15

<210> SEQ ID NO 366
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-23-CDR-3h

<400> SEQUENCE: 366

Ala Asp Tyr Asp Phe Trp Ser Gly Tyr Phe Asp Tyr
1               5                   10

<210> SEQ ID NO 367
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-23-CDR-1l

<400> SEQUENCE: 367

Arg Ala Ser Gln Gly Ile Arg Asn Asp Leu Gly
1               5                   10

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-23-CDR-2l

<400> SEQUENCE: 368

Ala Ala Ser Ser Leu Gln Ser
1               5

<210> SEQ ID NO 369
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-23-CDR-3l

<400> SEQUENCE: 369

Leu Gln His Asn Ser Tyr Pro Trp Thr
1               5

<210> SEQ ID NO 370
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: U1-24-CDR-1h

<400> SEQUENCE: 370

Gly Gly Ser Ile Ser Ser Gly Asp Tyr Tyr Trp Ser
1               5                   10

<210> SEQ ID NO 371
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-24-CDR-2h

<400> SEQUENCE: 371

Tyr Ile Tyr Tyr Ser Gly Ser Thr Tyr Tyr Asn Pro Ser Leu Lys Ser
1               5                   10                  15

<210> SEQ ID NO 372
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-24-CDR-3h

<400> SEQUENCE: 372

Ala Asp Tyr Asp Phe Trp Asn Gly Tyr Phe Asp Tyr
1               5                   10

<210> SEQ ID NO 373
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-24-CDR-1l

<400> SEQUENCE: 373

Arg Ala Ser Gln Gly Ile Arg Asn Asp Leu Gly
1               5                   10

<210> SEQ ID NO 374
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-24-CDR-2l

<400> SEQUENCE: 374

Ala Ala Ser Ser Leu Gln Ser
1               5

<210> SEQ ID NO 375
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: U1-24-CDR-3l

<400> SEQUENCE: 375

Leu Gln His Asn Asn Tyr Pro Trp Thr
1               5

<210> SEQ ID NO 376
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-25-CDR-1h

<400> SEQUENCE: 376

Gly Gly Ser Ile Ser Ser Gly Asp Tyr Tyr Trp Ser
1               5                   10

<210> SEQ ID NO 377
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-25-CDR-2h

<400> SEQUENCE: 377

Tyr Ile Tyr Tyr Ser Gly Ser Thr Tyr Tyr Asn Pro Ser Leu Lys Ser
1               5                   10                  15

<210> SEQ ID NO 378
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-25-CDR-3h

<400> SEQUENCE: 378

Ala Asp Tyr Asp Phe Trp Ser Gly Tyr Phe Asp Tyr
1               5                   10

<210> SEQ ID NO 379
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-25-CDR-1l

<400> SEQUENCE: 379

Arg Ala Ser Gln Gly Ile Arg Asn Asp Leu Gly
1               5                   10

<210> SEQ ID NO 380
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<223> OTHER INFORMATION: U1-25-CDR-2l

<400> SEQUENCE: 380

Ala Ala Ser Ser Leu Gln Asn
1               5

<210> SEQ ID NO 381
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-25-CDR-3l

<400> SEQUENCE: 381

Leu Gln His Asn Ser Tyr Pro Trp Thr
1               5

<210> SEQ ID NO 382
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-26-CDR-1h

<400> SEQUENCE: 382

Gly Gly Ser Ile Ser Ser Gly Asp Tyr Tyr Trp Ser
1               5                   10

<210> SEQ ID NO 383
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-26-CDR-2h

<400> SEQUENCE: 383

Tyr Ile Tyr Tyr Ser Gly Ser Thr Tyr Tyr Asn Pro Ser Leu Lys Ser
1               5                   10                  15

<210> SEQ ID NO 384
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-26-CDR-3h

<400> SEQUENCE: 384

Ala Asp Tyr Asp Phe Trp Ser Gly Tyr Phe Asp Phe
1               5                   10

<210> SEQ ID NO 385
<211> LENGTH: 11
<212> TYPE: PRT
<213> ORGANISM: Artificial Sequence
<220> FEATURE:

<223> OTHER INFORMATION: Description of Artificial Sequence: Synthetic
    peptide
<220> FEATURE:
<223> OTHER INFORMATION: U1-26-CDR-1l

<400> SEQUENCE: 385

Arg Ala Ser Gln Gly Ile Arg Asn Asp Leu Gly
1               5                   10

<210> SEQ ID NO 386
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: U1-26-CDR-2l

<400> SEQUENCE: 386

Ala Ala Ser Ser Leu Gln Ser
1               5

<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: U1-26-CDR-3l

<400> SEQUENCE: 387

Leu Gln His Asn Gly Tyr Pro Trp Thr
1               5

<210> SEQ ID NO 388
<211> LENGTH: 12
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: U1-27-CDR-1h

<400> SEQUENCE: 388

Gly Gly Ser Ile Ser Ser Gly Asp Tyr Tyr Trp Ser
1               5                   10

<210> SEQ ID NO 389
<211> LENGTH: 16
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: U1-27-CDR-2h

<400> SEQUENCE: 389

Tyr Ile Tyr Tyr Ser Gly Ser Thr Tyr Tyr Asn Pro Ser Leu Lys Ser
1               5                   10                  15

<210> SEQ ID NO 390
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: U1-27-CDR-3h

<400> SEQUENCE: 390

Ala Asp Tyr Asp Phe Trp Ser Gly Tyr Phe Asp Phe
1               5                   10

<210> SEQ ID NO 391
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-27-CDR-1l

<400> SEQUENCE: 391

Arg Ala Ser Gln Gly Ile Arg Asn Asp Leu Gly
1               5                   10

<210> SEQ ID NO 392
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-27-CDR-2l

<400> SEQUENCE: 392

Ala Ala Ser Ser Leu Gln Ser
1               5

<210> SEQ ID NO 393
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-27-CDR-3l

<400> SEQUENCE: 393

Leu Gln His Asn Gly Tyr Pro Trp Thr
1               5

<210> SEQ ID NO 394
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-28-CDR-1h

<400> SEQUENCE: 394

Gly Gly Ser Ile Ser Ser Gly Asp Tyr Tyr Trp Ser
1               5                   10

<210> SEQ ID NO 395
<211> LENGTH: 16
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-28-CDR-2h

<400> SEQUENCE: 395

Tyr Ile Tyr Tyr Ser Gly Ser Thr Tyr Tyr Asn Pro Ser Leu Lys Ser
1               5                   10                  15

<210> SEQ ID NO 396
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-28-CDR-1l

<400> SEQUENCE: 396

Ala Asp Tyr Asp Phe Trp Ser Gly Tyr Phe Asp Ser
1               5                   10

<210> SEQ ID NO 397
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-28-CDR-1l

<400> SEQUENCE: 397

Arg Ala Ser Gln Gly Ile Arg Asn Asp Leu Gly
1               5                   10

<210> SEQ ID NO 398
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-28-CDR-2l

<400> SEQUENCE: 398

Ala Ala Ser Ser Leu Gln Ser
1               5

<210> SEQ ID NO 399
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-28-CDR-3l

<400> SEQUENCE: 399

Leu Gln His Asn Gly Tyr Pro Trp Thr
1               5

<210> SEQ ID NO 400
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-29-CDR-1h

<400> SEQUENCE: 400

Gly Phe Thr Phe Asn Ser Tyr Asp Met His
1               5                   10

<210> SEQ ID NO 401
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-29-CDR-2h

<400> SEQUENCE: 401

Val Ile Trp Tyr Asp Gly Ser Asn Lys Tyr Tyr Ala Asp Ser Val Lys
1               5                   10                  15

Gly

<210> SEQ ID NO 402
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-29-CDR-3h

<400> SEQUENCE: 402

Asp Arg Leu Cys Thr Asn Gly Val Cys Tyr Glu Asp Tyr Gly Met Asp
1               5                   10                  15

Val

<210> SEQ ID NO 403
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-29-CDR-1l

<400> SEQUENCE: 403

Gln Ala Ser Gln Asp Ile Ser Asn Tyr Leu Asn
1               5                   10

<210> SEQ ID NO 404
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-29-CDR-2l

<400> SEQUENCE: 404

Asp Ala Ser Asn Leu Glu Thr
```

```
<210> SEQ ID NO 405
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-29-CDR-3l

<400> SEQUENCE: 405

Gln His Tyr Asp Thr Leu Pro Leu Thr
1               5

<210> SEQ ID NO 406
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-30-CDR-1h

<400> SEQUENCE: 406

Gly Gly Ser Ile Ser Ser Gly Asp Tyr Tyr Trp Ser
1               5                   10

<210> SEQ ID NO 407
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-30-CDR-2h

<400> SEQUENCE: 407

Tyr Ile Tyr Tyr Ser Gly Thr Thr Tyr Tyr Asn Pro Ser Leu Lys Ser
1               5                   10                  15

<210> SEQ ID NO 408
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-30-CDR-3h

<400> SEQUENCE: 408

Ala Asp Tyr Asp Phe Trp Ser Gly Tyr Phe Asp Tyr
1               5                   10

<210> SEQ ID NO 409
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-30-CDR-1l

<400> SEQUENCE: 409
```

Arg Ala Gly Gln Gly Ile Arg Asn Asp Leu Gly
1               5                   10

<210> SEQ ID NO 410
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-30-CDR-2l

<400> SEQUENCE: 410

Ala Ala Ser Ser Leu Gln Ser
1               5

<210> SEQ ID NO 411
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-30-CDR-3l

<400> SEQUENCE: 411

Leu Gln His Asn Ser Tyr Pro Trp Thr
1               5

<210> SEQ ID NO 412
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-31-CDR-1h

<400> SEQUENCE: 412

Gly Tyr Thr Phe Thr Asn Tyr Gly Ile Ser
1               5                   10

<210> SEQ ID NO 413
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-31-CDR-2h

<400> SEQUENCE: 413

Trp Ile Ser Ala Tyr Asp Gly Tyr Arg Asn Tyr Ala Gln Lys Leu Gln
1               5                   10                  15
Gly

<210> SEQ ID NO 414
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-31-CDR-3h

```
<400> SEQUENCE: 414

Asp Val Gln Asp Tyr Gly Asp Tyr Asp Tyr Phe Asp Tyr
1               5                   10

<210> SEQ ID NO 415
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-31-CDR-1l

<400> SEQUENCE: 415

Arg Ala Ser Gln Ser Ile Ser Ser Tyr Leu Asn
1               5                   10

<210> SEQ ID NO 416
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-31-CDR-2l

<400> SEQUENCE: 416

Ala Ala Ser Ser Leu Gln Ser
1               5

<210> SEQ ID NO 417
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-31-CDR-3l

<400> SEQUENCE: 417

Gln Gln Ser Tyr Ser Thr Pro Ile Thr
1               5

<210> SEQ ID NO 418
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-32-CDR-1h

<400> SEQUENCE: 418

Gly Gly Ser Ile Ser Ser Gly Asp Tyr Tyr Trp Ser
1               5                   10

<210> SEQ ID NO 419
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: U1-32-CDR-2h

<400> SEQUENCE: 419

Tyr Ile Tyr Tyr Ser Gly Thr Thr Tyr Tyr Asn Pro Ser Leu Lys Ser
1               5                   10                  15

<210> SEQ ID NO 420
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-32-CDR-3h

<400> SEQUENCE: 420

Ala Asp Tyr Asp Phe Trp Ser Gly Tyr Phe Asp Tyr
1               5                   10

<210> SEQ ID NO 421
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-32-CDR-1l

<400> SEQUENCE: 421

Arg Ala Gly Gln Gly Ile Arg Asn Asp Leu Gly
1               5                   10

<210> SEQ ID NO 422
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-32-CDR-2l

<400> SEQUENCE: 422

Ala Ala Ser Ser Leu Gln Ser
1               5

<210> SEQ ID NO 423
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-32-CDR-3l

<400> SEQUENCE: 423

Leu Gln His Asn Ser Tyr Pro Trp Thr
1               5

<210> SEQ ID NO 424
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: U1-33-CDR-1h

<400> SEQUENCE: 424

Gly Gly Ser Ile Ser Ser Gly Asp Tyr Tyr Trp Ser
1               5                   10

<210> SEQ ID NO 425
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-33-CDR-2h

<400> SEQUENCE: 425

Tyr Ile Tyr Tyr Ser Gly Ser Thr Tyr Tyr Asn Pro Ser Leu Lys Ser
1               5                   10                  15

<210> SEQ ID NO 426
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-33-CDR-3h

<400> SEQUENCE: 426

Ala Asp Tyr Asp Phe Trp Ser Gly His Phe Asp Cys
1               5                   10

<210> SEQ ID NO 427
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-33-CDR-1l

<400> SEQUENCE: 427

Arg Ala Ser Gln Gly Ile Arg Asp Asp Leu Gly
1               5                   10

<210> SEQ ID NO 428
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-33-CDR-2l

<400> SEQUENCE: 428

Ala Glu Ser Ser Leu Gln Ser
1               5

<210> SEQ ID NO 429
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: U1-33-CDR-3l

<400> SEQUENCE: 429

Leu Gln His His Ser Tyr Pro Trp Thr
1               5

<210> SEQ ID NO 430
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-34-CDR-1h

<400> SEQUENCE: 430

Gly Tyr Thr Phe Thr Asn Tyr Gly Ile Ser
1               5                   10

<210> SEQ ID NO 431
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-34-CDR-2h

<400> SEQUENCE: 431

Trp Ile Ser Ala Tyr Asp Gly Tyr Arg Asn Tyr Ala Gln Lys Leu Gln
1               5                   10                  15

Gly

<210> SEQ ID NO 432
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-34-CDR-3h

<400> SEQUENCE: 432

Asp Val Gln Asp Tyr Gly Asp Tyr Asp Tyr Phe Asp Tyr
1               5                   10

<210> SEQ ID NO 433
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-34-CDR-1l

<400> SEQUENCE: 433

Arg Ala Ser Gln Ser Ile Ser Ser Tyr Leu Asn
1               5                   10

<210> SEQ ID NO 434
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-34-CDR-2l

<400> SEQUENCE: 434

Ala Ala Ser Ser Leu Gln Ser
1               5

<210> SEQ ID NO 435
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-34-CDR-3l

<400> SEQUENCE: 435

Gln Gln Ser Tyr Ser Thr Pro Ile Thr
1               5

<210> SEQ ID NO 436
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-35-CDR-1h

<400> SEQUENCE: 436

Gly Phe Thr Phe Ser Asp Tyr Tyr Met Ser
1               5                   10

<210> SEQ ID NO 437
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-35-CDR-2h

<400> SEQUENCE: 437

Tyr Ile Ser Ser Ser Gly Asn Asn Ile Tyr His Ala Asp Ser Val Lys
1               5                   10                  15

Gly

<210> SEQ ID NO 438
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-35-CDR-3h

<400> SEQUENCE: 438

Glu Arg Tyr Ser Gly Tyr Asp Asp Pro Asp Gly Phe Asp Ile
1               5                   10
```

```
<210> SEQ ID NO 439
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-35-CDR-1l

<400> SEQUENCE: 439

Gln Ala Ser Gln Asp Ile Ser Asn Tyr Leu Ser
1               5                   10

<210> SEQ ID NO 440
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-35-CDR-2l

<400> SEQUENCE: 440

Asp Ala Ser Asn Leu Glu Thr
1               5

<210> SEQ ID NO 441
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-35-CDR-3l

<400> SEQUENCE: 441

Gln Gln Tyr Asp Asn Pro Pro Cys Ser
1               5

<210> SEQ ID NO 442
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-36-CDR-1h

<400> SEQUENCE: 442

Gly Gly Ser Ile Ser Ser Gly Tyr Tyr Tyr Trp Ser
1               5                   10

<210> SEQ ID NO 443
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-36-CDR-2h

<400> SEQUENCE: 443

Tyr Ile Tyr Tyr Ser Gly Thr Thr Tyr Tyr Asn Pro Ser Phe Lys Ser
1               5                   10                  15
```

<210> SEQ ID NO 444
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-36-CDR-3h

<400> SEQUENCE: 444

Ala Asp Tyr Asp Phe Trp Ser Gly His Phe Asp Tyr
1               5                   10

<210> SEQ ID NO 445
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-36-CDR-1l

<400> SEQUENCE: 445

Arg Ala Ser Gln Gly Ile Arg Asn Asp Leu Gly
1               5                   10

<210> SEQ ID NO 446
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-36-CDR-2l

<400> SEQUENCE: 446

Ala Ala Ser Ser Leu Gln Ser
1               5

<210> SEQ ID NO 447
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-36-CDR-3l

<400> SEQUENCE: 447

Leu Gln His Asn Ser Tyr Pro Trp Thr
1               5

<210> SEQ ID NO 448
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-37-CDR-1h

<400> SEQUENCE: 448

Gly Tyr Thr Phe Thr Ser Tyr Gly Ile Ser
1               5                   10

<210> SEQ ID NO 449
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-37-CDR-2h

<400> SEQUENCE: 449

Trp Ile Ser Ala Tyr Asp Gly His Thr Asn Tyr Ala Gln Lys Leu Gln
1               5                   10                  15

Gly

<210> SEQ ID NO 450
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-37-CDR-3h

<400> SEQUENCE: 450

Asp Pro His Asp Tyr Ser Asn Tyr Glu Ala Phe Asp Phe
1               5                   10

<210> SEQ ID NO 451
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-37-CDR-1l

<400> SEQUENCE: 451

Arg Ala Ser Gln Ser Ile Ser Ser Tyr Leu Asn
1               5                   10

<210> SEQ ID NO 452
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-37-CDR-2l

<400> SEQUENCE: 452

Ala Ala Ser Ser Leu Gln Ser
1               5

<210> SEQ ID NO 453
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-37-CDR-3l

<400> SEQUENCE: 453

Gln Gln Ser Tyr Ser Thr Pro Ile Thr
1               5

<210> SEQ ID NO 454
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-38-CDR-1h

<400> SEQUENCE: 454

Gly Phe Ser Leu Ser Thr Ser Gly Val Gly Val Gly
1               5                   10

<210> SEQ ID NO 455
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-38-CDR-2h

<400> SEQUENCE: 455

Leu Ile Tyr Trp Asn Asp Asp Lys Arg Tyr Ser Pro Ser Leu Lys Ser
1               5                   10                  15

<210> SEQ ID NO 456
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-38-CDR-3h

<400> SEQUENCE: 456

Arg Asp Glu Val Arg Gly Phe Asp Tyr
1               5

<210> SEQ ID NO 457
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-38-CDR-1l

<400> SEQUENCE: 457

Arg Ser Ser Gln Ser Leu Val Tyr Ser Asp Gly Tyr Thr Tyr Leu His
1               5                   10                  15

<210> SEQ ID NO 458
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-38-CDR-2l

```
<400> SEQUENCE: 458

Lys Val Ser Asn Trp Asp Ser
1               5

<210> SEQ ID NO 459
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-38-CDR-3l

<400> SEQUENCE: 459

Met Gln Gly Ala His Trp Pro Ile Thr
1               5

<210> SEQ ID NO 460
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-39-CDR-1h

<400> SEQUENCE: 460

Gly Phe Thr Val Ser Ser Asn Tyr Met Ser
1               5                   10

<210> SEQ ID NO 461
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-39-CDR-2h

<400> SEQUENCE: 461

Val Ile Tyr Ser Gly Gly Ser Thr Tyr Tyr Ala Asp Ser Val Lys Gly
1               5                   10                  15

<210> SEQ ID NO 462
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-39-CDR-3h

<400> SEQUENCE: 462

Gly Gln Trp Leu Asp Val
1               5

<210> SEQ ID NO 463
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-39-CDR-1l
```

```
<400> SEQUENCE: 463

Arg Ser Ser Gln Ser Leu Leu His Ser Asn Gly Tyr Asn Tyr Leu Asp
1               5                   10                  15

<210> SEQ ID NO 464
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-39-CDR-2l

<400> SEQUENCE: 464

Leu Gly Phe His Arg Ala Ser
1               5

<210> SEQ ID NO 465
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-39-CDR-3l

<400> SEQUENCE: 465

Arg Gln Ala Leu Gln Thr Pro Leu Thr
1               5

<210> SEQ ID NO 466
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-40-CDR-1h

<400> SEQUENCE: 466

Gly Gly Ser Ile Ser Ser Gly Gly Tyr Tyr Trp Ser
1               5                   10

<210> SEQ ID NO 467
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-40-CDR-2h

<400> SEQUENCE: 467

Tyr Ile Tyr Ser Ser Gly Ser Thr Tyr Tyr Asn Pro Ser Leu Lys Ser
1               5                   10                  15

<210> SEQ ID NO 468
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: U1-40-CDR-3h

<400> SEQUENCE: 468

Asp Arg Glu Leu Glu Leu Tyr Tyr Tyr Tyr Tyr Gly Met Asp Val
1               5                   10                  15

<210> SEQ ID NO 469
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-40-CDR-1l

<400> SEQUENCE: 469

Arg Ser Ser Gln Ser Leu Leu Tyr Ser Asn Gly Tyr Asn Tyr Leu Asp
1               5                   10                  15

<210> SEQ ID NO 470
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-40-CDR-2l

<400> SEQUENCE: 470

Leu Gly Ser Asn Arg Ala Ser
1               5

<210> SEQ ID NO 471
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-40-CDR-3l

<400> SEQUENCE: 471

Met Gln Ala Leu Gln Thr Pro Leu Thr
1               5

<210> SEQ ID NO 472
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-41-CDR-1h

<400> SEQUENCE: 472

Gly Gly Ser Ile Ser Ser Gly Gly Tyr Tyr Trp Ser
1               5                   10

<210> SEQ ID NO 473
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: U1-41-CDR-2h

<400> SEQUENCE: 473

Tyr Ile Tyr Tyr Ser Gly Ser Thr Tyr Tyr Asn Pro Ser Leu Lys Ser
1               5                   10                  15

<210> SEQ ID NO 474
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-41-CDR-3h

<400> SEQUENCE: 474

Asp Arg Glu Leu Glu Gly Tyr Ser Asn Tyr Tyr Gly Val Asp Val
1               5                   10                  15

<210> SEQ ID NO 475
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-41-CDR-1l

<400> SEQUENCE: 475

Arg Ala Ser Gln Ala Ile Ser Asn Tyr Leu Asn
1               5                   10

<210> SEQ ID NO 476
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-41-CDR-2l

<400> SEQUENCE: 476

Ala Ala Ser Ser Leu Gln Ser
1               5

<210> SEQ ID NO 477
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-41-CDR-3l

<400> SEQUENCE: 477

Gln Gln Asn Asn Ser Leu Pro Ile Thr
1               5

<210> SEQ ID NO 478
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
              peptide
<220> FEATURE:
<223> OTHER INFORMATION: U1-42-CDR-1h

<400> SEQUENCE: 478

Gly Tyr Ser Phe Thr Ser Tyr Trp Ile Gly
1               5                   10

<210> SEQ ID NO 479
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-42-CDR-2h

<400> SEQUENCE: 479

Ile Ile Tyr Pro Gly Asp Ser Asp Thr Arg Tyr Ser Pro Ser Phe Gln
1               5                   10                  15

Gly

<210> SEQ ID NO 480
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-42-CDR-3h

<400> SEQUENCE: 480

His Glu Asn Tyr Gly Asp Tyr Asn Tyr
1               5

<210> SEQ ID NO 481
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-42-CDR-1l

<400> SEQUENCE: 481

Arg Ala Ser Gln Ser Ile Arg Ser Tyr Leu Asn
1               5                   10

<210> SEQ ID NO 482
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-42-CDR-2l

<400> SEQUENCE: 482

Ala Ala Ser Ser Leu Gln Ser
1               5

<210> SEQ ID NO 483
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-42-CDR-3l

<400> SEQUENCE: 483

Gln Gln Ser Asn Gly Ser Pro Leu Thr
1               5

<210> SEQ ID NO 484
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-43-CDR-1h

<400> SEQUENCE: 484

Gly Gly Ser Ile Ser Ser Gly Gly Tyr Tyr Trp Ser
1               5                   10

<210> SEQ ID NO 485
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-43-CDR-2h

<400> SEQUENCE: 485

Tyr Ile Tyr Tyr Ser Gly Ser Thr Tyr Tyr Asn Pro Ser Leu Arg Ser
1               5                   10                  15

<210> SEQ ID NO 486
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-43-CDR-3h

<400> SEQUENCE: 486

Asp Arg Glu Arg Glu Trp Asp Asp Tyr Gly Asp Pro Gln Gly Met Asp
1               5                   10                  15

Val

<210> SEQ ID NO 487
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-43-CDR-1l

<400> SEQUENCE: 487

Arg Ala Ser Gln Ser Ile Ser Ser Tyr Leu His
1               5                   10
```

```
<210> SEQ ID NO 488
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-43-CDR-2l

<400> SEQUENCE: 488

Ala Ala Ser Ser Leu Gln Ser
1               5

<210> SEQ ID NO 489
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-43-CDR-3l

<400> SEQUENCE: 489

Gln Gln Ser Tyr Ser Asn Pro Leu Thr
1               5

<210> SEQ ID NO 490
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-44-CDR-1h

<400> SEQUENCE: 490

Gly Tyr Ser Phe Thr Ser Tyr Trp Ile Gly
1               5                   10

<210> SEQ ID NO 491
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-44-CDR-2h

<400> SEQUENCE: 491

Ile Ile Trp Pro Gly Asp Ser Asp Thr Ile Tyr Ser Pro Ser Phe Gln
1               5                   10                  15
Gly

<210> SEQ ID NO 492
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-44-CDR-3h

<400> SEQUENCE: 492

His Glu Asn Tyr Gly Asp Tyr Asn Tyr
```

<210> SEQ ID NO 493
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-44-CDR-1l

<400> SEQUENCE: 493

Arg Ala Ser Gln Ser Ile Arg Ser Tyr Leu Asn
1               5                   10

<210> SEQ ID NO 494
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-44-CDR-2l

<400> SEQUENCE: 494

Ala Ala Ser Ser Leu Gln Ser
1               5

<210> SEQ ID NO 495
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-44-CDR-3l

<400> SEQUENCE: 495

Gln Gln Ser Ile Ser Ser Pro Leu Thr
1               5

<210> SEQ ID NO 496
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-45-CDR-1h

<400> SEQUENCE: 496

Gly Tyr Thr Phe Thr Ser Tyr Asp Ile Asn
1               5                   10

<210> SEQ ID NO 497
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-45-CDR-2h

<400> SEQUENCE: 497

Trp Met Asn Pro Asn Ser Gly Asp Thr Gly Tyr Ala Gln Val Phe Gln
1               5                   10                  15
Gly

<210> SEQ ID NO 498
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-45-CDR-3h

<400> SEQUENCE: 498

Phe Gly Asp Leu Pro Tyr Asp Tyr Ser Tyr Tyr Glu Trp Phe Asp Pro
1               5                   10                  15

<210> SEQ ID NO 499
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-45-CDR-1l

<400> SEQUENCE: 499

Arg Ala Ser Gln Ser Ile Ser Ser Tyr Leu Asn
1               5                   10

<210> SEQ ID NO 500
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-45-CDR-2l

<400> SEQUENCE: 500

Ala Ala Ser Ser Leu Gln Ser
1               5

<210> SEQ ID NO 501
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-45-CDR-3l

<400> SEQUENCE: 501

Gln Gln Ser Tyr Ser Thr Pro Leu Thr
1               5

<210> SEQ ID NO 502
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-46-CDR-1h

```
<400> SEQUENCE: 502

Gly Asp Ser Val Ser Ser Asn Ser Ala Ala Trp Asn
1               5                   10

<210> SEQ ID NO 503
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-46-CDR-2h

<400> SEQUENCE: 503

Arg Thr Tyr Tyr Arg Ser Lys Trp Tyr Asn Asp Tyr Ala Val Ser Val
1               5                   10                  15

Lys Ser

<210> SEQ ID NO 504
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-46-CDR-3h

<400> SEQUENCE: 504

Asp Leu Tyr Asp Phe Trp Ser Gly Tyr Pro Tyr Tyr Tyr Gly Met Asp
1               5                   10                  15

Val

<210> SEQ ID NO 505
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-47-CDR-1h

<400> SEQUENCE: 505

Gly Asp Ser Val Ser Ser Asn Ser Ala Ala Trp Asn
1               5                   10

<210> SEQ ID NO 506
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-47-CDR-2h

<400> SEQUENCE: 506

Arg Thr Tyr Tyr Arg Ser Lys Trp Tyr Asn Asp Tyr Ala Val Ser Val
1               5                   10                  15

Lys Ser

<210> SEQ ID NO 507
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-47-CDR-3h

<400> SEQUENCE: 507

Asp Tyr Tyr Gly Ser Gly Ser Phe Tyr Tyr Tyr Gly Met Asp Val
1               5                   10                  15

<210> SEQ ID NO 508
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-47-CDR-1l

<400> SEQUENCE: 508

Arg Ala Ser Gln Ser Ile Ser Ser Tyr Leu Asn
1               5                   10

<210> SEQ ID NO 509
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-47-CDR-2l

<400> SEQUENCE: 509

Ala Ala Ser Asn Leu Gln Ser
1               5

<210> SEQ ID NO 510
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-47-CDR-3l

<400> SEQUENCE: 510

Gln Gln Ser Tyr Ser Thr Pro Arg Thr
1               5

<210> SEQ ID NO 511
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-48-CDR-1h

<400> SEQUENCE: 511

Gly Gly Ser Ile Ser Ser Tyr Tyr Trp Ser
1               5                   10

<210> SEQ ID NO 512
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-48-CDR-2h

<400> SEQUENCE: 512

His Ile Tyr Thr Ser Gly Ser Thr Asn Tyr Asn Pro Ser Leu Lys Ser
1               5                   10                  15

<210> SEQ ID NO 513
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-48-CDR-3h

<400> SEQUENCE: 513

Glu Ala Ile Phe Gly Val Gly Pro Tyr Tyr Tyr Tyr Gly Met Asp Val
1               5                   10                  15

<210> SEQ ID NO 514
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-49-CDR-1h

<400> SEQUENCE: 514

Gly Tyr Thr Phe Thr Gly Tyr Tyr Met His
1               5                   10

<210> SEQ ID NO 515
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-49-CDR-2h

<400> SEQUENCE: 515

Trp Ile Asn Pro Asn Ile Gly Gly Thr Asn Cys Ala Gln Lys Phe Gln
1               5                   10                  15

Gly

<210> SEQ ID NO 516
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-49-CDR-3h

<400> SEQUENCE: 516

Gly Gly Arg Tyr Ser Ser Ser Trp Ser Tyr Tyr Tyr Tyr Gly Met Asp
1               5                   10                  15
```

Val

<210> SEQ ID NO 517
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-49-CDR-1l

<400> SEQUENCE: 517

Lys Ser Ser Gln Ser Leu Leu Leu Ser Asp Gly Gly Thr Tyr Leu Tyr
1               5                   10                  15

<210> SEQ ID NO 518
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-49-CDR-2l

<400> SEQUENCE: 518

Glu Val Ser Asn Arg Phe Ser
1               5

<210> SEQ ID NO 519
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-49-CDR-3l

<400> SEQUENCE: 519

Met Gln Ser Met Gln Leu Pro Ile Thr
1               5

<210> SEQ ID NO 520
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-50-CDR-1h

<400> SEQUENCE: 520

Gly Gly Ser Val Ser Ser Gly Gly Tyr Tyr Trp Ser
1               5                   10

<210> SEQ ID NO 521
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-50-CDR-2h

<400> SEQUENCE: 521

```
Tyr Ile Tyr Tyr Ser Gly Ser Thr Asn Tyr Asn Pro Ser Leu Lys Ser
1               5                   10                  15

<210> SEQ ID NO 522
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-50-CDR-3h

<400> SEQUENCE: 522

Gly Gly Asp Ser Asn Tyr Glu Asp Tyr Tyr Tyr Tyr Gly Met Asp
1               5                   10                  15

Val

<210> SEQ ID NO 523
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-50-CDR-1l

<400> SEQUENCE: 523

Arg Ala Ser Gln Ser Ile Ser Ile Tyr Leu His
1               5                   10

<210> SEQ ID NO 524
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-50-CDR-2l

<400> SEQUENCE: 524

Ala Ala Ser Ser Leu Gln Ser
1               5

<210> SEQ ID NO 525
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-50-CDR-3l

<400> SEQUENCE: 525

Gln Gln Ser Tyr Thr Ser Pro Ile Thr
1               5

<210> SEQ ID NO 526
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: U1-51-CDR-1h

<400> SEQUENCE: 526

Gly Gly Ser Ile Ser Ser Tyr Tyr Trp Ser
1               5                   10

<210> SEQ ID NO 527
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-51-CDR-2h

<400> SEQUENCE: 527

Tyr Ile Tyr Tyr Ser Gly Ser Thr Asn Tyr Asn Pro Ser Leu Lys Ser
1               5                   10                  15

<210> SEQ ID NO 528
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-51-CDR-3h

<400> SEQUENCE: 528

Asp Ser Ser Tyr Tyr Asp Ser Ser Gly Tyr Tyr Leu Tyr Tyr Tyr Ala
1               5                   10                  15

Met Asp Val

<210> SEQ ID NO 529
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-51-CDR-1l

<400> SEQUENCE: 529

Lys Ser Ser Gln Ser Val Leu Tyr Ser Ser Asn Asn Lys Asn Tyr Leu
1               5                   10                  15

Ala

<210> SEQ ID NO 530
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-51-CDR-2l

<400> SEQUENCE: 530

Trp Ala Ser Thr Arg Glu Ser
1               5

<210> SEQ ID NO 531
<211> LENGTH: 9
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-51-CDR-3l

<400> SEQUENCE: 531

Gln Gln Tyr Tyr Thr Thr Pro Leu Thr
1               5

<210> SEQ ID NO 532
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-52-CDR-1h

<400> SEQUENCE: 532

Gly Gly Ser Ile Ser Ser Gly Gly Tyr Tyr Trp Ser
1               5                   10

<210> SEQ ID NO 533
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-52-CDR-2h

<400> SEQUENCE: 533

Asn Ile Tyr Tyr Ser Gly Ser Thr Tyr Tyr Asn Pro Ser Leu Lys Ser
1               5                   10                  15

<210> SEQ ID NO 534
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-52-CDR-3h

<400> SEQUENCE: 534

Gly Gly Thr Gly Thr Asn Tyr Tyr Tyr Tyr Gly Met Asp Val
1               5                   10                  15

<210> SEQ ID NO 535
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-52-CDR-1l

<400> SEQUENCE: 535

Arg Ala Ser Gln Ser Val Ser Ser Ser Tyr Leu Ala
1               5                   10

<210> SEQ ID NO 536
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-52-CDR-2l

<400> SEQUENCE: 536

Gly Ala Ser Ser Trp Ala Thr
1               5

<210> SEQ ID NO 537
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-52-CDR-3l

<400> SEQUENCE: 537

Gln Gln Tyr Gly Ser Ser Pro Leu Thr
1               5

<210> SEQ ID NO 538
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-53-CDR-1h

<400> SEQUENCE: 538

Gly Phe Thr Phe Ser Ile Tyr Ser Met Asn
1               5                   10

<210> SEQ ID NO 539
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-53-CDR-2h

<400> SEQUENCE: 539

Tyr Ile Ser Ser Ser Ser Ser Thr Ile Tyr Tyr Ala Asp Ser Val Lys
1               5                   10                  15
Gly

<210> SEQ ID NO 540
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-53-CDR-3h

<400> SEQUENCE: 540

Asp Arg Gly Asp Phe Asp Ala Phe Asp Ile
1               5                   10
```

<210> SEQ ID NO 541
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-53-CDR-1l

<400> SEQUENCE: 541

Gln Ala Ser Gln Asp Ile Thr Asn Tyr Leu Asn
1               5                   10

<210> SEQ ID NO 542
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-53-CDR-2l

<400> SEQUENCE: 542

Asp Ala Ser Asn Leu Glu Thr
1               5

<210> SEQ ID NO 543
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-53-CDR-3l

<400> SEQUENCE: 543

Gln Gln Cys Glu Asn Phe Pro Ile Thr
1               5

<210> SEQ ID NO 544
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-55.1-CDR-1h

<400> SEQUENCE: 544

Gly Gly Ser Val Ser Ser Gly Gly Tyr Tyr Trp Asn
1               5                   10

<210> SEQ ID NO 545
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-55.1-CDR-2h

<400> SEQUENCE: 545

Tyr Ile Asn Tyr Ser Gly Ser Thr Asn Tyr Asn Pro Ser Leu Lys Ser
1               5                   10                  15

```
<210> SEQ ID NO 546
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-55.1-CDR-3h

<400> SEQUENCE: 546

Asp Arg Glu Leu Glu Leu Tyr Tyr Tyr Tyr Tyr Gly Met Asp Val
1               5                   10                  15

<210> SEQ ID NO 547
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-55-CDR-1l

<400> SEQUENCE: 547

Arg Ser Ser Gln Ser Leu Leu Tyr Ser Asn Gly Tyr Lys Tyr Leu Asp
1               5                   10                  15

<210> SEQ ID NO 548
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-55-CDR-2l

<400> SEQUENCE: 548

Leu Gly Ser Asn Arg Ala Ser
1               5

<210> SEQ ID NO 549
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-55-CDR-3l

<400> SEQUENCE: 549

Met Gln Ala Leu Gln Thr Pro Ile Thr
1               5

<210> SEQ ID NO 550
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-57.1-CDR-1l

<400> SEQUENCE: 550

Arg Ser Ser Gln Ser Leu Leu Tyr Ser Asn Gly Tyr Lys Tyr Leu Asp
```

<210> SEQ ID NO 551
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: U1-57.1-CDR-2l

<400> SEQUENCE: 551

Leu Gly Ser Asn Arg Ala Ser
1               5

<210> SEQ ID NO 552
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: U1-57.1-CDR-3l

<400> SEQUENCE: 552

Met Gln Ala Leu Gln Thr Pro Ile Thr
1               5

<210> SEQ ID NO 553
<211> LENGTH: 12
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: U1-57_CDR-1h

<400> SEQUENCE: 553

Gly Gly Ser Val Ser Ser Gly Gly Tyr Tyr Trp Asn
1               5                   10

<210> SEQ ID NO 554
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: U1-57_CDR-2h

<400> SEQUENCE: 554

Tyr Ile Asn Tyr Ser Gly Ser Thr Asn Tyr Asn Pro Ser Leu Lys Ser
1               5                   10                  15

<210> SEQ ID NO 555
<211> LENGTH: 15
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: U1-57_CDR-3h

<400> SEQUENCE: 555

Asp Arg Glu Leu Glu Leu Tyr Tyr Tyr Tyr Gly Met Asp Val
1               5                   10                  15

<210> SEQ ID NO 556
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-58-CDR-1h

<400> SEQUENCE: 556

Gly Phe Thr Phe Ser Ser Tyr Gly Met His
1               5                   10

<210> SEQ ID NO 557
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-58-CDR-2h

<400> SEQUENCE: 557

Val Ile Trp Tyr Asp Gly Ser Asn Lys Tyr Tyr Ala Asp Ser Val Lys
1               5                   10                  15

Gly

<210> SEQ ID NO 558
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-58-CDR-3h

<400> SEQUENCE: 558

Ala Ala Arg Leu Asp Tyr Tyr Tyr Gly Met Asp Val
1               5                   10

<210> SEQ ID NO 559
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-58-CDR-1l

<400> SEQUENCE: 559

Arg Ala Ser Gln Ser Ile Asn Ser Tyr Leu Asn
1               5                   10

<210> SEQ ID NO 560
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-58-CDR-2l

<400> SEQUENCE: 560

Gly Ala Ser Gly Leu Gln Ser
1               5

<210> SEQ ID NO 561
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-58-CDR-3l

<400> SEQUENCE: 561

Gln Gln Ser Tyr Ser Ser Pro Leu Thr
1               5

<210> SEQ ID NO 562
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-59-CDR-1h

<400> SEQUENCE: 562

Gly Gly Ser Phe Ser Gly Tyr Tyr Trp Ser
1               5                   10

<210> SEQ ID NO 563
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-59-CDR-2h

<400> SEQUENCE: 563

Glu Ile Asn His Ser Gly Ser Thr Asn Tyr Asn Pro Ser Leu Lys Ser
1               5                   10                  15

<210> SEQ ID NO 564
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-59-CDR-3h

<400> SEQUENCE: 564

Asp Lys Trp Thr Trp Tyr Phe Asp Leu
1               5

<210> SEQ ID NO 565
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<223> OTHER INFORMATION: U1-59-CDR-1l

<400> SEQUENCE: 565

Arg Ser Ser Gln Ser Val Leu Tyr Ser Ser Ser Asn Arg Asn Tyr Leu
1               5                   10                  15
Ala

<210> SEQ ID NO 566
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-59-CDR-2l

<400> SEQUENCE: 566

Trp Ala Ser Thr Arg Glu Ser
1               5

<210> SEQ ID NO 567
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-59-CDR-3l

<400> SEQUENCE: 567

Gln Gln Tyr Tyr Ser Thr Pro Arg Thr
1               5

<210> SEQ ID NO 568
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-61.1-CDR-1h

<400> SEQUENCE: 568

Gly Val Ser Ile Ser Ser Gly Gly Tyr Tyr Trp Ser
1               5                   10

<210> SEQ ID NO 569
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-61.1-CDR-2h

<400> SEQUENCE: 569

Tyr Ile Tyr Tyr Ser Gly Ser Thr Tyr Tyr Asn Pro Ser Leu Lys Ser
1               5                   10                  15

<210> SEQ ID NO 570
<211> LENGTH: 16
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<223> OTHER INFORMATION: U1-61.1-CDR-3h

<400> SEQUENCE: 570

Asp Ser Glu Ser Glu Tyr Ser Ser Ser Asn Tyr Gly Met Asp Val
1               5                   10                  15

<210> SEQ ID NO 571
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-61.1-CDR-1l

<400> SEQUENCE: 571

Arg Ala Ser Gln Thr Ile Ser Ser Tyr Leu Asn
1               5                   10

<210> SEQ ID NO 572
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-61.1-CDR-2l

<400> SEQUENCE: 572

Ala Ala Ser Ser Leu Gln Gly
1               5

<210> SEQ ID NO 573
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-61.1-CDR-3l

<400> SEQUENCE: 573

Gln Gln Ser Tyr Ser Asn Pro Leu Thr
1               5

<210> SEQ ID NO 574
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-61-CDR-1h

<400> SEQUENCE: 574

Gly Val Ser Ile Ser Ser Gly Gly Tyr Tyr Trp Ser
1               5                   10

<210> SEQ ID NO 575
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: U1-61-CDR-2h

<400> SEQUENCE: 575

Tyr Ile Tyr Tyr Ser Gly Ser Thr Tyr Tyr Asn Pro Ser Leu Lys Ser
1               5                   10                  15

<210> SEQ ID NO 576
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-61-CDR-3h

<400> SEQUENCE: 576

Asp Ser Glu Ser Glu Tyr Ser Ser Ser Asn Tyr Gly Met Asp Val
1               5                   10                  15

<210> SEQ ID NO 577
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-62-CDR-1h

<400> SEQUENCE: 577

Gly Tyr Ser Phe Thr Ser Tyr Trp Ile Gly
1               5                   10

<210> SEQ ID NO 578
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-62-CDR-2h

<400> SEQUENCE: 578

Ile Ile Tyr Pro Gly Asp Ser Asp Thr Arg Tyr Ser Pro Ser Phe Gln
1               5                   10                  15

Gly

<210> SEQ ID NO 579
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-62-CDR-3h

<400> SEQUENCE: 579

Gln Met Ala Gly Asn Tyr Tyr Tyr Gly Met Asp Val
1               5                   10

<210> SEQ ID NO 580
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-62-CDR-1l

<400> SEQUENCE: 580

Arg Ala Ser Gln Ser Val Ile Ser Ile Tyr Leu Ala
1               5                   10

<210> SEQ ID NO 581
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-62-CDR-2l

<400> SEQUENCE: 581

Gly Ala Ser Ser Arg Ala Thr
1               5

<210> SEQ ID NO 582
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: U1-62-CDR-3l

<400> SEQUENCE: 582

Gln Gln Tyr Gly Ser Ser Pro Cys Ser
1               5

<210> SEQ ID NO 583
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 583

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Glu Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Trp Thr Trp Tyr Phe Asp Leu Trp Gly Arg Gly Thr Leu
            100                 105                 110
```

```
Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 584
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antibody

<400> SEQUENCE: 584

Asp Ile Glu Met Thr Gln Ser Pro Asp Ser Leu Ala Val Ser Leu Gly
1               5                   10                  15
```

Glu Arg Ala Thr Ile Asn Cys Arg Ser Ser Gln Ser Val Leu Tyr Ser
            20                  25                  30

Ser Ser Asn Arg Asn Tyr Leu Ala Trp Tyr Gln Gln Asn Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 585
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Gly Gly Phe Gly
1

<210> SEQ ID NO 586
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Asp Gly Gly Phe
1

<210> SEQ ID NO 587
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

```
Glu Gly Gly Phe
1

<210> SEQ ID NO 588
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588

Ser Gly Gly Phe
1

<210> SEQ ID NO 589
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589

Lys Gly Gly Phe
1

<210> SEQ ID NO 590
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Asp Gly Gly Phe Gly
1               5

<210> SEQ ID NO 591
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Gly Gly Phe Gly Gly
1               5

<210> SEQ ID NO 592
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 592

Asp Asp Gly Gly Phe Gly
1               5

<210> SEQ ID NO 593
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 593

Lys Asp Gly Gly Phe Gly
1               5

<210> SEQ ID NO 594
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 594

Gly Gly Phe Gly Gly Gly Phe
1               5
```

ANTI-HER3 ANTIBODY-DRUG CONJUGATE

CROSS-REFERENCE TO RELATED APPLICATIONS

The present application is a Continuation of U.S. patent application Ser. No. 15/285,156, filed on Oct. 4, 2016, which is a Bypass Continuation of International Patent Application No. PCT/JP2015/002020, filed on Apr. 10, 2015, which claims the benefit of priority to Japanese Patent Application No. 2014-081454, filed on Apr. 10, 2014. The entire contents of which are hereby incorporated by reference.

SEQUENCE LISTING

The instant application contains a Sequence Listing which has been submitted electronically in ASCII format and is hereby incorporated by reference in its entirety. Said ASCII copy, created on Jan. 9, 2018, is named 111119-0109_SL.txt and is 267,770 bytes in size.

TECHNICAL FIELD

The present invention relates to an antibody-drug conjugate having an anti-HER3 antibody and an antitumor drug conjugated to each other via a linker structure moiety, the conjugate being useful as an antitumor drug.

BACKGROUND ART

An antibody-drug conjugate (ADC) having a drug with cytotoxicity conjugated to an antibody which binds to an antigen expressed on a surface of cancer cells and capable of cellular internalization (the antibody which binds to the antigen is also capable of cellular internalization), can deliver the drug selectively to the cancer cells and is thus expected to cause accumulation of the drug in the cancer cells and to kill the cancer cells (see, Non Patent Literatures 1 to 3). As an ADC, Mylotarg (registered trademark; Gemtuzumab ozogamicin) in which calicheamicin is conjugated to an anti-CD33 antibody is approved as a therapeutic agent for acute myeloid leukemia. Further, Adcetris (registered trademark; Brentuximab vedotin), in which auristatin E is conjugated to an anti-CD30 antibody, has recently been approved as a therapeutic agent for Hodgkin's lymphoma and anaplastic large cell lymphoma (see, Non Patent Literature 4). The drugs contained in ADCs which have been approved until now target DNA or tubulin.

As an antitumor, low-molecular-weight compounds, camptothecin derivatives, which inhibit topoisomerase I to exhibit an antitumor effect, are known. Among them, an antitumor compound represented by the formula below (exatecan, chemical name: (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione) is a water soluble derivative of camptothecin (Patent Literature 1 and 2).

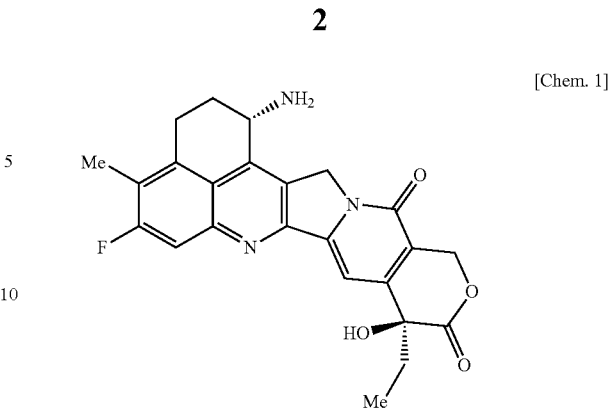

[Chem. 1]

Unlike irinotecan currently used in clinical settings, this compound does not require activation by an enzyme for exerting its antitumor effect. Further, compared to SN-38 as a main pharmaceutically active ingredient of irinotecan and topotecan also used in clinical settings, it has higher inhibitory activity on topoisomerase I and has higher cytocidal activity in vitro against various cancer cells. In particular, it exhibits the effect against cancer cells which have resistance to SN-38 or the like due to expression of P-glycoprotein. Further, in a mouse model with a human tumor subcutaneously transplanted, it exhibited a potent antitumor effect, and thus has undergone the clinical studies, but has not been put on the market yet (see, Non Patent Literatures 5 to 10). It remains unclear whether or not exatecan functions effectively as an ADC.

DE-310 is a complex in which exatecan is conjugated to a biodegradable carboxymethyldextran polyalcohol polymer via a GGFG peptide spacer (SEQ ID NO: 585) (Patent Literature 3). By making exatecan into a form of a polymer prodrug, a high blood retention property can be maintained and also a high penetration property to a tumor area is passively increased by utilizing the increased permeability of newly formed tumor vessels and retention property in tumor tissues. With DE-310, the peptide spacer is cleaved by an enzyme to continuously release exatecan as a main active ingredient and exatecan with glycine bonded to an amino group, and as a result, the pharmacokinetics are improved. According to various tumor evaluation models in non-clinical studies, it was found that higher effectiveness was obtained by DE-310 than exatecan administered alone even though the total amount of exatecan contained therein is lower than the case of administration of exatecan alone. A clinical study was conducted for DE-310, and effective cases were confirmed. There is also a report suggesting that the main active ingredient accumulates in a tumor than in normal tissues. However, there is also a report indicating that the accumulation of DE-310 and the main active ingredient in a tumor is not much different from the accumulation in normal tissues, and thus no passive targeting is observed in humans (see, Non Patent Literatures 11 to 14). As a result, DE-310 was not also commercialized, and it remains unclear whether or not exatecan effectively functions as a drug oriented for such targeting.

As a compound relating to DE-310, a complex in which a structure moiety represented by —NH—$(CH_2)_4$—C(=O)— is inserted between -GGFG-spacer (SEQ ID NO: 585) and exatecan to form -GGFG (SEQ ID NO: 585)-NH—$(CH_2)_4$—C(=O)— used as a spacer structure is also known (Patent Literature 4). However, the antitumor effect of the complex is not known at all.

The human epidermal growth factor receptor 3 (also known as HER3 and ErbB3) is a receptor protein tyrosine kinase and belongs to the epidermal growth factor receptor (EGFR) subfamily of receptor protein tyrosine kinases, which also includes HER1 (also known EGFR), HER2, and HER4 (see Non Patent Literatures 15 to 17). As with the prototypical epidermal growth factor receptor, the transmembrane receptor HER3 consists of an extracellular ligand-binding domain (ECD), a dimerization domain within the ECD, a transmembrane domain, and a carboxyl-terminal phosphorylation domain. HER1, HER2, and HER4 carry an intracellular protein tyrosine kinase domain (TKD) in addition to these domains, while HER3 lacks this domain and is thus unable to be autophosphorylated.

The ligand Heregulin (HRG) binds to the extracellular domain of HER3 and activates the receptor-mediated signaling pathway by promoting dimerization with other human epidermal growth factor receptor (HER) family members and transphosphorylation of its intracellular domain. The dimer formation of HER3 with other HER family members expands the signaling potential of HER3 and serves as means not only for signal diversification but also for signal amplification. For example, the HER2/HER3 heterodimer induces one of the most important mitogenic signals among HER family members. HER3 is overexpressed in several types of cancers such as breast, gastrointestinal, and pancreatic cancers. Interestingly, a correlation between the expression of HER2/HER3 and the progression from a non-invasive stage to an invasive stage has been shown (see Non Patent Literatures 18 to 20). Accordingly, agents that interfere with HER3-mediated signaling are desirable. Anti-HER3 antibodies and immunoconjugates thereof have been reported in, for example, Patent Literatures 5 to 10, respectively.

CITATION LIST

Patent Literature

[PTL 1] Japanese Patent Laid-Open No. 5-59061
[PTL 2] Japanese Patent Laid-Open No. 8-337584
[PTL 3] International Publication No. WO 1997/46260
[PTL 4] International Publication No. WO 2000/25825
[PTL 5] U.S. Pat. No. 5,968,511
[PTL 6] U.S. Pat. No. 5,480,968
[PTL 7] International Publication No. WO 2003/013602
[PTL 8] International Publication No. WO 2007/077028
[PTL 9] International Publication No. WO 2008/100624
[PTL 10] International Publication No. WO 2012/019024

Non Patent Literature

[NPL 1] Ducry, L., et al., Bioconjugate Chem. (2010) 21, 5-13.
[NPL 2] Alley, S. C., et al., Current Opinion in Chemical Biology (2010) 14, 529-537.
[NPL 3] Damle N. K. Expert Opin. Biol. Ther. (2004) 4, 1445-1452.
[NPL 4] Senter P. D., et al., Nature Biotechnology (2012) 30, 631-637.
[NPL 5] Kumazawa, E., Tohgo, A., Exp. Opin. Invest. Drugs (1998) 7, 625-632.
[NPL 6] Mitsui, I., et al., Jpn J. Cancer Res. (1995) 86, 776-786.
[NPL 7] Takiguchi, S., et al., Jpn J. Cancer Res. (1997) 88, 760-769.
[NPL 8] Joto, N. et al., Int J Cancer (1997) 72, 680-686.
[NPL 9] Kumazawa, E. et al., Cancer Chemother. Pharmacol. (1998) 42, 210-220.
[NPL 10] De Jager, R., et al., Ann N Y Acad Sci (2000) 922, 260-273.
[NPL 11] Inoue, K. et al. Polymer Drugs in the Clinical Stage, Edited by Maeda et al., (2003) 145-153.
[NPL 12] Kumazawa, E. et al., Cancer Sci (2004) 95, 168-175.
[NPL 13] Soepenberg, O. et al., Clinical Cancer Research, (2005) 11, 703-711.
[NPL 14] Wente M. N. et al., Investigational New Drugs (2005) 23, 339-347.
[NPL 15] Plowman, et al., Proc. Natl. Acad. Sci. U.S.A. (1990) 87, 4905-4909.
[NPL 16] Kraus et al., Proc. Natl. Acad. Sci. U.S.A. (1989) 86, 9193-9197.
[NPL 17] Kraus et al., Proc. Natl. Acad. Sci. U.S.A. (1993) 90, 2900-2094.
[NPL 18] Alimandi et al., Oncogene (1995) 10, 1813-1821.
[NPL 19] DeFazio et al., Int. J. Cancer (2000) 87, 487-498.
[NPL 20] Nadiu et al., Br. J. Cancer (1998) 78, 1385-1390.

SUMMARY OF INVENTION

Technical Problem

With regard to the treatment of tumor using an antibody, an insufficient antitumor effect may be observed even when the antibody recognizes an antigen and binds to tumor cells, and thus a more effective antitumor antibody is sometimes needed. Further, many antitumor low-molecular-weight compounds have a problem in safety like side effect and toxicity even the compounds have an excellent antitumor effect. As such, it remains as a subject to achieve a superior therapeutic effect by further enhancing the safety. Thus, an object of the present invention is to provide an antitumor drug having an excellent therapeutic effect, which is excellent in terms of antitumor effect and safety.

Solution to Problem

The inventors thought that, since the anti-HER3 antibody is an antibody capable of targeting tumor cells, that is, it is an antibody having a property of recognizing tumor cells, a property of binding to tumor cells, a property of internalizing in tumor cells, a cytocidal activity against tumor cells, or the like, when exatecan as an antitumor compound is converted into an antibody-drug conjugate by conjugation to the antibody via a linker structure moiety, the antitumor compound can be more surely delivered to tumor cells to specifically exhibit the antitumor effect of the compound in tumor cells, and thus the antitumor effect can be surely exhibited and also an enhanced cytocidal effect of the anti-HER3 antibody is expected, and a dose of the antitumor compound can be reduced compared to a case of administering the compound alone, and thus an influence of the antitumor compound on normal cells can be alleviated so that higher safety can be achieved.

In this connection, the inventors created a linker with a specific structure and succeeded in obtaining an antibody-drug conjugate in which the anti-HER3 antibody and exatecan are conjugated to each other via the linker, and confirmed an excellent antitumor effect exhibited by the conjugate to thereby complete the present invention.

Specifically, the present invention relates to the followings.

[1] An antibody-drug conjugate wherein an antitumor compound represented by the following formula

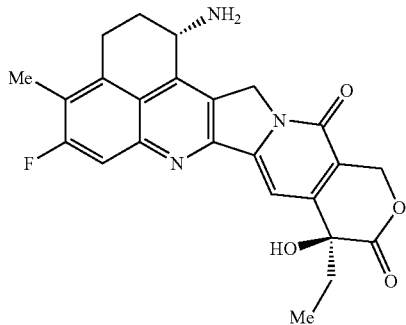
[Chem. 2]

is conjugated to an anti-HER3 antibody by a thioether bond which is formed at a disulfide bond moiety present in a hinge part of the anti-HER3 antibody via a linker having a structure represented by the following formula:

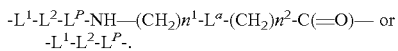

Here, the anti-HER3 antibody is connected to the terminal of $L^1$, the antitumor compound is connected to the carbonyl group of —$(CH_2)n^2$-$C(=O)$— moiety or the C terminal of $L^P$, with the nitrogen atom of the amino group at position 1 as a connecting position.
In the formula, $n^1$ represents an integer of 0 to 6,
$n^2$ represents an integer of 0 to 5,
$L^1$ represents -(Succinimid-3-yl-N)—$(CH_2)n^3$-$C(=O)$—,
wherein $n^3$ represents an integer of 2 to 8,
$L^2$ represents —NH—$(CH_2CH_2$—$O)n^4$-$CH_2CH_2$—$C(=O)$— or a single bond,
wherein $n^4$ represents an integer of 1 to 6,
$L^P$ represents a peptide residue consisting of 2 to 7 amino acids,
$L^a$ represents —O— or a single bond,
-(Succinimid-3-yl-N)— has a structure represented by the following formula:

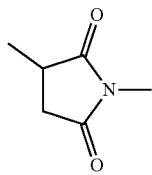
[Chem. 3]

which is connected to the anti-HER3 antibody at position 3 thereof and is connected on the nitrogen atom at position 1 to a methylene group in the linker structure containing this structure.

The present invention further relates to each of the followings.
[2] The antibody-drug conjugate according to [1], wherein the peptide residue of $L^P$ is a peptide residue comprising an amino acid selected from phenylalanine, glycine, valine, lysine, citrulline, serine, glutamic acid, and aspartic acid.
[3] The antibody-drug conjugate according to [1] or [2], wherein $L^P$ is a peptide residue selected from the following group

-GGF-,

-DGGF-, (SEQ ID NO: 586)

-(D-)D-GGF-,

-EGGF-, (SEQ ID NO: 587)

-GGFG-, (SEQ ID NO: 585)

-SGGF-, (SEQ ID NO: 588)

-KGGF-, (SEQ ID NO: 589)

-DGGFG-, (SEQ ID NO: 590)

-GGFGG-, (SEQ ID NO: 591)

-DDGGFG-, (SEQ ID NO: 592)

-KDGGFG-, (SEQ ID NO: 593)
and

-GGFGGGF-; (SEQ ID NO: 594)

(wherein, "(D-)D" represents D-aspartic acid).
[4] The antibody-drug conjugate according to [1] or [2], wherein $L^P$ is a peptide residue comprising 4 or 5 amino acids.
[5] The antibody-drug conjugate according to any one of [1] to [4], wherein $L^P$ is -GGFG- (SEQ ID NO: 585) or -DGGFG- (SEQ ID NO: 590).
[6] The antibody-drug conjugate according to any one of [1] to [4], wherein $L^P$ is -GGFG- (SEQ ID NO: 585).
[7] The antibody-drug conjugate according to any one of [1] to [6], wherein $n^3$ is an integer of 2 to 5 and $L^2$ is a single bond.
[8] The antibody-drug conjugate according to any one of [1] to [7], wherein the linker is -$L^1$-$L^2$-$L^P$-NH—$(CH_2)n^1$-$L^a$-$(CH_2)n^2$-$C(=O)$—.
[9] The antibody-drug conjugate according to [8], wherein $n^3$ is an integer of 2 to 5, $L^2$ is —NH—$(CH_2CH_2$—$O)n^4$-$CH_2CH_2$—$C(=O)$—, and $n^4$ is 2 or 4.
[10] The antibody-drug conjugate according to [8] or [9], wherein —NH—$(CH_2)n^1$-$L^a$-$(CH_2)n^2$-$C(=O)$— is a partial structure having chain length of 4 to 7 atoms.
[11] The antibody-drug conjugate according to [8] or [9], wherein —NH—$(CH_2)n^1$-$L^a$-$(CH_2)n^2$-$C(=O)$— is a partial structure having chain length of 5 or 6 atoms.
[12] The antibody-drug conjugate described in [10] or [11], wherein —NH—$(CH_2)n^1$-$L^a$-$(CH_2)n^2$-$C(=O)$— is
—NH—$CH_2CH_2$—$C(=O)$—,
—NH—$CH_2CH_2CH_2$—$C(=O)$—,
—NH—$CH_2CH_2CH_2CH_2$—$C(=O)$—,
—NH—$CH_2CH_2CH_2CH_2CH_2$—$C(=O)$—,
—NH—$CH_2$—O—$CH_2$—$C(=O)$—, or
—NH—$CH_2CH_2$—O—$CH_2$—$C(=O)$—.
[13] The antibody-drug conjugate according to [12], wherein —NH—$(CH_2)n^1$-$L^a$-$(CH_2)n^2$-$C(=O)$— is any one of the followings:
—NH—$CH_2CH_2CH_2$—$C(=O)$—,
—NH—$CH_2$—O—$CH_2$—$C(=O)$—, or
—NH—$CH_2CH_2$—O—$CH_2$—$C(=O)$—.

[14] The antibody-drug conjugate according to any one of [1] to [5], wherein the linker is -L$^1$-L$^2$-L$^P$-.

[15] The antibody-drug conjugate according to [14], wherein L$^P$ is -DGGFG- (SEQ ID NO: 590).

[16] The antibody-drug conjugate according to [15], wherein n$^3$ is an integer of 2 to 5 and L$^2$ is a single bond.

[17] The antibody-drug conjugate according to [1], wherein the drug-linker structure moiety in which a drug is bound to -L$^1$-L$^2$-L$^P$-NH—(CH$_2$)n$^1$-L$^a$-(CH$_2$)n$^2$-C(=O)— or -L$^1$-L$^2$-L$^P$- is one drug-linker structure selected from the following group:

```
(Succinimid-3-yl-N)-CH2CH2-C(=O)-
GGFG (SEQ ID NO: 585)-NH-CH2CH2-
C(=O)-(NH-DX), (Succinimid-3-yl-N)-CH2CH2-C(=O)-
GGFG (SEQ ID NO: 585)-NH-CH2CH2CH2-
C(=O)-(NH-DX), (Succinimid-3-yl-N)-CH2CH2CH2CH2CH2-
C(=O)-GGFG (SEQ ID NO: 585)-NH-
CH2CH2-C(=O)-(NH-DX), (Succinimid-3-yl-N)-CH2CH2CH2CH2CH2-
C(=O)-GGFG (SEQ ID NO: 585)-NH-
CH2CH2CH2-C(=O)-(NH-DX), (Succinimid-3-yl-N)-CH2CH2CH2CH2CH2-
C(=O)-GGFG (SEQ ID NO: 585)-NH-
CH2CH2CH2CH2-C(=O)-(NH-DX), (Succinimid-3-yl-N)-CH2CH2CH2CH2CH2-
C(=O)-GGFG (SEQ ID NO: 585)-NH-
CH2-O-CH2-C(=O)-(NH-DX), (Succinimid-3-yl-N)-CH2CH2CH2CH2CH2-
C(=O)-GGFG (SEQ ID NO: 585)-NH-
CH2CH2-O-CH2-C(=O)-(NH-DX), (Succinimid-3-yl-N)-CH2CH2CH2CH2CH2-
C(=O)-DGGFG (SEQ ID NO: 590)-NH-
CH2CH2-C(=O)-(NH-DX), (Succinimid-3-yl-N)-CH2CH2CH2CH2CH2-
C(=O)-DGGFG (SEQ ID NO: 590)-NH-
CH2CH2CH2-C(=O)-(NH-DX), (Succinimid-3-yl-N)-CH2CH2CH2CH2CH2-
C(=O)-DGGFG (SEQ ID NO: 590)-NH-
CH2CH2CH2CH2-C(=O)-(NH-DX), (Succinimid-3-yl-N)-CH2CH2-C(=O)-NH-
CH2CH2-O-CH2CH2-O-CH2CH2-C(=O)-
GGFG (SEQ ID NO: 585)-NH-CH2CH2-
C(=O)-(NH-DX), (Succinimid-3-yl-N)-CH2CH2-C(=O)-NH-
CH2CH2-O-CH2CH2-O-CH2CH2-C(=O)-
GGFG (SEQ ID NO: 585)-NH-CH2CH2CH2-
C(=O)-(NH-DX), (Succinimid-3-yl-N)-CH2CH2-C(=O)-NH-
CH2CH2-O-CH2CH2-O-CH2CH2-O-CH2CH2-O-
CH2CH2-C(=O)-GGFG (SEQ ID NO: 585)-
NH-CH2CH2-C(=O)-(NH-DX), (Succinimid-3-yl-N)-CH2CH2-C(=O)-NH-
CH2CH2-O-CH2CH2-O-CH2CH2-O-CH2CH2-O-
CH2CH2-C(=O)-GGFG (SEQ ID NO: 585)-
NH-CH2CH2CH2-C(=O)-(NH-DX), (Succinimid-3-yl-N)-CH2CH2-C(=O)-
GGFG (SEQ ID NO: 585)-(NH-DX), (Succinimid-3-yl-N)-CH2CH2-C(=O)-
DGGFG (SEQ ID NO: 590)-(NH-DX),
```

```
(Succinimid-3-yl-N)-CH2CH2CH2CH2CH2-
C(=O)-GGFG (SEQ ID NO: 585)-(NH-DX), (Succinimid-3-yl-N)-CH2CH2CH2CH2CH2-
C(=O)-DGGFG (SEQ ID NO: 590)-(NH-DX).
```

In the above, -(Succinimid-3-yl-N)— has a structure represented by the following formula:

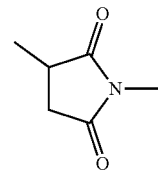

[Chem. 4]

which is connected to the anti-HER3 antibody at position 3 and is connected to a methylene group in the linker structure containing it on the nitrogen atom at position 1, -(NH-DX) represents a group represented by the following formula, wherein the nitrogen atom of the amino group at position 1 is the connecting position,

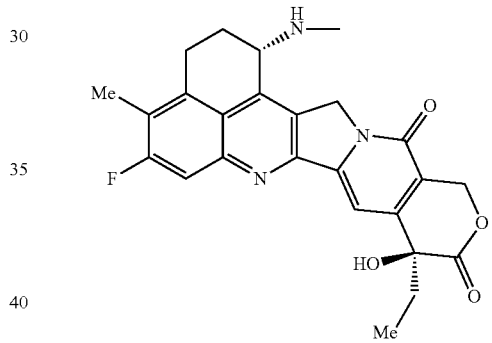

[Chem. 5]

-GGFG- (SEQ ID NO: 585) represents a tetrapeptide residue of -Gly-Gly-Phe-Gly- (SEQ ID NO: 585) and -DGGFG- (SEQ ID NO: 590) represents a pentapeptide residue of -Asp-Gly-Gly-Phe-Gly- (SEQ ID NO: 590).

[18] The antibody-drug conjugate described in [1], wherein the drug-linker structure moiety having a drug bonded to -L$^1$-L$^2$-L$^P$-NH—(CH$_2$)n$^1$-L$^a$-(CH$_2$)n$^2$-C(=O)— is one drug-linker structure selected from the following group:

```
(Succinimid-3-yl-N)-CH2CH2CH2CH2CH2-C(=O)-
GGFG (SEQ ID NO: 585)-NH-CH2CH2CH2-C(=O)-
(NH-DX), (Succinimid-3-yl-N)-CH2CH2CH2CH2CH2-C(=O)-
DGGFG (SEQ ID NO: 590)-NH-CH2CH2CH2-C(=O)-
(NH-DX), (Succinimid-3-yl-N)-CH2CH2CH2CH2CH2-C(=O)-
GGFG (SEQ ID NO: 585)-NH-CH2-O-CH2-C(=O)-
(NH-DX), (Succinimid-3-yl-N)-CH2CH2-C(=O)-NH-
CH2CH2-O-CH2CH2-O-CH2CH2-C(=O)-
GGFG (SEQ ID NO: 585)-NH-CH2CH2CH2-C(=O)-
(NH-DX),
```

```
(Succinimid-3-yl-N)-CH2CH2CH2CH2CH2-C(=O)-
DGGFG (SEQ ID NO: 590)-(NH-DX).
```

Here, -(Succinimid-3-yl-N)—, -(NH-DX), -GGFG (SEQ ID NO: 585)-, and -DGGFG- (SEQ ID NO: 590) are as described above.

[19] An antibody-drug conjugate comprising an antitumor compound represented by the following formula:

[Chem. 6]

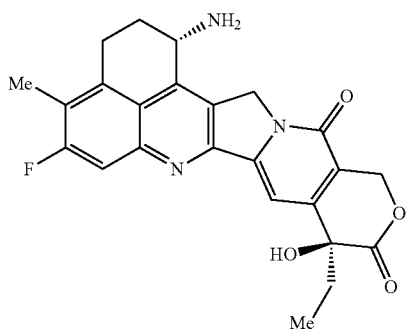

conjugated to an anti-HER3 antibody by a thioether bond which is formed at a disulfide bond moiety present in a hinge part of the anti-HER3 antibody via a linker having a structure represented by the following formula:

$-L^1-L^2-L^P-NH-(CH_2)n^1-L^a-(CH_2)n^2-C(=O)-$.

Here, the anti-HER3 antibody is connected to the terminal of $L^1$ and the antitumor compound is connected to the carbonyl group of $—(CH_2)n^2-C(=O)—$ moiety.

In the formula, $n^1$ represents an integer of 0 to 6,
$n^2$ represents an integer of 0 to 5,
$L^1$ represents $-(Succinimid-3-yl-N)—(CH_2)n^3-C(=O)—$,
wherein $n^3$ represents an integer of 2 to 8,
$L^2$ represents $—NH—(CH_2CH_2—O)n^4-CH_2CH_2—C(=O)—$ or a single bond,
wherein $n^4$ represents an integer of 1 to 6,
$L^P$ represents a tetrapeptide residue of -GGFG- (SEQ ID NO: 585),
$L^a$ represents $—O—$ or a single bond,
-(Succinimid-3-yl-N)— has a structure represented by the following formula:

[Chem. 7]

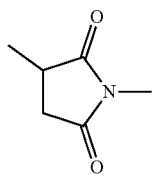

which is connected to the anti-HER3 antibody at position 3 thereof and binds on the nitrogen atom at position 1 to a methylene group in a linker structure containing this structure.

[20] The antibody-drug conjugate according to [19], wherein $n^1$ is 3, $n^2$ is 0, $n^3$ is 2, $L^2$ is $—NH—(CH_2CH_2—O)n^4-CH_2CH_2—C(=O)—$, $n^4$ is 2, and $L^a$ is a single bond, or
$n^1$ is 1, $n^2$ is 1, $n^3$ is 5, $L^2$ is a single bond, and $L^a$ is $—O—$, or
$n^1$ is 2, $n^2$ is 1, $n^3$ is 5, $L^2$ is a single bond, and $L^a$ is $—O—$.

[21] The antibody-drug conjugate according to [19] or [20], wherein $n^3$ is 2 or 5 and $L^2$ is a single bond.

[22] The antibody-drug conjugate according to [19] or [20], wherein $n^3$ is 2 or 5, $L^2$ is $—NH—(CH_2CH_2—O)n^4-CH_2CH_2—C(=O)—$, and $n^4$ is 2 or 4.

[23] The antibody-drug conjugate described in any one of [19] to [22], wherein $—NH—(CH_2)n^1-L^a-(CH_2)n^2-C(=O)—$ is
$—NH—CH_2CH_2CH_2—C(=O)—$,
$—NH—CH_2—O—CH_2—C(=O)—$, or
$—NH—CH_2CH_2—O—CH_2—C(=O)—$.

[24] The antibody-drug conjugate described in any one of [19] to [23], wherein the drug-linker structure moiety having a drug bonded to $-L^1-L^2-L^P-NH—(CH_2)n^1-L^a-(CH_2)n^2-C(=O)—$ is one drug-linker structure selected from the following group:

```
(Succinimid-3-yl-N)-CH2CH2-C(=O)-
GGFG (SEQ ID NO: 585)-NH-CH2CH2-C(=O)-
(NH-DX), (Succinimid-3-yl-N)-CH2CH2-C(=O)-
GGFG (SEQ ID NO: 585)-NH-CH2CH2CH2-C(=O)-
(NH-DX), (Succinimid-3-yl-N)-CH2CH2CH2CH2CH2-C(=O)-
GGFG (SEQ ID NO: 585)-NH-CH2CH2-C(=O)-
(NH-DX), (Succinimid-3-yl-N)-CH2CH2CH2CH2CH2-C(=O)-
GGFG (SEQ ID NO: 585)-NH-CH2CH2CH2-C(=O)-
(NH-DX), (Succinimid-3-yl-N)-CH2CH2CH2CH2CH2-C(=O)-
GGFG (SEQ ID NO: 585)-NH-CH2CH2CH2CH2CH2-
C(=O)-(NH-DX), (Succinimid-3-yl-N)-CH2CH2CH2CH2CH2-C(=O)-
GGFG (SEQ ID NO: 585)-NH-CH2-O-CH2-C(=O)-
(NH-DX), (Succinimid-3-yl-N)-CH2CH2CH2CH2CH2-C(=O)-
GGFG (SEQ ID NO: 585)-NH-CH2CH2-O-CH2-C(=O)-
(NH-DX), (Succinimid-3-yl-N)-CH2CH2-C(=O)-NH-CH2CH2-O-
CH2CH2-O-CH2CH2-C(=O)-GGFG (SEQ ID NO: 585)-
NH-CH2CH2-C(=O)-(NH-DX), (Succinimid-3-yl-N)-CH2CH2-C(=O)-NH-CH2CH2-O-
CH2CH2-O-CH2CH2-C(=O)-GGFG (SEQ ID NO: 585)-
NH-CH2CH2CH2-C(=O)-(NH-DX), (Succinimid-3-yl-N)-CH2CH2-C(=O)-NH-CH2CH2-O-
CH2CH2-O-CH2CH2-O-CH2CH2-O-CH2CH2-C(=O)-
GGFG (SEQ ID NO: 585)-NH-CH2CH2-C(=O)-(NH-DX);

(Succinimid-3-yl-N)-CH2CH2-C(=O)-NH-CH2CH2-O-
CH2CH2-O-CH2CH2-O-CH2CH2-O-CH2CH2-C(=O)-
GGFG (SEQ ID NO: 585)-NH-CH2CH2CH2-C(=O)-
(NH-DX),
```

In the above, -(Succinimid-3-yl-N)— has a structure represented by the following formula:

[Chem. 8]

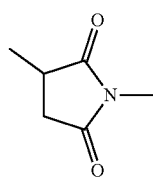

which is connected to the anti-HER3 antibody at position 3 thereof and is connected on the nitrogen atom at position 1 to a methylene group in a linker structure containing this structure. -(NH-DX) represents a group represented by the following formula, wherein the nitrogen atom of the amino group at position 1 is the connecting position:

[Chem. 9]

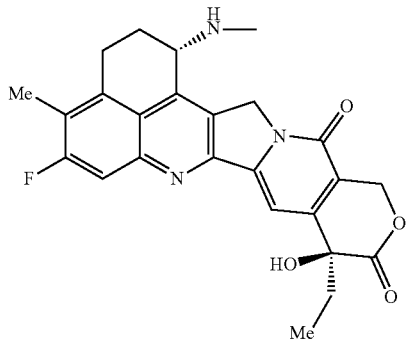

-GGFG- (SEQ ID NO: 585) represents a tetrapeptide residue of -Gly-Gly-Phe-Gly- (SEQ ID NO: 585).

[25] The antibody-drug conjugate described in any one of [19] to [23], wherein the drug-linker structure moiety having a drug connected to $-L^1-L^2-L^P-NH-(CH_2)n^1-L^a-(CH_2)n^2-C(=O)-$ is one drug-linker structure selected from the following group:

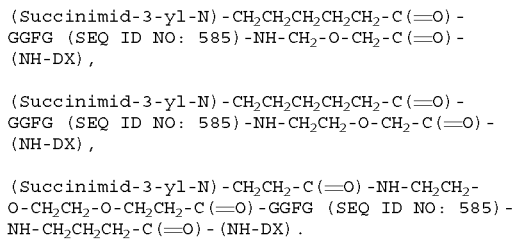

In the above, -(Succinimid-3-yl-N)—, -(NH-DX), and -GGFG (SEQ ID NO: 585)- are as defined above.

[26] The antibody-drug conjugate according to any one of [1] to [25], wherein the average number of units of the selected one drug-linker structure conjugated per antibody is in a range of from 1 to 10.

[27] The antibody-drug conjugate according to any one of [1] to [25], wherein the average number of units of the selected one drug-linker structure conjugated per antibody is in a range of from 2 to 8.

[28] The antibody-drug conjugate according to any one of [1] to [25], wherein the average number of units of the selected one drug-linker structure conjugated per antibody is in a range of from 3 to 8.

[29] A medicine comprising the antibody-drug conjugate according to any one of [1] to [28], a salt thereof or a hydrate thereof.

[30] An antitumor medicine and/or anticancer medicine comprising the antibody-drug conjugate according to any one of [1] to [28], a salt thereof or a hydrate thereof.

[31] The antitumor medicine and/or anticancer medicine according to [30], which is applied to lung cancer, kidney cancer, urothelial cancer, colorectal cancer, prostate cancer, glioblastoma multiforme, ovarian cancer, pancreatic cancer, breast cancer, melanoma, liver cancer, bladder cancer, stomach cancer, gastrointestinal stromal tumor, cervical cancer, head and neck cancer, esophageal cancer, epidermoid cancer, peritoneal cancer, adult glioblastoma multiforme, hepatic cancer, hepatocellular carcinoma, colon cancer, rectal cancer, colon and rectal cancer, endometrial cancer, uterus cancer, salivary cancer, renal cancer, vulval cancer, thyroid cancer, hepatic carcinoma, anus carcinoma, or penis cancer.

[32] A pharmaceutical composition comprising the antibody-drug conjugate according to any one of [1] to [28], a salt thereof or a hydrate thereof as an active component, and a pharmaceutically acceptable formulation component.

[33] The pharmaceutical composition according to [32], which is applied to lung cancer, kidney cancer, urothelial cancer, colorectal cancer, prostate cancer, glioblastoma multiforme, ovarian cancer, pancreatic cancer, breast cancer, melanoma, liver cancer, bladder cancer, stomach cancer, gastrointestinal stromal tumor, cervical cancer, head and neck cancer, esophageal cancer, epidermoid cancer, peritoneal cancer, adult glioblastoma multiforme, hepatic cancer, hepatocellular carcinoma, colon cancer, rectal cancer, colon and rectal cancer, endometrial cancer, uterus cancer, salivary cancer, renal cancer, vulval cancer, thyroid cancer, hepatic carcinoma, anus carcinoma, or penis cancer.

[34] A method for treating a tumor and/or cancer comprising administering the antibody-drug conjugate according to any one of [1] to [28], a salt thereof or a hydrate thereof.

[35] The medicine according to [29], the antitumor medicine and/or anticancer medicine according to [30] or [31], the pharmaceutical composition according to [32] or [33], or the treatment method according to [34], which is used in administration in combination with an additional medicine.

[36] The pharmaceutical composition according to [32] or [33], further comprising even an additional medicine as an active ingredient.

[35] A method for producing an antibody-drug conjugate comprising reacting a compound represented by the following formula:

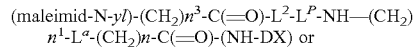

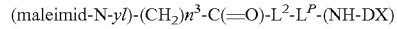

with an anti-HER3 antibody or a reactive derivative thereof and conjugating a drug-linker moiety to the antibody by a method for forming a thioether bond on a disulfide bond moiety present at a hinge part of the antibody.

In the formula, $n^3$ represents an integer of 2 to 8,
$L^2$ represents $-NH-(CH_2CH_2-O)n^4-CH_2CH_2-C(=O)-$ or a single bond wherein $n^4$ represents an integer of 1 to 6,
$L^P$ represents a peptide residue consisting of 2 to 7 amino acids selected from phenylalanine, glycine, valine, lysine, citrulline, serine, glutamic acid, and aspartic acid,
$n^1$ represents an integer of 0 to 6,
$n^2$ represents an integer of 0 to 5,
$L^a$ represents —O— or a single bond,
(maleimid-N-yl)- is a group represented by the following formula and has a nitrogen atom as a connecting position.

[Chem. 10]

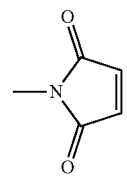

-(NH-DX) represents a group represented by the following formula, wherein the nitrogen atom of the amino group at position 1 is the connecting position:

[Chem. 11]

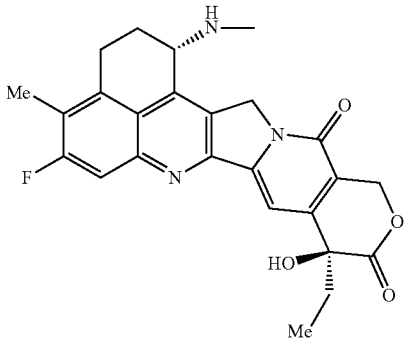

[36] The production method described in [35], wherein the method for conjugating a drug-linker moiety to an anti-HER3 antibody is a method of reducing the antibody for conversion into a reactive derivative.

[37] The production method described in [35] or [36], wherein the average number of units of the selected one drug-linker structure conjugated per antibody is in the range of from 1 to 10.

[38] The production method described in [35] or [36], wherein the average number of units of the selected one drug-linker structure conjugated per antibody is in the range of from 2 to 8.

[39] The production method described in [35] or [36], wherein the average number of units of the selected one drug-linker structure conjugated per antibody is in the range of from 3 to 8.

[40] An antibody-drug conjugate obtained by the production method according to any one of [35] to [39].

[41] An antibody-drug conjugate obtained by forming a thioether bond at a disulfide bond site present in a hinge part of an anti-HER3 antibody, wherein the anti-HER3 antibody is treated in a reducing condition and thereafter reacted with a compound selected from the compound group shown below:

(maleimid-N-yl)-$CH_2CH_2$-C(=O)-
GGFG (SEQ ID NO: 585)-NH-$CH_2CH_2$-C(=O)-
(NH-DX), (maleimid-N-yl)-$CH_2CH_2CH_2$-C(=O)-
GGFG (SEQ ID NO: 585)-NH-$CH_2CH_2$-C(=O)-
(NH-DX), (maleimid-N-yl)-$CH_2CH_2CH_2CH_2$-C(=O)-
GGFG (SEQ ID NO: 585)-NH-$CH_2CH_2$-C(=O)-
(NH-DX), (maleimid-N-yl)-$CH_2CH_2CH_2CH_2CH_2$-C(=O)-
GGFG (SEQ ID NO: 585)-NH-$CH_2CH_2$-C(=O)-
(NH-DX), (maleimid-N-yl)-$CH_2CH_2$-C(=O)-
GGFG (SEQ ID NO: 585)-NH-$CH_2CH_2CH_2$-C(=O)-
(NH-DX), (maleimid-N-yl)-$CH_2CH_2CH_2$-C(=O)-
GGFG (SEQ ID NO: 585)-NH-$CH_2CH_2CH_2$-C(=O)-
(NH-DX), (maleimid-N-yl)-$CH_2CH_2CH_2CH_2$-C(=O)-
GGFG (SEQ ID NO: 585)-NH-$CH_2CH_2CH_2$-C(=O)-
(NH-DX), (maleimid-N-yl)-$CH_2CH_2CH_2CH_2CH_2$-C(=O)-
GGFG (SEQ ID NO: 585)-NH-$CH_2CH_2CH_2$-C(=O)-
(NH-DX), (maleimid-N-yl)-$CH_2CH_2$-C(=O)-
GGFG (SEQ ID NO: 585)-NH-$CH_2CH_2CH_2CH_2$-C(=O)-
(NH-DX), (maleimid-N-yl)-$CH_2CH_2CH_2$-C(=O)-
GGFG (SEQ ID NO: 585)-NH-$CH_2CH_2CH_2CH_2$-C(=O)-
(NH-DX), (maleimid-N-yl)-$CH_2CH_2CH_2CH_2$-C(=O)-
GGFG (SEQ ID NO: 585)-NH-$CH_2CH_2CH_2CH_2$-C(=O)-
(NH-DX), (maleimid-N-yl)-$CH_2CH_2CH_2CH_2CH_2$-C(=O)-
GGFG (SEQ ID NO: 585)-NH-$CH_2CH_2CH_2CH_2$-C(=O)-
(NH-DX), (maleimid-N-yl)-$CH_2CH_2$-C(=O)-
GGFG (SEQ ID NO: 585)-NH-$CH_2CH_2CH_2CH_2CH_2$-C(=O)-
(NH-DX), (maleimid-N-yl)-$CH_2CH_2CH_2$-C(=O)-
GGFG (SEQ ID NO: 585)-NH-$CH_2CH_2CH_2CH_2CH_2$-C(=O)-
(NH-DX), (maleimid-N-yl)-$CH_2CH_2CH_2CH_2$-C(=O)-
GGFG (SEQ ID NO: 585)-NH-$CH_2CH_2CH_2CH_2CH_2$-C(=O)-
(NH-DX), (maleimid-N-yl)-$CH_2CH_2CH_2CH_2CH_2$-C(=O)-
GGFG (SEQ ID NO: 585)-NH-$CH_2CH_2CH_2CH_2CH_2$-C(=O)-
(NH-DX), (maleimid-N-yl)-$CH_2CH_2CH_2CH_2CH_2$-C(=O)-
DGGFG (SEQ ID NO: 590)-NH-$CH_2CH_2$-C(=O)-
(NH-DX), (maleimid-N-yl)-$CH_2CH_2CH_2CH_2CH_2$-C(=O)-
DGGFG (SEQ ID NO: 590)-NH-$CH_2CH_2CH_2$-
C(=O)-(NH-DX), (maleimid-N-yl)-$CH_2CH_2CH_2CH_2CH_2$-C(=O)-
DGGFG (SEQ ID NO: 590)-NH-$CH_2CH_2CH_2CH_2CH_2$-
C(=O)-(NH-DX), (maleimid-N-yl)-$CH_2CH_2$-C(=O)-
GGFG (SEQ ID NO: 585)-NH-$CH_2$-O-$CH_2$-C(=O)-
(NH-DX), (maleimid-N-yl)-$CH_2CH_2CH_2$-C(=O)-
GGFG (SEQ ID NO: 585)-NH-$CH_2$-O-$CH_2$-C(=O)-
(NH-DX), (maleimid-N-yl)-$CH_2CH_2CH_2CH_2$-C(=O)-
GGFG (SEQ ID NO: 585)-NH-$CH_2$-O-$CH_2$-C(=O)-
(NH-DX), (maleimid-N-yl)-$CH_2CH_2CH_2CH_2CH_2$-C(=O)-
GGFG (SEQ ID NO: 585)-NH-$CH_2$-O-$CH_2$-C(=O)-
(NH-DX), (maleimid-N-yl)-$CH_2CH_2$-C(=O)-
GGFG (SEQ ID NO: 585)-NH-$CH_2CH_2$-O-$CH_2$-
C(=O)-(NH-DX), (maleimid-N-yl)-$CH_2CH_2CH_2$-C(=O)-
GGFG (SEQ ID NO: 585)-NH-$CH_2CH_2$-O-$CH_2$-
C(=O)-(NH-DX), (maleimid-N-yl)-$CH_2CH_2CH_2CH_2$-C(=O)-
GGFG (SEQ ID NO: 585)-NH-$CH_2CH_2$-O-$CH_2$-
C(=O)-(NH-DX), (maleimid-N-yl)-$CH_2CH_2CH_2CH_2CH_2$-C(=O)-
GGFG (SEQ ID NO: 585)-NH-$CH_2CH_2$-O-$CH_2$-
C(=O)-(NH-DX), (maleimid-N-yl)-$CH_2CH_2$-C(=O)-NH-$CH_2CH_2$-
O-$CH_2CH_2$-O-$CH_2CH_2$-C(=O)-
GGFG (SEQ ID NO: 585)-NH-$CH_2CH_2$-C(=O)-
(NH-DX), (maleimid-N-yl)-$CH_2CH_2$-C(=O)-NH-$CH_2CH_2$-
O-$CH_2CH_2$-O-$CH_2CH_2O$-$CH_2CH_2$-C(=O)-
GGFG (SEQ ID NO: 585)-NH-$CH_2CH_2$-C(=O)-
(NH-DX), (maleimid-N-yl)-$CH_2CH_2$-C(=O)-NH-$CH_2CH_2$-
O-$CH_2CH_2$-O-$CH_2CH_2$-O-$CH_2CH_2$-O-$CH_2CH_2$-

-continued
```
C(=O)-GGFG (SEQ ID NO: 585)-NH-CH₂CH₂-
C(=O)-(NH-DX), (maleimid-N-yl)-CH₂CH₂-C(=O)-NH-CH₂CH₂-
O-CH₂CH₂-O-CH₂CH₂-C(=O)-
GGFG (SEQ ID NO: 585)-NH-CH₂CH₂CH₂-
C(=O)-(NH-DX), (maleimid-N-yl)-CH₂CH₂-C(=O)-NH-CH₂CH₂-
O-CH₂CH₂-O-CH₂CH₂-O-CH₂CH₂-C(=O)-
GGFG (SEQ ID NO: 585)-NH-CH₂CH₂CH₂-
C(=O)-(NH-DX), (maleimid-N-yl)-CH₂CH₂-C(=O)-NH-CH₂CH₂-
O-CH₂CH₂-O-CH₂CH₂-O-CH₂CH₂-O-CH₂CH₂-
C(=O)-GGFG (SEQ ID NO: 585)-NH-
CH₂CH₂CH₂-C(=O)-(NH-DX), (maleimid-N-yl)-CH₂CH₂-C(=O)-NH-CH₂CH₂-
O-CH₂CH₂-O-CH₂CH₂-C(=O)-
GGFG (SEQ ID NO: 585)-NH-CH₂-O-CH₂-
C(=O)-(NH-DX), (maleimid-N-yl)-CH₂CH₂-C(=O)-NH-CH₂CH₂-
O-CH₂CH₂-O-CH₂CH₂-O-CH₂CH₂-C(=O)-
GGFG (SEQ ID NO: 585)-NH-CH₂-O-CH₂-
C(=O)-(NH-DX), (maleimid-N-yl)-CH₂CH₂-C(=O)-NH-CH₂CH₂-
O-CH₂CH₂-O-CH₂CH₂-O-CH₂CH₂-O-CH₂CH₂-
C(=O)-GGFG (SEQ ID NO: 585)-NH-CH₂-O-
CH₂-C(=O)-(NH-DX), (maleimid-N-yl)-CH₂CH₂-C(=O)-NH-CH₂CH₂-
O-CH₂CH₂-O-CH₂CH₂-C(=O)-
GGFG (SEQ ID NO: 585)-NH-CH₂CH₂-O-CH₂-
C(=O)-(NH-DX), (maleimid-N-yl)-CH₂CH₂-C(=O)-NH-CH₂CH₂-
O-CH₂CH₂-O-CH₂CH₂-O-CH₂CH₂-C(=O)-
GGFG (SEQ ID NO: 585)-NH-CH₂CH₂-O-CH₂-
C(=O)-(NH-DX), (maleimid-N-yl)-CH₂CH₂-C(=O)-NH-CH₂CH₂O-
CH₂CH₂O-CH₂CH₂O-CH₂CH₂O-CH₂CH₂-C(=O)-
GGFG (SEQ ID NO: 585)-NH-CH₂CH₂-O-CH₂
-C(=O)-(NH-DX), (maleimid-N-yl)-CH₂CH₂-C(=O)-
GGFG (SEQ ID NO: 585)-(NH-DX), (maleimid-N-yl)-CH₂CH₂CH₂-C(=O)-
GGFG (SEQ ID NO: 585)-(NH-DX), (maleimid-N-yl)-CH₂CH₂CH₂CH₂-C(=O)-
GGFG (SEQ ID NO: 585)-(NH-DX), (maleimid-N-yl)-CH₂CH₂CH₂CH₂CH₂-C(=O)-
GGFG (SEQ ID NO: 585)-(NH-DX), (maleimid-N-yl)-CH₂CH₂-C(=O)-
DGGFG (SEQ ID NO: 590)-(NH-DX), (maleimid-N-yl)-CH₂CH₂CH₂-C(=O)-
DGGFG (SEQ ID NO: 590)-(NH-DX), (maleimid-N-yl)-CH₂CH₂CH₂CH₂-C(=O)-
DGGFG (SEQ ID NO: 590)-(NH-DX),
or (maleimid-N-yl)-CH₂CH₂CH₂CH₂CH₂-C(=O)-
DGGFG (SEQ ID NO: 590)-(NH-DX).
```

In the above, (maleimid-N-yl)- is a group represented by the following formula:

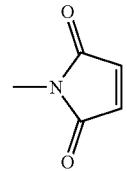

which has a nitrogen atom as a connecting position.
-(NH-DX) represents a group represented by the following formula, the nitrogen atom of the amino group at position 1 being a connecting position.

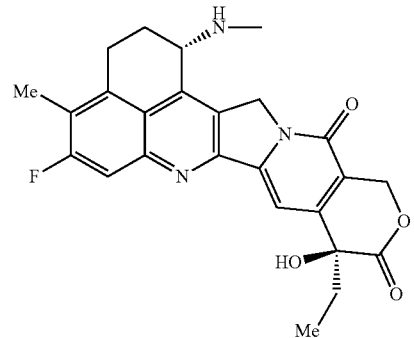

-GGFG- (SEQ ID NO: 585) represents a tetrapeptide residue of -Gly-Gly-Phe-Gly- (SEQ ID NO: 585) and -DGGFG- (SEQ ID NO: 590) represents pentapeptide residue of -Asp-Gly-Gly-Phe-Gly- (SEQ ID NO: 590).

[42] An antibody-drug conjugate obtained by forming a thioether bond at a disulfide bond site present in a hinge part of an anti-HER3 antibody, and characterized by treating the anti-HER3 antibody with a reducing condition and thereafter reacting with a compound selected from the compound group shown below:

```
(maleimid-N-yl)-CH₂CH₂-C(=O)-NH-CH₂CH₂-O-
CH₂CH₂-O-CH₂CH₂-C(=O)-
GGFG (SEQ ID NO: 585)-NH-CH₂CH₂CH₂-C(=O)-
(NH-DX), (maleimid-N-yl)-CH₂CH₂CH₂CH₂CH₂-C(=O)-
GGFG (SEQ ID NO: 585)-NH-CH₂-O-CH₂-C(=O)-
(NH-DX),
or (maleimid-N-yl)-CH₂CH₂CH₂CH₂CH₂-C(=O)-
GGFG (SEQ ID NO: 585)-NH-CH₂CH₂-O-CH₂-
C(=O)-(NH-DX).
```

In the above, (maleimid-N-yl)-, -(NH-DX), and -GGFG (SEQ ID NO: 585)- are as defined above.

[43] The antibody-drug conjugate according to [41] or [42], wherein an average conjugated number of the selected one drug-linker structure per antibody is in a range of from 1 to 10.

[44] The antibody-drug conjugate according to [41] or [42], wherein an average conjugated number of the selected one drug-linker structure per antibody is in a range of from 2 to 8.

[45] The antibody-drug conjugate according to [41] or [42], wherein an average conjugated number of the selected one drug-linker structure per antibody is in a range of from 3 to 8.

[46] A medicine comprising the antibody-drug conjugate according to any one of [40] to [45], a salt thereof or a hydrate thereof.

[47] An antitumor medicine and/or anticancer medicine comprising the antibody-drug conjugate according to any one of [40] to [45], a salt thereof or a hydrate thereof.

[48] The antitumor medicine and/or anticancer medicine according to [47], which is applied to lung cancer, kidney cancer, urothelial cancer, colorectal cancer, prostate cancer, glioblastoma multiforme, ovarian cancer, pancreatic cancer, breast cancer, melanoma, liver cancer, bladder cancer, stomach cancer, gastrointestinal stromal tumor, cervical cancer, head and neck cancer, esophageal cancer, epidermoid cancer, peritoneal cancer, adult glioblastoma multiforme, hepatic cancer, hepatocellular carcinoma, colon cancer, rectal cancer, colon and rectal cancer, endometrial cancer, uterus cancer, salivary cancer, renal cancer, vulval cancer, thyroid cancer, hepatic carcinoma, anus carcinoma, or penis cancer.

[49] A pharmaceutical composition comprising the antibody-drug conjugate according to any one of [40] to [45], a salt thereof or a hydrate thereof as an active component, and a pharmaceutically acceptable formulation component.

[50] The pharmaceutical composition according to [49], which is applied to lung cancer, kidney cancer, urothelial cancer, colorectal cancer, prostate cancer, glioblastoma multiforme, ovarian cancer, pancreatic cancer, breast cancer, melanoma, liver cancer, bladder cancer, stomach cancer, gastrointestinal stromal tumor, cervical cancer, head and neck cancer, esophageal cancer, epidermoid cancer, peritoneal cancer, adult glioblastoma multiforme, hepatic cancer, hepatocellular carcinoma, colon cancer, rectal cancer, colon and rectal cancer, endometrial cancer, uterus cancer, salivary cancer, renal cancer, vulval cancer, thyroid cancer, hepatic carcinoma, anus carcinoma, or penis cancer.

[51] A method for treating a tumor and/or cancer comprising administering the antibody-drug conjugate according to any one of [40] to [45], a salt thereof or a hydrate thereof.

[52] The medicine according to [46], the antitumor medicine and/or anticancer medicine according to [47] or [48], the pharmaceutical composition according to [49] or [50], or the treatment method according to [51], which is used in administration in combination with an additional medicine.

[53] The pharmaceutical composition according to [49] or [50], further comprising even an additional medicine as an active ingredient.

Advantageous Effects of Invention

With an anti-HER3 antibody-drug conjugate having an antitumor compound exatecan conjugated via a linker with a specific structure, an excellent antitumor effect and safety can be achieved.

BRIEF DESCRIPTION OF DRAWINGS

FIG. 1 shows the full-length amino acid sequence of a heavy chain of anti-HER3 human antibody U1-59 (SEQ ID NO: 583).

FIG. 2 shows the full-length amino acid sequence of a light chain of anti-HER3 human antibody U1-59 (SEQ ID NO: 584).

FIG. 6A shows cell growth or survival derived from the antibody-drug conjugate in the presence of 10% FBS. The data is indicated by mean+/−standard deviation of triplicates. The ordinate depicts a luminescence value indicating the ATP activity of each sample. The abscissa depicts the concentration of each antibody-drug conjugate. FIG. 6B shows the rate of reduction in luminescence caused by antibody-drug conjugate treatment when the luminescence of an untreated group was defined as 100%.

FIG. 7A shows cell growth or survival derived from the antibody-drug conjugate in the presence of 10% FBS. The ordinate depicts a luminescence value indicating the ATP activity of each sample. The abscissa depicts the concentration of each antibody-drug conjugate. The data is indicated by mean+/−standard deviation of triplicates. FIG. 7B shows the rate of reduction in luminescence caused by antibody-drug conjugate treatment when the luminescence of an untreated group was defined as 100%.

FIG. 8A shows cell growth or survival derived from the antibody-drug conjugate in the presence of 10% FBS. The ordinate depicts a luminescence value indicating the ATP activity of each sample. The abscissa depicts the concentration of each antibody-drug conjugate. The data is indicated by mean+/−standard deviation of triplicates. FIG. 8B shows the rate of reduction in luminescence caused by antibody-drug conjugate treatment when the luminescence of an untreated group was defined as 100%.

FIG. 9A shows cell growth or survival derived from the antibody-drug conjugate in the presence of 10% FBS. The ordinate depicts a luminescence value indicating the ATP activity of each sample. The abscissa depicts the concentration of each antibody-drug conjugate. The data is indicated by mean+/−standard deviation of triplicates. FIG. 9B shows the rate of reduction in luminescence caused by antibody-drug conjugate treatment when the luminescence of an untreated group was defined as 100%.

FIG. 10A shows cell growth or survival derived from the antibody-drug conjugate in the presence of 10% FBS. The ordinate depicts a luminescence value indicating the ATP activity of each sample. The abscissa depicts the concentration of each antibody-drug conjugate. The data is indicated by mean+/−standard deviation of triplicates. FIG. 10B shows the rate of reduction in luminescence caused by antibody-drug conjugate treatment when the luminescence of an untreated group was defined as 100%.

FIG. 11 shows results of comparing the rate of inhibition of cell growth or survival between the antibody-drug conjugate (3) and the antibody-drug conjugate (4). The left diagram shows the rate of inhibition of cell growth or survival derived from the antibody-drug conjugate in the presence of 10% FBS. The ordinate depicts luminescence indicating the ATP activity of each sample. The abscissa depicts the concentration of each antibody-drug conjugate. The data is indicated by mean+/−standard deviation of triplicates. The right diagram shows the comparison of the rate of reduction in luminescence caused by antibody-drug conjugate treatment between high drug loading (HDL) and middle drug loading (MDL) when the luminescence of an untreated group was defined as 100%.

DESCRIPTION OF EMBODIMENTS

Figure 3:
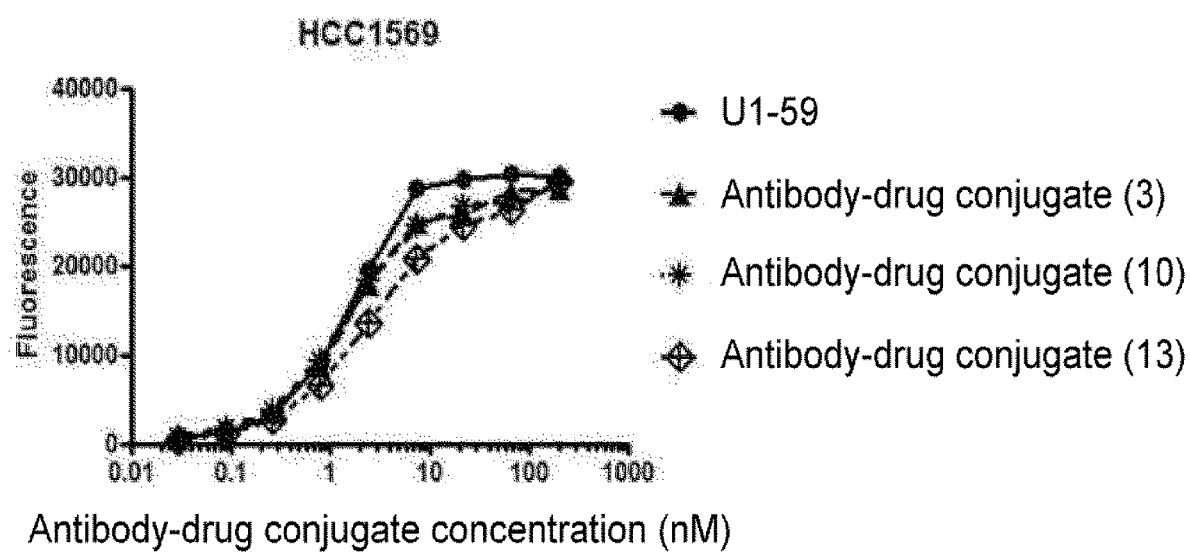
FIG. 3 shows the mean fluorescence intensity of HCC1569 treated with serial dilutions of U1-59 or each antibody-drug conjugate. KD and Bmax values were calculated using GraphPad Prism Software.

Hereinbelow, the preferred embodiments for carrying out the present invention are explained in view of the drawings. Meanwhile, the embodiments explained below are the examples of the representative embodiments of the present invention and the scope of the present invention shall not be narrowly interpreted based on them.

The present invention provides HER3 binding protein-drug conjugate. Preferably, the HER3 binding protein of the invention is a scaffold protein having an antibody like binding activity or an antibody, i.e. an anti-HER3 antibody.

The anti-HER3 antibody-drug conjugate of the present invention is an antitumor medicine in which an anti-HER3 antibody is conjugated to an antitumor compound via a linker structure moiety and explained in detail hereinbelow.

Within the context of the present invention, the term "scaffold protein", as used herein, means a polypeptide or protein with exposed surface areas in which amino acid insertions, substitutions or deletions are highly tolerable. Examples of scaffold proteins that can be used in accordance with the present invention are protein A from *Staphylococcus aureus*, the bilin binding protein from *Pieris brassicae* or other lipocalins, ankyrin repeat proteins, and human fibronectin (reviewed in Binz and Pluckthun, Curr Opin Biotechnol, 16, 459-69). Engineering of a scaffold protein can be regarded as grafting or integrating an affinity function onto or into the structural framework of a stably folded protein. Affinity function means a protein binding affinity according to the present invention. A scaffold can be structurally separable from the amino acid sequences conferring binding specificity. In general, proteins appearing suitable for the development of such artificial affinity reagents may be obtained by rational, or most commonly, combinatorial protein engineering techniques such as panning against HER3, either purified protein or protein displayed on the cell surface, for binding agents in an artificial scaffold library displayed in vitro, skills which are known in the art (Skerra, J. Mol. Recog., 2000; Binz and Pluckthun, 2005). In addition, a scaffold protein having an antibody like binding activity can be derived from an acceptor polypeptide containing the scaffold domain, which can be grafted with binding domains of a donor polypeptide to confer the binding specificity of the donor polypeptide onto the scaffold domain containing the acceptor polypeptide. Said inserted binding domains may be, for example, the complementarity determining region (CDR) of an antibody, in particular an anti-HER3 antibody. Insertion can be accomplished by various methods known to those skilled in the art including, for example, polypeptide synthesis, nucleic acid synthesis of an encoding amino acid as well by various forms of recombinant methods well known to those skilled in the art.

{Antibody}

Moreover, the term "antibody" or "anti-HER3 antibody", as used herein, means a monoclonal antibody, a polyclonal antibody, a recombinant antibody, a humanized antibody (Jones et al., Nature 321 (1986), 522-525; Riechmann et al., Nature 332 (1988), 323-329; and Presta, Curr. Op. Struct. Biol. 2 (1992), 593-596), a chimeric antibody (Morrison et al., Proc. Natl. Acad. Sci. U.S.A. 81 (1984), 6851-6855), a human antibody and fully human antibody, (Tomizuka, K. et al., Nature Genetics (1997) 16, p. 133-143; Kuroiwa, Y. et al., Nucl. Acids Res. (1998) 26, p. 3447-3448; Yoshida, H. et al., Animal Cell Technology: Basic and Applied Aspects vol. 10, p. 69-73 (Kitagawa, Y., Matsuda, T. and Iijima, S. eds.), Kluwer Academic Publishers, 1999.; Tomizuka, K. et al., Proc. Natl. Acad. Sci. USA (2000) 97, p. 722-727, International Publication No. WO 2007/077028, and so on), a multispecific antibody (e.g. a bispecific antibody) formed from at least two antibodies, or an antibody fragment thereof. The term "antibody fragment" comprises any portion of the afore-mentioned antibodies, preferably their antigen binding region or variable regions. Examples of antibody fragments include Fab fragments, Fab' fragments, F(ab')$_2$ fragments, Fv fragments, diabodies (Hollinger et al., Proc. Natl. Acad. Sci. U.S.A. 90 (1993), 6444-6448), single chain antibody molecules (Pluckthun in: The Pharmacology of Monoclonal Antibodies 113, Rosenburg and Moore, EDS, Springer Verlag, N.Y. (1994), 269-315) and other fragments as long as they exhibit the desired capability of binding to HER3.

In addition, the term "antibody" or "anti-HER3 antibody", as used herein, may include antibody-like molecules that contain engineered sub-domains of antibodies or naturally occurring antibody variants. These antibody-like molecules may be single-domain antibodies such as VH-only or VL-only domains derived either from natural sources such as camelids (Muyldermans et al., Reviews in Molecular Biotechnology 74, 277-302) or through in vitro display of libraries from humans, camelids or other species (Holt et al., Trends Biotechnol., 21, 484-90).

In accordance with the present invention, the "Fv fragment" is the minimum antibody fragment that contains a complete antigen-recognition and -binding site. This region consists of a dimer of one heavy- and one light-chain variable domain in tight, non-covalent association. It is in this configuration that the three CDR's of each variable domain interact to define an antigen-binding site on the surface of the VH-VL dimer. Collectively, the six CDR's confer antigen-binding specificity to the antibody. However, even a single variable domain (or half of an Fv comprising only three CDR's specific for an antigen) has the ability to recognize and bind the antigen, although usually at a lower affinity than the entire binding site.

The "Fab fragment" also contains the constant domain of the light chain and the first constant domain (CH1) of the heavy chain. The "Fab fragment" differs from the "Fab$^1$ fragment" by the addition of a few residues at the carboxy terminus of the heavy chain CH1 domain including one or more cysteines from the antibody hinge region. The "F(ab')$_2$ fragment" originally is produced as a pair of "Fab' fragments" which have hinge cysteines between them. Methods of preparing such antibody fragments, such as papain or pepsin digestion, are known to those skilled in the art.

In another preferred embodiment of the present invention, the anti-HER3 antibody of the invention is an anti-HER3 antibody directed against the extracellular domain (ECD) of HER3.

The anti-HER3 antibody used in an anti-HER3 antibody-drug conjugate of the present invention may be derived from any species. Preferred examples of the species can include humans, rats, mice, and rabbits. The anti-HER3 antibody derived from other than human species is preferably chimerized or humanized using a well known technique. The antibody of the present invention may be a polyclonal antibody or a monoclonal antibody and is preferably a monoclonal antibody.

The anti-HER3 antibody is may be those which are capable of targeting tumor cells and thus possesses the property of being capable of recognizing tumor cells, the property of being capable of binding to tumor cells, the property of being internalized into tumor cells, and cytocidal activity against tumor cells, etc. The anti-HER3 antibody can be conjugated with a compound having antitumor activity via a linker to form an antibody-drug conjugate.

The binding activity of the antibody against tumor cells can be confirmed using flow cytometry. The internalization of the antibody into tumor cells can be confirmed using (1) an assay of visualizing an antibody incorporated in cells under a fluorescence microscope using a secondary antibody (fluorescently labeled) binding to the therapeutic antibody (Cell Death and Differentiation (2008) 15, 751-761), (2) an assay of measuring the amount of fluorescence incorporated in cells using a secondary antibody (fluorescently labeled) binding to the therapeutic antibody (Molecular Biology of the Cell, Vol. 15, 5268-5282, December 2004), or (3) a Mab-ZAP assay using an immunotoxin binding to the therapeutic antibody wherein the toxin is released upon incorporation into cells to inhibit cell growth (Bio Techniques 28: 162-165, January 2000). A recombinant complex protein of a diphtheria toxin catalytic domain and protein G may be used as the immunotoxin.

The antitumor activity of the antibody can be confirmed in vitro by determining inhibitory activity against cell growth. For example, a cancer cell line overexpressing a target protein for the antibody is cultured, and the antibody is added at varying concentrations into the culture system to determine inhibitory activity against focus formation, colony formation, and spheroid growth. The antitumor activity can be confirmed in vivo, for example, by administering the antibody to a nude mouse with a transplanted tumor cell line highly expressing the target protein, and determining change in the cancer (tumor) cells.

Since the compound conjugated in the antibody-drug conjugate exerts an antitumor effect, it is preferred but not essential that the antibody itself should have an antitumor effect. For the purpose of exerting the cytotoxicity of the antitumor compound specifically and selectively for tumor cells, it is important and also preferred that the antibody should have the property of being internalized to migrate into tumor cells.

The anti-HER3 antibody can be obtained using a method usually carried out in the art, which involves immunizing animals with an antigenic polypeptide and collecting and purifying antibodies produced in vivo. The origin of the antigen is not limited to humans, and the animals may be immunized with an antigen derived from a non-human animal such as a mouse or a rat and the like. In this case, the cross-reactivity of antibodies binding to the obtained heterologous antigen with human antigens can be tested to screen for an antibody applicable to a human disease.

Alternatively, antibody-producing cells which produce antibodies against the antigen are fused with myeloma cells according to a method known in the art (e.g., Kohler and Milstein, Nature (1975) 256, p. 495-497; and Kennet, R. ed., Monoclonal Antibodies, p. 365-367, Plenum Press, N.Y. (1980)) to establish hybridomas, from which monoclonal antibodies can in turn be obtained.

The antigen can be obtained by genetically engineering host cells to produce a gene encoding the antigenic protein. Specifically, vectors that permit expression of the antigen gene are prepared and transferred to host cells so that the gene is expressed. The antigen thus expressed can be purified. The antibody can also be obtained by use of a method which involves immunizing animals with the genetically engineered antigen-expressing cells or a cell line with an expressed antigen.

The anti-HER3 antibody can be obtained by means known in the art.

The anti-HER3 antibody that can be used in the present invention is not particularly limited and is desirably, for example, any of antibodies having properties as described below.

(1) An anti-HER3 antibody having the following properties:
  (a) specifically binding to HER3, and/or
  (b) having the activity of being internalized into HER3-expressing cells through binding to HER3.
(2) The antibody according to (1), wherein the antibody binds to the extracellular domain of HER3.
(3) The antibody according to (1) or (2), wherein the antibody is a monoclonal antibody.
(4) The antibody according to any of (1) to (3), wherein the antibody has antibody-dependent cell-mediated cytotoxicity (ADCC) activity and/or complement-dependent cytotoxicity (CDC) activity.

(5) The antibody according to any of (1) to (4), wherein the antibody is a mouse monoclonal antibody, a chimeric monoclonal antibody, a humanized monoclonal antibody, or a human or fully human (monoclonal) antibody.
(6) The antibody according to any of (1) to (5), wherein the antibody is a humanized monoclonal antibody comprising a heavy chain comprising the amino acid sequence represented by SEQ ID NO: 1 and a light chain comprising the amino acid sequence represented by SEQ ID NO: 2.
(7) The antibody according to any of (1) to (6), wherein the antibody lacks a lysine residue at the carboxy terminus of the heavy chain.
(8) The antibody according to (7), wherein the antibody comprises a heavy chain variable region represented by the amino acid sequence represented by SEQ ID NO: 70 and a light chain variable region represented by the amino acid sequence represented by SEQ ID NO: 72.
(9) An antibody obtained by a method for producing the antibody according to any of (1) to (8), the method comprising the steps of: culturing a host cell transformed with an expression vector comprising a polynucleotide encoding the antibody; and collecting the antibody of interest from the cultures obtained in the preceding step.

Hereinafter, the anti-HER3 antibody used in the present invention will be described.

In the present specification, the terms "cancer" and "tumor" are used interchangeably.

In the present specification, the term "gene" includes not only DNA but its mRNA, cDNA, and cRNA thereof.

In the present specification, the term "polynucleotide" is used interchangeably with a nucleic acid and also includes DNA, RNA, probes, oligonucleotides, and primers.

In the present specification, the terms "polypeptide" and "protein" are used interchangeably.

In the present specification, the term "cell" also includes cells in animal individuals and cultured cells.

In the present specification, the term "HER3" is used interchangeably with HER3 protein.

In the present specification, the term "CDR" means a complementarity determining region (CDR). An antibody molecule is known to have three CDRs in each of heavy and light chains. CDRs, also called hypervariable domains, are located in the variable regions of the antibody heavy and light chains. These sites have a particularly highly variable primary structure and are separated at three positions on the respective primary structures of heavy and light chain polypeptide strands. In the present specification, the antibody CDRs are referred to as CDRH1, CDRH2, and CDRH3 from the amino terminus of the heavy chain amino acid sequence as to heavy chain CDRs and as CDRL1, CDRL2, and CDRL3 from the amino terminus of the light chain amino acid sequence as to light chain CDRs. These sites are proximal to each other on the three-dimensional structure and determine specificity for the antigen to be bound.

In the present invention, the phrase "hybridizing under stringent conditions" refers to hybridization at 68 C in a commercially available hybridization solution ExpressHyb Hybridization Solution (manufactured by Clontech Laboratories, Inc.), or identifiable hybridization under conditions involving hybridization at 68 C in the presence of 0.7 to 1.0 M NaCl using a DNA-immobilized filter, followed by washing at 68 C using 0.1 to 2×SSC solution (1×SSC is composed of 150 mM NaCl and 15 mM sodium citrate), or hybridization under conditions equivalent thereto.

1. HER3

The human epidermal growth factor receptor 3 (HER3, also known as ErbB3) is a receptor protein tyrosine kinase and belongs to the epidermal growth factor receptor (EGFR) subfamily of receptor protein tyrosine kinases, which also includes HER1 (also known as EGFR), HER2, and HER4. HER3 is a transmembrane receptor and consists of an extracellular ligand-binding domain (ECD), a dimerization domain within the ECD, a transmembrane domain, an intracellular protein tyrosine kinase domain (TKD) and a C-terminal phosphorylation domain. HER3 has been found to be overexpressed in several types of cancer such as breast, gastrointestinal and pancreatic cancers. A correlation between the expression of HER2/HER3 and the progression from a non-invasive to an invasive stage has been shown.

The HER3 protein used in the present invention can be used after direct purification from HER3-expressing human or non-human mammalian (rat, mouse, etc.) cells or can be used by preparing cell membrane fractions of the cells. Alternatively, HER3 may be synthesized in vitro or may be produced from host cells by genetic engineering. In the genetic engineering, specifically, HER3 cDNA is integrated into vectors that permit expression thereof, and HER3 can then be expressed by synthesis in a solution containing enzymes necessary for transcription and translation, substrates, and energy substances or by transformation of other host prokaryotic cells or host eukaryotic cells to yield the protein. Alternatively, the genetically engineered HER3-expressing cells described above or a cell line with expressed HER3 may be used as the HER3 protein.

An RNA sequence, a cDNA sequence, and an amino acid sequence of HER3 are available in public database, and can be referred to by an accession number such as AAA35979 (precursor including a signal sequence consisting of amino terminus 19 amino acid residue), M34309 (NCBI), for example.

The above amino acid sequence of HER3 consists of an amino acid sequence which is subjected to replacements, deletions, additions and/or insertions of at least one amino acid, and proteins having a biological activity equivalent to that of the protein are also included in HER3.

2. Production of Anti HER3 Antibody

The antibody against HER3 of the present invention can be obtained by immunizing an animal with HER3 or an arbitrary polypeptide selected from the amino acid sequence of HER3, and collecting and purifying the antibody produced in vivo according to a method usually carried out in the art. The biological species of HER3 to be used as an antigen is not limited to being human, and an animal can be immunized with HER3 derived from an animal other than humans such as a mouse or a rat. In this case, by examining the cross-reactivity between an antibody binding to the obtained heterologous HER3 and human HER3, an antibody applicable to a human disease can be selected.

Further, a monoclonal antibody can be obtained from a hybridoma established by fusing antibody-producing cells which produce an antibody against HER3 with myeloma cells according to a known method (for example, Kohler and Milstein, Nature, (1975) 256, pp. 495-497; Kennet, R. ed., Monoclonal Antibodies, pp. 365-367, Plenum Press, N.Y. (1980)).

HER3 to be used as an antigen can be obtained by expressing HER3 gene in a host cell using genetic engineering.

Specifically, a vector capable of expressing HER3 gene is produced, and the resulting vector is transfected into a host cell to express the gene, and then, the expressed HER3 is purified.

It is also possible to use HER3 expressing cells obtained by the genetic engineering or a cell line expressing HER3 as HER3 protein. Hereinbelow, a method for obtaining an antibody against HER3 is explained specifically.

(1) Preparation of Antigen

Examples of the antigen to be used for producing the anti HER3 antibody include HER3, a polypeptide consisting of a partial amino acid sequence comprising at least 6 consecutive amino acids of HER3, and a derivative obtained by adding a given amino acid sequence or carrier thereto.

HER3 can be purified directly from human tumor tissues or tumor cells and used. Further, HER3 can be obtained by synthesizing it in vitro or by producing it in a host cell by genetic engineering.

With respect to the genetic engineering, specifically, after HER3 cDNA is integrated into a vector capable of expressing HER3 cDNA, HER3 can be obtained by synthesizing it in a solution containing an enzyme, a substrate and an energy substance required for transcription and translation, or by expressing HER3 in another prokaryotic or eucaryotic transformed host cell.

Further, the antigen can also be obtained as a secretory protein by expressing a fusion protein obtained by ligating the extracellular domain of HER3, which is a membrane protein, to the constant region of an antibody in an appropriate host-vector system.

HER3 cDNA can be obtained by, for example, a so-called PCR method in which a polymerase chain reaction (referred to as "PCR"; see Saiki, R. K., et al., Science, (1988) 239, pp. 487-489) is performed using a cDNA library expressing HER3 cDNA as a template and primers which specifically amplify HER3 cDNA.

As the in vitro synthesis of the polypeptide, for example, Rapid Translation System (RTS) manufactured by Roche Diagnostics, Inc. can be exemplified, but it is not limited thereto.

Examples of the prokaryotic host cells include *Escherichia coli* and *Bacillus subtilis*. In order to transform the host cells with a target gene, the host cells are transformed by a plasmid vector comprising a replicon, i.e., a replication origin derived from a species compatible with the host, and a regulatory sequence. Further, the vector preferably has a sequence capable of imposing phenotypic selectivity on the transformed cell.

Examples of the eucaryotic host cells include vertebrate cells, insect cells, and yeast cells. As the vertebrate cells, for example, simian COS cells (Gluzman, Y., Cell, (1981) 23, pp. 175-182, ATCC CRL-1650; ATCC: American Type Culture Collection), murine fibroblasts NIH3T3 (ATCC No. CRL-1658), and dihydrofolate reductase-deficient strains (Urlaub, G. and Chasin, L. A., Proc. Natl. Acad. Sci. USA (1980) 77, pp. 4126-4220) of Chinese hamster ovarian cells (CHO cells; ATCC: CCL-61); and the like are often used, however, the cells are not limited thereto.

The thus obtained transformant can be cultured according to a method usually carried out in the art, and by the culturing of the transformant, a target polypeptide is produced intracellularly or extracellularly.

A suitable medium to be used for the culturing can be selected from various commonly used culture media depending on the employed host cells. If *Escherichia coli* is employed, for example, an LB medium supplemented with an antibiotic such as ampicillin or IPMG as needed can be used.

A recombinant protein produced intracellularly or extracellularly by the transformant through such culturing can be separated and purified by any of various known separation methods utilizing the physical or chemical property of the protein.

Specific examples of the methods include treatment with a common protein precipitant, ultrafiltration, various types of liquid chromatography such as molecular sieve chromatography (gel filtration), adsorption chromatography, ion exchange chromatography, and affinity chromatography, dialysis, and a combination thereof.

Further, by attaching a tag of six histidine residues to a recombinant protein to be expressed, the protein can be efficiently purified with a nickel affinity column. Alternatively, by attaching the IgG Fc region to a recombinant protein to be expressed, the protein can be efficiently purified with a protein A column.

By combining the above-described methods, a large amount of a target polypeptide can be easily produced in high yield and high purity.

It is also possible to use the aforementioned transformant itself as an antigen. It is also possible to use a cell line expressing HER3 as an antigen. Examples of the cell line include. However, as long as HER3 is expressed, it is not limited to those cell lines.

(2) Production of Anti HER3 Monoclonal Antibody

Examples of the antibody specific binding to HER3 include a monoclonal antibody specific binding to HER3, and a method of obtaining the antibody is as described below.

The production of a monoclonal antibody generally requires the following operational steps of (a) Purification of a biopolymer used as an antigen or preparation of cells expressing antigen;

(b) preparing antibody-producing cells by immunizing an animal by injection of the antigen, collecting the blood, assaying its antibody titer to determine when the spleen is excised;

(c) preparing myeloma cells (hereinafter referred to as "myeloma");

(d) fusing the antibody-producing cells with the myeloma;

(e) screening a group of hybridomas producing a desired antibody;

(f) dividing the hybridomas into single cell clones (cloning);

(g) optionally, culturing the hybridoma or rearing an animal implanted with the hybridoma for producing a large amount of a monoclonal antibody;

(h) examining the thus produced monoclonal antibody for biological activity and binding specificity, or assaying the same for properties as a labeled reagent; and the like.

Hereinafter, the method of producing a monoclonal antibody will be described in detail following the above steps, however, the method is not limited thereto, and, for example, antibody-producing cells other than spleen cells and myeloma can be used.

(a) Purification of Antigen

As the antigen, HER3 prepared by the method as described above or a partial peptide thereof can be used.

Further, a membrane fraction prepared from recombinant cells expressing HER3 or the recombinant cells expressing HER3 themselves, and also a partial peptide of the protein of the invention chemically synthesized by a method known to those skilled in the art can also be used as the antigen.

Further, a cell line expressing HER3 can be also used as an antigen.

(b) Preparation of Antibody-Producing Cells

The antigen obtained in the step (a) is mixed with an adjuvant such as Freund's complete or incomplete adjuvant or aluminum potassium sulfate and the resulting mixture is used as an immunogen to immunize an experimental animal. In an alternative method, a test animal is immunized with cells expressing antigen as an immunogen. As the experimental animal, any animal used in a known hybridoma production method can be used without any trouble. Specifically, for example, a mouse, a rat, a goat, sheep, cattle, a horse, or the like can be used. However, from the viewpoint of ease of availability of myeloma cells to be fused with the extracted antibody-producing cells, a mouse or a rat is preferably used as the animal to be immunized.

Further, the strain of a mouse or a rat to be used is not particularly limited, and in the case of a mouse, for example, various strains such as A, AKR, BALB/c, BDP, BA, CE, C3H, 57BL, C57BL, C57L, DBA, FL, HTH, HT1, LP, NZB, NZW, RF, R III, SJL, SWR, WB, and 129 and the like can be used, and in the case of a rat, for example, Wistar, Low, Lewis, Sprague, Dawley, ACI, BN, Fischer and the like can be used.

These mice and rats are commercially available from breeders/distributors of experimental animals, for example, CLEA Japan, Inc. and Charles River Laboratories Japan, Inc.

As the animal to be immunized, in consideration of compatibility of fusing with myeloma cells described below, in the case of a mouse, BALB/c strain, and in the case of a rat, Wistar and Low strains are particularly preferred.

Further, in consideration of antigenic homology between humans and mice, it is also preferred to use a mouse having decreased biological function to remove auto-antibodies, that is, a mouse with an autoimmune disease.

The age of such mouse or rat at the time of immunization is preferably 5 to 12 weeks of age, more preferably 6 to 8 weeks of age.

In order to immunize an animal with HER3 or a recombinant thereof, for example, a known method described in detail in, for example, Weir, D. M., Handbook of Experimental Immunology Vol. I. II. III., Blackwell Scientific Publications, Oxford (1987); Kabat, E. A. and Mayer, M. M., Experimental Immunochemistry, Charles C Thomas Publisher Springfield, Ill. (1964) or the like can be used.

Among these immunization methods, a preferred specific method in the invention is, for example, as follows.

That is, first, a membrane protein fraction serving as the antigen or cells caused to express the antigen is/are intradermally or intraperitoneally administered to an animal. However, the combination of both routes of administration is preferred for increasing the immunization efficiency, and when intradermal administration is performed in the first half and intraperitoneal administration is performed in the latter half or only at the last dosing, the immunization efficiency can be particularly increased.

The administration schedule of the antigen varies depending on the type of animal to be immunized, individual difference or the like. However, in general, an administration schedule in which the frequency of administration of the antigen is 3 to 6 times and the dosing interval is 2 to 6 weeks is preferred, and an administration schedule in which the frequency of administration of the antigen is 3 to 4 times and the dosing interval is 2 to 4 weeks is more preferred.

Further, the dose of the antigen varies depending on the type of animal, individual differences or the like, however, the dose is generally set to 0.05 to 5 mg, preferably about 0.1 to 0.5 mg.

A booster immunization is performed 1 to 6 weeks, preferably 1 to 4 weeks, more preferably 1 to 3 weeks after the administration of the antigen as described above. When the immunogen is a cell, $1\times10^6$ to $1\times10^7$ cells are used.

The dose of the antigen at the time of performing the booster immunization varies depending on the type or size of animal or the like, however, in the case of, for example, a mouse, the dose is generally set to 0.05 to 5 mg, preferably 0.1 to 0.5 mg, more preferably about 0.1 to 0.2 mg. When the immunogen is a cell, $1\times10^6$ to $1\times10^7$ cells are used.

Spleen cells or lymphocytes including antibody-producing cells are aseptically removed from the immunized animal 1 to 10 days, preferably 2 to 5 days, more preferably 2 to 3 days after the booster immunization. At this time, the antibody titer is measured, and if an animal having a sufficiently increased antibody titer is used as a supply source of the antibody-producing cells, the subsequent procedure can be carried out more efficiently.

Examples of the method of measuring the antibody titer to be used here include an RIA method and an ELISA method, but the method is not limited thereto. For example, if an ELISA method is employed, the measurement of the antibody titer in the invention can be carried out according to the procedures as described below.

First, a purified or partially purified antigen is adsorbed to the surface of a solid phase such as a 96-well plate for ELISA, and the surface of the solid phase having no antigen adsorbed thereto is covered with a protein unrelated to the antigen such as bovine serum albumin (hereinafter referred to as "BSA"). After washing the surface, the surface is brought into contact with a serially-diluted sample (for example, mouse serum) as a primary antibody to allow the antibody in the sample to bind to the antigen.

Further, as a secondary antibody, an antibody labeled with an enzyme against a mouse antibody is added and is allowed to bind to the mouse antibody. After washing, a substrate for the enzyme is added and a change in absorbance which occurs due to color development induced by degradation of the substrate or the like is measured and the antibody titer is calculated based on the measurement.

The separation of the antibody-producing cells from the spleen cells or lymphocytes of the immunized animal can be carried out according to a known method (for example, Kohler et al., Nature (1975), 256, p. 495; Kohler et al., Eur. J. Immunol. (1977), 6, p. 511; Milstein et al., Nature (1977), 266, p. 550; Walsh, Nature (1977), 266, p. 495). For example, in the case of spleen cells, a general method in which the antibody-producing cells are separated by homogenizing the spleen to yield the cells through filtration with a stainless steel mesh and suspending the cells in Eagle's Minimum Essential Medium (MEM) can be employed.

(c) Preparation of Myeloma Cells (Hereinafter Referred to as "Myeloma")

The myeloma cells to be used for cell fusion are not particularly limited and suitable cells can be selected from known cell lines. However, in consideration of convenience when a hybridoma is selected from fused cells, it is preferred to use an HGPRT (hypoxanthine-guanine phosphoribosyl transferase) deficient strain whose selection procedure has been established.

More specifically, examples of the HGPRT-deficient strain include X63-Ag8(X63), NS1-ANS/1(NS1), P3X63-Ag8.U1(P3U1), X63-Ag8.653(X63.653), SP2/0-Agl4(SP2/0), MPC11-45.6TG1.7(45.6TG), FO, S149/5XXO, and BU.1 derived from mice; 210.RSY3.Ag.1.2.3(Y3) derived from rats; and U266AR(SKO-007), GM1500.GTG-A12 (GM1500), UC729-6, LICR-LOW-HMy2(HMy2) and 8226AR/NIP4-1(NP41) derived from humans. These HGPRT-deficient strains are available from, for example, ATCC or the like.

These cell strains are subcultured in an appropriate medium such as an 8-azaguanine medium [a medium obtained by adding 8-azaguanine to an RPMI 1640 medium supplemented with glutamine, 2-mercaptoethanol, gentamicin, and fetal calf serum (hereinafter referred to as "FBS")], Iscove's Modified Dulbecco's Medium; IMDM), or Dulbecco's Modified Eagle Medium (hereinafter referred to as "DMEM"). In this case, 3 to 4 days before performing cell fusion, the cells are subcultured in a normal medium [for example, an ASF104 medium (manufactured by Ajinomoto Co., Ltd.) containing 10% FCS] to ensure not less than $2 \times 10^7$ cells on the day of cell fusion.

(d) Cell Fusion

Fusion between the antibody-producing cells and the myeloma cells can be appropriately performed according to a known method (Weir, D. M. Handbook of Experimental Immunology Vol. I. II. III., Blackwell Scientific Publications, Oxford (1987); Kabat, E. A. and Mayer, M. M., Experimental Immunochemistry, Charles C Thomas Publisher, Springfield, Ill. (1964), etc.), under conditions such that the survival rate of cells is not excessively reduced.

As such a method, for example, a chemical method in which the antibody-producing cells and the myeloma cells are mixed in a solution containing a polymer such as polyethylene glycol at a high concentration, a physical method using electric stimulation, or the like can be used. Among these methods, a specific example of the chemical method is as described below.

That is, in the case where polyethylene glycol is used in the solution containing a polymer at a high concentration, the antibody-producing cells and the myeloma cells are mixed in a solution of polyethylene glycol having a molecular weight of 1500 to 6000, more preferably 2000 to 4000 at a temperature of from 30 to 40 C, preferably from 35 to 38 C for 1 to 10 minutes, preferably 5 to 8 minutes.

(e) Selection of a Group of Hybridomas

The method of selecting hybridomas obtained by the above-described cell fusion is not particularly limited. Usually, an HAT (hypoxanthine, aminopterin, thymidine) selection method (Kohler et al., Nature (1975), 256, p. 495; Milstein et al., Nature (1977), 266, p. 550) is used.

This method is effective when hybridomas are obtained using the myeloma cells of an HGPRT-deficient strain which cannot survive in the presence of aminopterin. That is, by culturing unfused cells and hybridomas in an HAT medium, only hybridomas resistant to aminopterin are selectively allowed to survive and proliferate.

(f) Division into Single Cell Clone (Cloning)

As a cloning method for hybridomas, a known method such as a methylcellulose method, a soft agarose method, or a limiting dilution method can be used (see, for example, Barbara, B. M. and Stanley, M. S.: Selected Methods in Cellular Immunology, W. H. Freeman and Company, San Francisco (1980)). Among these methods, particularly, a three-dimensional culture method such as a methylcellulose method is preferred. For example, the group of hybridomas produced by cell fusion are suspended in a methylcellulose medium such as ClonaCell-HY Selection Medium D (manufactured by StemCell Technologies, inc., #03804) and cultured. Then, the formed hybridoma colonies are collected, whereby monoclonal hybridomas can be obtained. The collected respective hybridoma colonies are cultured, and a hybridoma which has been confirmed to have a stable antibody titer in an obtained hybridoma culture supernatant is selected as an anti-HER3 monoclonal antibody-producing hybridoma strain.

(g) Preparation of Monoclonal Antibody by Culturing Hybridoma

By culturing the thus selected hybridoma, a monoclonal antibody can be efficiently obtained. However, prior to culturing, it is preferred to perform screening of a hybridoma which produces a target monoclonal antibody.

In such screening, a known method can be employed.

The measurement of the antibody titer in the invention can be carried out by, for example, an ELISA method explained in item (b) described above.

The hybridoma obtained by the method described above can be stored in a frozen state in liquid nitrogen or in a freezer at −80 C or below.

After completion of cloning, the medium is changed from an HT medium to a normal medium, and the hybridoma is cultured.

Large-scale culture is performed by rotation culture using a large culture bottle or by spinner culture. From the supernatant obtained by the large-scale culture, a monoclonal antibody which specifically binds to the protein of the invention can be obtained by purification using a method known to those skilled in the art such as gel filtration.

Further, the hybridoma is injected into the abdominal cavity of a mouse of the same strain as the hybridoma (for example, the above-described BALB/c) or a Nu/Nu mouse to proliferate the hybridoma, whereby the ascites containing a large amount of the monoclonal antibody of the invention can be obtained.

In the case where the hybridoma is administrated in the abdominal cavity, if a mineral oil such as 2,6,10,14-tetramethyl pentadecane (pristane) is administrated 3 to 7 days prior thereto, a larger amount of the ascites can be obtained.

For example, an immunosuppressant is previously injected into the abdominal cavity of a mouse of the same strain as the hybridoma to inactivate T cells. 20 days thereafter, $10^6$ to $10^7$ hybridoma clone cells are suspended in a serum-free medium (0.5 mL), and the suspension is administrated in the abdominal cavity of the mouse. In general, when the abdomen is expanded and filled with the ascites, the ascites is collected from the mouse. By this method, the monoclonal antibody can be obtained at a concentration which is about 100 times or much higher than that in the culture solution.

The monoclonal antibody obtained by the above-described method can be purified by a method described in, for example, Weir, D. M.: Handbook of Experimental Immunology Vol. I, II, III, Blackwell Scientific Publications, Oxford (1978).

The thus obtained monoclonal antibody has high antigen specificity for HER3.

(h) Assay of Monoclonal Antibody

The isotype and subclass of the thus obtained monoclonal antibody can be determined as follows.

First, examples of the identification method include an Ouchterlony method, an ELISA method, and an RIA method.

An Ouchterlony method is simple, but when the concentration of the monoclonal antibody is low, a condensation operation is required.

On the other hand, when an ELISA method or an RIA method is used, by directly reacting the culture supernatant with an antigen-adsorbed solid phase and using antibodies corresponding to various types of immunoglobulin isotypes and subclasses as secondary antibodies, the isotype and subclass of the monoclonal antibody can be identified.

In addition, as a simpler method, a commercially available identification kit (for example, Mouse Typer Kit manufactured by Bio-Rad Laboratories, Inc.) or the like can also be used.

Further, the quantitative determination of a protein can be performed by the Folin Lowry method and a method of calculation based on the absorbance at 280 nm [1.4 (OD 280)=Immunoglobulin 1 mg/mL].

Further, even when the monoclonal antibody is separately and independently obtained by performing again the steps of (a) to (h) in (2), it is possible to yield an antibody having a cytotoxic activity equivalent to that of the anti-HER3 antibody. As one example of such an antibody, an antibody which binds to the same epitope as the anti-HER3 antibody can be exemplified. If a newly produced monoclonal antibody binds to a partial peptide or a partial tertiary structure to which the anti-HER3 antibody binds, it can be determined that the monoclonal antibody binds to the same epitope as the anti-HER3 antibody. Further, by confirming the competition by the monoclonal antibody for binding of the anti-HER3 antibody to HER3 (binding between the anti-HER3 antibody and HER3 is interfered by the monoclonal antibody), it can be determined that the monoclonal antibody binds to the same epitope as the anti-HER3 antibody even though a specific sequence or structure of the epitope has not been identified. Once the epitope is confirmed to be the same, it is strongly expected that the monoclonal antibody has the same antigen binding capacity or biological activity as the anti-HER3 antibody.

(3) Other Antibodies

The antibody of the invention includes not only the above-described monoclonal antibody against HER3 but also a recombinant antibody obtained by artificial modification for the purpose of decreasing heterologous antigenicity to humans such as a chimeric antibody, a humanized antibody and a human antibody. These antibodies can be produced using a known method.

As the chimeric antibody, an antibody in which antibody variable and constant regions are derived from different species, for example, a chimeric antibody in which a mouse- or rat-derived antibody variable region is connected to a human-derived constant region can be exemplified (see Proc. Natl. Acad. Sci. USA, 81, 6851-6855, (1984)).

As the humanized antibody, an antibody obtained by integrating only a complementarity determining region (CDR) into a human-derived antibody (see Nature (1986) 321, pp. 522-525), and an antibody obtained by grafting a part of the amino acid residues of the framework as well as the CDR sequence to a human antibody by a CDR-grafting method (WO 90/07861) can be exemplified.

The term "several" as used herein refers to 1 to 10, 1 to 9, 1 to 8, 1 to 7, 1 to 6, 1 to 5, 1 to 4, 1 to 3, or 1 or 2.

In accordance with the present invention, it is to be understood, that the amino acid sequence of the binding protein of the invention is not limited to the twenty conventional amino acids (See Immunology—A Synthesis ($2^{nd}$ Edition, E. S. Golub and D. R. Gren, Eds., Sinauer Associates, Sunderland, Mass. (1991)), which is incorporated herein by reference). For example, the amino acids may include stereoisomers (e.g. D-amino acids) of the twenty conventional amino acids, unnatural amino acids such as alpha-, alpha-disubstituted amino acids, N-alkyl amino acids, lactic acid, and other unconventional amino acids. Examples of unconventional amino acids, which may also be suitable components for the binding protein of the invention, include: 4-hydroxyproline, gamma-carboxyglutamate, epsilon-N,N,N-trimethyllysine, epsilon-N-acetyllysine, O-phosphoserine, N-acetylserine, N-formylmethionine, 3-methylhistidine, 5-hydroxylysine, sigma-N-methylarginine, and other similar amino acids and imino acids, e.g. 4-hydroxyproline.

As the amino acid substitution in this specification, a conservative amino acid substitution is preferred. The conservative amino acid substitution refers to a substitution occurring within a group of amino acids related to amino acid side chains. Preferred amino acid groups are as follows: an acidic group (aspartic acid and glutamic acid); a basic group (lysine, arginine, and histidine); a non-polar group (alanine, valine, leucine, isoleucine, proline, phenylalanine, methionine, and tryptophan); and an uncharged polar family (glycine, asparagine, glutamine, cysteine, serine, threonine, and tyrosine). More preferred amino acid groups are as follows: an aliphatic hydroxy group (serine and threonine); an amide-containing group (asparagine and glutamine); an aliphatic group (alanine, valine, leucine, and isoleucine); and an aromatic group (phenylalanine, tryptophan, and tyrosine). Such an amino acid substitution is preferably performed within a range which does not impair the properties of a substance having the original amino acid sequence. When the heavy and light chains of the antibody of the present invention have glutamate as the N-terminal amino acid, it may be cyclized (in the form of pyroglutamate). In the present invention, such pyroglutamate is not differentiated from normal glutamine on amino acid sequences. In the heavy and light chains of the antibody of the present invention, cysteine may be in the form of cysteinyl. In the present invention, such a cysteinyl form is not differentiated from normal cysteine on amino acid sequences.

Further, the antibody of the invention includes a human antibody which binds to the HER3. An anti HER3 human antibody refers to a human antibody having only a gene sequence of an antibody derived from a human chromosome. The anti HER3 human antibody can be obtained by a method using a human antibody-producing mouse having a human chromosome fragment comprising heavy and light chain genes of a human antibody (see Tomizuka, K. et al., Nature Genetics (1997) 16, pp. 133-143; Kuroiwa, Y. et al., Nucl. Acids Res. (1998) 26, pp. 3447-3448; Yoshida, H. et al., Animal Cell Technology: Basic and Applied Aspects vol. 10, pp. 69-73 (Kitagawa, Y., Matuda, T. and Iijima, S. eds.), Kluwer Academic Publishers, 1999; Tomizuka, K. et al., Proc. Natl. Acad. Sci. USA (2000) 97, pp. 722-727, etc.).

Such a human antibody-producing mouse can be created specifically as follows. A genetically modified animal in which endogenous immunoglobulin heavy and light chain gene loci have been disrupted, and instead, human immunoglobulin heavy and light chain gene loci have been introduced via a yeast artificial chromosome (YAC) vector or the like is created by producing a knockout animal and a transgenic animal and mating these animals.

Further, according to a recombinant DNA technique, by using cDNAs encoding each of such a heavy chain and a light chain of a human antibody, and preferably a vector comprising such cDNAs, eukaryotic cells are transformed, and a transformant cell which produces a recombinant human monoclonal antibody is cultured, whereby the antibody can also be obtained from the culture supernatant.

Here, as the host, for example, eukaryotic cells, preferably mammalian cells such as CHO cells, lymphocytes, or myeloma cells can be used.

With regard to preparation of a human antibody, detailed descriptions are given in International Publication No. WO 2007/077028. The contents of International Publication No. WO 2007/077028 are incorporated herein by reference.

Further, a method of obtaining a phage display-derived human antibody selected from a human antibody library (see Wormstone, I. M. et al., Investigative Ophthalmology & Visual Science. (2002) 43 (7), pp. 2301-2308; Carmen, S. et al., Briefings in Functional Genomics and Proteomics (2002), 1 (2), pp. 189-203; Siriwardena, D. et al., Ophthalmology (2002) 109 (3), pp. 427-431, etc.) is also known.

For example, a phage display method in which a variable region of a human antibody is expressed on the surface of a phage as a single-chain antibody (scFv), and a phage which binds to an antigen is selected (Nature Biotechnology (2005), 23, (9), pp. 1105-1116) can be used.

By analyzing the gene of the phage selected based on the binding to an antigen, a DNA sequence encoding the variable region of a human antibody which binds to an antigen can be determined.

If the DNA sequence of scFv which binds to an antigen is determined, a human antibody can be obtained by preparing an expression vector comprising the sequence and introducing the vector into an appropriate host to express it (WO 92/01047, WO 92/20791, WO 93/06213, WO 93/11236, WO 93/19172, WO 95/01438, WO 95/15388; Annu. Rev. Immunol. (1994) 12, pp. 433-455; Nature Biotechnology (2005) 23 (9), pp. 1105-1116).

One aspect of the present invention relates to an isolated protein that binds to HER3. In one embodiment of the present invention, an isolated HER3-binding protein of the invention comprises a heavy chain variable region amino acid sequence comprising: (a) CDRH1 comprised in the amino acid sequence represented by SEQ ID NO: 2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 or 230, (b) CDRH2 comprised in the amino acid sequence represented by SEQ ID NO: 2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 or 230, and (c) CDRH3 comprised in the amino acid sequence represented by SEQ ID NO: 2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 or 230, and a light chain variable region amino acid sequence comprising: (d) CDRL1 comprised in the amino acid sequence represented by SEQ ID NO: 4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 or 232, (e) CDRL2 comprised in the amino acid sequence represented by SEQ ID NO: 4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 or 232, and (f) CDRL3 comprised in the amino acid sequence represented by SEQ ID NO: 4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 or 232.

The isolated HER3-binding protein of the present invention preferably comprises a heavy chain amino acid sequence comprising (a) CDRH1 comprising the amino acid sequence represented by one selected from the group consisting of SEQ ID NOs: 236, 251, 252, and 256; (b) CDRH2 comprising the amino acid sequence represented by one selected from the group consisting of SEQ ID NOs: 258, 278, 280, and 282; and (c) CDRH3 comprising the amino acid sequence represented by one selected from the group consisting of SEQ ID NOs: 283, 285, 309, 313, and 315, and a light chain amino acid sequence comprising (d) CDRL1 comprising the amino acid sequence represented by one selected from the group consisting of SEQ ID NOs: 320, 334, 337, and 340; (e) CDRL2 comprising the amino acid sequence represented by one selected from the group consisting of SEQ ID NOs: 343, 356, 351, and 344; and (f) CDRL3 comprising the amino acid sequence represented by one selected from the group consisting of SEQ ID NOs: 360, 381, 385, and 387.

In another embodiment of the present invention, an isolated binding protein of the invention comprises a heavy chain variable region amino acid sequence selected from the group consisting of SEQ ID Nos: 2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 and 230, and/or a light chain variable region amino acid sequence selected from the group consisting of SEQ ID NOs: 4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 and 232.

In yet another embodiment of the present invention, an isolated binding protein of the invention comprises a heavy chain variable region amino acid sequence and a light chain variable region amino acid sequence represented by SEQ ID NOs: 2 and 4, 6 and 8, 10 and 12, 14 and 16, 18 and 20, 22 and 24, 26 and 28, 30 and 32, 36 and 38, 42 and 44, 46 and 48, 50 and 52, 54 and 56, 60 and 58, 62 and 64, 66 and 68, 70 and 72, 74 and 76, 78 and 82, 80 and 82, 84 and 86, 88 and 90, 92 and 94, 96 and 98, 100 and 102, 104 and 106, 108 and 110, 112 and 114, 116 and 118, 122 and 124, 126 and 128, 130 and 132, 134 and 136, 138 and 140, 142 and 144, 146 and 148, 150 and 152, 154 and 156, 158 and 160, 162 and 164, 166 and 168, 170 and 172, 174 and 176, 178 and 180, 182 and 184, 186 and 188, 190 and 192, 194 and 196, 198 and 200, 202 and 204, 206 and 208, 210 and 212, 214 and 216, 218 and 220, 222 and 224, 226 and 228 or 230 and 232, or, a heavy chain variable region amino acid sequence represented by SEQ ID NO: 34, 40, 60, 62 or 120 and a light chain variable region amino acid sequence represented by SEQ ID NO: 58 or 64, respectively.

The isolated HER3-binding protein of the present invention more preferably comprises a heavy chain variable region amino acid sequence represented by SEQ ID NO: 42, 54, 70, 92, or 96 and a light chain variable region amino acid sequence represented by SEQ ID NO: 44, 56, 72, 94, or 98.

An antibody comprising a heavy chain variable region amino acid sequence and a light chain variable region amino acid sequence represented by SEQ ID NOs: 2 and 4 is referred to as "U1-39", an antibody comprising a heavy chain variable region amino acid sequence and a light chain variable region amino acid sequence represented by SEQ ID NOs: 6 and 8 is referred to as "U1-40", an antibody comprising a heavy chain variable region amino acid sequence and a light chain variable region amino acid sequence represented by SEQ ID NOs: 10 and 12 is referred to as "U1-38", an antibody comprising a heavy chain variable region amino acid sequence and a light chain variable region amino acid sequence represented by SEQ ID NOs: 14 and 16 is referred to as "U1-41", an antibody comprising a heavy chain variable region amino acid sequence and a light chain variable region amino acid sequence represented by SEQ ID NOs: 18 and 20 is referred to as "U1-42", an antibody comprising a heavy chain variable region amino acid sequence and a light chain variable region amino acid sequence represented by SEQ ID NOs: 22 and 24 is referred to as "U1-43", an antibody comprising a heavy chain variable region amino acid sequence and a light chain variable region amino acid sequence represented by SEQ ID NOs: 26 and 28 is referred to as "U1-44", an antibody comprising a heavy chain variable region amino acid sequence and a light chain variable region amino acid sequence represented by SEQ ID NOs: 30 and 32 is referred to as "U1-45", an antibody comprising a heavy chain variable region amino acid sequence and a light chain variable region amino acid sequence represented by SEQ ID NOs: 36 and 38 is referred to as "U1-47", an antibody comprising a heavy chain variable region amino acid sequence and a light chain variable region amino acid sequence represented by SEQ ID NOs: 42 and 44 is referred to as "U1-49", an antibody comprising a heavy chain variable region amino acid sequence and a light chain variable region amino acid sequence represented by SEQ ID NOs: 46 and 48 is referred to as "U1-50", an antibody comprising a heavy chain variable region amino acid sequence and a light chain variable region amino acid sequence represented by SEQ ID NOs: 50 and 52 is referred to as "U1-51", an antibody comprising a heavy chain variable region amino acid sequence and a light chain variable region amino acid sequence represented by SEQ ID NOs: 54 and 56 is referred to as "U1-53", an antibody comprising a heavy chain variable region amino acid sequence and a light chain variable region amino acid sequence represented by SEQ ID NOs: 60 and 58 is referred to as "U1-55", an antibody comprising a heavy chain variable region amino acid sequence and a light chain variable region amino acid sequence represented by SEQ ID NOs: 62 and 64 is referred to as "U1-57", an antibody comprising a heavy chain variable region amino acid sequence and a light chain variable region amino acid sequence represented by SEQ ID NOs: 66 and 68 is referred to as "U1-58", an antibody comprising a heavy chain variable region amino acid sequence and a light chain variable region amino acid sequence represented by SEQ ID NOs: 70 and 72 is referred to as "U1-59", an antibody comprising a heavy chain variable region amino acid sequence and a light chain variable region amino acid sequence represented by SEQ ID NOs: 74 and 76 is referred to as "U1-52", an antibody comprising a heavy chain variable region amino acid sequence and a light chain variable region amino acid sequence represented by SEQ ID NOs: 78 and 82 is referred to as "U1-61", an antibody comprising a heavy chain variable region amino acid sequence and a light chain variable region amino acid sequence represented by SEQ ID NOs: 80 and 82 is referred to as "U1-61.1", an antibody comprising a heavy chain variable region amino acid sequence and a light chain variable region amino acid sequence represented by SEQ ID NOs: 84 and 86 is referred to as "U1-62", an antibody comprising a heavy chain variable region amino acid sequence and a light chain variable region amino acid sequence represented by SEQ ID NOs: 88 and 90 is referred to as "U1-2", an antibody comprising a heavy chain variable region amino acid sequence and a light chain variable region amino acid sequence represented by SEQ ID NOs: 92 and 94 is referred to as "U1-7", an antibody comprising a heavy chain variable region amino acid sequence and a light chain variable region amino acid sequence represented by SEQ ID NOs: 96 and 98 is referred to as "U1-9", an antibody comprising a heavy chain variable region amino acid sequence and a light chain variable region amino acid sequence represented by SEQ ID NOs: 100 and 102 is referred to as "U1-10", an antibody comprising a heavy chain variable region amino acid sequence and a light chain variable region amino acid sequence represented by SEQ ID NOs: 104 and 106 is referred to as "U1-12", an antibody comprising a heavy chain variable region amino acid sequence and a light chain variable region amino acid sequence represented by SEQ ID NOs: 108 and 110 is referred to as "U1-13", an antibody comprising a heavy chain variable region amino acid sequence and a light chain variable region amino acid sequence represented by SEQ ID NOs: 112 and 114 is referred to as "U1-14", an antibody comprising a heavy chain variable region amino acid sequence and a light chain variable region amino acid sequence represented by SEQ ID NOs: 116 and 118 is referred to as "U1-15", an antibody comprising a heavy chain variable region amino acid sequence and a light chain variable region amino acid sequence represented by SEQ ID NOs: 122 and 124 is referred to as "U1-20", an antibody comprising a heavy chain variable region amino acid sequence and a light chain variable region amino acid sequence represented by SEQ ID NOs: 126 and 128 is referred to as "U1-21", an antibody comprising a heavy chain variable region amino acid sequence and a light chain variable region amino acid sequence represented by SEQ ID NOs: 130 and 132 is referred to as "U1-22", an antibody comprising a heavy chain variable region amino acid sequence and a light chain variable region amino acid sequence represented by SEQ ID NOs: 134 and 136 is referred to as "U1-23", an antibody comprising a heavy chain variable region amino acid sequence and a light chain variable region amino acid sequence represented by SEQ ID NOs: 138 and 140 is referred to as "U1-24", an antibody comprising a heavy chain variable region amino acid sequence and a light chain variable region amino acid sequence represented by SEQ ID NOs: 142 and 144 is referred to as "U1-25", an antibody comprising a heavy chain variable region amino acid sequence and a light chain variable region amino acid sequence represented by SEQ ID NOs: 146 and 148 is referred to as "U1-26", an antibody comprising a heavy chain variable region amino acid sequence and a light chain variable region amino acid sequence represented by SEQ ID NOs: 150 and 152 is referred to as "U1-27", an antibody comprising a heavy chain variable region amino acid sequence and a light chain variable region amino acid sequence represented by SEQ ID NOs: 154 and 156 is referred to as "U1-28", an antibody comprising a heavy chain variable region amino acid sequence and a light chain variable region amino acid sequence represented by SEQ ID NOs: 158 and 160 is referred to as "U1-31", an antibody comprising a heavy chain variable region amino acid sequence and a light chain variable region amino acid sequence represented by SEQ ID NOs: 162 and 164 is referred to as "U1-32", an antibody comprising a heavy chain variable region amino acid sequence and a light chain variable region amino acid sequence represented by SEQ ID NOs: 166 and 168 is referred to as "U1-35", an antibody comprising a heavy chain variable region amino acid sequence and a light chain variable region amino acid sequence represented by SEQ ID NOs: 170 and 172 is referred to as "U1-36", an antibody comprising a heavy chain variable region amino acid sequence and a light chain variable region amino acid sequence represented by SEQ ID NOs: 174 and 176 is referred to as "U1-37", an antibody comprising a heavy chain variable region amino acid sequence and a light chain variable region amino acid sequence represented by SEQ ID NOs: 178 and 180 is referred to as "U1-34", an antibody comprising a heavy chain variable region amino acid sequence and a light chain variable region amino acid sequence represented by SEQ ID NOs: 182 and 184 is referred to as "U1-1", an antibody comprising a heavy chain variable region amino acid sequence and a light chain variable region amino acid sequence represented by SEQ ID NOs: 186 and 188 is referred to as "U1-3", an antibody comprising a heavy chain variable region amino acid sequence and a light chain variable region amino acid sequence represented by SEQ ID NOs: 190 and 192 is referred to as "U1-4", an antibody comprising a heavy chain variable region amino acid sequence and a light chain variable region amino acid sequence represented by SEQ ID NOs: 194 and 196 is referred to as "U1-5", an antibody comprising a heavy chain variable region amino acid sequence and a light chain variable region amino acid sequence represented by SEQ ID NOs: 198 and 200 is referred to as "U1-6", an antibody comprising a heavy chain variable region amino acid sequence and a light chain variable region amino acid sequence represented by SEQ ID NOs: 202 and 204 is referred to as "U1-8", an antibody comprising a heavy chain variable region amino acid sequence and a light chain variable region amino acid sequence represented by SEQ ID NOs: 206 and 208 is referred to as "U1-11", an antibody comprising a heavy chain variable region amino acid sequence and a light chain variable region amino acid sequence represented by SEQ ID NOs: 210 and 212 is referred to as "U1-16", an antibody comprising a heavy chain variable region amino acid sequence and a light chain variable region amino acid sequence represented by SEQ ID NOs: 214 and 216 is referred to as "U1-17", an antibody comprising a heavy chain variable region amino acid sequence and a light chain variable region amino acid sequence represented by SEQ ID NOs: 218 and 220 is referred to as "U1-18", an antibody comprising a heavy chain variable region amino acid sequence and a light chain variable region amino acid sequence represented by SEQ ID NOs: 222 and 224 is referred to as "U1-33", an antibody comprising a heavy chain variable region amino acid sequence and a light chain variable region amino acid sequence represented by SEQ ID NOs: 226 and 228 is referred to as "U1-29", an antibody comprising a heavy chain variable region amino acid sequence and a light chain variable region amino acid sequence represented by SEQ ID NOs: 230 and 232 is referred to as "U1-30", an antibody comprising a heavy chain variable region amino acid sequence represented by SEQ ID NO: 34 is referred to as "U1-46", an antibody comprising a heavy chain variable region amino acid sequence represented by SEQ ID NO: 40 is referred to as "U1-48", an antibody comprising a heavy chain variable region amino acid sequence and a light chain variable region amino acid sequence represented by SEQ ID NOs: 60 and 58 is referred to as "U1-55.1", an antibody comprising a heavy chain variable region amino acid sequence represented by SEQ ID NO: 120 is referred to as "U1-19", and an antibody comprising a heavy chain variable region amino acid sequence and a light chain variable region amino acid sequence represented by SEQ ID NOs: 62 and 64 is referred to as "U1-57.1". These antibodies are described in detail in Examples.

The isolated HER3-binding protein of the present invention even more preferably comprises a heavy chain variable region amino acid sequence and a light chain variable region amino acid sequence represented by SEQ ID NOs: 42 and 44, respectively, a heavy chain variable region amino acid sequence and a light chain variable region amino acid sequence represented by SEQ ID NOs: 54 and 56, respectively, a heavy chain variable region amino acid sequence and a light chain variable region amino acid sequence represented by SEQ ID NOs: 70 and 72, respectively, a heavy chain variable region amino acid sequence and a light chain variable region amino acid sequence represented by SEQ ID NOs: 92 and 94, respectively, or a heavy chain variable region amino acid sequence and a light chain variable region amino acid sequence represented by SEQ ID NOs: 96 and 98, respectively, and still even more preferably, the HER3-binding proteins is U1-49, U1-53, U1-59, U1-7, or U1-9, which are an anti-HER3 antibody.

```
[Chem. 14]
In the Sequence Listing below, SEQ ID NOS 1-232 are disclosed,
respectively, in order of appearance.
Sequence Listing
Antibody U1-39
1 Heavy Chain DNA:
GAGGTGCAGCTGGTGGAGTCTCGAGGAGGCTTGATCCAGCCTGGGGGGTCCCTGAGACTC

TCCTGTGCAGCCTCTGGGTTCACCGTCAGTACCAACTACATGAGCTGGGTCCGCCAGGCT

CCAGGGAAGGGGCTGGATTGGGTCTCAGTTATTTATAGCGGTGGTAGCACATACTACGCA

GACTCCGTGAAGGGCCGATTCACCATCTCCAGAGACAATTCCAAGAACACGCTGTATCTT

CAAATGAACAGCCTGAGAGCCGAGGACACGGCCGTGTATTACTGTGCGAGAGGGCAGTGG

CTGGACGTCTGGGGCCAAGGGACCACGGTCACGGTCTCCTCA

2 Heavy Chain Protein:
EVQLVESGGGLIQPGGSLRLSCAASGFTVSSNYMSWVRQAPGKGLDWVSVIYSGGSTYYA

DSVKGRFTISRDNSKNTLYLQMNSLRAEDTAVYYCARGQWLDVWGQGTTVTVSS

3 Light Chain DNA:
GATATTGTGATGACTCAGTCTCCACTCTCCCTGCCCGTCACCCCTGGAGAGCCGGCCTCC

ATCTCCTGCAGGTCAAGTCAGAGCCTCCTGCATAGTAATGGATACAACTATTTGCATTGG

TACCTGCAGAGGCCAGGGCAGTCPCCACAACTCCTGTTCTATTTGGGTTTTCATCGGGCC
```

```
TCCGGGGTCCCTGACAGGTTCAGTGGCAGTGGATCAGGCACAGATTTTACACTGAAAATC

AGCAGAGTGGAGGCTGAGGATGTTGGGGTTTATTACTGCAGGCAAGCTCTACAAACTCCG

CTCACTTTCGGCGGAGGGACCAAGGTGGAGATCAAA

4 Light Chain Protein:
DIVMTQSPLSLPVTPGEPASISCRSSQSLLHSNGYNYLDWYLQRPGQSPQLLFYLGFHRA

SGVPDRFSGSGSGTDFTLKISRVEAEDVGVYYCRQALQTPLTFGGGTKVEIK

Antibody U1-40
5 Heavy Chain DNA:
CAGGTGCAGCTCCAGGAGTCGGGCCCAGGACTGGTGAAGCCTTCACAGACCCTGTCCCTC

ACCTGTACTGTCTCTGGTGGCTCCATCAGCAGTGGTCGTTACTACTCGAGCTGGATCCGC

CAGCACCCAGGGAAGGGCCTGGAGTGGATTGGGTACATCTATTCCAGTGGGAGCACCTAC

TACAACCCGTCCCTCAACAGTCGAGTTACCATATCAGTAGACACGTCTAAGAACCAGTTC

TCCCTGAAGCTGAGCTCTGTGACTGCCGCGGACACGGCCGTSTATTACTGTCCCAGACAT

AGGGAACTGGAACTTTACTACTACTACGGTATGGACGTCTGGGGCCAAGGGACCACG

GTCACCGTCTCCTC

6 Heavy Chain Protein:
QVQLQESGPGLVKPSQTLSLTCTVSGGSISSGGYYWSWIRQHPGKGLEWIGYIYSSGSTY

YNPSLKSRVTISVDTSKNQFSLKLSSVTAADTAVYYCARDRELELYYYYGMDVWGQGTT

VTVS

7 Light Chain DNA:
GATATTGTGATGACTCAGTCTCCACTCTCCCTGCCCGTCACCCCTGGAGAGCCGGCCTCC

ATCTCCTGCAGGTCTAGTCAGAGCCTCCTGTATAGTAATGGATACAACTATTTGGATTGG

TACCTGCAGAAGCCAGGGCAGTCTCCACAGCTCCTGATCTATTTGGGTTCTAATCGGGCC

TCCGGGGTCCCTGACAGGTTCAGTCGCAGTGGATCAGGCACAGATTTTACACTGAAAATC

AGCAGAGTGGACGCTGAGGATGTTGGCATTTATTACTGCATGCAAGCTCTACAAACTCCG

CTCACTTTCGGCGGAGGCACCAAGGTGGAGATCAAA

8 Light Chain Protein:
DIVMTQSPLSLPVTPGEPASISCRSSQSLLYSNGYNYLDWYLQKPGQSPQLLIYLGSNRA

SGVPDRFSGSGSGTDFTLKISRVEAEDVGIYYCMQALQTPLTFGGGTKVEIK

Antibody U1-38
9 Heavy Chain DNA:
CAGATCACCTTGAAGGAGTCTGGTCCTACGCTGGTGAAACCCACACAGACCCTCACGCTG

ACCTGCACCTTCTCTGGGTTCTCACTCAGCACTACTGGAGTGGGTGTGGGCTGGATCCGT

CAGCCCCCAGGAAAGGCCCTGGACTGGCTTGCACTCATTTATTGGAATGATGATAAGCGC

TACACCCCATCTCTGAACACCAGGCTCACCATCACCAAGGACACCTCCAAAAACCAGGTG

GTCCTTACAATGACCAACATGGATCTTGTCGACACAGCCACATATTACTGTGTACACAGA

GACGAAGTTCGAGGGTTTGACTACTGGGGCCAGGGAACCCTGGTCACCGTCTCCTCA

10 Heavy Chain Protein:
QITLKESGPTLVKPTQTLTLTCTFSGFSLSTSGVGVGWIRQPPGKALDWLALIYWNDDKR

YSPSLKSRLTITKDTSKNQVVLTMTNMDLVDTATYYCVHRDEVRGFDYWGQGTLVTVSS

11 Light Chain DNA:
GATGTTGTGATGACTCAGTCTCCACTCTCCCTGCCCGTCACCCTTGGACAGCCGGCCTCC

ATCTCCTGCAGGTCTAGTCAAAGCCTCGTATACAGTGATGGATACACCTACTTGCATTGG

TTTCAGCAGAGGCCAGGCCAATCTCCAAGGCGCCTTATTTATAAGGTTTCTAACTGGGAC

TCTGGGGTCCCAGACAGATTCAGCGGCAGTGGGTCAGGCACTGATTTCACACTGAAAATC
```

-continued

AGCAGGGTGGAGGCTGAGGATGTTGGGGTTTATTACTGCATGCAAGGTGCACACTGGCCG

ATCACCTTCGGCCAAGGGACACGACTGGAGATTAAA

12 Light Chain Protein:
DVVMTQSPLSLPVTLGQPASISCRSSQSLVYSDGYTYLHWFQQRPGQSPRRLIYKVSNWD

SGVPDRFSGSGSGTDFTLKISRVEAEDVGVYYCMQGAHWPITFGQGTRLEIK

Antibody U1-41
13 Heavy Chain DNA:
CAGGTGCAGCTGCAGGAGTCGGGCCCAGGACTGGTGAAGCCTTCACAGACCCTGTCCCTC

ACCTGCACTGTCTCTGGTGGCTCCATCAGCAGTGGTGGGTACTACTGGAGCTGGATCCGC

CAGCACCCAGGGAAGGGCCTGGAGTGGATTGGGTACATCTATTACAGTGGGAGCACCTAC

TACAACCCGTCCCTCAAGAGTCGAGTTACCATATCAGTAGACACGTCTAAGAACCAGTTC

TCCCTGAAGCTGAGCTCTGTGACTGCCGCGGACACGGCCGTGTATTTCTGTGCGAGAGAT

CGGGAACTTGAGGGTTACTCCAACTACTACGGTGTGGACGTCTGGGGCCAAGGGACCACG

GTCACCGTCTCCTC

14 Heavy Chain Protein:
QVQLQESGPGLVKPSQTLSLTCTVSGGSISSGGYYWSWIRQHPGKGLEWIGYIYYSGSTY

YNPSLKSRVTISVDTSKNQFSLKLSSVTAADTAVYFCARDRELEGYSNYYGVDVWGQGTT

VTVS

15 Light Chain DNA:
GACATCCAGATGACCCAGTCTCCATCCTCCCTGTCTGCATCTGTAGGAGACAGAGTCACC

ATCACTTGCCGGGCAAGTCAGGCCATTAGCAACTATTTAAATTGGTATCAGCAGAAACCA

GGGAAAGCCCCTAAGCTCCTGATCTATGCTGCATCCAGTTTGCAAAGTGGGGTCCCATCA

AGGTTCAGTGGCAGTGGATCTGGGACAGATTTCACTCTCACCATCAGCAGCCTGCAGCCT

GAAGATTTTGCAACTTATTACTGTCAACAGAATAATAGTCTCCCGATCACCTTCGGCCAA

GGGACACGACTGGAGATTAAA

16 Light Chain Protein:
DIQMTQSPSSLSASVGDRVTITCRASQAISNYLNWYQQKPGKAPKLLIYAASSLQSGVPS

RFSGSGSGTDFTLTISSLQPEDFATYYCQQNNSLPITFGQGTRLEIK

Antibody U1-42
17 Heavy Chain DNA:
GAGGTGCAGCTGGTGCAGTCTGGAGCAGAGGTGAAAAAGCCCGGGGAGTCTCTGAAGATC

TCCTGTAAGGGTTCTGGATACAGCTTTACCAGCTACTGGATCGGCTGGGTGCGCCAGATG

CCCGGGAAAGGCCTGGAGTGGATGGGGATCATCTATCCTGGTGACTCTGATACCAGATAC

AGCCCGTCCTTCCAAGGCCAGGTCACCATCTCAGCCGACAAGTCCATCAGCACCGCCTAC

CTGCAGTGGAGCAGCCTGAAGGCCTCGGACACCGCCATGTATTACTGTGCGAGACATGAA

AACTACGGTGACTACAACTACTGGGGCCAGGGAACCCTGGTCACCGTCTCCTCA

18 Heavy Chain Protein:
EVQLVQSGAEVKKPGESLKISCKGSGYSFTSYWIGWVRQMPGKGLEWMGIIYPGDSDTRY

SPSFQGQVTISADKSISTAYLQWSSLKASDTAMYYCARHENYGDYNYWGQGTLVTVSS

19 Light Chain DNA:
GACATCCAGATGACCCAGTCTCCATCCTCCCTGTCTGCATCTGTCCGAGACAGAGTCACC

ATCACTTGCCGGGCAAGTCAGAGCATTCGCAGCTATTTAAATTGGTATCAGCAGAAACCA

GGGAAAGCCCCTAAGCTCCTGATCTATGCTGCTTCCAGTTTCCAAAGTGGGGTCCCATCA

AGGTTCAGTGGCAGTGGATCTGGGACAGATTTCACTCTCACCATCAGCAGTCTGCAACCT

GAAGATTTTGCACTTTACTGCTGTCAACAGAGTAACGGTTCCCCGCTCACTTTCGGCGGA

GGGACCAAGGTGGAGATCAAA

-continued

20 Light Chain Protein:
DIQMTQSPSSLSASVGDRVTITCRASQSIRSYLNWYQQKPGKAPKLLIYAASSLQSGVPS

RFSGSGSGTDFTLTISSLQPEDFALYCCQQSNGSPLTFGGGTKVEIK

Antibody U1-43
21 Heavy Chain DNA:
CAGGTCCAGCTGCAGGACTCGGGCCCAGGACTGGTGAAGCCTTCACAGACCCTGTCCCTC

ACCTGCACTGTCTCTGGTGGCTCCATCAGCAGTGGTGGTTACTACTGGAGCTGGATCCGC

CAGCACCCAGGGAAGGGCCTGGAGTGGATTGGGTACATCTATTACAGTGGGAGCACCTAC

TACAACCCGTCCCTCAGGAGTCGAGTTACCATATCAGTAGACACGTCTAAGAACCAGTTC

TCCCTGAAGCTGAGCTCTGTCACTGCCGCGGACACGGCCGTGTATTACTGTGCGAGAGAT

AGAGAGAGAGAGTGGGATGATTACGGTGACCCCCAAGGTATGGACGTCTGGGGCCAAGGG

ACCACGGTCACCGTCTCCTC

22 Heavy Chain Protein:
QVQLQESGPGLVKPSQTLSLTCTVSGGSISSGGYYWSWIRQHPGKGLEWIGYIYYSGSTY

YNPSLRSRVTISVDTSKNQFSLKLSSVTAADTAVYYCARDREREWDDYGDPQGMDVWGQG

TTVTVS

23 Light Chain DNA:
GACATCCAGATGACCCAGTCTCCATCCTCCCTGTCTGCATCTGTAGGAGACAGAGTCACC

ATCACTTGCCGGGCAAGTCAGAGCATTAGCAGCTATTTACATTGGTATCAGCAGAAACCA

GGGAAAGCCCCTAAGCTCCTGATCCATGCTGCATCCAGTTTACAAAGTGGGGTCCCATCA

AGGTTCAGTGGCAGTGGATCTGGGACAGATTTCACTCTCACCATCAGTAGTCTGCAACCT

GAAGATTTTCCAACTTACTACTGTCAACAGAGTTACAGTAACCCGCTCACTTTCGGCGGA

GGGACCAAGGTGGAGATCCAA

24 Light Chain Protein:
DIQMTQSPSSLSASVGDRVTITCRASQSISSYLHWYQQKPGKAPKLLIHAASSLQSGVPS

RFSGSGSGTDFTLTISSLQPEDFATYYCQQSYSNPLTFGGGTKVEIQ

Antibody U1-44
25 Heavy Chain DNA:
GAGGTGCAGCTGGTGCAGTCTGGAGCAGAGGTGAAAAAGCCCGGCGAGTCTCTGAAGATC

TCCTGTAAGGGTTCTGGATACAGCTTTACCAGCTACTGGATCGGCTGGGTGCGCCAGATG

CCCGGGAAAGGCCTGGAGTGGATGGGGATCATCTGGCCTGGTGACTCTGATACCATATAC

AGCCCGTCCTTCCAAGGCCAGGTCACCATCTCAGCCGACAAGTCCATCAGCACCGCCTAC

CTGCAGTGGAGCAGCCTGAAGGCCTCGGACACCGCCATGTATTACTGTGCCAGACATGAA

AACTACGGTGACTACAACTACTGGGGCCAGGGAACCCTGGTCACCGTCTCCTCA

26 Heavy Chain Protein:
EVQLVQSGAEVKKPGESLKISCKGSGYSFTSYWIGWVRQMPGKGLEWMGIIWPGDSDTIY

SPSFQGQVTISADKSISTAYLQWSSLKASDTAMYYCARHENYGDYNYWGQGTLVTVSS

27 Light Chain DNA:
GACATCCAGATGACCCAGTCTCCATCCTCCCTGTCTGCATCTGTGGGAGACAGAGTCACC

ATCACTTGCCGGGCAAGTCAGAGCATTCGAAGTTATTTAAATTGGTATCAGCAGAAACCG

GGGAATGCCCCTAAACTCCTGATCTATGCTGCATCCAGTTTGCAAAGTGGGGTCCCATCA

AGGTTCAGTGGCAGTGGATCTGGGACAGATTTCACTCTCACCATCAGCAGTCTGCAACCT

GAAGATTTTGCACTTTACTACTGTCAACAGAGTATCAGTTCCCCGCTCACTTTCGGCGGA

GGGACCAAGGTGGAGATCAAA

-continued

28 Light Chain Protein:
DIQMTQSPSSLSASVGDRVTITCRASQSIRSYLNWYQQKPGNAPKLLIYAASSLQSGVPS

RFSGSGSGTDFTLTISSLQPEDFALYYCQQSISSPLTFGGGTKVEIK

Antibody (U1-45)
29 Heavy Chain DNA:
CAGGTGCAGCTGGTGCAGTCTGGGGCTGAGGTGAAGAAGCCTGGGGCCTCAGTGAAGGTC

TCCTGCAAGGCTTCTGGATACACCTTCACCAGTTATGATATCAACTGGGTGCGACAGGCC

ACTGGACAAGGGCTTGAGTGGATGGGATGGATGAACCCTAACAGTGGTGACACTGGCTAT

GCACAGGTGTTCCAGGGCAGAGTCACCATGACCTGGAACACCTCCATAAGCACAGCCTAC

ATGGAACTGAGCAGCCTGAGATCTGAGGACACGGCCGTGTATTACTGTGCGAGATTTGGG

GATCTCCCGTATGACTACAGTTACTACGAATGGTTCGACCCCTGGGGCCAGGGAACCCTG

GTCACCGTCTCCTC

30 Heavy Chain Protein:
QVQLVQSGAEVKKPGASVKVSCKASGYTFTSYDINWVRQATGQGLEWMGWMNPNSGDTGY

AQVFQGRVTMTWNTSISTAYMELSSLRSEDTAVYYCARFGDLPYDYSYYEWFDPWGQGTL

VTVS

31 Light Chain DNA:
GACATCCAGATGACCCAGTCTCCATCCTCCCTGTCTGCATCTGTAGGAGACAGAGTCACC

ATGACTTGCCGGGCAAGCCAGAGCATTAGCAGCTATTTAPATTGGTATCAGCAGAGACCA

GGGAAAGCCCCTAAGCTCCTGATCTATGCAGCATCCAGTTTGCAAAGTGGGGTCCCATCA

AGGTTCAGTGGCAGTGGATCTGGGACAGATTTCACTCTCACCATCAGCAGTCTGCAACCT

GAAGATTTTGCAACTTACTACTGTCAACAGAGTTACAGTACCCCGCTCACTTTCGCCCGA

GGGACCAAGGTGGAGATCAAA

32 Light Chain Protein:
DIQMTQSPSSLSASVGDRVTITCRASQSISSYLNWYQQRPGKAPKLLIYAASSLQSGVPS

RFSGSGSGTDFTLTISSLQPEDFATYYCQQSYSTPLTFGGGTKVEIK

Antibody (U1-46
33 Heavy Chain DNA:
CAGGTACAGCTGCAGCAGTCAGGTCCAGGACTGGTGAAGCCCTCGCAGACCCTCTCACTC

ACCTGTGCCATGTCCGGGGACAGTGTCTCTAGCAACAGTGCTGCTTGGAACTGGATCAGG

CAGTCCCCATCGAGAGGCCTTGAGTGGCTGGGAAGGACATACTACAGGTCCAAGTGGTAT

AATGATTATGCAGTATCTGTGAAAAGTCGAATAACCATCAACCCAGACACATCCAAGAAC

CAGTTCTCCCTGCAGCTGAACTCTGTGACTCCCGAGGACACGGCTGTGTATTACTGTGCA

AGAGATCTCTACGATTTTTGGAGTGGTTATCCCTACTACTACGGTATGGACGTCTGGGGC

CAAGGGACCACGGTCACCGTCTCCTC

34 Heavy Chain Protein:
QVQLQQSGPGLVKPSQTLSLTCAISGDSVSSNSAAWNWIRQSPSRGLEWLGRTYYRSKWY

NDYAVSVKSRITINPDTSKNQFSLQLNSVTPEDTAVYYCARDLYDFWSGYPYYYGMDVWG

QGTTVTVS

Antibody U1-47
35 Heavy Chain DNA:
CAGGTACAGCTGCAGCAGTCAGGTCCAGGACTGGTGAAGCCCTCGCAGACCCTCTCACTC

ACCTGTGCCATCTCCGGGGACAGTGTCTCTAGCAACAGTGCTGCTTGGAACTGGATCAGG

CAGTCCCCATCGAGAGGCCTTGAGTGGCTGGGAAGGACATACTACAGGTCCAAGTGGTAT

AATGATTATGCAGTATCTGTGAAAAGTCGAATAACCATCAACCCAGACACATCCAAGAAC

CAGTTCTCCCTGCAGCTGAACTCTGTGACTCCCGAGGACACGGCTGTGTATTACTGTGCA

```
AGAGATTACTATGGTTCGGGGAGTTTCTACTACTACTACGGTATGGACGTCTGGGGCCAA

GGGACCACGGTCACCGTCTCCTC

36 Heavy Chain Protein:
QVQLQQSGPGLVKPSQTLSLTCAISGDSVSSNSAAWNWIRQSPSRGLEWLGRTYYRSKWY

NDYAVSVKSRITINPDTSKNQFSLQLNSVTPEDTAVYYCARDYYGAGAFYYYYGMDVWGQ

GTTVTVS

37 Light Chain DNA:
GACATCCAGATGACCCAGTCTCCATCCTCCCTGTCTGCATCTGTAGGAGACAGAGTCACC

ATCACTTGCCGGGCAAGTCAGAGCATTAGCAGCTATTTAAATTGGTATCAGCAGAAACCA

GGGAAAGCCCCTAAGGTCCTGATCTATGCTGCATCCAATTTGCAAAGTGGGGTCCCATCA

AGGTTCAGTGGCAGTGGATCTGGGACAGATTTCACTCTCACCATCAGCAGTCTGCAACCT

GAAGATTTTGCAACTTACTACTGTCAACAGAGTTACAGTACCCCTCGGACGTTCGGCCAA

GGGACCAAGGTGGAAATCAAA

33 Light Chain Protein:
DIQMTQSPSSLSASVGDRVTITCRASQSISSYLNWYQQKPGKAPKVLIYAASNLQSGVPS

RFSGSGSGTDFTLTISSLQPEDFATYYCQQSYSTPRTFGQGTKVEIK

Antibody U1-48
39 Heavy Chain DNA:
CAGGTGCAGCTGCAGGAGTCGGGCCCAGGACTGGTGAAGCCTTCGGAGACCCTGTCCCTC

ACCTGCACTGTCTCTGGTGGCTCCATCAGTAGTTACTACTGGAGCTGGATCCGGCAGCCC

GCCGGGAAGGGACTGGAGTGGATTGGGCATATCTATACCAGTGGGAGCACCAACTACAAC

CCCTCCCTCAAGAGTCGAGTCACCATGTCACTAGACACGTCCAAGAACCAGTTCTCCCTG

AAGCTGAGCTCTGTGACCGCCGCGGACACGGCCCTGTATTACTGTGCGAGAGAAGCGATT

TTTGGAGTGGGCCCCTACTACTACTACGGTATGGACGTCTGGGGCCAAGGGACCACGGTC

ACCGTCTCCTC

40 Heavy Chain Protein:
QVQLQESGPGLVKPSETLSLTCTVSGGSISSYYWSWIRQPAGKGLEWIGHIYTSGSTNYN

PSLKSRVTMSVDTSKNQFSLKLSSVTAADTAVYYCAREAIFGVGPYYYYGMDVWGQGTTV

TVS

Antibody U1-49
41 Heavy Chain DNA:
CAGGTGCAGCTGGTGCAGTCTGGGGCTGAGGTGAAGAAGCCTGGGGCCTCAGTGAAGGTC

TCCTGCAAGGCTTCTGGATACACCTTCACCGGCTACTATATGCACTGGGTGCGACAGGCC

CCTGGACAAGGGCTTGAGTGGATGGGATGGATCAACCCTAATATTGGTGGCACAAACTGT

GCACAGAAGTTTCAGGGCAGGGTCACCATGACCAGGGACACGTCCATCAGCACAGCCTAC

ATGGAGCTGAGCAGGCTGAGATCTGACGACACGGCCGTGTATTACTGTGCGAGAGGGGGA

CGGTATAGCAGCAGCTGGTCCTACTACTACTACGGTATGGACGTCTGGGGCCAAGGGACC

ACGGTCACCGTCTCCTC

42 Heavy Chain Protein:
QVQLVQSGAEVKKPGASVKVSCKASGYTFTGYYMHWVRQAPGQGLEWMGWINPNIGGTNC

AQKFQGRVTMTRDTSISTAYMELSRLRSDDTAVYYCARGGRYSSSWSYYYYGMDVWGQGT

TVTVS

43 Light Chain DNA:
GATATTCTGATGACCCAGACTCCACTCTCTCTGTCCGTCACCCCTGGACAGCCGGCCTCC

ATCTCCTGCAAGTCTAGTCAGAGCCTCCTGCTTAGTGATGGAGGGACCTATTTGTATTGG
```

-continued

```
TACCTGCAGAAGCCAGGCCAGCCTCCACAGCTCCTGATCTATGAAGTTTCCAACCGGTTC

TCTGGAGTGCCAGATAGGTTCAGTGGCAGCGGGTCAGGGACAGATTTCACACTGAAAATC

AGCCGGGTGGAGGCTGAGGATGTTGGGGTTTATTACTGCATGCAAAGTATGCAGCTTCCG

ATCACCTTCGGCCAAGGGACACGACTGGAAATTAAA
```

44 Light Chain Protein:
```
DILMTQTPLSLSVTPGQPASISCKSSQSLLLSDGGTYLYWYLQKPGQPPQLLIYEVSNRF

SGVPDRFSGSGSGTDFTLKISRVEAEDVGVYYCMQSMQLPITFGQTRLEIK
```

Antibody U1-50
45 Heavy Chain DNA:
```
CAGGTGCAGCTGCAGGAGTCGGGCCCAGGACTGGTGAAGCCTTCGGAGACCCTGTCCCTC

ACCTGCACTGTCTCTGGTGGCTCCGTCAGCAGTGGTGGTTACTACTGGAGCTGGATCCGG

CAGCCCCCAGGGAAGGGACTGGAGTGGATTGGGTATATCTATTACAGTGGGAGCACCAAC

TACAACCCCTCCCTCAAGAGTCGAGTCACCATATCAGTAGACACGTCCAAGAACCAGTTC

TCCCTGAAGCTGAGCTCTGTGACCGCTGCGGACACGGCCGTGTATTACTGTGCGAGAGGG

GGGGACAGTAACTACGAGGATTACTACTACTACTACGGTATGGACGTCTGGGGCCAAGGG

ACCACGGTCACCGTCTCCTC
```

46 Heavy Chain Protein:
```
QVQLQESGPGLVKPSETLSLTCTVSGGSVSSGGYYWSWIRQPPGKGLEWIGYIYYSGSTN

YNPSLKSRVTISVDTSKNQFSLKLSSVTAADTAVYYCARGGDSNYEDYYYYGMDVWGQG

TTVTVS
```

47 Light Chain DNA:
```
GACATCCAGATGACCCAGTCTCCATCCTCCCTGTCTGCATCTGTAGGAGACAGAGTCACC

ATCACTTGCCGGGCAAGTCAGAGCATTAGCATCTATTTACATTGGTATCAGCAGAAACCA

GGGAAAGCCCCTAAGCTCTTGATCTCTGCTGCATCCAGTTTGCAAAGTGGGGTCCCGTCA

AGGTTCAGTGGCAGTGGATCTGGGACAGATTTCACTCTCACCATCAGAAGTCTGCAACCT

GAAGATTTTGCAACTTACTACTGTCAACAGAGTTACACTTCCCCGATCACCTTCGGCCAA

GGGACACGACTGGAGATTAAA
```

48 Light Chain Protein:
```
DIQMTQSPSSLSASVGDRVTITCRASQSISIYLHWYQQKPGKAPKLLISAASSLQSGVPS

RFSGSGSGTDFTLTIRSLQPEDFATYYCQQSYTSPITFGQTRLEIK
```

49 Antibody U1-51
Heavy Chain DNA:
```
CAGGTGCAGCTGCAGGAGTCGGGCCCAGGACTGGTGAAGCCTTCGGAGACCCTGTCCCTC

ACCTGCACTGTCTCTGGTGGCTCCATCAGTAGTTACTACTGGAGCTGGATCCGGCAGCCC

CCAGGGAAGGGACTGGAGTGGATTGGGTATATCTATTACAGTGGGAGCACCAACTACAAC

CCCTCCCTCAAGAGTCGAGTCACCATATCAGTAGACACGTCCAAGCACCAGTTCTCCCTG

AAGCTGAGCTCTGTGACCGCTGCGGACACGGCCGTGTATTACTGTGCGAGAGATTCGAGT

TACTATGATAGTAGTGGTTATTACTTATACTACTACGCTATGGACGTCTGGGGCCAAGGG

ACCACGGTCACCGTCTCCTC
```

50 Heavy Chain Protein:
```
QVQLQESGPGLVKPSETLSLTCTVSGGSISSYYWSWIRQPPGKGLEWIGYIYYSGSTNYN

PSLKSRVTISVDTSKHQFSLKLSSVTAADTAVYYCARDSSYYDSSGYYLYYYAMDVWGQG

TTVTVS
```

51 Light Chain DNA:
```
GACATCGTGATGACCCAGTCTCCAGACTCCCTGGCTGTGTCTCTGGGCGAGAGGGCCACC

ATCAACTGCAAGTCCAGCCAGAGTGTTTTATACAGCTCCAACAATAAGAACTACTTAGCT
```

TGGTACCAGCAGAAACCAGGACAGCCTCCTAAGCTGCTCATTTCCTGGGCATCTACCCGG

GAATCCGGGGTCCCTGACCGATTCAGTGGCAGCGGGTCTGGGACAGATTTCACTCTCACC

ATCAGCAGCCTGCAGGCTGAAGATGTGGCAGTTTATTACTGTCAGCAATATTATACTACT

CCTCTCACTTTCGGCCCTGGGACCAAAGTGGATATCAAA

52 Light Chain Protein:
DIVMTQSPDSLAVSLGERATINCKSSQSVLYSSNNKNYLAWYQQKPGQPPKLLISWASTR

ESGVPDRFSGSGSGTDFTLTISSLQAEDVAVYYCQQYYTTPLTFGPGTKVDIK

Antibody U1-53
53 Heavy Chain DNA:
GAGGTGCAACTGGTGGAGTCTGGGGGAGGCTTGGTACAGCCTGGGGGGTCCCTGAGACTC

TCCTGTGCAGCCTCTGGATTCACCTTCAGTATCTATAGCATGAACTGGGTCCGCCAGGCT

CCAGGGAAGGGGCTGGAGTGGGTTTCATACATTAGTAGTAGTAGTAGTACCATATACTAC

GCAGACTCTGTGAAGGGCCGATTCACCATCTCCAGAGACAATGCCAAGAACTCACTGTAT

CTGCAAATGAACAGCCTGAGAGACGAGGACACGGCTGTGTATTACTGTGCGAGAGATAGG

GGTGACTTCGATGCTTTTGATATCTGGGGCCAAGGGACAATGGTCACCGTCTCTTCA

54 Heavy Chain Protein:
EVQLVESGGGLVQPGGSLRLSCAASGFTFSIYSMNWVRQAPGKGLEWVSYISSSSSTIYY

ADSVKGRFTISRDNAKNSLYLQMNSLRDEDTAVYYCARDRGDFDAFDIWGQGTMVTVSS

55 Light Chain DNA:
GACATCCAGATCACCCAGTCTCCATCCTCCCTGTCTGCATCTCTAGGAGACACAGTCACC

ATCACTTGCCAGGCGAGTCAGGACATTACCAACTATTTGAATTCGTATCAGCAGAAACCA

GGGAAAGCCCCTAAGCTCCTGATCTACGATCCATCCAATTTGGAAACAGGGGTCCCATCA

AGGTTCAGTGGAAGTGGATCTGGGACAGATTTTACTTTCACCATCAGCAGCCTGCAGCCT

GAAGATATTCCAACATATAACTGTCAACACTGTGAAAATTTCCCGATCACCTTCGGCCAA

GGGACACGACTGGAGATTAAA

56 Light Chain Protein:
DIQMTQSPSSLSASVGDRVTITCQASQDITNYLNWYQQKPGKAPKLLIYDASNLETGVPS

RFSGSGSGTDFTFTISSLQPEDIATYNCQQCENFPITFGQGTRLEIK

Antibody U1-55
57 Light Chain DNA:
GATATTGTGATGACTCAGTCTCCACTCTCCCTGCCCGTCACCCCTGGAGAGCCGGCCTCC

ATCTCCTGCAGGTCTAGTCAGAGCCTCCTGTATAGTAATGGATACAAGTATTTGGATTGG

TACCTGCAGAAGCCAGGGCAGTCTCCACAGCTCCTGATCTATTTGGGTTCTAATCGGGCC

TCCGGGGTCCCTGACAGGTTCAGTGGCAGTGGATCAGGCACAGATTTTACACTGAAAATC

AGCAGAGTGGAGGCTGAGGATGTTGGGGTTTATTATTGCATGCAGGCTCTACAAACTCCG

ATCACCTTCGGCCAAGGGACACGACTGGAGATTAAA

58 Light Chain Protein:
DIVMTQSPLSLPVTPGEPASISCRSSQSLLYSNGYKYLDWYLQKPGQSPQLLIYLGSNRA

SGVPDRFSGSGSGTDFTLKISRVEAEDVGVYYCMQALQTPITFGQGTRLEIK

Antibody (U1-55.1)
59 Heavy Chain DNA:
CAGGTGCAGCTGCAGGAGTCGGGCCCAGGACTGGTGAAGCCTTCGGAGACCCTGTCCCTC

ACCTGCACTGTCTCTGGTGGCTCCGTCAGCAGTGGTGGTTACTACTGGAACTGGATCCGG

CAGCCCCCAGGGAAGGGACTGGAGTGGATTGGGTATATCAATTACAGTGGGAGCACCAAC

TACAACCCCTCCCTCAAGAGTCGAGTCACCATATCAGTAGACACGTCCAAGAACCAGTTC

TCCCTGAAGCTGAGCTCTGTGACCGCTGCCGACACGGCCGTGTATTACTGTGCGAGAGAT

```
CGAGAACTGGAACTTTACTACTACTACTACGGTATGGACGTCTGGGGCCAAGGGACCACG

GTCACCGTCTCCTC

60 Heavy Chain Protein:
QVQLQESGPGLVKPSETLSLTCTVSGGSVSSGGYYWNWIRQPPGKGLEWIGYINYSGSTN

YNPSLKSRVTISVDTSKNQFSLKLSSVTAADTAVYYCARDRELELYYYYYGMDVWGQGTT

VTVS

Antibody (U1-57)
61 Heavy Chain DNA:
CAGGTGCAGCTGCAGGAGTCGGGCCCAGGACTGGTGAAGCCTTCTGAGACCCTGTCCCTC

ACCTGCACTGTCTCTGGTGGCTCCGTCAGCAGTGGTGGTTACTACTGGAACTGGATCCGG

CAGCCCCCAGGGAAGGGACTGGAGTGGATTGGGTATATCAATTACAGTGGGAGCACCAAC

TACAACCCCTCCCTCAAGAGTCGAGTCACCATATCAGTAGACACGTCCAAGAACCAGTTC

TCCCTGAAGCTGAGCTCTGTGACCGCTGCGGACACGGCCGTGTATTACTGTGCGAGAGAT

CGAGAACTGGAACTTTACTACTACTACTACGGTATGGACGTCTGGGGCCAAGGGACCACG

GTCACCGTCTCCTC

62 Heavy Chain Protein:
QVQLQESGPGLVKPSETLSLTCTVSGGSVSSGGYYWNWIRQPPGKGLEWIGYINYSGSTN

YNPSLKSRVTISVDTSKNQFSLKLSSVTAADTAVYYCARDRELELYYYYYGMDVWGQGTT

Antibody U1-57.1
63 Light Chain DNA:
GATATTGTGATGACTCAGTCTCCACTCTCCCTGCCCGTCACCCCTGGAGAGCCGGCCTCC

ATCTCCTGCAGGTCTAGTCAGAGCCTCCTGTATAGTAATGGATACAAGTATTTGGATTGG

TACCTGCAGAAGCCAGGGCAGTCTCCACAGCTCATGATCTATTTGGGTTCTAATCGGGCC

TCCGGGGTCCCTGACAGGTTCAGTGGCAGTGGATCAGGCACAGATTTTACACTGAAAATC

AGCAGAGTGGAGGCTGAGGATGTTGGGGTTTATTATTGCATGCAGGCTCTACAAACTCCG

ATCACCTTCGGCCAAGGGACACGACTGGAGATTAAA

64 Light Chain Protein:
DIVMTQSPLSLPVTPGEPASISCRSSQSLLYSNGYKYLDWYLQKPGQSPQLMIYLGSNRA

SGVPDRFSGSGSGTDFTLKISRVEAEDVGVYYCMQALQTPITFGQGTRLEIK

Antibody U1-58
65 Heavy Chain DNA:
GAGGTGCAGCTGGTGGAGTCTGGGCCAGGCGTGGTCCAGCCTGGGAGGTCCCTGAGACTC

TCCTGTGCAGCCTCTGGATTCAGCTTCAGTAGCTATGCCATGCACTGGGTCCGCCAGGCT

CCAGGCAAGGGGCTGGAGTGGGTGCCACTTATATCGTATCATGGAACTAATAAATACTAT

GCAGACTCCGTGAAGGGCCGATTCACCATCTGCAGAGACAATTCCAACAACACGCTCTAT

CTGCAAATGAACAGCCTGAGAGCCCAGGACACGGCTGTCTATTACTGTGCGAGAGCACCT

CGCCTTCACTACTACTACGGTATGGACGTCTGCGGCCAAGGGACCACGGTCACCGTCTCC

TCA

66 Heavy Chain Protein:
QVQLVESGGGVVQPGRSLRLSCAASGFTFSSYGMHWVRQAPGKGLEWVAVIWYDGSNKYY

ADSVKGRFTISRDNSKNTLYLQMNSLRAEDTAVYYCARAARLDYYYGMDVWGQGTTVTVS

S

67 Light Chain DNA:
GACATCCAGATGACCCAGTCTCCATCCTCCCTGTCTGCATCTCTAGGAGAGAGAGTCTCC

ATCACTTGCCGGCCAAGTCAGACCATTAACAGCTATTTAAATTGGTTTCAGCAGAAGCCA

GGGAAAGCCCCTCAGCTCCTGATCTTTGGTGCATCCGGTTTCCAAACTGGCGTCCCATCA
```

AGGTTCAGTCGCAGTGGATCTGGGACAGATTTCACTCTCACCATCAACAGTCTGCAACCT

GAAGATTTTGCAACTTACTACTGTCAACAGAGTTACAGTTCCCCGCTCACCTTCCGCCAA

GGGACACGACTGGAGATTAAA

68 Light Chain Protein:
DIQMTQSPSSLSASVGDRVSITCRASQSINSYLNWFQQKPGKAPQLLIFGASGLQSGVPS

RFSGSGSGTDFTLTINSLQPEDFATYYCQQSYSSPLTFGQGTRLEIK

Antibody U1-59
69 Heavy Chain DNA:
CAGGTGCAGCTACAGCAGTGGGGCGCAGGACTGTTGAAGCCTTCGGAGACCCTGTCCCTC

ACCTGCGCTGTCTATGGTGGGTCCTTCAGTGGTTACTACTGGAGCTGGATCCGCCAGCCC

CCAGGGAAGGGGCTGGAGTGGATTGGGGAAATCAATCATAGTGGAAGCACCAACTACAAC

CCGTCCCTCAAGAGTCGAGTCACCATATCAGTAGAAACGTCCAAGAACCAGTTCTCCCTG

AAGCTGAGCTCTGTGACCGCCGCGGACACGGCTGTGTATTACTGTGCGAGAGATAAGTGG

ACCTGGTACTTCGATCTCTGGGGCCGTGGCACCCTGGTCACTGTCTCCTCA

70 Heavy Chain Protein:
QVQLQQWGAGLLKPSETLSLTCAVYGGSFSGYYWSWIRQPPGKGLEWIGEINHSGSTNYN

PSLKSRVTISVETSKNQFSLKLSSVTAADTAVYYCARDKWTWYFDLWGRGTLVTVSS

71 Light Chain DNA:
GACATCGAGATGACCCAGTCTCCAGACTCCCTGGCTGTGTCTCTGGGCGAGAGGGCCACC

ATCAACTGCAGGTCCAGCCAGAGTGTTTTATACAGCTCCAGCAATAGGAACTACTTAGCT

TGGTACCAGCAGAACCCAGGACAGCCTCCTAAGCTGCTCATTTACTGGGCTTCTACCCGG

GAATCCGGGGTCCCTGACCGATTCAGTGGCAGCGGGTCTGGGACAGATTTCACTCTCACC

ATCAGCAGCCTGCAGGCTGAAGATGTGGCAGTTTATTACTGTCAGCAATATTATAGTACT

CCTCGGACGTTCGGCCAAGGGACCAAGGTGGAAATCAAA

72 Light Chain Protein:
DIEMTQSPDSLAVSLGERATINCRSSQSVLYSSSNRNYLAWYQQNPGQPPKLLIYWASTR

ESGVPDRFSGSGSGTDFTLTISSLQAEDVAVYYCQQYYSTPRTFGQGTKVEIK

Antibody U1-52
73 Heavy Chain DNA:
CAGGTGCAGCTGCAGGAGTCGGGCCCAGGACTGGTGAAGCCTTCACAGACCCTGTCCCTC

ACCTGCACTGTCTCTGGTGGCTCCATCAGCAGTGGTGGTTACTACTGGAGCTGGATCCGC

CAGCACCCAGGGAAGGGCCTGGAGTGGATGGGGAACATCTATTACAGTGGGAGCACCTAC

TACAACCCGTCCCTCAAGAGTCGAGTTACCATATCAGTAGACACGTCTGAGAACCAGTTC

TCCCTGAAGCTGAACTCTGTGACTGCCGCGGACACGGCCGTATATTACTGTGCGAGAGGG

GGAACTGGAACCAATTACTACTACTACTACGGTATGGACGTCTGGGGCCAAGGGACCACG

GTCACCGTCTCCTC

74 Heavy Chain Protein:
QVQLQESGPGLVKPSQTLSLTCTVSGGSISSGGYYWSWIRQHPGKGLEWMGNIYYSGSTY

YNPSLKSRVTISVDTSENQFSLKLNSVTAADTAVYYCARGGTGTNYYYYYGMDVWGQGTT

VTVS

75 Light Chain DNA:
GAAATTGTGTTGACGCAGTCTCCAGGCACCCTGTCTTTGTCTCCAGGGGAAAGAGCCACC

CTCTCCTGCAGGGCCAGTCAGAGTGTTAGCAGCAGCTACTTAGCCTGGTACCAGCAGAAA

CCTGGCCAGGCTCCCAGGCTCCTCATCTATGGTGCATCCAGCTGGGCCACTGGCATCCCA

AACAGGTTCAGTGGCAGTGGGTCTGGGACAGACTTCACTCTCACCATCAGCAGACTGGAG

```
                       -continued
CCTGAAGATTTTGCAGTGTATTACTGTCAGCAGTATGGTAGCTCACCGCTCACTTTCGGC

GGAGGGACCAAGGTGGAGATCAAA

76 Light Chain Protein:
EIVLTQSPGTLSLSPGERATLSCRASQSVSSSYLAWYQQKPGQAPRLLIYGASSWATGIP

NRFSGSGSGTDFTLTISRLEPEDFAVYYCQQYGSSPLTFGGGTKVEIK

Antibody U1-61
77 Heavy Chain DNA:
CAGGTGCAGCTGCAGGAGTCGGGCCCAGGACTGGTGAAGCCTTCACAGACCCTGTCCCTC

ACCTGCACTGTCTCTGGTGTCTCCATCAGCAGTGGTGGTTACTACTGGAGCTGGATCCGC

CAGCACCCAGGGATGGGCCTGGAGTGGATTGGGTACATCTATTACAGTGGGAGCACCTAC

TACAACCCGTCCCTCAAGAGTCGAGTCACCATATCAGAAGACACGTCTAAGAACCAGTTC

TCCCTGAAGCTGAGCTCTGTGACTGCCGCGGACACGGCCGTGTATTACTGTGCGAGAGAT

TCCGAGTCCGAGTATAGCAGCTCGTCGAACTACGGTATGGACGTCTGGGGCCAAGGGACC

ACGGTCACCGTCTCCTC

78 Heavy Chain Protein:
QVQLQESGPGLVKPSQTLSLTCTVSGVSISSGGYYWSWIRQHPGMGLEWIGYIYYSGSTY

YNPSLKSRVTISEDTSKNQFSLKLSSVTAADTAVYYCARDSESEYSSSSNYGMDVWGQGT

TVTVS

Antibody U1-61.1
79 Heavy Chain DNA:
CAGGTGCAGCTGCAGGAGTCSGGCCCAGGACTGGTGAAGCCTTCACAGACCCTGTCCCTC

ACCTGCACTGTCTCTGGTGTCTCCATCAGCAGTGGTGGTTACTACTGGAGCTGGATCCGC

CACCACCCAGGGATGGGCCTGGAGTGGATTGGGTACATCTATTACAGTGGGAGCACCTAC

TACAACCCGTCCCTCAAGAGTCGAGTCACCATATCAGAACACACGTCTAAGAACCAGTTC

TCCCTGAAGCTGAGCTCTGTGACTGCCGCGGACACGGCCGTGTATTACTGTGCGAGAGAT

TCCGAGTCCGAGTATAGCAGCTCGTCGAACTACGGTATGGACGTCTCGGGCCAAGGGACC

ACGCTCACCGTCTCCTC

80 Heavy Chain Protein:
QVQLQESGPGLVKPSQTLSLTCTVSGVSISSGGYYWSWIRQHPGMGLEWIGYIYYSGSTY

YNPSLKSRVTISEDTSKNQFSLKLSSVTAADTAVYYCARDSESEYSSSSNYGMDVWGQGT

TVTVS

81 Light Chain DNA:
GACATCCAGATGACCCAGTCTCCATCCTCCCTGTCTGCATCTGTAGGAGACAGAATCACC

ATCACTTGCCGGGCAAGTCAGACCATTAGCAGCTATTTAAATTGGTATCAGCAGAAACCA

GGGAAAGCCCCTAAGCTCCTGATCTATGCTGCATCCAGTTTGCAAGGTGGGGTCCCATCA

AGGTTCAGTGGCAGTGTATCTGGGACAGATTTCACCCTCACCGTCAGCAGTCTGCAACCT

GAAGATTTTGCAACTTACTACTGTCAACAGAGTTACAGTAACCCGCTCACTTTCGGCGGA

GGGACCAAGGTGGAGATCAAA

82 Light Chain Protein:
DIQMTQSPSSLSASVGDRITITCRASQTISSYLNWYQQKPGKAPKLLIYAASSLQGGVPS

RFSGSVSGTDFTLTVSSLQPEDFATYYCQQSYSNPLTFGGGTKVEIK

Antibody U1-62 (2.9.1)
83 Heavy Chain DNA:
GAGGTGCAGCTGGTGCAGTCTGGAGCAGAGGTGAAAAAGCCCGGGGAGTCTCTGAAGATC

TCCTGTAAGGGTTCTGGATACAGTTTTACCAGCTACTGGATCGGCTGGGTGCGCCAGATG

CCCGGGAAAGGCCTGGAGTGGATGGGGATCATCTATCCTGGTGACTCTGATACCAGATAC
```

```
AGCCCGTCCTTCCAAGGCCAGGTCACCATGTCAGCCGACAAGTCCATCAGTACCGCCTAC

CTGCAGCTGAGCAGCCATGAAGGCCTCGGACACCGCCATGTATTACTGTGCGAGACAGAT

GGCTGGAAACTACGTACATCACGGGTGATCGAGACGTCCTGGGGCCAAGGGACCACGGTC

ACCGTCTCCTC

84 Heavy Chain Protein:
EVQLVQSGAEVKKPGESLKISCKGSGYSFTSYWIGWVRQMPGKGLEWMGIIYPGDSDTRY

SPSPQGQVTMSADKSISTAYLQLSSHEGLGHRHVLLCETDGWKLRTSRVIETSWGQGTTV

TVS

85 Light Chain DNA:
GAAATTGTGTTGACGCAGTCTCCAGGCACCCTGTCTTTGTCTCCAGGGGAAAGAGCCACC

CTCTCCTGCAGGGCCAGTCAGAGTGTTATCAGCATCTACTTAGCCTGGTACCAGCAGAAA

CCTGGCCAGGCTCCCAGGCTCCTCATCTATGGTGCATCCAGCAGGGCCACTGGCATCCCA

GACAGGTTCAGTGGCAGTGGGTCTGGGACAGACTTCACTCTCACCATCAGCAGACTGGAG

CCTGAAGATTTTGCAGTGTATTACTGTCAGCAGTATGGTAGCTCACCGTGCAGTTTTGGC

CAGGGGACCAAACTGGAGATCAAA

86 Light Chain Protein:
EIVLTQSPGTLSLSPGERATLSCRASQSVISIYLAWYQQKPGQAPRLLIYGASSRATGIP

DRFSGSGSGTDFTLTISRLEPEDFAVYYCQQYGSSPCSFGQGTKLEIK

Antibody U1-2
87 Heavy Chain DNA:
CAGGTGCAGCTGCAGGAGTCGGGCCCAGGACTGGTGAAGCCTTCACAGACCCTGTCCCTC

ACCTGCACTGTCTCTGGTGGCTCCATCAGCAGTGGTGATTACTACTGGAGCTGGATCCGC

CAGCACCCAGGGAAGGGCCTGGAGTGGATTGGGTACATCTATTACAGTGGGAGCACCTAC

TACAACCCGTCCCTCAGGAGTCGAGTTACCATATCAGTAGACACGTCTAAGAACCAGTTC

TCCCTGAAGCTGAGCTCTGTGACTGCCGCGGACACGGCCGTGTATTACTGTGCGAGAGCG

GATTACGATTTTTGGAGTGGTTATTTTGACTACTGGGGCCAGGGAACCCTGGTCACCGTC

TCCTCA

88 Heavy Chain Protein:
QVQLQESGPGLVKPSQTLSLTCTVSGGSISSGDYYWSWIRQHPGKGLEWIGYIYYSGSTY

YNPSLRSRVTISVDTSKNQFSLKLSSVTAADTAVYYCARADYDFWSGYFDYWGQGTLVTV

SS

89 Light Chain DNA:
GACATCCAGATGACCCAGTCTCCATCCTCCCTGTCTGCATCTGTAGGAGACAGAGTCACC

ATCACTTGCCGGGCAAGTCAGGGCATTAGAAATGATTTAGGCTGGTATCAGCAGATACCT

GGGAAAGCCCCTAAGCGCCTGATCTATGCTGCATCCAGTTTGCAAAGTGGGGTCCCATCA

AGGTTCAGCGGCAGTGGATCTGGGACAGAATTCACTCTCACAATCAACAGCCTGCAGCCT

GAAGATTTTGCAACTTATTACTGTCTACAGCATAATGGTTACCCGTGGACGTTCGGCCAA

GGGACCAAGGTGGAAATCAAAC

90 Light Chain Protein:
DIQMTQSPSSLSASVGDRVTITCRASQGIRNDLGWYQQIPGKAPKRLIYAASSLQSGVPS

RFSGSGSGTEFTLTINSLQPEDFATYYCLQHNGYPWTFGQGTKVEIK

Antibody U1-7
91 Heavy Chain DNA:
CAGGTGCAGCTGCAGGAGTCGGGCCCAGGACTGGTGAAGCCTTCACAGACCCTGTCCCTC

ACCTGCACTGTCTCTGGTGGCTCCATCAGCAGTGGTGATTACTACTGGAGCTGGATCCGC

CAGCACCCAGGGAAGGGCCTGGAGTGGATTGGATACATCTATTACAGTGGGAGCACCTAC
```

TACAACCCGTCCCTCAAGAGTCGAGTTACCATATCAGTAGACACGTCTAAGAACCAGTTC

TCCCTGAAGCTGAGCTCTGTGACTGCCGCGGACACGGCCGTGTATTACTGTGCGAGAGCG

GATTACGATTTTTGGAGTGGTTATTTTGACTACTGGGGCCAGGGAACCCTGGTCACCGTC

TCCTCA

92 Heavy Chain Potein:
QVQLQESGPGLVKPSQTLSLTCTVSGGSISSGDYYWSWIRQHPGKGLEWIGYIYYSGSTY

YNPSLKSRVTISVDTSKNQFSLKLSSVTAADTAVYYCARADYDFWSGYFDYWGQGTLVTV

SS

93 Light Chain DNA:
GACTTCCAGATGACCCAGTCTCCATCCTCCCTGTCTGCATCTGTAGGAGACAGAGTCACC

ATCACTTGCCGGGCAAGTCAGGACATTCGAAATGATTTAGGCTGGTATCGGCAGAAACCT

GGGAAAGCCCCTAAGCGCCTGATCTATGCTGCATCCAGTTTGCAAAGTGGGGTCCCATCA

AGGTTCAGCGGCAGTGGATCTGGGACAGAATTCACTCTCACAATCAGCAGCCTGCAGCCT

GAAGATTTTGCAACTTATTACTGTCTACAGCATAATAGTTACCCGTGGACGTTCGGCCAA

GGGACCAAGGTGGAAATCAAAC

94 Light Chain Protein:
DFQMTQSPSSLSASVGDRVTITCRASQDIRNDLGWYRQKPGKAPKRLIYAASSLQSGVPS

RFSGSGSGTEFTLTISSLQPEDFATYYCLQHNSYPWTFGQGTKVEIK

Antibody U1-9
95 Heavy Chain DNA:
CAGGTGCAGCTGCAGGAGTCGGGCCCAGGACTGGTGAAGCCTTCACAGACCCTGTCCCTC

ACCTGCACTGTCTCTGGTGGCTCCATCAGCAGTGGTGATTACTACTGGAGCTGGATCCGC

CAGCACCCAGGGAAGGGCCTGGAGTGGATTGGATACATCTATTACAGTGGGAGCACCTAC

TACAACCCGTCCCTCAAGAGTCGAGTTACCATATCAATAGACACGTCTAAGAACCAGTTC

TCCCTGAAGCTGAGCTCTGTGACTGCCGCGGACACGGCCGTGTATTACTGTGCGAGAGCG

GATTACGATTTTTGGAATGGTTATTTTGACTACTGGGGCCAGGGAACCCTGGTCACCGTC

TCCTCA

96 Heavy Chain Protein:
QVQLQESGPGLVKPSQTLSLTCTVSGGSISSGDYYWSWIRQHPGKGLEWIGYIYYSGSTY

YNPSLKSRVTISIDTSKNQFSLKLSSVTAADTAVYYCARADYDFWNGYFDYWGQGTLVTV

SS

97 Light Chain DNA:
GACATCCAGATGACCCAGTCTCCATCCTCCCTGTCTGCATCTGTAGGAGACAGAGTCACC

ATCACTTGCCGGGCAAGTCAGGACATTAGAAATGATTTAGGCTGGTATCGGCAGAAACCT

GGGAAAGCCCCTAAGCGCCTGATCTATGCTGCATCCAGTTTGCAAAGTGGGGTCCCATCA

AGGTTCAGCGGCAGTGGATCTGGGACAGAATTCACTCTCACAATCAGCAGCCTGCAGCCT

GAAGATTTTGCAACTTATTACTGTCTACAGCATAATAGTTACCCGTGGACGTTCGGCCAA

GGGACCAAGGTGGAAATCAAA

98 Light Chain Protein:
DIQMTQSPSSLSASVGDRVTITCRASQDIRNDLGWYRQKPGKAPKRLIYAASSLQSGVPS

RFSGSGSGTEFTLTISSLQPEDFATYYCLQHNSYPWTFGQGTKVEIK

Antibody U1-10
99 Heavy Chain DNA:
CAGGTGCAGCTGCAGGAGTCGGGCCCAGGACTGGTGAAGCCTACACAGACCCTGTCCCTC

ACCTGCACTGTCTCTGGTGGCTCCATCAGCAGTGGTGATTACTACTGGAGCTGGATCCGC

-continued
CACCACCCAGGGAAGGGCCTGGAGTGGATTGGGTACATCTATTACAGTGGGAGCACCTAC

TACAACCCGTCCCTCAAGAGTCGACTTACCATATCAGTAGACACGTCTAAGAACCAGTTC

TCCCTGAAGCTGAGCTCTGTGACTGCCGCGGACACGGCCGTGTATTACTGTGCGAGAGCA

GATTACGATTTTTGGAGTGGTTACTTTGACTACTGGGGCCAGGGAACCCTGGTCACCGTC

TCCTCA

100 Heavy Chain Protein:
QVQLQESGPGLVKPTQTLSLTCTVSGGSISSGDYYWSWIRQHPGKGLEWIGYIYYSGSTY

YNPSLKSRLTISVDTSKNQFSLKLSSVTAADTAVYYCARADYDFWSGYFDYWGQGTLVTV

SS

101 Light Chain DNA:
GACATCCAGATGACCCAGTCTCCATCCTCCCTGTCTGCATCTGTAGGAGACAGAGTCACC

ATCACTTGCCGGGCAAGTCAGGGCATTAGAAATGATTTAGGCTGGTATCAGCAGAAACCA

GGGAAAGCCCCTAAGCGCCTGATCTATGCTGCATCCAGTTTGCAAAGTGGGGTCCCATCA

AGGTTCAGCGGCAGTGGATCTGGGACAGAATTCACTCTCACAATCAGCAGCCTGCAGCCT

GAAGATTTTGCAACTTATTACTGTCTACAGCATAATAATTACCCGTGGACGTTCGGCCAA

GGGACCAAGGTGGAAATCAAA

102 Light Chain Protein:
DIQMTQSPSSLSASVGDRVTITCRASQGIRNDLGWYQQKPGKAPKRLIYAASSLQSGVPS

RFSGSGSGTEFTLTISSLQPEDFATYYCLQHNNYPWTFGQGTKVEIK

Antibody U1-12
103 Heavy Chain DNA
CAGGTGCAGCTGCAGGAGTCGGGCCCAGGACTGGTGAAGCCTTCACAGACCCTGTCCCTC

ACCTGCACTGTCTCTGGTGGCTCCATCAGTAGTGGTGATTACTACTGGAGCTGGATCCGC

CAGCACCCAGGGAAGGGCCTGGAGTGGATTGGGTACATCTATTACAGTGGGAGCACCTAC

TACAACCCGTCCCTCAAGAGTCGAGTTACCATATCAGTAGACACGTCTAAGAACCAGTTC

TCCCTGAAGTTGAGCTCTGTGACTGCCGCGGACACGGCCGTGTATTACTGTGCGAGAGCC

GATTACGATTTTTGGAGTGGTTATTTTGACTACTGGGGCCAGGGAACCCTGGTCACCGTC

TCCTCA

104 Heavy Chain Protein:
QVQLQESGPGLVKPSQTLSLTCTVSGGSISSGDYYWSWIRQHPGKGLEWIGYIYYSGSTY

YNPSLKSRVTISVDTSKNQFSLKLSSVTAADTAVYYCARADYDFWSGYFDYWGQGTLVTV

SS

105 Light Chain DNA:
GACATCCAGATGACCCAGTCTCCATCCTCCCTGTCTGCATCTGTAGGAGACAGAGTCACC

ATCACTTGCCGGGCAAGTCAGGGCATTAGAAATGATTTAGGCTGGTATCAGCAGAAACCA

GGGAAAGCCCCTAAGCGCCTGATCTATGCTGCATCCAGTTTGCAAAGTGGGGTCCCATCA

AGGTTCAGCGGCAGTGGATCTGGGACAGAATTCACTCTCACAATCAGCAGCCTGCAGCCT

GAAGATTTTGCAACTTATTACTGTCTACAGCATAATAATTACCCGTGGACGTTCGGCCAA

GGGACCAAGGTGGAAATCAAA

106 Light Chain Protein:
DIQMTQSPSSLSASVGDRVTITCRASQGIRNDLGWYQQKPGKAPKRLIYAASSLQSGVPS

RFSGSGSGTEFTLTISSLQPEDFATYYCLQHNNYPWTFGQGTKVEIK

Antibody U1-13
107 Heavy Chain DNA:
CAGGTGCAGCTGCAGGAGTCGGGCCCAGGACTGGTGAAGCCTTCACAGACCCTGTCCCTC

ACCTGCACTGTCTCTGGTGGCTCCATCAGCAGTGGTGGTTACTACTGGAGCTGGATCCGC

-continued

```
CAGCACCCAGGGAAGGGCCTGGAGTGGATTGGGTACATCTATTACAGTGGGAGCACCTAC

TACAACCCGTCCCTCAAGAGTCGAGTTACCATATCAGTAGACACGTCTAAGAACCAGTTC

TCCCTGAAGCTGAGCTCTGTGACTGCCGCGGACACGGCCGTGTATTACTGTGCGAGAGAG

GACGACGGTATGGACGTCTGGGGCCAAGGGACCACGGTCACCGTCTCCTCA

108 Heavy Chain Protein:
QVQLQESGPGLVKPSQTLSLTCTVSGGSISSGGYYWSWIRQHPKGLEWIGYIYYSGSTY

YNPSLKSRVTISVDTSKNQFSLKLSSVTAADTAVYYCAREDDGMDVWGQGTTVTVSS

109 Light Chain DNA:
GATATTGTGATGACTCAGTCTCCACTCTCCCTGCCCGTCACCCCTGGAGAGCCGGCCTCC

ATTTCCTGCAGGTCTAGTCAGAGCCTCCTGCATAGTAATGGATACAACTATTTGGAATGG

TACCTGCAGAAGCCAGGGCAGTCCCCACAGTTCATGATTTATTTCGGGTCTAATCGGGCC

TCCGGGGTCCCTGACAGGTTCAGTGGCAGTCGATCAGGCACAGATTTTACACTGAAAATC

ACCAGAGTGGAGGCTGAGGATGTTCGGGTTTATTACTGCATGCAAGCTCTACAAACTCCG

ATCACCTTCGGCCAAGGGACACGACTGGAGATTAAA

110 Light Chain Protein:
DIVMTQSPLSLPVTPGEPASISCRSSQSLLHSNGYNYLEWYLQKPGQSPQFMIYLGSNRA

SGVPDRFSGSGSGTDFTLKISRVEAEDVGVYYCMQALQTPITFGQGTRLEIK

Antibody U1-14
111 Heavy Chain DNA:
CAGGTGCAGCTGCAGGAGTCGGGCCCAGGACTGGTGAAGCCTTCACAGACCCTGTCCCTC

ACCTGCACTGTCTCTGGTGGCTCCATCAGCAGTGGTGATTACTACTGGAGCTGGATCCGC

CAGTACCCAGGGAAGGGCCTGGAGTGGATTGGGTACATCTATTACAGTGGGAGCACCTAC

TACAACCCGTCCCTCAAGAGTCGAGTTACCATATCAGTAGACACGTCTAAGAACCAGTTC

TCCCTGAAGCTGAGGTCTGTGACTGCCGCGGACACGGCCGTGTATTACTGTGCGAGAGCG

GATTACGATTTTTGGAGTGGTTATTTTGACTACTGGGGCCAGGGAACCCTGGTCACCGTC

TCCTCA

112 Heavy Chain Protein:
QVQLQESGPGLVKPSQTLSLTCTVSGGSISSGDYYWSWIRQYPGKGLEWIGYIYYSGSTY

YNPSLKSRVTISVDTSKNQFSLKLRSVTAADTAVYYCARADYDFWSGYFDYWGQGTLVTV

SS

113 Light Chain DNA:
GACATCCAGATGACCCAGTCTCCATCCTCCCTGTCTGCATCTGTAGGAGACAGAGTCACC

ATCACTTGCCGGGCAAGTCAGGGCATTAGAAATGATTTAGGCTGGTATCAGCAGAAACCA

GGGAAAGCCCCTAAGCGCCTGATCTATGCTGCATCCAGTTTGCAAAGTGGGGTCCCATCA

AGGTTCAGCGGCAGTGGATCTGGGACAGAATTCACTCTCACAATCAGCAGCCTGCAGCCT

GAAGATTTTGCAACTTATTACTGTCTACAGCATAATACTTACCCGTGGACGTTCGGCCAA

GGGACCAAGGTGGAAATCAAAC

114 Light Chain Protein:
DIQMTQSPSSLSASVGDRVTITCRASQGIRNDLGWYQQKPGKAPKRLIYAASSLQSGVPS

RFSGSGSGTEFTLTISSLQPEDFATYYCLQHNTYPWTFGQGTKVEIK

Antibody U1-15
115 Heavy Chain DNA:
CAGGTGCAGCTGCAGGAGTCGGGCCCAGGACTGGTGAAGCCTTCGGAGACCCTGTCCCTC

ACCTGCACTGTCTCTGGTGGCTCCGTCAGCAGTGGTGGTTACTACTGGAGCTGGATCCGG

CAGCCCCCAGGGAAGGGACTGGAGTGGATTGGGTATATCTATTACAGTGGGAGCACCAAC
```

TACAACCCCTCCCTCAAGAGTCGAGTCACCATATCAGTAGACACGTCCAAGAACCAGTTC

TCCCTGAAGCTGAGCTCTGTGACCGCTGCGGACACGGCCGTGTATTACTGTGCGAGAGAT

GGGGACGTGGATACAGCTATGGTCGATGCTTTTGATATCTGGGGCCAAGGGACAATGGTC

ACCGTCTCCTCA

116 Heavy Chain Protein:
QVQLQESGPGLVKPSETLSLTCTVSGGSVSSGGYYWSWIRQPPGKGLEWIGYIYYSGSTN

YNPSLKSRVTISVDTSKNQFSLKLSSVTAADTAVYYCARDGDVDTAMVDAFDIWGQGTMV

TVSS

117 Light Chain DNA:
GAAATTGTATTGACGCAGTCTCCAGGCACCCTGTCTTTGTCTCCAGGGGAAAGAGCCACC

CTCTCCTGCAGGGCCAGTCAGAGTTTAAGCGGCAACTACTTAGCCTGGTACCAGCAGAAG

CCTGGCCAGGCTCCCAGGCTCATCATCTGTGGTGCATCCAGCAGGGCCACTGGCATCCCA

GACAGGTTCAGTGGCAGTGGGTCTGGGACAGACTTCACTCTCACCATCACAAGACTGGAG

CCTGAAGATTTTGCAGTGTATTACTGTCAGCAGTATGATAGGTCACCGCTCACTTTCGGC

GGAGGGACCAAGGTGGAGATCAAA

118 Light Chain Protein:
EIVLTQSPGTLSLSPGERATLSCRASQSLSGNYLAWYQQKPGQAPRLIICGASSRATGIP

DRFSGSGSGTDFTLTITRLEPEDFAVYYCQQYDRSPLTFGGGTKVEIK

Antibody U1-19
119 Heavy Chain DNA:
CAGGTGCAGGTGCAGGAGTCGGGCCCAGGACTGGTGAAGCCTTCACAGACCCTGTCCCTC

ACCTGCACTGTCTCTGGTGGCTCCATCAGCAGTGGTGATTACTACTGGAGCTGGATCCGC

CAGCACCCAGGGAAGGGCCTGGAGTGGATTGGGTACATCTATTACAGTGGGAGCACCTAC

TACAACCCGTCCCTCAAGAGTCGAGTTACCATATCAGTAGACACGTCTAAGAACCAGTTC

TCCCTGAAGCTGAGCTCTGTGACTGCCGCGGACACGGCCGTGTATTACTGTGCGAGAGGA

GATTACGATTTTTGGAGTGGAGAGTTTGACTACTGGGGCCAGGGAACCCTGGTCACCGTC

TCCTCA

120 Heavy Chain Protein:
QVQLQESGPGLVKPSQTLSLTCTVSGGSISSGDYYWSWIRQHPGKGLEWIGYIYYSGSTY

YNPSLKSRVTISVDTSKNQFSLKLSSVTAADTAVYYCARGDYDFWSGEFDYWGQGTLVTV

SS

Antibody U1-20
121 Heavy Chain DNA:
CAGGTCCAGCTGCAGGAGTCGGGCCCAGGACTGGTGAAGCCTTCACAGACCCTGTCCCTC

ACCTGCACTGTCTCTGGTGGCTCCATCAGCAGTGGTGGTTACTACTGGAGCTGGATCCGC

CAGCACCCAGGGAAGGGCCTGGAGTGGATTGGGTACATCTATGACAGTGGGAGCACCTAC

TACAACCCGTCCCTCAAGAGTCGAGTTACCATATCAGTAGACACGTCTAAGAACCAGTTC

TCCCTGAAGCTGAGGTCTGTGACTGCCGCGGACACGGCCGTGTATTACTGTGCGAGAGAT

CAGGGGCAGGACGGATACAGCTATGGTTACGGCTACTACTACGGTATGGACGTCTGGGGC

CAAGGGACCACGGTCACCGTCTCCTC

122 Heavy Chain Protein:
QVQLQESGPGLVKPSQTLSLTCTVSGGSISSGGYYWSWIRQHPGKGLEWIGYIYDSGSTY

YNPSLKSRVTISVDTSKNQFSLKLRSVTAADTAVYYCARDQGQDGYSYGYGYYYGMDVWG

QGTTVTVS

123 Light Chain DNA:
GACATCCAGATGACCCAGTCTCCATCCTCCCTGTCTGCATCTGTAGGAGACAGAGTCACC

```
ATCACTTGCCAGGCGAGTCAGGACATTAGCAATTATTTAAATTGGTATCAGCAGAAACCA

GGGAAAGCCCCTAAACTCCTGATCTACGTTGCATCCAATTTGGAAACAGGGGTCCCATCA

AGGTTCAGTGGAAGTGGATCTGGGACAGATTTTACTTTCACCATCAGCAGCCTGCAGCCT

GAAGATATTGCAACATATTACTGTCAACAGTGTGATAATCTCCCTCTCACTTTCGGCGGA

GGGACCAAGGTGGAGATCAAA
```

124 Light Chain Protein:
124 Light Chain Protein:
```
DIQMTQSPSSLSASVGDRVTITCQASQDISNYLNWYQQKPGKAPKLLIYVASNLETGVPS

RFSGSGSGTDFTFTISSLQPEDIATYYCQQCDNLPLTFGGGTKVEIK
```

Antibody U1-21
125 Heavy Chain DNA:
```
CAGGTGCAGCTGCAGGAGTCCCGCCCAGGACTGGTGAAGCCTTCACAGACCCTGTCCCTC

ACCTCCACTGTCTCTGGTGGCTCCATCAGCAGTGGTGATTACTACTGGAGCTCGATCCGC

CAGCACCCAGGGAAGGGCCTGGAGTCGATTGGATACATCTATTACAGTGCGAGCACCTAC

TACAACCCGTCCCTCAAGAGTCGAGTTACCATATCAGTAGACACGTCTAAGAACCAGTTC

TCCCTGAAGCTGAGCTCTCTGACTGCCGCGGACACCGCCGTGTATTACTGTGCGAGAGCG

GATTACGATTTTGGAGTGGTTATTTTGACTACTGGGCCCAGGGAACCCTGGTCACCGTC

TCCTC
```

126 Heavy Chain Protein:
```
QVQLQESGPGLVKPSQTLSLTCTVSGGSISSGDYYWSSIRQHPGKGLEWIGYIYYSGSTY

YNPSLKSRVTISVDTSKNQFSLKLSSVTAADTAVYYCARADYDFWSGYFDYWGQGTLVTV

S
```

127 Light Chain DNA:
```
GACATCCAGATCACCCAGTCTCCATCCTCCCTGTCTGCATCTGTAGGAGACAGAGTCACC

ATCACTTGCCGGGCAAGTCAGGACATTAGAAATCATTTAGGCTGCTATCCGCAGAAACCT

GGGAAAGCCCCTAAGCGCCTGATCTATGCTGCATCCCGTTTGCAAACTGGGGTCCCATCA

AGGTTCAGCGCCAGTGGATCTGCGACAGAATTCACTCTCACAATCACCACCCTGCACCCT

GAAGATTTTGCAACTTATTACTGTCTACAGCATAATAGTTACCCGTGGACGTTCGGCCAA

GGGACCAAGGTGGAAATCAAAC
```

128 Light Chain Protein:
```
DIQMTQSPSSLSASVGDRVTITCRASQDIRNDLGWYRQKPGKAPKRLIYAASRLQSGVPS

RFSGSGSGTEFTLTISSLQPEDFATYYCLQHNSYPWTFGQGTKVEIK
```

Antibody U1-22
129 Heavy Chain DNA:
```
CAGGTGCAGCTGCAGGAGTCGGGCCCAGGACTGGTGAAGCCTTCACAGACCCTGTCCCTC

ACCTGCACTGTCTCTGGTGGCTCCATCAGCAGTGGTGATTACTACTGGAGCTGGATCCGC

CAGCACCCAGGGAAGGGCCTGGAGTGGATTGGGTACATCTATTACAGTGGGAGCACCTAC

TACAACCCGTCCCTCAAGAGTCGAGTTACCATATCAGTAGACACGTCTAAGAACCAGTTC

TCCCTGAAGCTGAGCTCTGTGACTGCCGCGGACACGGCCGTGTATTACTGTGCGAGAGCC

GATTACGATTTTGGAGTGGTTATTTTGACTACTGGGGCCAGGGAACCCTGGTCACCGTC

TCCTCA
```

130 Heavy Chain Protein:
```
QVQLQESGPGLVKPSQTLSLTCTVSGGSISSGDYYWSWIRQHPGKGLEWICYIYYSGSTY

YNPSLKSRVTISVDTSKNQFSLKLSSVTAADTAVYYCARADYDFWSGYFDYWGQGTLVTV

SS
```

131 Light Chain DNA:
GACATCCAGATCACCCAGTCTCCATCCTCCCTGTCTGCATCTGTAGGAGACAGAGTCACC

ATCACTTGCCGGGCAAGTCAGGGCATTAGAAATGATTTAGCCTGCTATCACCAGAAACCA

GGGAAAGCCCCTAAGCGCCTCATCTATGCTGCATCCACTTTGCAAAATGGGGTCCCATCA

AGGTTCAGCGGCAGTGGATCTGGGACAGAATTCACTCTCACAATCACCAGCCTGCAGCCT

GAAGATTTTGCAACTTATTACTGTCTACAGCATAATAGTTACCCGTGGACGTTCGGCCAA

CCGACCAAGGTGGAAATCAAAC

132 Light Chain Protein:
DIQMTQSPSSLSASVGDRVTITCRASQGIRNDLGWYQQKPGKAPKRLIYAASSLQNGVPS

RFSGSGSGTEFTLTISSLQPEDFATYYCLQHNSYPWTFGQGTKVEIK

Antibody U1-23
Antibody U1-23
133 Heavy Chain DNA:
CACGTGCAGCTGCAGGAGTCGGGCCCAGGACTGGTGAAGCCTTCACAGACCCTGTCCCTC

ACCTGCACTGTCTCTGGTGGCTCCATCACCAGTGGTGATTACTACTGGAGCTGGATCCGC

CAGCACCCAGGGAAGGGCCTGGAGTGGATTGGGTACATCTATTACAGTGGGAGCACCTAC

TACAACCCGTCCCTCAAGAGTCGACTTACCATATCAGTAGACACGTCTAAGAACCAGTTC

TCCCTGAAGCTGAGCTCTGTGACTGCCGCGCACACGGCCGTGTATTACTGTGCGAGAGCG

GATTACGATTTTGGAGTCGTTATTTTGACTACTGGGGCCAGGGAATCCTGGTCACCGTC

TCCTC

134 Heavy Chain Protein:
QVQLQESGPGLVKPSQTLSLTCTVSGGSISSGDYYWSWIRQHPGKGLEWIGYIYYSGSTY

YNPSLKSRVTISVDTSKNQFSLKLSSVTAADTAVYYCARADYDFWSGYFDYWGQGILVTV

S

135 Light Chain DNA:
GACATCCAGATGACCCAGTCTCCATCCTCCCTGTCTGCATCTGTAGGAGACAGAGTCACC

ATCACTTGCCGGGCAAGTCAGGCCATTAGAAATGATTTAGGCTGGTATCAGCAGAAACCA

GGGAAAGCCCCTAACCGCCTGATTTATGCTGCATCCAGTTTGCAAAGTGGGGTCCCATCA

AGGTTCAGCGGCAGTGCATCTGGGACACAATTCACTCTCACAATCAGCAGCCTGCAGCCT

GAAGATTTTCCAACTTATTACTGTCTACAGCATAATAGTTACCCGTGGACGTTCGGCCAA

GGGACCAAGGTGGAAATCAAAC

136 Light Chain Protein:
DIQMTQSPSSLSASVGDRVTITCRASQGIRNDLGWYQQKPGKAPKRLIYAASSLQSGVPS

RFSGSGSGTEFTLTISSLQPEDFATYYCLQHNSYPWTFGQGTKVEIK

Antibody U1-24
137 Heavy Chain DNA:
CAGGTGCAGCTGCAGGAGTCGGGCCCAGGACTGGTGAAGCCTTCACACACCCTGTCCCTC

ACCTGCACTGTCTCTGGTGGCTCCATCAGTAGTGGTGATTACTACTGGAGCTGGATCCGC

CAGCACCCAGGGAAGGGCCTGGAGTGGATTGGGTACATCTATTACAGTGGGAGCACCTAC

TACAACCCGTCCCTCAAGAGTCGAGTTACCATATCAGTAGACACGTCTAAGAACCAGTTC

TCCCTGAAGTTGAGCTCTGTGACTGCCGCGGACACGGCCGTGTATTACTGTGCGAGAGCC

GATTACGATTTTGGAATGGTTATTTTGACTACTGGGGCCAGGGAACCCTGGTCACCGTC

TCCTCA

138 Heavy Chain Protein:
QVQLQESGPGLVKPSQTLSLTCTVSGGSISSGDYYWSWIRQHPGKGLEWIGYIYYSGSTY

YNPSLKSRVTISVDTSKNQFSLKLSSVTAADTAVYYCARADYDFWNGYFDYWGQGTLVTV

SS

139 Light Chain DNA:
GACATCCAGATGACCCAGTCTCCATCCTCCCTGTCTGCATCTGTAGGAGACAGAGTCACC

ATCACTTGCCGCGCAAGTCAGGGCATTAGAAATGATTTAGCCTGGTATCAGCAGAAACCA

GGGAAAGCCCCTAAGCGCCTGATCTATGCTGCATCCAGTTTGCAAAGTGGGGTCCCATCA

AGGTTCACCGCCAGTGGATCTGGGACAGAATTCACTCTCACAATCAGCAGCCTGCAGCCT

GAAGATTTTGCAACTTATTACTGTCTACAGCATAATAATTACCCGTGGACGTTCGGCCAA

GGGACCAAGGTGGAAATCAAA

140 Light Chain Protein:
DIQMTQSPSSLSASVGDRVTITCRASQGIRNDLGWYQQKPGKAPKRLIYAASSLQSGVPS

RFSGSGSGTEFTLTISSLQPEDFATYYCLQHNNYPWTPGQGTKVEIK

Antibody U1-25
141 Heavy Chain DNA:
CAGGTGCAGCTGCAGGAGTCGGGCCCAGGACTGGTGAAGCCTTCACAGACCCTGTCCCTC

ACCTGCACTGTCTCTGGTGGCTCCATCAGCAGTGGTGATTACTACTGGAGCTGGATCCGC

CAGCACCCAGGGAAGGGCCTGGAGTGGATTGGGTACATCTATTACAGTGGGAGCACCTAC

TACAACCCGTCCCTCAAGAGTCGAGTTACCATATCAGTAGACACGTCTAAGAACCAGTTC

TCCCTGAAGCTGAGCTCTGTGACTGCCGCGGACACGGCCGTGTATTACTGTGCGAGAGCC

GATTACGATTTTTGGAGTGGTTATTTTGACTACTGGGGCCAGGGAACCCTGGTCACCGTC

TCCTCA

142 Heavy Chain Protein:
QVQLQESGPGLVKPSQTLSLTCTVSGGSISSGDYYWSWIRQHPGKGLEWIGYIYYSGSTY

YNPSLKSRVTISVDTSKNQFSLKLSSVTAADTAVYYCARADYDFWSGYFDYWGQGTLVTV

SS

143 Light Chain DNA:
GACATCCAGCTGACCCAGTCTCCATCCTCCCTGTCTGCATCTGTAGGAGACAGAGTCACC

ATCACTTGCCGGGCAAGTCAGGGCATTAGAAATGATTTAGGCTGGTATCAGCAGAAACCA

GGGAAAGCCCCTAAGCGCCTGATCTATGCTGCATCCAGTTTGCAAAATGGGGTCCCATCA

AGGTTCAGCGGCAGTGGATCTGGGACACAATTCACTCTCACAATCAGCAGCCTGCAGCCT

GAAGATTTTGCAACTTATTACTGTCTACAGCATAATAGTTACCCGTGGAGGTTCGGCCAA

GGGACCAAGGTGGAAATCAAAC

144 Light Chain Protein:
DIQLTQSPSSLSASVGDRVTITCRASQGIRNDLGWYQQKPGKAPKRLIYAASSLQNGVPS

RFSGSGSGTEFTLTISSLQPEDFATYYCLQHNSYPWTFGQGTKVEIK

Antibody U1-26
145 Heavy Chain DNA:
CAGGTGCAGCTGCAGGAGTCGGGCCCAGGACTGGTGAAGCCTTCACAGACCCTGTCCCTC

ACCTGCACTGTCTCTGGTGGCTCCATCAGCAGTGGTGATTACTAGTGGACCTGGATCCGC

CAGTACCCAGGGAAGGGCCTGGAGTGGATTGGGTACATCTATTACAGTGGGAGCACCTAC

TACAACCCGTCGCTCAAGAGTCCAGTTACCATATCAGTAGACACGTCTAAGAACCAGTTC

TCCCTGAAGCTGGGCTCTGTGACTGCCGCGGAGACGGCCGTGTATTTCTGTGCGAGAGCC

GATTACGATTTTTGGAGTGGTTATTTTGACTTCTGGGGCCAGGGAACCCTGGTCACCGTC

TCCTC

-continued

146 Heavy Chain Protein:
QVQLQESGPGLVKPSQTLSLTCTVSGGSISSGDYYWSWIRQYPGKGLEWIGYIYYSGSTV

YNPSLKSRVTISVDTSKNQFSLKLGSVTAADTAVYFCARADYDFWSGYFDFWGQGTLVTV

S

147 Light Chain DNA:
GACATCCAGATGACCCAGTCTCCATCCTCCCTGTCTGCATCTGTAGGAGACAGAGTCACC

ATCACTTGCCGGGCAAGTCAGGGCATTAGAAATGATTTAGGCTCGTATCAGCAGAAACCA

GGGAAAGCCCCTAAGCCCCTGATCTATGCTGCATCCAGTTTGCAAAGTGGGGTCCCATCA

AGGTTCACCGGCAGTGGATCTGGGACAGAATTCACTCTCACAATCAGCAGCCTGCAGCCT

GAAGATTTTGCAACTTATTACTGTCTACAGCATAATGGTTACCCGTGGACGTTCGGCCAA

GGGACCAAGGTGGAAATCAAAC

148 Light Chain Protein:
DIQMTQSPSSLSASVGDRVTITCRASQGIRNDLGWYQQKPGKAPKRLIYAASSLQSGVPS

RFSGSGSGTEFTLTISSLQPEDFATYYCLQHNGYPWTFGQGTKVEIK

Antibody U1-27
149 Heavy Chain DNA:
CAGGTGCAGCTGCAGGAGTCGGGCCCAGGACTGGTGAAGCCTTCACAGACCCTGTCCCTC

ACCTGCACTGTCTCTGGTGGCTCCATCACCAGTGGTGATTACTACTGGAGCTGGATCCGC

CAGTACGCAGGGAAGGGCCTGGAGTGGATTGGGTACATCTATTACAGTGGGAGCACCTAG

TACAACCCGTCCCTCAAGAGTCGAGTTACCATATCAGTAGACACGTCTAAGAACCAGTTC

TCCCTGAAGCTGGGCTCTGTGACTGCCGCGGACACGGCCGTGTATTTCTGTGCGAGAGCC

GATTACGATTTTTGGAGTGGTTATTTTGACTTCTGGGGCCAGGGAACCCTGGTCACCGTC

TCCTC

150 Heavy Chain Protein:
QVQLQESGPGLVKPSQTLSLTCTVSGGSISSGDYYWSWIRQYPGKGLEWIGYIYYSGSTY

YNPSLKSRVTISVDTSKNQFSLKLGSVTAADTAVYFCARADYDFWSGYFDFWGQGTLVTV

S

151 Light Chain DNA:
CACATCCAGATCACCCAGTCTCCATCCTCCCTGTCTGCATCTGTAGGAGACAGAGTCACC

ATCACTTGCCGGGCAAGTCAGGGCATTAGAAATCATTTAGGCTGGTATCAGCAGAAACCA

GGGAAAGCCCCTAAGCGCCTGATCTATGCTGCATCCAGTTTGCAAAGTGGGGTCCCATCA

AGGTTCACCGGCAGTGGATCTGGGACAGAATTCACTCACACAATCAGCAGCCTCCAGCCT

GAAGATTTTGCAACTTATTACTGTCTACAGCATAATCGTTACCCGTGGACGTTCGGCCAA

GGGACCAACGTGGAAATCAAAC

152 Light Chain Protein:
DIQMTQSPSSLSASVGDRVTITCRASQGIRNDLGWYQQKPGKAPKRLIYAASSLQSGVPS

RFSGSGSGTEFTLTISSLQPEDFATYYCLQHNGYPWTFGQGTKVEIK

Antibody U1-28
153 Heavy Chain DNA:
CAGGTGCAGCTGCAGGAGTCGGGCCCAGGACTCCTGAAGCCTTCACACACCCTGTCCCTC

ACCTCCACTGTCTCTGGTGGCTCCATCAGTAGTGGTGATTACTACTGGAGCTGGATCCGC

CAGCACCCAGGGAAGGGCCTGGAGTGGATTGGGTACATCTATTACAGTCCCAGCACCTAC

TACAACCCSTCCCTCAAGAGTCCAGPTACCATATCAGTAGACACGTCTAAGAACCAGTTC

TCCCTGAAGCTGACCTCTGTGACTGCCGCGSACACGGCCGTGTATTACTGTGCGAGAGCG

```
GATTACGATTTTTGGACTGGTTATTTTGACTCCTGGGGCCAGGGAACCCTGGTCACCGTC

TCCTCA

154 Heavy Chain Protein:
QVQLQESGPGLVKPSQTLSLTCTVSGGSISSGDYYWSWIRQHPGKGLEWIGYIYYSGSTY

YNPSLKSRVTISVDTSKNQFSLKLSSVTAADTAVYYCARADYDFWSGYFDSWGQGTLVTV

SS

155 Light Chain DNA:
GACATCCACATGACCCAGTCTCCATCCTCCCTGTCTGCATCTGTAGGAGACAGAGTCACC

ATCACTTCCCGGGCAAGTCAGGGCATTAGAAATGATTTAGGCTGGTATCAGCAGATACCT

GGGAAAGCCCCTAAGCGCCTGATCTATGCTGCATCCAGTTTGCAAAGTGGGGTCCCATCA

AGGTTCAGCGGCAGTGGATCTGGGACAGAATTCACTCTCACAATCAGCAGCCTGCAGCCT

GAAGATTTTGCAACTTATTACTGTCTACAGCATAATGGTTACCCGTGGACGTTCGGCCAA

CGGACCAAGGTGGAAATCAAA

156 Light Chain Protein:
DIQMTQSPSSLSASVGDRVTITCRASQGIRNDLGWYQQIPGKAPKRLIYAASSLQSGVPS

RFSGSGSGTEFTLTISSLQPEDFATYYCLQHNGYPWTFGQGTKVEIK

Antibody U1-31
157 Heavy Chain DNA:
CAGGTTCAGCTGGTGCAGTCTGGAGCTGAGGTGAAGAAGCCTGGGGCCTCAGTGAAGGTC

TCCTGCAAGGCTTCTCGTTACACCTTTACCAACTATGGTATCAGCTGGGTGCGGCAGGCC

CCTGGACAAGGGCTTGAGTGGATGGGATGGATCAGCGCTTACGATGGTTACAGAAACTAT

GCACAGAAGCTCCACGGCAGAGTCACCATGACCACAGACACATCCACGACCACTGCCTAC

ATGGAGCTCAGGAGCCTGAGATCTGACGACACGGCCGTGTATTACTGTGCCAGACATGTT

CAAGACTACGGTGACTACGACTACTTTGACTACTGGGGCCAGGGAACCCTGGTCACCCTC

TCCTCA

158 Heavy Chain Protein:
QVQLVQSGAEVKKPGASVKVSCRASGYTFTNYGISWVRQAPGQGLEWMGWISAYDGYRNY

AQKLQGRVTMTTDTSTTTAYMELRSLRSDDTAVYYCARDVQDYGDYDYFDYWGQGTLVTV

SS

159 Light Chain DNA:
CACATCCAGATGACCCAGTCTCCATCCTCCCTGTCTGCATCTGTAGGAGACAGAGTCACC

ATCACTTGCCGGGCAAGTCAGAGCATTAGCAGTTATTTAAATTGCTATCAGCAGAAACCA

GGGAAAGCCCCTAACCTCCTGATCTATCCTGCATCCACTTTGCAAAGTGGGGTCCCATGA

AGATTCAGGCGCAGTGGATCTGGGACAGATTTCACTCTCACCATCACCAGTCTGCAACCT

GAAGATTTTCCAACTTACTACTGTCAACAGAGTTACAGTACCCCCATCACCTTCGGCCAA

GGGACACGACTGGAGATTAAA

160 Light Chain Protein:
DIQMTQSPSSLSASVGDRVTITCRASQSISSYLNWYQQKPGKAPNLLIYAASSLQSGVPS

RFRGSGSGTDFTLTISSLQPEDFATYYCQQSYSTPITFGQGTRLEIK

Antibody U1-32
161 Heavy Chain DNA:
CAGGTGCAGCTGCAGGAGTCGGGCCCAGGACTGCTGAAGCCTTTACAGACCCTGTCCCTC

ACCTGCACTGTCTCTGGTGGCTCCATCAGCAGTGGTGATTACTACTGGAGCTGGATCCGC

CAGCACCCAGGGAAGGGCCTGGAGTGGATTGGGTACATCTATTACAGTGGGACCACCTAC

TACAACCCGTCCGTCAAGAGTCGAGTTACCATATCAGTAGACACGTCTAAGAACCAGTTC
```

-continued
GCCCTGAAGCTGAACTCTGTGACTGCCGCGGAGACGGCCGTGTATTACTGTGCGAGAGCC

GATTACCATTTTTGGAGTCGTTATTTTCACTACTGGGGCCAGGGAACCCTGGTCACCGTC

TCCTCA

162 Heavy Chain Protein:
QVQLQESGPGLVKPLQTLSLTCTVSGGSISSGDYYWSWIRQHPGKGLEWIGYIYYSGTTY

YNPSLKSRVTISVDTSKNQFALKLNSVTAADTAVYYCARADYDFWSGYFDYWGQGTLVTV

SS

163 Light Chain DNA:
GACATCCAGATGACCCAGTCTCCATCCTCCCTGTCTGCATCTGTAGGAGACAGAGTCACC

ATCACTTGCCGGGCAGGTCAGGCCATTAGAAATGATTTAGGCTGGTATCAGGAGAAACCA

GGGAAAGCCCCTCAGCGCCTGATCTATGCTGCATCCAGTTTGCAAAGTGGGGTCCCATCA

AGGTTCAGCGGCAGTGGATCTGGGACAGAATTCTCTCTCACAATGTCCAGCCTGCAGCCT

GAAGATTTTGCAACTTATTACTGTCTACAGCATAATAGTTACCCGTGGACGTTCGGCCAA

GGGACCAAGGTGGAAATCAAAG

164 Light Chain Protein:
DIQMTQSPSSLSASVGDRVTITCRAGQGIRNDLGWYQQKPGKAPQRLIYAASSLQSGVPS

RFSGSGSGTEFSLTISSLQPEDFATYYCLQHNSYPWTFGQGTKVEIK

Antibody U1-35
165 Heavy Chain DNA:
CAGGTGCAGCTGGTGGAGTCTGGGGGAGGCTTGGTCAAGCCTGGAGGGTCCCTGAGACTC

TCCTGTGCAGCCTCTGGATTCACCTTCAGTGACTACTACATGAGCTGGATCCGCCAGGCT

CCAGGGAAGGGGCTGGAGTGGGTTTCATATATTAGTAGTAGTGGTAATAACATATACCAC

GCAGACTGTGTGAAGGGCCGATTCACCATCTCCAGGGACAACGCCAAGAACTCACTGTAT

CTGCAAATGAACAGCCTGAGAGCCGACGACACGGCCGTGTATTACTGTGCGAGAGAGAGA

TATAGTGGCTACGACGACCCTGATGGTTTTGATATCTGGGGCCAAGGGACAATGGTCACC

GTCTCTTCA

166 Heavy Chain Protein:
QVQLVESGGGLVKPGGSLRLSCAASGFTFSDYYMSWIRQAPGKGLEWVSYISSSGNNIYH

ADSVKGRFTISRDNAKNSLYLQMNSLRAEDTAVYYCARERYSGYDDFDGFDIWGQGTMVT

VSS

167 Light Chain DNA:
GACATCCAGATGACCCAGTCTCCATCCTCCCTGTCTGCATGTGTAGGAGACAGAGTCACC

ATCACTTGCCAGGCGAGTCAGGACATTAGCAACTATTTAAGTTGGTTTCAGCAGAAACCA

GGGAAAGCCCCTAAGCTCCTGATCCACGATGCATCCAATTTGGAAACAGGGGTCCCTTCA

AGGTTCAGTGGAAGTGGATCTGGGACAGATTTTACTTTCACCATCAGCAGCCTGCAGGCT

GAAGATATTGCAACATATTACTGTCAACAGTATGATAATCCCCCGTGCAGTTTTGGCCAG

GGGACCAAGCTGGAGATCAAA

168 Light Chain Protein:
DIQMTQSPSSLSASVGDRVTITCQASQDISNYLSWFQQKPGKAPKLLIHDASNLETGVPS

RFSGSGSGTDFTFTISSLQPEDIATYYCQQYDNPPCSFGQGTKLEIK

Antibody U1-36
169 Heavy Chain DNA:
CAGGTGCAGCTGCAGGAGTCGGGCCCACGACTGGTGAAGCCTTCACAGACCCTGTCCCTC

ACCTGCACTGTCTCTGGTGGCTCCATCAGCAGTGGTTATTACTACTGGAGCTCCATCCGC

CAGCACCCAGGGAAGGGCCTGGAGTCCATTGGGTACATCTATTACAGTGGGACCACCTAC

TACAATCCGTCCTTCAAGAGTCGAGTTACCATATCAGTAGACACGTCTAAGAACCAGTTC

-continued

```
TCCCTGAAACTGAGCTCTGTGACTGCCGCGGACACCGCCGTGTATTACTGTGCGAGAGCC

GATTACGATTTTTGGAGTGGTCACTTTGACTACTGGGGCCAGGGAACCCTCGTCACCGTC

TCCTCA
```

170 Heavy Chain Protein:
QVQLQESGPGLVKPSQTLSLTCTVSGGSISSGYYYWSWIRQHPGKGLEWIGYIYYSGTTY

YNPSFKSRVTISVDTSKNQFSLKLSSVTAADTAVYYCARADYDFWSGHFDYWGQGTLVTV

SS

171 Light Chain DNA:
```
GACATCCAGATGACCCAGTCTCCATCCTCCCTGTCTGCATCTGTAGGAGACAGAGTCACC

ATCACTTGCCGGGCAAGTCAGGGCATTAGAAATGATTTAGGCTGGTATCAGCAGAAACCA

GGCAAACCCCCTAAGCGCCTGATCTATGCTGCATCCAGTTTGCAAAGTGGGGTCCCATCA

AGGTTCAGCGGCAGTGGATCTGGGACAGAATTCACTCTCACAATCAGCAGCCTGCAGCCT

GAAGATTTTGCAACTTATTACTGTCTACAGCATAATAGTTACCCGTGGACGTTCGGCCAA

GGGACCAAGGTGGAAATCAAA
```

172 Light Chain Protein:
DIQMTQSPSSLSASVGDRVTITCRASQGIRNDLGWYQQKPGKAPKRLIYAASSLQSGVPS

RFSGSGSGTEFTLTISSLQPEDFATYYCLQHNSYPWTFGQGTKVEIK

Antibody U1-37
173 Heavy Chain DNA:
```
CAGGTTCACCTGGTGCAGTCTCCAGCTGAGGTGAAGAAGCCTGGGGCCTCAGTGAAGGTC

TCCTGCAAGGCTTCTGGTTACACCTTTACCAGCTATGGTATCAGCTGGGTGCGACAGGCC

CCTGGACAAGGACTTGAGTGGATCGGATGGATCAGCGCTTACGATGGTCACACAAACTAT

CCACAGAAGCTCCAGGGCAGAGTCACCATGACCACAGACACATCCACCAACACAGCCTAC

ATGGAGCTGAGGAGCCTGACATCTGACGACACGGCCGTTTATTACTGTGCGAGAGACCCC

CATCACTACAGTAACTACCACGCTTTTGACTTCTGGGGCCAGGGAACCCTGGTCACCGTC

TCCTC
```

174 Heavy Chain Protein:
QVQLVQSGAEVKKPGASVKVSCKASGYTFTSYGISWVRQAPGQGLEWMGWISAYDGHTNY

AQKLQGRVTMTTDTSTNTAYMELRSLRSDDTAVYYCARDPHDYSNYEAFDFWGQGTLVTV

S

175 Light Chain DNA
```
atgaggtcccctgctcagctcctggggctcctgctactctggctccgaggtgccagatgtg acatccagatgacccagtctccatcctccctgtctgcatctgtaggagacagagtcaccat cacttgccgggcaagtcagagcattagcagttatttaaattggtatcagcagaaaccaggg aaagcccctaacctcctgatctatgctgcatccagtttgcaaagtggggtcccatcaagat tcagtggcagtggatctgggacagatttcactctcaccatcagcagtctgcaacctgaaga ttttgcaacttactactgtcaacagagttacagtaccccatcaccttcggccaagggaca cgactggagattaaacgaactgtggctgcaccatctgtcttcatcttcccgccatctgatg agcagttgaaatctggaactgcctctgttgtgtgcctgctgaataacttctatcccagaga ggccaaagtacagtggaaggtggataacgcc
```

176 Light Chain Protein:
DIQMTQSPSSLSASVGDRVTITCRASQSISSYLNWYQQKPGKAPNLLIYAASSLQGVPSR

FSGSGSGTDFTLTISSLQPEDFATYYCQQSYSTPITFGQGTRLEIK

Antibody U1-34
177 Heavy Chain DNA:

-continued
```
accatggactggacctggagggtccttttcttggtggcagcagcaacaggtgcccactccca ggttcagctggtgcagtctggagctgaggtgaagaagcctggggcctcagtgaaggtctcct gcaaggcttctggttacacctttaccaactatggtatcagctgggtgcggcaggcccctgga caagggcttgagtggatgggatggatcagcgcttacgatggttacagaaactatgcacagaa gctccagggcagagtcaccatgaccacagacacatccacgaccactgcctacatggagctga ggagcctgagatctgacgacacggccgtgtattactgtgcgagagatgttcaagactacggt gactacgactactttgactactggggccagggaaccctggtcaccgtctcctcagcttccac caagggcccatccgtcttccccctggtgccctgctccaggagcacctccgagagcacagccg ccctgggctgcctggtcaaggactacttccccgaaccg
```

178 Heavy Chain Protein
QVQLVQSGAEVKKPGASVKVSCKASGYTFTNYGISWVRQAPGQGLEWMGWISAYDGYRNYA

QKLQGRVTMTTDTSTTTAYMELRSLRSDDTAVYYCARDVQDYGDYDYFDYWGQGTLVTVSS

179 Light Chain DNA:
```
cagctcctgggctcctgctactctggctccgaggtgccagatgtgacatccagatgaccc agtctccatcctccctgtctgcatctgtaggagacagagtcaccatcacttgccgggcaag tcagagcattagcagttatttaaattggtatcagcagaaaccagggaaagcccctaacctc ctgatctatgctgcatccagtttgcaaagtggggtcccatcaagattcagtggcagtggat ctgggacagatttcactctcaccatcagcagtctgcaacctgaagattttgcaacttacta ctgtcaacagagttacagtaccccatcaccttcggccaagggacacgactggagattaaa cgaactgtggctgcaccatctgtcttcatcttcccgccatctgatgagcagttgaaatctg gaactgcctctgttgtgtgcctgctgaataacttctatcccagagaggccaaagtacagtg gaaggtggataacgcc
```

180 Light Chain Protein:
DIQMTQSPSSLSASVGDRVTITCRASQSISSYLNWYQQKPGKAPNLLIYAASSLQSGVPSR

FSGSGSGTDFTLTISSLQPEDFATYYCQQSYSTPITFGQGTRLEIK

Antibody U1-1
181 Heavy Chain DNA:
```
catctgtggttcttcctcctgctggtggcagctcccagatgggtcctgtcccaggtgcagc tgcaggagtcgggcccaggactggtgaagccttcacagaccctgtcctcacctgcactgt ctctggtggctccatcaacagtggtgattactactggagctggatccgccagcacccaggg aagggcctggagtggattgggtacatctattacagtgggagcacctactacaacccgtccc tcaagagtcgagttaccatatcagtagacacgtctaagaaccagttctccctgaagctgag ctctgtgactgccgcggacacggccgtgtattactgtgcgagagcagattacgattttggg agtggttactttgactactggggccagggaaccctggtcaccgtctcctcagcctccacca agggcccatcggtcttccccctggcaccctcctccaagagcacctctgggggcacaacggc cctgg
```

182 Heavy Chain Protein
QVQLQESGPGLVKPSQTLSLTCTVSGGSINSGDYYWSWIRQHPGKGLEWIGYIYYSGSTYY

NPSLKSRVTISVDTSKNQFSLKLSSVTAADTAVYYCARADYDFWSGYFDYWGQGTLVTVSS

183 Light Chain DNA:
```
atgagggtccctgctcagctcctggggctcctgctgctctggttcccaggtgccaggtgtga catccagatgacccagtctccatcctccctgcctgcatctgtaggagacagagtcaccatca cttgccgggcaagtcagggcattagaaatgatttaggctggtatcagcagaaaccagggaaa gcccctaagcgcctgatctatgctgcatccagtttgcaaagtggggtcccatcaaggttcag
```

```
cggcagcggatctgagacagaattcactctcacaatcagcagcctgcagcctgaagattttg caacttattactgtctacagcataatagttacccgtggacgttcggccaagggaccaaggtg gaaatcaaacgaactgtggctgcaccatctgtcttcatcttcccgccatctgatgagcagtt gaaatctggaactgcctctgttgtgtgcctgctgaataacttctatcccagagaggccaaag tacagtggaaggtggataacgc
```

184 Light Chain Protein
```
DIQMTQSPSSLSASVGDRVTITCRASQGIRNDLGWYQQKPGKAPKRLIYAASSLQSGVPSR

FSGSGSGTEFTLTISSLQPEDFATYYCLQHNSYPWTFGQGTKVETK
```

Antibody U1-3
185 Heavy Chain DNA:
```
tggttcttccttctgctggtggcagctcccagatgggtcctgtcccaggtgcagctgcagga gtcgggcccaggactggtgaagccttcacagaccctgtcctcacctgcactgtctctggtg gctccatcagcagtggtggttactactggagctggatccgccagcacccagggaagggcctg gagtggattgggtacatctattacagtgggagcacctactacaacccgtccctcaagagtcg agttaccatatcagtagacacgtctaagaaccagttctccctgaagctgagctctgtgactg ccgcggacacggccgtgtattactgtgcgagagatggctatgatagtagtggttattaccac ggctactttgactactggggccagggaaccctggtcaccgtctcctcagcctccaccaaggg cc
```

186 Heavy Chain Protein
```
QVQLQESGPGLVKPSQTLSLTCTVSGGSISSGGYYWSWIRQHPGKGLEWIGYIYYSGSTYY

NPSLKSRVTISVDTSKNQFSLKLSSVTAADTAVYYCARDGYDSSGYYHGYFDYWGQGTLVT

VSS
```

187 Light Chain DNA:
H3_130_1N1K
```
caggtcttcatttctctgttgctctggatctctggtgcctacggggacatcgtgatgaccc agtctccagactccctggctgtgtctctgggcgagagggccaccatcaactgcaagtccag ccagagtgttttatacagctccaacaataagaactacttagcttggtaccagcagaaacca ggacagcctcctaagctgctcatttactgggcatctacccgggaatccggggtccctgacc gattcagtggcagcgggtctgggacagatttcactctcaccatcagcagcctgcaggctga agatgtggcagtttattactgtcagcaatattatagtactccgctcactttcggcggaggg accaaggtggagatcaaacgaactgtggctgcaccatctgtcttcatcttcccgccatctg atgagcagttgaaatctggaactgcctctgttgtgtgcctgctgaataacttctatcccag agaggccaaagtacagtggaaggtggataacgc
```

188 Light Chain Protein:
```
DIVMTQSPDSLAVSLGERATINCKSSQSVLYSSNNKNYLAWYQQKPGQPPKLLIYWASTRE

SGVPDRFSGSGSGTDFTLTISSLQAEDVAVYYCQQYYSTPLTFGGGTKVEIK
```

Antibody U1-4
H3_133_1N1G1
189 Heavy Chain DNA
```
ctgtggttcttcctcctgctggtggcagctcccagatgggtcctgtcccaggtgcagctgca ggagtcgggcccaggactggtgaagccttcacagaccctgtcctcacctgcactgtctctg gtggctccatcagtagtggtgattactactggagctggatccgccagcacccagggaagggc ctggagtggattgggtacatctattacagtgggagcacctactacaacccgtccctcaagag tcgagttaccatatcagtagacacgtctaagaaccagttctccctgaagttgagctctgtga ctgccgcggacacggccgtgtattactgtgcgagagccgattacgattttttggagtggttat tttgactactggggccagggaaccctggtcaccgtctcctcagcctccaccaagggcccatc
``` ggtcttcccctggcaccctc

190 Heavy Chain Protein
QVQLQESGPGLVKPSQTLSLTCTVSGGSISSGDYYWSWIRQHPGKGLEWIGYIYYSGSTYY

NPSLKSRVTISVDTSKNQFSLKLSSVTAADTAVYYCARADYDFWSGYFDYWGQGTLVTVSS

191 Light Chain DNA
H3_133_1N1K
gtgcccgctcagcgcctggggctcctgctgctctggttcccaggtgccaggtgtgacatcc agatgacccagtctccatcctccctgtctgcatctgtaggagacagagtcaccatcacttg ccgggcaagtcagggcattagaaatgatttaggctggtatcagcagaaaccagggaaagcc cctaagcgcctgatctatgctgcatccagtttgcaaagtggggtcccatcaaggttcagcg gcagtggatctgggacagaattcactctcacaatcagcagcctgcagcctgaagattttgc aacttattactgtctacagcataataattacccgtggacgttcggccaagggaccaaggtg gaaatcaaacgaactgtggctgcaccatctgtcttcatcttcccgccatctgatgagcagt tgaaatctggaactg 192 Light Chain Protein
DIQMTQSPSSLSASVGDRVTITCRASQGIRNDLGWYQQKPGKAPKRLIYAASSLQSGVPSRF

SGSGSGTEFTLTISSLQPEDFATYYCLQHNNYPWTFGQGTKVEIK

Antibody U1-5
193 Heavy Chain DNA:
H3_138_1N1G1
tggttcttccttctgctggtggcagctcccagatgggtcctgtcccaggtgcagctgcagga gtcgggcccaggactggtgaagccttcacagaccctgtcctcacctgcactgtctctggtg gctccatcagcagtggtgattactactggagctggatccgccagcacccagggaagggcctg gagtggattgggtacatctattacagtgggagcacctactacaacccgtccctcaagagtcg agttaccatatcagtagacacgtctaagaaccagttctccctgaagctgagctctgtgactg ccgcggacacggccgtgtattttctgtgcgagagccgattacgattttttggagtggttattttt gactactggggccagggaaccctggtcaccgtctcctcagcctccaccaagggcc 194 Heavy Chain Protein
QVQLQESGPGLVKPSQTLSLTCTVSGGSISSGDYYWSWIRQHPGKGLEWIGYIYYSGSTYYN

PSLKSRVTISVDTSKNQFSLKLSSVTAADTAVYFCARADYDFWSGYFDYWGQGTLVTVSS

195 Light Chain DNA:
H3_138_1N1K
atgagggtcccgctcagctcctggggctcctgctgctctggttcccaggtgccaggtgtga catccagatgacccagtctccatcctccctgtctgcatctgtaggcgacagagtcaccatca cttgccgggcaagtcagggcattagaaatgatttaggccggtatcagcagaaaccagggaaa gcccctaagcgcctgatctatgctgcatccagtttgcaaagtggggtcccatcaaggttcag cggcagtggatctgggacagaattcactctcacaatcagcagcctgcagcccgaagattttg caacttattactgtctacagcataatacttacccgtggacgttcggccaagggaccaaggtg gaaatcaaacgaactgtggctgcaccatctgtcttcatcttcccgccatctgatgagcagtt gaaatctggaactgcctctgttgtgtgcctgctgaataacttctatcccagagaggccaaag tacagtggaaggtggataacgc 196 Light Chain Protein
DIQMTQSPSSLSASVGDRVTITCRASQGIRNDLGWYQQKPGKAPKRLIYAASSLQSGVPS

RFSGSGSGTEFTLTISSLQPEDFATYYCLQHNTYPWTFGQGTKVEIK

Antibody U1-6
197 Heavy Chain DNA:
H3_162_1N1G1

-continued tggttcttccttctgctggtggcagctcccagatgggtcctgtcccaggtgcagctgcagga gtcgggcccaggactggtgaagccttcacagaccctgtccctcacctgcactgtctctggtg gctccatcagcagtggtgattactactggagctggatccgccagcacccagggaagggcctg gagtggattgggtacatctattacagtgggagcacctactacaacccgtccctcaagagtcg agttaccatatcagtagacacgtctaagaaccagttctccctgaagctgagctctgtgactg ccgcggacacggccgtgtatttctgtgcgagagccgattacgattttttggaatggttatttt gactactggggccagggaaccctggtcaccgtctcctcagcctccaccaagggccc 198 Heavy Chain Protein
QVQLQESGPGLVKPSQTLSLTCTVSGGSISSGDYYWSWIRQHPGKGLEWIGYIYYSGSTY

YNPSLKSRVTISVDTSKNQFSLKLSSVTAADTAVYFCARADYDFWNGYFDYWGQGTLVTV

SS

199 Light Chain DNA:
H3_162_1N1K
atgagggtccccgctcagctcctggggctcctgctgctctggttcccaggtgccaggtgtga catccagatgacccagtctccatcctccctgtctgcatctgtaggagacagagtcaccatca cttgccgggcaagtcagggcattagaaatgatttaggctggtatcagcagaaaccagggaaa gcccctaagcgcctgatctatgctgcttccagtttgcaaagtggggtcccatcaaggttcag cggcagtggatctgggacagaattcactctcacaatcagcagcctgcagcctgaagattttg caacttattactgtctacagcataatacttacccgtggacgttcggccaagggaccaaggtg gaaatcaaacgaactgtggctgcaccatctgtcttcatcttcccgccatctgatgagcagtt gaaatctggaactgcctctgttgtgtgcctgctgaataacttctatcccagagaggccaaag tacagtggaaggtggataacgcc 200 Light Chain Protein
DIQMTQSPSSLSASVGDRVTITCRASQGIRNDLGWYQQKPGKAPKRLIYAASSLQSGVPS

RFSGSGSGTEFTLTISSLQPEDFATYYCLQHNTYPWTFGQGTKVEIK

Antibody U1-8
201 Heavy Chain DNA:
H3_174_1N1G1
ttggtggcagcagctacaggcacccacgcccaggtccagctggtacagtctggggctgaggt gaagaagcctggggcctcagtgaaggtctcctgcaaggtttccggatacaccctcactgaat tatccatgtactgggtgcgacaggctcctggaaaagggcttgagtggatgggaggttttgat cctgaagatggtgaaacaatctacgcacagaagttccagggcagagtcaccatgaccgagga cacatctacagacacagcctacatggagctgagcagcctgagatctgaggacacggccgtgt attactgtgcaactgggtggaactacgtctttgactactggggccagggaaccctggtcacc gtctcctcagcctccaccaagggccc 202 Heavy Chain Protein
QVQLVQSGAEVKKPGASVKVSCKVSGYTLTELSMYWVRQAPGKGLEWMGGFDPEDGETIYA

QKFQGRVTMTEDTSTDTAYMELSSLRSEDTAVYYCATGWNYVFDYWGQGTLVTVSS

203 Light Chain DNA:
H3_174_1N1K
ggatccagtggggatattgtgatgactcagtctccactctccctgcccgtcacccctggaga gccggcctccatctcctgcaggtccagtcagagcctcctgcatagtaatggatacaactatt tggattggtacctgcagaagccagggcagtctccacagctcctgatctatttggattctcat cgggcctccggggtccctgacaggttcagtggcagtggatcaggcacagattttacactgaa aatcagcagagtggaggctgaggatgttggggtttattactgcatgcaagctctacaaactc cgctcactttcggcggagggaccaaggtggagatcaaacgaactgtggctgcaccatctgtc ttcatcttcccgccat 204 Light Chain Protein
DIVMTQSPLSLPVTPGEPASISCRSSQSLLHSNGYNYLDWYLQKPGQSPQLLIYLDSHRA

SGVPDRFSGSGSGTDFTLKISRVEAEDVGVYYCMQALQTPLTFGGGTKVEIK

Antibody U1-11
205 Heavy Chain DNA:
H3_178_1N1G1
tggttcttccttctgctggtggcagctcccagatgggtcctgtcccaggtgcagctgcagga gtcgggcccaggactggtgaagccttcacagaccctgtccctcacctgcactgtctctggtg gctccatcagcagtggtgattactactggagctggatccgccagcacccagggaagggcctg gagtggattgggtacatctattacagtgggagcacctactacaacccgtccctcaagagtcg agttaccatatcagtagacacgtctaagaaccagttctccctgaagctgagctctgtgactg ccgcggacacggccgtgtatttctgtgcgagagccgattacgattttggagtggttatttt gactactggggccagggaaccctggtcaccgtctcctcagcctccaccaagggcccatcgag tcttccccctgg 206 Heavy Chain Protein
QVQLQESGPGLVKPSQTLSLTCTVSGGSISSGDYYWSWIRQHPGKGLEWIGYIYYSGSTY

YNPSLKSRVTISVDTSKNQFSLKLSSVTAADTAVYFCARADYDFWSGYFDYWGQGTLVTV

SS

207 Light Chain DNA:
H3_178_1N1K
atgagggtccccgctcagctcctgggctcctgctgctctggttcccaggtgccaggtgtg acatccagatgacccagtctccatcctccctgtctgcatctgtaggagacagagtcaccat cacttgccgggcaagtcagggcattagaaatgatttaggctggtatcagcagaaaccaggg aaagcccctaagcgcctgatctatgctgcatccagtttgcaaagtggggtcccatcaaggt tcagcggcagtggatctgggacaaaattcactctcactatcagcagcctgcagcctgaaga ttttgcaacttattactgtctacagcataatatacccgtggacgttcggccaagggacc aaggtggaaatcagacgaactgtggctgcaccatctgtcttcatcttcccgccatctgatg agcagttgaaatctggaactgcctctgttgtgtgcctgctgaataacttctatcccagaga ggccaaagtacagtggaaggtggataacgcc 208 Light Chain Protein
DIQMTQSPSSLSASVGDRVTITCRASQGIRNDLGWYQQKPGKAPKRLIYAASSLQSGVP

SRPSGSGSGTKFTLTISSLQPEDFATYYCLQHNTYPWTFGQGTKVEIR

Antibody U1-16
209 Heavy Chain DNA:
H3_221_1N1G1
accatgaaacatctgtggttcttcctcctgctggtggcagctcccagatgggtcctgtccc aggtgcagctgcaggagtcgggcccaggactggtgaagccttcacagaccctgtccctcac ctgcactgtctctggtggctccatcagcagtggtgattactactggagctggatccgccag cacccagggaagggcctggagtggattgggtacatctattacagtgggagcacctactaca acccgtccctcaagagtcgagttaccatatcagtagacacgtctaagaaccagttctccct gaagctgagctctgtgactgccgcggacacggccgtgtattactgtgcgagagcggattac gattttggagtggttattttgactactggggccagggaatcctggtcaccgtctcctcag cctccaccaagggcccatcggtcttcccctggcaccctcctccaagaacacctctggggg -continued cacagcggccctgggctgcctggtcaaggactacttccccgaaccggtgacggtgtcctgg aactcaggcgccctg 210 Heavy Chain Protein
QVQLQESGPGLVKPSQTLSLTCTVSGGSISSGDYYWSWIRQHPGKGLEWIGYIYYSGSTYY

NPSLKSRVTISVDTSKNQFSLKLSSVTAADTAVYYCARADYDFWSGYFDYWGQGILVTVSS

211 Light Chain DNA:
H3_221_1N1K
atgagggtccccgctcagctcctggggctcctgctgctctggttcccaggtgccaggtgt gacatccagatgacccagtctccatcctccctgtctgcatctgtaggagacagagtcacc atcacttgccgggcaagtcagggcattagaaatgatttaggctggtatcagcagaaacca gggaaagcccctaagcgcctgatctatgctgcatccagtttgcaaagtggggtcccatca aggttcagcggcagtggatctgggacagaattcactctcacaatcagcagcctgcagcct gaagattttgcaacttattactgtctacagcataatagttacccgtggacgttcggccaa gggaccaaggtggaaatcaaacgaactgtggctgcaccatctgtcttcatcttcccgcca tctgatgagcagttgaaatctggaactgcctctgttgtgtgcctgctgaataacttctat cccagagaggccaaagtacagtggaaggtggataacgcc 212 Light Chain Protein
DIQMTQSPSSLSASVGDRVTITCRASQGIRNDLGWYQQKPGKAPKRLIYAASSLQSGVPSR

FSGSGSGTEFTLTISSLQPEDFATYYCLQHNSYPWTFGQGTKVEIK

Antibody U1-17
213 Heavy Chain DNA:
H3_224_1N1G1
tggttcttccttctgctggtggcagctcccagatgggtcctgtcccaggtgcagctgcagg agtcgggcccaggactggtgaagccttcacagaccctgtccctcacctgcactgtctctgg tggctccatcagcagtggtgattactactggagctggatccgccagcacccagggaagggc ctggagtggattggatacatctattacagtgggagcacctactacaattcgtccctcaaga gtcgagttaccatatcagtagacacgtctaagaaccagttctccctgaagctgagctctgt gactgccgcggacacggccgtgtattactgtgcgagagcggattacgattttttggagtggt tattttgactactggggccagggaaccctggtcaccgtctcctcagcctccaccaagggcc catcg 214 Heavy Chain Protein
QVQLQESGPGLVKPSQTLSLTCTVSGGSISSGDYYWSWIRQHPGKGLEWIGYIYYSGSTYY

NSSLKSRVTISVDTSKNQFSLKLSSVTAADTAVYYCARADYDFWSGYFDYWGQGTLVTVSS

215 Light Chain DNA:
H3_224_1N1K
ggtgccaggtgtgacatccagatgacccagtctccatcctccctgtctgcatctgtaggag acagagtcaccatcacttgccgggcaagtcagggcattagaaatgatttaggctggtatca gcagaaacctgggaaagcccctaagcgcctgatctatgctgcatccagtttgcaaagtggg gtcccatcaaggttcagcggcagtggatctgggacagaattcactctcacaatcagcagcc tgcagcctgaagattttgcaacttattactgtctacagcacaatagttacccgtggacgtt cggccaagggaccaaggtggaaatcaaacgaactgtggctgcaccatctgtcttcatcttc ccgcca 216 Light Chain Protein
DIQMTQSPSSLSASVGDRVTITCRASQGIRNDLGWYQQKPGKAPKRLIYAASSLQGVPS

RFSGSGSGTEFTLTISSLQPEDFATYYCLQHNSYPWTFGQGTKVEIK

Antibody U1-18

217 Heavy Chain DNA:
H3_227_1N1G1
aggttcttccttctgctggtggcagctcccagatgggtcctgtcccaggtgcagctgcagg agtcgggcccaggactggtgaagccttcacagaccctgtccctcacctgcactgtctctgg tggctccatcagcagtggtgattactactggagctggatccgccagcacccagggaagggc ctggagtggattggatacatctattacagtgggagcacctactacaacccgtccctcaaga gtcgagttaccatatcagtagacacgtctaagaaccagttctccctgaagctgagctctgt gactgccgcggacacggccgtgtattactgtgcgagagccgattacgattttggagtggt tattttgactactggggccagggaaccctggtcaccgtctcctcagcctccaccaagggcc catcggtcttccccctggcaccctcctccaagagcacctctgggggcacagcggccctggg ctgcctggtcaaggactacttccccgaaccggtgacggtgtcgtggaactcaggcgccct 218 Heavy Chain Protein
QVQLQESGPGLVKPSQTLSLTCTVSGGSISSGDYYWSWIRQHPGKGLEWIGYIYYSGSTYY

NPSLKSRVTISVDTSKNQFSLKLSSVTAADTAVYYCARADYDFWSGYFDYWGQGTLVTVSS

219 Light Chain DNA:
H3_227_1N1K
atgagggtccccgctcagctcctggggctcctgctgctctggttcccaggtgccaggtgtga catccagatgacccagtctccatcctccctgtctgcatctgtaggagacagagtcaccatca cttgccgggcaagtcagggcattagaaatgatttaggctggtatcagcagaaaccagggaaa gcccctaagcgcctgatctatgctgcatccagtttgcaaagtggggtcccatcaaggttcag cggcagtggatctgggacagaattcactctcacaatcagcagcctgcagcctgaagattttg caacttattactgtctacagcataatagttacccgtggacgttcggccaagggaccaaggtg gaaatcaaacgaactgtggctgcaccatctgtcttcatcttcccgccatctgatgagcagtt gaaatctggaactgcctctgttgtgtgcctgctgaataacttctatcccagagaggccaaag tacagtggaaggtggataacg 220 Light Chain Protein
DIQMTQSPSSLSASVGDRVTITCRASQGIRNDLGWYQQKPGAPKRLIYAASSLQSGVPS

RFSGSGSGTEFTLTISSLQPEDFATYYCLQHNSYPWTGQGTKVEIK

Antibody U1-33
221 Heavy Chain DNA:
H4_14_1N1G4
ctgtggttcttccttctgctggtggcagctcccagatgggtcctgtcccaggtgcagctgc aggagtcgggcccaggactggtgaagccttcacagaccctgtccctcacctgcactgtctc tggtggctccatcagcagtggtgattactactggagctggatccgccagcacccagggaag ggcctggagtggattgggtacatctattacagtgggagcacctactacaacccgtccctca agagtcgagttaccatgtcagtagacacgtctaagaaccagttctccctgaagctgagctc tgtgactgccgcggacacggccgtgtattactgtgcgagagccgattacgattttggagt ggtcactttgactgctggggccagggaaccctggtcaccgtctcctcagcttccaccaagg gcccatccgtcttccccc 222 Heavy Chain Protein
QVQLQESGPGLVKPSQTLSLTCTVSGGSISSGDYYWSWIRQHPGKGLEWIGYIYYSGSTYY

NPSLKSRVTMSVDTSKNQFSLKLSSVTAADTAVYYCARADYDFWSGHFDCWGQGTLVTVSS

223 Light Chain DNA:
H4_14_1N1K
atgagggtccccgctcagctcctggggctcctgctgctctggttcccaggtgccaggtgtga catccagatgacccagtctccatcctccctgtctgcatctgtaggagacagagtcaccatca cttgccgggcaagtcagggcattagagatgatttaggctggtatcagcagaaaccagggaaa -continued gcccctaagcgcctgatctatgctgaatccagtttgcaaagtggggtcccatcaaggttcag cggcagtggatctgggacagaattcactctcacaatcagcagcctgcagcctgaagattttg caacttattactgtctacagcatcatagttacccgtggacgttcggccaagggaccaaggtg gaaatcaaacgaactgtggctgcaccatctgtcttcatcttcccgcc 224 Light Chain Protein
DIQMTQSPSSLSASVGDRVTITCRASQGIRDDLGWYQQKPGKAPKRLIYAESSLQSGVPSR

FSGSGSGTEFTLTISSLQPEDFATYYCLQHHSYPWTFGQGTKVEIK

Antibody U1-29
225 Heavy Chain DNA:
H4_107_1N1G4
tggctgagctgggttttcctcgttgctcttttaagaggtgtccagtgtcaggtgcagctgg tggagtctgggggaggcgtggtccagcctggggaggtccctgagactctcctgtgcagcgtc tggattcaccttcaatagctatgacatgcactgggtccgccaggctccaggcaaggggctg gagtgggtggcagttatatggtatgatggaagtaataaatactatgcagactccgtgaagg gccgattcaccatctctagagacaattccaagaacacgctgtatctgcaaatgaacagcct gagagccgaggacacggctgtgtattactgtgcgagagaccgcttgtgtagtaatggtgta tgctatgaagactacggtatggacgtctggggccaagggaccacggtcaccgtctcctcag cttccaccaagggcccatccgtcttccccctggcgccctgctccaggagcacctccgagag cacagccgccctgggc 226 Heavy Chain Protein
QVQLVESGGGVVQPGRSLRLSCAASGFTFNSYDMHWVRQAPGKGLEWVAVIWYDGSNKYYA

DSVKGRFTISRDNSKNTLYLQMNSLRAEDTAVYYCARDRLCTNGVCYEDYGMDVWGQGTTV

TVSS

227 Light Chain DNA:
H4_107_1N1K
atgagggtccctgctcagctcctggggctcctgctgctctggctctcaggtgccagatgtga catccagatgacccagtctccatcctccctgtctgcatctgtaggagacagagtcaccatca cttgccaggcgagtcaggacattagcaactatttaaattggtatcagcagaaaccagggaaa gcccctaaggtcctgatctacgatgcatccaatttggaaacaggggtcccatcaaggttcag tggaagtggatctgggacagattttactttcaccatcagcagcctgcagcctgaagatgttg caacatattactgtcaaacactatgatactctcccgctcactttcggcggagggaccaaggtg gagatcaaacgaactgtggctgcaccatctgtcttcatcttcccgccatctgatgagcagtt gaaatctggaactgcctctgttgtgtgcctgctgaataacttctatcccagagaggccaaag tacagtgg 228 Light Chain Protein
DIQMTQSPSSLSASVGDRVTITCQASQDISNYLNWYQQKPGKAPKVLIYDASNLETGVPSR

FSGSGSGTDFTFTISSLQPEDVATYYCQHYDTLPLTFGGGTKVEIK

Antibody U1-30
229 Heavy Chain DNA:
H4_116_1_1N1G4
ggactgtgcaagaacatgaaacacctgtggttcttcctcctgctggtggcagctcccagatg ggtcctgtcccaggtgcagctgcaggagtcgggcccaggactggtgaagcctttacagaccc tgtccctcacctgcactgtctctggtggctccatcagcagtggtgattactactggagctgg atccgccagcacccagggaagggcctggagtggattgggtacatctattacagtgggaccac ctactacaacccgtccctcaagagtcgagttaccatatcagtagacacgtctaagaaccagt tcgccctgaagctgaactctgtgactgccgcggacacggccgtgtattactgtgcgagagcc -continued

```
gattacgattttttggagtggttattttgactactggggccagggaaccctggtcaccgtctc ctcagcttccaccaagggcccatccgtcttccccctgg
```

230 Heavy Chain Protein
QVQLQESGPGLVKPLQTLSLTCTVSGGSISSGDYYWSWIRQHPGKGLEWIGYIYYSGTTYY

NPSLKSRVTISVDTSKNQFALKLNSVTAADTAVYYCARADYDFWSGYFDYWGQGTLVTVSS

231 Light Chain DNA:
H4_116_1_1N1K
```
atgagggtccctgctcagctcctggggctcctgctgctctggttcccaggtgccaggtgtg acatccagatgacccagtctccatcctccctgtctgcatctgtaggagacagagtcaccat cacttgccgggcaggtcagggcattagaaatgatttaggctggtatcagcagaaaccaggg aaagcccctcagcgcctgatctatgctgcatccagtttgcaaagtggggtcccatcaaggt tcagcggcagtggatctgggacagaattctctctcacaatctccagcctgcagcctgaaga ttttgcaacttattactgtctacagcataatagttacccgtggacgttcggccaagggacc aaggtggaaatcaaacgaactgtggctgcaccatctgtcttcatcttcccgccatctgatg agcagttgaaatctggaactgcctctgttgtgtgcctgctgaataacttctatcccagaga ggccaaagtacagtggaaggtggataacgcccttccaatcggg
```

232 Light Chain Protein
DIQMTQSPSSLSASVGDRVTITCRAGQGIRNDLGWYQQKPGKAPQRLIYAASSLQSGVPSR

FSGSGSGTEFSLTISSLQPEDFATYYCLQHNSYPWTFGQGTKVEIK

[Chem 15]
In the Table below SEQ ID NOS 235-582 are disclosed, respectively, in order of appearance.
Sequence List of ODR

| Chain antibodies | Pat. number: | CDR1 | CDR2 | CDR3 |
|---|---|---|---|---|
| Heavy | U1-1 | GGSINSGDYYWS | YIYYSGSTYYNPSLKS | ADYDFWSGYFDY |
| Light | | RASQGIRNDLG | AASSLQS | LQHNSYPWT |
| Heavy | U1-2 | GGSISSGDYYWS | YIYYSGSTYYNPSLRS | ADYDFWSGYFDY |
| Light | | RASQGIRNDLG | AASSLQS | LQHNGYPWT |
| Heavy | U1-3 | GGSISSGGYYWS | YIYYSGSTYYNPSLKS | DGYDSSGYYHGYFDY |
| Light | | KSSQSVLYSSNNKNYLA | WASTRES | QQYYSTPLT |
| Heavy | U1-4 | GGSISSGDYYWS | YIYYSGSTYYNPSLKS | ADYDFWSGYFDY |
| Light | | RASQGIRNDLG | AASSLQS | LQHNNYPWT |
| Heavy | U1-5 | GGSISSGDYYWS | YIYYSGSTYYNPSLKS | ADYDFWSGYFDY |
| Light | | RASQGIRNDLG | AASSLQS | LQHNNYPWT |
| Heavy | U1-6 | GGSISSGDYYWS | YIYYSGSTYYNPSLKS | ADYDFWNGYFDY |
| Light | | RASQGIRNDLG | AASSLQS | LQHNTYPWT |
| Heavy | U1-7 | GGSISSGDYYWS | YIYYSGSTYYNPSLKS | ADYDFWSGYFDY |
| Light | | RASQDIRNDLG | AASSLQS | LQHNSYPWT |
| Heavy | U1-8 | GYTLTELSMY | GFDPEDGETIYAQKFQG | GWNYVFDY |
| Light | | RSSQSLLHSNGYNYLD | LDSHRAS | MQALQTPLT |
| Heavy | U1-9 | GGSISSGDYYWS | YIYYSGSTYYNPSLKS | ADYDFWNGYFDY |
| Light | | RASQDIRNDLG | AASSLQS | LQHNSYPWT |

[Chem 15]
In the Table below SEQ ID NOS 235-582 are disclosed, respectively, in order of appearance.

Sequence List of ODR

| Chain antibodies | Pat. number: | CDR1 | CDR2 | CDR3 |
|---|---|---|---|---|
| Heavy | U1-10 | GGSISSGDYYWS | YIYYSGSTYYNPSLKS | ADYDFWSGYFDY |
| Light | | RASQGIRNDLG | AASSLQS | LQHNNYPWT |
| Heavy | U1-11 | GGSISSGDYYWS | YIYYSGSTYYNPSLKS | ADYDFWSGYFDY |
| Light | | RASQGIRNDLG | AASSLQS | LQHNTYPWT |
| Heavy | U1-12 | GGSISSGDYYWS | YIYYSGSTYYNPSLKS | ADYDFWSGYFDY |
| Light | | RASQGIRNDLG | AASSLQS | LQHNNYPWT |
| Heavy | U1-13 | GGSISSGGYYWS | YIYYSGSTYYNPSLKS | EDDGMDV |
| Light | | RSSQSLLHSNGYNYLE | LGSNRAS | MQALQTPIT |
| Heavy | U1-14 | GGSISSGDYYWS | YIYYSGSTYYNPSLKS | ADYDFWSGYFDY |
| Light | | RASQGIRNDLG | AASSLQS | LQHNTYPWT |
| Heavy | U1-15 | GGSVSSGGYYWS | YIYYSGSTNYNPSLKS | DGDVDTAMVDAFDI |
| Light | | RASQSLSGNYLA | GASSRAT | QQYDRSPLT |
| Heavy | U1-16 | GGSISSGDYYWS | YIYYSGSTYYNPSLKS | ADYDFWSGYFDY |
| Light | | RASQGIRNDLG | AASSLQS | LQHNSYPWT |
| Heavy | U1-17 | GGSISSGDYYWS | YIYYSGSTYYNSSLKS | ADYDFWSGYFDY |
| Light | | RASQGIRNDLG | AASSLQS | LQHNSYPWT |
| Heavy | U1-18 | GGSISSGDYYWS | YIYYSGSTYYNPSLKS | ADYDFWSGYFDY |
| Light | | RASQGIRNDLG | AASSLQS | LQHNSYPWT |
| Heavy | U1-19 | GGSISSGDYYWS | YIYYSGSTYYNPSLKS | GDYDFWSGEFDY |
| Light | | | sequence not available | |
| Heavy | U1-20 | GGSISSGGYYWS | YIYDSGSTYYNPSLKS | DQGQDGYSYGYGYYYGMDV |
| Light | | QASQDISNYLN | VASNLET | QQCDNLPLT |
| Heavy | U1-21 | GGSISSGDYYWS | YIYYSGSTYYNPSLKS | ADYDFWSGYFDY |
| Light | | RASQDIRNDLG | AASRLQS | LQHNSYPWT |
| Heavy | U1-22 | GGSISSGDYYWS | YIYYSGSTYYNPSLKS | ADYDFWSGYFDY |
| Light | | RAWQGIRNDLG | AASSLQN | LQHNSYPWT |
| Heavy | U1-23 | GGSISSGDYYWS | YIYYSGSTYYNPSLKS | ADYDFWSGYFDY |
| Light | | RASQGIRNDLG | AASSLQS | LQHNSYPWT |
| Heavy | U1-24 | GGSISSGDYYWS | YIYYSGSTYYNPSLKS | ADYDFWNGYFDY |
| Light | | RASQGIRNDLG | AASSLQS | LQHNNYPWT |
| Heavy | U1-25 | GGSISSGDYYWS | YIYYSGSTYYNPSLKS | ADYDFWSGYFDY |
| Light | | RASQGIRNDLG | AASSLQN | LQHNSYPWT |
| Heavy | U1-26 | GGSISSGDYYWS | YIYYSGSTYYNPSLKS | ADYDFWSGYFDF |
| Light | | RASQGIRNDLG | AASSLQS | OQHNGYPWT |
| Heavy | U1-27 | GGSISSGDYYWS | YIYYSGSTYYNPSLKS | ADYDFWSGYFDF |

-continued

[Chem 15]
In the Table below SEQ ID NOS 235-582 are disclosed, respectively, in order of appearance.
Sequence List of ODR

| Chain antibodies | Pat. number: | CDR1 | CDR2 | CDR3 |
|---|---|---|---|---|
| Light | | RASQGIRNDLG | AASSLQS | LQHNGYPWT |
| Heavy | U1-28 | GGSISSGDYYWS | YIYYSGSTYYNPSLKS | ADYDFWSGYFDS |
| Light | | RASQGIRNDLG | AASSLQS | LQHNGYPWT |
| Heavy | U1-29 | GFTFNSYDMH | VIWYDGSNKYYADSVKG | DRLCTNGVCYEDYGMDV |
| Light | | QASQDISNYLN | DASNLET | QHYDTLPLT |
| Heavy | U1-30 | GGSISSGDYYWS | YIYYSGTTYYNPSLKS | ADYDFWSGYFDY |
| Light | | RAGQGIRNDLG | AASSLQS | LQHNSYPWT |
| Heavy | U1-31 | GYTFTNYGIS | WISAYDGYRNYAQKLQG | DVQDYGDYDYFDY |
| Light | | RASQSISSYLN | AASSLQS | QQSYSTPIT |
| Heavy | U1-32 | GGSISSGDYYWS | YIYYSGTTYYNPSLKS | ADYDFWSGYFDY |
| Light | | RAGQGIRNDLG | AASSLQS | LQHNSYPWT |
| Heavy | U1-33 | GGSISSGDYYWS | YIYYSGSTYYNPSLKS | ADYDFWSGHFDC |
| Light | | RASQGIRDDLG | AESSLQS | LQHHSYPWT |
| Heavy | U1-34 | GYTFTNYGIS | WISAYDGYRNYAQKLQG | DVQDYGDYDYFDY |
| Light | | RASQSISSYLN | AASSLQS | QQSYSTPIT |
| Heavy | U1-35 | GFTFSDYYMS | YISSSGNNIYHADSVKG | ERYSGYDDPDGFDI |
| Light | | QASQDISNYLS | DASNLET | QQYDNPPCS |
| Heavy | U1-36 | GGSISSGYYYWS | YIYYSGTTYYNPSFKS | ADYDFWSGHFDY |
| Light | | RASQGIRNDLG | AASSLQS | LQHNSYPWT |
| Heavy | U1-37 | GYTFTSYGIS | WISAYDGHTNYAQKLQG | DPHDYSNYEAFDF |
| Light | | RASQSISSYLN | AASSLQS | QQSYSTPIT |
| Heavy | U1-38 | GFSLSTSGVGVG | LIYWNDDKRYSPSLKS | RDEVRGFDY |
| Light | | RSSQSLVYSDGYTYLH | KVSNWDS | MQGAHWPIT |
| Heavy | U1-39 | GFTVSSNYMS | VIYSGGSTYYADSVKG | GQWLDV |
| Light | | RSSQSLLHSNGYNYLD | LGFHRAS | RQALQTPLT |
| Heavy | U1-40 | GGSISSGGYYWS | YISSSGSTYYNPSLKS | DRELELYYYYGMDV |
| Light | | RSSQSLLYSNGYNYLD | LGSNRAS | MQALQTLPLT |
| Heavy | U1-41 | GGSISSGGYYWS | YIYYSGSTYYNPSLKS | DRELEGYSNYYGVDV |
| Light | | RASQAISNYLN | AASSLQS | QQNNSLPIT |
| Heavy | U1-42 | GYSFTSYWIG | IIYPGDSDTRYSPSFQG | HENYGDYNY |
| Light | | RASQSIRSYLN | AASSLQS | QQSNGSPLT |
| Heavy | U1-43 | GGSISSGGYYWS | YIYYSGSTYYNPSLRS | DREREWDDYGDPQGMDV |
| Light | | RASQSISSYLH | AASSLQS | QQSYSNPLT |
| Heavy | U1-44 | GYSFTSYWIG | IIWPGDSDTIYSPSGQG | HENYGDYNY |
| Light | | RASQSIRSYLN | AASSLQS | QQSISSPLT |

[Chem 15]
In the Table below SEQ ID NOS 235-582 are disclosed, respectively, in order of appearance.

Sequence List of ODR

| Chain antibodies | Pat. number: | CDR1 | CDR2 | CDR3 |
|---|---|---|---|---|
| Heavy | U1-45 | GYTFTSYDIN | WMNPNSGDTGYAQVFQG | FGDLPYDYSYYEWFDP |
| Light | | RASQSISSYLN | AASSLQS | QQSYSTPLT |
| Heavy | U1-46 | GDSVSSNSAAWN | RTYYRSKWYNDYAVSVKS | DLYDFWSGYPYYYGMDV |
| Light | | | sequence not available | |
| Heavy | U1-47 | GDSVSSNSAAWN | RTYYRSKWYNDYAVSVKS | DYYGSGSFYYYYGMDV |
| Light | | RASQSISSYLN | AASNLQS | QQSYSTPRT |
| Heavy | U1-48 | GGSISSYYWS | HIYTSGSTNYNPSLKS | EAIPGVGPYYYYGMDV |
| Light | | | sequence not available | |
| Heavy | U1-49 | GYTFTGYYMH | WINPNIGGTNCAQKFQG | GGRYSSSWSYYYYGMDV |
| Light | | KSSQSLLLSDGGTYLY | EVSNRFS | MQSMQLPIT |
| Heavy | U1-50 | GGSVSSGGYYWS | YIYYSGSTNYNPSLKS | GGDSNYEDYYYYGMDV |
| Light | | RASQSISIYLH | AASSLQS | QQSYTSPIT |
| Heavy | U1-51 | GGSISSYYWS | YIYYSGSTNYNPSLKS | DSSYYDSSGYYLYYYAMDV |
| Light | | KSSQSVLYSSNNKNYLA | WASTRES | QQYYTTPLT |
| Heavy | U1-52 | GGSISSGGYYWS | NIYYSGSTYYNPSLKS | GGTGTNYYYYYGMDV |
| Light | | RASQSVSSSYLA | GASSWAT | QQYGSSPLT |
| Heavy | U1-53 | GFTFSIYSMN | YISSSSSTIYYADSVKG | DRGDFDAFDI |
| Light | | QASQDITNYLN | DASNLET | QQCENFPIT |
| Heavy | U1-54 | GGSVSSGGYYWN | YINYSGSTNYNPSLKS | DRELELYYYYGMDV |
| Light | | | Identical with U1-55 | |
| Heavy | U1-55 | | Identical with U1-55.1 | |
| Light | | RSSQSLLYSNGYKYLD | LGSNRAS | MQALQTPIT |
| Heavy | U1-57.1 | | Identical with U1-57 | |
| Light | | RSSQSLLYSNGYKYLD | LGSNRAS | MQALQTPIT |
| Heavy | U1-57 | GGSVSSGGYYWN | YINYSGSTNYNPSLKS | DRELELYYYYGMDV |
| Light | | | Identical with U1-57.1 | |
| Heavy | U1-58 | GFTFSSYGMII | VIWYDGSNKYYADSVKG | AARLDYYYGMDV |
| Light | | RASQSINSYLN | GASGLQS | QQSYSSPLT |
| Heavy | U1-59 | GGSFSGYYWS | EINHSGSTMYNPSLKS | DKWTWYFDL |
| Light | | RSSQSVLYSSSNRNYLA | WASTRES | QQYYSTPRT |
| Heavy | U1-61.1 | GVSISSGGYYWS | YIWWSGSTYYNPSLKS | DSESEYSSSSNYGMDV |
| Light | | RASQTISSYLN | AASSLQG | QQSYSNPLT |
| Heavy | U1-61 | GVSISSGGYYWS | YIYYSGSTYYNPSLKS | DSESEYSSSSNYGMDV |
| Light | | | Identical with U1-61.1 | |

-continued

[Chem 15]
In the Table below SEQ ID NOS 235-582 are disclosed, respectively, in order of appearance.
Sequence List of ODR

| Chain antibodies | Pat. number: | CDR1 | CDR2 | CDR3 |
|---|---|---|---|---|
| Heavy | U1-62 | GYSFTSYWIG | IIYPGDSDTRYSPSFQG | QMAGNYYYGMDV |
| Light | | RASQSVISIYLA | GASSRAT | QQYGSSPCS |

When a newly produced monoclonal antibody binds to a partial peptide or a partial tertiary structure to which the U1-49, U1-53, U1-59, U1-7, or U1-9 antibody binds, it can be determined that the antibody binds to the same epitope as the U1-49, U1-53, U1-59, U1-7, or U1-9 antibody. Further, by confirming that the antibody competes with the U1-49, U1-53, U1-59, U1-7, or U1-9 antibody for binding to HER3 (that is, the antibody inhibits the binding between the U1-49, U1-53, U1-59, U1-7, or U1-9 antibody and HER3), it can be determined that the antibody binds to the same epitope as the U1-49, U1-53, U1-59, U1-7, or U1-9 antibody even when the specific sequence or structure of an epitope is not defined. Once the epitope is confirmed to be the same, it is strongly expected that the antibody has a biological activity equivalent to that of the U1-49, U1-53, U1-59, U1-7, or U1-9 antibody.

According to the present invention, the binding protein of the invention interacts with at least one epitope in the extracellular part of HER3. The epitopes are preferably located in domain L1 (aa 19-184), which is the amino terminal domain, in domain S1 (aa 185-327) and S2 (aa 500-632), which are the two Cysteine-rich domains, in domain L2 (328-499), which is flanked by the two Cysteine-rich domains or in a combination of HER3 domains. The epitopes may also be located in combinations of domains such as but not limited to an epitope comprised by parts of L1 and S1. Moreover, the binding protein of the invention is further characterized in that its binding to HER3 reduces HER3-mediated signal transduction. In accordance with the present invention, a reduction of HER3-mediated signal transduction may, e.g. be caused by a downregulation of HER3 resulting in an at least partial disappearance of HER3 molecules from the cell surface or by a stabilization of HER3 on the cell surface in a substantially inactive form, i.e. a form which exhibits a lower signal transduction compared to the non-stabilized form. Alternatively, a reduction of HER3-mediated signal transduction may also be caused by influencing, e.g. decreasing or inhibiting, the binding of a ligand or another member of the HER family to HER3, of GRB2 to HER-2 or of GRB2 to SHC, by inhibiting receptor tyrosine phosphorylation, AKT phosphorylation, PYK2 tyrosine phosphorylation or ERK2 phosphorylation, or by decreasing tumor invasiveness. Alternatively, a reduction of HER3 mediated signal transduction may also be caused by influencing, e.g., decreasing or inhibiting, the formation of HER3 containing dinners with other HER family members. One example among others may be the decreasing or inhibiting of the HER3-EGFR protein complex formation.

Furthermore, in accordance with the present invention, minor variations in the amino acid sequences shown in SEQ ID NOs: 1-232 are contemplated as being encompassed by the present invention, providing that even the variations in the amino acid sequence still maintain at least 75%, more preferably at least 80%, 90%, 95%, and most preferably 99% of the sequences shown in SEQ ID NOs: 1-232. The variations may occur within the framework regions (i.e. outside the CDRs), within the CDRs, or within the framework regions and the CDRs. Preferred variations in the amino acid sequences shown in SEQ ID NOs: 1-232, i.e. deletions, insertions and/or replacements of at least one amino acid, occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other binding proteins of known structure and/or function. Methods to identify protein sequences that fold into a known three-dimensional structure are known. See e.g. Bowie et al, Science 253, 164 (1991); Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at., Nature 354, 105 (1991), which are all incorporated herein by reference. Thus, those of skill in the art can recognize sequence motifs and structural conformations that may be used to define structural and functional domains in accordance with the invention. Among antibodies obtained by combining heavy and light chains having variations in such an amino acid sequences, an antibody equivalent to the original antibody (parent antibody) or more excellent than a parent antibody may be selected. As mentioned above, the HER3-binding protein, the anti-HER3 antibody, and the like of the present invention maintain the HER3-binding activity even if having variations in their amino acid sequences.

In the present invention, the term "homology" has the same meaning as the "identity". The homology between two amino acid sequences can be determined using default parameters of Blast algorithm version 2.2.2 (Altschul, Stephen F., Thomas L. Madden, Alejandro A. Schaeffer, Jinghui Zhang, Zheng Zhang, Webb Miller, and David J. Lipman (1997), "Gapped BLAST and PSI-BLAST: a new generation of protein database search programs", Nucleic Acids Res. 25: 3389-3402). The Blast algorithm can be used also through the Internet by accessing the site ncbi.nlm.nih.gov/blast.

The chimeric antibody, humanized antibody, or human antibody obtained by the aforementioned method can be subjected to a known method for evaluating the binding property to an antigen for selecting preferable antibodies.

In the anti-HER3 antibody of the present invention, MEHD-7945A (or duligotuzumab), RG-7116, MM-111, MM-121 (or seribantumab, MM-141, LJM-716, huHER3-8, tri-specific anti-EGFR/ErbB3 zybody, GSK-2849330, REGN-1400, KTN-3379, AV-203, monospecific surrobody (ErbB3), lumretuzumab, MP-EV-20, ZW-9, Dimercept™, anti-Erb3 surrobody(SL-175 or SL-176), SYM-013, variants, active fragments, modified products thereof, and the like are also included.

As one example of another index for use in the comparison of the properties of antibodies, the stability of antibodies can be exemplified. The differential scanning calorimetry (DSC) is a device capable of quickly and accurately measuring a thermal denaturation midpoint temperature (Tm) to be used as a favorable index of the relative conformational stability of proteins. By measuring the Tm values using DSC and comparing the values, a difference in thermal stability can be compared. It is known that the storage stability of antibodies shows some correlation with the thermal stability of antibodies (Lori Burton, et. al., Pharmaceutical Development and Technology (2007) 12, pp. 265-273), and a preferred antibody can be selected by using thermal stability as an index. Examples of other indices for selecting antibodies include the following features: the yield in an appropriate host cell is high; and the aggregability in an aqueous solution is low. For example, an antibody which shows the highest yield does not always show the highest thermal stability, and therefore, it is necessary to select an antibody most suitable for the administration to humans by making comprehensive evaluation based on the above-described indices.

The antibody of the present invention encompasses a modified product of the antibody. The modified variant refers to a variant obtained by subjecting the antibody of the invention to chemical or biological modification. Examples of the chemically modified variant include variants chemically modified by linking a chemical moiety to an amino acid skeleton, variants chemically modified with an N-linked or O-linked carbohydrate chain, etc. Examples of the biologically modified variant include variants obtained by modification after translation (such as N-linked or O-linked glycosylation, N- or C-terminal processing, deamidation, isomerization of aspartic acid, or oxidation of methionine), and variants in which a methionine residue has been added to the N terminus by being expressed in a prokaryotic host cell. Further, an antibody labeled so as to enable the detection or isolation of the antibody or an antigen of the invention, for example, an enzyme-labeled antibody, a fluorescence-labeled antibody, and an affinity-labeled antibody are also included in the meaning of the modified variant. Such a modified variant of the antibody of the invention is useful for improving the stability and blood retention of the antibody, reducing the antigenicity thereof, detecting or isolating the antibody or the antigen, and so on.

Further, by regulating the modification of a glycan which is linked to the antibody of the invention (glycosylation, defucosylation, etc.), it is possible to enhance an antibody-dependent cellular cytotoxic activity. As the technique for regulating the modification of a glycan of antibodies, International Publication WO 1999/54342, WO 2000/61739, WO 2002/31140, etc. are known. However, the technique is not limited thereto. In the antibody of the invention, an antibody in which the modification of a glycan is regulated is also included.

In the case where an antibody is produced by first isolating an antibody gene and then introducing the gene into an appropriate host, a combination of an appropriate host and an appropriate expression vector can be used. Specific examples of the antibody gene include a combination of a gene encoding a heavy chain sequence of an antibody and a gene encoding a light chain sequence thereof described in this specification. When a host cell is transformed, it is possible to insert the heavy chain sequence gene and the light chain sequence gene into the same expression vector, and also into different expression vectors separately.

In the case where eukaryotic cells are used as the host, animal cells, plant cells, and eukaryotic microorganisms can be used. As the animal cells, mammalian cells, for example, simian COS cells (Gluzman, Y., Cell, (1981) 23, pp. 175-182, ATCC CRL-1650), murine fibroblasts NIH3T3 (ATCC No. CRL-1658), and dihydrofolate reductase-deficient strains (Urlaub, G. and Chasin, L. A., Proc. Natl. Acad. Sci. USA (1980) 77, pp. 4126-4220) of Chinese hamster ovarian cells (CHO cells; ATCC: CCL-61) can be exemplified.

In the case where prokaryotic cells are used, for example, *Escherichia coli* and *Bacillus subtilis* can be exemplified.

By introducing a desired antibody gene into these cells through transformation, and culturing the thus transformed cells in vitro, the antibody can be obtained. In the above-described culture method, the yield may sometimes vary depending on the sequence of the antibody, and therefore, it is possible to select an antibody which is easily produced as a pharmaceutical by using the yield as an index among the antibodies having an equivalent binding activity. Therefore, in the antibody of the invention, an antibody obtained by a method of producing an antibody, characterized by including a step of culturing the transformed host cell and a step of collecting a desired antibody or a functional fragment of the antibody from a cultured product obtained in the culturing step is also included.

It is known that a lysine residue at the carboxyl terminus of the heavy chain of an antibody produced in a cultured mammalian cell could be deleted/eliminated (Journal of Chromatography A, 705: 129-134 (1995)), and it is also known that two amino acid residues (glycine and lysine) at the carboxyl terminus of the heavy chain of an antibody produced in a cultured mammalian cell could be deleted/eliminated and a proline residue newly located at the carboxyl terminus could be amidated (Analytical Biochemistry, 360: 75-83 (2007)). However, such deletion/elimination and modification of the heavy chain sequence do not affect the antigen-binding affinity and the effector function (the activation of a complement, the antibody-dependent cellular cytotoxicity, etc.) of the antibody. Therefore, in the antibody of the invention, an antibody and a functional fragment of the antibody subjected to such modification are also included, and a deletion variant in which one or two amino acids have been deleted at the carboxyl terminus of the heavy chain, a variant obtained by amidation of the deletion variant (for example, a heavy chain in which the carboxyl terminal proline residue has been amidated), and the like are also included. The type of deletion variant having a deletion at the carboxyl terminus of the heavy chain of the antibody according to the invention is not limited to the above variants as long as the antigen-binding affinity and the effector function are conserved. The two heavy chains constituting the antibody according to the invention may be of one type selected from the group consisting of a full-length heavy chain and the above-described deletion variant, or may be of two types in combination selected therefrom. The ratio of the amount of each deletion variant can be affected by the type of cultured mammalian cells which produce the antibody according to the invention and the culture conditions, however, a case where one amino acid residue at the carboxyl terminus has been deleted in both of the two heavy chains contained as main components in the antibody according to the invention can be exemplified. The scope of the whole antibody (in the present invention, also simply referred to as an "antibody") of the present invention also includes deletion variants thereof, mixtures containing one or two or more deletion variants thereof, etc. The "antibody" of the present invention includes an antibody comprising a heavy or light chain in which N-terminal glutamate is in the form of pyroglutamate by cyclization and/or a heavy or light chain in which a portion of cysteine residues are in the form of cysteinyl.

In a preferred embodiment of the present invention, the anti-HER3 antibody of the invention is of the IgA, IgD-, IgE$_1$ IgG- or IgM-type, preferably of the IgG- or IgM-type including, but not limited to, the IgGI-, IgG2-, IgG3-, IgG4-, IgMI- and IgM2-type. In most preferred embodiments, the antibody is of the IgGI-, IgG2- or IgG4-type.

As the biological activity of the antibody, generally, an antigen-binding activity, activity of internalizing an antigen in cells expressing the antigen by binding with the antigen, an activity of neutralizing the activity of an antigen, an activity of enhancing the activity of an antigen, an antibody-dependent cellular cytotoxicity (ADCC) activity, a complement-dependent cytotoxicity (CDC) activity, and an antibody-dependent cell-mediated phagocytosis (ADCP) can be exemplified. The function of the antibody according to the invention is a binding activity to HER3, preferably, activity of internalizing HER3 in HER3 expressing cells by binding with HER3. Further, the antibody of the invention may have an ADCC activity, a CDC activity and/or an ADCP activity in addition to the cell internalization activity.

In certain respects, e.g. in connection with the generation of antibodies as therapeutic candidates against HER3, it may be desirable that the anti-HER3 antibody of the invention is capable of fixing complement and participating in complement-dependent cytotoxicity (CDC). There are a number of isotypes of antibodies that are capable of the same including without limitations the following: murine IgM, murine IgG2a, murine IgG2b, murine IgG3, human IgM, human IgGI, human IgG3, and human IgA. It will be appreciated that antibodies that are generated need not initially possess such an isotype but, rather the antibody as generated can possess any isotype and the antibody can be isotype switched by appending the molecularly cloned V region genes or cDNA to molecularly cloned constant region genes or cDNAs in appropriate expression vectors using conventional molecular biological techniques that are well known in the art and then expressing the antibodies in host cells using techniques known in the art. The isotype-switched antibody may also possess an Fc region that has been molecularly engineered to possess superior CDC over naturally occurring variants (Idusogie et al., J Immunol., 166, 2571-2575) and expressed recombinantly in host cells using techniques known in the art. Such techniques include the use of direct recombinant techniques (see e.g. U.S. Pat. No. 4,816,397), cell-cell fusion techniques (see e.g. U.S. Pat. Nos. 5,916,771 and 6,207,418), among others. In the cell-cell fusion technique, a myeloma or other cell line such as CHO is prepared that possesses a heavy chain with any desired isotype and another myeloma or other cell line such as CHO is prepared that possesses the light chain. Such cells can, thereafter, be fused and a cell line expressing an intact antibody can be isolated. By way of example, a human anti-HER3 IgG4 antibody, that possesses the desired binding to the HER3 antigen, could be readily isotype switched to generate a human IgM, human IgGI or human IgG3 isotype, while still possessing the same variable region (which defines the antibody's specificity and some of its affinity). Such molecule might then be capable of fixing complement and participating in CDC.

Moreover, it may also be desirable for the anti-HER3 antibody of the invention to be capable of binding to Fc receptors on effector cells, such as monocytes and natural killer (NK) cells, and participate in antibody-dependent cellular cytotoxicity (ADCC). There are a number of isotypes of antibodies that are capable of the same, including without limitations the following: murine IgG2a, murine IgG2b, murine IgG3, human IgGI and human IgG3. It will be appreciated that antibodies that are generated need not initially possess such an isotype but, rather the antibody as generated can possess any isotype and the antibody can be isotype switched by appending the molecularly cloned V region genes or cDNA to molecularly cloned constant region genes or cDNAs in appropriate expression vectors using conventional molecular biological techniques that are well known in the art and then expressing the antibodies in host cells using techniques known in the art. The isotype-switched antibody may also possess an Fc region that has been molecularly engineered to possess superior ADCC over naturally occurring variants (Shields et al. J Biol Chem., 276, 6591-6604) and expressed recombinantly in host cells using techniques known in the art. Such techniques include the use of direct recombinant techniques (see e.g. U.S. Pat. No. 4,816,397), cell-cell fusion techniques (see e.g. U.S. Pat. Nos. 5,916,771 and 6,207,418), among others. In the cell-cell fusion technique, a myeloma or other cell line such as CHO is prepared that possesses a heavy chain with any desired isotype and another myeloma or other cell line such as CHO is prepared that possesses the light chain. Such cells can, thereafter, be fused and a cell line expressing an intact antibody can be isolated. By way of example, a human anti-HER3 IgG4 antibody, that possesses the desired binding to the HER3 antigen, could be readily isotype switched to generate a human IgGI or human IgG3 isotype, while still possessing the same variable region (which defines the antibody's specificity and some of its affinity). Such molecule might then be capable of binding to FcγR on effectors cells and participating in ADCC.

The obtained antibody can be purified to be homogeneous. The separation and purification of the antibody may be performed employing a conventional protein separation and purification method. For example, the antibody can be separated and purified by appropriately selecting and combining column chromatography, filter filtration, ultrafiltration, salt precipitation, dialysis, preparative polyacrylamide gel electrophoresis, isoelectric focusing electrophoresis, and the like (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but the method is not limited thereto.

Examples of such chromatography include affinity chromatography, ion exchange chromatography, hydrophobic chromatography, gel filtration chromatography, reverse phase chromatography, and adsorption chromatography.

Such chromatography can be performed employing liquid chromatography such as HPLC or FPLC.

As a column to be used in affinity chromatography, a Protein A column and a Protein G column can be exemplified. For example, as a column using a Protein A column, Hyper D, POROS, Sepharose FF (Pharmacia Corp.) and the like can be exemplified.

Further, by using a carrier having an antigen immobilized thereon, the antibody can also be purified utilizing the binding property of the antibody to the antigen.

{Antitumor Compound}

The antitumor compound to be conjugated to the anti-HER3 antibody-drug conjugate of the present invention is explained. The antitumor compound used in the present invention is not particularly limited if it is a compound having an antitumor effect and a substituent or a partial structure allowing connecting to a linker structure. When a part or whole linker of the antitumor compound is cleaved in tumor cells, the antitumor compound moiety is released to exhibit the antitumor effect. As the linker is cleaved at a connecting position with a drug, the antitumor compound is released in its unmodified structure to exhibit its intrinsic antitumor effect.

As an antitumor compound used in the present invention, exatecan, a camptothecin derivative ((1S,9S)-1-amino-9-ethyl-5-fluoro-2,3-dihydro-9-hydroxy-4-methyl-1H,12H-benzo[de]pyrano[3',4':6,7]indolizino[1,2-b]quinolin-10,13 (9H,15H)-dione shown in the following formula) can be preferably used.

[Chem. 16]

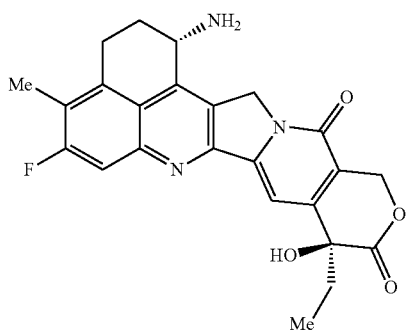

Although having an excellent antitumor effect, exatecan has not been commercialized as an antitumor drug. The compound can be easily obtained by a known method and the amino group at position 1 can be preferably used as a connecting position to the linker structure. Further, exatecan can be also released in tumor cells while part of the linker is still attached thereto. However, it is an excellent compound exhibiting an excellent antitumor effect even in such structure.

Because exatecan has a camptothecin structure, it is known that the equilibrium shifts to a structure with a closed lactone ring (closed ring) in an acidic aqueous medium (for example, pH 3 or so) but it shifts to a structure with an open lactone ring (open ring) in a basic aqueous medium (for example, pH 10 or so). A drug conjugate being introduced with an exatecan residue corresponding to the closed ring structure and the open ring structure is also expected to have the same antitumor effect and it is needless to say that any of them is within the scope of the present invention.

Examples of other antitumor compounds include doxorubicin, daunorubicin, mitomycin C, bleomycin, cyclocytidine, vincristine, vinblastine, methotrexate, platinum-based antitumor agent (cisplatin or derivatives thereof), taxol or derivatives thereof, and other camptothecin or derivatives thereof (antitumor agent described in Japanese Patent Laid-Open No. 6-87746).

With regard to the antibody-drug conjugate, the number of conjugated drug molecules per antibody molecule is a key factor having an influence on the efficacy and safety. Production of the antibody-drug conjugate is performed by defining the reaction condition including the amounts of use of raw materials and reagents for reaction so as to have a constant number of conjugated drug molecules, a mixture containing different numbers of conjugated drug molecules is generally obtained unlike the chemical reaction of a low-molecular-weight compound. The number of drugs conjugated in an antibody molecule is expressed or specified by the average value, that is, the average number of conjugated drug molecules. Unless specifically described otherwise as a principle, the number of conjugated drug molecules means an average value except in a case in which it represents an antibody-drug conjugate having a specific number of conjugated drug molecules that is included in an antibody-drug conjugate mixture having different number of conjugated drug molecules.

The number of exatecan molecules conjugated to an antibody molecule is controllable, and as an average number of conjugated drug molecules per antibody, about 1 to 10 exatecans can be bound. Preferably, it is 2 to 8, and more preferably 3 to 8. Meanwhile, a person skilled in the art can design a reaction for conjugating a required number of drug molecules to an antibody molecule based on the description of the Examples of the present application and can obtain an antibody-drug conjugate with a controlled number of conjugated exatecan molecules.

The antibody-drug conjugate of the present invention is unlikely to have an occurrence of aggregation, insolubility, fragmentation, or the like, even when the number of conjugated drug molecules per antibody molecule is increased.

{Linker Structure}

With regard to the anti-HER3 antibody-drug conjugate of the present invention, the linker structure for conjugating an antitumor compound to the anti-HER3 antibody is explained. The linker has the following structure:

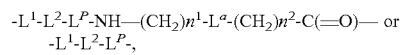

the antibody is connected to the terminal of $L^1$ (opposite terminal to which $L^2$ is connected), and the antitumor compound is connected to the carbonyl group of $-L^a-(CH_2)n^2-C(=O)-$ moiety or the C terminal of $L^P$.

$n^1$ represents an integer of 0 to 6, preferably, an integer of 1 to 5, and more preferably 1 to 3.

1. $L^1$ $L^1$ is represented by a structure shown below:
-(Succinimid-3-yl-N)—$(CH_2)n^3$-C(=O)—

In the above, $n^3$ is an integer of 2 to 8, and "-(Succinimid-3-yl-N)—" has a structure represented by the following formula:

[Chem. 17]

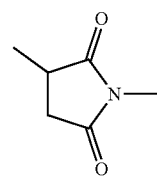

Position 3 of the above partial structure is the connecting position to the anti-HER3 antibody. The connection to the antibody at position 3 is characterized by forming a thioether bond. The nitrogen atom at position 1 of the structure moiety is connected to the carbon atom of methylene which is present within the linker including the structure. Specifically, -(Succinimid-3-yl-N)—$(CH_2)n^3$-C(=O)-$L^2$- is a structure represented by the following formula (herein, "antibody —S—" is derived from an antibody).

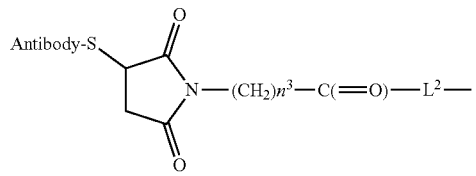

In the formula, n³ is an integer of 2 to 8, and preferably 2 to 5.

Specific examples of $L^1$ include the followings.
-(Succinimid-3-yl-N)—CH₂CH₂—C(=O)—,
-(Succinimid-3-yl-N)—CH₂CH₂CH₂—C(=O)—,
-(Succinimid-3-yl-N)—CH₂CH₂CH₂CH₂—C(=O)—,
-(Succinimid-3-yl-N)—CH₂CH₂CH₂CH₂CH₂—C(=O)—
2. $L^2$ $L^2$ has a structure represented by the following formula:

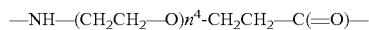

$L^2$ may not be present, and in such a case, $L^2$ is a single bond. In the drug-linker structure of the present invention, in particular, $L^P$ may be directly connected to a drug, and in such a case, $L^2$ is particularly preferably a single bond. n⁴ is an integer of 1 to 6, and preferably 2 to 4. $L^2$ is connected to $L^1$ at its terminal amino group and is connected to $L^P$ at the carbonyl group of the opposite terminal.

Specific examples of $L^2$ include the followings.
—NH—CH₂CH₂—O—CH₂CH₂—C(=O)—,
—NH—CH₂CH₂—O—CH₂CH₂—O—CH₂CH₂—C(=O)—,
—NH—CH₂CH₂—O—CH₂CH₂—O—CH₂CH₂—O—CH₂CH₂—C(=O)—,
—NH—CH₂CH₂—O—CH₂CH₂—O—CH₂CH₂—O—CH₂CH₂—O—CH₂CH₂—C(=O)—,
—NH—CH₂CH₂—O—CH₂CH₂—O—CH₂CH₂—O—CH₂CH₂—O—CH₂CH₂—C(=O)—,
—NH—CH₂CH₂—O—CH₂CH₂—O—CH₂CH₂—O—CH₂CH₂—O—CH₂CH₂—O—CH₂CH₂—C(=O)—
3. $L^P$ $L^P$ is a peptide residue consisting of 2 to 7 amino acids. Specifically, it consists of an oligopeptide residue in which 2 to 7 amino acids are linked by a peptide bond. $L^P$ is connected to $L^2$ at N terminal and it is connected to the amino group of —NH—(CH₂)n¹-$L^a$-(CH₂)n²-C(=O)— moiety of the linker at C terminal.

The amino acid constituting $L^P$ is not particularly limited, and the examples thereof include an L- or a D-amino acid, preferably an L-amino acid. Further, it can be an amino acid having a structure such as beta-alanine, epsilon-aminocaproic acid, or gamma-aminobutyric acid in addition to an alpha-amino acid, further, it can be a non-natural type amino acid such as N-methylated amino acid.

Sequence of the amino acid of $L^P$ is not particularly limited, but examples of the constituting amino acid include phenylalanine (Phe; F), tyrosine (Tyr; Y), leucine (Leu; L), glycine (Gly; G), alanine (Ala; A), valine (Val; V), lysine (Lys; K), citrulline (Cit), serine (Ser; S), glutamic acid (Glu; E), and aspartic acid (Asp; D). Among them, preferred examples include phenylalanine, glycine, valine, lysine, citrulline, serine, glutamic acid, and aspartic acid. Depending on the type of the amino acid, drug release pattern can be controlled. The number of the amino acid can be between 2 to 7.

Specific examples of $L^P$ include the followings.

-GGF-,

-DGGF-, (SEQ ID NO: 586)

-(D-)D-GGF-, (SEQ ID NO: 587)

-EGGF-, (SEQ ID NO: 585)

-GGFG-, (SEQ ID NO: 588)

-SGGF-, (SEQ ID NO: 589)

-KGGF-, (SEQ ID NO: 590)

-DGGFG-, (SEQ ID NO: 591)

-GGFGG-, (SEQ ID NO: 592)

-DDGGFG-, (SEQ ID NO: 593)

-KDGGFG-, (SEQ ID NO: 594)

-GGFGGGF-

The "(D-)D" described above means D-aspartic acid. Examples of the particularly preferred L of the antibody-drug conjugate of the present invention include -GGFG- (SEQ ID NO: 585) and -DGGFG- (SEQ ID NO: 590) peptide residue. Further, in the drug-linker structure of the present invention, $L^P$ may be directly connected to the drug, and for such a case, preferred examples of $L^P$ include a pentapeptide residue of -DGGFG- (SEQ ID NO: 590).

4. $L^a$-(CH₂)n²-C(=O)—

$L^a$ in $L^a$-(CH₂)n²-C(=O)— is a structure of —O— or a single bond. n² is an integer of 0 to 5, preferably, 0 to 3, and more preferably 0 or 1.

Examples of $L^a$-(CH₂)n²-C(=O)— include the followings.
—O—CH₂—C(=O)—,
—O—CH₂CH₂—C(=O)—,
—O—CH₂CH₂CH₂—C(=O)—,
—O—CH₂CH₂CH₂CH₂—C(=O)—,
—O—CH₂CH₂CH₂CH₂CH₂—C(=O)—,
—CH₂—C(=O)—,
—CH₂CH₂—C(=O)—,
—CH₂CH₂CH₂—C(=O)—,
—CH₂CH₂CH₂CH₂—C(=O)—,
—CH₂CH₂CH₂CH₂CH₂—C(=O)—.

Among them, those with
—O—CH₂—C(=O)—,
—O—CH₂CH₂—C(=O)—
or those in which $L^a$ is a single bond and n² is 0 are preferable.

Specific examples of the linker structure represented by —NH—(CH₂)n¹-$L^a$-(CH₂)n²-C(=O)— include the followings.
—NH—CH₂—C(=O)—,
—NH—CH₂CH₂—C(=O)—,
—NH—CH₂—O—CH₂—C(=O)—,
—NH—CH₂CH₂—O—C(=O)—,
—NH—CH₂CH₂—O—CH₂—C(=O)—, —NH—CH$_2$CH$_2$CH$_2$—C(=O)—,
—NH—CH$_2$CH$_2$CH$_2$CH$_2$—C(=O)—,
—NH—CH$_2$CH$_2$CH$_2$CH$_2$CH$_2$—C(=O)—

Among them, the examples are more preferably the followings.
—NH—CH$_2$CH$_2$CH$_2$—C(=O)—,
—NH—CH$_2$—O—CH$_2$—C(=O)—,
—NH—CH$_2$CH$_2$—O—C(=O)—

As for the linker —NH—(CH$_2$)n$^1$-L$^a$-(CH$_2$)n$^2$-C(=O)—, the chain length of 4 to 7 atoms is preferable, and more preferably, are those having the chain length of 5 or 6 atoms.

With regard to the anti-HER3 antibody-drug conjugate of the present invention, when it is transferred to the inside of tumor cells, it is thought that the linker moiety is cleaved and the drug derivative having a structure represented by NH$_2$—(CH$_2$)n$^1$-L$^a$-(CH$_2$)n$^2$-C(=O)-(NH-DX) is released to express an antitumor action. Examples of the antitumor derivative exhibiting an antitumor effect by releasing from the antibody-drug conjugate of the present invention include an antitumor derivative having a structure moiety in which the terminal of the structure represented by —NH—(CH$_2$)n$^1$-L$^a$-(CH$_2$)n$^2$-C(=O)— of the linker is an amino group, and the particularly preferred include the followings.

NH$_2$—CH$_2$CH$_2$—C(=O)—(NH-DX),
NH$_2$—CH$_2$CH$_2$CH$_2$—C(=O)—(NH-DX),
NH$_2$—CH$_2$—O—CH$_2$—C(=O)—(NH-DX),
NH$_2$—CH$_2$CH$_2$—O—CH$_2$—C(=O)—(NH-DX).

Meanwhile, in case of NH$_2$—CH$_2$—O—CH$_2$—C(=O)-(NH-DX), it was confirmed that, as the aminal structure in the molecule is unstable, it again undergoes a self-degradation to release the following HO—CH$_2$—C(=O)-(NH-DX). Those compounds can be also preferably used as a production intermediate of the antibody-drug conjugate of the present invention.

Further, in the drug-linker structure of the present invention, there arises a case in which L$^P$ may be directly connected to the drug. In such a case, when the C terminal of L$^P$ is glycine, the antitumor drug to be released is exatecan itself or a compound having glycine bonded to the amino group of exatecan.

For the antibody-drug conjugate of the present invention in which exatecan is used as a drug, the drug-linker structure moiety having the following structure
-L$^1$-L$^2$-L$^P$-NH—(CH$_2$)n$^1$-L$^a$-(CH$_2$)n$^2$-C(=O)-(NH-DX) or
-L$^1$-L$^2$-L$^P$-(NH-DX)
to which the antibody is connected is preferable. The conjugated number of these drug-linker structure moiety may be from 1 to 10 as the average conjugated number per antibody, preferably, 2 to 8, and more preferably 3 to 8.

(SEQ ID NO: 585)
-(Succinimid-3-yl-N)-CH$_2$CH$_2$-C(=O)-GGFG
-NH-CH$_2$CH$_2$-C(=O)-(NH-DX), (SEQ ID NO: 585)
-(Succinimid-3-yl-N)-CH$_2$CH$_2$-C(=O)-GGFG
-NH-CH$_2$CH$_2$CH$_2$-C(=O)-(NH-DX), (SEQ ID NO: 585)
-(Succinimid-3-yl-N)-CH$_2$CH$_2$CH$_2$CH$_2$CH$_2$-C(=O)-GGFG
-NH-CH$_2$CH$_2$-C(=O)-(NH-DX), (SEQ ID NO: 585)
-(Succinimid-3-yl-N)-CH$_2$CH$_2$CH$_2$CH$_2$CH$_2$-C(=O)-GGFG
-NH-CH$_2$CH$_2$CH$_2$-C(=O)-(NH-DX), (SEQ ID NO: 585)
-(Succinimid-3-yl-N)-CH$_2$CH$_2$CH$_2$CH$_2$CH$_2$-C(=O)-GGFG
-NH-CH$_2$CH$_2$CH$_2$CH$_2$CH$_2$-C(=O)-(NH-DX), (SEQ ID NO: 590)
-(Succinimid-3-yl-N)-CH$_2$CH$_2$CH$_2$CH$_2$CH$_2$-C(=O)-DGGFG
-NH-CH$_2$CH$_2$-C(=O)-(NH-DX), (SEQ ID NO: 590)
-(Succinimid-3-yl-N)-CH$_2$CH$_2$CH$_2$CH$_2$CH$_2$-C(=O)-DGGFG
-NH-CH$_2$CH$_2$CH$_2$-C(=O)-(NH-DX), (SEQ ID NO: 590)
-(Succinimid-3-yl-N)-CH$_2$CH$_2$CH$_2$CH$_2$CH$_2$-C(=O)-DGGFG
-NH-CH$_2$CH$_2$CH$_2$CH$_2$CH$_2$-C(=O)-(NH-DX), (SEQ ID NO: 585)
-(Succinimid-3-yl-N)-CH$_2$CH$_2$CH$_2$CH$_2$CH$_2$-C(=O)-GGFG
-NH-CH$_2$-O-CH$_2$-C(=O)-(NH-DX), (SEQ ID NO: 585)
-(Succinimid-3-yl-N)-CH$_2$CH$_2$CH$_2$CH$_2$CH$_2$-C(=O)-GGFG
-NH-CH$_2$CH$_2$-O-CH$_2$-C(=O)-(NH-DX), (SEQ ID NO: 585)
-(Succinimid-3-yl-N)-CH$_2$CH$_2$-C(=O)-NH-CH$_2$CH$_2$-O-CH$_2$CH$_2$-O-CH$_2$CH$_2$-C(=O)-GGFG
-NH-CH$_2$CH$_2$-C(=O)-(NH-DX), (SEQ ID NO: 585)
-(Succinimid-3-yl-N)-CH$_2$CH$_2$-C(=O)-NH-CH$_2$CH$_2$-O-CH$_2$CH$_2$-O-CH$_2$CH$_2$-C(=O)-GGFG
-NH-CH$_2$CH$_2$CH$_2$-C(=O)-(NH-DX), (SEQ ID NO: 585)
-(Succinimid-3-yl-N)-CH$_2$CH$_2$-C(=O)-NH-CH$_2$CH$_2$-O-CH$_2$CH$_2$-O-CH$_2$CH$_2$-O-CH$_2$CH$_2$-C(=O)-GGFG
-NH-CH$_2$CH$_2$-C(=O)-(NH-DX), (SEQ ID NO: 585)
-(Succinimid-3-yl-N)-CH$_2$CH$_2$-C(=O)-NH-CH$_2$CH$_2$-O-CH$_2$CH$_2$-O-CH$_2$CH$_2$O-CH$_2$CH$_2$-O-CH$_2$CH$_2$-C(=O)-GGFG
-NH-CH$_2$CH$_2$CH$_2$-C(=O)-(NH-DX), (SEQ ID NO: 585)
-(Succinimid-3-yl-N)-CH$_2$CH$_2$-C(=O)-GGFG
-(NH-DX), (SEQ ID NO: 590)
-(Succinimid-3-yl-N)-CH$_2$CH$_2$-C(=O)-DGGFG
-(NH-DX), (SEQ ID NO: 585)
-(Succinimid-3-yl-N)-CH$_2$CH$_2$CH$_2$CH$_2$-C(=O)-GGFG
-(NH-DX), (SEQ ID NO: 590)
-(Succinimid-3-yl-N)-CH$_2$CH$_2$CH$_2$CH$_2$-C(=O)-DGGFG
-(NH-DX).

Among them, the more preferred are the followings.

-(Succinimid-3-yl-N)-CH₂CH₂-C(=O)-GGFG (SEQ ID NO: 585)
-NH-CH₂CH₂CH₂-C(=O)-(NH-DX), -(Succinimid-3-yl-N)-CH₂CH₂CH₂CH₂CH₂-C(=O)-GGFG (SEQ ID NO: 585)
-NH-CH₂CH₂CH₂-C(=O)-(NH-DX), -(Succinimid-3-yl-N)-CH₂CH₂CH₂CH₂CH₂-C(=O)-DGGFG (SEQ ID NO: 590)
-NH-CH₂CH₂CH₂-C(=O)-(NH-DX), -(Succinimid-3-yl-N)-CH₂CH₂CH₂CH₂CH₂-C(=O)-GGFG (SEQ ID NO: 585)
-NH-CH₂-O-CH₂-C(=O)-(NH-DX), -(Succinimid-3-yl-N)-CH₂CH₂CH₂CH₂CH₂-C(=O)-GGFG (SEQ ID NO: 585)
-NH-CH₂CH₂-O-CH₂-C(=O)-(NH-DX), -(Succinimid-3-yl-N)-CH₂CH₂-C(=O)-NH-CH₂CH₂-O-CH₂CH₂-O-CH₂CH₂-C(=O)-GGFG (SEQ ID NO: 585)
-NH-CH₂CH₂CH₂-C(=O)-(NH-DX), -(Succinimid-3-yl-N)-CH₂CH₂-C(=O)-NH-CH₂CH₂-O-CH₂CH₂-O-CH₂CH₂-O-CH₂CH₂-C(=O)-GGFG (SEQ ID NO: 585)
-NH-CH₂CH₂CH₂-C(=O)-(NH-DX), -(Succinimid-3-yl-N)-CH₂CH₂-C(=O)-DGGFG (SEQ ID NO: 590)
-(NH-DX), -(Succinimid-3-yl-N)-CH₂CH₂CH₂CH₂CH₂-C(=O)-DGGFG (SEQ ID NO: 590)
-(NH-DX).

The still more preferred are the followings.

-(Succinimid-3-yl-N)-CH₂CH₂CH₂CH₂CH₂-C(=O)-GGFG (SEQ ID NO: 585)
-NH-CH₂-O-CH₂-C(=O)-(NH-DX), -(Succinimid-3-yl-N)-CH₂CH₂CH₂CH₂CH₂-C(=O)-GGFG (SEQ ID NO: 585)
-NH-CH₂CH₂-O-CH₂-C(=O)-(NH-DX), -(Succinimid-3-yl-N)-CH₂CH₂-C(=O)-NH-CH₂CH₂-O-CH₂CH₂-O-CH₂CH₂-C(=O)-GGFG (SEQ ID NO: 585)
-NH-CH₂CH₂CH₂-C(=O)-(NH-DX), -(Succinimid-3-yl-N)-CH₂CH₂CH₂CH₂CH₂-C(=O)-DGGFG (SEQ ID NO: 590)
-(NH-DX).

The particularly preferred are the followings.

-(Succinimid-3-yl-N)-CH₂CH₂CH₂CH₂CH₂-C(=O)-GGFG (SEQ ID NO: 585)
-NH-CH₂-O-CH₂-C(=O)-(NH-DX), -(Succinimid-3-yl-N)-CH₂CH₂CH₂CH₂CH₂-C(=O)-GGFG (SEQ ID NO: 585)
-NH-CH₂CH₂-O-CH₂-C(=O)-(NH-DX), -(Succinimid-3-yl-N)-CH₂CH₂-C(=O)-NH-CH₂CH₂-O-CH₂CH₂-O-CH₂CH₂-C(=O)-GGFG (SEQ ID NO: 585)
-NH-CH₂CH₂CH₂-C(=O)-(NH-DX).

With regard to the linker structure for conjugating the anti-HER3 antibody and a drug in the antibody-drug conjugate of the present application, the preferred linker can be constructed by connecting preferred structures shown for each part of the linker explained above. As for the linker structure, those with the following structure can be preferably used. Meanwhile, the left terminal of the structure is a connecting position to the antibody and the right terminal is a connecting position to the drug.

-(Succinimid-3-yl-N)-CH₂CH₂-C(=O)-GGFG (SEQ ID NO: 585)
-NH-CH₂CH₂-C(=O)-,

-(Succinimid-3-yl-N)-CH₂CH₂-C(=O)-GGFG (SEQ ID NO: 585)
-NH-CH₂CH₂CH₂-C(=O)-,

-(Succinimid-3-yl-N)-CH₂CH₂CH₂CH₂CH₂-C(=O)-GGFG (SEQ ID NO: 585)
-NH-CH₂CH₂-C(=O)-, -(Succinimid-3-yl-N)-CH₂CH₂CH₂CH₂CH₂-C(=O)-GGFG (SEQ ID NO: 585)
-NH-CH₂CH₂CH₂-C(=O)-, -(Succinimid-3-yl-N)-CH₂CH₂CH₂CH₂CH₂-C(=O)-GGFG (SEQ ID NO: 585)
-NH-CH₂CH₂CH₂CH₂CH₂-C(=O)-, -(Succinimid-3-yl-N)-CH₂CH₂CH₂CH₂CH₂-C(=O)-DGGFG (SEQ ID NO: 590)
-NH-CH₂CH₂-C(=O)-, -(Succinimid-3-yl-N)-CH₂CH₂CH₂CH₂CH₂-C(=O)-DGGFG (SEQ ID NO: 590)
-NH-CH₂CH₂CH₂-C(=O)-, -(Succinimid-3-yl-N)-CH₂CH₂CH₂CH₂CH₂-C(=O)-DGGFG (SEQ ID NO: 590)
-NH-CH₂CH₂CH₂CH₂CH₂-C(=O)-, -(Succinimid-3-yl-N)-CH₂CH₂CH₂CH₂CH₂-C(=O)-GGFG (SEQ ID NO: 585)
-NH-CH₂-O-CH₂-C(=O)-, -(Succinimid-3-yl-N)-CH₂CH₂CH₂CH₂CH₂-C(=O)-GGFG (SEQ ID NO: 585)
-NH-CH₂CH₂-O-CH₂-C(=O)-, -(Succinimid-3-yl-N)-CH₂CH₂-C(=O)-NH-CH₂CH₂-O-CH₂CH₂-O-CH₂CH₂-C(=O)-GGFG (SEQ ID NO: 585)
-NH-CH₂CH₂-C(=O)-, -continued (SEQ ID NO: 585)
-(Succinimid-3-yl-N)-CH₂CH₂-C(=O)-NH-CH₂CH₂-O-
CH₂CH₂-O-CH₂CH₂-C(=O)-GGFG

-NH-CH₂CH₂CH₂-C(=O)-, (SEQ ID NO: 585)
-(Succinimid-3-yl-N)-CH₂CH₂-C(=O)-NH-CH₂CH₂-O-
CH₂CH₂-O-CH₂CH₂-O-CH₂CH₂-C(=O)-GGFG

-NH-CH₂CH₂-C(=O)-, (SEQ ID NO: 585)
-(Succinimid-3-yl-N)-CH₂CH₂-C(=O)-NH-CH₂CH₂-O-
CH₂CH₂-O-CH₂CH₂-O-CH₂CH₂-C(=O)-GGFG

-NH-CH₂CH₂CH₂-C(=O)-, (SEQ ID NO: 585)
-(Succinimid-3-yl-N)-CH₂CH₂-C(=O)-GGFG-, (SEQ ID NO: 590)
-(Succinimid-3-yl-N)-CH₂CH₂-C(=O)-DGGFG-, (SEQ ID NO: 585)
-(Succinimid-3-yl-N)-CH₂CH₂CH₂CH₂CH₂-C(=O)-GGFG-, (SEQ ID NO: 590)
-(Succinimid-3-yl-N)-CH₂CH₂CH₂CH₂CH₂-C(=O)-DGGFG-.

Among them, more preferred are the followings.

(SEQ ID NO: 585)
-(Succinimid-3-yl-N)-CH₂CH₂-C(=O)-GGFG

-NH-CH₂CH₂CH₂-C(=O)-, (SEQ ID NO: 585)
-(Succinimid-3-yl-N)-CH₂CH₂CH₂CH₂CH₂-C(=O)-GGFG

-NH-CH₂CH₂CH₂-C(=O)-, (SEQ ID NO: 590)
-(Succinimid-3-yl-N)-CH₂CH₂CH₂CH₂CH₂-C(=O)-DGGFG

-NH-CH₂CH₂CH₂-C(=O)-, (SEQ ID NO: 585)
-(Succinimid-3-yl-N)-CH₂CH₂CH₂CH₂CH₂-C(=O)-GGFG

-NH-CH₂-O-CH₂-C(=O)-, (SEQ ID NO: 585)
-(Succinimid-3-yl-N)-CH₂CH₂CH₂CH₂CH₂-C(=O)-GGFG

-NH-CH₂CH₂-O-CH₂-C(=O)-, (SEQ ID NO: 585)
-(Succinimid-3-yl-N)-CH₂CH₂-C(=O)-NH-CH₂CH₂-O-
CH₂CH₂-O-CH₂CH₂-C(=O)-GGFG

-NH-CH₂CH₂CH₂-C(=O)-, (SEQ ID NO: 585)
-(Succinimid-3-yl-N)-CH₂CH₂-C(=O)-NH-CH₂CH₂-O-
CH₂CH₂-O-CH₂CH₂-O-CH₂CH₂-C(=O)-GGFG

-NH-CH₂CH₂CH₂-C(=O)-, (SEQ ID NO: 590)
-(Succinimid-3-yl-N)-CH₂CH₂-C(=O)-DGGFG-, (SEQ ID NO: 590)
-(Succinimid-3-yl-N)-CH₂CH₂CH₂CH₂CH₂-C(=O)-DGGFG-.

Still more preferred are the followings.

(SEQ ID NO: 585)
-(Succinimid-3-yl-N)-CH₂CH₂CH₂CH₂CH₂-C(=O)-GGFG

-NH-CH₂-O-CH₂-C(=O)-, (SEQ ID NO: 585)
-(Succinimid-3-yl-N)-CH₂CH₂CH₂CH₂CH₂-C(=O)-GGFG

-NH-CH₂CH₂-O-CH2-C(=O)-, (SEQ ID NO: 585)
-(Succinimid-3-yl-N)-CH₂CH₂-C(=O)-NH-CH₂CH₂-O-
CH₂CH₂-O-CH₂CH₂-C(=O)-GGFG

-NH-CH₂CH₂CH₂-C(=O)-, (SEQ ID NO: 590)
-(Succinimid-3-yl-N)-CH₂CH₂CH₂CH₂CH₂-C(=O)-DGGFG-.

Particularly preferred are the followings.

(SEQ ID NO: 585)
-(Succinimid-3-yl-N)-CH₂CH₂CH₂CH₂CH₂-C(=O)-GGFG

-NH-CH₂-O-CH₂-C(=O)-, (SEQ ID NO: 585)
-(Succinimid-3-yl-N)-CH₂CH₂CH₂CH₂CH₂-C(=O)-GGFG

-NH-CH₂CH₂-O-CH₂-C(=O)-, (SEQ ID NO: 585)
-(Succinimid-3-yl-N)-CH₂CH₂-C(=O)-NH-CH₂CH₂-O-
CH₂CH₂-O-CH₂CH₂-C(=O)-GGFG

-NH-CH₂CH₂CH₂-C(=O)-.

{Production Method}

Next, explanations are given for the representative method for producing the antibody-drug conjugate of the present invention or a production intermediate thereof. Meanwhile, the compounds are hereinbelow described with the number shown in each reaction formula. Specifically, they are referred to as a "compound of the formula (1)", a "compound (1)", or the like. The compounds with numbers other than those are also described similarly.

1. Production Method 1

The antibody-drug conjugate represented by the formula (1) in which the antibody is conjugated to the drug-linker structure via thioether can be produced by the following method, for example.

[Chem. 19]

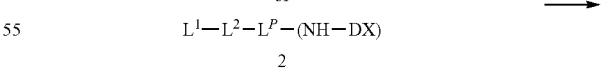

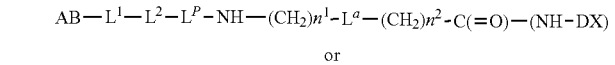

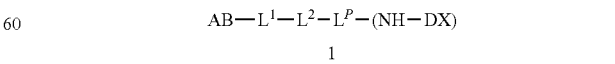

[in the formula, AB represents an antibody with a sulfhydryl group and $L^{1'}$ corresponds to $L^1$ having a structure in which the linker terminal is converted to a maleimidyl group (formula shown below).

[Chem. 20]

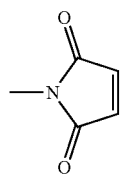

(in the formula, the nitrogen atom is the connecting position)

Specifically, it represents a linker having a structure which, within the structure of $L^1$ represented as -(Succinimid-3-yl-N)—$(CH_2)n^2$-C(=O)—, said -(Succinimid-3-yl-N)— moiety is converted into a maleimidyl group. Further, the -(NH-DX) represents a structure represented by the following formula:

[Chem. 21]

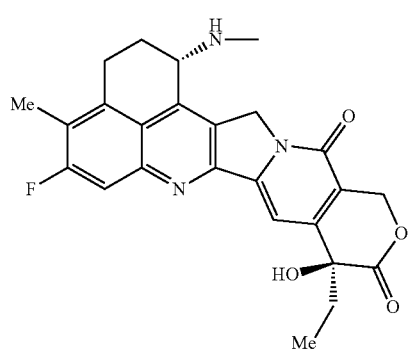

and it represents a group that is derived by removing one hydrogen atom of the amino group at position 1 of exatecan.]

Further, the compound of the formula (1) in the above reaction formula can be interpreted as a structure in which one structure moiety from drug to the linker terminal is connected to one antibody. However, it is only the description given for the sake of convenience, and there are actually many cases in which a plurality of said structure moieties is connected to one antibody molecule. The same applies to the explanation of the production method described below.

Specifically, the antibody-drug conjugate (1) can be produced by reacting the compound (2), which is obtainable by the method described below, with the antibody (3a) having a sulfhydryl group.

The antibody (3a) having a sulfhydryl group can be obtained by a method well known in the art (Hermanson, G. T, Bioconjugate Techniques, pp. 56-136, pp. 456-493, Academic Press (1996)). Examples include: Traut's reagent is reacted with the amino group of the antibody; N-succinimidyl S-acetylthioalkanoates are reacted with the amino group of the antibody followed by reaction with hydroxylamine; after reacting with N-succinimidyl 3-(pyridyldithio)propionate, it is reacted with a reducing agent; the antibody is reacted with a reducing agent such as dithiothreitol, 2-mercaptoethanol, and tris(2-carboxyethyl)phosphine hydrochloride (TCEP) to reduce the disulfide bond at a hinge part in the antibody to form a sulfhydryl group, but it is not limited thereto.

Specifically, using 0.3 to 3 molar equivalents of TCEP as a reducing agent per disulfide bonds at hinge part in the antibody and reacting with the antibody in a buffer solution containing a chelating agent, the antibody which the disulfide bonds at hinge part in the antibody is partially or completely reduced can be obtained. Examples of the chelating agent include ethylenediamine tetraacetic acid (EDTA) and diethylenetriamine pentaacetic acid (DTPA). It can be used at concentration of 1 mM to 20 mM. Examples of the buffer solution which may be used include a solution of sodium phosphate, sodium borate, or sodium acetate. Specifically, by reacting the antibody with TCEP at 4 C to 37 C for 1 to 4 hours, the antibody (3a) having partially or completely reduced sulfhydryl groups can be obtained.

Meanwhile, by performing an addition reaction of a sulfhydryl group to a drug-linker moiety, the drug-linker moiety can be conjugated by a thioether bond.

Using 2 to 20 molar equivalents of the compound (2) per the antibody (3a) having a sulfhydryl group, the antibody-drug conjugate (1) in which 2 to 8 drug molecules are conjugated per antibody can be produced. Specifically, it is sufficient that the solution containing the compound (2) dissolved therein is added to a buffer solution containing the antibody (3a) having a sulfhydryl group for the reaction. Herein, examples of the buffer solution which may be used include sodium acetate solution, sodium phosphate, and sodium borate. pH for the reaction is 5 to 9, and more preferably the reaction is performed near pH 7. Examples of the solvent for dissolving the compound (2) include an organic solvent such as dimethyl sulfoxide (DMSO), dimethylformamide (DMF), dimethylacetamide (DMA), and N-methyl-2-pyrrolidone (NMP).

The reaction may be carried out by adding the organic solvent solution containing the compound (2) dissolved therein at 1 to 20% v/v to a buffer solution containing the antibody (3a) having a sulfhydryl group. The reaction temperature is 0 to 37 C, more preferably 10 to 25 C, and the reaction time is 0.5 to 2 hours. The reaction can be terminated by deactivating the reactivity of unreacted compound (2) with a thiol-containing reagent. Examples of the thiol-containing reagent include cysteine and N-acetyl-L-cysteine (NAC). More specifically, by adding 1 to 2 molar equivalents of NAC to the compound (2) used and, by incubating at room temperature for 10 to 30 minutes, the reaction can be terminated.

The produced antibody-drug conjugate (1) can be subjected to, after concentration, buffer exchange, purification, and measurement of antibody concentration and average number of conjugated drug molecules per antibody molecule according to common procedures described below, to make an identification of the antibody-drug conjugate (1).

Common Procedure A: Concentration of Aqueous Solution of Antibody or Antibody-Drug Conjugate To a Amicon Ultra (50,000 MWCO, Millipore Corporation) container, a solution of antibody or antibody-drug conjugate was added and the solution of the antibody or antibody-drug conjugate was concentrated by centrifugation (centrifuge for 5 to 20 minutes at 2000 G to 3800 G) using a centrifuge (Allegra X-15R, Beckman Coulter, Inc.)

Common Procedure B: Measurement of Antibody Concentration

Using a UV detector (Nanodrop 1000, Thermo Fisher Scientific Inc.), measurement of the antibody concentration was performed according to the method defined by the manufacturer. Here, 280 nm absorption coefficient can be estimated from the amino acid sequence of an antibody using a known calculation method (Protein Science, 1995, vol. 4, 2411-2423), and 280 nm absorption coefficient different for each antibody was used (1.3 mLmg$^{-1}$ cm$^{-1}$ to 1.8 mLmg$^{-1}$ cm$^{-1}$). In the case of U1-59, 280 nm absorption coefficient of 1.768 mLmg$^{-1}$ cm$^{-1}$ was used as an estimated value according to its amino acid sequence.

Common Procedure C: Buffer Exchange for Antibody

NAP-25 column (Cat. No. 17-0852-02, GE Healthcare Japan Corporation) using Sephadex G-25 carrier was equilibrated with phosphate buffer (10 mM, pH 6.0; it is referred to as PBS6.0/EDTA in the specification) containing sodium chloride (137 mM) and ethylene diamine tetraacetic acid (EDTA, 5 mM) according to the method defined by the manufacturer. Aqueous solution of the antibody was applied in an amount of 2.5 mL to single NAP-25 column, and then the fraction (3.5 mL) eluted with 3.5 mL of PBS6.0/EDTA was collected. The resulting fraction was concentrated by the Common procedure A. After measuring the concentration of the antibody using the Common procedure B, the antibody concentration was adjusted to 10 mg/mL using PBS6.0/EDTA.

Common Procedure D: Purification of Antibody-Drug Conjugate

NAP-25 column was equilibrated with acetate buffer containing sorbitol (5%) (10 mM, pH 5.5; it is referred to as ABS in the specification). Aqueous reaction solution of the antibody-drug conjugate (about 2.5 mL) was applied to the NAP-25 column, and then eluted with the buffer in an amount as defined by the manufacturer to collect the antibody fraction. By conducting a gel filtration purification process, in which said collected fraction was again applied to the NAP-25 column and eluted with buffer, was repeated 2 to 3 times in total, the antibody-drug conjugate excluding non-conjugated drug linker and a low-molecular-weight compound (tris(2-carboxyethyl)phosphine hydrochloride (TCEP), N-acetyl-L-cysteine (NAC), and dimethyl sulfoxide) was obtained.

Common Procedure E: Measurement of Antibody Concentration in Antibody-Drug Conjugate and Average Number of Conjugated Drug Molecules Per Antibody Molecule (1)

The conjugated drug concentration in the antibody-drug conjugate can be calculated by measuring UV absorbance of an aqueous solution of the antibody-drug conjugate at two wavelengths of 280 nm and 370 nm, followed by performing the calculation shown below.

Because the total absorbance at any wavelength is equal to the sum of the absorbance of every light-absorbing chemical species that are present in a system [additivity of absorbance], when the molar absorption coefficients of the antibody and the drug remain the same before and after conjugation between the antibody and the drug, the antibody concentration and the drug concentration in the antibody-drug conjugate are expressed with the following equations.

$$A_{280} = A_{D,280} + A_{A,280} = E_{D,280}C_D + E_{A,280}C_A \quad \text{Equation (1)}$$

$$A_{370} = A_{D,370} + A_{A,370} = E_{D,370}C_D + E_{A,370}C_A \quad \text{Equation (2)}$$

In the above, $A_{280}$ represents the absorbance of an aqueous solution of the antibody-drug conjugate at 280 nm, $A_{370}$ represents the absorbance of an aqueous solution of the antibody-drug conjugate at 370 nm, $A_{A,280}$ represents the absorbance of an antibody at 280 nm, $A_{A,370}$ represents the absorbance of an antibody at 370 nm, $A_{D,280}$ represents the absorbance of a conjugate precursor at 280 nm, $A_{D,370}$ represents the absorbance of a conjugate precursor at 370 nm, $E_{A,280}$ represents the molar absorption coefficient of an antibody at 280 nm, $E_{A,370}$ represents the molar absorption coefficient of an antibody at 370 nm, $E_{D,280}$ represents the molar absorption coefficient of a conjugate precursor at 280 nm, $E_{D,370}$ represents the molar absorption coefficient of a conjugate precursor at 370 nm, $C_A$ represents the antibody concentration in an antibody-drug conjugate, and $C_D$ represent the drug concentration in an antibody-drug conjugate.

As for $E_{A,280}$, $E_{A,370}$, $E_{D,280}$, and $E_{D,370}$ in the above, previously prepared values (estimated value based on calculation or measurement value obtained by UV measurement of the compound) are used. For example, $E_{A,280}$ can be estimated from the amino acid sequence of an antibody using a known calculation method (Protein Science, 1995, vol. 4, 2411-2423). $E_{A,370}$ is generally zero. In the case of U1-59, $E_{A,280}$ of 259400 was used as an estimated value according to its amino acid sequence. $E_{D,280}$ and $E_{D,370}$ can be obtained based on Lambert-Beer's law (Absorbance=molar concentration×molar absorption coefficient×cell path length) by measuring the absorbance of a solution in which the conjugate precursor to be used is dissolved at a certain molar concentration. By measuring $A_{280}$ and $A_{370}$ of an aqueous solution of the antibody-drug conjugate and solving the simultaneous equations (1) and (2) using the values, $C_A$ and $C_D$ can be obtained. Further, by diving $C_D$ by $C_A$, the average drug binding number per antibody can be obtained.

In the present invention, the method for determining the average number of conjugated drug molecules per antibody as described above is referred to as a "UV method".

Common Procedure F: Measurement of Average Number of Conjugated Drug Molecules Per Antibody Molecule in Antibody-Drug Conjugate—(2)

The average number of conjugated drug molecules per antibody molecule in the antibody-drug conjugate can also be determined by high-performance liquid chromatography (HPLC) analysis using the following method, in addition to the aforementioned Common procedure E.

{F-1. Preparation of Sample for HPLC Analysis (Reduction of Antibody-Drug Conjugate)}

An antibody-drug conjugate solution (about 1 mg/mL, 60 u ("u" represents "micro")L) is mixed with an aqueous solution of dithiothreitol (DTT) (100 mM, 15 uL). By incubating the mixture at 37 C for 30 minutes, the disulfide bond between the L and H chains of the antibody-drug conjugate is cleaved. The resulting sample is used in HPLC analysis.

{F-2. HPLC Analysis}

The HPLC analysis is carried out under the following measurement conditions.

HPLC system: Agilent 1290 HPLC system (Agilent Technologies)

Detector: Ultraviolet absorption spectrometer (measurement wavelength: 280 nm)

Column: PLRP-S (2.1×50 mm, 8 um, 1000 angstroms; Agilent Technologies, P/N PL1912-1802)

Column temperature: 80 C

Mobile phase A: 0.04% aqueous trifluoroacetic acid (TFA) solution

Mobile phase B: Acetonitrile solution containing 0.04% TFA

Gradient program: 29%-36% (0 min.-12.5 min.), 36%-42% (12.5-15 min.), 42%-29% (15 min.-15.1 min.), 29%-29% (15.1 min.-25 min.)

Sample injection: 15 uL

{F-3. Data Analysis}

[F-3-1] Compared with non-conjugated antibody L ($L_0$) and H ($H_0$) chains, drug-conjugated L (L chain bound to one drug molecule: $L_1$) and H (H chain bound to one drug molecule: $H_1$, H chain bound to two drug molecule: $H_2$, H chain bound to three drug molecules: $H_3$) chains exhibit higher hydrophobicity in proportion to the number of conjugated drug molecules and thus have a larger retention time.

These chains are therefore eluted in the order of $L_0$ and $L_1$ or $H_0$, $H_1$, $H_2$, and $H_3$. Detection peaks can be assigned to any of $L_0$, $L_0$, $H_0$, $H_1$, $H_2$, and $H_3$ by the comparison of retention times with $L_0$ and $H_0$.

[F-3-2] Since the drug linker has UV absorption, peak area values are corrected in response to the number of conjugated drug linker molecules according to the following expression using the molar absorption coefficients of the L or H chain and the drug linker.

$$\text{Corrected value of the peak area of the L chain } (L_i) = \text{Peak area} \times \frac{\text{Molar absorption coefficient of the L chain}}{\text{Molar absorption coefficient of the L chain} + \text{The number of conjugated drug molecules} \times \text{Molar absorption coefficient of the drug linker}}$$ [Math. 1]

$$\text{Corrected value of the peak area of the H chain } (H) = \text{Peak area} \times \frac{\text{Molar absorption coefficient of the H chain}}{\text{Molar absorption coefficient of the H chain} + \text{The number of conjugated drug molecules} \times \text{Molar absorption coefficient of the drug linker}}$$ [Math. 2]

Here, a value estimated from the amino acid sequence of the L or H chain of each antibody using a known calculation method (Protein Science, 1995, vol. 4, 2411-2423) can be used as the molar absorption coefficient (280 nm) of the L or H chain of each antibody. In the case of U1-59, a molar absorption coefficient of 34690 and a molar absorption coefficient of 95000 were used as estimated values for the L and H chains, respectively, according to its amino acid sequence. The actually measured molar absorption coefficient (280 nm) of a compound in which the maleimide group has been converted to succinimide thioether by the reaction of each drug linker with mercaptoethanol or N-acetylcysteine was used as the molar absorption coefficient (280 nm) of the drug linker.

[F-3-3] The peak area ratio (%) of each chain is calculated for the total of the corrected values of peak areas.

$$\text{Peak area ratio of the L chain} = \frac{A_{Li}}{A_{L0} + A_{L1}} \times 100$$ [Math. 3]

$$\text{Peak area ratio of the H chain} = \frac{A_{Hi}}{A_{H0} + A_{H1} + A_{H2} + A_{H3}} \times 100$$

Corrected Values of Respective Peak Areas of $A_{Li}$, $A_{Hi}$:$L_i$, $H_i$

[F-3-4] The average number of conjugated drug molecules per antibody molecule in the antibody-drug conjugate is calculated according to the following expression.

Average number of conjugated drug molecules=($L_0$ peak area ratio×0+$L_0$ peak area ratio×1+$H_0$ peak area ratio×0+$H_1$ peak area ratio×1+$H_2$ peak area ratio×2+$H_3$ peak area ratio×3)/100×2

Hereinbelow, production intermediate compounds used in Production method 1 are described. The compound represented by the formula (2) in the production method 1 is a compound represented by the following formula:
(maleimid-N-yl)-$(CH_2)n^3$-C(=O)-$L^P$-$L^P$-NH—$(CH_2)n^1$-$L^a$-$(CH_2)n^2$-C(=O)-(NH-DX) or
(maleimid-N-yl)-$(CH_2)n^3$-C(=O)-$L^2$-$L^P$-(NH-DX).
In the formula, $n^3$ represents an integer of 2 to 8,
$L^2$ represents —NH—$(CH_2CH_2$—O$)n^4$-$CH_2CH_2$—C(=O)— or a single bond,
wherein $n^4$ represents an integer of 1 to 6,
$L^P$ represents a peptide residue consisting of 2 to 7 amino acids selected from phenylalanine, glycine, valine, lysine, citrulline, serine, glutamic acid, and aspartic acid,
$n^1$ represents an integer of 0 to 6,
$n^2$ represents an integer of 0 to 5,
$L^a$ represents —O— or a single bond,
(maleimid-N-yl)- is a maleimidyl group (2,5-dioxo-2,5-dihydro-1H-pyrrol-1-yl group) represented by the following formula:

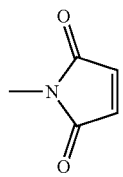

[Chem. 22]

wherein the nitrogen atom is the connecting position, and -(NH-DX) is a group represented by the following formula:

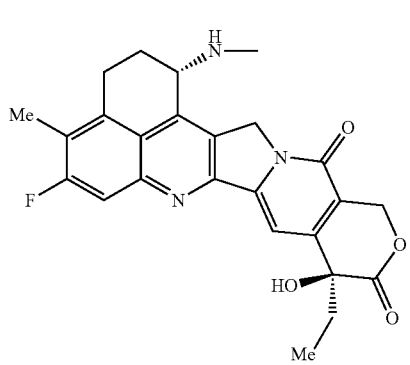 [SMILES: CC[C@@]1(O)C(=O)OCc2c1cc1n(c2=O)Cc2c-1nc1cc(F)c(C)c3c1c2[C@@H](NC)CC3]

[Chem. 23]

wherein the nitrogen atom of the amino group at position 1 is the connecting position.

As for the peptide residue $L^P$, those consisting of an amino acid selected from phenylalanine, glycine, valine, lysine, citrulline, serine, glutamic acid, and aspartic acid is preferred as a production intermediate. Among the peptide residue $L^P$, those consisting of 4 or 5 amino acids is preferred as a production intermediate. More specifically, those in which $L^P$ is a tetrapeptide residue of -GGFG- (SEQ ID NO: 585) or a pentapeptide of -DGGFG- (SEQ ID NO: 590) is preferred as a production intermediate, more preferably, -GGFG- (SEQ ID NO: 585).

Further, as for the —NH—$(CH_2)n^1$-$L^a$-$(CH_2)n^2$-, those having —NH—$CH_2CH_2$—, —NH—$CH_2CH_2CH_2$—, —NH—$CH_2CH_2CH_2CH_2$—, —NH—$CH_2CH_2CH_2CH_2CH_2$—, —NH—$CH_2$—O—$CH_2$—, or —NH—$CH_2CH_2$—O—$CH_2$— is preferred as a production intermediate. A compound of —NH—$CH_2CH_2CH_2$—, —NH—$CH_2$—O—$CH_2$—, or —NH—$CH_2CH_2$—O—$CH_2$ is more preferred.

As for $n^3$, those in which it is an integer of 2 to 8 is preferred as a production intermediate.

As for $L^2$, those in which it is a single bond or —NH—$(CH_2CH_2$—O$)n^4$-$CH_2CH_2$—C(=O)— and $n^4$ is an integer of 2 to 4 is preferred as a production intermediate.

Further, those in which $n^3$ is an integer of 2 to 5, $L^2$ is a single bond, and —NH—$(CH_2)n^1$-$L^a$-$(CH_2)n^2$— is —NH—$CH_2CH_2$—, —NH—$CH_2CH_2CH_2$—, —NH—$CH_2CH_2CH_2CH_2$—, —NH—$CH_2CH_2CH_2CH_2CH_2$—, —NH—$CH_2$—O—$CH_2$—, or —NH—$CH_2CH_2$—O—$CH_2$— is preferred as a production intermediate. Further, more preferred among them is those in which —NH—$(CH_2)n^1$-$L^a$-$(CH_2)n^2$- is —NH—$CH_2CH_2$—, —NH—$CH_2CH_2CH_2$—, —NH—$CH_2$—O—$CH_2$—, or —NH—$CH_2CH_2$—O—$CH_2$—. Further, those in which $n^3$ is an integer of 2 or 5 is preferred.

Further, those in which $n^3$ is an integer of 2 to 5, $L^2$ is —NH—$(CH_2CH_2$—O$)n^4$-$CH_2CH_2$—C(=O)—, $n^4$ is an integer of 2 to 4, and —NH—$(CH_2)n^1$-$L^a$-$(CH_2)n^2$- is —NH—$CH_2CH_2$—, —NH—$CH_2CH_2CH_2$—, —NH—$CH_2CH_2CH_2CH_2$—, —NH—$CH_2CH_2CH_2CH_2CH_2$—, —NH—$CH_2$—O—$CH_2$—, or —NH—$CH_2CH_2$—O—$CH_2$— is preferred as a production intermediate. More preferred among them is those in which $n^4$ is an integer of 2 or 4. Further, those in which —NH—$(CH_2)n^1$-$L^a$- is —NH—$CH_2CH_2CH_2$—, —NH—$CH_2$—O—$CH_2$—, or —NH—$CH_2CH_2$—O—$CH_2$— is preferred.

Preferred examples of the intermediate that are useful for production of the compound of the present invention include those exemplified below:

(SEQ ID NO: 585)
(maleimid-N-yl)-$CH_2CH_2$-C(=O)-GGFG
-NH-$CH_2CH_2$-C(=O)-(NH-DX), (SEQ ID NO: 585)
(maleimid-N-yl)-$CH_2CH_2CH_2$-C(=O)-GGFG
-NH-$CH_2CH_2$-C(=O)-(NH-DX), (SEQ ID NO: 585)
(maleimid-N-yl)-$CH_2CH_2CH_2CH_2$-C(=O)-GGFG
-NH-$CH_2CH_2$-C(=O)-(NH-DX), (SEQ ID NO: 585)
(maleimid-N-yl)-$CH_2CH_2CH_2CH_2CH_2$-C(=O)-GGFG
-NH-$CH_2CH_2$-C(=O)-(NH-DX), (SEQ ID NO: 585)
(maleimid-N-yl)-$CH_2CH_2$-C(=O)-GGFG
-NH-$CH_2CH_2CH_2$-C(=O)-(NH-DX), (SEQ ID NO: 585)
(maleimid-N-yl)-$CH_2CH_2CH_2$-C(=O)-GGFG
-NH-$CH_2CH_2CH_2$-C(=O)-(NH-DX), (SEQ ID NO: 585)
(maleimid-N-yl)-$CH_2CH_2CH_2CH_2$-C(=O)-GGFG
-NH-$CH_2CH_2CH_2$-C(=O)-(NH-DX), (SEQ ID NO: 585)
(maleimid-N-yl)-$CH_2CH_2CH_2CH_2CH_2$-C(=O)-GGFG
-NH-$CH_2CH_2CH_2$-C(=O)-(NH-DX), (SEQ ID NO: 585)
(maleimid-N-yl)-$CH_2CH_2$-C(=O)-GGFG
-NH-$CH_2CH_2CH_2CH_2$-C(=O)-(NH-DX), (SEQ ID NO: 585)
(maleimid-N-yl)-$CH_2CH_2CH_2$-C(=O)-GGFG
-NH-$CH_2CH_2CH_2CH_2$-C(=O)-(NH-DX), (SEQ ID NO: 585)
(maleimid-N-yl)-$CH_2CH_2CH_2CH_2$-C(=O)-GGFG
-NH-$CH_2CH_2CH_2CH_2$-C(=O)-(NH-DX), (SEQ ID NO: 585)
(maleimid-N-yl)-$CH_2CH_2$-C(=O)-GGFG
-NH-$CH_2CH_2CH_2CH_2CH_2$-C(=O)-(NH-DX), (SEQ ID NO: 585)
(maleimid-N-yl)-$CH_2CH_2CH_2$-C(=O)-GGFG
-NH-$CH_2CH_2CH_2CH_2CH_2$-C(=O)-(NH-DX), (SEQ ID NO: 585)
(maleimid-N-yl)-$CH_2CH_2CH_2CH_2$-C(=O)-GGFG
-NH-$CH_2CH_2CH_2CH_2CH_2$-C(=O)-(NH-DX), (SEQ ID NO: 585)
(maleimid-N-yl)-$CH_2CH_2CH_2CH_2CH_2$-C(=O)-GGFG
-NH-$CH_2CH_2CH_2CH_2CH_2$-C(=O)-(NH-DX), (SEQ ID NO: 590)
(maleimid-N-yl)-$CH_2CH_2CH_2CH_2CH_2$-C(=O)-DGGFG
-NH-$CH_2CH_2CH_2$-C(=O)-(NH-DX), (SEQ ID NO: 590)
(maleimid-N-yl)-$CH_2CH_2CH_2CH_2CH_2$-C(=O)-DGGFG
-NH-$CH_2CH_2CH_2CH_2$-C(=O)-(NH-DX), (SEQ ID NO: 590)
(maleimid-N-yl)-$CH_2CH_2CH_2CH_2CH_2$-C(=O)-DGGFG
-NH-$CH_2CH_2CH_2CH_2CH_2$-C(=O)-(NH-DX), (SEQ ID NO: 585)
(maleimid-N-yl)-$CH_2CH_2$-C(=O)-GGFG
-NH-$CH_2$-O-$CH_2$-C(=O)-(NH-DX), (SEQ ID NO: 585)
(maleimid-N-yl)-$CH_2CH_2CH_2$-C(=O)-GGFG
-NH-$CH_2$-O-$CH_2$-C(=O)-(NH-DX), (SEQ ID NO: 585)
(maleimid-N-yl)-$CH_2CH_2CH_2CH_2$-C(=O)-GGFG
-NH-$CH_2$-O-$CH_2$-C(=O)-(NH-DX), (SEQ ID NO: 585)
(maleimid-N-yl)-$CH_2CH_2CH_2CH_2CH_2$-C(=O)-GGFG
-NH-$CH_2$-O-$CH_2$-C(=O)-(NH-DX), (SEQ ID NO: 585)
(maleimid-N-yl)-$CH_2CH_2$-C(=O)-GGFG
-NH-$CH_2CH_2$-O-$CH_2$-C(=O)-(NH-DX), (SEQ ID NO: 585)
(maleimid-N-yl)-$CH_2CH_2$-C(=O)-GGFG
-NH-$CH_2CH_2$-O-$CH_2$-C(=O)-(NH-DX), (maleimid-N-yl)-CH₂CH₂CH₂CH₂-C(=O)-GGFG (SEQ ID NO: 585)

-NH-CH₂CH₂-O-CH₂-C(=O)-(NH-DX), (maleimid-N-yl)-CH₂CH₂CH₂CH₂CH₂-C(=O)-GGFG (SEQ ID NO: 585)

-NH-CH₂CH₂-O-CH₂-C(=O)-(NH-DX), (maleimid-N-yl)-CH₂CH₂-C(=O)-NH-CH₂CH₂-O-CH₂CH₂-O-CH₂CH₂-C(=O)-GGFG (SEQ ID NO: 585)

-NH-CH₂CH₂CH₂-C(=O)-(NH-DX), (maleimid-N-yl)-CH₂CH₂-C(=O)-NH-CH₂CH₂-O-CH₂CH₂-O-CH₂CH₂-O-CH₂CH₂-C(=O)-GGFG (SEQ ID NO: 585)

-NH-CH₂CH₂CH₂-C(=O)-(NH-DX), (maleimid-N-yl)-CH₂CH₂-C(=O)-NH-CH₂CH₂-O-CH₂CH₂-O-CH₂CH₂-O-CH₂CH₂-O-CH₂CH₂-C(=O)-GGFG (SEQ ID NO: 585)

-NH-CH₂CH₂CH₂-C(=O)-(NH-DX), (maleimid-N-yl)-CH₂CH₂-C(=O)-GGFG (SEQ ID NO: 585)

-(NH-DX), (maleimid-N-yl)-CH₂CH₂CH₂-C(=O)-GGFG (SEQ ID NO: 585)

-(NH-DX), (maleimid-N-yl)-CH₂CH₂CH₂CH₂-C(=O)-GGFG (SEQ ID NO: 585)

-(NH-DX), (maleimid-N-yl)-CH₂CH₂CH₂CH₂CH₂-C(=O)-GGFG (SEQ ID NO: 585)

-(NH-DX), (maleimid-N-yl)-CH₂CH₂-C(=O)-DGGFG (SEQ ID NO: 590)

-(NH-DX), (maleimid-N-yl)-CH₂CH₂CH₂-C(=O)-DGGFG (SEQ ID NO: 590)

-(NH-DX), (maleimid-N-yl)-CH₂CH₂CH₂CH₂-C(=O)-DGGFG (SEQ ID NO: 590)

-(NH-DX),
or (maleimid-N-yl)-CH₂CH₂CH₂CH₂CH₂-C(=O)-DGGFG (SEQ ID NO: 590)

-(NH-DX).

By the reaction of the drug-linker compound selected from the aforementioned group of intermediate compounds with an anti-Her3 antibody or a reactive derivative thereof, a thioether bond can be formed at a disulfide bond moiety present in a hinge part of the anti-Her3 antibody, and as a result, the anti-Her3 antibody-drug conjugate of the present invention can be produced. In this case, it is preferable to use a reactive derivative of an anti-Her3 antibody. A reactive derivative obtained by reducing an anti-Her3 antibody is particularly preferred.

The followings are a compound which is more preferred as a production intermediate.

(maleimid-N-yl)-CH₂CH₂-C(=O)-GGFG (SEQ ID NO: 585)

-NH-CH₂CH₂-C(=O)-(NH-DX), (maleimid-N-yl)-CH₂CH₂-C(=O)-GGFG (SEQ ID NO: 585)

-NH-CH₂CH₂CH₂-C(=O)-(NH-DX), (maleimid-N-yl)-CH₂CH₂CH₂CH₂CH₂-C(=O)-GGFG (SEQ ID NO: 585)

-NH-CH₂CH₂-C(=O)-(NH-DX), (maleimid-N-yl)-CH₂CH₂CH₂CH₂CH₂-C(=O)-GGFG (SEQ ID NO: 585)

-NH-CH₂CH₂CH₂-C(=O)-(NH-DX), (maleimid-N-yl)-CH₂CH₂CH₂CH₂CH₂-C(=O)-GGFG (SEQ ID NO: 585)

-NH-CH₂CH₂CH₂CH₂CH₂-C(=O)-(NH-DX), (maleimid-N-yl)-CH₂CH₂CH₂CH₂CH₂-C(=O)-DGGFG (SEQ ID NO: 590)

-NH-CH₂CH₂CH₂-C(=O)-(NH-DX), (maleimid-N-yl)-CH₂CH₂CH₂CH₂CH₂-C(=O)-GGFG (SEQ ID NO: 585)

-NH-CH₂-O-CH₂-C(=O)-(NH-DX), (maleimid-N-yl)-CH₂CH₂CH₂CH₂CH₂-C(=O)-GGFG (SEQ ID NO: 585)

-NH-CH₂CH₂-O-CH₂-C(=O)-(NH-DX), (maleimid-N-yl)-CH₂CH₂-C(=O)-NH-CH₂CH₂-O-CH₂CH₂-O-CH₂CH₂-C(=O)-GGFG (SEQ ID NO: 585)

-NH-CH₂CH₂CH₂-C(=O)-(NH-DX), (maleimid-N-yl)-CH₂CH₂-C(=O)-NH-CH₂CH₂-O-CH₂CH₂-O-CH₂CH₂-C(=O)-GGFG (SEQ ID NO: 585)

-NH-CH₂CH₂CH₂-C(=O)-(NH-DX), (maleimid-N-yl)-CH₂CH₂-C(=O)-NH-CH₂CH₂-O-CH₂CH₂-O-CH₂CH₂-O-CH₂CH₂-C(=O)-GGFG (SEQ ID NO: 585)

-NH-CH₂CH₂CH₂-C(=O)-(NH-DX), (maleimid-N-yl)-CH₂CH₂-C(=O)-DGGFG (SEQ ID NO: 590)

-(NH-DX), (maleimid-N-yl)-CH₂CH₂CH₂-C(=O)-DGGFG (SEQ ID NO: 590)

-(NH-DX), (maleimid-N-yl)-CH₂CH₂CH₂CH₂-C(=O)-DGGFG (SEQ ID NO: 590)

-(NH-DX), (maleimid-N-yl)-CH₂CH₂CH₂CH₂CH₂-C(=O)-DGGFG (SEQ ID NO: 590)

-(NH-DX).

Further, among the aforementioned intermediate compound group, the intermediates represented by the following formula are a more preferred compound:

(SEQ ID NO: 585)
(maleimid-N-yl)-CH$_2$CH$_2$-C(=O)-NH-CH$_2$CH$_2$-O-CH$_2$CH$_2$-O-CH$_2$CH$_2$-C(=O)-GGFG

-NH-CH$_2$CH$_2$CH$_2$-C(=O)-(NH-DX), (SEQ ID NO: 585)
(maleimid-N-yl)-CH$_2$CH$_2$CH$_2$CH$_2$CH$_2$-C(=O)-GGFG

-NH-CH$_2$-O-CH$_2$-C(=O)-(NH-DX), (SEQ ID NO: 585)
(maleimid-N-yl)-CH$_2$CH$_2$CH$_2$CH$_2$CH$_2$-C(=O)-GGFG

-NH-CH$_2$CH$_2$-O-CH$_2$-C(=O)-(NH-DX), (SEQ ID NO: 590)
(maleimid-N-yl)-CH$_2$CH$_2$CH$_2$CH$_2$CH$_2$-C(=O)-DGGFG -NH-CH$_2$CH$_2$CH$_2$-C(=O)-(NH-DX),
or (SEQ ID NO: 590)
(maleimid-N-yl)-CH$_2$CH$_2$CH$_2$CH$_2$CH$_2$-C(=O)-DGGFG

-(NH-DX).

Particularly preferred are the compounds that are represented by the following formula:

(SEQ ID NO: 585)
(maleimid-N-yl)-CH$_2$CH$_2$-C(=O)-NH-CH$_2$CH$_2$-O-CH$_2$CH$_2$-O-CH$_2$CH$_2$-C(=O)-GGFG

-NH-CH$_2$CH$_2$CH$_2$-C(=O)-(NH-DX), (SEQ ID NO: 585)
(maleimid-N-yl)-CH$_2$CH$_2$CH$_2$CH$_2$CH$_2$-C(=O)-GGFG -NH-CH$_2$-O-CH$_2$-C(=O)-(NH-DX),
or (SEQ ID NO: 585)
(maleimid-N-yl)-CH$_2$CH$_2$CH$_2$CH$_2$CH$_2$-C(=O)-GGFG

-NH-CH$_2$CH$_2$-O-CH$_2$-C(=O)-(NH-DX).

2. Production Method 2

The compound represented by the formula (2) or a pharmacologically acceptable salt thereof used as an intermediate in the previous production method can be produced by the following method, for example.

[Chem. 24]
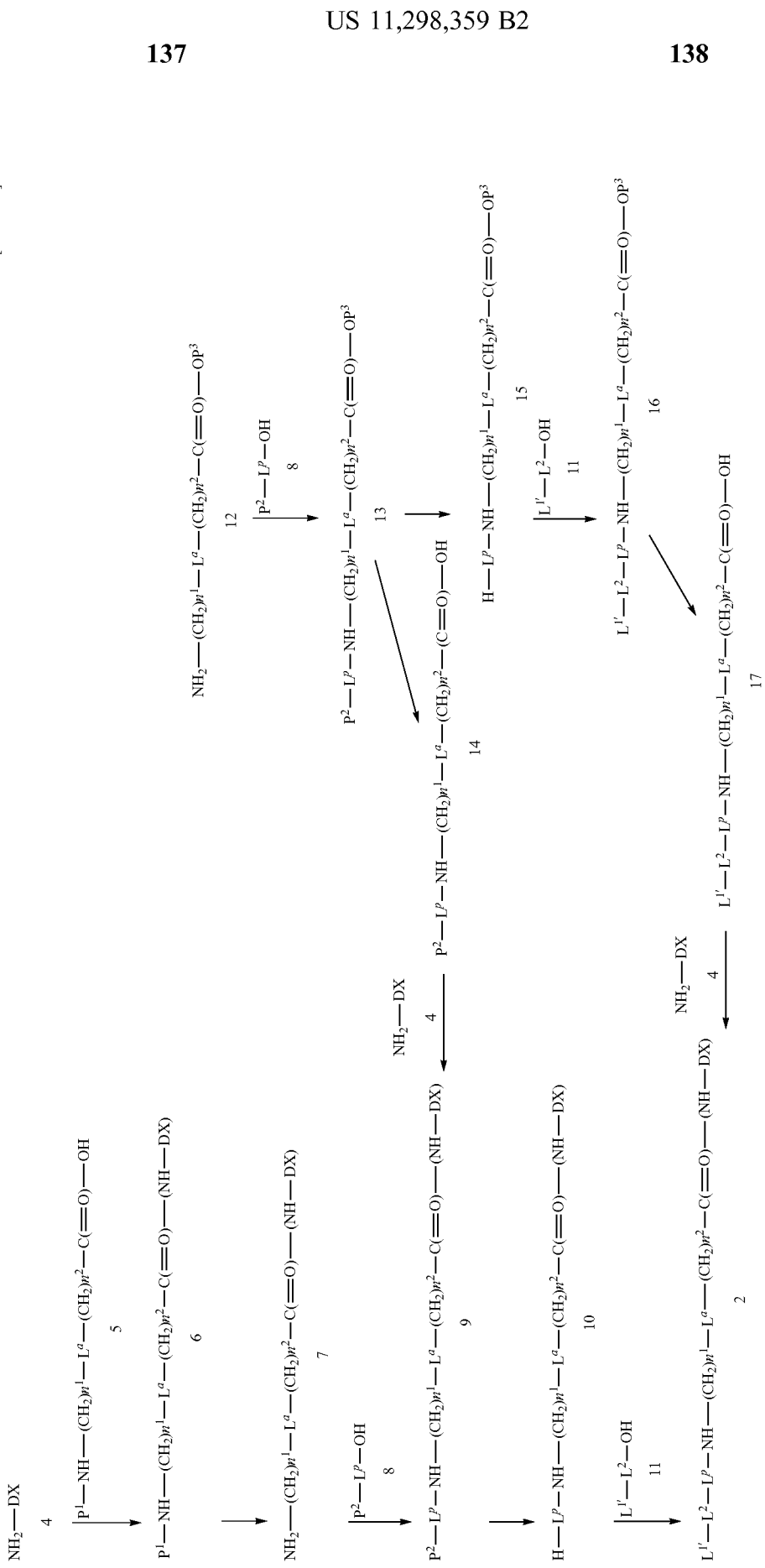

[in the formula, $L^{1'}$ corresponds to $L^1$ having a structure in which the terminal is converted to a maleimidyl group and $P^1$, $P^2$, and $P^3$ represent a protecting group].

The compound (6) can be produced by derivatizing the carboxylic acid (5) into an active ester, mixed acid anhydride, acid halide, or the like and, in the presense of base, reacting it with NH$_2$-DX [indicating exatecan; chemical name: (1S,9S)-1-amino-9-ethyl-5-fluoro-2,3-dihydro-9-hydroxy-4-methyl-1H, 12H-benzo[de]pyrano[3',4': 6,7]indolizino[1,2-b]quinolin-10,13(9H,15H)-dione] (4) or a pharmacologically acceptable salt thereof.

Reaction reagents and conditions that are commonly used for peptide synthesis can be employed for the reaction. There are various kinds of active ester, for example, it can be produced by reacting phenols such as p-nitrophenol, N-hydroxy benzotriazole, N-hydroxy succinimide, or the like, with the carboxylic acid (5) using a condensing agent such as N,N'-dicyclohexylcarbodiimide or 1-ethyl-3-(3-dimethylaminopropyl)carbodiimide hydrochloride; further, the active ester can be also produced by a reaction of the carboxylic acid (5) with pentafluorophenyl trifluoroacetate or the like; a reaction of the carboxylic acid (5) with 1-benzotriazolyl oxytripyrrolidinophosphonium hexafluorophosphite; a reaction of the carboxylic acid (5) with diethyl cyanophosphonate (Shioiri method); a reaction of the carboxylic acid (5) with triphenylphosphine and 2,2'-dipyridyl disulfide (Mukaiyama method); a reaction of the carboxylic acid (5) with a triazine derivative such as 4-(4,6-dimethoxy-1,3,5-triazin-2-yl)-4-methylmorpholinium chloride (DMTMM); or the like. Further, the reaction can be also performed by, e.g., an acid halide method by which the carboxylic acid (5) is treated with acid halide such as thionyl chloride and oxalyl chloride in the presence of a base.

By reacting the active ester, mixed acid anhydride, or acid halide of the carboxylic acid (5) obtained as above with the compound (4) in the presence of a suitable base in an inert solvent at a reaction temperature of -78 C to 150 C, the compound (6) can be produced. Meanwhile, "inert solvent" indicates a solvent which does not inhibit a desired reaction for which the solvent is used.

Specific examples of the base used for each step described above include a carbonate, an alkoxide, a hydroxide or a hydride of an alkali metal or an alkali earth metal such as sodium carbonate, potassium carbonate, sodium ethoxide, potassium butoxide, sodium hydroxide, potassium hydroxide, sodium hydride, or potassium hydride; organometallic base represented by an alkyl lithium such as n-butyl lithium, or dialkylamino lithium such as lithium diisopropylamide; organometallic base such as bissilylamine including lithium bis(trimethylsilyl)amide; and organic base such as pyridine, 2,6-lutidine, collidine, 4-dimethylaminopyridine, triethylamine, N-methyl morpholine, diisopropylethylamine, and diazabicyclo[5.4.0]undec-7-ene (DBU).

Examples of the inert solvent which is used for the reaction of the present invention include a halogenated hydrocarbon solvent such as dichloromethane, chloroform, and carbon tetrachloride; an ether solvent such as tetrahydrofuran, 1,2-dimethoxyethane, and dioxane; an aromatic hydrocarbon solvent such as benzene and toluene; and an amide solvent such as N,N-dimethylformamide, N,N-dimethylacetamide, and N-methylpyrrolidin-2-one. In addition to them, a sulfoxide solvent such as dimethyl sulfoxide and sulfolane; a ketone solvent such as acetone and methyl ethyl ketone; and an alcohol solvent such as methanol and ethanol may be used in some case. Alternatively, these solvents may be used as a mixed solvent.

As for the protecting group $P^1$ for the terminal amino group of the compound (6), a protecting group for an amino group which is generally used for peptide synthesis, for example, tert-butyloxy carbonyl group, 9-fluorenylmethyloxy carbonyl group, and benzyloxy carbonyl group, can be used. Examples of the other protecting group for an amino group include an alkanoyl group such as acetyl group; an alkoxycarbonyl group such as methoxycarbonyl group and ethoxycarbonyl group; an arylmethoxy carbonyl group such as paramethoxybenzyloxy carbonyl group, and para (or ortho)nitroybenzyloxy carbonyl group; an arylmethyl group such as benzyl group and triphenyl methyl group; an aroyl group such as benzoyl group; and an aryl sulfonyl group such as 2,4-dinitrobenzene sulfonyl group and orthonitrobenzene sulfonyl group. The protecting group $P^1$ can be selected depending on, e.g., properties of a compound having an amino group to be protected.

By deprotecting the protecting group $P^1$ for the terminal amino group of the compound (6) obtained, the compound (7) can be produced. In this deprotection, reagents and conditions can be selected depending on the protecting group.

The compound (9) can be produced by derivatizing the peptide carboxylic acid (8) having the N terminal protected with $P^2$ into an active ester, mixed acid anhydride, or the like and reacting it with the compound (7) obtained. The reaction conditions, reagents, base, and inert solvent used for a peptide bond formation between the peptide carboxylic acid (8) and the compound (7) can be suitably selected from those described for the synthesis of the compound (6). The protecting group $P^2$ can be suitably selected from those described for the protecting group of the compound (6), and the selection can be made based on, e.g., the properties of the compound having an amino group to be protected. As it is generally used for peptide synthesis, by repeating sequentially the reaction and deprotection of the amino acid or peptide constituting the peptide carboxylic acid (8) for elongation, the compound (9) can be also produced.

By deprotecting $P^2$ as the protecting group for the amino group of the compound (9) obtained, the compound (10) can be produced. In this deprotection, reagents and conditions can be selected depending on the protecting group.

It is possible to produce the compound (2) by derivatizing the carboxylic acid (11) into an active ester, mixed acid anhydride, acid halide, or the like and reacting it with the compound (10) obtained. The reaction conditions, reagents, base, and inert solvent used for forming a peptide bond between the carboxylic acid (11) and the compound (10) can be suitably selected from those described for the synthesis of the compound (6).

The compound (9) can be also produced by the following method, for example.

The compound (13) can be produced by derivatizing the peptide carboxylic acid (8) having the N terminal protected with $P^2$ into active ester, mixed acid anhydride, or the like and reacting it with the amine compound (12) having the carboxy group protected with $P^3$ in the presence of a base. The reaction conditions, reagents, base, and inert solvent used for forming a peptide bond between the peptide carboxylic acid (8) and the compound (12) can be suitably selected from those described for the synthesis of the compound (6).

The protecting group $P^2$ for the amino group of the compound (13) is not particularly limited if it is a protecting group which is commonly used. Specifically, examples of the protecting group for a hydroxyl group include an alkoxymethyl group such as methoxymethyl group; an arylmethyl group such as benzyl group, 4-methoxybenzyl group, and triphenylmethyl group; an alkanoyl group such as acetyl group; an aroyl group such as benzoyl group; and a silyl group such as tert-butyl diphenylsilyl group. Carboxy group can be protected by an ester with an alkyl group such as methyl group, ethyl group, and tert-butyl group, an allyl group, or an arylmethyl group such as benzyl group. As for the amino group, an alkyloxy carbonyl group such as tert-butyloxy carbonyl group, methoxycarbonyl group, and ethoxycarbonyl group; an arylmethoxy carbonyl group such as allyloxycarbonyl group, 9-fluorenylmethyloxy carbonyl group, benzyloxy carbonyl group, paramethoxybenzyloxy carbonyl group, and para (or ortho)nitroybenzyloxy carbonyl group; an alkanoyl group such as acetyl group; an arylmethyl group such as benzyl group and triphenyl methyl group; an aroyl group such as benzoyl group; and an aryl sulfonyl group such as 2,4-dinitrobenzene sulfonyl group or orthonitrobenzene sulfonyl group can be mentioned.

As for the protecting group $P^3$ for a carboxy group, a protecting group commonly used as a protecting group for a carboxy group in organic synthetic chemistry, in particular, peptide synthesis can be used. A carboxyl group can be protected as an ester with an alkyl group such as a methyl group, an ethyl group, or a tert-butyl, an allyl group, and an arylmethyl group such as a benzyl group.

In such case, it is preferable that the protecting group for an amino group and the protecting group for a carboxy group can be removed by a different method or different conditions. For example, a representative example includes a combination in which $P^2$ is a tert-butyloxy carbonyl group and $P^3$ is a benzyl group. The protecting groups can be selected from the aforementioned ones depending on, e.g., the properties of a compound having an amino group and a carboxy group to be protected. For removal of the protecting groups, reagents and conditions can be selected depending on the protecting group.

By deprotecting the protecting group $P^3$ for the carboxy group of the compound (13) obtained, the compound (14) can be produced. In this deprotection, reagents and conditions are selected depending on the protecting group.

The compound (9) can be produced by derivatizing the compound (14) obtained into active ester, mixed acid anhydride, acid halide, or the like and reacting with the compound (4) in the presence of a base. For the reaction, reaction reagents and conditions that are generally used for peptide synthesis can be also used, and the reaction conditions, reagents, base, and inert solvent used for the reaction can be suitably selected from those described for the synthesis of the compound (6).

The compound (2) can be also produced by the following method, for example.

By deprotecting the protecting group $P^2$ for the amino group of the compound (13), the compound (15) can be produced. In this deprotection, reagents and conditions can be selected depending on the protecting group.

The compound (16) can be produced by derivatizing the carboxylic acid derivative (11) into active ester, mixed acid anhydride, acid halide, or the like and reacting it with the compound (15) obtained in the presence of a base. The reaction conditions, reagents, base, and inert solvent used for forming an amide bond between the peptide carboxylic acid (11) and the compound (15) can be suitably selected from those described for the synthesis of the compound (6).

By deprotecting the protecting group for the carboxy group of the compound (16) obtained, the compound (17) can be produced. In this deprotection, it can be carried out similar to deprotecting carboxy group for producing the compound (14).

The compound (2) can be produced by derivatizing the compound (17) into active ester, mixed acid anhydride, acid halide, or the like and reacting it with the compound (4) in the presence of a base. For the reaction, reaction reagents and conditions that are generally used for peptide synthesis can be also used, and the reaction conditions, reagents, base, and inert solvent used for the reaction can be suitably selected from those described for the synthesis of the compound (6).

3. Production Method 3

The compound represented by the formula (2) used as an intermediate can be also produced by the following method.

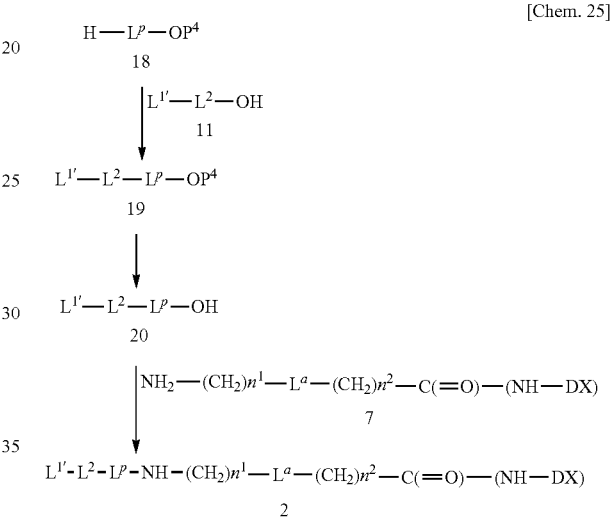

[Chem. 25]

[in the formula, $L^{1'}$ corresponds to $L^1$ having a structure in which the terminal is converted to a maleimidyl group and $P^4$ represents a protecting group].

The compound (19) can be produced by derivatizing the compound (11) into active ester, mixed acid anhydride, or the like and reacting it with the peptide carboxylic acid (18) having the C terminal protected with $P^4$ in the presence of a base. The reaction conditions, reagents, base, and inert solvent used for forming a peptide bond between the peptide carboxylic acid (18) and the compound (11) can be suitably selected from those described for the synthesis of the compound (6). The protecting group $P^4$ for the carboxy group of the compound (18) can be suitably selected from the aforementioned protective groups.

By deprotecting the protecting group for the carboxy group of the compound (19) obtained, the compound (20) can be produced. In this deprotecion, it can be performed similar to the deprotection of the carboxy group for producing the compound (14).

The compound (2) can be produced by derivatizing the compound (20) obtained into active ester, mixed acid anhydride, or the like and reacting it with the compound (7). For the reaction, reaction reagents and conditions that are generally used for peptide synthesis can be also used, and the reaction conditions, reagents, base, and inert solvent used for the reaction can be suitably selected from those described for the synthesis of the compound (6).

4. Production Method 4

Hereinbelow, within the production intermediate (10) described in production method 2, the method for producing the compound (10b) having $n^1=1$ and $L^a=0$ is described in detail. The compound represented by the formula (10b), a salt or a solvate thereof can be produced according to the following method, for example.

[Chem. 26]

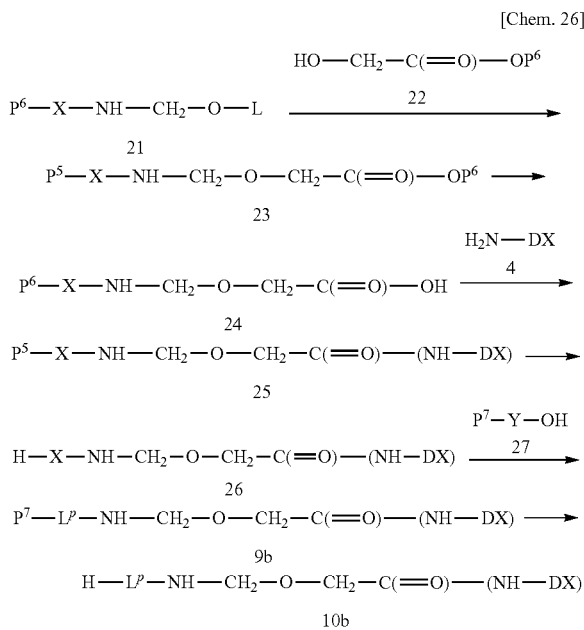

[in the formula, $L^P$ is as defined above, L represents an acyl group including an alkanoyl group such as acetyl group or an aroyl group such as benzoyl group, or represents a hydrogen atom or the like, X and Y represent an oligopeptide consisting of 1 to 3 amino acids, $P^5$ and $P^7$ represent a protecting group for an amino group, and $P^6$ represents a protecting group for a carboxy group].

A compound represented by the formula (21) can be produced by using or applying the method described in Japanese Patent Laid-Open No. 2002-60351 or the literature (J. Org. Chem., Vol. 51, page 3196, 1986), and if necessary, by removing the protecting groups or modifying the functional groups. Alternatively, it can be also obtained by treating an amino acid with a protected terminal amino group or acid amide of oligopeptide with protected amino group with aldehyde or ketone.

By reacting the compound (21) with the compound (22) having a hydroxyl group under temperature conditions ranging from under cooling to room temperature in an inert solvent in the presence of an acid or a base, the compound (23) can be produced.

Here, examples of the acid which may be used can include inorganic acid such as hydrofluoric acid, hydrochloric acid, sulfuric acid, nitric acid, phosphoric acid, and boric acid; an organic acid such as acetic acid, citric acid, paratoluene sulfonic acid, and methane sulfonic acid; and a Lewis acid such as tetrafluoroborate, zinc chloride, tin chloride, aluminum chloride, and iron chloride. Among them, sulfonic acids are preferable, and paratoluene sulfonic acid is particularly preferable. As for the base, any one of the aforementioned base can be suitably selected and used. Preferred examples thereof include an alkali metal alkoxide such as potassium tert-butoxide, an alkali metal or alkaline earth metal hydroxide such as sodium hydroxide and potassium hydroxide; alkali metal hydride such as sodium hydride and potassium hydride; organometallic base represented by dialkylamino lithium such as lithium diisopropylamide; and organometallic base of bissilylamine such as lithium bis(trimethylsilyl) amide.

Examples of the solvent to be used for the reaction include an ether solvent such as tetrahydrofuran and 1,4-dioxane; and an aromatic hydrocarbon solvent such as benzene and toluene. Those solvents can be prepared as a mixture with water.

Further, the protecting group for an amino group as represented as $P^5$ is not particularly limited if it is a group commonly used for protection of an amino group. Representative examples can include the protecting groups for an amino group that are described in Production method 2. However, the protecting group for an amino group as drepresented as $P^5$ may be cleaved off within the course of the reaction. In such case, a protecting group can be reintroduced by appropriately performing a reaction with a suitable reagent for protecting an amino group as required.

The compound (24) can be derived by removing the protecting group $P^6$ of the compound (23). Herein, although the representative examples of the protecting group for a carboxy group as represented as $P^6$ are described in Production method 2, it can be appropriately selected from these examples. In the compound (23), it is desirable that the protecting group $P^5$ for an amino group and the protecting group $P^6$ for a carboxy group are the protecting groups that can be removed by a different method or different conditions. For example, a representative example can include a combination in which $P^5$ is a 9-fluorenylmethyloxy carbonyl group and $P^6$ is a benzyl group. The protecting groups can be selected depending on, e.g., the properties of a compound having an amino group and a carboxy group to be protected. For removal of the protecting groups, reagents and conditions are selected depending on the protecting group.

The compound (26) can be produced by derivatizing the compound (24) into active ester, mixed acid anhydride, acid halide, or the like and reacting it with the compound (4) or a pharmacologically acceptable salt thereof in the presence of a base to produce the compound (25) followed by removing the protecting group $P^5$ of the compound (25) obtained. For the reaction between the compound (4) and the carboxylic acid (24) and the reaction for removing the protecting group $P^6$, the same reagents and reaction conditions as those described for Production method 2 can be used.

The compound (10b) can be produced by reacting the compound (26) with an amino acid with protected terminal amino group or the oligopeptide (27) with protected amino group to produce the compound (9b) and removing the protective group $P^7$ of the compound (9b) obtained. The protective group for an amino group as represented as $P^7$ is not particularly limited if it is generally used for protection of an amino group. Representative examples thereof include the protecting groups for an amino group that are described in Production method 2. For removing the protective group, reagents and conditions are selected depending on the protecting group. For the reaction between the compound (26) and the compound (27), reaction reagents and conditions that are commonly used for peptide synthesis can be employed. The compound (10b) produced by the aforementioned method can be derivatized into the compound (1) of the present invention according to the method described above.

5. Production Method 5 The compound represented by the formula (2) as an intermediate can be also produced by the method shown below.

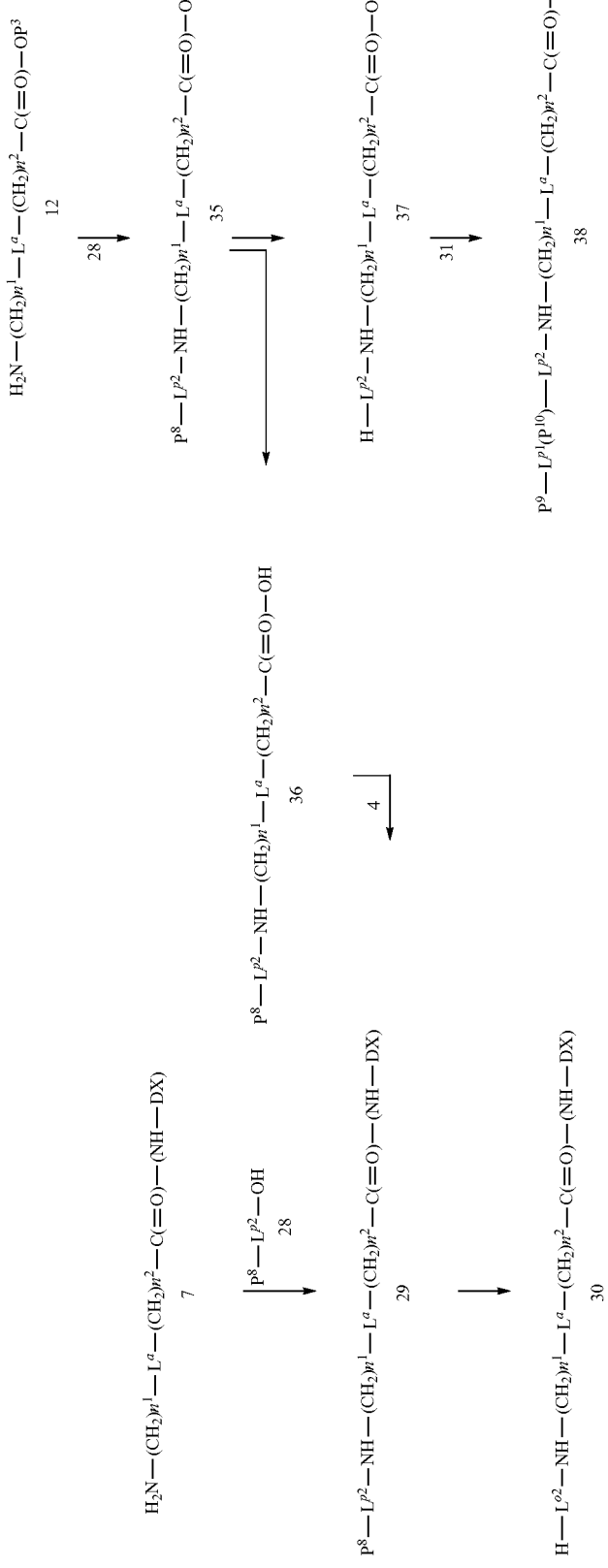

-continued $L^1-L^2-L^{p1}(P^{10})-L^{p2}-NH-(CH_2)n^1-L^a-(CH_2)n^2-C(=O)-OP^3$
41

$\xrightarrow{4}$ $L^1-L^2-L^{p1}(P^{10})-L^{p2}-NH-(CH_2)n^1-L^a-(CH_2)n^2-C(=O)-OH$
42

$\xrightarrow{30}$ $L^1-L^2-L^{p1}(P^{10})-L^{p2}-OH$
46

$\downarrow 46$ $L^1-L^2-L^{p1}(P^{10})-L^{p2}-OP^{12}$
47

$\uparrow 11$ $H-L^{p1}(P^{10})-L^{p2}-OP^{12}$
50

$\uparrow$ $P^3-L^{o1}(P^{10})-L^{p2}-OP^{12}$
49

$\uparrow 24$ $H-L^{o2}-OP^{12}$
46

$L^1-L^2-L^{p1}(P^{10})-L^{p2}-OP^{11}$
44

$\uparrow 11$ $H-L^{p1}(P^{10})-OP^{11}$
43

$H-L^{p1}(P^{10})-L^{p2}-NH-(CH_2)n^1-L^a-(CH_2)n^2-C(=O)-(NH-DX)$
33

$\downarrow \begin{array}{c} L^1-L^2-OH \\ 11 \end{array}$ $L^1-L^2-L^{p1}(P^{10})-L^{p2}-NH-(CH_2)n^1-L^a-(CH_2)n^2-C(=O)-(NH-DX)$
34

$\xleftarrow{7}$ $L^1-L^2-L^{p1}(P^{10})-L^{p2}-OH$
48

$\downarrow$ $L^1-L^2-L^o-NH-(CH_2)n^1-L^a-(CH_2)n^2-C(=O)-(NH-DX)$
2

[in the formula, $L^{1'}$ corresponds to $L^1$ having a structure in which the terminal is converted to a maleimidyl group, $L^P$ represents a structure consisting of -$L^{P1}$-$L^{P2}$-, and $P^3$, $P^8$, $P^9$, $P^{10}$, $P^{11}$, and $P^{12}$ represent a protecting group].

Because $L^P$ is formed by connecting $L^{P1}$ to $L^{P2}$, the hydrophilic amino acid at N terminal of $L^P$ is derived from $L^{P1}$, and thus, those that having a hydrophilic amino acid at the N terminal are suitably employed as $L^{P1}$. Meanwhile, plural hydrophilic amino acids may be present therein. Further, when $L^{P2}$ with hydrophilic amino acid is employed, $L^P$ having plural hydrophilic amino acids at the N terminal of $L^P$ or at the N terminal and at other positions can be produced depending on the location of the hydrophilic amino acid.

The compound (29) can be produced by derivatizing the peptide or amino acid (28) having the N terminal protected with $P^2$ into active ester, mixed acid anhydride, or the like and reacting it with the compound (7) obtained. The reaction conditions, reagents, base, and solvent used for forming an amide bond between the peptide or amino acid (28) and the compound (7) can be suitably selected from those described for the synthesis of the compound (6). The protecting group $P^8$ for an amino group can be suitably selected from those described for the protecting group of the compound (6), and the selection can be made based on the properties of the compound or the like. As it is generally used for peptide synthesis, by repeating sequentially the reaction and deprotection of the amino acid or peptide constituting the peptide or amino acid (28) for elongation, the compound (29) can be also produced.

By deprotection of $P^8$ as a protecting group of the amino group of the compound (29) obtained, the compound (23) can be produced. In this deprotection, reagents and conditions can be selected depending on the protecting group.

The compound (32) can be produced by derivatizing the amino acid or peptide (31) having the N terminal protected with $P^8$ and the protected carboxy group, hydroxy group, or amino group in side chain protected into active ester, mixed acid anhydride, or the like and reacting it with the compound (30) obtained. The reaction conditions, reagents, base, and inert solvent used for forming a peptide bond between the amino acid or peptide (31) and the compound (30) can be suitably selected from those described for the synthesis of the compound (6). As for the protecting groups $P^8$ and $P^9$, the protecting groups can be suitably selected from those described as protecting group for an amino group, carboxy group, or hydroxy group of the compound (6). However, in such case, it is necessary that the protecting group $P^9$ for an amino group and the protecting group $P^{10}$ for a functional group in side chain can be removed by a different method or different conditions. For example, a representative example includes a combination in case $P^9$ is a 9-fluorenylmethyloxy carbonyl group and $P^{10}$ is a tert-butyl group or the like as a protecting group for a carboxy group, a methoxymethyl group or the like as a protecting group for a hydroxy group, or a tert-butyloxycarbonyl group or the like as a protecting group for an amino group. The protective group $P^{10}$ for a functional group in a side chain is preferably a protecting group which can be deprotected by a treatment under acidic conditions. However, it is not limited thereto, and it can be selected from the aforementioned ones depending on, e.g., the properties of amino group, carboxy group, or a hydroxy group of a compound to be protected. For removal of the protecting groups, reagents and conditions are selected depending on the protecting group. As it is generally used for peptide synthesis, by repeating sequentially the reaction and deprotection of the constituting amino acid or peptide for elongation, the compound (32) can be also produced.

By deprotection of $P^9$ as a protecting group of the terminal amino group of the compound (32) obtained, the compound (33) can be produced. In this deprotection, reagents and conditions can be selected depending on the protecting group.

It is possible to produce the compound (34) by derivatizing the carboxylic acid derivative (11) into active ester, mixed acid anhydride, acid halide, or the like and reacting it with the compound (33) obtained. Herein, the carboxylic acid derivative (11) is a compound with a structure in which the linker terminal of $L^{1'}$ has a maleimidyl group.

The reaction conditions, reagents, base, and solvent used for forming a peptide bond between the carboxylic acid derivative (11) and the compound (33) can be suitably selected from those described for the synthesis of the compound (6).

By deprotecting the protecting group $P^{10}$ for the carboxy group, hydroxy group, or amino group in the amino acid side chain of the peptide moiety of the compound (34) obtained, the compound (2) can be produced. Reagents and conditions can be selected depending on the protecting group.

The compound (29) can be also produced by the following method, for example.

The compound (35) can be produced by derivatizing the peptide or amino acid (28) having the N terminal protected with $P^8$ into active ester, mixed acid anhydride, or the like and reacting it with the amine compound (12) having the terminal carboxy group protected with $P^3$ in the presence of a base. The reaction conditions, reagents, base, and solvent used for forming a peptide bond between the peptide or amino acid (28) and the compound (12) can be suitably selected from those described for the synthesis of the compound (6). The protecting group $P^8$ for an amino group of the compound (35) can be suitably selected and used from those described as a protecting group for the compound (6). As for the protecting group $P^3$ for a carboxy group, a protecting group commonly used as a protecting group for a carboxy group in organic synthetic chemistry, in particular, peptide synthesis can be used. Specific examples include alkyl ester such as methyl group, ethyl group, and tert-butyl, allyl ester, and benzyl ester, and it can be suitably selected and used from the protecting groups that are described for the compound (6). In such case, it is necessary that the protecting group $P^8$ for an amino group and the protecting group $P^3$ for a carboxy group can be removed by a different method or different conditions. For example, a representative example includes a combination in which $P^8$ is a tert-butyloxy carbonyl group and $P^3$ is a benzyl group. The protecting groups can be selected from the aforementioned ones depending on, e.g., the properties of a compound having an amino group and a carboxy group to be protected. For removal of the protecting groups, reagents and conditions are selected depending on the protecting group.

By deprotecting the protecting group $P^3$ for the carboxy group of the compound (35) obtained, the compound (36) can be produced. In this deprotection, reagents and conditions are selected depending on the protecting group.

The compound (29) can be produced by derivatizing the compound (36) obtained into active ester, mixed acid anhydride, acid halide, or the like and reacting it with the compound (4) in the presence of a base. For the reaction, reaction reagents and conditions that are generally used for peptide synthesis can be also used, and the reaction conditions, reagents, base, and solvent used for the reaction can be suitably selected from those described for the synthesis of the compound (6).

The compound (32) can be also produced by the following method, for example.

By deprotecting the protecting group $P^8$ for the amino group of the compound (35), the compound (37) can be produced. In this deprotection, reagents and conditions can be selected depending on the protecting group.

The compound (38) can be produced by derivatizing the amino acid or peptide (31) into active ester, mixed acid anhydride, acid halide, or the like and reacting it with the compound (37) obtained in the presence of a base. The reaction conditions, reagents, base, and solvent used for forming an amide bond between the amino acid or peptide (31) and the compound (37) can be suitably selected from those described for the synthesis of the compound (6). In such case, it is necessary that the protecting group $P^9$ and $P^{10}$ for the amino acid or peptide (31) and the protecting group $P^3$ for the compound (37) can be removed by a different method or different conditions. For example, a representative example includes a combination in which $P^9$ is a 9-fluorenylmethyloxy carbonyl group, $P^{10}$ is a tert-butyloxy carbonyl group, tert-butyl group, or a methoxymethyl group, and $P^3$ is a benzyl group. Further, the protective group $P^{10}$ for a functional group in a side chain is preferably a protecting group which can be deprotected by a treatment under acidic conditions as described above. However, it is not limited thereto, and it can be selected from the aforementioned ones depending on, e.g., the properties of amino group, carboxy group, or a hydroxy group of a compound to be protected. For removal of the protecting groups, reagents and conditions are selected depending on the protecting group.

By deprotecting the protecting group $P^3$ for the carboxy group of the compound (38) obtained, the compound (39) can be produced. In this deprotection, reagents and conditions can be selected depending on the protecting group.

The compound (32) can be produced by derivatizing the compound (39) into active ester, mixed acid anhydride, acid halide, or the like and reacting it with the compound (4) in the presence of a base. For the reaction, reaction reagents and conditions that are generally used for peptide synthesis can be also used, and the reaction conditions, reagents, base, and solvent used for the reaction can be suitably selected from those described for the synthesis of the compound (6).

The compound (34) can be also produced by the following method, for example.

By deprotecting the protecting group $P^9$ for the amino group of the compound (38), the compound (40) can be produced. In this deprotection, reagents and conditions can be selected depending on the protecting group.

The compound (41) can be produced by derivatizing the carboxylic acid derivative (11) into active ester, mixed acid anhydride, acid halide, or the like and reacting it with the compound (40) obtained in the presence of a base. The reaction conditions, reagents, base, and solvent used for forming an amide bond between the carboxylic acid derivative (11) and the compound (40) can be suitably selected from those described for the synthesis of the compound (6).

By deprotecting the protecting group $P^3$ for the carboxy group of the compound (41) obtained, the compound (42) can be produced. In this deprotection, reagents and conditions can be selected depending on the protecting group.

The compound (34) can be produced by derivatizing the compound (42) into active ester, mixed acid anhydride, acid halide, or the like and reacting it with the compound (4) in the presence of a base. For the reaction, reaction reagents and conditions that are generally used for peptide synthesis can be also used, and the reaction conditions, reagents, base, and solvent used for the reaction can be suitably selected from those described for the synthesis of the compound (6).

The compound (34) can be also produced by the following method, for example.

The compound (44) can be produced by derivatizing the carboxylic acid derivative (11) into active ester, mixed acid anhydride, acid halide, or the like and reacting it with the amino acid or peptide (43) having the carboxy group protected with $P^{11}$ and the carboxy group, hydroxy group, or amino group in side chain protected with $P^{10}$ in the presence of a base. The reaction conditions, reagents, base, and solvent used for forming an amide bond between the carboxylic acid derivative (11) and the compound (43) can be suitably selected from those described for the synthesis of the compound (6). As for the protecting groups $P^{10}$ and $P^{11}$ of the compound (44), the protecting groups can be suitably selected from those described as protecting group for a carboxy group, hydroxy group, or amino group of the compound (6). Meanwhile, in such case, it is necessary that the protecting group $P^{11}$ for a carboxy group and the protecting group $P^{10}$ for a functional group in side chain can be removed by a different method or different conditions. For example, a representative example includes a combination in which $P^{11}$ is a benzyl group and $P^{10}$ is a tert-butyl group or the like as a protecting group for a carboxy group, a methoxymethyl group or the like as a protecting group for a hydroxy group, or a tert-butyloxycarbonyl group or the like as a protecting group for an amino group. The protective group $P^{10}$ for a functional group in a side chain is preferably a protecting group which can be deprotected by a treatment under acidic conditions. However, it is not limited thereto, and it can be selected from the aforementioned ones depending on, e.g., the properties of amino group, carboxy group, or a hydroxy group of a compound to be protected. For removing the protecting group, the reagents and conditions can be selected depending on the protecting group.

By deprotecting the protecting group $P^{11}$ for the carboxy group of the compound (44) obtained, the compound (45) can be produced. In this deprotection, reagents and conditions can be selected depending on the protecting group.

The compound (34) can be produced by derivatizing the compound (45) into active ester, mixed acid anhydride, acid halide, or the like and reacting it with the compound (30) in the presence of a base. For the reaction, reaction reagents and conditions that are generally used for peptide synthesis can be also used, and the reaction conditions, reagents, base, and solvent used for the reaction can be suitably selected from those described for the synthesis of the compound (6).

The compound (47) can be produced by derivatizing the compound (45) into active ester, mixed acid anhydride, acid halide or the like and reacting it with the amino acid or peptide (46) having the carboxy group protected with $P^{12}$ in the presence of a base. For the reaction, the reaction reagents and conditions commonly used for peptide synthesis can be used and the reaction conditions, reagents, base, and solvent can be suitably selected from those described for the synthesis of the compound (6). As for the protecting groups $P^{10}$ and $P^{12}$ of the compound (47), the protecting groups can be suitably selected and used from those described as protecting group for a carboxy group, hydroxy group, or amino group of the compound (6). Meanwhile, in such case, it is necessary that the protecting group $P^{12}$ for a carboxy group and the protecting group $P^{10}$ for a functional group in side chain can be removed by a different method or different conditions. For example, a representative example includes a combination in which $P^{12}$ is a benzyl group and $P^{10}$ is a tert-butyl group or the like as a protecting group for a carboxy group, a methoxymethyl group or the like as a protecting group for a hydroxy group, or a tert-butyloxycarbonyl group or the like as a protecting group for an amino group. The protective group $P^{10}$ for a functional group in a side chain is preferably a protecting group which can be deprotected by a treatment under acidic conditions. However, it is not limited thereto, and it can be selected from the aforementioned ones depending on, e.g., the properties of amino group, carboxy group, or a hydroxy group of a compound to be protected. For removing the protecting group, the reagents and conditions can be selected depending on the protecting group. Further, the compound (47) can be also produced by repeating sequentially the reaction and deprotection of constituting amino acid or peptide for elongation.

By deprotecting the protecting group $P^{12}$ for the carboxy group of the compound (47) obtained, the compound (48) can be produced. Reagents and conditions can be selected depending on the protecting group.

The compound (34) can be produced by derivatizing the compound (48) into active ester, mixed acid anhydride, acid halide, or the like and reacting it with the compound (7) in the presence of a base. For the reaction, reaction reagents and conditions that are generally used for peptide synthesis can be also used, and the reaction conditions, reagents, base, and solvent used for the reaction can be suitably selected from those described for the synthesis of the compound (6).

The compound (47) can be also produced by the following method, for example.

The peptide (49) can be produced by derivatizing the amino acid or peptide (46) into active ester, mixed acid anhydride, acid halide, or the like and reacting it with the amino acid or peptide (31) having the N terminal protected with $P^9$ and the carboxy group, hydroxy group, or amino group in side chain protected with $P^{10}$ in the presence of a base. The reaction conditions, reagents, base, and solvent used for forming a peptide bond between the amino acid or peptide (46) and the amino acid or peptide (31) can be suitably selected from those described for the synthesis of the compound (6). Meanwhile, in this case, it is necessary that the protecting group $P^{12}$ for a carboxy group of the amino acid or peptide (46) and the protecting group $P^9$ and $P^{10}$ for the amino acid or peptide (31) can be removed in the same manner as described above but by a different method or different conditions. For example, a representative example includes a combination in which $P^9$ is a 9-fluorenylmethyloxy carbonyl group, $P^{10}$ is a tert-butyl group or the like as a protecting group for a carboxy group, a methoxymethyl group or the like as a protecting group for a hydroxy group, or a tert-butyloxycarbonyl group as a protecting group or the like for an amino group, and $P^{12}$ is a benzyl group. The protective group $P^{10}$ for a functional group in a side chain is preferably a protecting group which can be deprotected by a treatment under acidic conditions. However, it is not limited thereto, and it can be selected from the aforementioned ones depending on, e.g., the properties of amino group, carboxy group, or a hydroxy group of a compound to be protected. For removing the protecting group, the reagents and conditions can be selected depending on the protecting group.

By deprotecting the protecting group $P^9$ for the N terminal of the peptide (49) obtained, the compound (50) can be produced. Reagents and conditions can be selected depending on the protecting group.

The compound (47) can be produced by derivatizing the carboxylic acid derivative (11) into active ester, mixed acid anhydride, acid halide, or the like and reacting it with the peptide (50) obtained in the presence of a base. The reaction conditions, reagents, base, and solvent used for forming an amide bond between the carboxylic acid derivative (11) and the peptide (50) can be suitably selected from those described for the synthesis of the compound (6).

6. Production Method 6

Within the production intermediate (2), those in which the linker has a structure represented by $-L^1-L^2-L^P-$, and said $L^P$ is the peptide residue containing a hydrophilic amino acid at the N terminal and said hydrophilic amino acid located at the N terminal is other than glycine, can be also produced by the following method.

[Chem. 28]

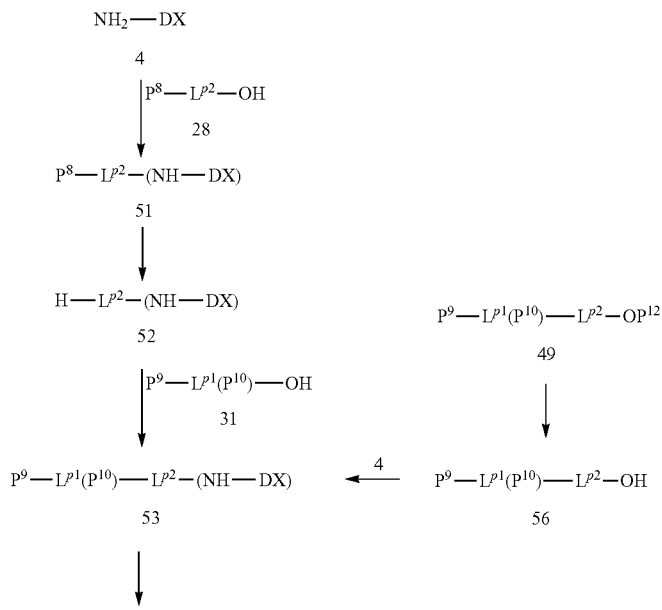

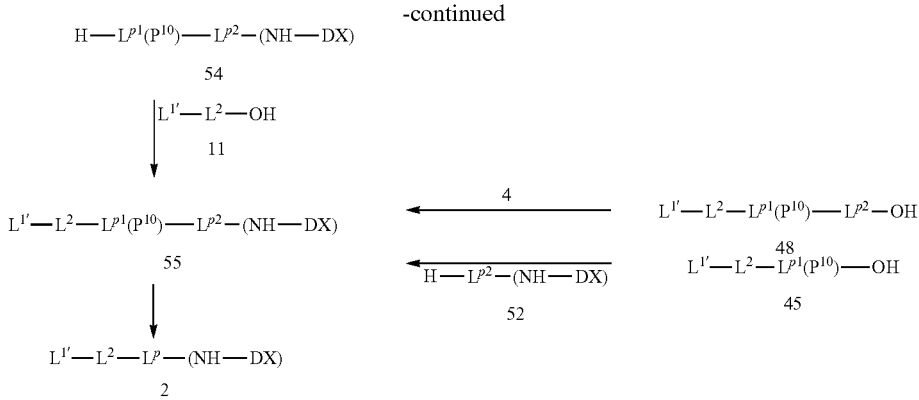

[in the formula, $L^{1'}$ corresponds to $L^1$ having a structure in which the terminal is modified to maleimidyl group, $L^P$ represents a structure consisting of -$L^{P1}$-$L^{P2}$-, and $P^8$, $P^9$, $P^{10}$, and $P^{12}$ represent a protecting group].

Because $L^P$ is formed by connecting $L^{P1}$ to $L^{P2}$, the hydrophilic amino acid at N terminal of $L^P$ is derived from $L^{P1}$, and thus, those that having a hydrophilic amino acid at the N terminal are suitably employed as $L^{P1}$. Meanwhile, plural hydrophilic amino acids may present therein. Further, when $L^{P2}$ with hydrophilic amino acid is employed, $L^P$ having plural hydrophilic amino acids at the N terminal of $L^P$ or at the N terminal and at other positions can be produced depending on its location of hydrophilic amino acid.

The compound (51) can be produced by derivatizing the peptide or amino acid (28) described in Production method 5, which has the N terminal protected with $P^8$, into active ester, mixed acid anhydride, or the like, and reacting with the compound (4) and a salt thereof. The reaction conditions, reagents, base, and solvent used for forming a peptide bond between the peptide or amino acid (28) and the compound (4) can be suitably selected from those described for the synthesis of the compound (6). The protective group $P^8$ can be suitably selected and used from those described as the protecting group for the compound (6), and it can be selected depending on, e.g., a property of the compound having an amino group to be protected. Further, as it is generally used for peptide synthesis, by repeating sequentially the reaction and deprotection of the amino acid or peptide constituting the peptide or amino acid (28) for elongation, the compound (51) can be also produced.

By deprotecting the protecting group $P^8$ for the amino group of the compound (51) obtained, the compound (52) can be produced. In this deprotection, reagents and conditions can be selected depending on the protecting group.

The compound (53) can be produced by derivatizing the amino acid or peptide (31) having the N terminal protected with $P^9$ and the carboxy group, hydroxy group, or amino group in side chain protected with $P^{10}$ as described in Production method 4 into active ester, mixed acid anhydride, or the like and reacting it with the compound (52) obtained. The reaction conditions, reagents, base, and solvent used for forming a peptide bond between the amino acid or peptide (31) and the compound (52) can be suitably selected from those described for the synthesis of the compound (6). The protecting group $P^9$ and $P^{10}$ are the same as those described in Production method 5. Further, as it is generally used for peptide synthesis, by repeating sequentially the reaction and deprotection of the constituting amino acid or peptide for elongation, the compound (53) can be also produced.

By deprotection of $P^9$ as the protecting group of the amino group of the compound (53) obtained, the compound (54) can be produced. In this deprotection, reagents and conditions can be selected depending on the protecting group.

It is possible to produce the compound (55) by derivatizing the carboxylic acid derivative (11) into active ester, mixed acid anhydride, acid halide, or the like and reacting it with the compound (54) obtained. The reaction conditions, reagents, base, and solvent used for forming a peptide bond between the carboxylic acid derivative (11) and the compound (54) can be suitably selected from those described for the synthesis of the compound (6).

By deprotecting the protecting group $P^{10}$ for the carboxy group, hydroxy group, or amino group of the compound (55) obtained, the compound (2) can be produced. In this deprotection, reagents and conditions can be selected depending on the protecting group.

The compound (53) can be also produced by the following method, for example.

By deprotecting the protecting group $P^{12}$ for the carboxy group of the compound (49) described in Production method 5, the peptide (56) can be produced. In this deprotection, reagents and conditions can be selected depending on the protecting group.

The compound (53) can be produced by derivatizing the peptide (56) obtained into active ester, mixed acid anhydride, acid halide, or the like and reacting it with the compound (4) or a salt thereof. The reaction conditions, reagents, base, and solvent used for forming a peptide bond between the compound (56) and the compound (4) can be suitably selected from those described for the synthesis of the compound (6).

The compound (55) can be also produced by the following method, for example.

The compound (55) can be produced by derivatizing the compound (48) described in Production method 5 into active ester, mixed acid anhydride, or the like, and reacting it with the compound (4) in the presence of a base, or derivatizing the amino acid or peptide (45) described in Production method 5 into active ester, mixed acid anhydride, or the like, and reacting it with the compound (52) in the presence of a base. The reaction conditions, reagents, base, and solvent used for forming each peptide bond can be suitably selected from those described for the synthesis of the compound (6).

7. Production Method 7

Within the production intermediate represented by the formula (2), those having the linker structure of -$L^1$-$L^2$-$L^P$-

$NH$—$(CH_2)n^1$-$L^a$-$NH$—$(CH_2)n^2$-$C(=O)$—, and said $L^P$ is the peptide residue having a hydrophilic amino acid at the N terminal, and said hydrophilic amino acid located at N terminal is other than glycine can be also produced by the following method.

[Chem. 29]

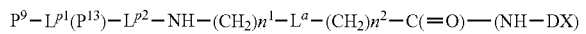
57

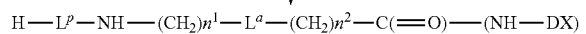
58

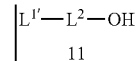

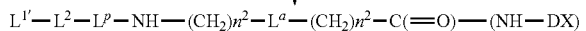
2

$P^9$—$L^{p1}(P^{13})$—$L^{p2}$—$(NH$—$DX)$
59

$H$—$L^p$—$(NH$—$DX)$
60

$L^{1'}$—$L^2$—$L^p$—$(NH$—$DX)$
2

[in the formula, $L^{1'}$ corresponds to $L^1$ having a structure in which the terminal is modified to maleimidyl group, $L^P$ represents a structure consisting of -$L^{p1}$-$L^{p2}$-, and $P^9$ and $P^{13}$ represent a protecting group].

The production intermediate represented by the formula (2) includes the following two modes, that is, a structure in which the linker is represented by -$L^1$-$L^2$-$L^P$-NH—$(CH_2)n^1$-$L^a$-NH—$(CH_2)n^2$-$C(=O)$— and a structure in which the linker is represented by -$L^1$-$L^2$-$L^P$-.

The compound (2) with a structure in which the linker is represented by -$L^1$-$L^2$-$L^P$-NH—$(CH_2)n^1$-$L^a$-NH—$(CH_2)n^2$-$C(=O)$— can be produced as follows.

The compound (57) can be synthesized in the same manner as the compound (32) described in Production method 5. However, unlike the compound (32), it is not necessary that the protecting group $P^9$ for the amino group and the protecting group $P^{13}$ for the functional group in side chain can be removed by a different method or different conditions. The functional group in side chain is a carboxy group or a hydroxy group, and the protecting group $P^9$ for the amino group and the protecting group $P^{13}$ for the carboxy group or hydroxy group in side chain can be simultaneously deprotected. For example, a representative example includes a combination in which $P^9$ is a tert-butyloxy carbonyl group and $P^{13}$ is a tert-butyl group or a trityl group, or $P^3$ is a benzyloxy carbonyl group and $P^{13}$ is a benzyl group. The protecting groups can be suitably selected from the aforementioned ones with regard to the protecting groups for the compound (6) depending on, e.g., the properties of an amino group, a carboxy group, or a hydroxy group of the compound to be protected. For removal of the protecting groups, reagents and conditions are selected depending on the protecting group. By using the protected amino acid or peptide satisfying above properties, the compound (57) can be synthesized in the same manner as Production method 5.

By sequential or simultaneous deprotection of the protecting group $P^9$ and $P^{13}$ of the compound (57), the compound (51) can be produced. Reagents and conditions can be selected depending on the protecting group.

A functional group in hydrophilic side chain of $L^P$ in the compound (58) is not particularly protected, however, by reaction with the compound (11) derivatized into active ester, mixed acid anhydride, or the like in the presence of a base, the compound (2) can be produced. The reaction conditions, reagents, base, and solvent used for forming each peptide bond can be suitably selected from those described for the synthesis of the compound (6).

The compound (2) with a structure in which the linker is represented by -$L^1$-$L^2$-$L^P$- can be produced as follows.

The compound (59) can be also synthesized in the same manner as the compound (53) described in Production method 6. However, unlike the compound (53), it may not be necessary that the protecting group $P^3$ for the amino group and the protecting group $P^8$ for the functional group in side chain can be removed by a different method or different conditions. The functional group in side chain is a carboxy group or a hydroxy group, and the protecting group $P^9$ for the amino group and the protecting group $P^{13}$ for the carboxy group or hydroxy group in side chain can be simultaneously deprotected. For example, a representative example includes a combination in which $P^9$ is a tert-butyloxy carbonyl group and $P^{13}$ is a tert-butyl group or a trityl group, or $P^3$ is a benzyloxy carbonyl group and $P^{13}$ is a benzyl group. The protecting groups can be suitably selected from the aforementioned ones with regard to the protecting groups for the compound (6) depending on, e.g., the properties of an amino group, a carboxy group, or a hydroxy group of the compound to be protected. For removal of the protecting groups, reagents and conditions are selected depending on the protecting group. By using the protected amino acid or peptide satisfying above properties, the compound (59) can be synthesized in the same manner as Production method 6.

By sequential or simultaneous deprotection of the protecting group $P^9$ and $P^{13}$ of the compound (59), the compound (53) can be produced. Reagents and conditions can be selected depending on the protecting group.

A functional group in hydrophilic side chain of $L^P$ in the compound (60) is not particularly protected. However, by reaction with the compound (11) derivatized into active ester, mixed acid anhydride, or the like in the presence of a base, the compound (2) can be produced. The reaction conditions, reagents, base, and solvent used for forming each peptide bond can be suitably selected from those described for the synthesis of the compound (6).

8. Production Method 8

The compound (43) shown in Production method 5 in which the linker -$L^P$- has a structure of -$L^{p1}$-Gly-Gly-Phe-Gly- (SEQ ID NO: 585) can be also produced by the following method.

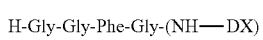
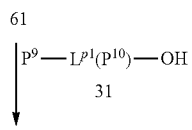
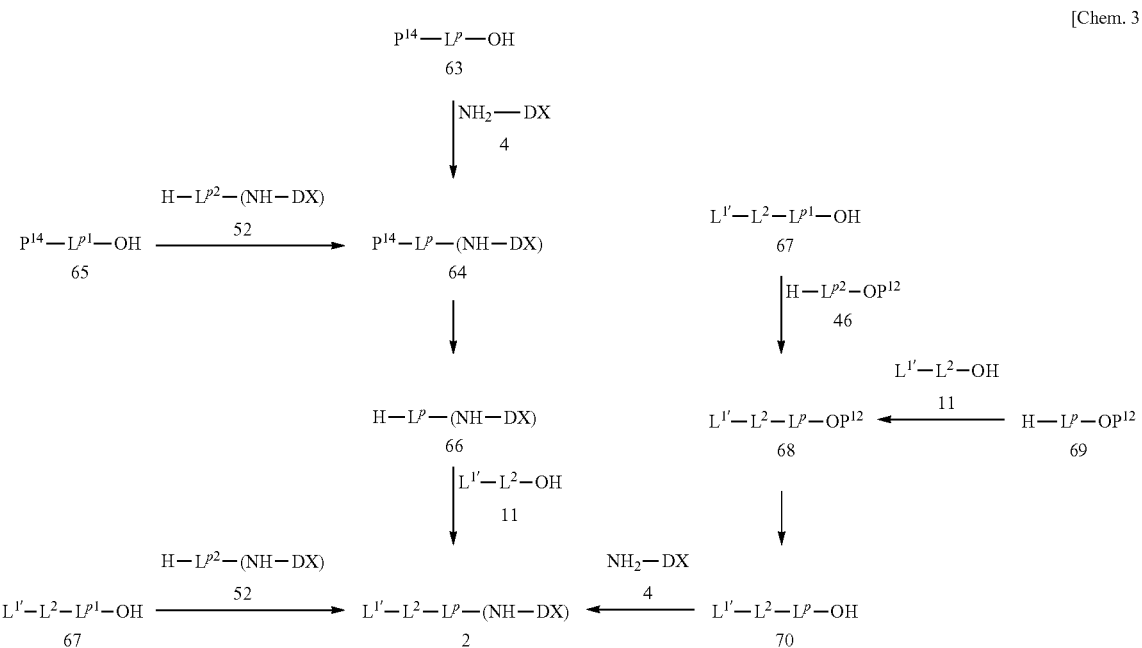

9. Production Method 9

Among the compounds represented by the formula (2), a compound, in which the linker has a structure represented by -$L^1$-$L^2$-$L^P$-, and said $L^P$ is the oligopeptide in which the C terminal is composed of 2 or 3 or more glycines and is connected to a drug, and the N terminal of said peptide residue is glycine in case a hydrophilic amino acid is present at N terminal, can be also produced according to the following method.

-continued

P⁹—L$^{p1}$(P¹⁰)—Gly-Gly-Phe-Gly-(NH—DX)
62

"Gly-Gly-Phe-Gly" disclosed as SEQ ID NO: 585.

[in the formula, P⁹ and P¹⁰ represent a protecting group].

The compound (62) can be produced by derivatizing the amino acid or peptide (31) described in Production method 5 into active ester, mixed acid anhydride, acid halide, or the like and reacting it with glycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide (that is, free form of the pharmaceutical compound disclosed in International Publication No. WO 1997/46260) (61) or a salt thereof in the presence of a base. The reaction conditions, reagents, base, and solvent used for forming a peptide bond between the amino acid or peptide (31) and the compound (61) can be suitably selected from those described for the synthesis of the compound (6). The protecting group P³ for N terminal and the protecting group P¹⁰ for the functional group in side chain are the same as those described in Production method 5. Meanwhile, the protecting group P¹⁰ for the functional group in side chain may not be present, and by performing the reaction using the amino acid or peptide (31) with N terminal protected only, the compound (62) can be obtained.

[in the formula, $L^{1'}$ corresponds to $L^1$ having a structure in which the terminal is converted to maleimidyl group, $L^P$ represents a structure consisting of $L^{p1}$-$L^{p2}$, and P¹² and P¹⁴ represent a protecting group].

Because $L^P$ is formed by connecting $L^{p1}$ to $L^{p2}$, the number of glycines for constituting the C terminal of $L^P$ contained therein can be designed in consideration of the number of glycines at C terminal in $L^P$ and the number of repeated use thereof during the reaction.

The peptide (63) is an oligopeptide in which the C terminal is composed of 2 or 3 or more glycines, and the N terminal is glycine in case the N terminal of said peptide residue is a hydrophilic amino acid, and further, said N terminal is protected with P¹⁴. As commonly employed for peptide synthesis, the peptide (63) can be synthesized by repeating sequentially the condensation reaction of the constituting amino acid or peptide and deprotection.

The compound (64) can be produced by derivatizing the peptide (63) into active ester, mixed acid anhydride, or the like and reacting it with the compound (4) or a salt thereof. The reaction conditions, reagents, base, and solvent used for forming a peptide bond between peptide (63) and the compound (4) can be suitably selected from those described for the synthesis of the compound (6). The protecting group P¹⁴ can be suitably selected and used from those described for synthesis of the compound (6).

The compound (64) can be also produced by derivatizing the amino acid or peptide (65) with the N terminal protected with P[14] into active ester, mixed acid anhydride, or the like and reacting it with the compound (52) described in Production method 6. The reaction conditions, reagents, base, and solvent used for forming a peptide bond between amino acid or peptide (65) and the compound (52) can be suitably selected from those described for the synthesis of the compound (6). The protecting group P[14] can be suitably selected and used from those described for synthesis of the compound (6).

By deprotecting the protecting group P[14] for the amino group of the compound (64) obtained, the compound (66) can be produced. Reagents and conditions can be selected depending on the protecting group.

The compound (2) can be produced by derivatizing the carboxylic acid derivative (11) into active ester, mixed acid anhydride, acid halide, or the like and reacting it with the compound (66) obtained. The reaction conditions, reagents, base, and solvent used for forming an amide bond between the carboxylic acid derivative (11) and the compound (66) can be suitably selected from those described for the synthesis of the compound (6).

The compound (2) can be also produced by the following method.

In the compound (67), of which glycine at N terminal of $L^{P1}$ is connected to $L^2$, and it can be produced in the same manner as the compound (45) described in Production method 5. The compound (68) can be produced by derivatizing the amino acid or peptide (46) described in Production method 5 into active ester, mixed acid anhydride, acid halide, or the like and reacting it with the compound (67). Herein, the amino acid or peptide (46) is an oligopeptide consisting of glycine or having C terminal consisting of 2 or 3 or more glycines, in which the C terminal is protected with P[12]. The reaction conditions, reagents, base, and solvent used for forming an amide bond between amino acid or peptide (46) and the compound (67) can be suitably selected from those described for the synthesis of the compound (6).

The compound (68) can be also produced by derivatizing the compound (11) into active ester, mixed acid anhydride, or the like and reacting it with the peptide (69) having the C terminal protected with P[12]. Herein, the peptide (69) is an oligopeptide in which the C terminal is composed of 2 or 3 or more glycines and the N terminal is glycine in case the N terminal of said peptide residue is a hydrophilic amino acid. As commonly employed for peptide synthesis, the peptide (69) can be produced by repeating sequentially the condensation reaction of the constituting amino acid or peptide and deprotection. The reaction conditions, reagents, base, and solvent used for forming a peptide bond between the peptide (69) and the compound (11) can be suitably selected from those described for the synthesis of the compound (6). The protecting group P[12] is preferably a protecting group which can be deprotected under acidic conditions but it is not limited thereto, and can be suitably selected and used from those described for synthesis of the compound (6).

By deprotecting the protecting group P[12] for the carboxy group of the compound (68) obtained, the compound (70) can be produced. In this deprotection, reagents and conditions can be selected depending on the protecting group.

The compound (2) can be produced by derivatizing the compound (70) into active ester, mixed acid anhydride, or the like and reacting it with the compound (4) or a salt thereof. The reaction conditions, reagents, base, and solvent used for forming a peptide bond between the compound (70) and the compound (4) can be suitably selected from those described for the synthesis of the compound (6).

In addition to above, the compound (2) can be also produced according to the following method.

The compound (2) can be produced by derivatizing the compound (52) described in Production method 6 into active ester, mixed acid anhydride, or the like and reacting it with the compound (67) in the presence of a base. The reaction conditions, reagents, base, and solvent used for forming a peptide bond between the compound (67) and the compound (52) can be suitably selected from those described for the synthesis of the compound (6).

Meanwhile, it is also possible that all of the intermediate compounds of Production method 1 to Production method 9 may be present as in form of salt and/or hydrate.

The antibody-drug conjugate of the present invention may absorb moisture to have adsorption water, for example, or turn into a hydrate when it is left in air or subjected to purification procedures such as recrystallization. Such a compound or a salt containing water are also included in the present invention.

A compound labeled with various radioactive or non-radioactive isotopes is also included in the present invention. One or more atoms constituting the antibody-drug conjugate of the present invention may contain an atomic isotope at non-natural ratio. Examples of the atomic isotope can include deuterium ($^2$H), tritium ($^3$H), iodine-125 ($^{125}$I), and carbon-14 ($^{14}$C). Further, the compound of the present invention may be radioactive-labeled with a radioactive isotope such as tritium ($^3$H), iodine-125 ($^{125}$I), carbon-14 ($^{14}$C), copper-64 ($^{64}$Cu), zirconium-89 ($^{89}$Zr), iodine-124 ($^{124}$I), fluorine-18 ($^{18}$F), indium-111 (111I), carbon-11 ($^{11}$C), or iodine-131 ($^{131}$I). The compound labeled with a radioactive isotope is useful as a therapeutic or prophylactic agent, a reagent for research such as an assay reagent and an agent for diagnosis such as an in vivo diagnostic imaging agent. Without being related to radioactivity, any isotope variant type of the antibody-drug conjugate of the present invention is within the scope of the present invention.

{Pharmaceuticals/Medicines}

The anti-HER3 antibody-drug conjugate of the present invention exhibits a cytotoxic activity against cancer cells, and thus, as a medicine, it can be particularly used as a therapeutic agent and/or prophylactic agent for cancer.

Specifically, the anti-HER3 antibody-drug conjugate of the present invention can be selectively used as a medicine for chemotherapy, which is a major method for treating cancer, and as a result, can delay development of cancer cells, inhibit growth thereof, and further destroy the cancer cells. This can allow cancer patients to be free from symptoms caused by cancer or achieve improvement in QOL of cancer patients and attains a therapeutic effect by sustaining the lives of the cancer patients. Even if the anti-HER3 antibody-drug conjugate of the present invention does not reach to destroying cancer cells, it can achieve higher QOL of cancer patients while achieving long-term survival, by inhibiting or controlling the growth of cancer cells.

The anti-HER3 antibody-drug conjugate of the present invention can be used as a medicine alone in such medicinal therapy. In addition, the anti-HER3 antibody-drug conjugate of the present invention can be used as a medicine in combination with an additional therapy in adjuvant therapy and can be combined with surgical operation, radiotherapy, hormone therapy, or the like. Furthermore, the anti-HER3 antibody-drug conjugate of the present invention can also be used as a medicine for drug therapy in neoadjuvant therapy.

In addition to the therapeutic use as described above, the effect of suppressing the growth of tiny metastatic cancer cells and further destroying them can also be expected.

Particularly, when the expression of HER3 is confirmed in primary cancer cells, inhibition of cancer metastasis or a prophylactic effect can be expected by administering the anti-HER3 antibody-drug conjugate of the present invention. For example, the effect of inhibiting and destroying cancer cells in a body fluid in the course of metastasis or the effect of, for example, inhibiting and destroying tiny cancer cells immediately after implantation in any tissue can be expected. Accordingly, inhibition of cancer metastasis or a prophylactic effect can be expected, particularly, after surgical removal of cancer.

The anti-HER3 antibody-drug conjugate of the present invention can be expected to produce a therapeutic effect by administration as systemic therapy to patients as well as by local administration to cancer tissues.

The antibody-drug conjugate (1) had excellent antitumor activity, safety, and physical properties and exhibited anti-breast cancer, anti-lung cancer, and anti-melanoma effects in vitro.

The antibody-drug conjugate (2) had excellent antitumor activity, safety, and physical properties and exhibited anti-breast cancer, anti-lung cancer, anti-colorectal cancer, and anti-melanoma effects in vitro and stronger anti-breast cancer and anti-melanoma effects in vivo than those of U1-59.

The antibody-drug conjugate (3) had excellent antitumor activity, safety, and physical properties and exhibited anti-breast cancer, anti-lung cancer, anti-ovarian, anti-colorectal cancer, and anti-melanoma effects in vitro and stronger anti-breast cancer, anti-lung cancer, anti-stomach cancer, and anti-melanoma effects in vivo than those of U1-59.

The antibody-drug conjugate (4) had excellent antitumor activity, safety, and physical properties and exhibited an anti-breast cancer effect in vitro.

The antibody-drug conjugate (5) had excellent antitumor activity, safety, and physical properties and exhibited anti-breast cancer, anti-lung cancer, and anti-melanoma effects in vitro.

The antibody-drug conjugate (6) had excellent antitumor activity, safety, and physical properties and exhibited anti-breast cancer, anti-lung cancer, and anti-melanoma effects in vitro and a stronger anti-breast cancer effect in vivo than that of U1-59.

The antibody-drug conjugate (7) had excellent antitumor activity, safety, and physical properties and exhibited anti-breast cancer, anti-lung cancer, and anti-melanoma effects in vitro.

The antibody-drug conjugate (8) had excellent antitumor activity, safety, and physical properties and exhibited anti-breast cancer, anti-lung cancer, and anti-melanoma effects in vitro and a stronger anti-breast cancer effect in vivo than that of U1-59.

The antibody-drug conjugate (9) had excellent antitumor activity, safety, and physical properties and exhibited anti-breast cancer, anti-lung cancer, anti-ovarian cancer, anti-colorectal cancer, and anti-melanoma effects in vitro.

The antibody-drug conjugate (10) had excellent antitumor activity, safety, and physical properties and exhibited anti-breast cancer, anti-lung cancer, anti-colorectal cancer, and anti-melanoma effects in vitro and stronger anti-breast cancer, anti-lung cancer, anti-colorectal cancer, anti-stomach cancer, and anti-melanoma effects in vivo than those of U1-59.

The antibody-drug conjugate (11) had excellent antitumor activity, safety, and physical properties and exhibited an anti-breast cancer effect in vitro.

The antibody-drug conjugate (12) had excellent antitumor activity, safety, and physical properties and exhibited anti-breast cancer, anti-lung cancer, anti-ovarian cancer, anti-colorectal cancer, and anti-melanoma effects in vitro.

The antibody-drug conjugate (13) had excellent antitumor activity, safety, and physical properties and exhibited anti-breast cancer, anti-lung cancer, anti-colorectal cancer, and anti-melanoma effects in vitro and stronger anti-breast cancer (including triple-negative breast cancer), anti-lung cancer, anti-stomach cancer, anti-pancreatic cancer, and anti-melanoma effects in vivo than those of U1-59.

The antibody-drug conjugate (14) had excellent antitumor activity, safety, and physical properties and exhibited an anti-breast cancer effect in vitro.

The antibody-drug conjugate (16a) had excellent antitumor activity, safety, and physical properties and exhibited an anti-breast cancer (including luminal and triple negative), anti-melanoma, anti-ovarian cancer, anti-bladder cancer, anti-lung cancer, anti-head and neck cancer, and anti-gastric cancer effects in vivo when it was administered alone or in combination with trastuzumab, gefinitib, cetuximab, panitumumab or pertuzumab.

Examples of the cancer type to which the anti-HER3 antibody-drug conjugate of the present invention is applied include lung cancer, kidney cancer, urothelial cancer, colorectal cancer, prostate cancer, glioblastoma multiforme, ovarian cancer, pancreatic cancer, breast cancer, metastatic breast cancer, luminal breast cancer, melanoma, liver cancer, bladder cancer, gastric (stomach) cancer, gastrointestinal stromal tumor, cervical cancer, head and neck cancer, esophageal cancer, epidermoid cancer, peritoneal cancer, adult glioblastoma multiforme, hepatic cancer, hepatocellular carcinoma, colon cancer, rectal cancer, colon and rectal cancer, endometrial cancer, uterus cancer, salivary cancer, renal cancer, vulval cancer, thyroid cancer, hepatic carcinoma, anus carcinoma, penis cancer. Chemotherapy is the only current treatment indicated for particularly triple negative breast cancer (that lacks the expression of HER2, estrogen, and progesteron receptors) among breast cancers, which is said to have a poor prognosis. There have been almost no reports of HER3 expression in triple negative breast cancer. However if HER3 expression is observed in patients with triple negative breast cancer, then the anti-HER3 antibody-drug conjugate of the present invention can be used as a therapeutic agent and/or a preventive agent. However, it is not limited to them as long as it is a cancer cell expressing, in a cancer cell as a treatment subject, a protein which the antibody of the antibody-drug conjugate can recognize.

The treatment using the anti-HER3 antibody-drug conjugate of the present invention can target a cancer cell expressing, in a cancer cell as a treatment subject, HER3 protein which the antibody of the antibody-drug conjugate can recognize. In the present specification, the "cancer expressing HER3 protein" is cancer comprising cells having HER3 protein on their surface or cancer secreting HER3 protein into blood. The HER3 protein is overexpressed in various human tumors and can be evaluated using a method usually carried out, such as immunohistochemical staining method (IHC) for evaluating the overexpression of the HER3 protein in tumor (primary, metastatic) specimens, fluorescence in situ hybridization method (FISH) for evaluating the amplification of the HER3 gene, or enzyme-linked immunosorbent assay (ELISA) for evaluating the overexpression of the HER3 protein in blood specimens.

The anti-HER3 antibody-drug conjugate of the present invention exhibits an antitumor effect by recognizing and further internalizing HER3 protein expressed on cancer cell surface. Thus, the treatment subject of the anti-HER3 antibody-drug conjugate of the present invention is not limited to the "cancer expressing HER3 protein" and can also be, for example, leukemia, malignant lymphoma, plasmacytoma, myeloma, or sarcoma.

The anti-HER3 antibody-drug conjugate of the present invention can be preferably administered to a mammal, but it is more preferably administered to a human.

Substances used in a pharmaceutical composition comprising the anti-HER3 antibody-drug conjugate of the present invention can be suitably selected and applied from formulation additives or the like that are generally used in the art, in view of the dosage or administration concentration.

The anti-HER3 antibody-drug conjugate of the present invention can be administered as a pharmaceutical composition comprising at least one pharmaceutically compatible ingredient. For example, the pharmaceutical composition typically comprises at least one pharmaceutical carrier (for example, sterilized liquid). As described herein, examples of the liquid include water and oil (petroleum oil and oil of animal origin, plant origin, or synthetic origin). The oil may be, for example, peanut oil, soybean oil, mineral oil, sesame oil or the like. Water is a more typical carrier when the pharmaceutical composition is intravenously administered. Saline solution, an aqueous dextrose solution, and an aqueous glycerol solution can be also used as a liquid carrier, in particular, for an injection solution. A suitable pharmaceutical vehicle can be appropriately selected from those known in the art. If desired, the composition may also comprise a trace amount of a moisturizing agent, an emulsifying agent, or a pH buffering agent. Examples of suitable pharmaceutical carrier are disclosed in "Remington's Pharmaceutical Sciences" by E. W. Martin. The formulations correspond to an administration mode.

Various delivery systems are known and they can be used for administering the anti-HER3 antibody-drug conjugate of the present invention. Examples of the administration route can include intradermal, intramuscular, intraperitoneal, intravenous, and subcutaneous routes, but not limited thereto. The administration can be made by injection or bolus injection, for example. According to a specific preferred embodiment, the administration of the ligand-drug conjugate is performed by injection. Parenteral administration is a preferred administration route.

According to a representative embodiment, the pharmaceutical composition is prescribed, as a pharmaceutical composition suitable for intravenous administration to human, according to the conventional procedures. The composition for intravenous administration is typically a solution in a sterile and isotonic aqueous buffer solution. If necessary, the drug may contain a solubilizing agent and local anesthetics to alleviate pain at injection area (for example, lignocaine). Generally, the ingredient is provided individually as any one of lyophilized powder or an anhydrous concentrate contained in a container which is obtained by sealing in an ampoule or a sachet having an amount of the active agent or as a mixture in a unit dosage form. When the pharmaceutical is the form to be administered by injection, it may be administered from an injection bottle containing water or saline of sterile pharmaceutical grade. When the pharmaceutical is administered by injection, an ampoule of sterile water or saline for injection may be provided such that the aforementioned ingredients are admixed with each other before administration.

The pharmaceutical composition of the present invention may comprise only the anti-HER3 antibody-drug conjugate of the present application as an active ingredient or may comprise the anti-HER3 antibody-drug conjugate and at least one medicine (e.g., cancer-treating agent) other than the conjugate. The anti-HER3 antibody-drug conjugate of the present invention can be administered with another cancer-treating agent, and the anti-cancer effect may be enhanced accordingly. For example, another medicine such as an anti-cancer agent used for such purpose may be administered before administration of the pharmaceutical composition comprising the anti-HER3 antibody-drug conjugate of the present invention as an active ingredient or after administration of the pharmaceutical composition comprising the anti-HER3 antibody-drug conjugate as an active ingredient, or may be administered simultaneously with, separately (individually) from, or subsequently to the antibody-drug conjugate, and it may be administered while varying the administration interval for each. In the present invention, the case where the anti-HER3 antibody-drug conjugate of the present invention is administered simultaneously with another medicine as a single formulation containing the antibody-drug conjugate and the medicine and the case where the anti-HER3 antibody-drug conjugate of the present invention and another medicine are administered simultaneously or subsequently as separate formulations or administered while varying the administration interval for each are both included in the scope of the "pharmaceutical composition comprising the antibody-drug conjugate and another medicine". Examples of the cancer-treating agent include 5-FU, trastuzumab, trastuzumabb emtansine (T-DM1), cetuximab, gefitinib, panitumumab, pertuzumab, abraxane, erlotinib, carboplatin, cisplatin, gemcitabine, capecitabine, irinotecan (CPT-11), paclitaxel, docetaxel, pemetrexed, sorafenib, vinblastine, vinorelbine, vemurafenib, medicines described in International Publication No. WO 2003/038043, LH-RH analogues (leuprorelin, goserelin, or the like), estramustine phosphate, estrogen antagonist (tamoxifen, raloxifene, or the like), and an aromatase inhibitor (anastrozole, letrozole, exemestane, or the like), but it is not limited as long as it is a medicine having an antitumor activity. These cancer-treating agents can be classified, according to their targets, into: anti-FGER agents such as cetuximab, gefitinib, and panitumumab; anti-HER2 agents such as trastuzumab, T-DM1, and pertuzumab; anti-HER3 agents such as patritumab, MM-121, and MM-111; anti-VEGF agents such as infliximab and adalimumab; etc. Further, they can be classified into: anti-EGFR antibodies such as cetuximab and panitumumab; anti-HER2 antibodies such as trastuzumab and pertuzumab; anti-HER3 antibodies such as patritumab, MM-121, and MM-111; anti-VEGF antibodies such as infliximab and adalimumab; etc. The anti-HER3 antibody-drug conjugate of the present invention exerts an excellent therapeutic effect when administered in combination with an anti-HER2 agent or an anti-HER2 antibody in i) the treatment of stomach cancer, breast cancer, triple-negative breast cancer, or the like or when administered in combination with an anti-EGFR agent or an anti-EGFR antibody in ii) the treatment of lung cancer, head and neck cancer, stomach cancer, breast cancer, triple-negative breast cancer, or the like. One or two or more medicines other than the conjugate can be used, and these medicines may be anti-cancer agents or may be medicines for alleviating side effect caused by companion medicines.

In the present invention, the "pharmaceutical composition comprising the anti-HER3 antibody-drug conjugate and another medicine" has the same meaning as a "pharmaceutical composition in which the anti-HER3 antibody-drug conjugate is to be administered in combination with another medicine". In the present invention, the phrase "administered in combination" used for the anti-HER3 antibody-drug conjugate and another medicine means that the anti-HER3 antibody-drug conjugate and another medicine are incorporated in the body of a recipient within a certain period. A single formulation containing the anti-HER3 antibody-drug conjugate and another medicine may be administered, or the anti-HER3 antibody-drug conjugate and another medicine may be separately formulated and administered as separate formulations. In the case of the separate formulations, the timings of administration thereof are not particularly limited, and the formulations may be administered at the same time or may be administered at different times or different days in a staggered manner. In the case where the anti-HER3 antibody-drug conjugate and another medicine are separately administered at different times or different days, the order of administration thereof is not particularly limited. Since separate formulations are usually administered according to their respective administration methods, the frequency of administration thereof may be the same or may be different. Further, such separate formulations may be administered by the same administration method (administration route) or different administration methods (administration routes). It is not necessary that the anti-HER3 antibody-drug conjugate and another medicine exist in the body at the same time, and it is sufficient that the anti-HER3 antibody-drug conjugate and another medicine are incorporated in the body within a certain period (e.g., 1 month, preferably 1 week, more preferably several days, even more preferably 1 day). Alternatively, when one of the active ingredients is administered, the other active ingredient may have already disappeared from the body.

Examples of the dosage form of the "pharmaceutical composition in which the anti-HER3 antibody-drug conjugate is to be administered in combination with another medicine" can include: 1) the administration of a single formulation comprising the anti-HER3 antibody-drug conjugate and another medicine, 2) the simultaneous administration through the same administration route of two formulations obtained by separately formulating the anti-HER3 antibody-drug conjugate and another medicine, 3) the administration in a staggered manner through the same administration route of two formulations obtained by separately formulating the anti-HER3 antibody-drug conjugate and another medicine, 4) the simultaneous administration through different administration routes of two formulations obtained by separately formulating the anti-HER3 antibody-drug conjugate and another medicine, and 5) the administration in a staggered manner through different administration routes of two formulations obtained by separately formulating the anti-HER3 antibody-drug conjugate and another medicine. The dose, dosing interval, dosage form, formulation, etc., of the "pharmaceutical composition in which the anti-HER3 antibody-drug conjugate is to be administered in combination with another medicine" abide by those of the pharmaceutical composition containing the anti-HER3 antibody-drug conjugate of the present invention, but are not limited thereto.

Such a pharmaceutical composition formulated in two different formulations may be in the form of a kit containing them.

In the present invention, the "combination" of the anti-HER3 antibody-drug conjugate and another medicine means that the anti-HER3 antibody-drug conjugate and the medicine are "administered in combination".

The pharmaceutical composition can be formulated into a lyophilization formulation or a liquid formulation as a formulation having desired composition and required purity. When formulated as a lyophilization formulation, it may be a formulation containing suitable formulation additives that are used in the art. Also for a liquid formulation, it can be formulated as a liquid formulation containing various formulation additives that are used in the art.

Constituents and concentration of the pharmaceutical composition may vary depending on administration method. However, the anti-HER3 antibody-drug conjugate comprised in the pharmaceutical composition of the present invention can exhibit the pharmaceutical effect even at a small dosage when the antibody-drug conjugate has higher affinity for an antigen, that is, higher affinity (=lower Kd value) in terms of the dissociation constant (that is, Kd value) for the antigen. Thus, for determining dosage of the antibody-drug conjugate, the dosage can be determined in view of a situation relating to the affinity between the antibody-drug conjugate and antigen. When the antibody-drug conjugate of the present invention is administered to a human, for example, about 0.001 to 100 mg/kg can be administered once or administered several times with an interval of one time for 1 to 180 days.

EXAMPLES

The present invention is specifically described in view of the examples shown below. However, the present invention is not limited to them. Further, it is by no means interpreted in a limited sense. Further, unless specifically described otherwise, the reagent, solvent, and starting material described in the specification can be easily obtained from a commercial supplier.

Reference Example 1 Production of U1-59

U1-59 was produced on the basis of the method described in International Publication No. WO 2007/077028.

Example 1 Antibody-Drug Conjugate (1)

[Chem. 32]

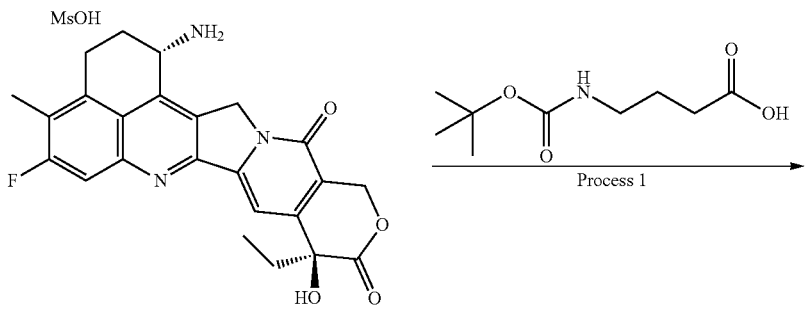

-continued
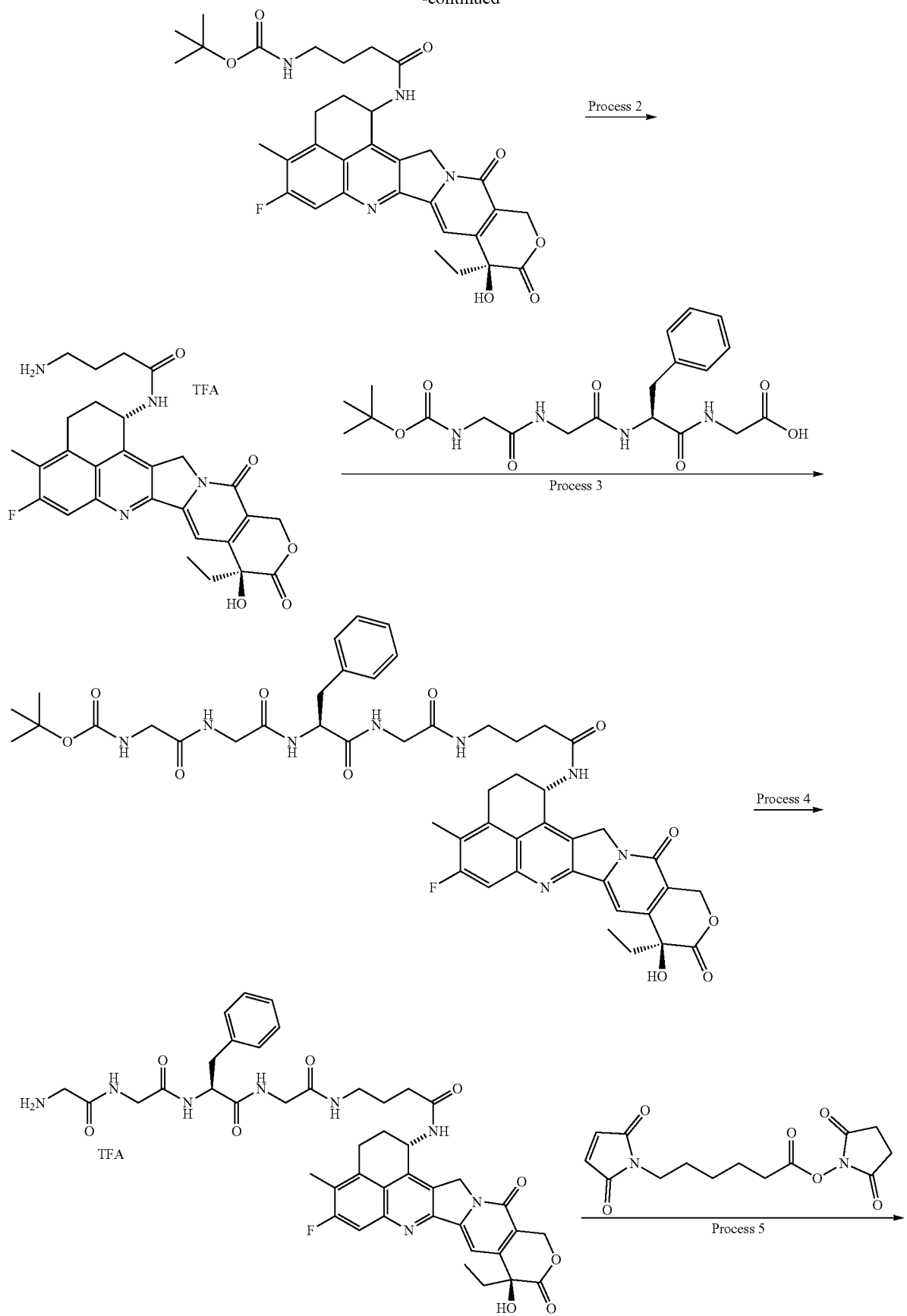

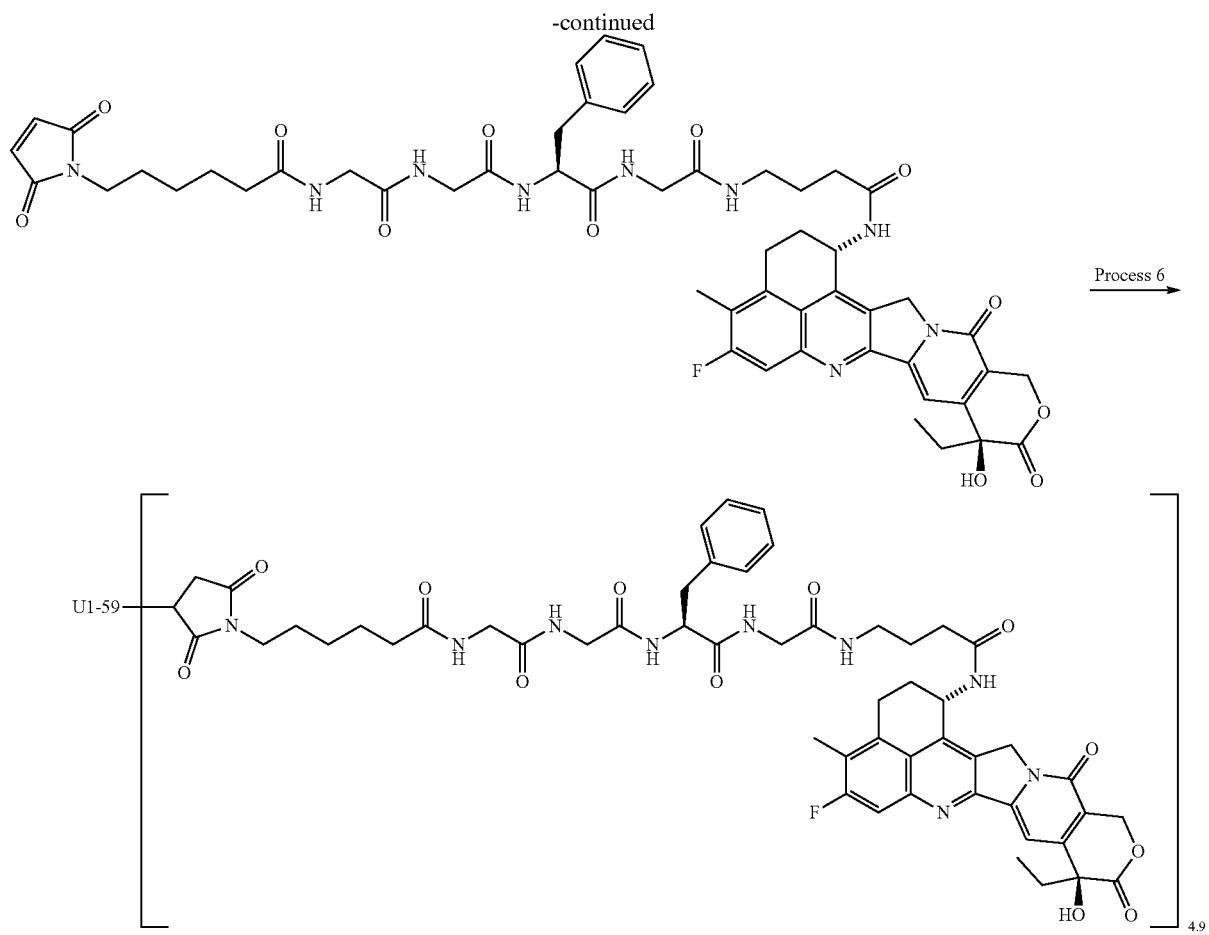

Process 1: tert-Butyl (4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)carbamate 4-(tert-Butoxycarbonylamino)butanoic acid (0.237 g, 1.13 mmol) was dissolved in dichloromethane (10 mL), charged with N-hydroxysuccinimide (0.130 g, 1.13 mmol) and 1-ethyl-3-(3-dimethylaminopropyl)carbodiimide hydrochloride (0.216 g, 1.13 mmol), and stirred for 1 hour. The reaction solution was added dropwise to an N,N-dimethylformamide solution (10 mL) charged with exatecan mesylate (0.500 g, 0.94 mmol) and triethylamine (0.157 mL, 1.13 mmol), and stirred at room temperature for 1 day. The solvent was removed under reduced pressure and the obtained residues were purified by silica gel column chromatography [chloroform-chloroform:methanol=8:2 (v/v)] to yield the titled compound (0.595 g, quantitative).

$^1$H-NMR (400 MHz, DMSO-$d_6$) delta: 0.87 (3H, t, J=7.2 Hz), 1.31 (9H, s), 1.58 (1H, t, J=7.2 Hz), 1.66 (2H, t, J=7.2 Hz), 1.89-1.82 (2H, m), 2.12-2.21 (3H, m), 2.39 (3H, s), 2.92 (2H, t, J=6.5 Hz), 3.17 (2H, s), 5.16 (1H, d, J=19.2 Hz), 5.24 (1H, d, J=18.8 Hz), 5.42 (2H, s), 5.59-5.55 (1H, m), 6.53 (1H, s), 6.78 (1H, t, J=6.3 Hz), 7.30 (1H, s), 7.79 (1H, d, J=11.0 Hz), 8.40 (1H, d, J=8.6 Hz).

MS (APCI) m/z: 621 (M+H)$^+$.

Process 2: 4-Amino-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]butanamide trifluoroacetate The compound (0.388 g, 0.61 mmol) obtained in above Process 1 was dissolved in dichloromethane (9 mL). After adding trifluoroacetic acid (9 mL), it was stirred for 4 hours. The solvent was removed under reduced pressure and the obtained residues were purified by silica gel column chromatography [chloroform-partitioned organic layer of chloroform:methanol:water=7:3:1 (v/v/v)] to yield the titled compound (0.343 g, quantitative).

$^1$H-NMR (400 MHz, DMSO-$d_6$) 0.87 (3H, t, J=7.2 Hz), 1.79-1.92 (4H, m), 2.10-2.17 (2H, m), 2.27 (2H, t, J=7.0 Hz), 2.40 (3H, s), 2.80-2.86 (2H, m), 3.15-3.20 (2H, m), 5.15 (1H, d, J=18.8 Hz), 5.26 (1H, d, J=18.8 Hz), 5.42 (2H, s), 5.54-5.61 (1H, m), 6.55 (1H, s), 7.32 (1H, s), 7.72 (3H, brs), 7.82 (1H, d, J=11.0 Hz), 8.54 (1H, d, J=8.6 Hz).

MS (APCI) m/z: 521 (M+H)$^+$.

Process 3: N-(tert-butoxycarbonyl)glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H, 12H-benzo[de]pyrano[3',4':6,7]indolizino[1,2-b]quinolin-1-yl]amino}-4-oxobutyl)glycinamide N-(tert-butoxycarbonyl)glycylglycyl-L-phenylalanylglycine (0.081 g, 0.19 mmol) was dissolved in dichloromethane (3 mL), charged with N-hydroxysuccinimide (0.021 g, 0.19 mmol) and 1-ethyl-3-(3-dimethylaminopropyl)carbodiimide hydrochloride (0.036 g, 0.19 mmol), and stirred for 3.5 hours. The reaction solution was added dropwise to an N,N-dimethylformamide solution (1.5 mL) charged with the compound (0.080 g, 0.15 mmol) which has been obtained in above Process 2 and stirred at room temperature for 4 hours. The solvent was removed under reduced pressure and the obtained residues were purified by silica gel column chromatography [chloroform-chloroform:methanol=8:2 (v/v)] to yield the titled compound (0.106 g, 73%).

$^1$H-NMR (400 MHz, DMSO-$d_6$) delta: 0.87 (3H, t, J=7.4 Hz), 1.36 (9H, s), 1.71 (2H, m), 1.86 (2H, t, J=7.8 Hz), 2.15-2.19 (4H, m), 2.40 (3H, s), 2.77 (1H, dd, J=12.7, 8.8 Hz), 3.02 (1H, dd, J=14.1, 4.7 Hz), 3.08-3.11 (2H, m), 3.16-3.19 (2H, m), 3.54 (2H, d, J=5.9 Hz), 3.57-3.77 (4H, m), 4.46-4.48 (1H, m), 5.16 (1H, d, J=19.2 Hz), 5.25 (1H, d, J=18.8 Hz), 5.42 (2H, s), 5.55-5.60 (1H, m), 6.53 (1H, s), 7.00 (1H, t, J=6.3 Hz), 7.17-7.26 (5H, m), 7.31 (1H, s), 7.71 (1H, t, J=5.7 Hz), 7.80 (1H, d, J=11.0 Hz), 7.92 (1H, t, J=5.7 Hz), 8.15 (1H, d, J=8.2 Hz), 8.27 (1H, t, J=5.5 Hz), 8.46 (1H, d, J=8.2 Hz).

MS (APCI) m/z: 939 (M+H)$^+$.

Process 4: Glycylglycyl-L-phenylalanyl-N-(4-{[(1S, 9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide trifluoroacetate The compound (1.97 g, 2.10 mmol) obtained in above Process 3 was dissolved in dichloromethane (7 mL). After adding trifluoroacetic acid (7 mL), it was stirred for 1 hour. The solvent was removed under reduced pressure, and it was charged with toluene for azeotropic distillation. The obtained residues were purified by silica gel column chromatography [chloroform-partitioned organic layer of chloroform:methanol:water=7:3:1 (v/v/v)] to yield the titled compound (1.97 g, 99%).

$^1$H-NMR (400 MHz, DMSO-$d_6$) delta: 0.87 (3H, t, J=7.4 Hz), 1.71-1.73 (2H, m), 1.82-1.90 (2H, m), 2.12-2.20 (4H, m), 2.40 (3H, s), 2.75 (1H, dd, J=13.7, 9.4 Hz), 3.03-3.09 (3H, m), 3.18-3.19 (2H, m), 3.58-3.60 (2H, m), 3.64 (1H, d, J=5.9 Hz), 3.69 (1H, d, J=5.9 Hz), 3.72 (1H, d, J=5.5 Hz), 3.87 (1H, dd, J=16.8, 5.9 Hz), 4.50-4.56 (1H, m), 5.16 (1H, d, J=19.2 Hz), 5.25 (1H, d, J=18.8 Hz), 5.42 (2H, s), 5.55-5.60 (1H, m), 7.17-7.27 (5H, m), 7.32 (1H, s), 7.78-7.81 (2H, m), 7.95-7.97 (3H, m), 8.33-8.35 (2H, m), 8.48-8.51 (2H, m).

MS (APCI) m/z: 839 (M+H)$^+$.

Process 5: N-[6-(2,5-dioxo-2,5-dihydro-1H-pyrrol-1-yl)hexanoyl]glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide To an N,N-dimethylformamide (1.2 mL) solution of the compound (337 mg, 0.353 mmol) obtained in above Process 4, triethylamine (44.3 mL, 0.318 mmol) and N-succinimidyl 6-maleimidehexanoate (119.7 mg, 0.388 mmol) were added and stirred at room temperature for 1 hour. The solvent was removed under reduced pressure and the obtained residues were purified by silica gel column chromatography [chloroform-chloroform:methanol=5:1 (v/v)] to yield the titled compound as a pale yellow solid (278.0 mg, 76%).

$^1$H-NMR (400 MHz, DMSO-$d_6$) delta: 0.87 (3H, t, J=7.3 Hz), 1.12-1.22 (2H, m), 1.40-1.51 (4H, m), 1.66-1.76 (2H, m), 1.80-1.91 (2H, m), 2.05-2.21 (6H, m), 2.39 (3H, s), 2.79 (1H, dd, J=14.0, 9.8 Hz), 2.98-3.21 (5H, m), 3.55-3.77 (8H, m), 4.41-4.48 (1H, m), 5.15 (1H, d, J=18.9 Hz), 5.24 (1H, d, J=18.9 Hz), 5.40 (1H, d, J=17.1 Hz), 5.44 (1H, d, J=17.1 Hz), 5.54-5.60 (1H, m), 6.53 (1H, s), 6.99 (2H, s), 7.20-7.27 (5H, m), 7.30 (1H, s), 7.70 (1H, t, J=5.5 Hz), 7.80 (1H, d, J=11.0 Hz), 8.03 (1H, t, J=5.8 Hz), 8.08 (1H, t, J=5.5 Hz), 8.14 (1H, d, J=7.9 Hz), 8.25 (1H, t, J=6.1 Hz), 8.46 (1H, d, J=8.5 Hz).

MS (APCI) m/z: 1032 (M+H)$^+$.

Process 6: Antibody-Drug Conjugate (1)

Reducing the antibody: U1-59 produced in Reference Example 1 was prepared to have antibody concentration of 10 mg/mL by replacing the medium with PBS6.0/EDTA by using the Common procedure B and Common procedure C described in Production method 1. The solution (1.00 mL) was added to a 2.0 mL polypropylene tube and charged with an aqueous solution of 10 mM TCEP (Tokyo Chemical Industry Co., Ltd.) (0.0307 mL; 4.6 equivalents per antibody molecule) and a 1 M aqueous solution of dipotassium hydrogen phosphate (Nacalai Tesque, Inc.; 0.050 mL). After confirming that the solution has pH of 7.4+/−0.1, the disulfide bond at hinge part in the antibody was reduced by incubating at 37 C for 1 hour.

Conjugation between antibody and drug linker: After incubating the solution in a water bath at 22 C for 10 minutes, dimethyl sulfoxide (Sigma-Aldrich Co. LLC; 0.0586 mL) and a dimethyl sulfoxide solution (0.0615 mL; 9.2 equivalents per antibody molecule) containing 10 mM of the compound obtained in above Process 5 were added thereto and incubated in a water bath at 22 C for 40 minutes for conjugating the drug linker to the antibody. Next, an aqueous solution (0.0123 mL) of 100 mM NAC (Sigma-Aldrich Co. LLC) was added thereto and stirred by using a tube rotator (MTR-103, manufactured by AS ONE Corporation) at room temperature for 20 minutes to terminate reaction of the drug linker.

Purification: The above solution was subjected to purification using the Common procedure D (ABS is used as buffer solution) described in Production method 1 to yield 6 mL of a solution containing the titled antibody-drug conjugate.

Physicochemical characterization: By using the Common procedure E described in Production method 1 (as molar absorption coefficient of the drug linker, $E_{D,280}$=7280 and $E_{D,370}$=23400 were used), the following characteristic values were obtained.

Antibody concentration: 1.29 mg/mL, antibody yield: 7.74 mg (77%), and average number of conjugated drug molecules (n) per antibody molecule measured by Common procedure E: 4.9.

Example 2 Antibody-Drug Conjugate (2)

[Chem. 33]

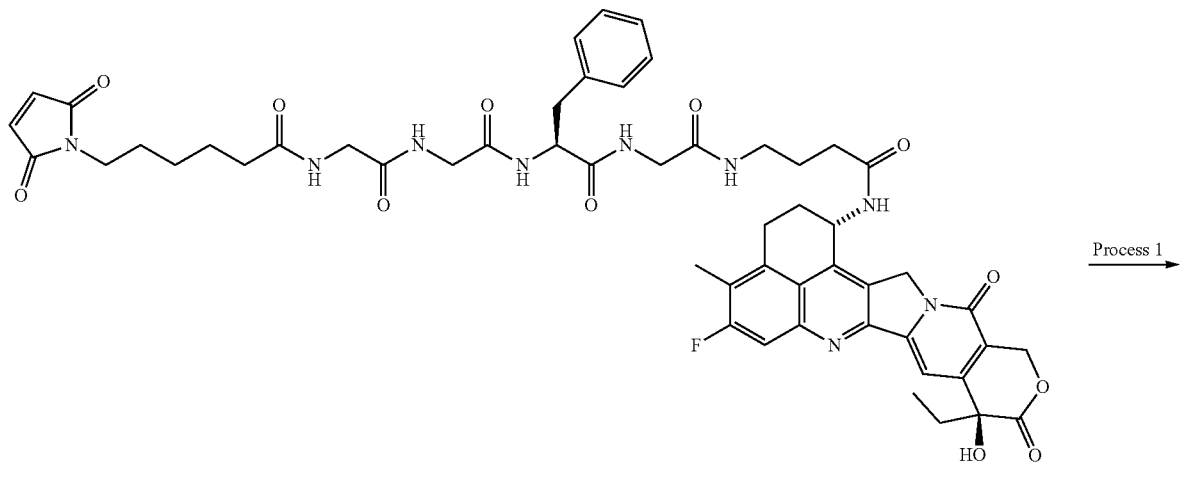

Process 1 →

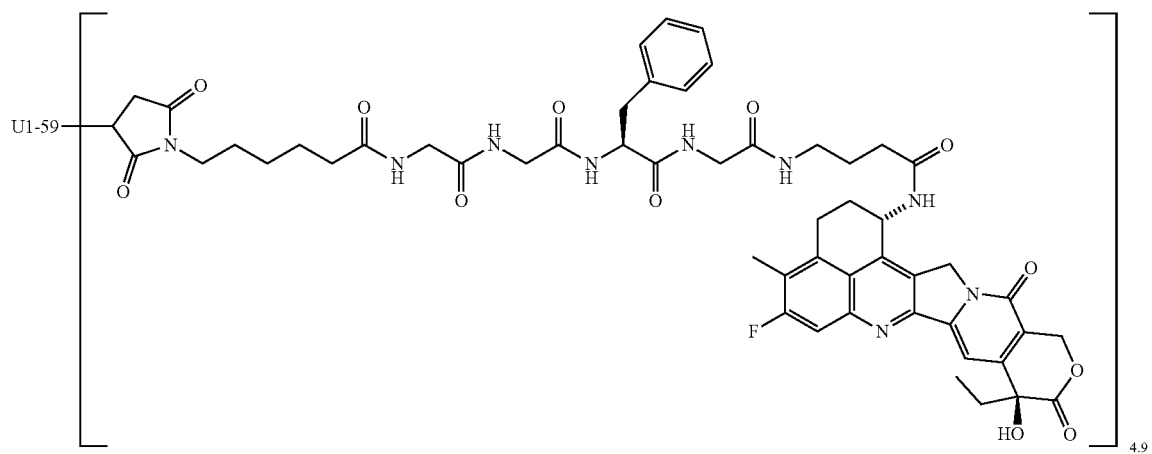

Process 1: Antibody-Drug Conjugate (2)

By using U1-59 produced in Reference Example 1 and the compound obtained in above Process 5 of Example 1, the titled antibody-drug conjugate was obtained in the same manner as Process 6 of Example 1.

Antibody concentration: 12.0 mg/mL, antibody yield: 226.8 mg (91%), and average number of conjugated drug molecules (n) per antibody molecule measured by Common procedure E: 4.9.

Example 3 Antibody-Drug Conjugate (3)

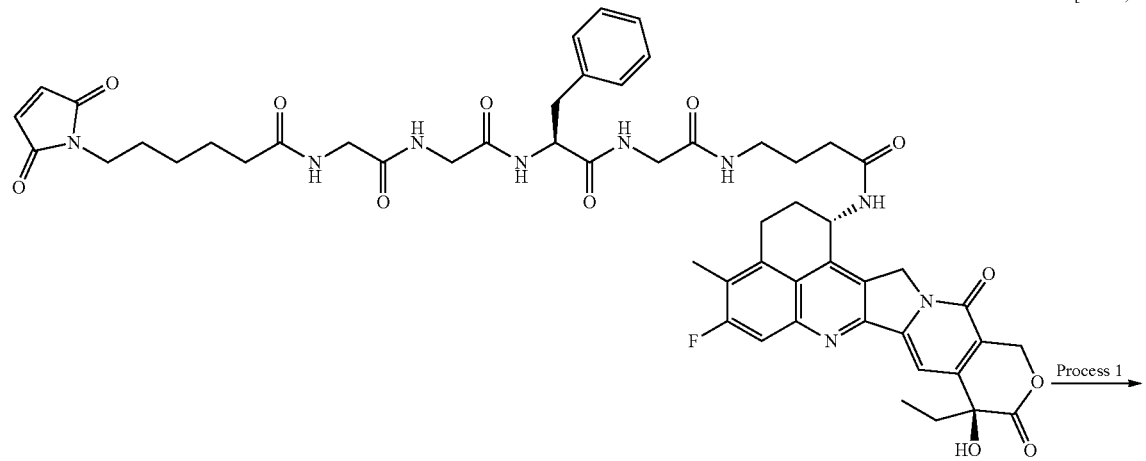

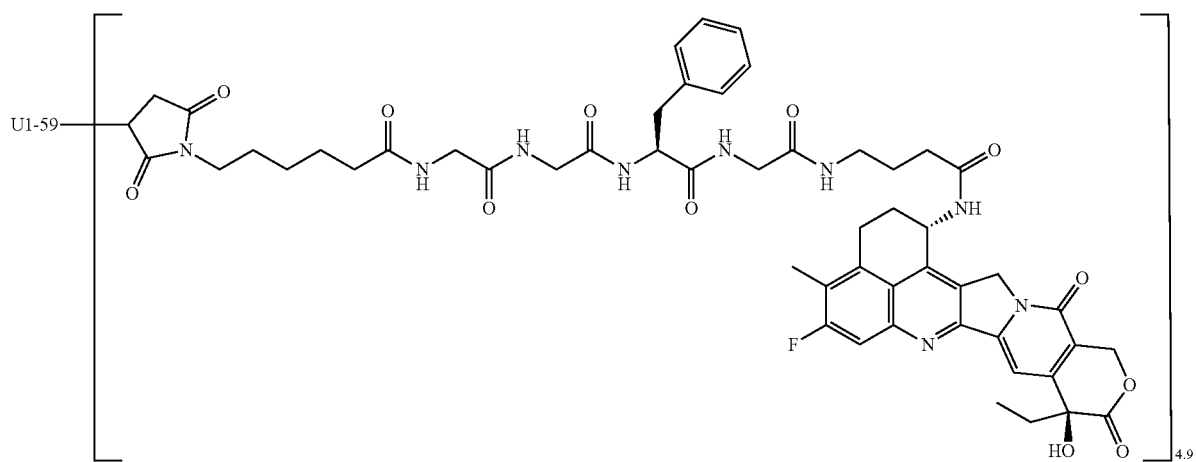

Process 1: Antibody-Drug Conjugate (3)

By using U1-59 produced in Reference Example 1 and the compound obtained in Process 5 of Example 1, the titled antibody-drug conjugate was obtained in the same manner as Process 6 of Example 1.

Antibody concentration: 16.9 mg/mL, antibody yield: 219.7 mg (88%), and average number of conjugated drug molecules (n) per antibody molecule measured by Common procedure E: 4.9.

Example 4 Antibody-Drug Conjugate (4)

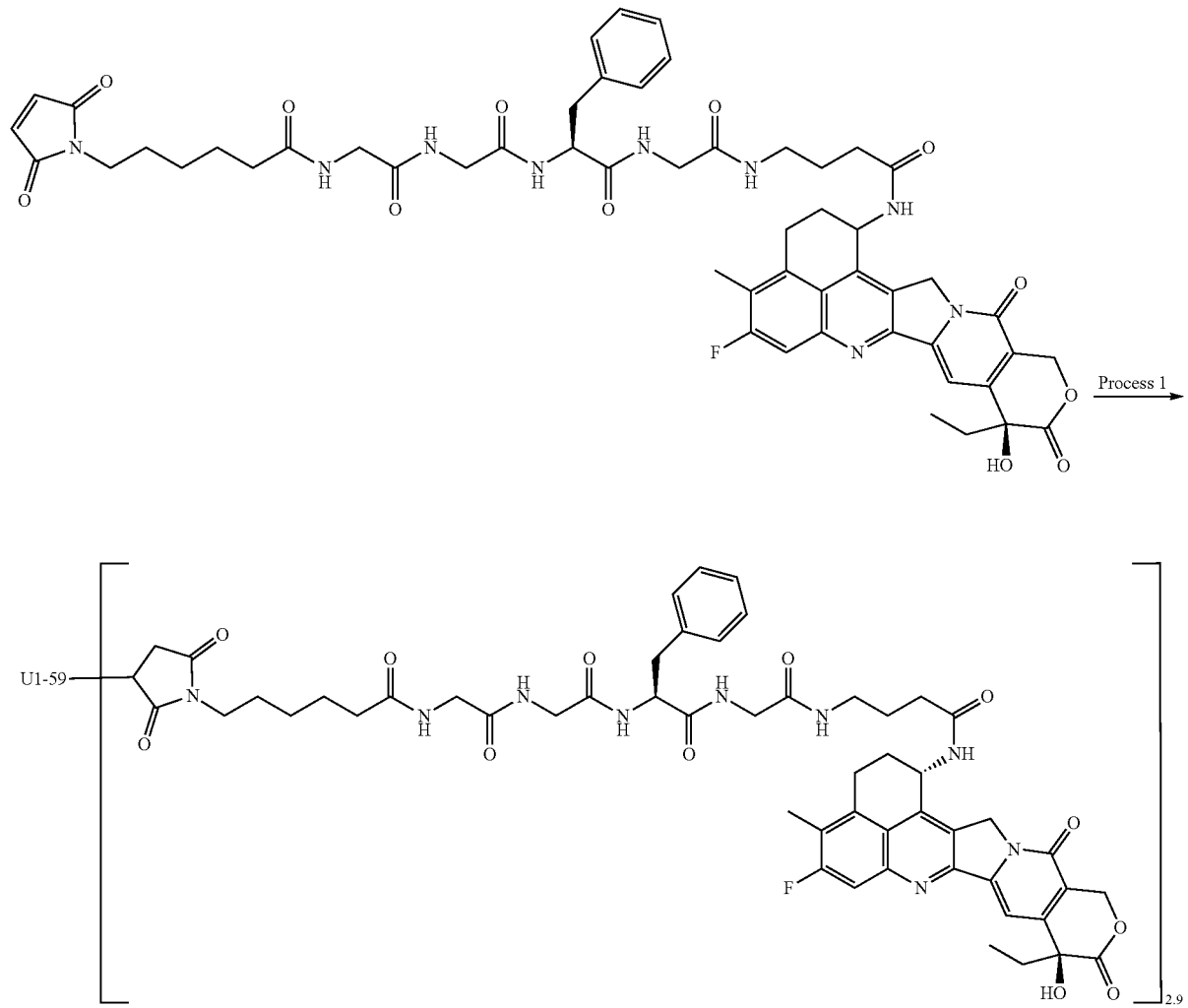

Process 1: Antibody-Drug Conjugate (4)

Reducing the antibody: U1-59 produced in Reference Example 1 was prepared to have antibody concentration of 10 mg/mL by replacing the medium with PBS6.0/EDTA by using the Common procedure B and Common procedure C described in Production method 1. The solution (1.00 mL) was added to a 1.5 mL polypropylene tube and charged with an aqueous solution of 10 mM TCEP (Tokyo Chemical Industry Co., Ltd.) (0.0187 mL; 2.8 equivalents per antibody molecule) and a 1 M aqueous solution of dipotassium hydrogen phosphate (Nacalai Tesque, Inc.; 0.0170 mL). After confirming that the solution has pH of 7.0+/−0.1, the disulfide bond at hinge part in the antibody was reduced by incubating at 37 C for 1 hour.

Conjugation between antibody and drug linker: After adding a dimethyl sulfoxide solution (0.0314 mL; 4.7 equivalents per antibody molecule) containing 10 mM of the compound obtained in above Process 5 to the solution at room temperature, it was incubated at 15 C for 1 hour for conjugating the drug linker to the antibody. Next, an aqueous solution (0.0123 mL; 18.4 equivalents per antibody molecule) of 100 mM NAC (Sigma-Aldrich Co. LLC) was added thereto and incubated at room temperature for another 20 minutes to terminate reaction of the drug linker.

Purification: The above solution was subjected to purification using the Common procedure D (ABS is used as buffer solution) described in Production method 1 to yield 6 mL of a solution containing the titled antibody-drug conjugate. After that, the solution was concentrated by the Common procedure A.

Physicochemical characterization: By using the Common procedure E described in Production method 1 (as molar absorption coefficient of the drug linker, $E_{D,280}$=5000, and $E_{D,370}$=19000 were used), the following characteristic values were obtained.

Antibody concentration: 1.02 mg/mL, antibody yield: 6.1 mg (61%), and average number of conjugated drug molecules (n) per antibody molecule measured by Common procedure E: 2.9; and average number of conjugated drug molecules (n) per antibody molecule measured by Common procedure F (as molar absorption coefficient of the drug linker, $E_{D,280}$=5000 were used): 3.2.

Example 5 Antibody-Drug Conjugate (5)
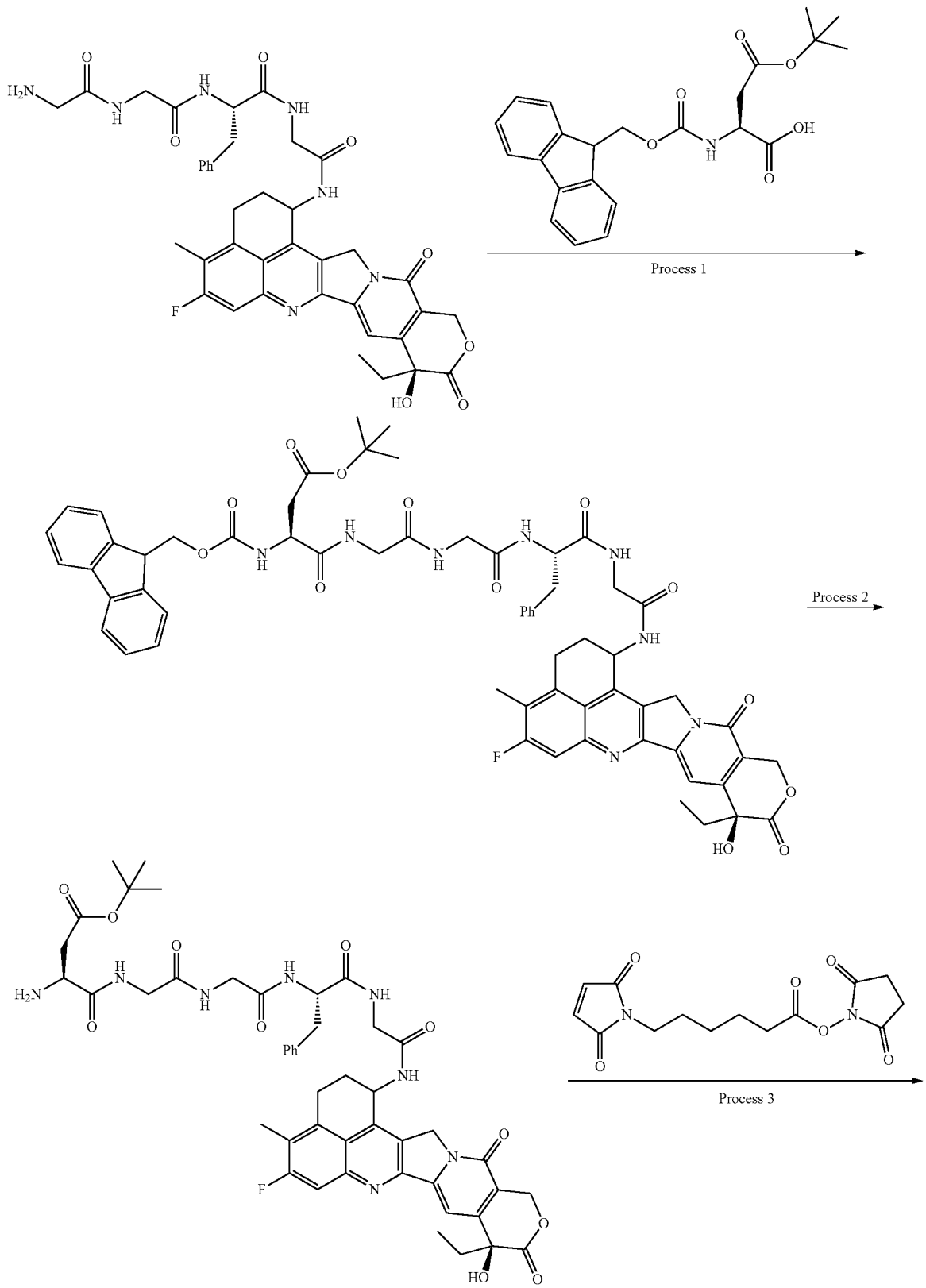

-continued
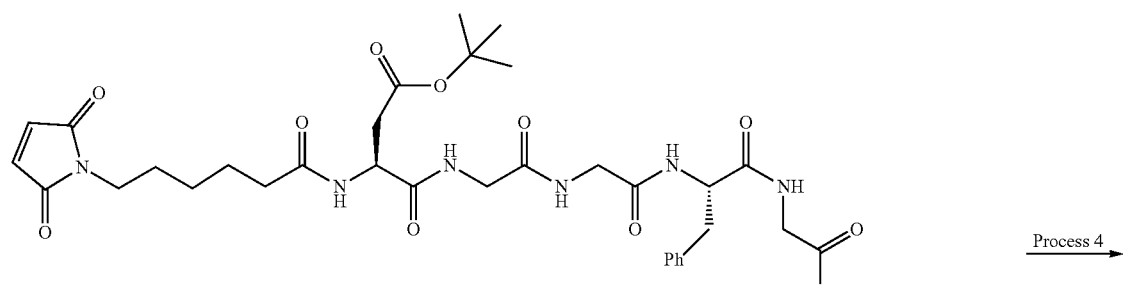
Process 4
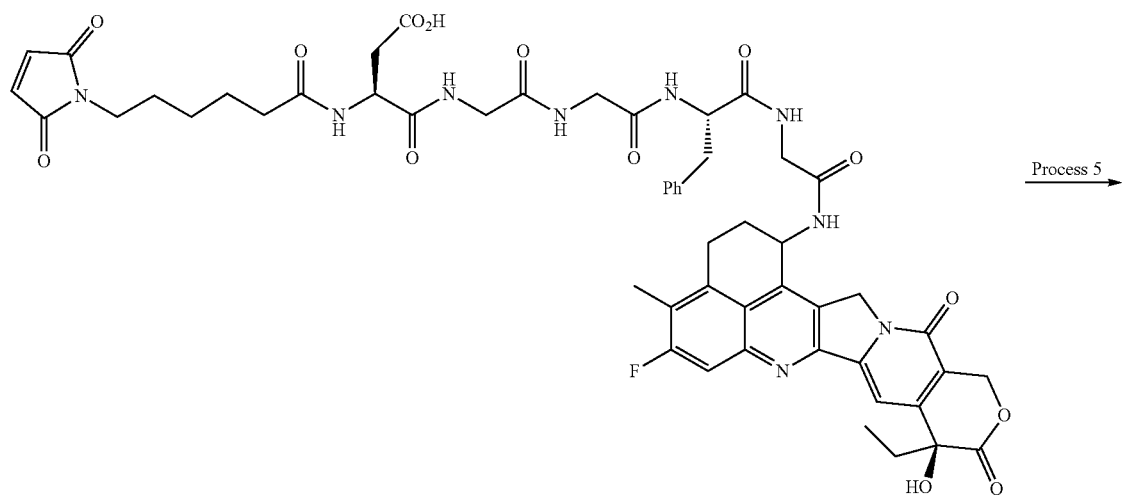
Process 5
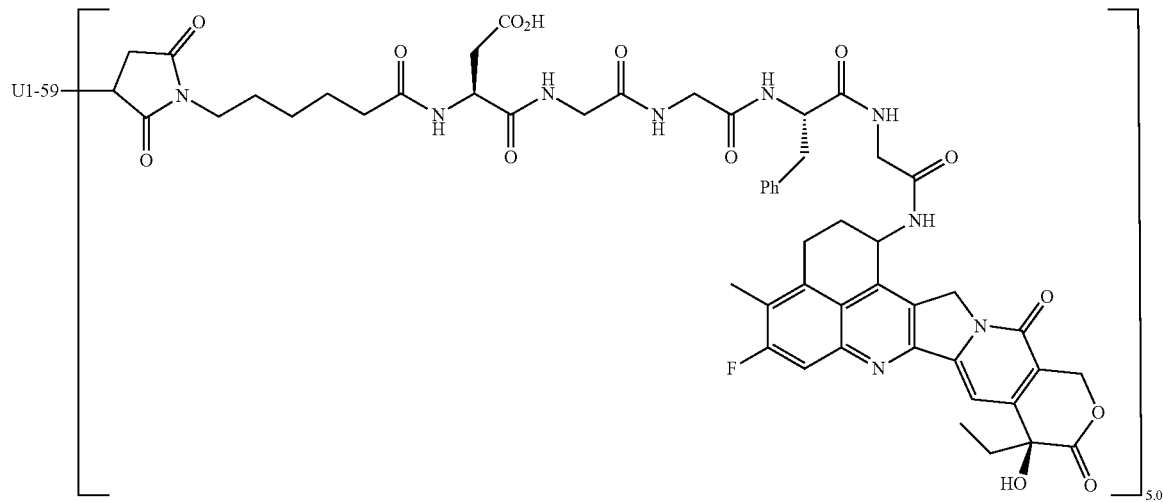

Process 1: tert-Butyl (5S,14S)-5-benzyl 1-{[(1S, 9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-14-{[(9H-fluoren-9-ylmethoxy)carbonyl]amino}-1,4,7,10,13-pentaoxo-3,6,9,12-tetraazahexadecan-16-oate Under ice cooling, to an N,N-dimethylformamide (10.0 mL) solution of glycylglycyl-L-phenylalanyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide (free form of the pharmaceutical compound described in International Publication No. WO 1997/46260; 0.250 g, 0.332 mmol), N-hydroxysuccinimide (57.2 mg, 0.497 mmol), and 4-tert-butyl N-[(9H-fluoren-9-ylmethoxy)carbonyl]-L-aspartic acid (0.205 g, 0.497 mmol), N,N'-dicyclohexylcarbodiimide (0.123 g, 0.497 mmol) was added and stirred at room temperature for 2 days. The solvent was removed under reduced pressure and the obtained residues were purified by silica gel column chromatography [chloroform-chloroform:methanol=9:1 (v/v)] to yield the titled compound as a pale yellow solid (0.278 g, 73%).

$^1$H-NMR (400 MHz, DMSO-$d_6$) delta: 0.86 (3H, t, J=7.1 Hz), 1.35 (9H, s), 1.79-1.90 (2H, m), 2.03-2.25 (2H, m), 2.40 (3H, s), 2.40-2.51 (2H, m), 2.64-2.82 (2H, m), 2.98 (1H, dd, J=13.7, 4.6 Hz), 3.16 (2H, brs), 3.55 (1H, dd, J=16.7, 5.7 Hz), 3.63-3.80 (4H, m), 4.16-4.34 (3H, m), 4.36-4.50 (2H, m), 5.23 (2H, s), 5.37 (1H, d, J=16.5 Hz), 5.43 (1H, d, J=16.5 Hz), 5.51-5.62 (1H, m), 6.52 (1H, s), 7.10-7.25 (5H, m), 7.26-7.33 (3H, m), 7.39 (2H, t, J=7.3 Hz), 7.65-7.72 (3H, m), 7.80 (1H, d, J=11.0 Hz), 7.86 (2H, d, J=7.3 Hz), 7.98 (1H, t, J=5.5 Hz), 8.07 (1H, d, J=7.8 Hz), 8.15 (1H, t, J=5.5 Hz), 8.31 (1H, t, J=5.5 Hz), 8.41 (1H, d, J=8.7 Hz).

MS (ESI) m/z: 1147 (M+H)$^+$.

Process 2: tert-Butyl (5S,14S)-14-amino-5-benzyl-1-{[(1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl]amino}-1,4,7,10,13-pentaoxo-3,6,9,12-tetraazahexadecan-16-oate To an N,N-dimethylformamide (2.00 mL) solution of the compound (0.279 g, 0.242 mmol) obtained in above Process 1, piperidine (0.240 mL, 2.42 mmol) was added and stirred at room temperature for 1 hour. The solvent was removed under reduced pressure and the obtained residues were purified by silica gel column chromatography [chloroform-chloroform:methanol=2:1 (v/v)] to yield the titled compound as a pale yellow solid (0.265 g, quantitative).

$^1$H-NMR (400 MHz, DMSO-$d_6$) delta: 0.88 (3H, t, J=7.2 Hz), 1.39 (9H, s), 1.81-1.94 (1H, m), 2.07-2.28 (2H, m), 2.37 (1H, dd, J=15.8, 8.0 Hz), 2.43 (3H, s), 2.60 (1H, dd, J=15.8, 4.9 Hz), 2.75-2.82 (1H, m), 3.00 (1H, dd, J=13.9, 4.5 Hz), 3.16-3.25 (2H, m), 3.50-3.61 (2H, m), 3.65-3.81 (5H, m), 4.40-4.51 (1H, m), 5.27 (2H, dd, J=24.1, 19.0 Hz), 5.43 (2H, dd, J=21.3, 16.2 Hz), 5.56-5.65 (1H, m), 6.55 (1H, s), 7.15-7.28 (5H, m), 7.33 (1H, s), 7.83 (1H, d, J=11.0 Hz), 8.04 (1H, t, J=5.7 Hz), 8.09 (1H, d, J=8.2 Hz), 8.26-8.39 (2H, m), 8.44 (1H, d, J=8.2 Hz).

Process 3: tert-Butyl (5S,14S)-5-benzyl-14-{[6-(2,5-dioxo-2,5-dihydro-1H-pyrrol-1-yl)hexanoyl]amino}-1-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-1,4,7,10,13-pentaoxo-3,6,9,12-tetraazahexadecan-16-oate To an N,N-dimethylformamide (2.00 mL) solution of the compound (0.100 g, 0.108 mmol) obtained in above Process 2, N-succinimidyl 6-maleimide hexanoate (40.0 mg, 0.130 mmol) was added and stirred at room temperature for 2 days. The solvent was removed under reduced pressure and the obtained residues were purified by silica gel column chromatography [chloroform-chloroform:methanol=9:1 (v/v)] to yield the titled compound as a pale yellow solid (80.0 mg, 66%).

$^1$H-NMR (400 MHz, DMSO-$d_6$) delta: 0.88 (3H, t, J=7.2 Hz), 1.13-1.23 (2H, m), 1.37 (9H, s), 1.42-1.54 (4H, m), 1.80-1.96 (2H, m), 2.08-2.25 (4H, m), 2.35-3.76 (15H, m), 2.43 (3H, s), 4.39-4.49 (1H, m), 4.55-4.67 (1H, m), 5.21-5.34 (2H, m), 5.43 (2H, dd, J=21.1, 16.4 Hz), 5.56-5.64 (1H, m), 6.55 (1H, s), 7.01 (2H, d, J=0.8 Hz), 7.16-7.26 (5H, m), 7.33 (1H, s), 7.83 (1H, d, J=11.3 Hz), 8.04-8.18 (3H, m), 8.30-8.37 (1H, m), 8.43 (1H, d, J=8.6 Hz).

MS (ESI) m/z: 1118 (M+H)$^+$.

Process 4: N-[6-(2,5-dioxo-2,5-dihydro-1H-pyrrol-1-yl)hexanoyl]-L-alpha-aspartylglycylglycyl-L-phenylalanyl-N-[(1S,9S)-9-ethyl-5-fluoro-9-hydroxy-4-methyl-10,13-dioxo-2,3,9,10,13,15-hexahydro-1H, 12H-benzo[de]pyrano[3',4':6,7]indolizino[1,2-b]quinolin-1-yl]glycinamide Under ice cooling, trifluoroacetic acid (4.00 mL) was added to the compound (70.0 mg, 62.6 u moL) obtained in above Process 3 and stirred at room temperature for 1 hour. The solvent was removed under reduced pressure to yield the titled compound as a pale yellow solid (55.0 mg, 83%).

$^1$H-NMR (400 MHz, DMSO-$d_6$) delta: 0.88 (3H, t, J=7.4 Hz), 1.14-1.24 (2H, m), 1.41-1.53 (4H, m), 1.79-1.95 (2H, m), 2.08-2.28 (4H, m), 2.37-2.60 (2H, m), 2.42 (3H, s), 2.63-2.82 (2H, m), 2.99 (1H, dd, J=14.1, 5.1 Hz), 3.12-3.25 (2H, m), 3.29-3.44 (1H, m), 3.52-3.80 (6H, m), 4.38-4.48 (1H, m), 4.56 (1H, dd, J=13.7, 7.4 Hz), 5.27 (2H, dd, J=24.3, 18.8 Hz), 5.43 (2H, dd, J=21.5, 16.4 Hz), 5.57-5.62 (1H, m), 6.55 (1H, s), 7.01 (2H, s), 7.15-7.26 (5H, m), 7.33 (1H, s), 7.82 (1H, d, J=11.0 Hz), 7.98 (1H, brs), 8.08 (1H, d, J=6.7 Hz), 8.15 (1H, d, J=7.8 Hz), 8.34 (1H, brs), 8.44 (1H, d, J=8.6 Hz), 12.26 (1H, brs).

MS (ESI) m/z: 1062 (M+H)$^+$.

Process 5: Antibody-Drug Conjugate (5)

By using U1-59 produced in Reference Example 1 and the compound obtained in above Process 4, the titled antibody-drug conjugate was obtained in the same manner as Process 6 of Example 1.

Antibody concentration: 1.36 mg/mL, antibody yield: 8.16 mg (82%), and average number of conjugated drug molecules (n) per antibody molecule measured by Common procedure E (as molar absorption coefficient of the drug linker, $E_{D,280}$=7620, $E_{D,370}$=23700 were used): 5.0.

Example 6 Antibody-Drug Conjugate (6)

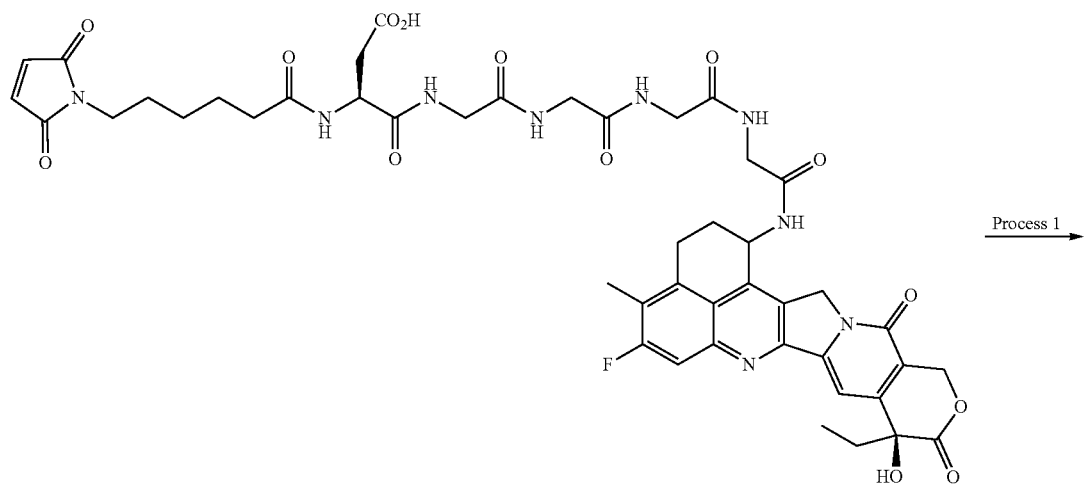

Process 1

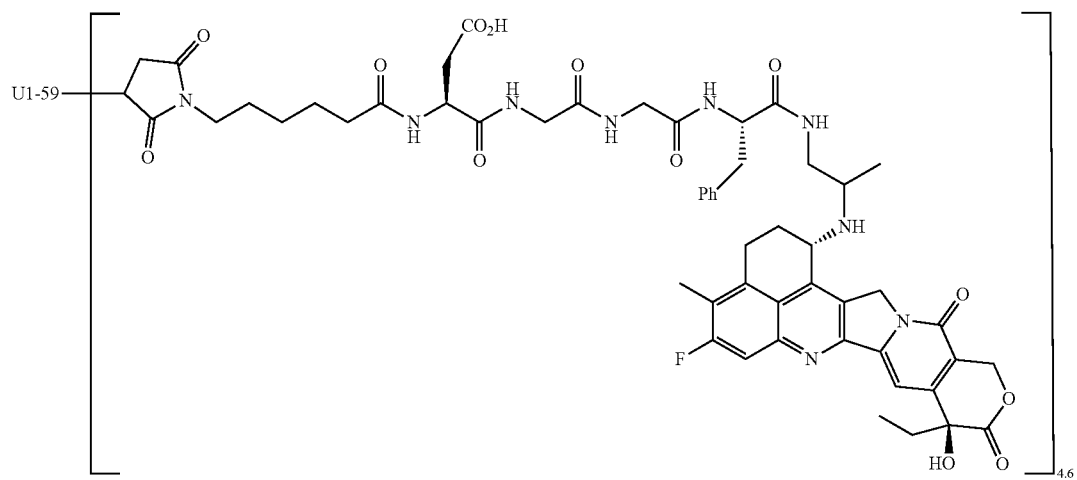

Process 1: Antibody-Drug Conjugate (6)

By using U1-59 produced in Reference Example 1 and the compound obtained in above Process 4 of Example 5, the titled antibody-drug conjugate was obtained in the same manner as Process 6 of Example 1.

Antibody concentration: 11.5 mg/mL, antibody yield: 224.2 mg (90%), and average number of conjugated drug molecules (n) per antibody molecule measured by Common procedure E (as molar absorption coefficient of the drug linker, $E_{D,280}$=7620, $E_{D,370}$=23700 were used): 4.6.

Example 7 Antibody-Drug Conjugate (7)
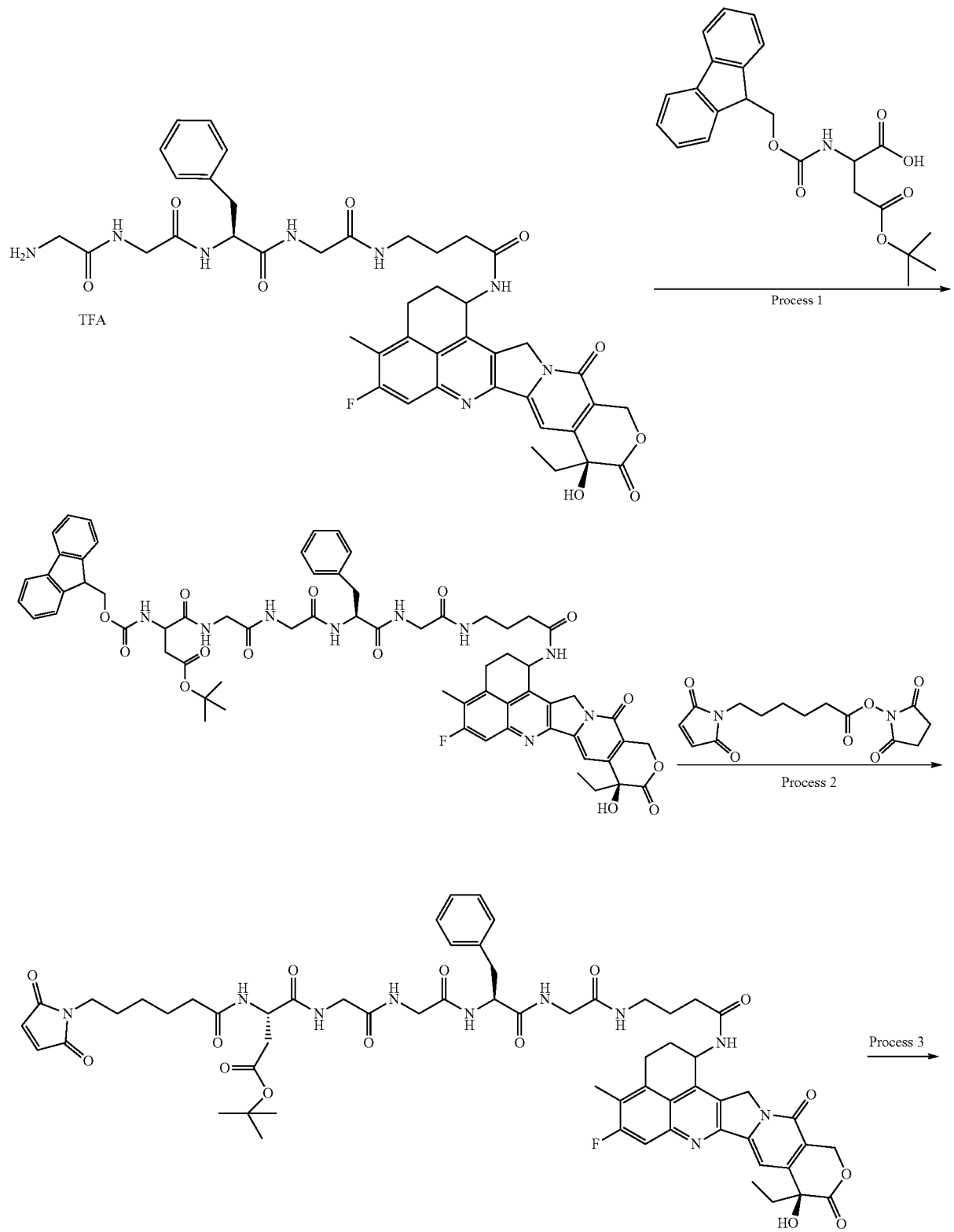

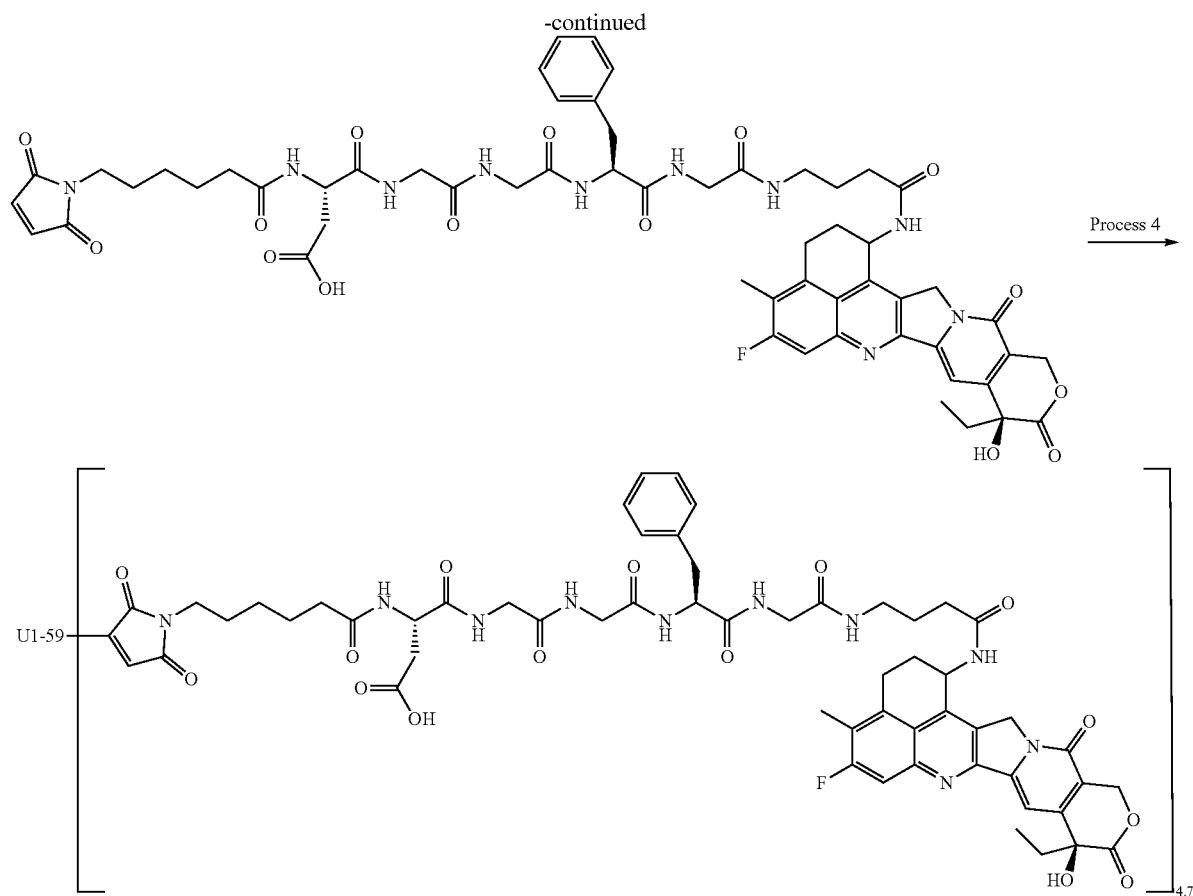

Process 1 tert-Butyl (3S,12S)-12-benzyl-21-{[(1S, 9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl]amino}-3-{[(9H-fluoren-9-ylmethoxy)carbonyl]amino}-4,7,10,13,16,21-hexaoxo-5,8,11,14,17-pentaazahenicosan-1-oate (2S)-4-tert-Butoxy-2-{[(9H-fluoren-9-ylmethoxy)carbonyl]amino}-4-oxobutanoic acid (0.625 g, 1.52 mmol) was dissolved in dichloromethane (10.0 mL), charged with N-hydroxysuccinimide (0.175 g, 1.52 mol) and 1-(3-dimethylaminopropyl)-3-ethylcarbodiimide hydrochloride (0.291 g, 1.52 mmol), and stirred for 1 hour. The reaction solution was added dropwise to an N,N-dimethylformamide solution (10.0 mL) charged with the compound (1.00 g, 1.01 mmol) obtained in above Process 4 of Example 1 and stirred at room temperature for 20 hours. The solvent was removed under reduced pressure and the obtained residues were purified by silica gel column chromatography [chloroform-chloroform:methanol=8:2 (v/v)] to yield the titled compound as a pale yellow solid (0.873 g, 70%).

$^1$H-NMR (400 MHz, DMSO-$d_6$) delta: 0.88 (3H, t, J=7.4 Hz), 1.37 (9H, s), 1.68-1.78 (2H, m), 1.81-1.93 (2H, m), 2.10-2.23 (4H, m), 2.41 (3H, s), 2.68-2.85 (3H, m), 2.99-3.22 (5H, m), 3.58-3.81 (6H, m), 4.19-4.36 (3H, m), 4.38-4.52 (2H, m), 5.17 (1H, d, J=19.2 Hz), 5.25 (1H, d, J=19.2 Hz), 5.43 (2H, s), 5.54-5.62 (1H, m), 6.55 (1H, s), 7.15-7.34 (8H, m), 7.41 (2H, t, J=7.2 Hz), 7.66-7.75 (4H, m), 7.81 (1H, d, J=11.0 Hz), 7.88 (2H, d, J=7.4 Hz), 8.01-8.06 (1H, m), 8.14 (1H, d, J=8.2 Hz), 8.17-8.22 (1H, m), 8.25-8.30 (1H, m), 8.47 (1H, d, J=8.6 Hz).

MS (APCI) m/z: 1232 (M+H)$^+$.

Process 2: tert-Butyl (3S,12S)-12-benzyl-3-{[6-(2,5-dioxo-2,5-dihydro-1H-pyrrol-1-yl)hexanoyl]amino}-21-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4,7,10,13,16,21-hexaoxo-5,8,11,14,17-pentaazahenicosan-1-oate The compound (0.800 g, 0.649 mmol) obtained in above Process 1 was dissolved in N,N-dimethylformamide (3.00 mL), charged with piperidine (0.643 mL, 6.49 mmol), and stirred for 1 hour. The solvent was removed to dryness under reduced pressure and the obtained residues were dissolved in N,N-dimethylformamide (10 mL). After adding N-succinimidyl 6-maleimide hexanoate (0.300 g, 0.974 mmol), it was stirred for 20 hours. The solvent was removed under reduced pressure and the obtained residues were purified by silica gel column chromatography [chloroform-chloroform:methanol=8:2 (v/v)] to yield the titled compound as a pale yellow solid (0.224 g, 29%).

$^1$H-NMR (400 MHz, DMSO-$d_6$) delta: 0.87 (3H, t, J=7.6 Hz), 1.15-1.22 (2H, m), 1.35 (9H, s), 1.44-1.47 (4H, m), 1.71-1.73 (2H, m), 1.80-1.91 (2H, m), 2.08 (2H, t, J=7.6 Hz), 2.13-2.20 (4H, m), 2.40 (3H, s), 2.67 (1H, dt, J=11.1, 4.8 Hz), 2.78 (1H, dd, J=13.6, 9.4 Hz), 2.99-3.17 (6H, m), 3.31-3.36 (2H, m), 3.57-3.76 (6H, m), 4.45-4.47 (1H, m), 4.57-4.60 (1H, m), 5.16 (1H, d, J=18.7 Hz), 5.25 (1H, d, J=18.7 Hz), 5.42 (2H, s), 5.55-5.60 (1H, m), 6.53 (1H, s), 6.99 (2H, s), 7.15-7.27 (5H, m), 7.31 (1H, s), 7.70 (1H, t, J=5.4 Hz), 7.80 (1H, d, J=10.9 Hz), 7.99 (1H, t, J=5.7 Hz), 8.09-8.12 (3H, m), 8.25 (1H, t, J=6.0 Hz), 8.45 (1H, d, J=9.1 Hz).

MS (APCI) m/z: 1203 (M+H)$^+$.

Process 3: N-[6-(2,5-dioxo-2,5-dihydro-1H-pyrrol-1-yl)hexanoyl]-L-alpha-aspartylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (0.224 g, 0.186 mmol) obtained in above Process 2 was reacted in the same manner as Process 2 of Example 1 to yield the titled compound as a pale yellow solid (21.2 mg, 10%).

$^1$H-NMR (400 MHz, DMSO-d$_6$) delta: 0.87 (3H, t, J=7.2 Hz), 1.13-1.21 (2H, m), 1.42-1.45 (6H, m), 1.70-1.72 (2H, m), 1.85-1.88 (2H, m), 2.06-2.20 (6H, m), 2.39 (3H, s), 2.63-2.67 (1H, m), 2.78-2.81 (1H, m), 3.04-3.12 (6H, m), 3.63-3.70 (6H, m), 4.46-4.52 (2H, m), 5.16 (1H, d, J=19.2 Hz), 5.25 (1H, d, J=18.8 Hz), 5.42 (2H, s), 5.55-5.58 (1H, m), 6.53 (1H, s), 6.99 (2H, s), 7.18-7.23 (6H, m), 7.30 (1H, s), 7.71 (1H, t, J=5.5 Hz), 7.79 (1H, d, J=10.9 Hz), 7.99-8.02 (1H, m), 8.10-8.11 (3H, m), 8.27-8.30 (1H, m), 8.47-8.50 (1H, m).

MS (APCI) m/z: 1147 (M+H)$^+$.

Process 4: Antibody-Drug Conjugate (7)

By using U1-59 produced in Reference Example 1 and the compound obtained in above Process 3, the titled antibody-drug conjugate was obtained in the same manner as Process 6 of Example 1.

Antibody concentration: 1.39 mg/mL, antibody yield: 8.34 mg (83%), and average number of conjugated drug molecules (n) per antibody molecule measured by Common procedure E (as molar absorption coefficient of the drug linker, $E_{D,280}$=7670, $E_{D,370}$=24800 were used): 4.7.

Example 8 Antibody-Drug Conjugate (8)

[Chem. 39]

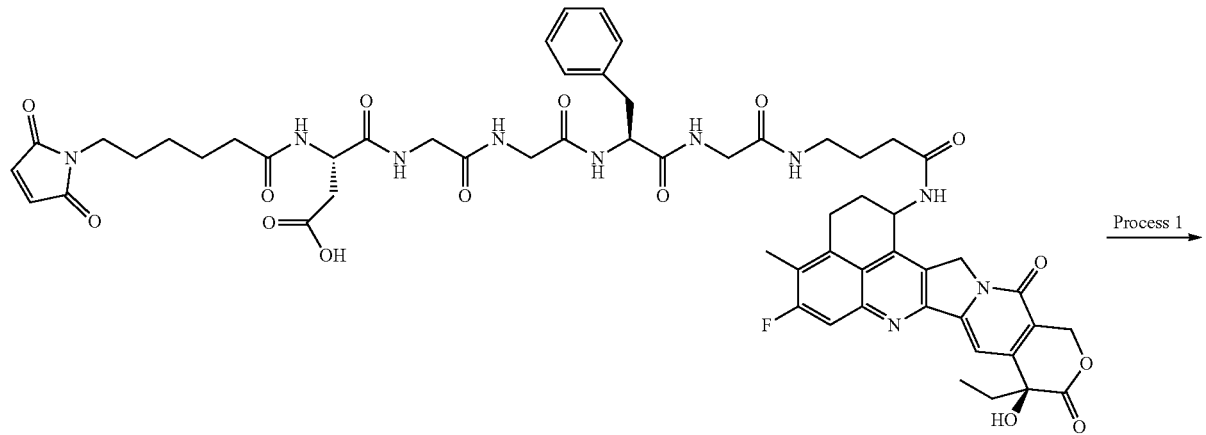

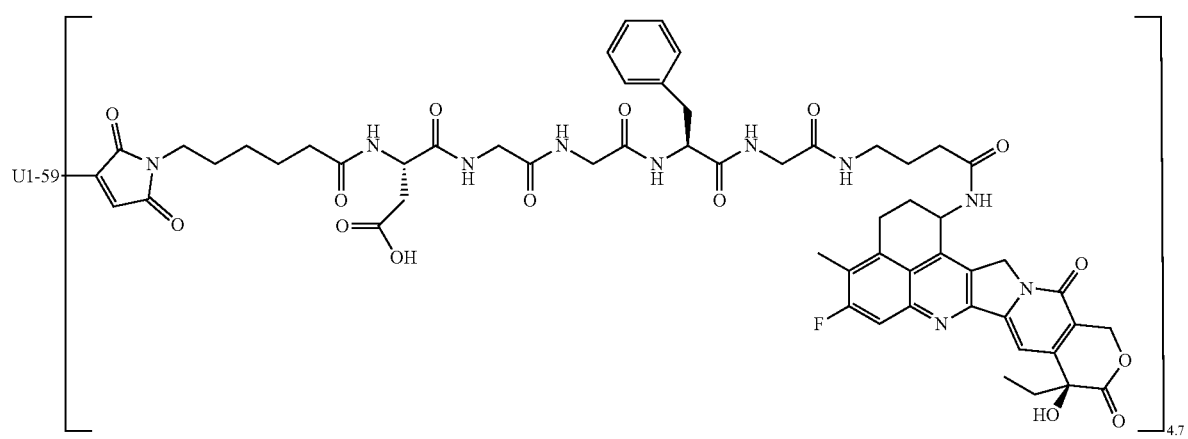

Process 1: Antibody-Drug Conjugate (8)

By using U1-59 produced in Reference Example 1 and the compound obtained in above Process 3 of Example 7, the titled antibody-drug conjugate was obtained in the same manner as Process 6 of Example 1.

Antibody concentration: 11.2 mg/m, antibody yield: 228.5 mg (91%), and average number of conjugated drug molecules (n) per antibody molecule measured by Common procedure E (as molar absorption coefficient of the drug linker, $E_{D,280}=7670$, $E_{D,370}=24800$ were used): 4.7.

Example 9 Antibody-Drug Conjugate (9)

[Chem. 40]

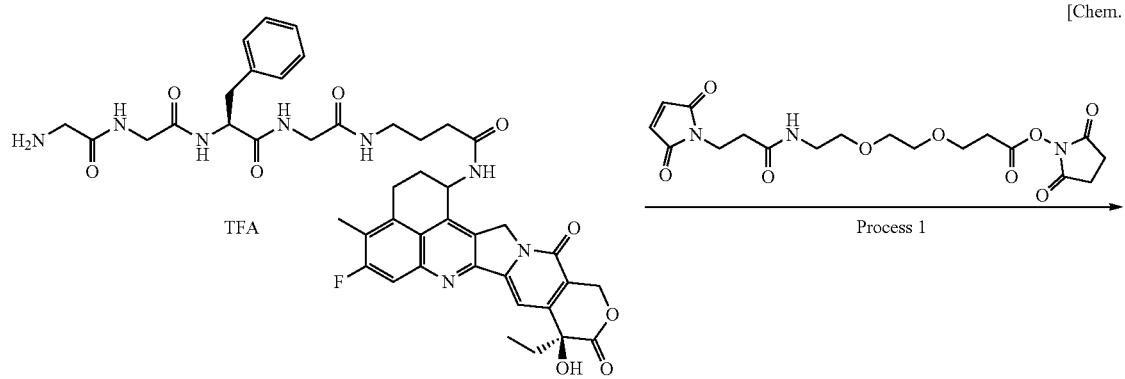

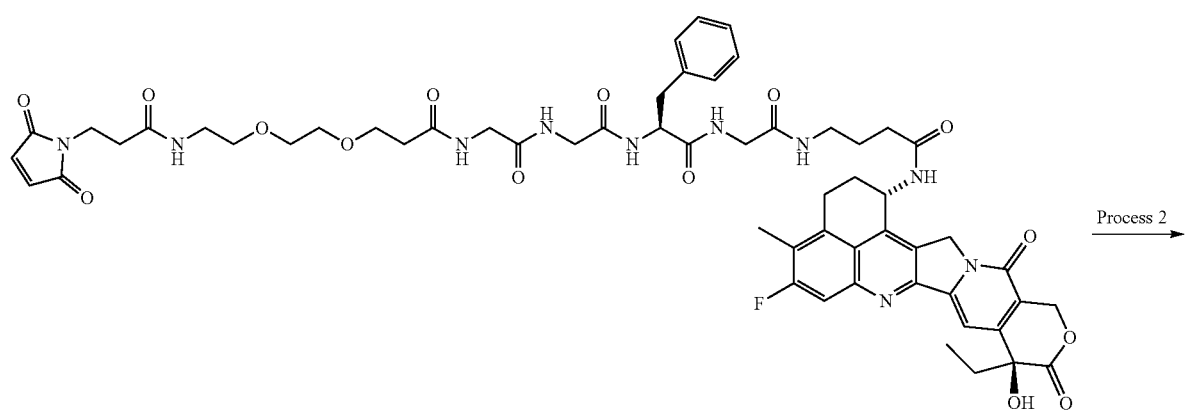

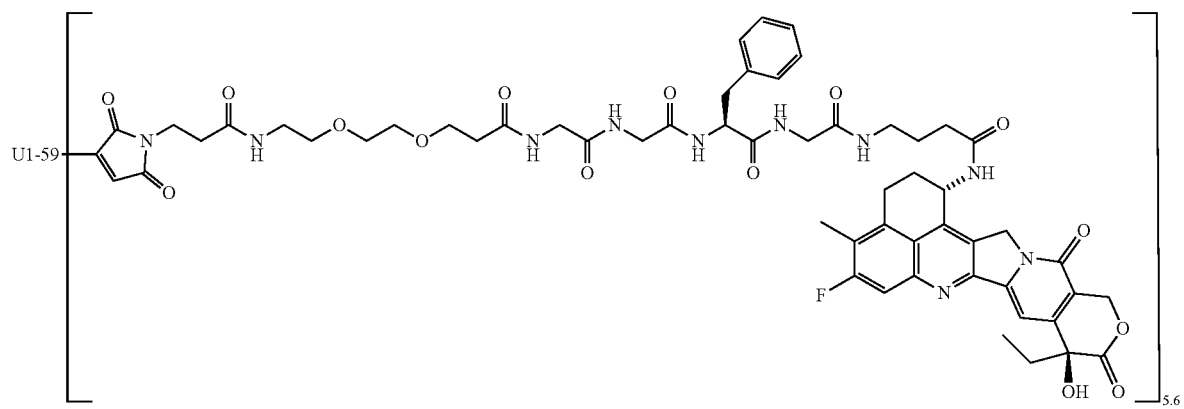

Process 1: N-{3-[2-(2-{[3-(2,5-dioxo-2,5-dihydro-1H-pyrrol-1-yl)propanoyl]amino}ethoxy)ethoxy]propanoyl}glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl]amino}-4-oxobutyl)glycinamide The compound (100 mg, 0.119 mmol) obtained in above Process 4 of Example 1 was reacted in the same manner as Process 5 of Example 1 by using N-succinimidyl 3424243-maleinimidepropanamide)ethoxy)ethoxy)propanoate (50.7 mg, 0.119 mmol) instead of N-succinimidyl 6-maleimide hexanoate to yield the titled compound as a pale yellow solid (66.5 mg, 48%).

$^1$H-NMR (400 MHz, DMSO-$d_6$) delta: 0.85 (3H, t, J=7.4 Hz), 1.65-1.74 (2H, m), 1.77-1.90 (2H, m), 2.07-2.19 (4H, m), 2.30 (2H, t, J=7.2 Hz), 2.33-2.36 (2H, m), 2.38 (3H, s), 2.76 (1H, dd, J=13.7, 9.8 Hz), 2.96-3.18 (9H, m), 3.42-3.44 (4H, m), 3.53-3.76 (10H, m), 4.43 (1H, td, J=8.6, 4.7 Hz), 5.14 (1H, d, J=18.8 Hz), 5.23 (1H, d, J=18.8 Hz), 5.38 (1H, d, J=17.2 Hz), 5.42 (1H, d, J=17.2 Hz), 5.52-5.58 (1H, m), 6.52 (1H, s), 6.98 (2H, s), 7.12-7.17 (1H, m), 7.18-7.25 (4H, m), 7.29 (1H, s), 7.69 (1H, t, J=5.5 Hz), 7.78 (1H, d, J=11.3 Hz), 7.98-8.03 (2H, m), 8.11 (1H, d, J=7.8 Hz), 8.16 (1H, t, J=5.7 Hz), 8.23 (1H, t, J=5.9 Hz), 8.44 (1H, d, J=9.0 Hz).

MS (APCI) m/z: 1149 (M+H)$^+$.

Process 2: Antibody-Drug Conjugate (9)

By using U1-59 produced in Reference Example 1 and the compound obtained in above Process 1, the titled antibody-drug conjugate was obtained in the same manner as Process 6 of Example 1.

Antibody concentration: 2.08 mg/mL, antibody yield: 18.7 mg (94%), and average number of conjugated drug molecules (n) per antibody molecule measured by Common procedure E (as molar absorption coefficient of the drug linker, $E_{D,280}$=4964, $E_{D,370}$=18982 were used): 5.6.

Example 10 Antibody-Drug Conjugate (10)

[Chem. 41]

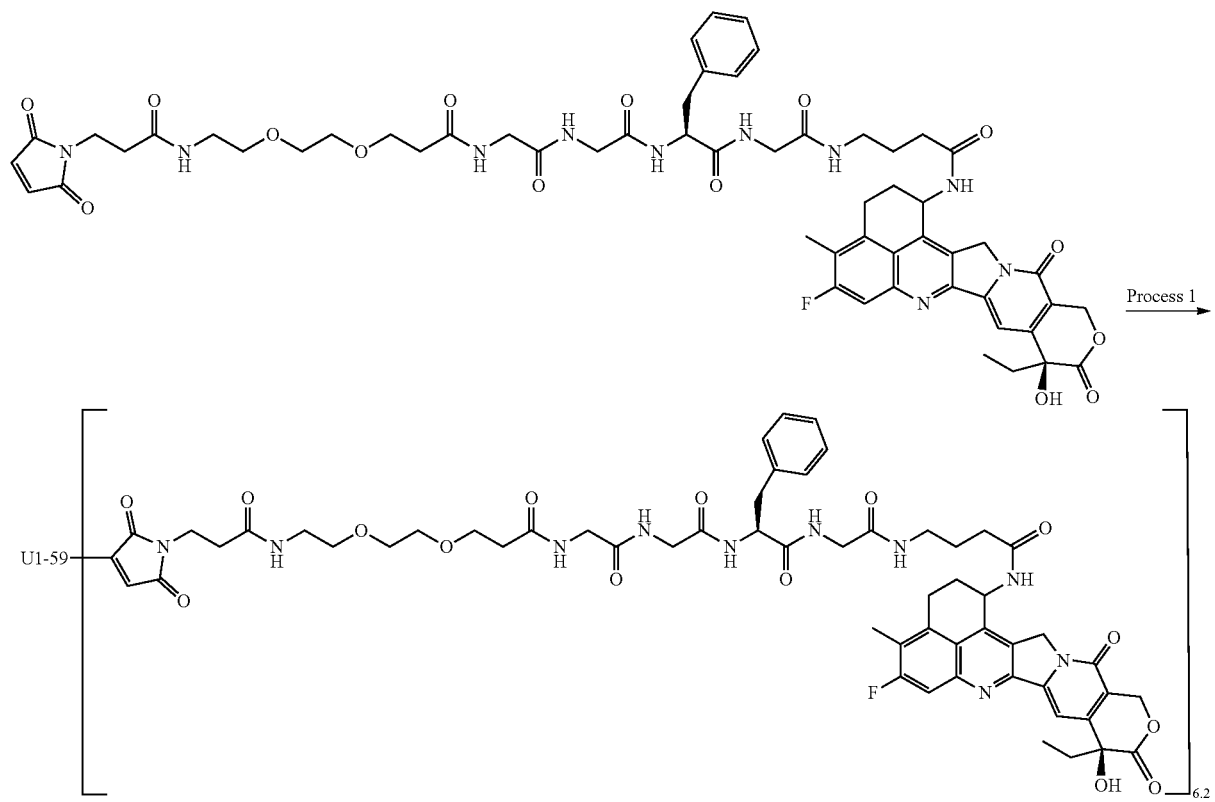

Process 1: Antibody-Drug Conjugate (10)

By using U1-59 produced in Reference Example 1 and the compound obtained in above Process 1 of Example 9, the titled antibody-drug conjugate was obtained in the same manner as Process 6 of Example 1.

Antibody concentration: 19.7 mg/mL, antibody yield: 236.4 mg (95%), and average number of conjugated drug molecules (n) per antibody molecule measured by Common procedure E (as molar absorption coefficient of the drug linker, $E_{D,280}$=4964, $E_{D,370}$=18982 were used): 6.2; and average number of conjugated drug molecules (n) per antibody molecule measured by Common procedure F (as molar absorption coefficient of the drug linker, $E_{D,280}$=4964 were used): 6.4.

Example 11 Antibody-Drug Conjugate (11)

[Chem. 42]

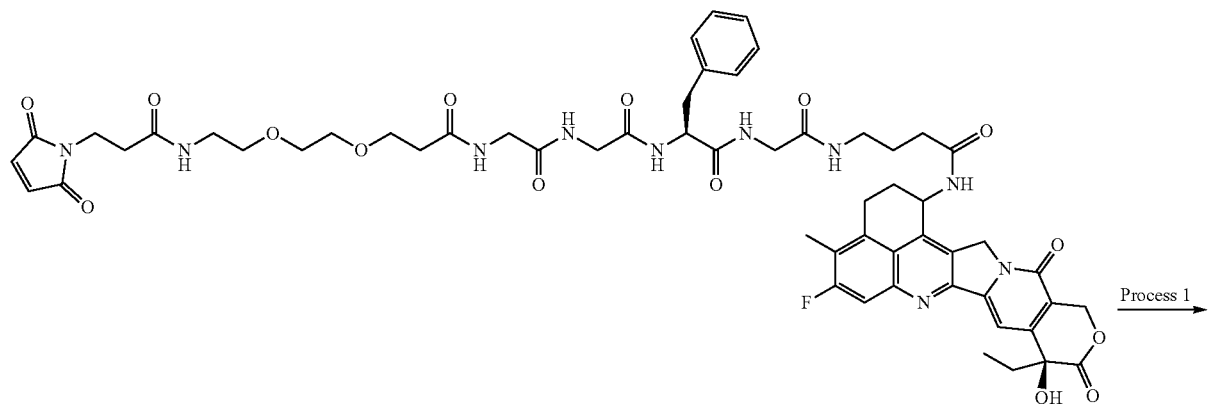

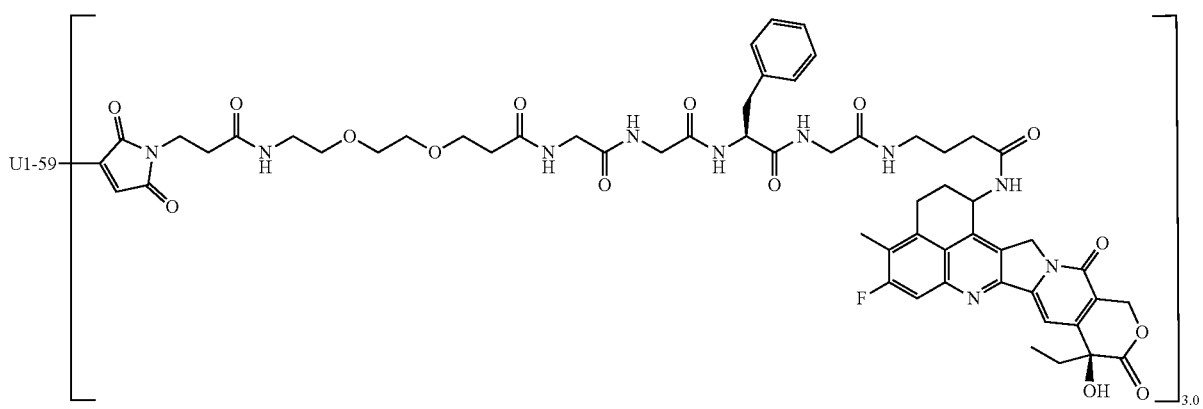

Process 1: Antibody-Drug Conjugate (11)

By using U1-59 produced in Reference Example 1 and the compound obtained in above Process 1 of Example 9, the titled antibody-drug conjugate was obtained in the same manner as Process 1 of Example 4.

Antibody concentration: 0.88 mg/mL, antibody yield: 5.28 mg (53%), and average number of conjugated drug molecules (n) per antibody molecule measured by Common procedure E (as molar absorption coefficient of the drug linker, $E_{D,280}$=4964, $E_{D,370}$=18982 were used): 3.0; and average number of conjugated drug molecules (n) per antibody molecule measured by Common procedure F (as molar absorption coefficient of the drug linker, $E_{D,280}$=4964 were used): 3.3.

Example 12 Antibody-Drug Conjugate (12)

[Chem. 43]

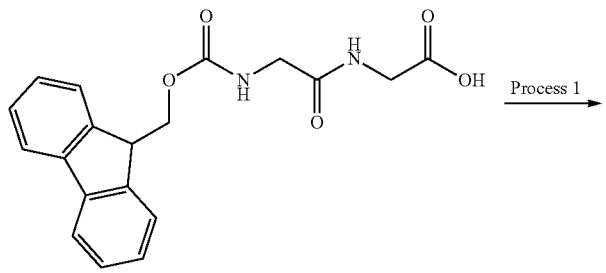

-continued
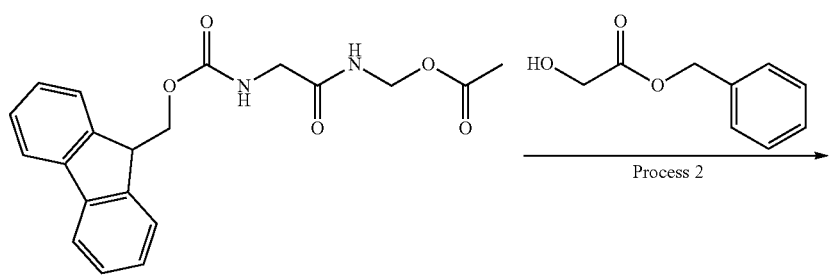
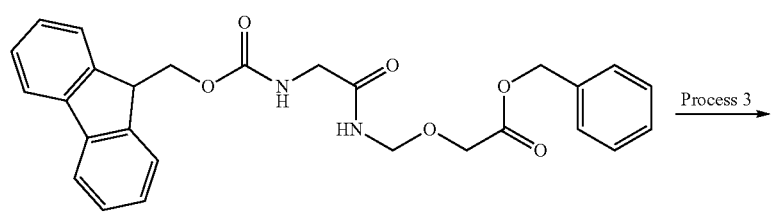
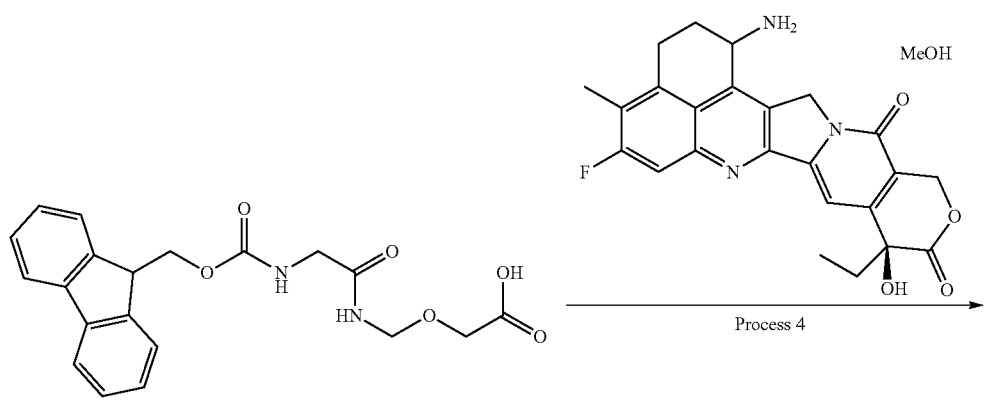
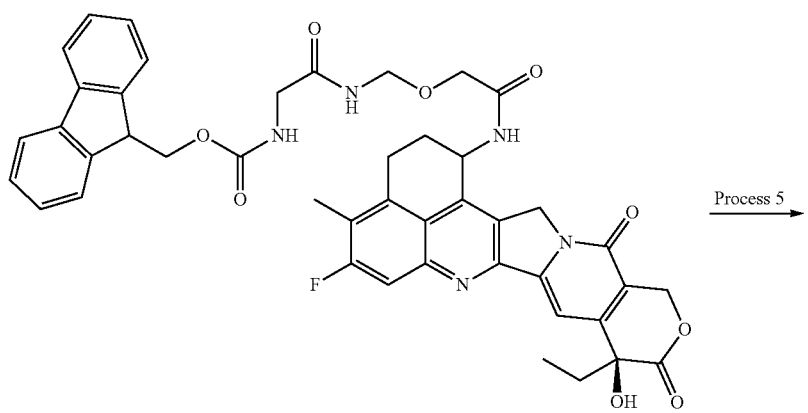

-continued
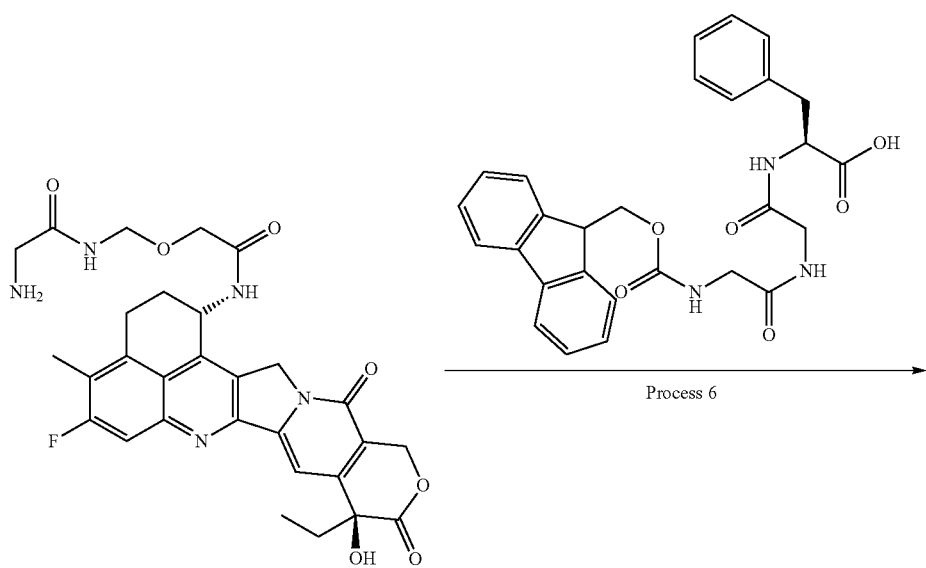
Process 6
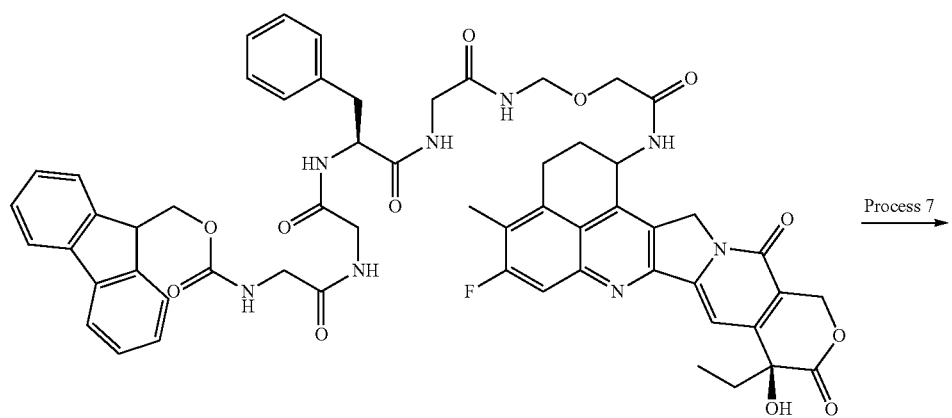
Process 7
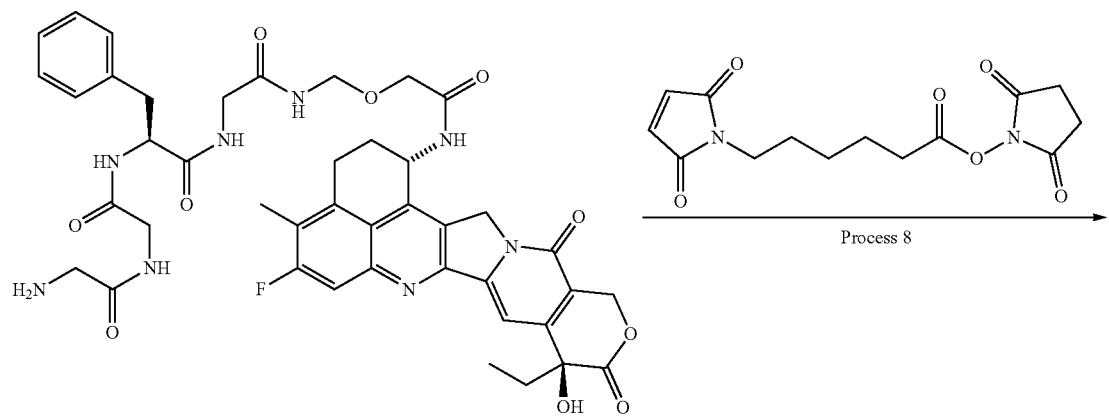
Process 8

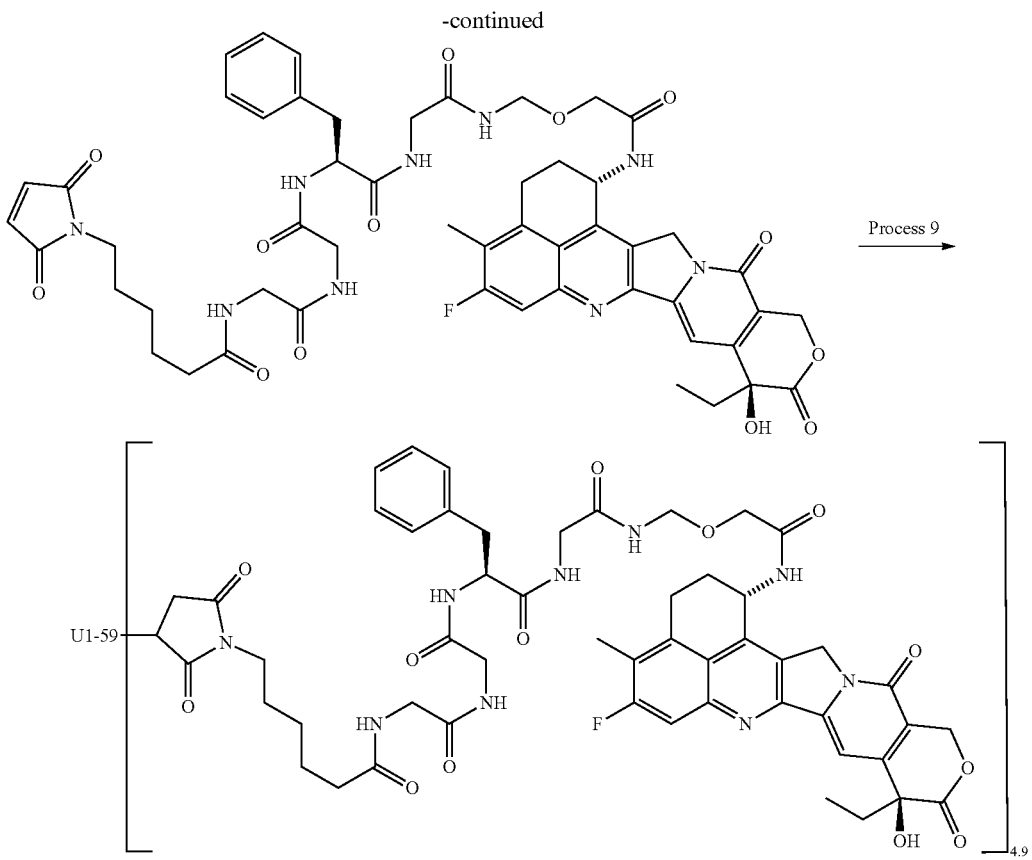

Process 1 ({N-[(9H-fluoren-9-ylmethoxy)carbonyl]glycyl}amino)methyl acetate

To a mixture containing N-9-fluorenylmethoxycarbonylglycylglycine (4.33 g, 12.2 mmol), tetrahydrofuran (120 ml), and toluene (40.0 ml), pyridine (1.16 mL, 14.7 mmol) and lead tetraacetate (6.84 g, 14.7 mmol) were added and refluxed under heating for 5 hours. After the reaction solution was cooled to room temperature, the insoluble material was removed by filtration through Celite, and the filtrate was concentrated under reduced pressure. The obtained residues were dissolved in ethyl acetate, washed with water and saturated brine, and then the organic layer was dried over anhydrous magnesium sulfate. After the solvent was removed under reduced pressure, the obtained residues were purified by silica gel column chromatography [hexane:ethyl acetate=9:1 (v/v)-ethyl acetate] to yield the titled compound as colorless solid (3.00 g, 67%).

$^1$H-NMR (400 MHz, CDCl$_3$) delta: 2.07 (3H, s), 3.90 (2H, d, J=5.1 Hz), 4.23 (1H, t, J=7.0 Hz), 4.46 (2H, d, J=6.6 Hz), 5.26 (2H, d, J=7.0 Hz), 5.32 (1H, brs), 6.96 (1H, brs), 7.32 (2H, t, J=7.3 Hz), 7.41 (2H, t, J=7.3 Hz), 7.59 (2H, d, J=7.3 Hz), 7.77 (2H, d, J=7.3 Hz).

Process 2: Benzyl [({N-[(9H-fluoren-9-ylmethoxy)carbonyl]glycyl}amino)methoxy]acetate To a tetrahydrofuran (40.0 mL) solution of the compound (3.68 g, 10.0 mmol) obtained in above Process 1 and benzyl glycolate (4.99 g, 30.0 mmol), potassium tert-butoxide (2.24 g, 20.0 mmol) was added at 0 C and stirred at room temperature for 15 minutes. The reaction solution was charged with ethyl acetate and water at 0 C and extracted with ethyl acetate and chloroform. The obtained organic layer was dried over sodium sulfate and filtered. The solvent was removed under reduced pressure. The obtained residues were dissolved in dioxane (40.0 mL) and water (10.0 mL), charged with sodium hydrogen carbonate (1.01 g, 12.0 mmol) and 9-fluorenylmethyl chloroformate (2.59 g, 10.0 mmol), and stirred at room temperature for 2 hours. The reaction solution was charged with water and extracted with ethyl acetate. The obtained organic layer was dried over sodium sulfate and filtered. The solvent was removed under reduced pressure and the obtained residues were purified by silica gel column chromatography [hexane:ethyl acetate=100:0 (v/v)-0:100] to yield the titled compound in colorless oily substance (1.88 g, 40%).

$^1$H-NMR (400 MHz, CDCl$_3$) delta: 3.84 (2H, d, J=5.5 Hz), 4.24 (3H, t, J=6.5 Hz), 4.49 (2H, d, J=6.7 Hz), 4.88 (2H, d, J=6.7 Hz), 5.15-5.27 (1H, m), 5.19 (2H, s), 6.74 (1H, brs), 7.31-7.39 (7H, m), 7.43 (2H, t, J=7.4 Hz), 7.61 (2H, d, J=7.4 Hz), 7.79 (2H, d, J=7.4 Hz).

Process 3: [({N-[(9H-fluoren-9-ylmethoxy)carbonyl]glycyl}amino)methoxy]acetic Acid The compound (1.88 g, 3.96 mmol) obtained in above Process 2 was dissolved in ethanol (40.0 mL) and ethyl acetate (20.0 mL). After adding palladium carbon catalyst (376 mg), it was stirred at room temperature under hydrogen atmosphere for 2 hours. The insoluble material was removed by filtration through Celite, and the solvent of the filtrate was removed under reduced pressure to yield the titled compound as colorless solid (1.52 g, quantitative).

$^1$H-NMR (400 MHz, DMSO-d$_6$) delta: 3.62 (2H, d, J=6.3 Hz), 3.97 (2H, s), 4.18-4.32 (3H, m), 4.60 (2H, d, J=6.7 Hz), 7.29-7.46 (4H, m), 7.58 (1H, t, J=5.9 Hz), 7.72 (2H, d, J=7.4 Hz), 7.90 (2H, d, J=7.4 Hz), 8.71 (1H, t, J=6.5 Hz).

Process 4: 9H-Fluoren-9-ylmethyl(2-{[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]amino}-2-oxoethyl)carbamate Under ice cooling, to an N,N-dimethylformamide (10.0 mL) solution of exatecan mesylate (0.283 g, 0.533 mmol), N-hydroxysuccinimide (61.4 mg, 0.533 mmol), and the compound (0.205 g, 0.533 mmol) obtained in above Process 3, N,N-diisopropylethylamine (92.9 uL, 0.533 mmol) and N,N'-dicyclohexylcarbodiimide (0.143 g, 0.693 mmol) were added and stirred at room temperature for 3 days. The solvent was removed under reduced pressure and the obtained residues were purified by silica gel column chromatography [chloroform-partitioned organic layer of chloroform:methanol:water=7:3:1 (v/v/v)] to yield the titled compound as a pale brown solid (0.352 g, 82%).

$^1$H-NMR (400 MHz, DMSO-d$_6$) delta: 0.81 (3H, t, J=7.4 Hz), 1.73-1.87 (2H, m), 2.06-2.20 (2H, m), 2.34 (3H, s), 3.01-3.23 (2H, m), 3.58 (2H, d, J=6.7 Hz), 3.98 (2H, s), 4.13-4.25 (3H, m), 4.60 (2H, d, J=6.7 Hz), 5.09-5.22 (2H, m), 5.32-5.42 (2H, m), 5.50-5.59 (1H, m), 6.49 (1H, s), 7.24-7.30 (3H, m), 7.36 (2H, t, J=7.4 Hz), 7.53 (1H, t, J=6.3 Hz), 7.66 (2H, d, J=7.4 Hz), 7.75 (1H, d, J=11.0 Hz), 7.84 (2H, d, J=7.4 Hz), 8.47 (1H, d, J=8.6 Hz), 8.77 (1H, t, J=6.7 Hz).

MS (ESI) m/z: 802 (M+H)$^+$.

Process 5: N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide To an N,N-dimethylformamide (11.0 mL) solution of the compound (0.881 g, 1.10 mmol) obtained in above Process 4, piperidine (1.1 mL) was added and stirred at room temperature for 2 hours. The solvent was removed under reduced pressure to yield a mixture containing the titled compound. The mixture was used for the next reaction without further purification.

Process 6: N-[(9H-fluoren-9-ylmethoxy)carbonyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H, 12H-benzo[de]pyrano[3',4':6,7]indolizino[1,2-b]quinolin-1-yl]amino}-2-oxoethoxy)methyl]glycinamide Under ice cooling, to an N,N-dimethylformamide (50.0 mL) solution of the mixture (0.439 mmol) obtained in above Process 5, N-hydroxysuccinimide (0.101 g, 0.878 mmol), and N-[(9H-fluoren-9-ylmethoxy)carbonyl]glycylglycyl-L-phenylalanine (the compound described in Japanese Patent Laid-Open No. 2002-60351; 0.440 g, 0.878 mmol), N,N'-dicyclohexylcarbodiimide (0.181 g, 0.878 mmol) was added and stirred at room temperature for 4 days. The solvent was removed under reduced pressure and the obtained residues were purified by silica gel column chromatography [chloroform-chloroform:methanol=9:1 (v/v)] to yield the titled compound as a pale orange solid (0.269 g, 58%).

MS (ESI) m/z: 1063 (M+H)$^+$.

Process 7: Glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide To an N,N-dimethylformamide (4.00 mL) solution of the compound (0.269 g, 0.253 mmol) obtained in above Process 6, piperidine (0.251 mL, 2.53 mmol) was added and stirred at room temperature for 2 hours. The solvent was removed under reduced pressure to yield a mixture containing the titled compound. The mixture was used for the next reaction without further purification.

Process 8: N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide To an N,N-dimethylformamide (10.0 mL) solution of the compound (0.253 mmol) obtained in above Process 7, N-succinimidyl 6-maleimide hexanoate (0.156 g, 0.506 mmol) was added and stirred at room temperature for 3 days. The solvent was removed under reduced pressure and the obtained residues were purified by silica gel column chromatography [chloroform-chloroform:methanol=9:1 (v/v)] to yield the titled compound as a pale yellow solid (0.100 g, 38%).

$^1$H-NMR (400 MHz, DMSO-d$_6$) delta: 0.83 (3H, t, J=7.2 Hz), 1.09-1.21 (2H, m), 1.33-1.47 (4H, m), 1.75-1.90 (2H, m), 2.00-2.23 (4H, m), 2.36 (3H, s), 2.69-2.81 (1H, m), 2.94-3.03 (1H, m), 3.06-3.22 (2H, m), 3.23-3.74 (6H, m), 3.98 (2H, s), 4.39-4.50 (1H, m), 4.60 (2H, d, J=6.7 Hz), 5.17 (2H, s), 5.39 (2H, s), 5.53-5.61 (1H, m), 6.50 (1H, s), 6.96 (2H, s), 7.11-7.24 (5H, m), 7.28 (1H, s), 7.75 (1H, d, J=11.0 Hz), 7.97 (1H, t, J=5.7 Hz), 8.03 (1H, t, J=5.9 Hz), 8.09 (1H, d, J=7.8 Hz), 8.27 (1H, t, J=6.5 Hz), 8.48 (1H, d, J=9.0 Hz), 8.60 (1H, t, J=6.5 Hz).

MS (ESI) m/z: 1034 (M+H)$^+$.

Process 9: Antibody-Drug Conjugate (12)

By using U1-59 produced in Reference Example 1 and the compound obtained in above Process 8, the titled antibody-drug conjugate was obtained in the same manner as Process 6 of Example 1.

Antibody concentration: 2.11 mg/mL, antibody yield: 19.0 mg (95%), and average number of conjugated drug molecules (n) per antibody molecule measured by Common procedure E (as molar absorption coefficient of the drug linker, $E_{D,280}$=5178, $E_{D,370}$=20217 were used): 4.9.

Example 13 Antibody-Drug Conjugate (13)

[Chem. 44]

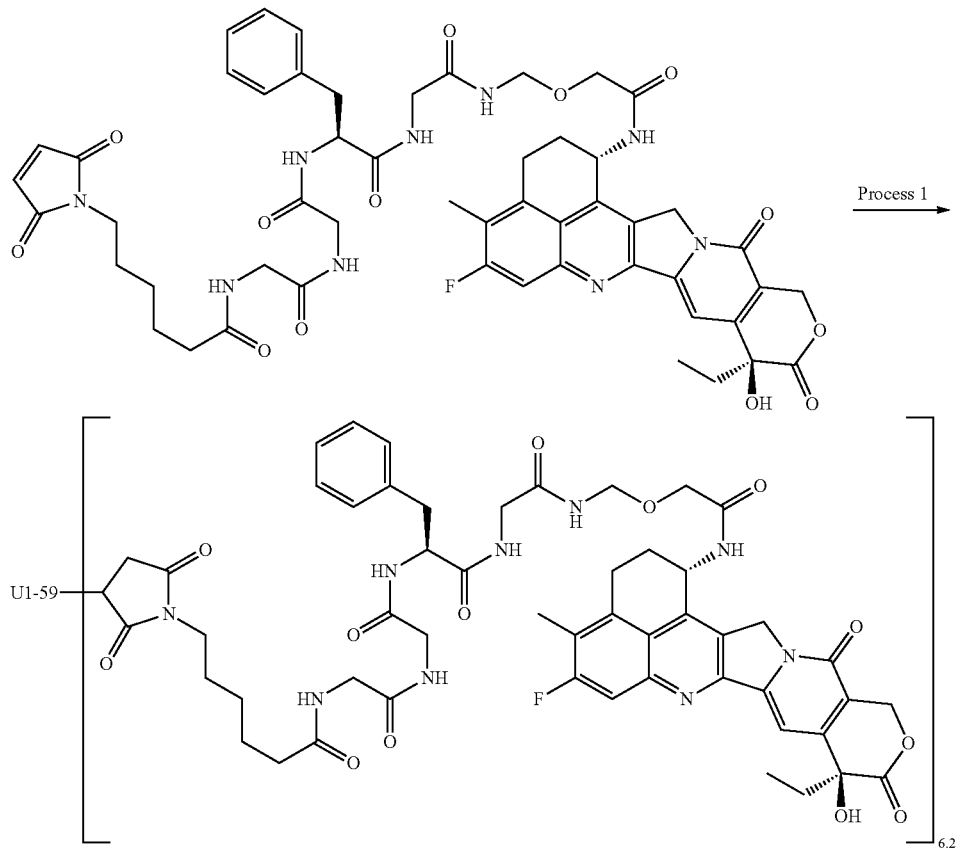

Process 1: Antibody-Drug Conjugate (13)

By using U1-59 produced in Reference Example 1 and the compound obtained in above Process 8 of Example 12, the titled antibody-drug conjugate was obtained in the same manner as Process 6 of Example 1.

Antibody concentration: 22.2 mg/mL, antibody yield: 244.2 mg (98%), and average number of conjugated drug molecules (n) per antibody molecule measured by Common procedure E (as molar absorption coefficient of the drug linker, $E_{D,280}$=5178, $E_{D,370}$=20217 were used): 6.2; and average number of conjugated drug molecules (n) per antibody molecule measured by Common procedure F (as molar absorption coefficient of the drug linker, $E_{D,280}$=5178 were used): 7.0.

Example 14 Antibody-Drug Conjugate (14)

[Chem. 45]

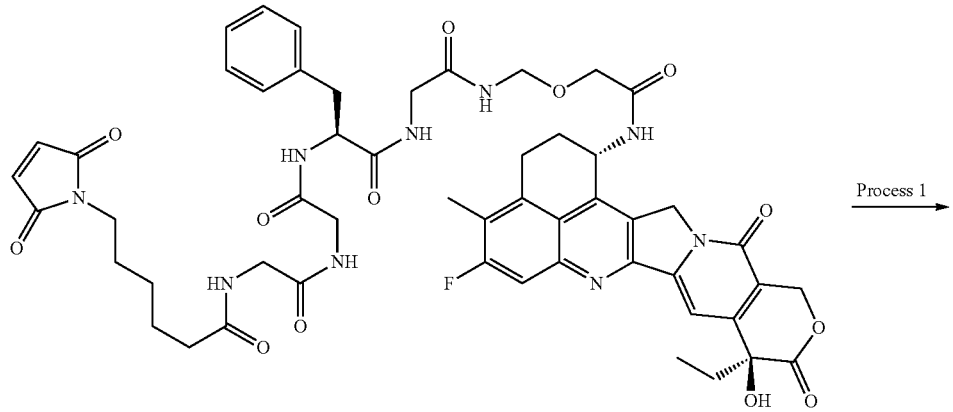

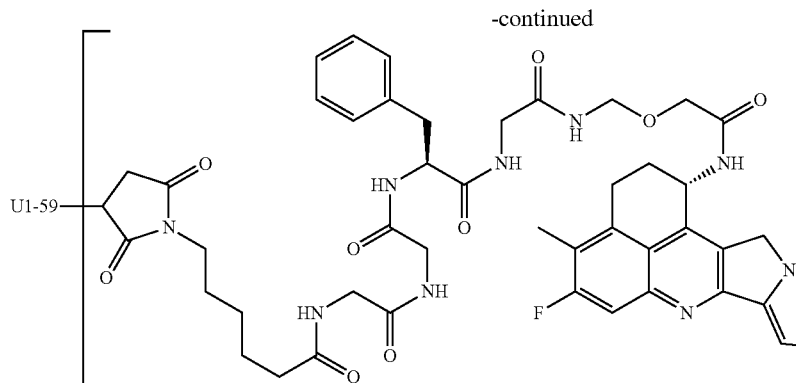

Process 1: Antibody-drug conjugate (14)

Reduction of the antibody: U1-59 produced in Reference Example 1 was prepared to have antibody concentration of 10 mg/mL by replacing the medium with PBS6.0/EDTA by using the Common procedure B and Common procedure C described in Production method 1. The solution (1.00 mL) was added to a 2.0 mL polypropylene tube and charged with an aqueous solution of 10 mM TCEP (Tokyo Chemical Industry Co., Ltd.) (0.0160 mL; 2.4 equivalents per antibody molecule) and a 1 M aqueous solution of dipotassium hydrogen phosphate (Nacalai Tesque, Inc.; 0.0150 mL). After confirming that the solution has pH of 7.0+/−0.1, the disulfide bond at hinge part in the antibody was reduced by incubating at 37 C for 1 hour.

Conjugation between antibody and drug linker: After incubating the solution in a water bath at 15 C for 10 minutes, dimethyl sulfoxide (Sigma-Aldrich Co. LLC; 0.0209 mL) and a dimethyl sulfoxide solution (0.0315 mL; 5.0 equivalents per antibody molecule) containing 10 mM of the compound obtained in above Process 8 of Example 12 was added thereto and incubated in a water bath at 15 C for 60 minutes for conjugating the drug linker to the antibody. Next, an aqueous solution (0.0050 mL) of 100 mM NAC (Sigma-Aldrich Co. LLC) was added thereto and stirred by using a tube rotator (MTR-103, manufactured by AS ONE Corporation) at room temperature for another 20 minutes to terminate reaction of the drug linker.

According to the same purification processes and physicochemical characterizations as Process 6 of Example 1, the following characteristics values were obtained.

Antibody concentration: 1.46 mg/mL, antibody yield: 8.76 mg (88%), and average number of conjugated drug molecules (n) per antibody molecule measured by Common procedure E (as molar absorption coefficient of the drug linker, $E_{D,280}=5178$, $E_{D,370}=20217$ were used): 2.5; and average number of conjugated drug molecules (n) per antibody molecule measured by Common procedure F (as molar absorption coefficient of the drug linker, $E_{D,280}=5178$ were used): 2.9.

Example 15 Antibody-Drug Conjugate (15)

[Chem. 46]

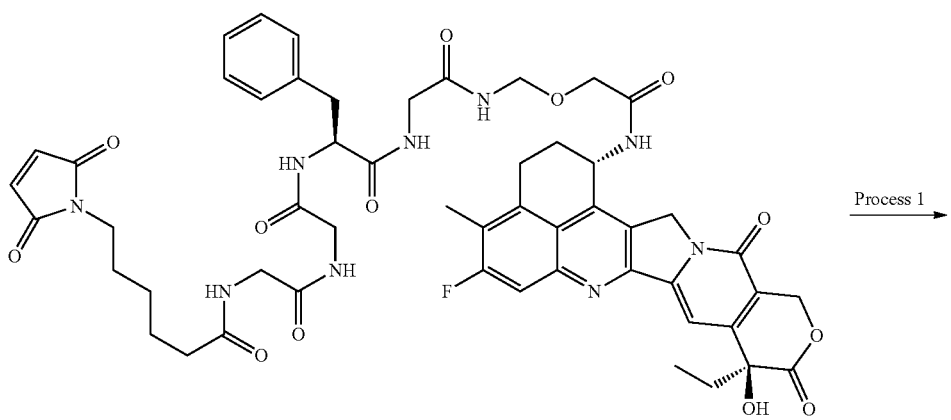

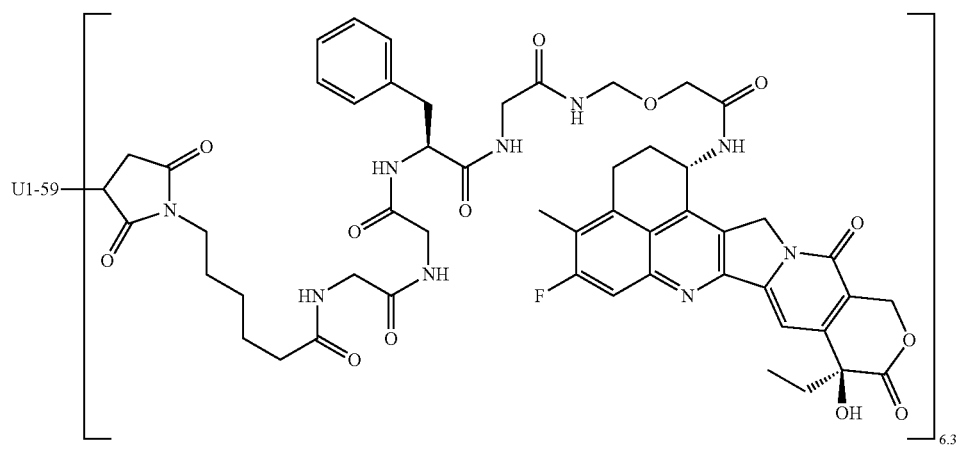

Process 1: Antibody-Drug Conjugate (15)

Reduction of the antibody: U1-59 produced in Reference Example 1 was prepared to have antibody concentration of 10 mg/mL by replacing the medium with PBS6.0/EDTA by using the Common procedure B and Common procedure C described in Production method 1. The solution (100 mL) was added to a 250 mL polycarbonate Erlenmeyer flask and charged with a 1 M aqueous solution of dipotassium hydrogen phosphate (1.70 mL) and then an aqueous solution of 10 mM TCEP (4.010 mL; 6.0 equivalents per antibody molecule) at room temperature with stirring using a magnetic stirrer. After confirming that the solution has pH of 7.0+/−0.1, the stirring was stopped, and the disulfide bond at hinge part in the antibody was reduced by incubating at 37 C for 1 hour.

Conjugation between antibody and drug linker: After cooling the above solution to 15 C, a DMSO solution (6.684 mL; 10.0 equivalents per antibody molecule) containing 10 mM of the compound obtained in above Process 8 of Example 12 was gradually added thereto with stirring. The mixture was stirred at 15 C for the first 30 minutes and, after stopping the stirring, incubated for another 1 hour for conjugating the drug linker to the antibody. Next, an aqueous solution (0.862 mL; 12.9 equivalents per antibody molecule) of 100 mM NAC was added thereto with stirring and incubated at room temperature for 20 minutes to terminate the reaction of unreacted drug linker.

Purification: A 20% aqueous acetic acid solution (about 0.6 mL) and ABS (100 mL) were gradually added to the solution with stirring to adjust pH of the solution to 5.5+/−0.1. This solution was subjected to microfiltration (Millipore Corp. Millex-HV filter, 0.45 um, PVDF membrane) to remove whitish matter. This solution was subjected to ultrafiltration purification using a ultrafiltration apparatus constituted by a ultrafiltration membrane (Merck Japan, Ltd., Pellicon XL Cassette, Biomax 50 KDa), a tube pump (Cole-Parmer International, USA, MasterFlex pump model 77521-40, pump head model 7518-00), and a tube (Cole-Parmer International, USA, MasterFlex tube L/S16). Specifically, by adding ABS dropwise (a total of 1600 mL) as a buffer solution for purification to the reaction solution while carrying out ultrafiltration purification, non-conjugated drug linkers and other low-molecular-weight reagents were removed while the buffer solution was replaced with ABS and further the solution was concentrated. The obtained purified solution was subjected to microfiltration (0.22 um (Millipore Corp. Millex-GV filter, PVDF membrane) to yield 37.5 mL of a solution containing the titled antibody-drug conjugate.

Antibody concentration: 26.5 mg/mL, antibody yield: 993.0 mg (90%), average number of conjugated drug molecules (n) per antibody molecule measured by Common procedure E (as molar absorption coefficient of the drug linker, $E_{D,280}=5178$ and $E_{D,370}=20217$ were used): 6.3, and average number of conjugated drug molecules (n) per antibody molecule measured by Common procedure F (as molar absorption coefficient of the drug linker, $E_{D,280}=5178$ was used): 7.3.

Example 16a Antibody-Drug Conjugate (16a)

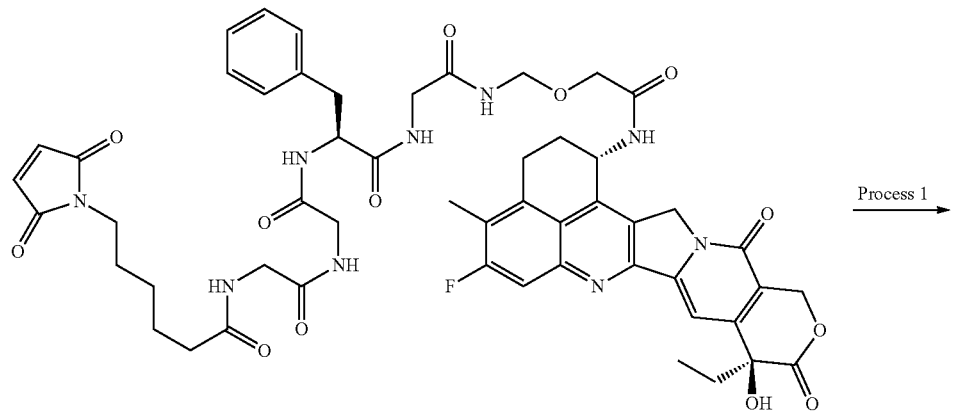

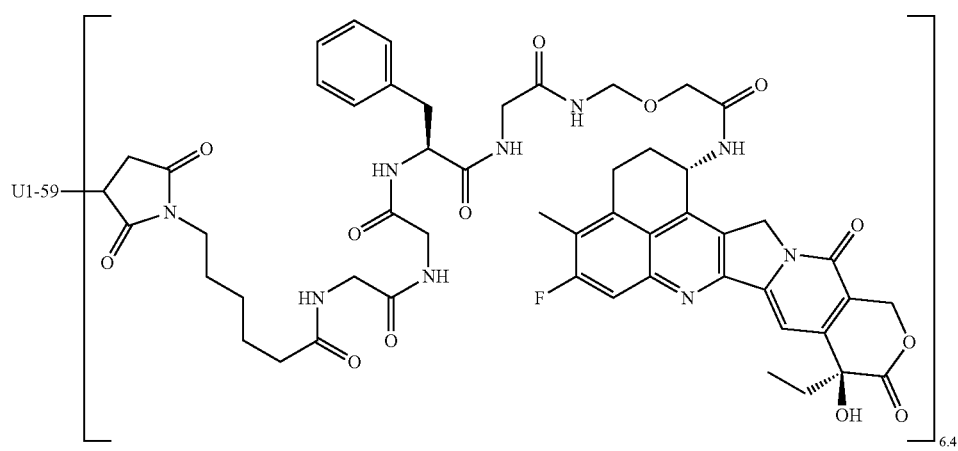

Process 1: Antibody-Drug Conjugate (16a)

Reduction of the antibody: U1-59 produced in Reference Example 1 was prepared to have antibody concentration of 10 mg/mL by replacing the medium with PBS6.0/EDTA by using the Common procedure B and Common procedure C described in Production method 1. The solution (15 mL) was added to a 50 mL polyethylene terephthalate container and charged with a 1 M aqueous solution of dipotassium hydrogen phosphate (0.255 mL) and then an aqueous solution of 10 mM TCEP (0.601 mL; 6.0 equivalents per antibody molecule) at room temperature with stirring using a magnetic stirrer. After confirming that the solution has pH of 7.0+/−0.1, the disulfide bond at hinge part in the antibody was reduced by incubating at 37 C for 2 hours.

Conjugation between antibody and drug linker: After cooling the above solution to 15 C, a DMSO solution (1.002 mL; 10.0 equivalents per antibody molecule) containing 10 mM of the compound obtained in above Process 8 of Example 12 was gradually added thereto with stirring. The mixture was stirred at 15 C for 30 minutes for conjugating the drug linker to the antibody. Next, an aqueous solution (0.129 mL; 12.9 equivalents per antibody molecule) of 100 mM NAC was added thereto with stirring and incubated at room temperature for 20 minutes to terminate the reaction of unreacted drug linker. According to the same purification processes and physicochemical characterizations as Process 6 of Example 1, the following characteristic values were obtained.

Antibody concentration: 2.36 mg/mL, antibody yield: 140 mg (59.5 mL) (94%), average number of conjugated drug molecules (n) per antibody molecule measured by Common procedure E (as molar absorption coefficient of the drug linker, $E_{D,280}$=5178 and $E_{D,370}$=20217 were used): 6.4, and average number of conjugated drug molecules (n) per antibody molecule measured by Common procedure F (as molar absorption coefficient of the drug linker, $E_{D,280}$=5178 was used): 7.7.

Example 16b Antibody-Drug Conjugate (16b)

[Chem. 48]

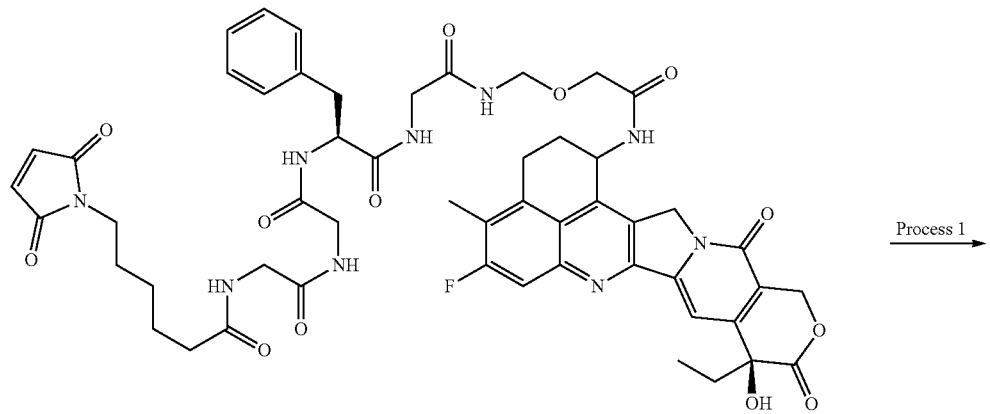

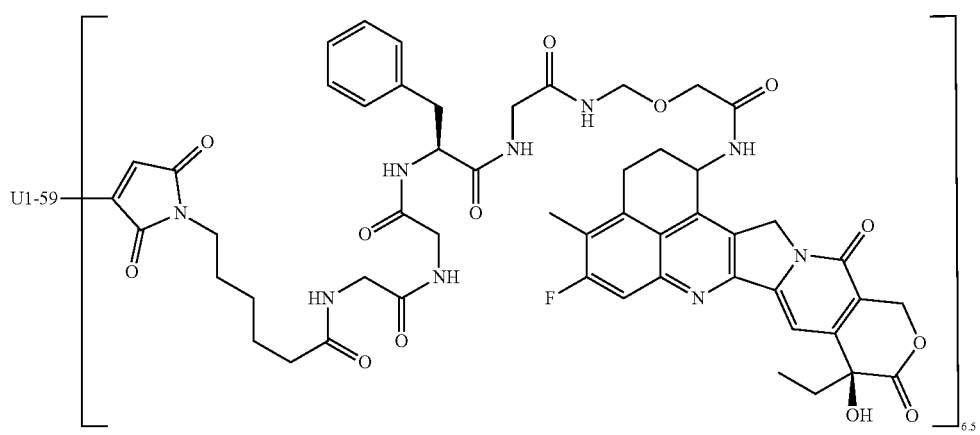

Reduction of the antibody: U1-59 produced in Reference Example 1 was prepared to have antibody concentration of 10 mg/mL by replacing the medium with PBS6.0/EDTA by using the Common procedure B and Common procedure C described in Production method 1. The solution (900 mL) was added to a 2000 mL polycarbonate Erlenmeyer flask and charged with a 1 M aqueous solution of dipotassium hydrogen phosphate (15.3 mL) and then an aqueous solution of 10 mM TCEP (36.1 mL; 6.0 equivalents per antibody molecule) at room temperature with stirring using a magnetic stirrer. After confirming that the solution has pH of 7.0+/−0.1, the stirring was stopped, and the disulfide bond at hinge part in the antibody was reduced by incubating at 37 C for 2 hours.

Conjugation between antibody and drug linker: After cooling the above solution to 15 C, a DMSO solution (60.16 mL; 10.0 equivalents per antibody molecule) containing 10 mM of the compound obtained from Process 8 of Example 12 was gradually added thereto with stirring. The mixture was stirred at 15 C for 30 minutes for conjugating the drug linker to the antibody. Next, an aqueous solution (7.76 mL; 12.9 equivalents per antibody molecule) of 100 mM NAC was added thereto with stirring and incubatedat room temperature for 20 minutes to terminate the reaction of unreacted drug linker.

Purification: A 20% aqueous acetic acid solution (about 5 mL) and ABS (1000 mL) were gradually added to the solution with stirring to adjust pH of the solution to 5.5+/−0.1. This solution was subjected to microfiltration (Millipore Corp. Stericup, 0.45 um, PVDF membrane) to remove whitish matter. This solution was subjected to ultrafiltration purification using a ultrafiltration apparatus constituted by a ultrafiltration membrane (Merck Japan, Ltd., Pellicon 2 mini cassette, Ultracel 30 KDa, 0.1 m$^2$), a tube pump (Cole-Parmer International, USA, MasterFlex pump model 7528-20, pump head model 77800-62), and a tube (Cole-Parmer International, USA, MasterFlex tubes L/S24 and 25). Specifically, by adding ABS dropwise (a total of 16 L) as a buffer solution for purification to the reaction solution while carrying out ultrafiltration purification, non-conjugated drug linkers and other low-molecular-weight reagents were removed while the buffer solution was replaced with ABS and further the solution was concentrated to yield about 500 mL of a solution containing the titled antibody-drug conjugate.

Antibody concentration: 19.66 mg/mL, antibody yield: 9830 mg (109%), and average number of conjugated drug molecules (n) per antibody molecule measured by Common procedure E (as molar absorption coefficient of the drug linker, $E_{D,280}$=5178 and $E_{D,370}$=20217 were used): 6.5.

Example 16c Antibody-Drug Conjugate (16c)

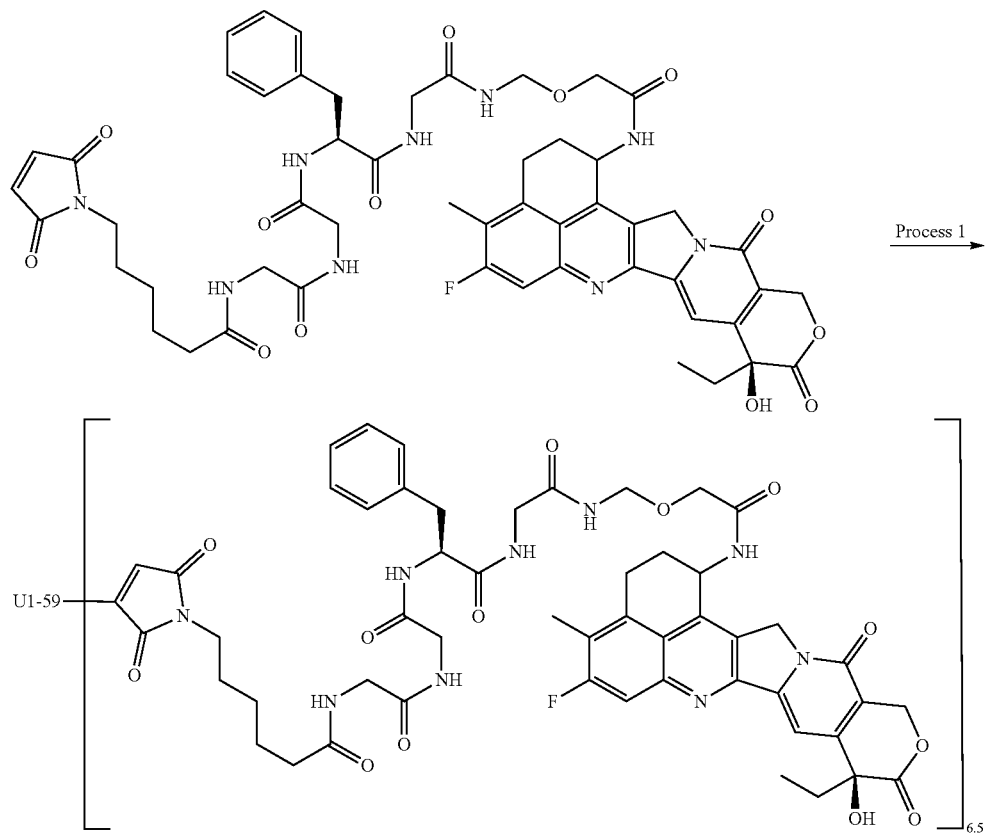

[Chem. 49]

By using U1-59 produced in Reference Example 1 and the compound obtained in above Process 8 of Example 12, the titled antibody-drug conjugate was obtained in the same manner as Example 16b.

Antibody concentration: 16.21 mg/mL, antibody yield: 9726 mg (600 mL, 108%), and average number of conjugated drug molecules (n) per antibody molecule measured by Common procedure E (as molar absorption coefficient of the drug linker, $E_{D,280}=5178$ and $E_{D,370}=20217$ were used): 6.5.

Example 16d Antibody-Drug Conjugate (16d)

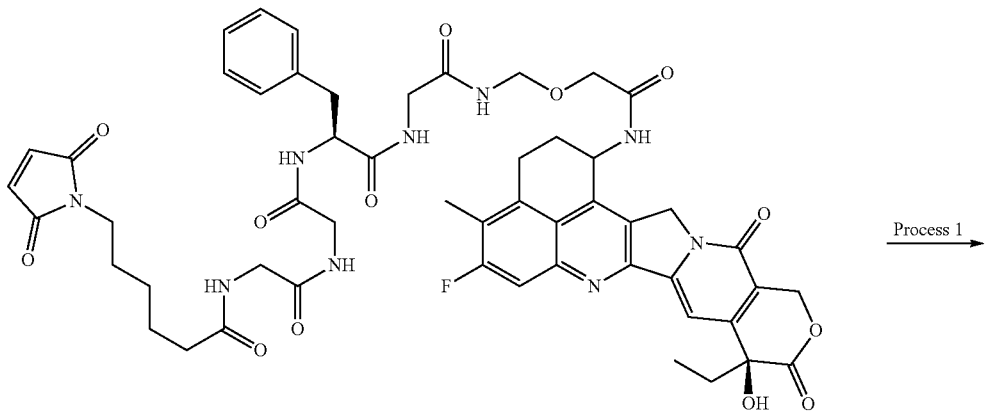

[Chem. 50]

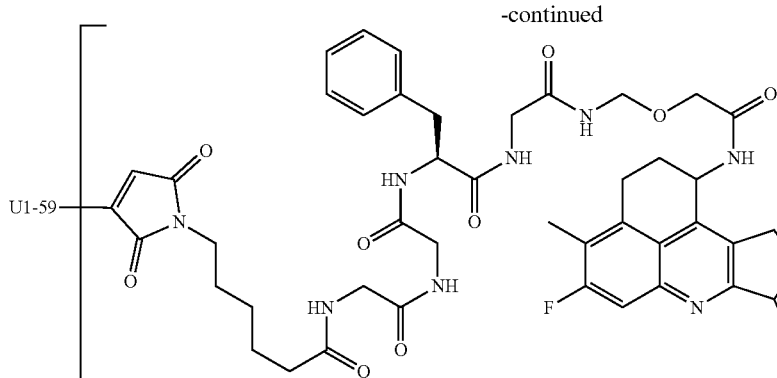

The antibody-drug conjugates (16a), (16b), and (16c) produced in Examples 16a, 16b, and 16c, respectively, were mixed (a total of about 18 g) and further subjected to ultrafiltration in the same manner as Example 16b (11 L of ABS was used). The obtained purified solution was subjected to microfiltration (Millipore Corp. Stericup, 0.45 um and 0.22 um, PVDF membrane) to yield 745 mL of a solution containing the titled antibody-drug conjugate. By further adding 110 mL of ABS, 855 mL of a solution containing the titled antibody-drug conjugate was obtained.

Antibody concentration: 20.0 mg/mL, antibody yield: 17.1 g (94%), average number of conjugated drug molecules (n) per antibody molecule measured by Common procedure E (as molar absorption coefficient of the drug linker, $E_{D,280}=5178$ and $E_{D,370}=20217$ were used): 6.5, and average number of conjugated drug molecules (n) per antibody molecule measured by Common procedure F (as molar absorption coefficient of the drug linker, $E_{D,280}=5178$ was used): 7.8.

Test Example 1 HER3 Binding Affinity of Antibody-Drug Conjugate Compared with U1-59 Method A human breast cancer cell line HCC1569 (CRL-2330) from ATCC was cultured in an RPMI1640 medium (purchased from Invitrogen Corp., containing 10% bovine serum albumin (manufactured by Invitrogen Corp.) and 2 mM L-glutamine (manufactured by Invitrogen Corp.)). The cells were dissociated from the culture plate using ACCUTASE® SOLUTION (Millipore Corp., SCR005) or EDTA (5 mM, phosphate buffered saline (PBS, 137 mM sodium chloride, 2.7 mM potassium chloride, 1.47 mM potassium dihydrogen phosphate, and 10.5 mM disodium hydrogen phosphate)), and the number of living cells was measured by trypan blue treatment. The same numbers of cells suspended in a fluorescence-activated cell sorting (FACS) buffer (PBS containing 3% FBS and 0.004% sodium azide) were inoculated to 96-well U-bottom plates, and the cells were precipitated by centrifugation and suspended in 100 uL of an ice-cooled antibody or antibody-drug conjugate dilution or FACS buffer.

The antibody or each antibody-drug conjugate was serially diluted at a ratio of 1/3 with a FACS buffer and adjusted to 30 ug/mL to 5 ng/mL (200 nM to 0.03 nM). Cells treated with a FACS buffer without the addition of a primary antibody were used as a control group.

U1-59, the antibody-drug conjugate (3), the antibody-drug conjugate (10), or the antibody-drug conjugate (13) was evaluated as the antibody or the antibody-drug conjugates.

The cells of each group were reacted with a primary antibody dilution for 45 minutes on ice and then washed with a FACS buffer. Further, 100 uL of a FACS buffer or a reaction solution of a secondary antibody diluted 1/100 (phycoerythrin (PE)-coupled anti human antibody, Dianova GmbH #709-116-149) was added thereto. The cells were treated for 45 minutes on ice in the dark and then washed with a FACS buffer, and dead cells were excluded using a FACS buffer or a FACS buffer supplemented with 7-aminoactinomycin D (7AAD, Sigma-Aldrich Co. LLC, #A9400, 1.1 ug/mL).

Fluorescence signals from living cells were evaluated using Accuri C6 Flow cytometer (BD Biosciences/Accuri® Cytometers Inc., serial number 1424) and CFlow software (CFlow sampler Version 1.0.264.13).

For the correction of PE- and 7-AAD-derived signals, the fluorescence signals of U1-59 (30 ug/mL) and cells stained with the PE-labeled secondary antibody or 7-AAD were evaluated.

In order to quantify U1-59-specific fluorescence signals in the cells, values obtained by the subtraction of FL-2 signals of cells treated with only the secondary antibody or 7-AAD were used. The equilibrium binding affinity (KD) and the maximum binding strength (Bmax) were calculated using GraphPad Prism software (version 5.04 for Windows® (one-site-specific binding)).

The results are shown in FIG. 3 and Table 1. FIG. 3 and Table 1 show the mean fluorescence intensity of HCC1569 treated with serial dilutions of U1-59 or each antibody-drug conjugate. The equilibrium binding affinity KD and the maximum binding strength Bmax were calculated using GraphPad Prism software.

TABLE 1

|  | U1-59 | Antibody-drug conjugate (3) | Antibody-drug conjugate (10) | Antibody-drug conjugate (13) |
|---|---|---|---|---|
| Bmax | 31830 | 28981 | 28841 | 28415 |
| Kd (nM) | 1.672 | 1.653 | 1.554 | 2.727 |

The antibody-drug conjugate (3) or the antibody-drug conjugate (10) exhibited average binding affinity KD for HCC-1569 equivalent to KD of the non-conjugated anti- HER3 antibody U1-59. The antibody-drug conjugate (13) also exhibited average binding affinity KD equivalent to KD of the non-conjugated anti-HER3 antibody U1-59 (2.7 nM vs. 1.6 nM). The KD values of the different antibody-drug conjugates suggested that the antibody-drug conjugation processes do not significantly impair the binding affinity of U1-59.

Test Example 2 Inhibition of HER3 Signal by Anti-HER3 Antibody-Drug Conjugate Method A human lung cancer cell line A549 (CRS-300114) from Cell Lines Service was dissociated by trypsin treatment, and 50,000 living cells were inoculated to 3 mL of DMEM/F12 (Invitrogen Corp., #21331-020)+10% FBS (Invitrogen Corp., #10270-106) in each of 6 wells. After culturing the cells for 3 days, the medium was replaced with 2 mL of a fresh medium.

The antibody or each antibody-drug conjugate was added directly to 2 mL of a medium in each of the 6 wells such that the final concentration was 10 ug/mL (20 uL of a stock solution of 1 ug/uL antibody or antibody-drug conjugate was added).

U1-59, the antibody-drug conjugate (3), the antibody-drug conjugate (10), or the antibody-drug conjugate (13) was used as the antibody or the antibody-drug conjugate. An untreated group was used as a control.

The cells were cultured for 2 days, washed once with PBS, and treated with 100 uL of an ice-cooled buffer (50 mM 4-(2-hydroxyethyl)-1-piperazineethanesulfonic acid (HEPES), pH 7.5, 150 mM sodium chloride, 1 mM ethylenediaminetetraacetic acid (EDTA), 12.5% glycerin, 1% Triton X-100, and 10 mM sodium pyrophosphate tetrabasic supplemented with proteinase inhibitors (Roche Diagnostics, Inc., #11697 498 001), 10 mM sodium fluoride, 1 mM sodium vanadate, 1 mM phenyl-methane-sulfonyl-fluoride (PMSF), and 10 ug/mL aprotinin (Sigma-Aldrich Co. LLC, A1153)) for 30 minutes at 4 C for lysis. The lysate was washed for 20 minutes at 13000 rpm at 4 C, and the supernatant was used in protein concentration measurement by Bradford assay (Sigma-Aldrich Co. LLC, #B6916, BSA standard was from Thermo Fisher Scientific Inc., #23209). To each sample (amount of proteins: 120 ug), a 4-fold concentration of an LDS buffer (Invitrogen Corp., containing DTT (final concentration: 166.67 mM)) was added, and its volume was finally adjusted to 40 uL with water. The sample was boiled for 10 minutes at 70 C and added to wells of NuPage Mini Bis-Tris gel (4%-12%, 1.5 mm thick, 10 slots/gel, Invitrogen Corp.). As protein standards, 7.5 uL of Novex® sharp ladder (Invitrogen Corp., P/N 57318) was added. The sample was electrophoresed for 70 minutes at 175 V with 1×MOPS Running buffer (Invitrogen Corp.) containing NuPage antioxidant (Invitrogen Corp., NP0005, Lot 1356629 added to the internal chamber. Proteins separated by the gel electrophoresis were transferred to a nitrocellulose membrane (GE Healthcare Life Sciences) having a pore size of 0.45 um using NuPage transfer buffer (Invitrogen Corp.) containing 10% methanol and NuPage antioxidant (Invitrogen Corp., NP0005, Lot 1356629, 1:1000 dilution). The proteins were transferred for 80 minutes at a constant volume of 30 V.

The transfer membrane was cut, separated into fractions of 100 kDa or larger and 30 to 100 kDa, washed twice with PBS containing 0.1% Tween-20, and blocked by shaking for 1 hour at room temperature using Odyssey Blocking solution (LI-COR, Inc., #927-40000). The transfer membrane thus blocked was treated overnight at 4 C with a solution of a diluted primary antibody (mixture of Odyssey blocking solution and PBS in equal amounts).

An anti-HER3 antibody (Santa Cruz Biotechnology, Inc., SC-81455, dilution 1:500) and an anti-phosphorylated HER antibody (Cell Signaling Technology, Inc., #4791, 1:1000) were used as the primary antibody, and an anti-actin antibody (Neomarkers, #MS1295, dilution 1:3333) was used as an electrophoresis control.

The transfer membrane was washed three times (5 minutes for each) with PBS containing 0.1% Tween-20 and reacted with a dilution containing a secondary antibody (mixture of Odyssey blocking solution and PBS in equal amounts) for 1 hour at room temperature in a dark room.

Goat anti mouse IRDye 680RD (LI-COR, Inc., #926-68070, dilution 1:25000) or goat anti rabbit IR Dye 800CW (LI-COR, Inc., #926-32211, dilution 1:10000) was used as the secondary antibody. The transfer membrane was washed three times (6 minutes for each) with PBS containing 0.1% Tween-20, followed by signal detection using Odyssey infrared imager (LI-COR, Inc.).

Figure 4:
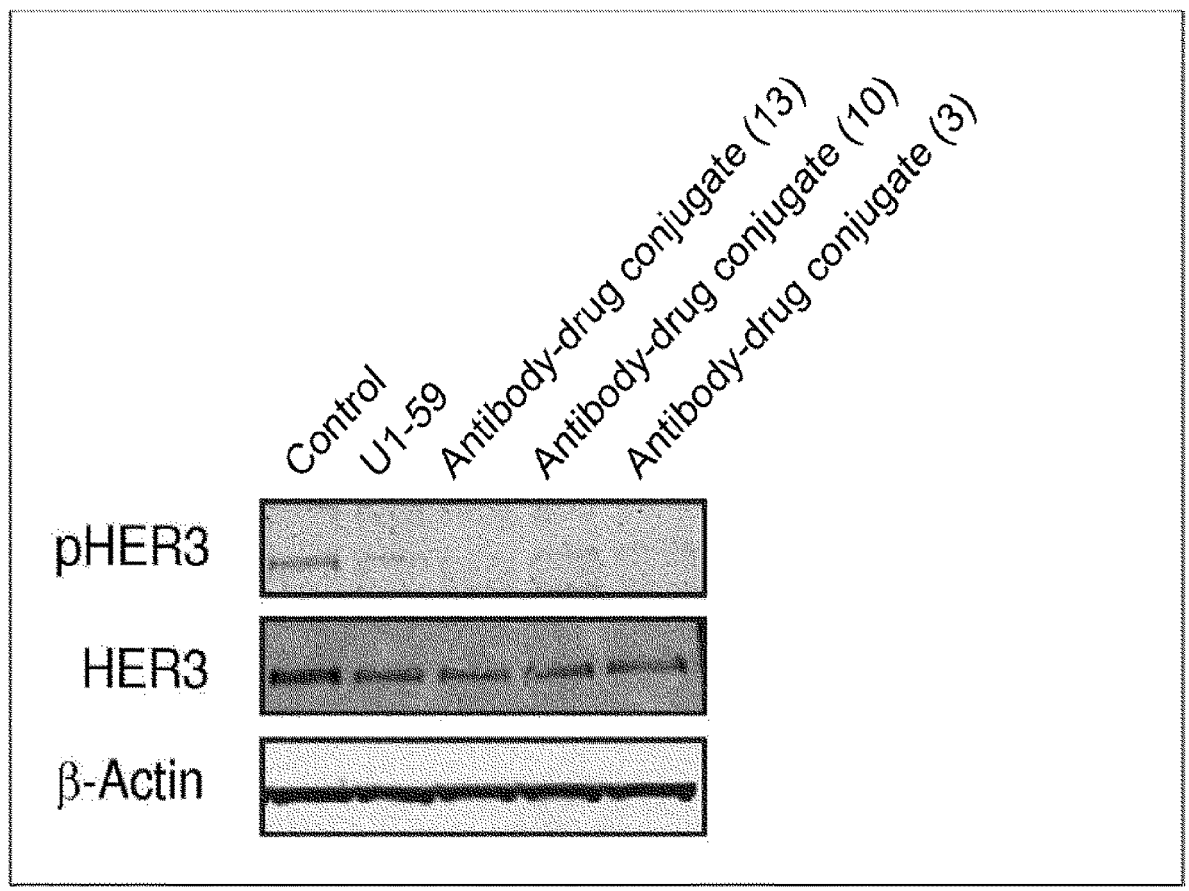
FIG. 4 A549 cells were cultured for 2 days with U1-59 or varied antibody-drug conjugates. HER3 or phosphorylated HER3 was evaluated by Western blotting. pan-Actin was detected as an electrophoresis control.

The results are shown in FIG. 4. A549 cells were cultured for 2 days with U1-59 or different antibody-drug conjugates. HER3 or phosphorylated HER3 was evaluated by Western blotting. pan-Actin was detected as an electrophoresis control.

As a result of culturing A549 for 2 days with 10 ug/mL U1-59 or antibody-drug conjugate, HER3 phosphorylation was reduced as compared with untreated cells. This reduction in HER3 phosphorylation was equivalent between U1-59 and the antibody-drug conjugate, suggesting that a plurality of drug conjugation processes did not impair a HER3 signal-inhibiting function derived from U1-59.

When A549 was treated with U1-59 or each antibody-drug conjugate for 2 days, reduction in HER3 expression was also observed as compared with untreated cells. The degree of this reduction in expression was equivalent between U1-59 and the antibody-drug conjugate. This suggests that a plurality of drug conjugation processes did not impair U1-59-mediated internalization (see Test Example regarding internalization) and U1-59-induced HER downregulation (see Test Example regarding signal inhibition).

Test Example 3 Reduction in Expression of HER3 on Cell Surface by U1-59 and Antibody-Drug Conjugate Method:

HER3 internalization by U1-59 and each antibody-drug conjugate was evaluated by flow cytometry. 70,000 living cells of HCC1569 (from ATCC) were suspended in 0.5 mL of RPMI1640 (Invitrogen Corp., #31870-025) (containing 10% FBS (Invitrogen Corp., #10270-106 or PAN Biotech GmbH, #1505-P131304) and 2 mM glutamine (Invitrogen Corp., #25030-024)) and inoculated to each well of a 24-well plate. The cells were cultured for 4 days, and the medium was replaced with 0.5 mL of a fresh medium before the start of the internalization test. 5 ug of the antibody or each antibody-drug conjugate was added to 0.5 mL in each well of the 24-well plate such that the final concentration was 10 ug/mL. The cells were cultured for 1 hour at 37 C in the presence of the antibody or the antibody-drug conjugate. U1-59, the antibody-drug conjugate (3), the antibody-drug conjugate (10), or the antibody-drug conjugate (13) was used as the antibody or the antibody-drug conjugate. Cells as a positive control or a negative control were untreated in some procedures.

For flow cytometry analysis, the cells were washed once with PBS and dissociated from the plate using 5 mM EDTA (100 uL/well) dissolved in ACCUTASE® SOLUTION (Millipore Corp., SCR005) or PBS. The cells were suspended in 200 uL of an ice-cooled FACS buffer (PBS containing 3% FBS and 0.004% sodium azide), then added to each well of a 96-well U-bottom plate, and left on ice. The cells were washed once with a FACS buffer. To each sample, 100 uL of U1-59 (10 ug/mL) diluted with a FACS buffer or only a FACS buffer was added. The cells were treated for 45 minutes with shaking on ice and then washed with a FACS buffer, and 100 uL of a PE-labeled secondary antibody anti-human antibody (Dianova GmbH, 709-116-149) dissolved at a ratio of 1:100 in a FACS buffer, or only a FACS buffer was added to each well. The cells were treated for 45 minutes in a dark room with shaking on ice. The cells were washed with a FACS buffer and treated with a FACS buffer or a FACS buffer containing 7AAD (Sigma-Aldrich Co. LLC, A9400, 1.1 ug to 1.25 ug/mL) for staining dead cells. The fluorescence signals of living cells were measured using Accuri C6 Flow cytometer. For the correction of PE and 7-AAD signals, U1-59 (10 ug/mL) and cells stained with only the PE-labeled secondary antibody or 7-AAD were used.

In order to quantify HER3-specific signals, values of cells stained with only the secondary antibody or 7-AAD were subtracted from FL-2 values of cells stained with the primary antibody and the secondary antibody, and further 7-AAD.

When the FL-2 signals of cells untreated with U1-59 or the antibody-drug conjugate (without internalization) were defined as the maximum value, reduction in HER3 (internalization) on the surface of the cells treated with U1-59 or the antibody-drug conjugate at 37 C was calculated.

An average value calculated from 2 to 3 wells was used for the positive control (without treatment at 37 C) and the negative control (without the addition of the primary antibody), and internalization in the wells of each treatment group was quantified.

Figure 5:
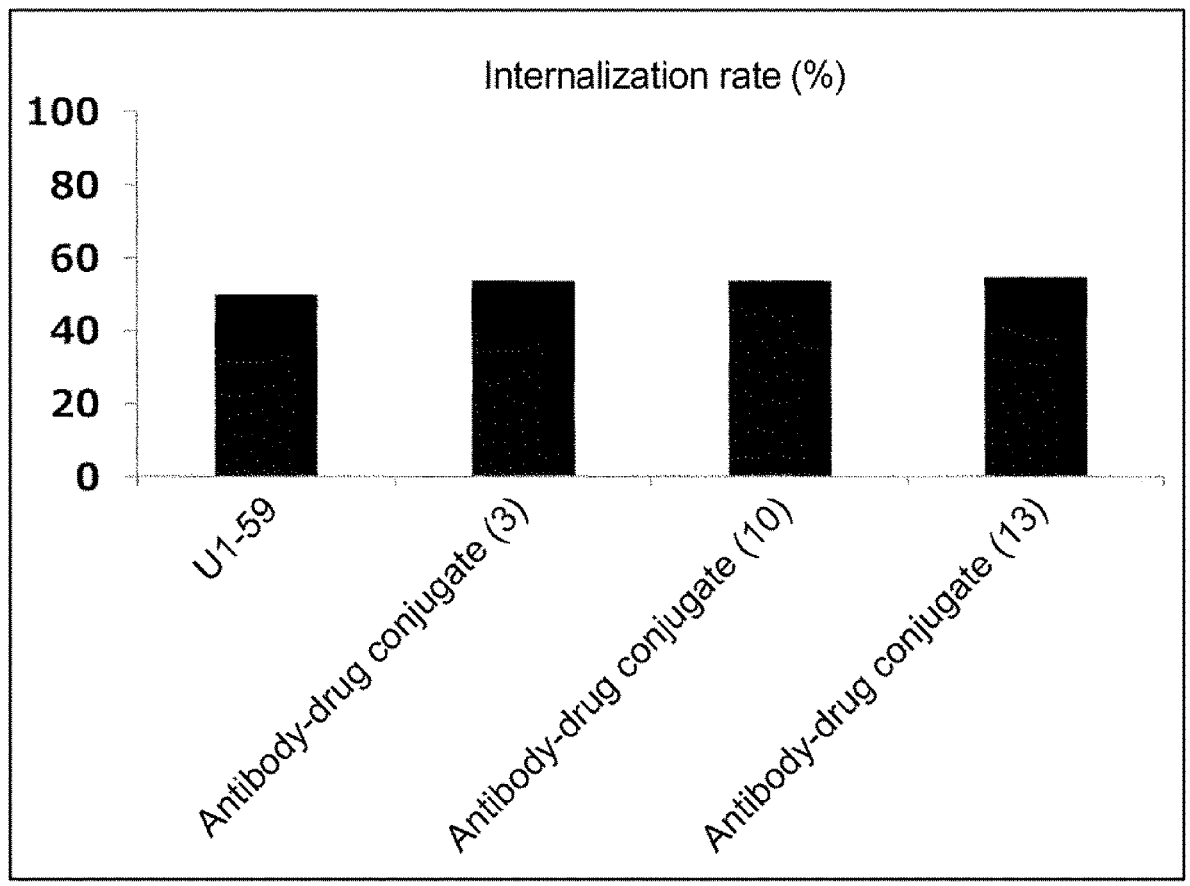
FIG. 5 shows an average value of reduction in HER3 expression on the surface of HCC1569 cells treated with U1-59 or each antibody-drug conjugate (37 C ("C" represents "degrees Celsius"), 1 hr).
Figure 6B:
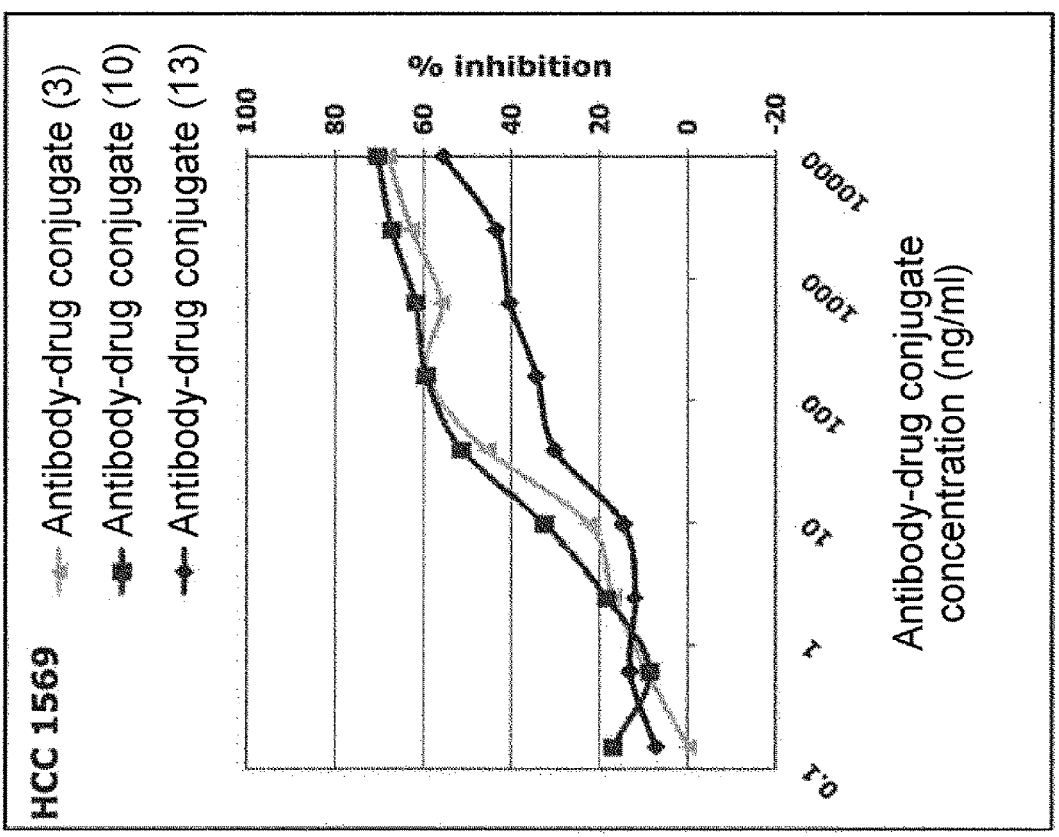
FIGS. 6A and 6B show results of a test on the inhibition of mitogenic or survival signals by each HER3 antibody-drug conjugate in a human breast cancer line (HCC1569).
Figure 6A:
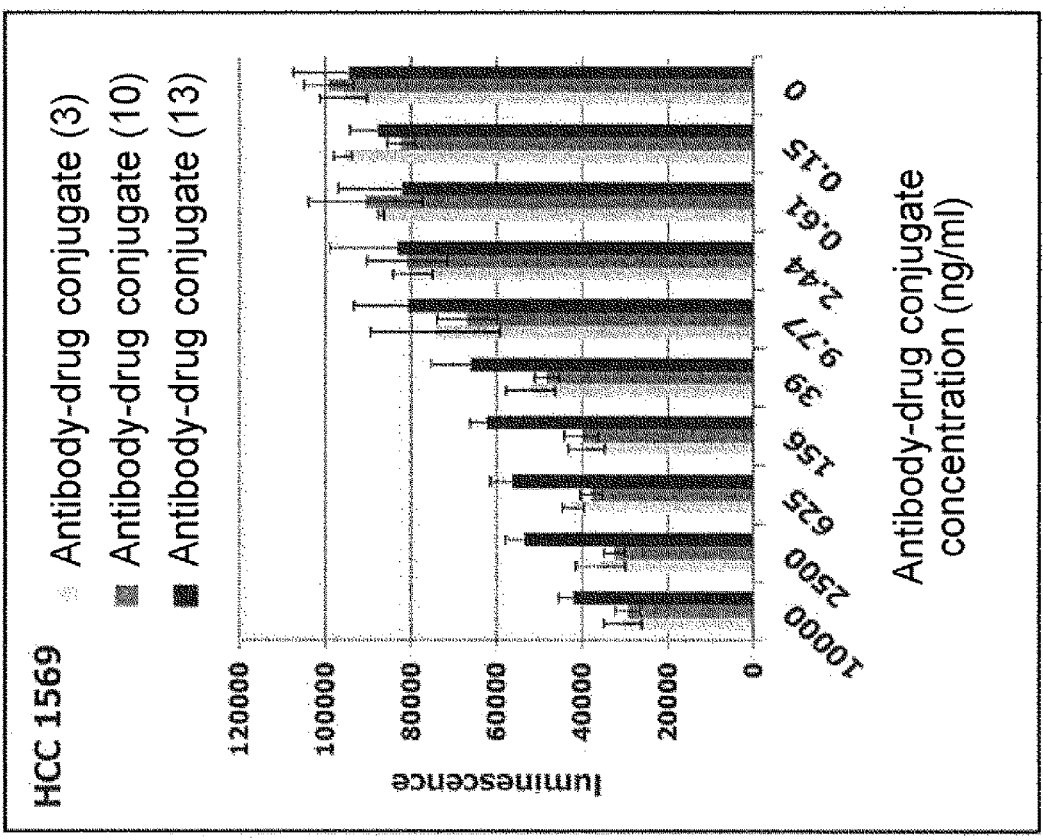
Figure 7B:
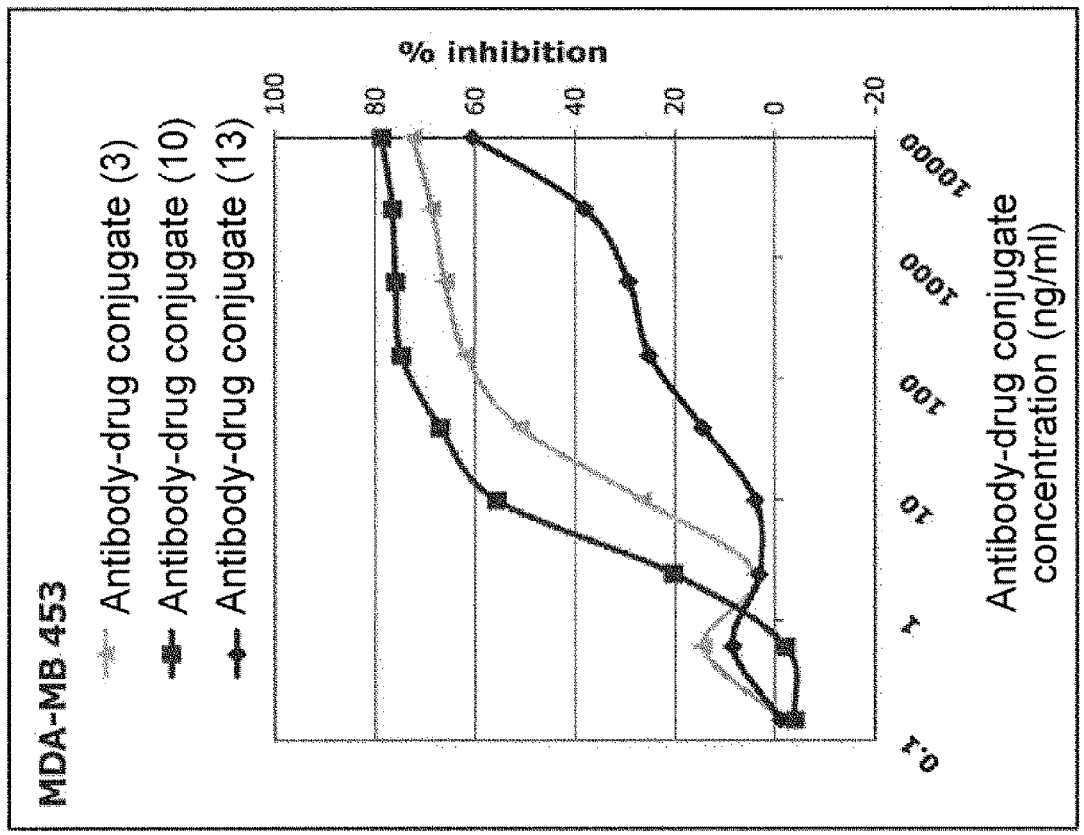
FIGS. 7A and 7B show results of a test on the inhibition of mitogenic or survival signals by each HER3 antibody-drug conjugate in a human breast cancer line (MDA-MB 453).
Figure 7A:
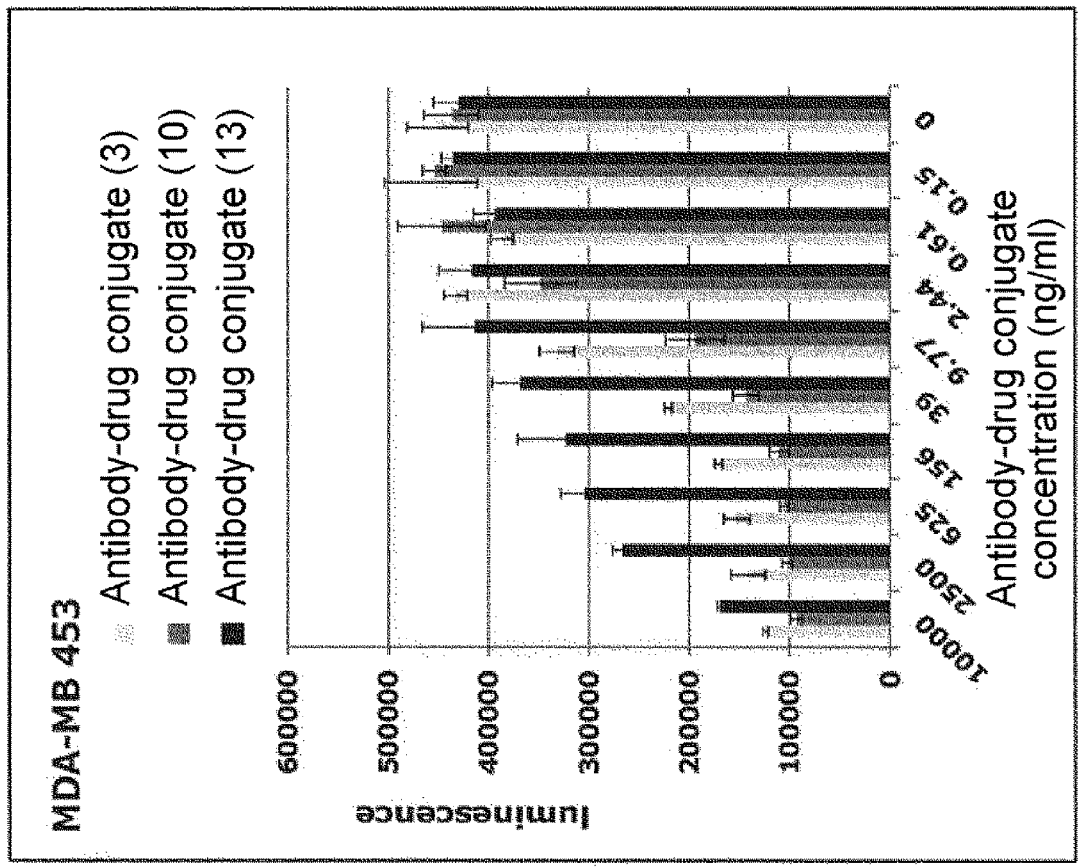

The results are shown in FIG. 5. This diagram shows an average value of reduction in HER3 expression on the surface of HCC1569 cells treated with U1-59 or each antibody-drug conjugate (37 C, 1 hr). The HER3 expression of a group without the addition of U1-59 or the antibody-drug conjugate was defined as the maximum value of HER3 expression in cells. The values of groups treated with only the secondary antibody or 7-AAD were used as backgrounds. Groups treated with U1-59 or each antibody-drug conjugate for 1 hour were used as treatment groups. The FL-2 values were almost the same between U1-59 and the antibody-drug conjugate.

Reduction in generated fluorescence caused by the treatment of HCC-1569 with U1-59 or each antibody-drug conjugate indicates reduction in HER3 expression. As compared with about 50% reduction in HER3 expression by U1-59, reduction in HER3 expression by each antibody-drug conjugate also exhibited a value equivalent to or higher than it, suggesting that the drug conjugation processes of the antibody did not impair the HER3-internalizing function of the antibody.

Test Example 4 Inhibition of In Vitro Mitogenic or Survival Signal by HER3 Antibody-Drug Conjugate in Human Cancer Cell Line Method:

The inhibitory activity of each HER3 antibody-drug conjugate against mitogenic or survival signals was measured in the presence of 10% FBS. The growth and development of cells were evaluated by measuring adenosine triphosphate (ATP) activity in untreated and antibody-drug conjugate-treated groups. Adherent cancer cell lines (human breast cancer cell line HCC1569 (CRL-2330) from ATCC, human breast cancer cell line MDA-MB-453 (CLB-22) from ATCC, and human colorectal cancer cell line HT-29 (CPQ-57) from ProQinase GmbH) were cultured in 2D culture systems, and floating (non-adherent) cancer cell lines (human melanoma cell line A375 (CRL-1619) from ATCC and human lung cancer cell line A549 (CRS-300114) from Cell Lines Service) were cultured in 3D culture systems.

Treatment of Adherent Cell

Each cancer cell line was suspended in 100 uL of each medium at a low density (500 cells/well for HT-29, 800 cells/well for MDA-MB-453, and 1000 cells/well for HCC-1569) and inoculated to 96-MicroWell Optical Bottom plate (Thermo Fisher Scientific Inc./Nunc, #165306, white wall and clear bottom). As for HCC-1569 and MDA-MB-453, the cells were cultured in an RPMI1640 medium (Invitrogen Corp., 31870-025) containing 10% FBS (Invitrogen Corp., 10270-106) and 2 mM glutamine (Invitrogen Corp., 25030-024). As for HT-29, the cells were cultured in a McCoy's 5A medium (Invitrogen Corp., 26600-023) containing 10% FBS (Invitrogen Corp., 10270-106) and 2 mM glutamine (Invitrogen Corp., 25030-024). The edge wells of each plate were filled with 100 uL of a medium.

The cells were cultured for 3 days, and the medium was replaced with 95 uL of a fresh medium before antibody-drug conjugate treatment.

The antibody-drug conjugate (3), the antibody-drug conjugate (10), and the antibody-drug conjugate (13) were used. An untreated group was set as a control for measuring normal cell growth.

By adding 5 uL of each antibody-drug conjugate concentrated into a 20-fold concentration to 95 uL of a culture medium (10% FBS) contained in each well of the 96-well plate, the final concentration was established. Only 5 uL of a medium was added to each control well. The test was conducted in triplicate per sample.

In order to calculate the concentration of the antibody-drug conjugate at which the growth or survival of cells was reduced by 50%, concentrations of the antibody-drug conjugate were prepared by 4-fold dilutions (10 ug/mL to 0.15 ng/mL or 40 ug/mL to 0.15 ng/mL), and the cells were treated with these concentrations of the antibody-drug conjugate and compared with the untreated group in terms of ATP activity. Evaluation was carried out by 5-day culture of HT-29 and 7-day culture of HCC-1569 and MDA-MB-453 thus supplemented with the antibody-drug conjugate. CellTiter-Glo® Luminescent Cell Viability Assay was used for evaluating the activity of the antibody-drug conjugate. This method involves measuring living cells having metabolic activity on the basis of ATP activity and finally estimating the number of living cells and employed CellTiter-Glo® Luminescent Cell (Promega K.K., G7573) as a kit.

100 uL of CellTiter-Glo® reagent was added to each well of the 96-well plate and stored for 25 minutes to 65 minutes at room temperature in a dark room before measurement using Wallac Victor2 1420 Multilabel Counter (program luminescence, measurement time: 0.5 s). Wells containing only a culture solution without the inoculation of the cells were assayed as blanks. In order to measure reduction in ATP activity, an average luminescence value of 3 wells was calculated under each condition (Microsoft Excel 2010). In order to remove cell-independent signals, the average luminescence value of the blanks was subtracted from the average luminescence value of the cells treated with the antibody-drug conjugate (Microsoft Excel 2010). The rate of reduction (%) in luminescence was calculated by comparison with the cells of the untreated group (Microsoft Excel 2010). This value was interpreted as the rate of inhibition (%) of cell growth or survival.

Treatment of Floating Cells

Since A375 and A549 have a faster growth rate than that of other cell lines, growth measurement was carried out in non-adherent 3D culture systems.

Each cancer cell line was suspended in 75 uL of each medium at a low density (500 cells/well for A375 and 1500 cells/well for A549) and inoculated to a 96-well round-bottom non-adherent 3D culture plate (Prime Surface 96U; Sumitomo Bakelite Co, Ltd.; order no. MS-9096U). As for A375, the cells were cultured in a DMEM medium (Invitrogen Corp., 41965-039) containing 10% FBS (Invitrogen Corp., 10270-106) and 2 mM glutamine (Invitrogen Corp., 25030-024). As for A549, the cells were cultured in a DMEM/F12 medium (Invitrogen Corp., 21331-020) containing 10% FBS (Invitrogen Corp., 10270-106) and 2 mM glutamine (Invitrogen Corp., 25030-024). The edge wells of each plate were filled with 150 uL of a medium. The cells were cultured for 3 days, and the final dose was adjusted to 142.5 uL or 150 uL by adding 67.5 or 75 uL of a fresh medium before antibody-drug conjugate addition. The antibody-drug conjugate (3), the antibody-drug conjugate (10), and the antibody-drug conjugate (13) were used. An untreated group was set as a control for measuring normal cell growth.

By adding 7.5 or 8 uL of each antibody-drug conjugate concentrated into a 20-fold concentration to 142.5 or 150 uL of a culture medium (10% FBS) contained in each well of the 96-well plate, the final concentration was established. The final dose was set to 150 uL or 158 uL. Only 7.5 or 8 uL of a medium was added to each control well. The test was conducted in triplicate per sample.

In order to calculate the concentration of the antibody-drug conjugate at which the growth or survival of cells was reduced by 50%, concentrations of the antibody-drug conjugate were prepared by 4-fold dilutions (10 ug/mL to 0.15 ng/mL or 40 ug/mL to 0.15 ng/mL), and the cells were treated with these concentrations of the antibody-drug conjugate and compared with the untreated group in terms of ATP activity. Evaluation was carried out by 7-day culture of the cells thus supplemented with the antibody-drug conjugate. CellTiter-Glo® Luminescent Cell Viability Assay was used for evaluating the activity of the antibody-drug conjugate. This method involves measuring living cells having metabolic activity on the basis of ATP activity and finally estimating the number of living cells and employed CellTiter-Glo® Luminescent Cell (Promega K.K., G7573) as a kit.

Before measurement, 50 uL of the medium was removed from each well, and 100 uL of CellTiter-Glo® reagent was added to each well of the 96-well plate and stored for 30 minutes to 55 minutes at room temperature in a dark room before measurement using Wallac Victor2 1420 Multilabel Counter (program luminescence, measurement time: 0.5 s). Before measurement, 180 uL was collected from each well and transferred to measurable 96-MicroWell Optical Bottom white plate. Wells containing only a culture solution without the inoculation of the cells were assayed as blanks. The method for calculating the concentration of the antibody-drug conjugate at which the growth or survival of cells was inhibited by 50% was described in the evaluation method as to the adherent cells.

Figure 8B:
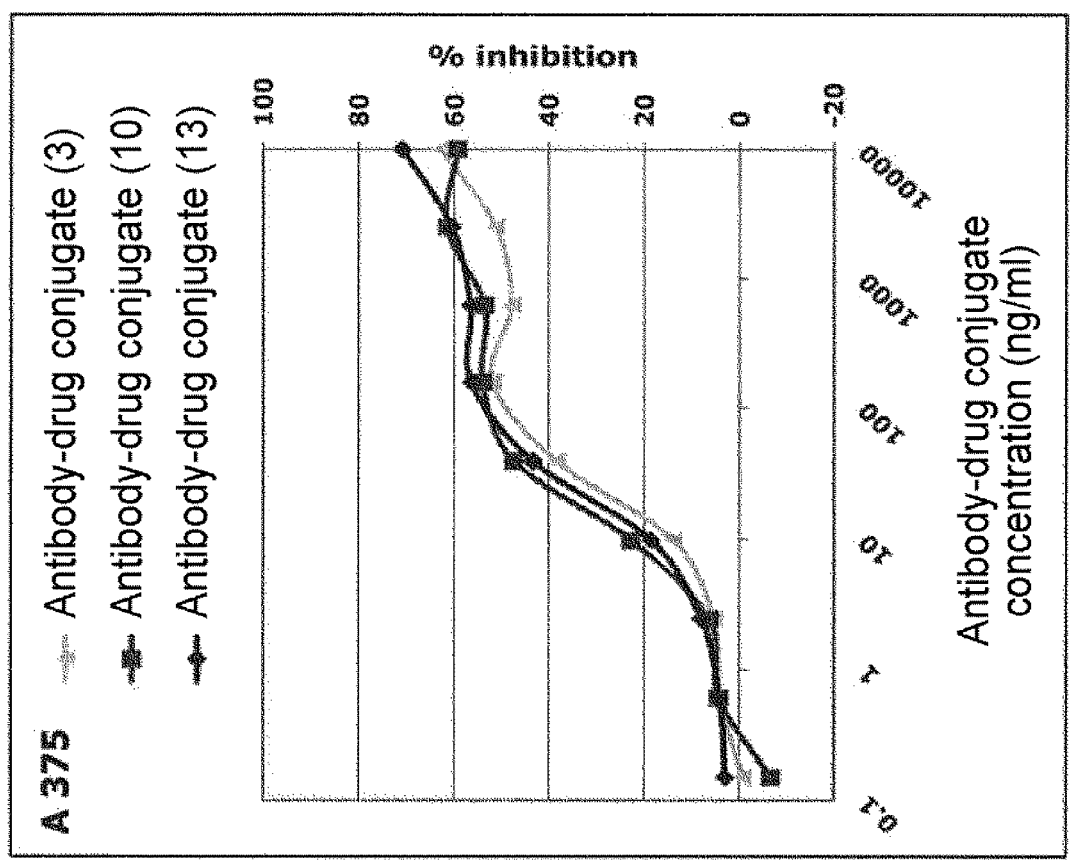
FIGS. 8A and 8B show results of a test on the inhibition of mitogenic or survival signals by each HER3 antibody-drug conjugate in a human melanoma line (A375).
Figure 8A:
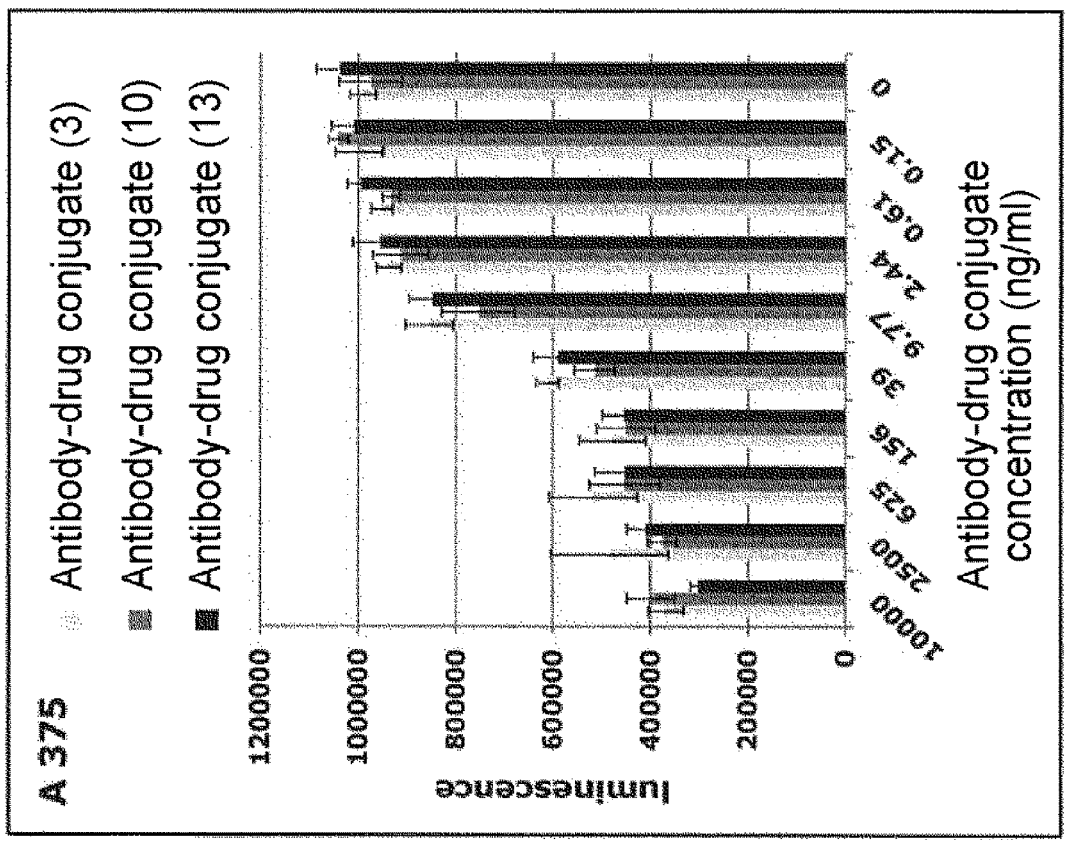
Figure 9A:
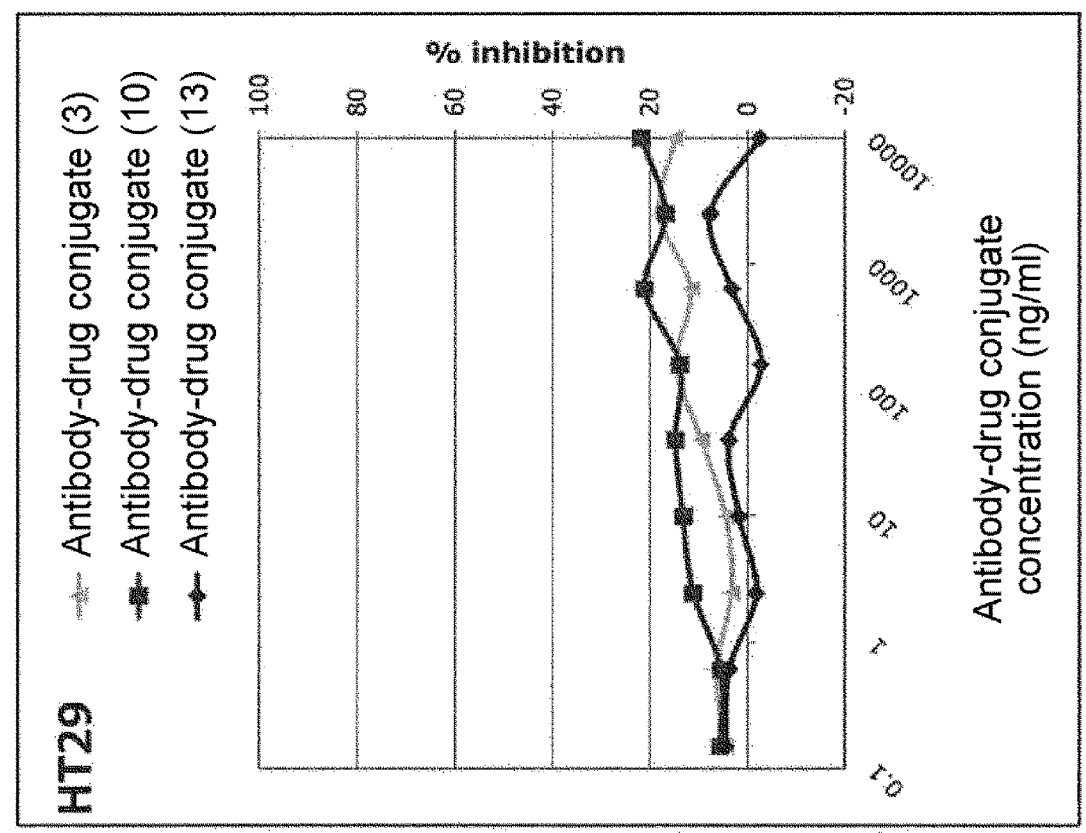
FIGS. 9A and 9B show results of a test on the inhibition of mitogenic or survival signals by each HER3 antibody-drug conjugate in a human colorectal cancer line (HT29).
Figure 9B:
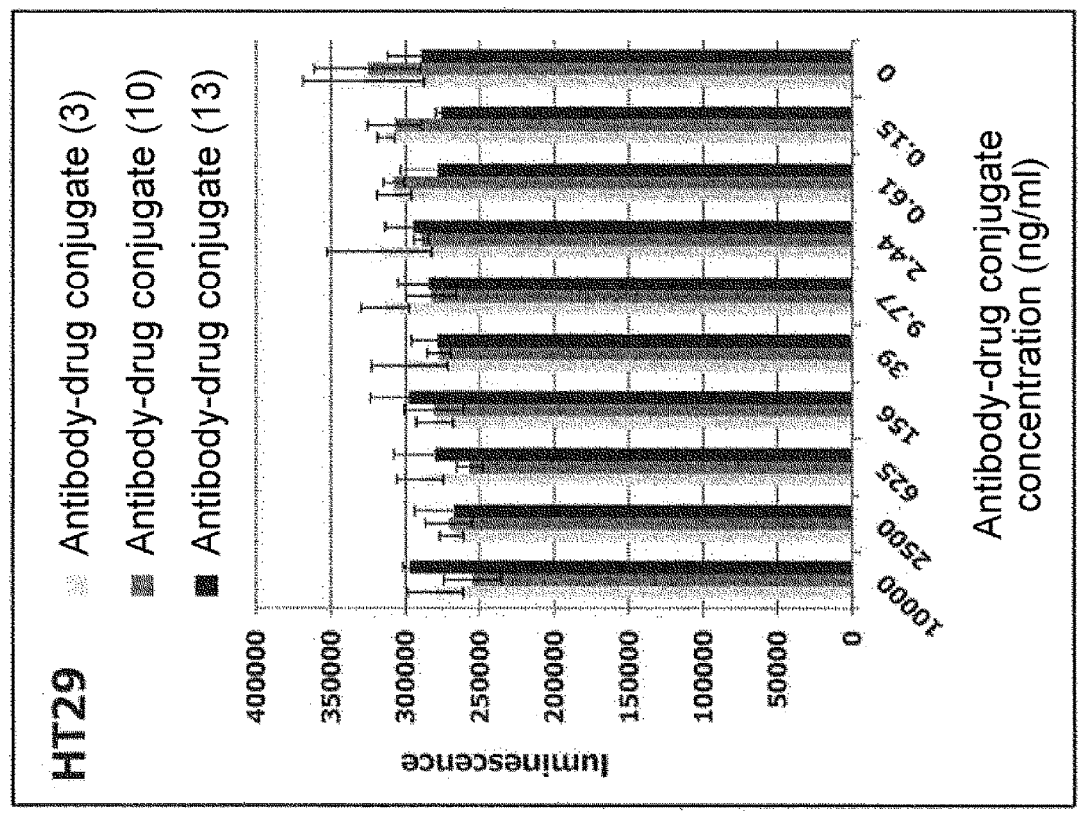
Figure 10A:
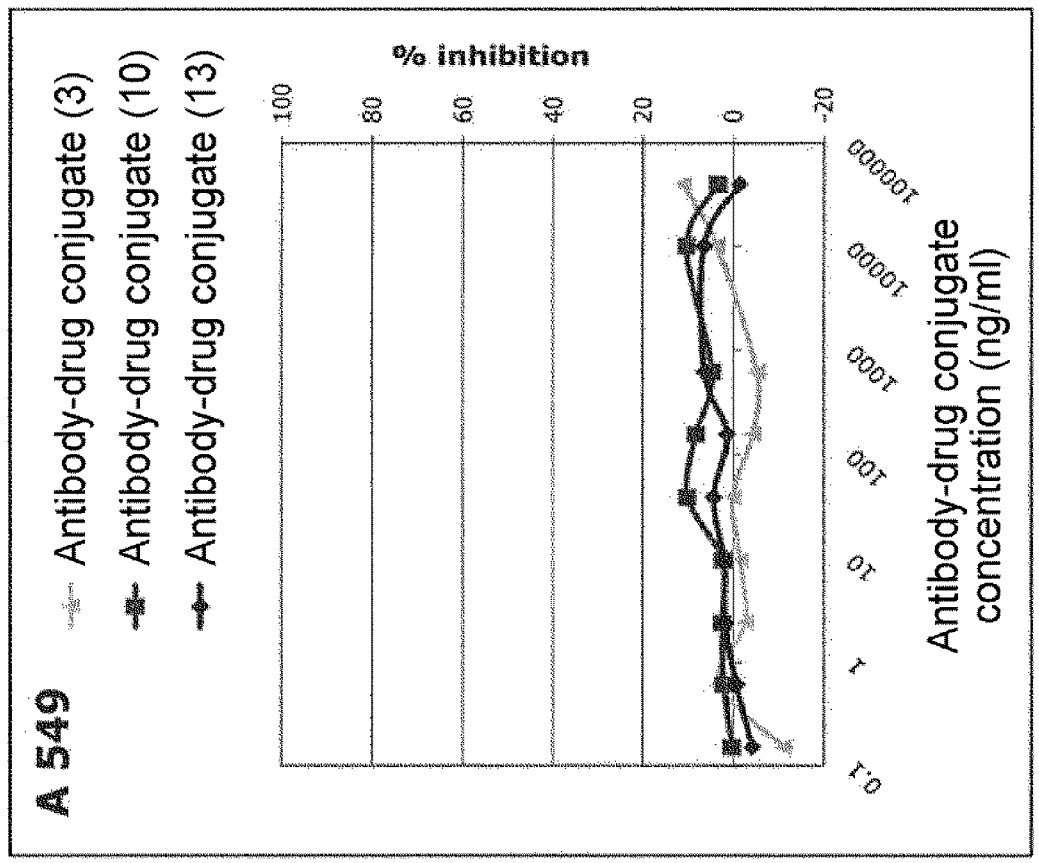
FIGS. 10A and 10B show results of a test on the inhibition of mitogenic or survival signals by each HER3 antibody-drug conjugate in a human lung cancer line (A549).
Figure 10B:
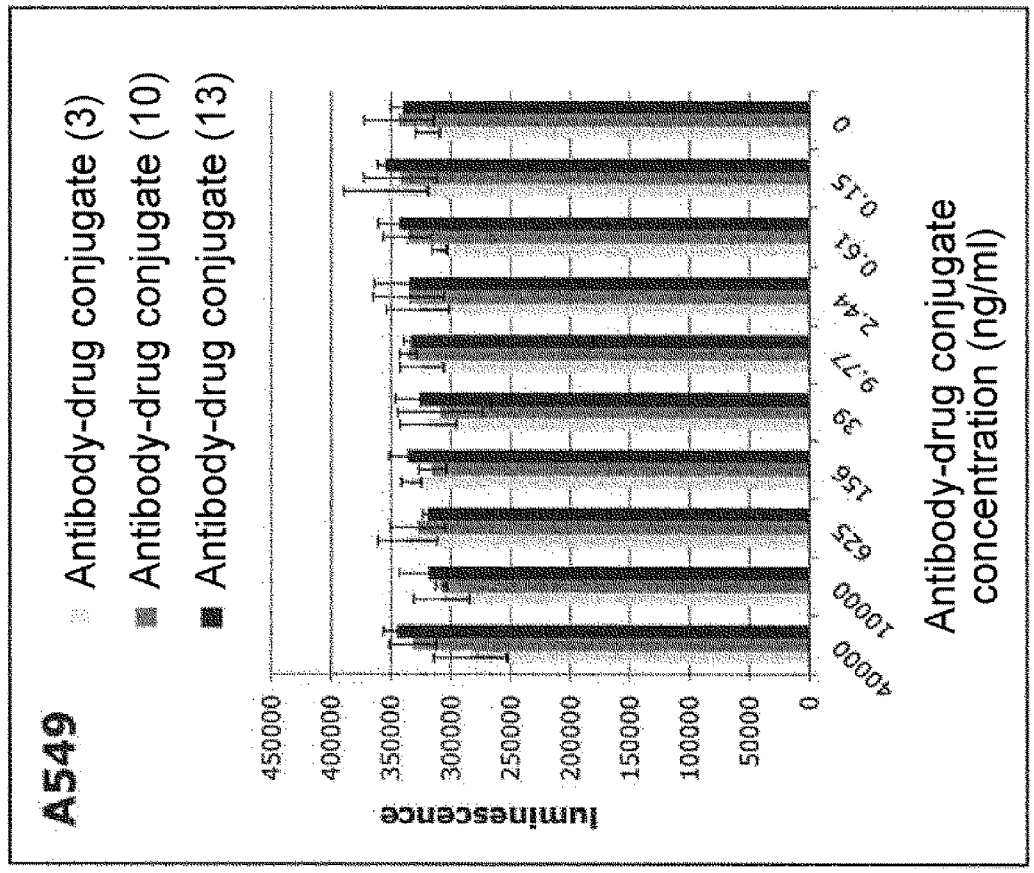

The results about the human breast cancer lines HCC1569 and MDA-MB453 are shown in FIGS. 6A-6B, and 7A-7B, respectively. The results about the human melanoma line A375 is shown in FIGS. 8A and 8B. The results about the human colorectal cancer line HT29 are shown in FIGS. 9A and 9B. The results about the human lung cancer line A549 are shown in FIGS. 10A and 10B. A of each figure shows cell growth or survival derived from the antibody-drug conjugate in the presence of 10% FBS. The ordinate depicts a luminescence value indicating the ATP activity of each sample. The abscissa depicts the concentration of each antibody-drug conjugate. The data is indicated by mean+/−standard deviation of triplicates. B of each figure shows the rate of reduction in luminescence caused by antibody-drug conjugate treatment when the luminescence of an untreated group was defined as 100%.

Three types of antibody-drug conjugates were added to various human cancer cell lines in the presence of 10% FBS and evaluated for in vitro growth in 2D or 3D systems. The rate of inhibition of cell growth or development in the untreated group or by each antibody-drug conjugate was calculated from the CellTiter-Glo® assay of ATP activity. In the evaluation of the ATP activity, these antibody-drug conjugates strongly inhibited the cell growth or survival of two types of breast cancer cell lines (HCC-1569 and MDA-MB-453) and one type of human melanoma line (A375).

The addition of each antibody-drug conjugate and culture (in the presence of 10% FBS) for 7 days reduced the ATP activity by 55 to 75% in HCC1569, by 60 to 83% in MDA-MB-453, and by 60 to 70% in A375. The inhibitory activity of the antibody-drug conjugate against cell growth or survival was not strong in the human colorectal cancer line HT-29 and the human lung cancer line A549 compared with the human breast cancer and human melanoma lines. In HCC-1569 and MDA-MB-453, the antibody-drug conjugate (10) exhibited strong inhibitory activity, which did not largely differ from the inhibitory activity of the antibody-drug conjugate (3) in vitro. By contrast, in both of the human breast cancer lines, the antibody-drug conjugate (13) exhibited low activity and required a concentration of 15 nM for achieving 50% inhibition of cell growth or survival, though the antibody-drug conjugate (3) or the antibody-drug conjugate (10) achieved this inhibition at 1 nM or lower. In the human melanoma line compared with the human breast cancer lines, the activity of the antibody-drug conjugate (13) was equivalent to that of the antibody-drug conjugate (3) or the antibody-drug conjugate (10).

All of the antibody-drug conjugates supported a maximum rate of inhibition on the order of 61 to 68%. The antibody-drug conjugates achieved 50% inhibition of ATP activity at a concentration of 1 to 4 nM.

In addition to the aforementioned test, the inhibitory activity of the antibody-drug conjugate (13) against the cell growth or survival of a human ovarian cancer cell line OVCAR-8 was also confirmed in vitro (data not shown).

Test Example 5 Comparison of Rate of Inhibition of In Vitro Cell Growth or Survival of Human Cancer Cell Line Depending on the Number of Drug Molecules (High or Medium) Loaded on Antibody-Drug Conjugate Method:

Antibody-drug conjugates differing in the number of loaded drug molecules were evaluated for in vitro inhibitory activity against cell growth or survival. The high drug loading represents the state where 5 to 7 drug molecules are conjugated with an antibody, and the middle drug loading represents the state where about 3 drug molecules are conjugated with an antibody. The average number of drug molecules conjugated with one antibody was measured by the UV method (described in other parts of the present invention).

The average number of drug molecules conjugated with one antibody:
  High drug loading <HDL>
  Antibody-drug conjugate (3): 4.9
  Antibody-drug conjugate (10): 6.2
  Antibody-drug conjugate (13): 6.2
  Middle drug loading <MDL>
  Antibody-drug conjugate (4): 2.9
  Antibody-drug conjugate (11): 3.0
  Antibody-drug conjugate (14): 2.5

The inhibitory activity of each HER3 antibody-drug conjugate against mitogenic or survival signals was measured in the presence of 10% FBS. The growth and development of cells were evaluated by measuring adenosine triphosphate (ATP) activity in untreated and antibody-drug conjugate-treated groups. The cancer cell line was suspended in 100 uL of each medium at a low density (750 cells/well for a human breast cancer cell line MDA-MB-453 (CLB-22)) from ATCC) and inoculated to 96-MicroWell Optical Bottom white plate (Thermo Fisher Scientific Inc./Nunc, #165306). The cells were cultured in an RPMI1640 medium (Invitrogen Corp., 31870-025) containing 10% FBS (Invitrogen Corp., 10270-106) and 2 mM glutamine (Invitrogen Corp., 25030-024). The edge wells of each plate were filled with 100 uL of a medium.

The cells were cultured for 3 days, and the medium was replaced with 95 uL of a fresh medium before antibody-drug conjugate addition. The antibody-drug conjugate (3), the antibody-drug conjugate (10), the antibody-drug conjugate (13), the antibody-drug conjugate (4), the antibody-drug conjugate (11), and the antibody-drug conjugate (14) were used. An untreated group was set as a control for measuring normal cell growth.

By adding 5 uL of each antibody-drug conjugate concentrated into a 20-fold concentration to 95 uL of a culture medium (10% FBS) contained in each well of the 96-well plate, the final concentration was established. Only 5 ul of a medium was added to each control well. The test was conducted in triplicate per sample. In order to calculate the concentration of the antibody-drug conjugate at which the growth or survival of cells was reduced by 50%, concentrations of the antibody-drug conjugate were prepared by 4-fold dilutions (10 ug/mL to 0.15 ng/mL), and the cells were treated with these concentrations of the antibody-drug conjugate and compared with the untreated group in terms of ATP activity. Evaluation was carried out by 7-day culture of the cells thus supplemented with the antibody-drug conjugate. CellTiter-Glo® Luminescent Cell Viability Assay was used for evaluating the activity of the antibody-drug conjugate. This method involves measuring living cells having metabolic activity on the basis of ATP activity and finally estimating the number of living cells and employed CellTiter-Glo® Luminescent Cell (Promega K.K., G7573) as a kit. 100 uL of CellTiter-Glo® reagent was added to each well of the 96-well plate and stored for 25 minutes to 55 minutes at room temperature in a dark room before measurement using Wallac Victor2 1420 Multilabel Counter (program luminescence, measurement time: 0.5 s). Wells containing only a culture solution without the inoculation of the cells were assayed as blanks. In order to measure reduction in ATP activity, an average luminescence value of 3 wells was calculated under each condition (Microsoft Excel 2010). In order to remove cell-independent signals, the average luminescence value of the blanks was subtracted from the average luminescence value of the cells treated with the antibody-drug conjugate (Microsoft Excel 2010). The rate of reduction (%) in luminescence was calculated by comparison with the cells of the untreated group (Microsoft Excel 2010). This value was interpreted as the rate of inhibition (%) of cell growth or survival.

Figure 12:
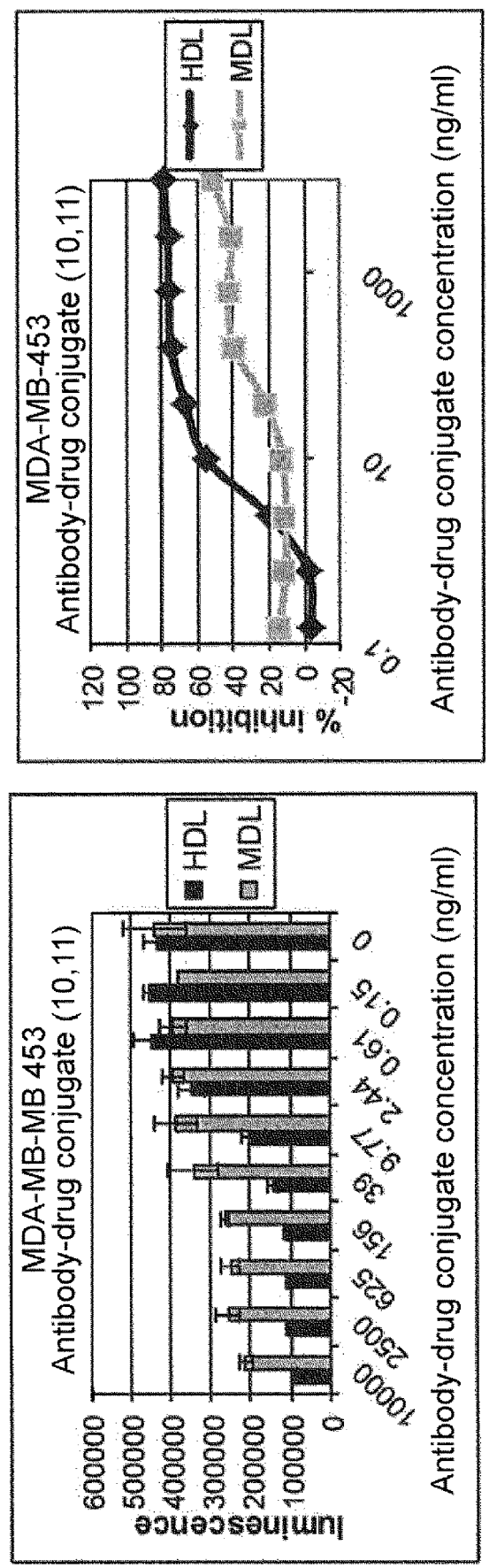
FIG. 12 shows results of comparing the rate of inhibition of cell growth or survival between the antibody-drug conjugate (10) and the antibody-drug conjugate (11). The left diagram shows the rate of inhibition of cell growth or survival derived from the antibody-drug conjugate in the presence of 10% FBS. The ordinate depicts luminescence indicating the ATP activity of each sample. The abscissa depicts the concentration of each antibody-drug conjugate. The data is indicated by mean+/−standard deviation of triplicates. The right diagram shows the comparison of the rate of reduction in luminescence caused by antibody-drug conjugate treatment between high drug loading (HDL) and middle drug loading (MDL) when the luminescence of an untreated group was defined as 100%.
Figure 13:
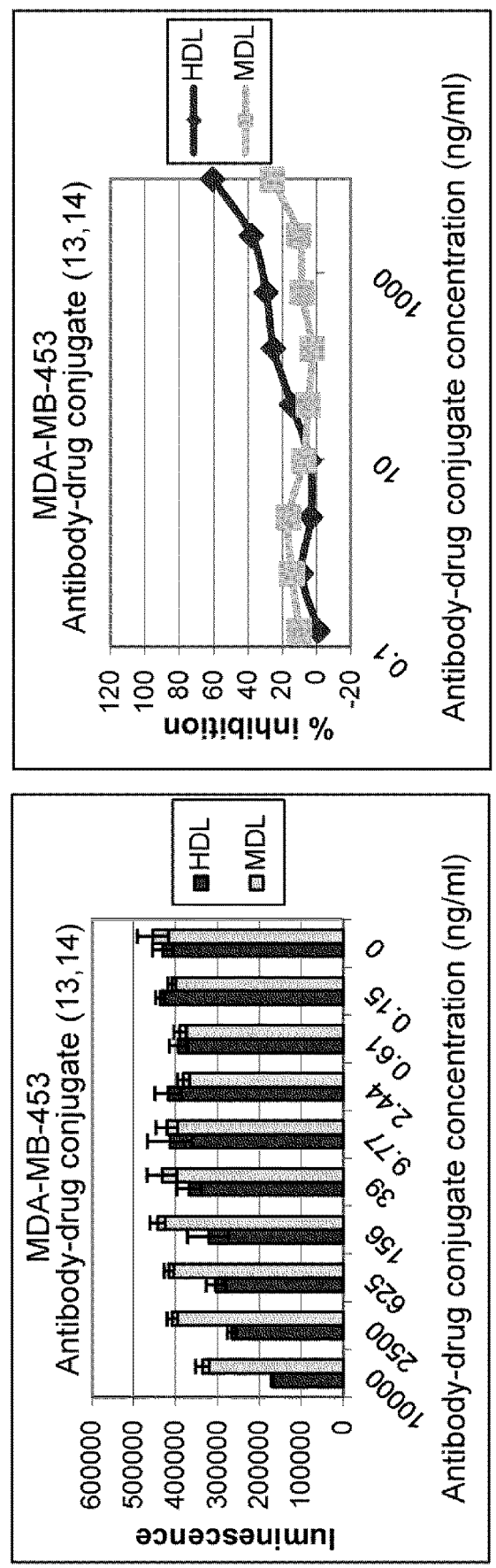
FIG. 13 shows results of comparing the rate of inhibition of cell growth or survival between the antibody-drug conjugate (13) and the antibody-drug conjugate (14). The left diagram shows the rate of inhibition of cell growth or survival derived from the antibody-drug conjugate in the presence of 10% FBS. The ordinate depicts luminescence indicating the ATP activity of each sample. The abscissa depicts the concentration of each antibody-drug conjugate. The data is indicated by mean+/−standard deviation of triplicates. The right diagram shows the comparison of the rate of reduction in luminescence caused by antibody-drug conjugate treatment between high drug loading (HDL) and middle drug loading (MDL) when the luminescence of an untreated group was defined as 100%.

The results are shown in FIGS. 11 to 13. FIG. 11 shows the results of comparing the antibody-drug conjugate (3) with the antibody-drug conjugate (4). FIG. 12 shows the results of comparing the antibody-drug conjugate (10) with the antibody-drug conjugate (11). FIG. 13 shows the results of comparing the antibody-drug conjugate (13) with the antibody-drug conjugate (14). In each figure, the left diagram shows the rate of inhibition of cell growth or survival derived from the antibody-drug conjugate in the presence of 10% FBS in one of the triplicate tests. The ordinate depicts luminescence indicating the ATP activity of each sample. The abscissa depicts the concentration of each antibody-drug conjugate. The right diagram shows the comparison of the rate of reduction in luminescence caused by antibody-drug conjugate treatment between high drug loading (HDL) and middle drug loading (MDL) when the luminescence of an untreated group was defined as 100%.

The high drug loading and middle drug loading antibody-drug conjugates inhibited cell growth or survival through the treatment and 7-day culture of MDA-MB-453. As already shown in the results about the high drug loading, the middle drug loading antibody-drug conjugate (11) exhibited high activity at the same level as that of the antibody-drug conjugate (4). In the comparison between the numbers of loaded drug molecules, the antibody-drug conjugates having a high number of loaded drug molecules exhibited higher reduction in ATP than that of the middle drug loading ones. The antibody-drug conjugate (3), the antibody-drug conjugate (10), and the antibody-drug conjugate (13) having a high number of loaded drug molecules exhibited rates of inhibition of 68%, 76%, and 56%, respectively, at a concentration of 10 ug/mL, whereas the antibody-drug conjugate (4), the antibody-drug conjugate (11), and the antibody-drug conjugate (14) having a middle number of loaded drug molecules merely exhibited rates of inhibition of 44%, 47%, and 27%, respectively, at this concentration. The antibody-drug conjugates having a high number of loaded drug molecules were superior in 50% inhibition concentration of cancer cell growth or survival to the antibody-drug conjugates having a middle number of loaded drug molecules. The antibody-drug conjugate (3) or the antibody-drug conjugate (10) having a high number of loaded drug molecules required 15 ng/mL (1 nM) of the antibody-drug conjugate for reducing the ATP activity value by 50%. The antibody-drug conjugate (13) reduced the ATP activity by 50% at least at the highest concentration tested. By contrast, reduction in ATP activity corresponding to this was not observed at 1000 ng/mL (67 nM) or lower within the range of concentrations of the evaluated antibody-drug conjugates having a middle number of loaded drug molecules. The in vitro comparison between the high number of loaded drug molecules and the middle number of loaded drug molecules suggested that an antibody-drug conjugate having a high number of loaded drug molecules is also superior in in vivo inhibitory activity against the growth of cancer cells.

Test Example 6 Antibody-Drug Conjugates (3), (10), and (13) Exhibited Antitumor Effect in In Vivo Antitumor Test Using Human Breast Cancer Five-week-old female BALB/C nude mice having a body weight of 15 to 20 g after acclimation were used. The mice were placed in individually ventilated cages (IVC, 4 mice at maximum per cage) which were kept at room temperature and a constant humidity. After randomization, the body weights of the mice were measured every other day, and the behaviors of the animals were recorded every day. $5 \times 10^6$ cells of a human breast cancer cell line HCC1569 (CRL-2330) from ATCC were suspended in a solution prepared from 50 uL of PBS and Matrigel (PBS: PAA #H21-002, Matrigel: BD #354230) mixed at a ratio of 1:1, and subcutaneously transplanted to the right side area of the body of each BALB/C nude mouse using a 29 G needle.

The body weights were measured using a weight scale (Mettler Toledo PB602-L). The major axis and minor axis of the tumor were measured twice a week using an electronic digital caliper (manual caliper, OMC Fontana), and the tumor volume (mm$^3$) was calculated. The calculation was carried out according to the following expression (the same holds true for Test Examples described below).

Tumor volume (mm$^3$)=½×Major axis (mm)×[Minor axis (mm)]$^2$

At Day 19 when the tumor size reached about 150 mm$^3$, 70 animals were randomly divided into 7 groups on the basis of their tumor sizes. At the same day, the antibody-drug conjugate (3), (10), or (13) or PBS for a control group were administered into the tail vein of each animal at the following doses.

Administration group: PBS was intravenously injected once a week at the same dose as the antibody-drug conjugate.

Administration group: The antibody-drug conjugate (3) was intravenously injected once a week at 3 or 10 mg/kg.

Administration group: The antibody-drug conjugate (10) was intravenously injected once a week at 3 or 10 mg/kg.

Administration group: The antibody-drug conjugate (13) was intravenously injected once a week at 3 or 10 mg/kg.

All data were indicated by mean+/−SEM. The tumor sizes and the body weights were evaluated by mean+/−SEM. All data were analyzed using Microsoft Excel 2009 (the same holds true for Test Examples described below).

Figure 14:
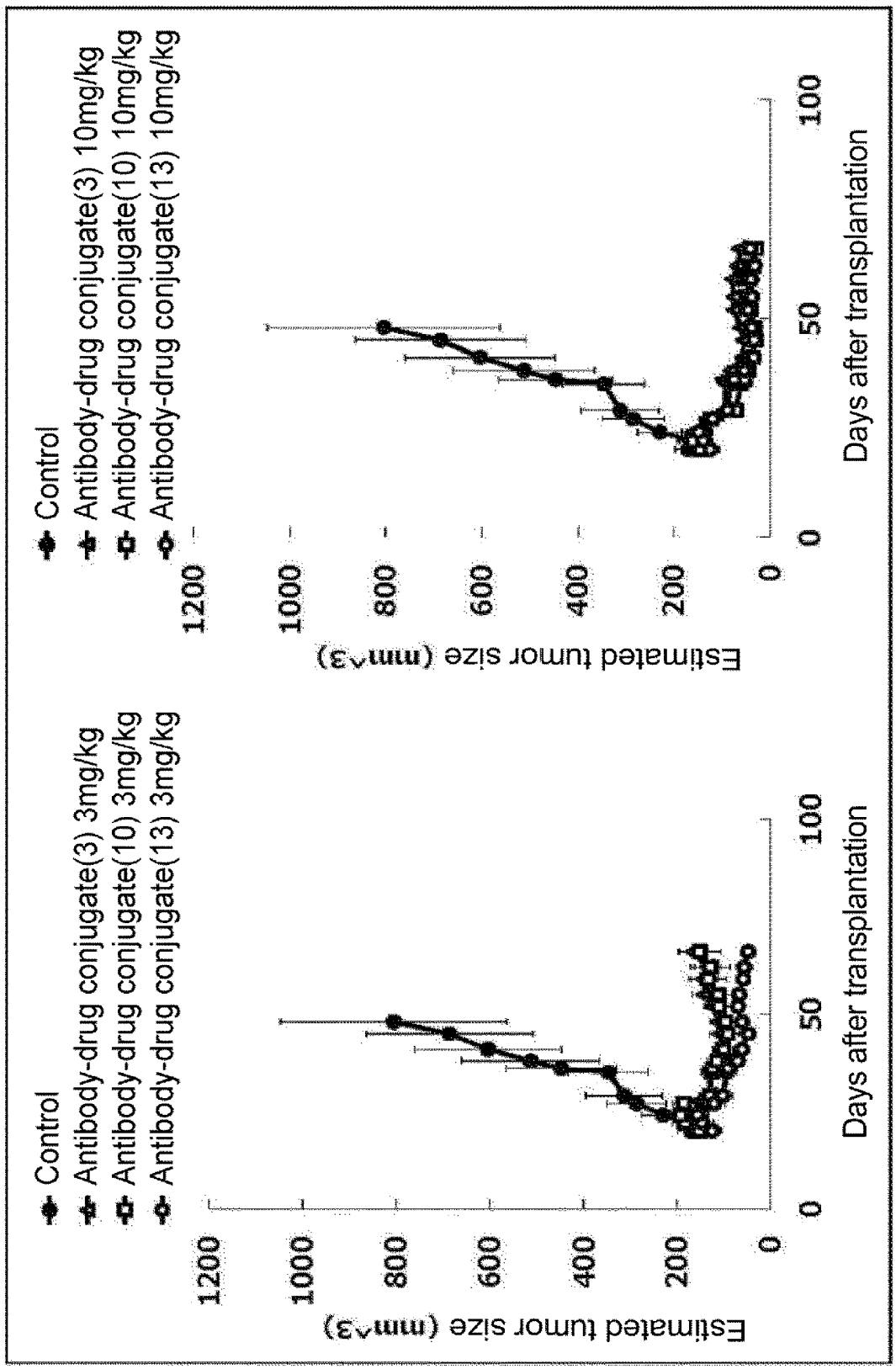
FIG. 14 shows results of a human breast cancer (HCC1569) antitumor test using the antibody-drug conjugate (3), (10), or (13). The ordinate depicts an average tumor volume. The abscissa depicts the number of days from cell transplantation. All values are indicated by mean+/−standard deviation. The initial tumor volume and the initial mouse weight were analyzed on the basis of descriptive data (mean and standard deviation) using Microsoft Excel 2009.

The results are shown in FIG. 14. The PBS administration group was euthanized at Day 53 after the transplantation, because the tumor sizes exceeded the acceptable maximum level. The inhibition of tumor growth of the human breast cancer cell line was observed in all of the antibody-drug conjugate administration groups compared with the control group. No weight loss was observed in the mice of the treated groups.

Test Example 7 Antibody-Drug Conjugates (3), (10), and (13) Exhibited Antitumor Effect in Antitumor Test Using Human Melanoma Five- to 6-week-old female NMRI nude mice having a body weight of 22 to 26 g after acclimation were used. The mice were placed in individually ventilated cages (IVC, 4 mice at maximum per cage) which were kept at room temperature and a constant humidity. After randomization, the body weights of the mice were measured every other day, and the behaviors of the animals were recorded every day.

$5 \times 10^6$ cells of a human melanoma cell line HT-144 (HTB-63) from ATCC were suspended in a solution prepared from 50 uL of PBS and Matrigel (PBS: PAA #H21-002, Matrigel: BD #354230) mixed at a ratio of 1:1, and subcutaneously transplanted to the right side area of the body of each NMRI nude mouse using a 29 G needle.

The measurement of the body weights and the tumor sizes and the measurement and calculation of the tumor volumes were carried out in the same manner as Test Example 6.

At Day 22 when the tumor size reached about 150 mm$^3$, 80 animals were randomly divided into 8 groups on the basis of their tumor sizes. At the same day, U1-59 or the antibody-drug conjugate (3), (10), or (13) or PBS for a control group were administered into the tail vein of each animal at the following doses.

Administration group: PBS was intravenously injected once a week at the same dose as the antibody-drug conjugate.

Administration group: U1-59 was subcutaneously injected twice a week at 25 mg/kg.

Administration group: The antibody-drug conjugate (3) was intravenously injected once a week at 3 or 10 mg/kg.

Administration group: The antibody-drug conjugate (10) was intravenously injected once a week at 3 or 10 mg/kg.

Administration group: The antibody-drug conjugate (13) was intravenously injected once a week at 3 or 10 mg/kg.

Figure 15:
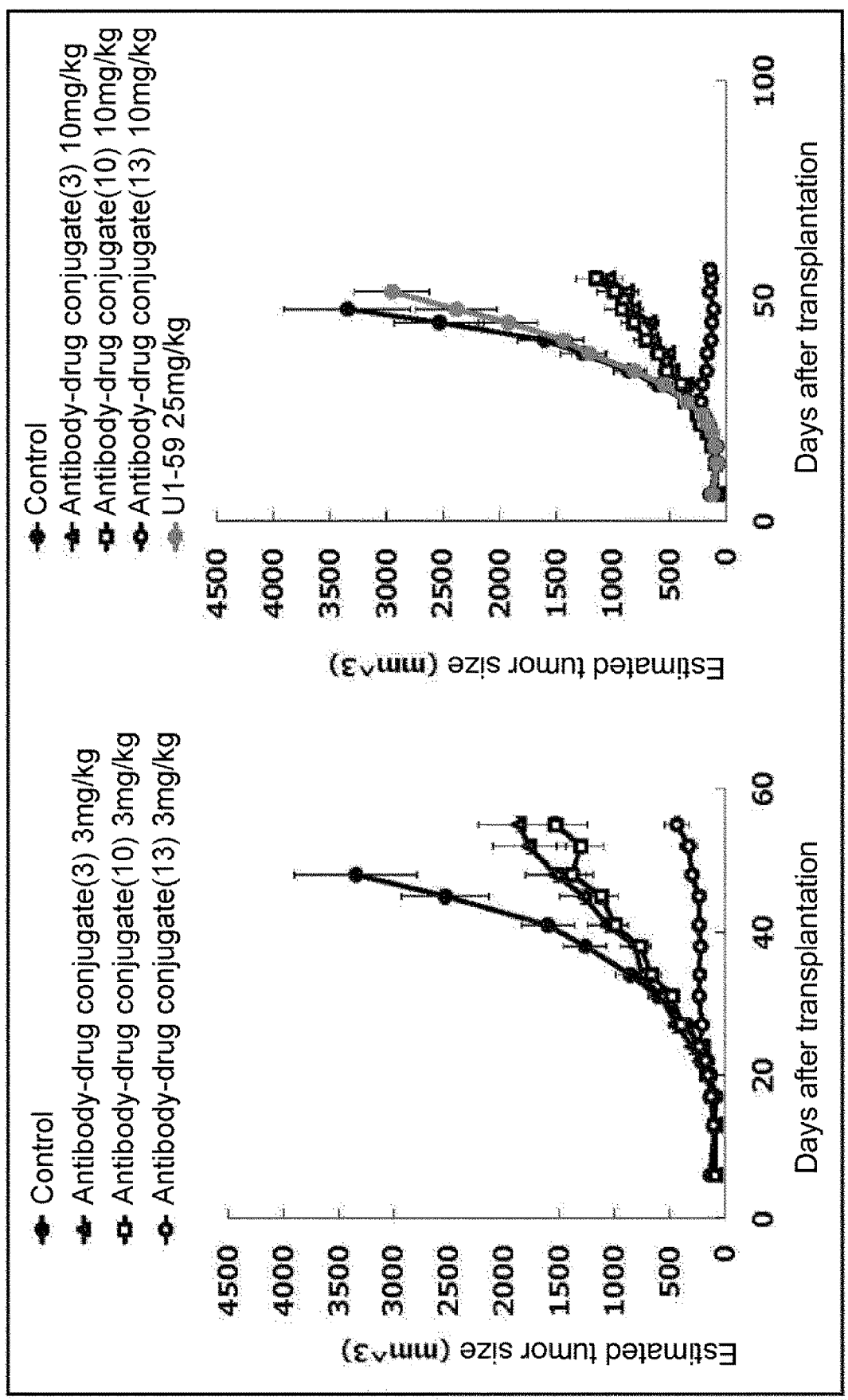
FIG. 15 shows results of a human melanoma (HT-144) antitumor test using the antibody-drug conjugate (3), (10), or (13). The ordinate depicts an average tumor volume. The abscissa depicts the number of days from cell transplantation. All values are indicated by mean+/−standard deviation. The initial tumor volume and the initial mouse weight were analyzed on the basis of descriptive data (mean and standard deviation) using Microsoft Excel 2009.

The results are shown in FIG. 15. The PBS and U1-59 administration groups were euthanized at Days 48 and 52, respectively, after the transplantation, because the tumor sizes exceeded the acceptable maximum level. The inhibition of tumor growth of the human melanoma cell line was observed in all of the antibody-drug conjugate administration groups compared with the control group and the U1-59 administration group.

Test Example 8 Antibody-Drug Conjugates (3), (10), and (13) Exhibited Antitumor Effect in Antitumor Test Using Human Breast Cancer Line Sixteen-week-old female SCID nude mice having a body weight of 17 to 25.5 g after acclimation were used. The mice were placed in individually ventilated cages which were kept at room temperature and a constant humidity.

For solid tumors derived from a human breast cancer cell line MDA-MB-453 (CLB-22) from ATCC, MDA-MB-453 in the first passage (Batch 1089) was transplanted to 3 mice (two areas per mouse: right and left side areas of the body). After 13 to 17 weeks, tumor sections were recovered and cryopreserved. For the second passage, the tumor section (2×2×2 mm) of the first passage was further subcutaneously transplanted (10 mice, two areas per mouse: right and left side areas of the body) and allowed to grow for tumor formation for 7 weeks. The tumor thus formed was prepared into a tumor section (2×2×2 mm, second passage) and transplanted to the right side area of the body of each SCID nude mouse.

The body weights were measured using a weight scale. The major axis (length) and diameter of the tumor were measured using an electronic digital caliper (Pro-Max 150 mm hand-held calipers, Fred V. Fowler Co., Inc.), and the tumor volume (mm³) was calculated. The calculation was carried out according to the following expression.

$$\text{Tumor volume (mm}^3\text{)} = \text{pi}/6 \times \text{Major axis (mm)} \times [\text{Diameter (mm)}]^2$$

At Day 40 when the tumor size reached about 143 mm³, 72 animals were randomly divided into 8 groups on the basis of their tumor sizes. At the same day, U1-59 or the antibody-drug conjugate (3), (10), or (13) or PBS for a control group were administered into the tail vein of each animal at the following doses.

Administration group: PBS was intravenously injected once a week at the same dose as the antibody-drug conjugate.

Administration group: U1-59 was subcutaneously injected twice a week at 25 mg/kg.

Administration group: The antibody-drug conjugate (3) was intravenously injected once a week at 3 or 10 mg/kg.

Administration group: The antibody-drug conjugate (10) was intravenously injected once a week at 3 or 10 mg/kg.

Administration group: The antibody-drug conjugate (13) was intravenously injected once a week at 3 or 10 mg/kg.

Figure 16:
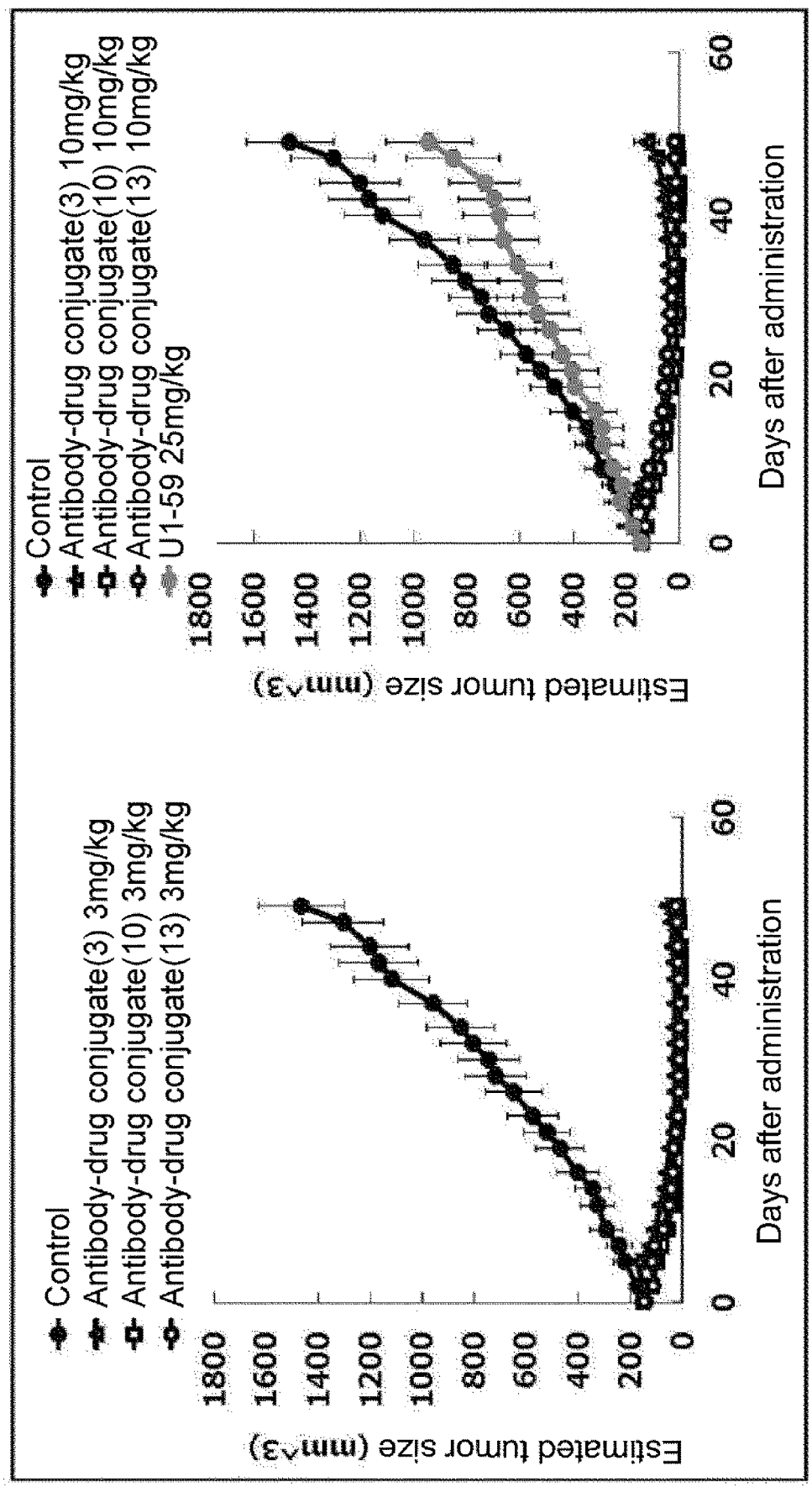
FIG. 16 shows results of a human breast cancer (MDA-MB-453) antitumor test using the antibody-drug conjugate (3), (10), or (13). The ordinate depicts an average tumor volume. The abscissa depicts the number of days from administration. All values are indicated by mean+/−standard deviation. The initial tumor volume and the initial mouse weight were analyzed on the basis of descriptive data (mean and standard deviation) using Microsoft Excel 2009.

The results are shown in FIG. 16. The inhibition of tumor growth of the human breast cancer cell line was observed in all of the antibody-drug conjugate administration groups compared with the control group and the U1-59 administration group. No weight loss was observed in the mice of the treated groups. Further, in other antitumor test using human breast cancer cell line HCC1954 or JIMT1-PR10 (trastzumab-,pertuzumab- and T-DM1-resistant), the inhibition of tumor growth was also observed in the antibody-drug conjugate (16a) administration group compared with the control group.

Test Example 9 Antibody-Drug Conjugates (3), (10), and (13) Exhibited Antitumor Effect in Antitumor Test Using Human Colorectal Cancer Line Five- to 6-week-old female NMRI nude mice having a body weight of 15 to 20 g after acclimation were used. The mice were placed in individually ventilated cages (IVC, 4 mice at maximum per cage) which were kept at room temperature and a constant humidity. After randomization, the body weights of the mice were measured every other day, and the behaviors of the animals were recorded every day.

4×10⁶ cells of a human colorectal cancer cell line HT-29 (CPQ-57) from ProQinase GmbH were suspended in a solution prepared from PBS and Matrigel (PBS: PAA #H21-002, Matrigel: BD #354230) mixed at a ratio of 1:1, and subcutaneously transplanted to the right side area of the body of each NMRI nude mouse using a 29 G needle.

The measurement of the body weights and the tumor sizes and the measurement and calculation of the tumor volumes were carried out in the same manner as Test Example 6.

At Day 8 when the tumor size reached about 150 mm³, 70 animals were randomly divided into 7 groups on the basis of their tumor sizes. At the same day, the antibody-drug conjugate (3), (10), or (13) or PBS for a control group were administered into the tail vein of each animal at the following doses.

Administration group: PBS was intravenously injected once a week at the same dose as the antibody-drug conjugate.

Administration group: The antibody-drug conjugate (3) was intravenously injected once a week at 3 or 10 mg/kg.

Administration group: The antibody-drug conjugate (10) was intravenously injected once a week at 3 or 10 mg/kg.

Administration group: The antibody-drug conjugate (13) was intravenously injected once a week at 3 or 10 mg/kg.

Figure 17:
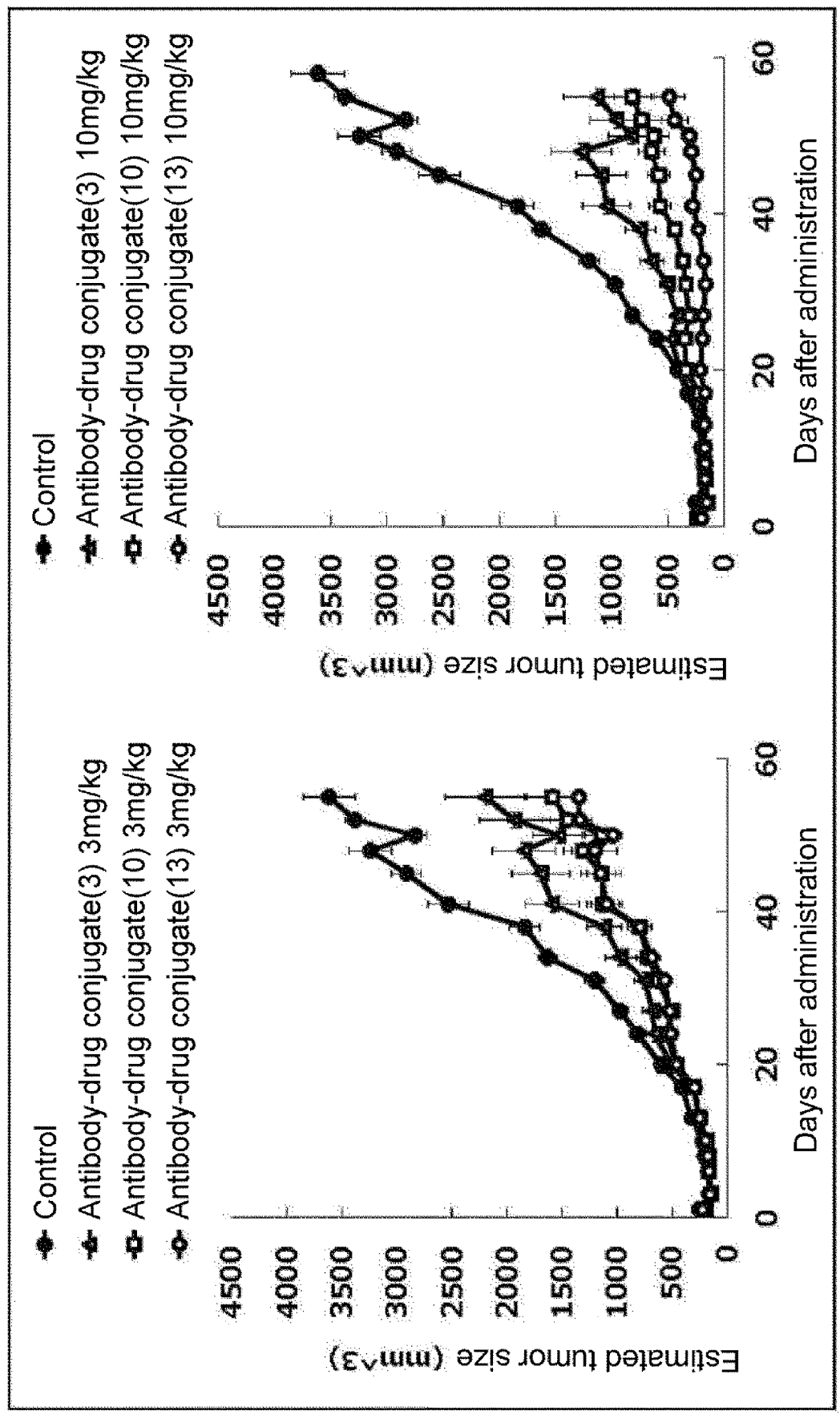
FIG. 17 shows results of a human colorectal cancer line (HT-29) antitumor test using the antibody-drug conjugate (3), (10), or (13). The ordinate depicts an average tumor volume. The abscissa depicts the number of days from administration. All values are indicated by mean+/−standard deviation. The initial tumor volume and the initial mouse weight were analyzed on the basis of descriptive data (mean and standard deviation) using Microsoft Excel 2009.

The results are shown in FIG. 17. The PBS administration group (6 out of the 10 mice), the groups given the antibody-drug conjugate (3) at 3 mg/kg (3 out of the 10 mice) and at 10 mg/kg (4 out of the 10 mice), the groups given the antibody-drug conjugate (10) at 3 mg/kg (2 out of the 10 mice) and at 10 mg/kg (2 out of the 10 mice), and the group given the antibody-drug conjugate (13) at 3 mg/kg (2 out of the 10 mice) were euthanized at Day 50 after the transplantation, because the tumor sizes exceeded the acceptable maximum level or ulcer was formed. The inhibition of tumor growth of the human colorectal cancer cell line was observed in all of the antibody-drug conjugate administration groups compared with the control group. The antibody-drug conjugate (13) exhibited stronger antitumor activity than that of the antibody-drug conjugate (3) or the antibody-drug conjugate (10). No weight loss was observed in the mice of the treated groups.

Test Example 10 Antibody-Drug Conjugates (3), (10), and (13) Exhibited Antitumor Effect in Antitumor Test Using Human Lung Cancer Line Five- to 6-week-old female CD1 nude mice having a body weight of 24 to 28 g after acclimation were used. The mice were placed in individually ventilated cages (IVC, 4 mice at maximum per cage) which were kept at room temperature and a constant humidity. After randomization, the body weights of the mice were measured every other day, and the behaviors of the animals were recorded every day.

5×10⁶ cells of a human lung cancer cell line A549 (CRS-300114) from Cell Lines Service were suspended in a solution prepared from 200 uL of PBS and Matrigel (PBS: PAA #H21-002, Matrigel: BD #354230) mixed at a ratio of 1:1, and subcutaneously transplanted to the right side area of the body of each CD1 nude mouse using a 29 G needle.

The measurement of the body weights and the tumor sizes and the measurement and calculation of the tumor volumes were carried out in the same manner as Test Example 6.

At Day 38 when the tumor size reached about 200 mm³, 70 animals were randomly divided into 7 groups on the basis of their tumor sizes. At the same day, the antibody-drug conjugate (3), (10), or (13) or PBS for a control group were administered into the tail vein of each animal at the following doses.

Administration group: PBS was intravenously injected once a week at the same dose as the antibody-drug conjugate.

Administration group: The antibody-drug conjugate (3) was intravenously injected once a week at 3 or 10 mg/kg.

Administration group: The antibody-drug conjugate (10) was intravenously injected once a week at 3 or 10 mg/kg.

Administration group: The antibody-drug conjugate (13) was intravenously injected once a week at 3 or 10 mg/kg.

Figure 18:
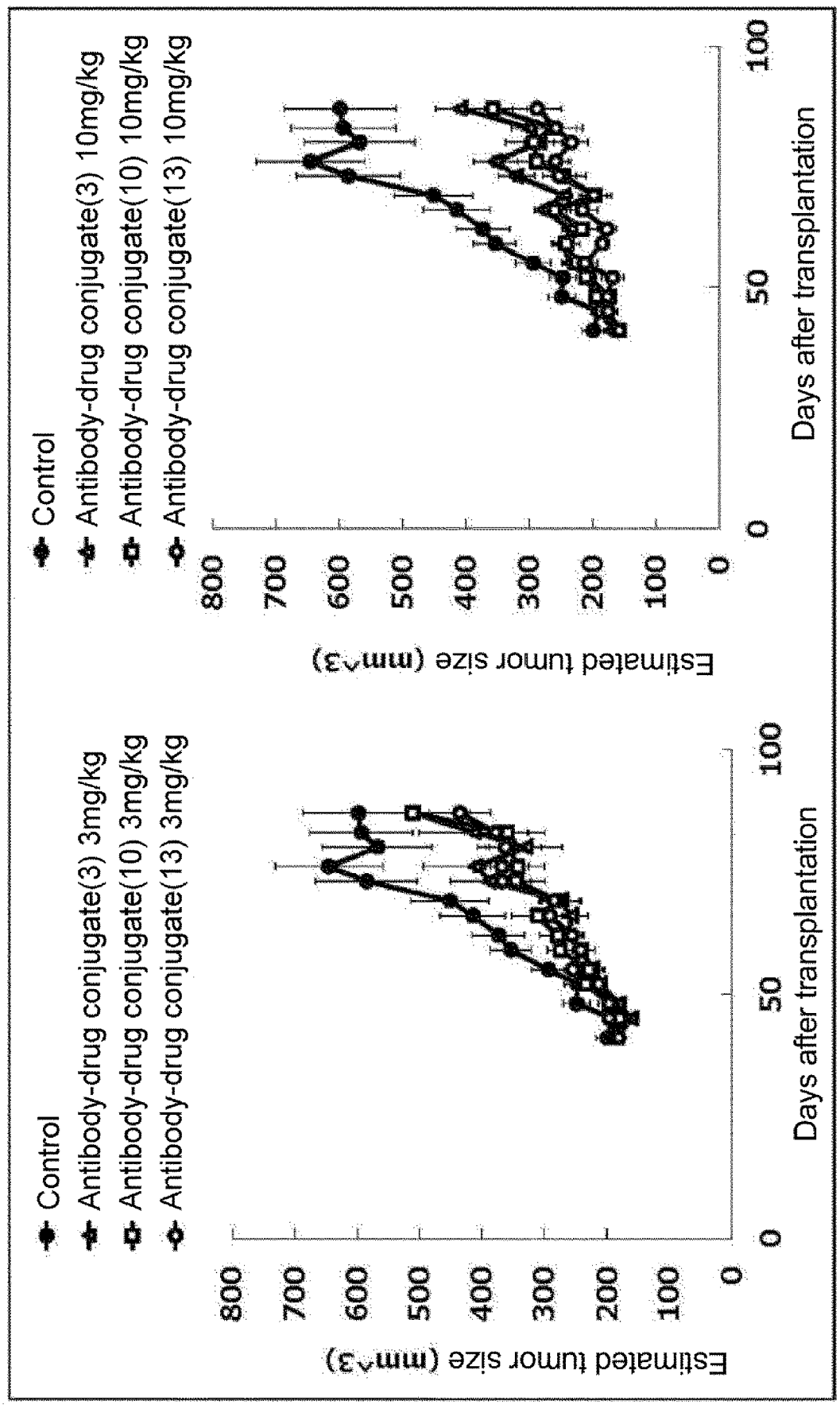
FIG. 18 shows results of a human lung cancer line (A549) antitumor test using the antibody-drug conjugate (3), (10), or (13). The ordinate depicts an average tumor volume. The abscissa depicts the number of days from cell transplantation. All values are indicated by mean+/−standard deviation. The initial tumor volume and the initial mouse weight were analyzed on the basis of descriptive data (mean and standard deviation) using Microsoft Excel 2009.

The results are shown in FIG. 18. The inhibition of tumor growth of the human lung cancer cell line was observed in all of the antibody-drug conjugate administration groups compared with the control group. No weight loss was observed in the mice of the treated groups.

Test Example 11 Antibody-Drug Conjugate (13) Exhibited Antitumor Effect in In Vivo Antitumor Test Using Human Triple-Negative Breast Cancer Line The triple-negative breast cancer refers to a breast cancer that neither expresses hormone receptors (estrogen receptor and progesterone receptor) nor expresses HER2. Since these receptors are not expressed, hormone treatment (tamoxifen, etc.) or anti-HER2 treatment (trastuzumab, trastuzumab emtansine, or pertuzumab) cannot be applied to the cancer. This breast cancer therefore leads to low survival rates, and many therapeutic agents are still under clinical trial. As the expression of HER3 was confirmed in a human triple-negative breast cancer line MDA-MB-468 (data not shown), the antitumor activity of the antibody-drug conjugate was evaluated.

Five- to 6-week-old female CAnN.Cg-Foxn1[nu]/CrlCrlj 〔Foxn1nu/Foxn1nu〕nude mice (Charles River Laboratories Japan, Inc.) having a body weight of 15 to 20 g after acclimation were used. The mice were placed in individually ventilated cages (IVC, 4 mice at maximum per cage) which were kept at room temperature and a constant humidity. After randomization, the body weights of the mice were measured every other day, and the behaviors of the animals were recorded every day.

$5 \times 10^6$ cells of a human triple-negative breast cancer cell line MDA-MB-468 (CRL-2322) from ATCC were suspended in a solution prepared from 200 uL of PBS and Matrigel (PBS: PAA #10010-023, Matrigel: BD #354234) mixed at a ratio of 1:1, and subcutaneously transplanted to the right side area of the body of each nude mouse using a 29 G needle. The body weights were measured using a weight scale (Mettler Toledo PB602-L).

The major axis and minor axis of the tumor were measured using an electronic digital caliper (CD-15CX, Mitsutoyo Corp), and the tumor volume ($mm^3$) was calculated. The calculation was carried out according to the following expression.

Tumor volume ($mm^3$)=½×Major axis (mm)×[Minor axis (mm)]$^2$

At Day 20 when the tumor size reached about 170 $mm^3$, 18 animals were randomly divided into 3 groups on the basis of their tumor sizes. At the same day, U1-59 or the antibody-drug conjugate (13) or PBS for a control group were administered into the tail vein of each animal at the following doses.

Administration group: PBS was intravenously injected once a week at the same dose as the antibody-drug conjugate.

Administration group: U1-59 was intravenously injected once a week at 10 mg/kg.

Administration group: The antibody-drug conjugate (13) was intravenously injected once a week at 10 mg/kg.

Figure 19:
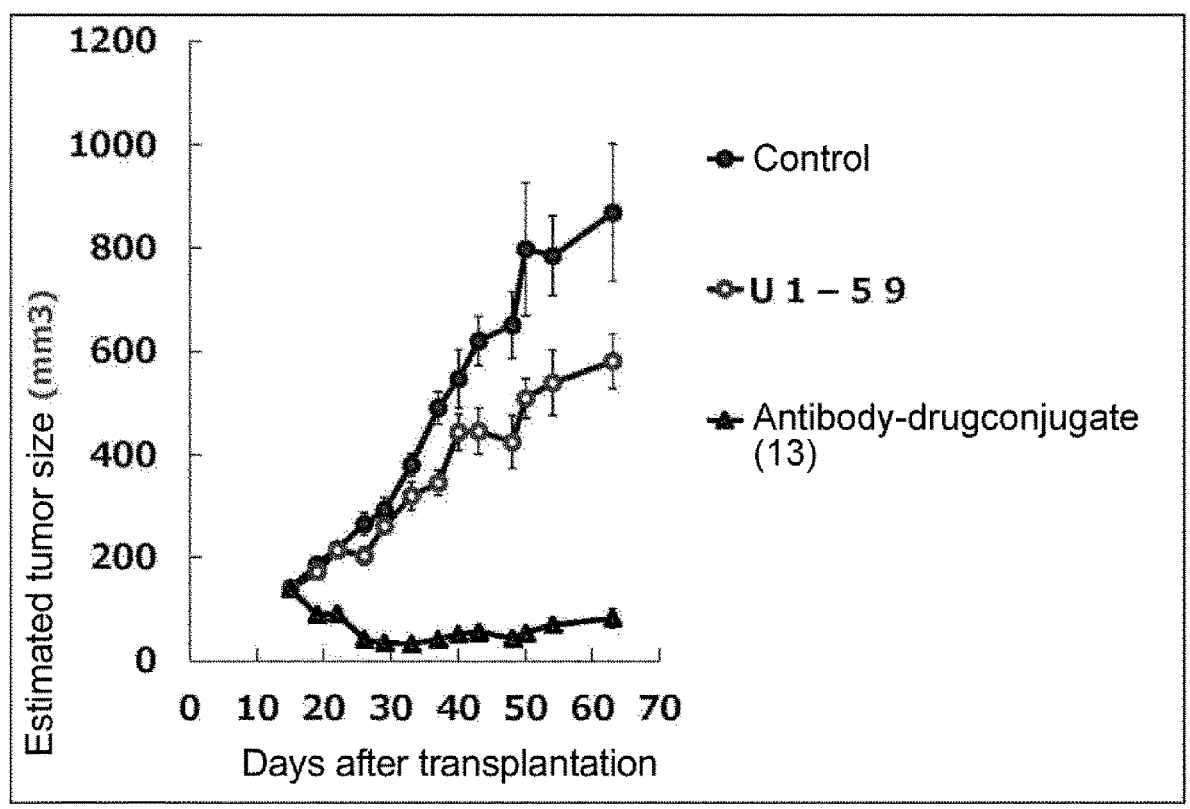
FIG. 19 shows results of a human triple-negative breast cancer line (MDA-MB-468) antitumor test using the antibody-drug conjugate (13). The ordinate depicts an average tumor volume. The abscissa depicts the number of days from cell transplantation. All values are indicated by mean+/−standard deviation. The initial tumor volume and the initial mouse weight were analyzed on the basis of descriptive data (mean and standard deviation) using Microsoft Excel 2009.

The results are shown in FIG. 19. The inhibition of tumor growth of the human triple-negative breast cancer line was observed in the antibody-drug conjugate administration group compared with the control group and the U1-59 administration group. No weight loss was observed in the mice of the treated groups.

Test Example 12 Antibody-Drug Conjugate (16a) Exhibited Antitumor Effect in In Vivo Antitumor Test Using Human Luminal Breast Cancer Line The human luminal breast cancer refers to a breast cancer that expresses hormone receptors (estrogen receptor), but expresses no HER2. Since these receptors are not expressed, anti-HER2 treatment (trastuzumab, trastuzumab emtansine, pertuzumab) cannot be applied to the cancer. This breast cancer therefore leads to low survival rates, and many therapeutic agents are still under clinical trial. As the expression of HER3 was confirmed in a human luminal breast cancer line MCF-7 (data not shown), the antitumor activity of the antibody-drug conjugate was evaluated.

Five- to 6-week-old female athymic nude mice Nude-Foxn1$^{nu}$ (ProQinase GmbH) having a body weight of 15 to 20 g after acclimation were used. The mice were placed in individually ventilated cages (IVC, 4 mice at maximum per cage) which were kept at room temperature and a constant humidity. After randomization, the body weights of the mice were measured every other day, and the behaviors of the animals were recorded every day.

$5 \times 10^6$ cells of a human luminal breast cancer cell line MCF-7 (CRQ-#327) were suspended in a solution prepared from 200 uL of PBS and Matrigel (PBS: PAA #10010-023, Matrigel: BD #354234) mixed at a ratio of 1:1, and subcutaneously transplanted to the right side area of the body of each nude mouse using a 29 G needle. The body weights were measured using a weight scale (Mettler Toledo PB602-L).

The major axis and minor axis of the tumor were measured using an electronic digital caliper (CD-15CX, Mitsutoyo Corp), and the tumor volume ($mm^3$) was calculated. The calculation was carried out according to the following expression.

Tumor volume ($mm^3$)=½×Major axis (mm)×[Minor axis (mm)]$^2$

At Day 11 when the tumor size reached about 250 $mm^3$, 20 animals were randomly divided into 2 groups on the basis of their tumor sizes. At the same day, the antibody-drug conjugate (16a) or PBS for a control group were administered at the following doses.

Administration group: PBS was intravenously injected at the same single dose as the antibody-drug conjugate.

Administration group: The antibody-drug conjugate (16a) was intravenously injected at a single dose of 10 mg/kg.

Figure 20:
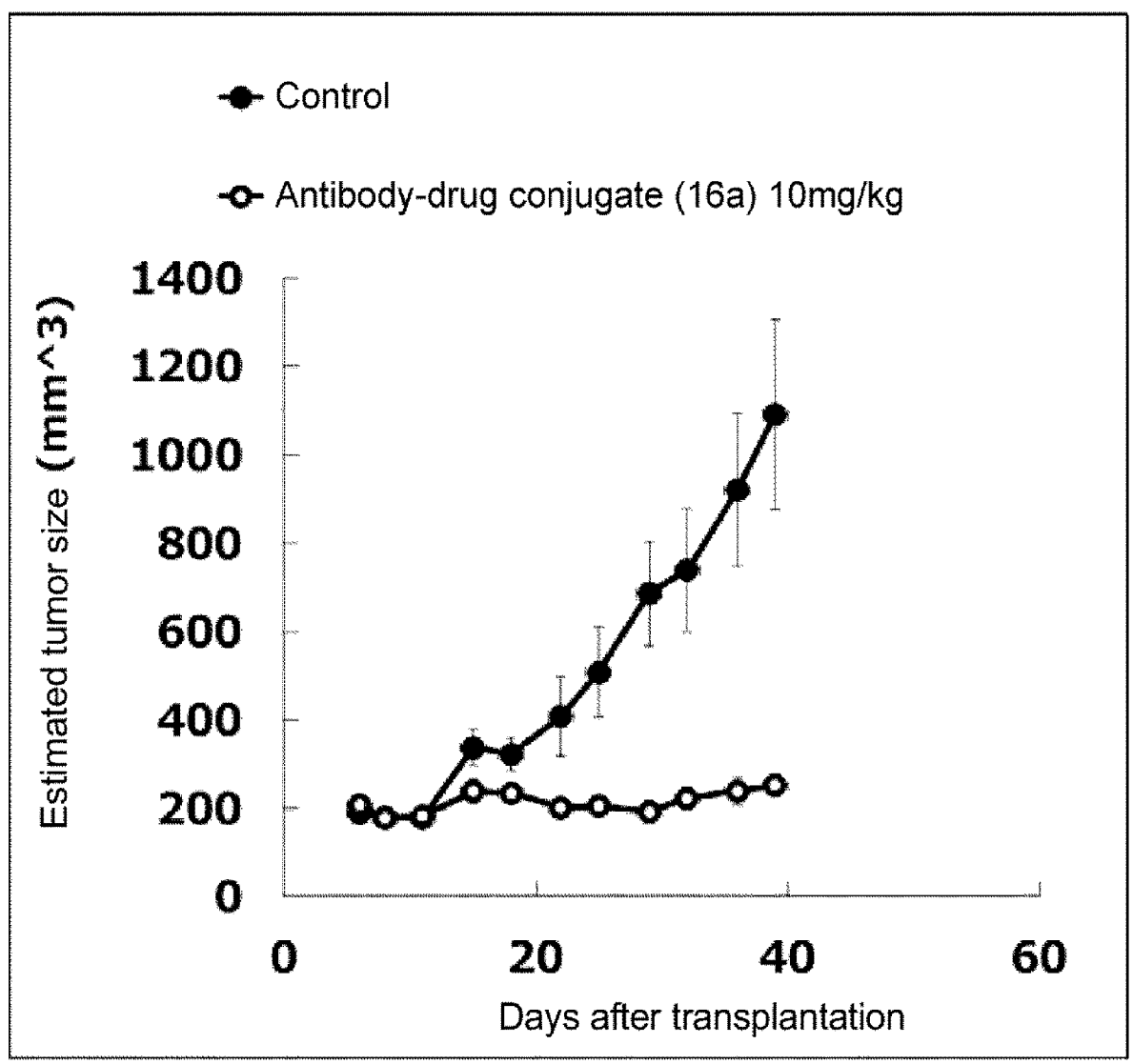
FIG. 20 shows results of a human luminal breast cancer line (MCF-7) antitumor test using the antibody-drug conjugate (16a). The ordinate depicts an average tumor volume. The abscissa depicts the number of days from cell transplantation. All values are indicated by mean+/−standard deviation. The initial tumor volume and the initial mouse weight were analyzed on the basis of descriptive data (mean and standard deviation) using Microsoft Excel 2009.

The results are shown in FIG. 20. The inhibition of tumor growth of the human luminal breast cancer line was observed in the antibody-drug conjugate administration group compared with the control group. No weight loss was observed in the mice of the treated groups.

Test Example 13 Antibody-Drug Conjugate (16a) Exhibited Antitumor Effect in In Vivo Antitumor Test Using Human Melanoma Line Five- to 6-week-old female CAnN.Cg-Foxn1[nu]/CrlCrlj 〔CFoxn1nu/Foxn1nu〕nude mice (Charles River Laboratories Japan, Inc.) having a body weight of 15 to 20 g after acclimation were used. The mice were placed in individually ventilated cages (IVC, 4 mice at maximum per cage) which were kept at room temperature and a constant humidity. After randomization, the body weights of the mice were measured every other day, and the behaviors of the animals were recorded every day.

$3 \times 10^6$ cells of a human melanoma cell line WM-266-4 (CRL-1676) from ATCC were mixed and suspended in Matrigel (BD #354234) and subcutaneously transplanted to the right side area of the body of each nude mouse using a 29 G needle. The body weights were measured using a weight scale (Mettler Toledo PB602-L).

The major axis and minor axis of the tumor were measured using an electronic digital caliper (CD-15CX, Mitsutoyo Corp), and the tumor volume ($mm^3$) was calculated. The calculation was carried out according to the following expression.

Tumor volume ($mm^3$)=½×Major axis (mm)×[Minor axis (mm)]$^2$

At Day 19 when the tumor size reached about 220 mm$^3$, 8 animals were randomly divided into 2 groups on the basis of their tumor sizes. At the same day, the antibody-drug conjugate (16a) or PBS for a control group were administered at the following doses.

Administration group: PBS was intravenously injected at the same single dose as the antibody-drug conjugate.

Administration group: The antibody-drug conjugate (16a) was intravenously injected at a single dose of 10 mg/kg.

Figure 21:
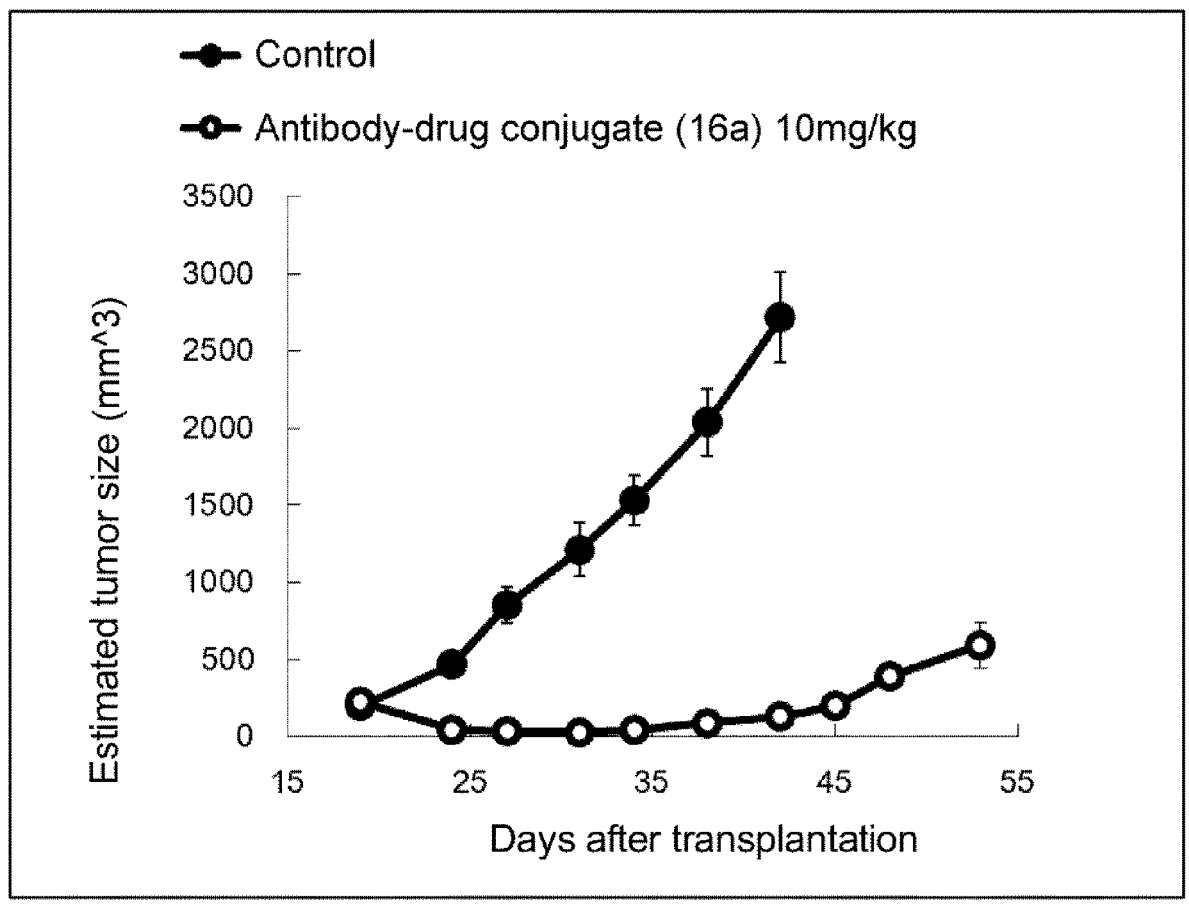
FIG. 21 shows results of a human melanoma line (WM-266-4) antitumor test using the antibody-drug conjugate (16a). The ordinate depicts an average tumor volume. The abscissa depicts the number of days from cell transplantation. All values are indicated by mean+/−standard deviation. The initial tumor volume and the initial mouse weight were analyzed on the basis of descriptive data (mean and standard deviation) using Microsoft Excel 2009.

The results are shown in FIG. 21. The inhibition of tumor growth of the human melanoma line was observed in the antibody-drug conjugate administration group compared with the control group. No weight loss was observed in the mice of the treated groups. In other human melanoma model C32, the inhibition of tumor growth was also observed in the antibody-drug conjugate (16a) administration group compared with the control group.

Test Example 14 Antibody-Drug Conjugate (16a) Exhibited Antitumor Effect in In Vivo Antitumor Test Using Human Ovarian Cancer Line Five- to 6-week-old female CAnN.Cg-Foxn1[nu]/CrlCrlj 〔Foxn1nu/Foxn1nu〕nude mice (Charles River Laboratories Japan, Inc.) having a body weight of 15 to 20 g after acclimation were used. The mice were placed in individually ventilated cages (IVC, 4 mice at maximum per cage) which were kept at room temperature and a constant humidity. After randomization, the body weights of the mice were measured every other day, and the behaviors of the animals were recorded every day.

5×10$^6$ cells of a human ovarian cancer cell line OVCAR-8 (HTB-161) from ATCC were mixed and suspended in Matrigel (BD #354234) and subcutaneously transplanted to the right side area of the body of each nude mouse using a 29 G needle. The body weights were measured using a weight scale (Mettler Toledo PB602-L).

The major axis and minor axis of the tumor were measured using an electronic digital caliper (CD-15CX, Mitsutoyo Corp), and the tumor volume (mm$^3$) was calculated. The calculation was carried out according to the following expression.

Tumor volume (mm$^3$)=½×Major axis (mm)×[Minor axis (mm)]$^2$

At Day 21 when the tumor size reached about 140 mm$^3$, 8 animals were randomly divided into 2 groups on the basis of their tumor sizes. At the same day, the antibody-drug conjugate (16a) or PBS for a control group were administered at the following doses.

Administration group: PBS was intravenously injected at the same single dose as the antibody-drug conjugate.

Administration group: The antibody-drug conjugate (16a) was intravenously injected at a single dose of 10 mg/kg.

Figure 22:
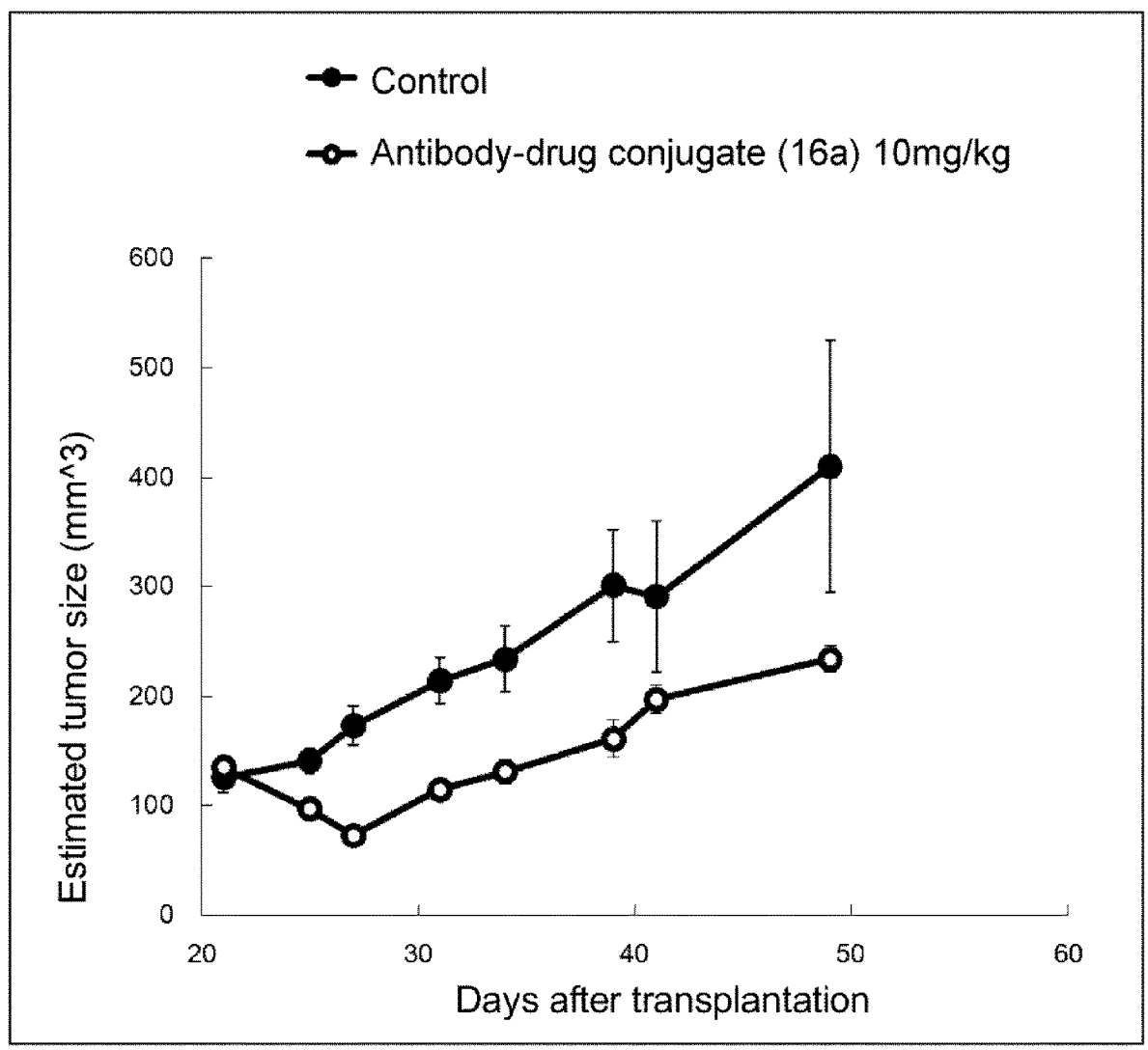
FIG. 22 shows results of a human ovarian cancer line (OVCAR-8) antitumor test using the antibody-drug conjugate (16a). The ordinate depicts an average tumor volume. The abscissa depicts the number of days from cell transplantation. All values are indicated by mean+/−standard deviation. The initial tumor volume and the initial mouse weight were analyzed on the basis of descriptive data (mean and standard deviation) using Microsoft Excel 2009.

The results are shown in FIG. 22. The inhibition of tumor growth of the human ovarian cancer line was observed in the antibody-drug conjugate administration group compared with the control group. No weight loss was observed in the mice of the treated groups.

Test Example 15 Antibody-Drug Conjugate (16a) Exhibited Antitumor Effect in In Vivo Antitumor Test Using Human Bladder Cancer Line Five- to 6-week-old female CAnN.Cg-Foxn1[nu]/CrlCrlj 〔Foxn1nu/Foxn1nu〕nude mice (Charles River Laboratories Japan, Inc.) having a body weight of 15 to 20 g after acclimation were used. The mice were placed in individually ventilated cages (IVC, 4 mice at maximum per cage) which were kept at room temperature and a constant humidity. After randomization, the body weights of the mice were measured every other day, and the behaviors of the animals were recorded every day.

8×10$^6$ cells of a human bladder cancer cell line SW-780 (CRL-2169) from ATCC were mixed and suspended in Matrigel (BD #354234) and subcutaneously transplanted to the right side area of the body of each nude mouse using a 29 G needle. The body weights were measured using a weight scale (Mettler Toledo PB602-L).

The major axis and minor axis of the tumor were measured using an electronic digital caliper (CD-15CX, Mitsutoyo Corp), and the tumor volume (mm$^3$) was calculated. The calculation was carried out according to the following expression.

Tumor volume (mm$^3$)=½×Major axis (mm)×[Minor axis (mm)]$^2$

At Day 7 when the tumor size reached about 190 mm$^3$, 10 animals were randomly divided into 2 groups on the basis of their tumor sizes. At the same day, the antibody-drug conjugate (16a) or PBS for a control group were administered at the following doses.

Administration group: PBS was intravenously injected at the same single dose as the antibody-drug conjugate.

Administration group: The antibody-drug conjugate (16a) was intravenously injected at a single dose of 10 mg/kg.

Figure 23:
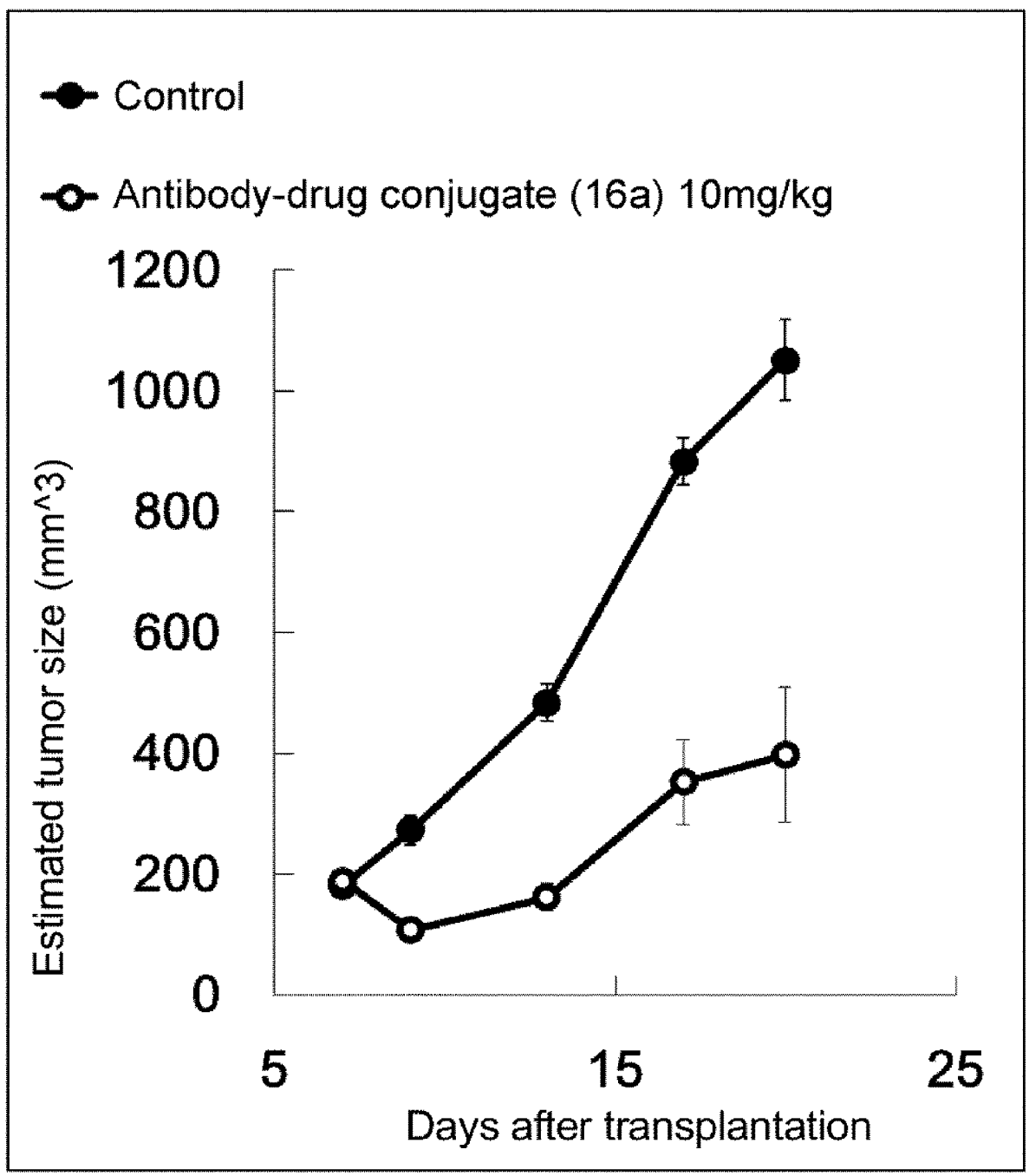
FIG. 23 shows results of a human bladder cancer line (SW-780) antitumor test using the antibody-drug conjugate (16a). The ordinate depicts an average tumor volume. The abscissa depicts the number of days from cell transplantation. All values are indicated by mean+/−standard deviation. The initial tumor volume and the initial mouse weight were analyzed on the basis of descriptive data (mean and standard deviation) using Microsoft Excel 2009.

The results are shown in FIG. 23. The inhibition of tumor growth of the human bladder cancer line was observed in the antibody-drug conjugate administration group compared with the control group. No weight loss was observed in the mice of the treated groups.

Test Example 16 Antibody-Drug Conjugate (16a) Exhibited HER3-Dependent Antitumor Effect in In Vivo Antitumor Test Using Human Breast Cancer Line The human breast cancer line MDA-MB-453 expresses HER3 and responds to the antibody-drug conjugate (13) as described in Test Example 8. However, as it had not been demonstrated that this pharmaceutical effect was mediated by HER3 yet, HER3 was veiled by administering U1-59 beforehand, and whether or not to reduce the pharmaceutical effect was evaluated.

Five- to 6-week-old female CAnN.Cg-Foxn1[nu]/CrlCrlj 〔Foxn1nu/Foxn1nu〕nude mice (Charles River Laboratories Japan, Inc.) having a body weight of 15 to 20 g after acclimation were used. The mice were placed in individually ventilated cages (IVC, 4 mice at maximum per cage) which were kept at room temperature and a constant humidity. After randomization, the body weights of the mice were measured every other day, and the behaviors of the animals were recorded every day.

1×10$^7$ cells of a human breast cancer cell line MDA-MB-453 (CLB-22) from ATCC were mixed and suspended in Matrigel (BD #354234) and subcutaneously transplanted to the right side area of the body of each nude mouse using a 29 G needle. The body weights were measured using a weight scale (Mettler Toledo PB602-L).

The major axis and minor axis of the tumor were measured using an electronic digital caliper (CD-15CX, Mitsutoyo Corp), and the tumor volume (mm$^3$) was calculated. The calculation was carried out according to the following expression.

Tumor volume (mm$^3$)=½×Major axis (mm)×[Minor axis (mm)]$^2$

At Day 11 when the tumor size reached about 130 mm$^3$, 16 animals were randomly divided into 4 groups on the basis of their tumor sizes. At the same day, the antibody-drug conjugate (16a) and/or U1-59 or PBS for a control group were administered at the following doses.

Administration group: PBS was intravenously injected at the same single dose as the antibody-drug conjugate.

Administration group: U1-59 was intravenously injected at a single dose of 30 mg/kg.

Administration group: The antibody-drug conjugate (16a) was intravenously injected at a single dose of 3 mg/kg.

Administration group: 30 minutes after administration (intravenous injection at a single dose) of U1-59, the antibody-drug conjugate (16a) was intravenously injected at a single dose of 3 mg/kg.

Figure 24:
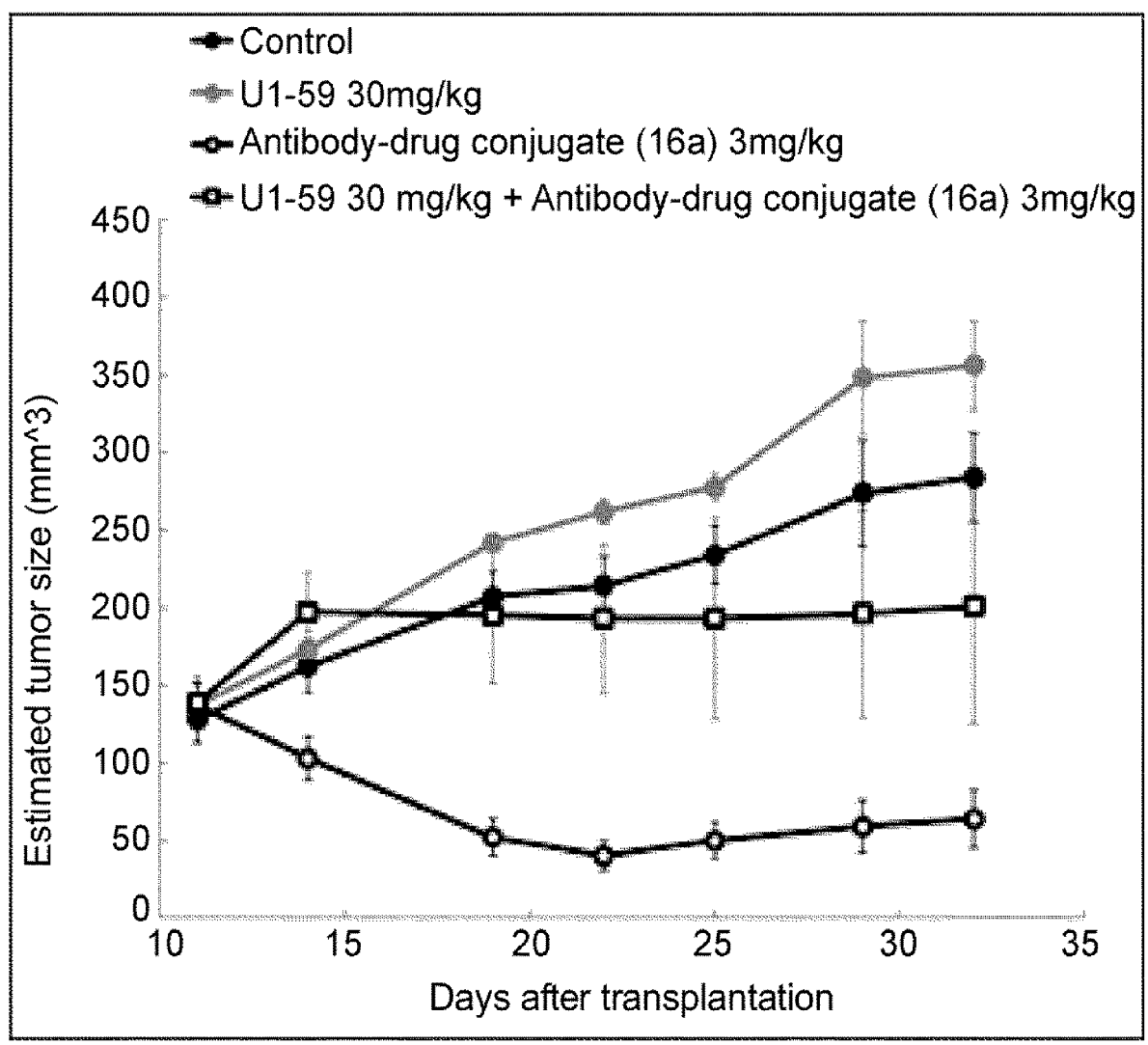
FIG. 24 shows results of a human breast cancer line (MDA-MB-453) antitumor test using the antibody-drug conjugate (16a). The ordinate depicts an average tumor volume. The abscissa depicts the number of days from cell transplantation. All values are indicated by mean+/−standard deviation. The initial tumor volume and the initial mouse weight were analyzed on the basis of descriptive data (mean and standard deviation) using Microsoft Excel 2009.

The results are shown in FIG. 24. The inhibition of tumor growth of the human breast cancer line was observed in the antibody-drug conjugate administration group compared with the control group, whereas this tumor inhibitory effect was attenuated by administering U1-59 beforehand. These results demonstrated that the tumor inhibitory effect of the antibody-drug conjugate is a pharmaceutical effect mediated by HER3. No weight loss was observed in the mice of the treated groups.

Test Example 17 Antibody-Drug Conjugate (16a) Exhibited Antitumor Effect in Combined Use with Trastuzumab in In Vivo Antitumor Test Using Human Breast Cancer Line Trastuzumab has been approved as a therapeutic agent for human HER2-positive breast cancer. However, trastuzumab resistance is known, and a mutation in PIK3CA <H1047R or H420R> has been reported to participate in one of the mechanisms underlying this resistance. In this test, whether or not the combined use of trastuzumab and the antibody-drug conjugate was effective for a trastuzumab-resistant breast cancer line was evaluated.

Five- to 6-week-old female CAnN.Cg-Foxn1[nu]/CrlCrlj 〔Foxn1nu/Foxn1nu〕 nude mice (Charles River Laboratories Japan, Inc.) having a body weight of 15 to 20 g after acclimation were used. The mice were placed in individually ventilated cages (IVC, 4 mice at maximum per cage) which were kept at room temperature and a constant humidity. After randomization, the body weights of the mice were measured every other day, and the behaviors of the animals were recorded every day.

$1 \times 10^7$ cells of a human breast cancer cell line MDA-MB-453 (CLB-22, H1047R mutation in PIK3CA) from ATCC were mixed and suspended in Matrigel (PBS: PAA #10010-023, Matrigel: BD #354234) and subcutaneously transplanted to the right side area of the body of each nude mouse using a 29 G needle. The body weights were measured using a weight scale (Mettler Toledo PB602-L).

The major axis and minor axis of the tumor were measured using an electronic digital caliper (CD-15CX, Mitsutoyo Corp), and the tumor volume ($mm^3$) was calculated. The calculation was carried out according to the following expression.

Tumor volume ($mm^3$)=½×Major axis (mm)×[Minor axis (mm)]$^2$

At Day 11 when the tumor size reached about 130 $mm^3$, 16 animals were randomly divided into 4 groups on the basis of their tumor sizes. At the same day, the antibody-drug conjugate (16a), trastuzumab, combined use of the conjugate and trastuzumab, or PBS for a control group were administered at the following doses.

Administration group: PBS was intravenously injected at the same single dose as the antibody-drug conjugate.

Administration group: Trastuzumab (Roche Diagnostics, Inc.) was intravenously injected at a single dose of 1 mg/kg.

Administration group: The antibody-drug conjugate (16a) was intravenously injected at a single dose of 3 mg/kg.

Administration group: 30 minutes after administration (intravenous injection at a single dose) of trastuzumab (Roche Diagnostics, Inc.), the antibody-drug conjugate (16a) was intravenously injected at a single dose of 3 mg/kg.

Figure 25:
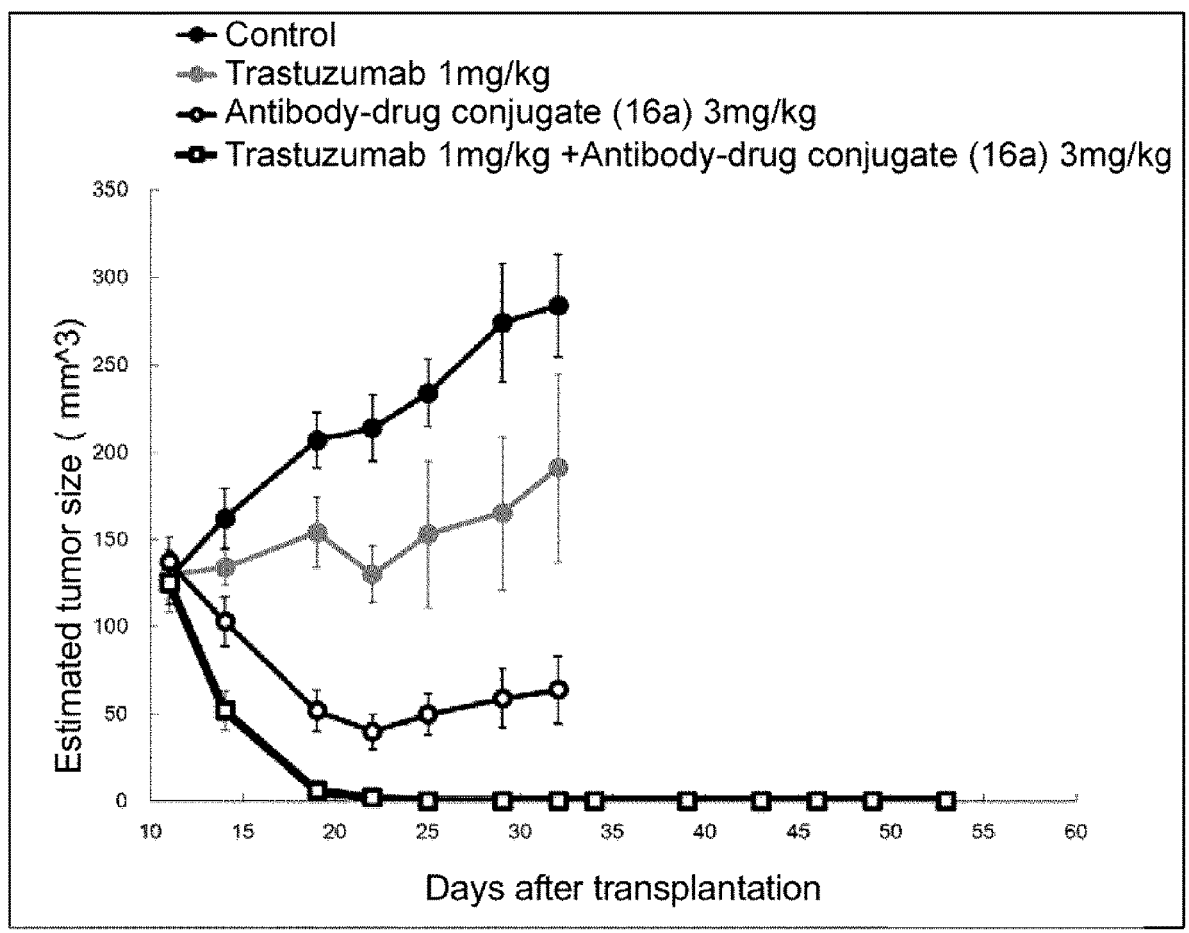
FIG. 25 shows results of a human breast cancer line (MDA-MB-453) antitumor test using the antibody-drug conjugate (16a). The ordinate depicts an average tumor volume. The abscissa depicts the number of days from cell transplantation. All values are indicated by mean+/−standard deviation. The initial tumor volume and the initial mouse weight were analyzed on the basis of descriptive data (mean and standard deviation) using Microsoft Excel 2009.

The results are shown in FIG. 25. The antitumor effect brought about by combined use on the human breast cancer line (PIK3CA H1047R) was observed in the administration of trastuzumab and the antibody-drug conjugate compared with the administration of each medicine alone. These results demonstrated that the pharmaceutical effect of the antibody-drug conjugate is potentiated by the combined use thereof with trastuzumab. No weight loss was observed in the mice of the treated groups. In other antitumor test using a human breast cancer cell line HCC1954(PIK3CA H1047R), the combined antitumor effect was also observed in the administration of trastuzumab and the antibody-drug conjugate (16a) compared with the administration of each medicine alone.

Test Example 18 Antibody-Drug Conjugate (15) Exhibited Antitumor Effect in Combined Use with Trastuzumab in In Vivo Antitumor Test Using Human Breast Cancer Line Trastuzumab has been approved as a therapeutic agent for human HER2-positive breast cancer. However, trastuzumab resistance is known, and a mutation in PIK3CA <H1047R or H420R> has been reported to participate in one of the mechanisms underlying this resistance. In this test, whether or not the combined use of trastuzumab and the antibody-drug conjugate was effective for a trastuzumab-resistant breast cancer line was evaluated.

Five- to 6-week-old female CAnN.Cg-Foxn1[nu]/CrlCrlj 〔Foxn1nu/Foxn1nu〕 nude mice (Charles River Laboratories Japan, Inc.) having a body weight of 15 to 20 g after acclimation were used. The mice were placed in individually ventilated cages (IVC, 4 mice at maximum per cage) which were kept at room temperature and a constant humidity. After randomization, the body weights of the mice were measured every other day, and the behaviors of the animals were recorded every day.

$5 \times 10^6$ cells of a human breast cancer cell line JIMT-1 (ACC-589, H420R mutation in PIK3CA) from ATCC were suspended in PBS (PAA #10010-023) and subcutaneously transplanted to the right side area of the body of each nude mouse using a 29 G needle. The body weights were measured using a weight scale (Mettler Toledo PB602-L).

The major axis and minor axis of the tumor were measured using an electronic digital caliper (CD-15CX, Mitsutoyo Corp), and the tumor volume ($mm^3$) was calculated. The calculation was carried out according to the following expression.

Tumor volume ($mm^3$)=½×Major axis (mm)×[Minor axis (mm)]$^2$

At Day 10 when the tumor size reached about 200 $mm^3$, 24 animals were randomly divided into 4 groups on the basis of their tumor sizes. At the same day, the antibody-drug conjugate (15), trastuzumab, combined use of the conjugate and trastuzumab, or PBS for a control group were administered at the following doses.

Administration group: PBS was intravenously injected once a week at the same dose as the antibody-drug conjugate.

Administration group: Trastuzumab (Roche Diagnostics, Inc.) was intravenously injected once a week at 10 mg/kg.

Administration group: The antibody-drug conjugate (15) was intravenously injected once a week at 10 mg/kg.

Administration group: 30 minutes after administration (intravenous injection once a week) of trastuzumab (Roche Diagnostics, Inc.), the antibody-drug conjugate (15) was intravenously injected once a week at 10 mg/kg.

Figure 26:
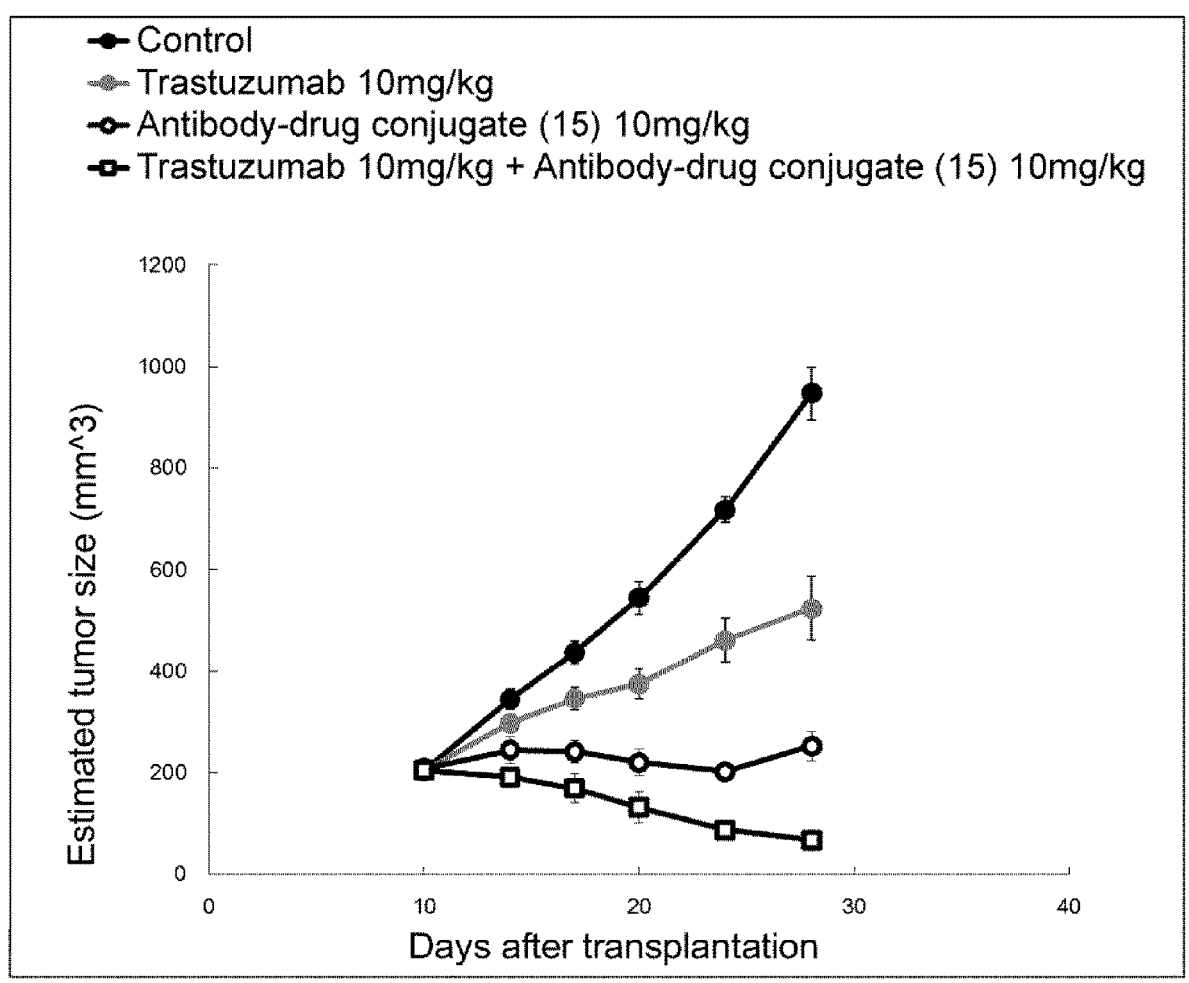
FIG. 26 shows results of a human breast cancer line (JIMT-1) antitumor test using the antibody-drug conjugate (15). The ordinate depicts an average tumor volume. The abscissa depicts the number of days from cell transplantation. All values are indicated by mean+/−standard deviation. The initial tumor volume and the initial mouse weight were analyzed on the basis of descriptive data (mean and standard deviation) using Microsoft Excel 2009.

The results are shown in FIG. 26. The antitumor effect brought about by combined use on the human breast cancer line (PIK3CA H420R) was observed in the administration of trastuzumab and the antibody-drug conjugate compared with the administration of each medicine alone. These results demonstrated that the pharmaceutical effect of the antibody-drug conjugate is potentiated by the combined use thereof with trastuzumab. No weight loss was observed in the mice of the treated groups.

Test Example 19 Antibody-Drug Conjugate (16a) Exhibited Antitumor Effect in Combined Use with Gefitinib in In Vivo Antitumor Test Using Human Lung Cancer Line Gefitinib has been approved as a therapeutic agent for human lung cancer. In this test, whether or not the combined use of gefitinib and the antibody-drug conjugate was effective was evaluated.

Five- to 6-week-old female CAnN.Cg-Foxn1[nu]/CrlCrlj 〔Foxn1nu/Foxn1nu〕 nude mice (Charles River Laboratories Japan, Inc.) having a body weight of 15 to 20 g after acclimation were used. The mice were placed in individually ventilated cages (IVC, 4 mice at maximum per cage) which were kept at room temperature and a constant humidity. After randomization, the body weights of the mice were measured every other day, and the behaviors of the animals were recorded every day.

$3\times10^6$ cells of a human lung cancer cell line PC-9 (RCB0446) from ATCC were suspended in PBS (PAA #10010-023) and subcutaneously transplanted to the right side area of the body of each nude mouse using a 29 G needle. The body weights were measured using a weight scale (Mettler Toledo PB602-L).

The major axis and minor axis of the tumor were measured using an electronic digital caliper (CD-15CX, Mitsutoyo Corp), and the tumor volume (mm$^3$) was calculated. The calculation was carried out according to the following expression.

Tumor volume (mm$^3$)=½×Major axis (mm)×[Minor axis (mm)]$^2$

At Day 14 when the tumor size reached about 270 mm$^3$, 16 animals were randomly divided into 4 groups on the basis of their tumor sizes. At the same day, the antibody-drug conjugate (16a), gefitinib, combined use of the conjugate and gefitinib, or PBS for a control group were administered at the following doses.

Administration group: PBS was intravenously injected once a week at the same dose as the antibody-drug conjugate.

Administration group: Gefitinib (AstraZeneca) was orally administered once a day at 6 mg/kg.

Administration group: The antibody-drug conjugate (16a) was intravenously injected once a week at 10 mg/kg.

Administration group: 30 minutes after administration (oral administration once a day) of gefitinib (AstraZeneca), the antibody-drug conjugate (16a) was intravenously injected once a week at 10 mg/kg.

Figure 27:
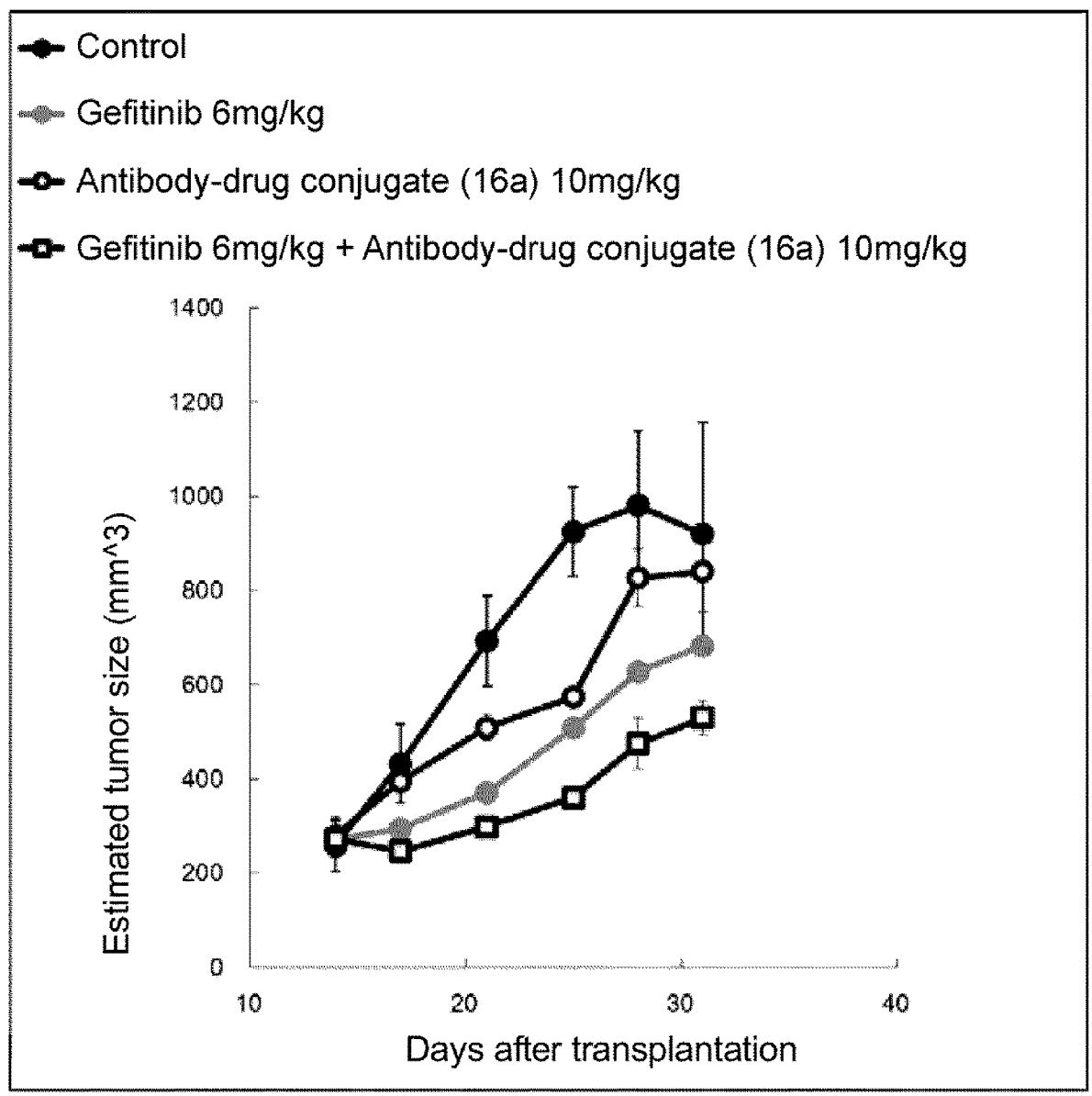
FIG. 27 shows results of a human lung cancer line (PC9) antitumor test using the antibody-drug conjugate (16a). The ordinate depicts an average tumor volume. The abscissa depicts the number of days from cell transplantation. All values are indicated by mean+/−standard deviation. The initial tumor volume and the initial mouse weight were analyzed on the basis of descriptive data (mean and standard deviation) using Microsoft Excel 2009.

The results are shown in FIG. 27. The antitumor effect brought about by combined use on the human lung cancer line was observed in the administration of gefitinib and the antibody-drug conjugate compared with the administration of each medicine alone. These results demonstrated that the pharmaceutical effect of the antibody-drug conjugate is potentiated by the combined use thereof with gefitinib. No weight loss was observed in the mice of the treated groups.

Test Example 20 Antibody-Drug Conjugate (16a) Exhibited Antitumor Effect in Combined Use with Cetuximab or Panitumumab in In Vivo Antitumor Test Using Human Triple-Negative Breast Cancer Line An anti-EGFR antibody cetuximab or panitumumab is under clinical trial against human triple-negative breast cancer. In this test, whether or not the combined use of cetuximab or panitumumab and the antibody-drug conjugate was effective was evaluated.

Five- to 6-week-old female CAnN.Cg-Foxn1[nu]/CrlCrlj 〔Foxn1nu/Foxn1nu〕 nude mice (Charles River Laboratories Japan, Inc.) having a body weight of 15 to 20 g after acclimation were used. The mice were placed in individually ventilated cages (IVC, 4 mice at maximum per cage) which were kept at room temperature and a constant humidity. After randomization, the body weights of the mice were measured every other day, and the behaviors of the animals were recorded every day.

$5\times10^6$ cells of a human triple-negative breast cancer cell line MDA-MB-468 (CRL-2322) from ATCC were suspended in a solution prepared from 200 uL of PBS and Matrigel (PBS: PAA #10010-023, Matrigel: BD #354234) mixed at a ratio of 1:1, and subcutaneously transplanted to the right side area of the body of each nude mouse using a 29 G needle. The body weights were measured using a weight scale (Mettler Toledo PB602-L).

The major axis and minor axis of the tumor were measured using an electronic digital caliper (CD-15CX, Mitsutoyo Corp), and the tumor volume (mm$^3$) was calculated. The calculation was carried out according to the following expression.

Tumor volume (mm$^3$)=½×Major axis (mm)×[Minor axis (mm)]$^2$

At Day 21 when the tumor size reached about 160 mm$^3$, 30 animals were randomly divided into 6 groups on the basis of their tumor sizes. At the same day, the antibody-drug conjugate (16a), cetuximab or panitumumab, combined use of the conjugate and cetuximab or panitumumab, or PBS for a control group were administered at the following doses.

Administration group: PBS was administered at the same single dose as the antibody-drug conjugate.

Administration group: Cetuximab (Bristol-Myers Squibb Company) was administered at a single dose of 10 mg/kg.

Administration group: Panitumumab (Amgen Inc.) was administered at a single dose of 10 mg/kg.

Administration group: The antibody-drug conjugate (16a) was administered at a single dose of 10 mg/kg.

Administration group: 30 minutes after administration (administration at a single dose) of cetuximab (Bristol-Myers Squibb Company), the antibody-drug conjugate (16a) was administered at a single dose of 10 mg/kg.

Administration group: 30 minutes after administration (administration at a single dose) of panitumumab (Amgen Inc.), the antibody-drug conjugate (16a) was administered at a single dose of 10 mg/kg.

Figure 28A:
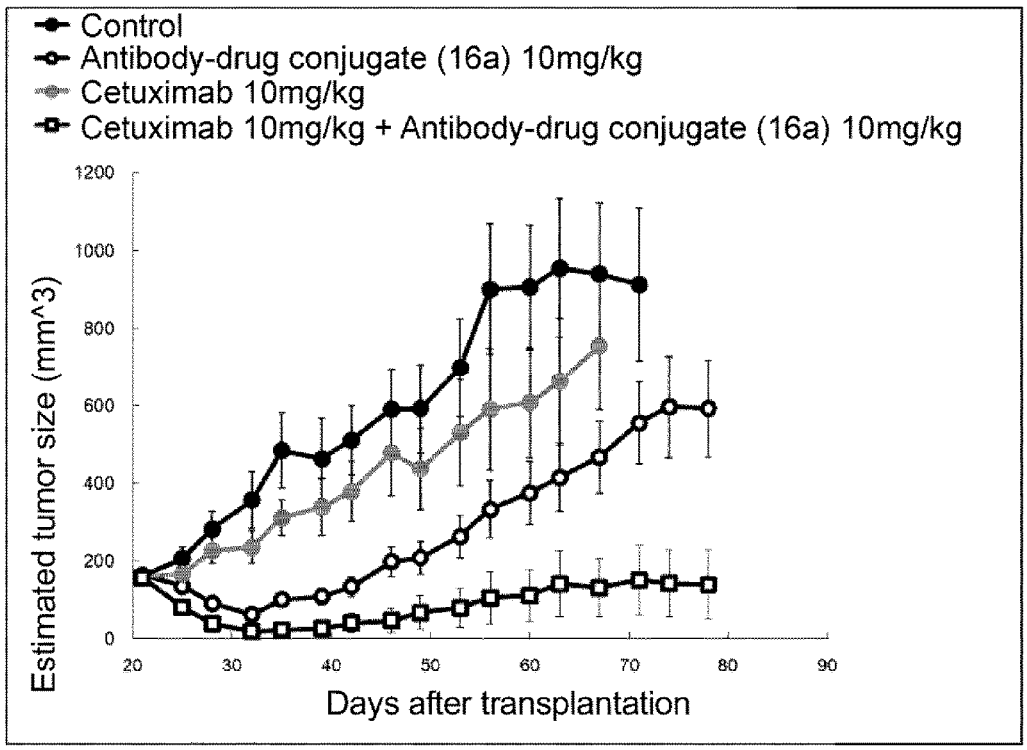
FIGS. 28A and 28B show results of a human triple-negative breast cancer line (MDA-MB-468) antitumor test using the antibody-drug conjugate (16a). The ordinate depicts an average tumor volume. The abscissa depicts the number of days from cell transplantation. All values are indicated by mean+/−standard deviation. The initial tumor volume and the initial mouse weight were analyzed on the basis of descriptive data (mean and standard deviation) using Microsoft Excel 2009.
Figure 28B:
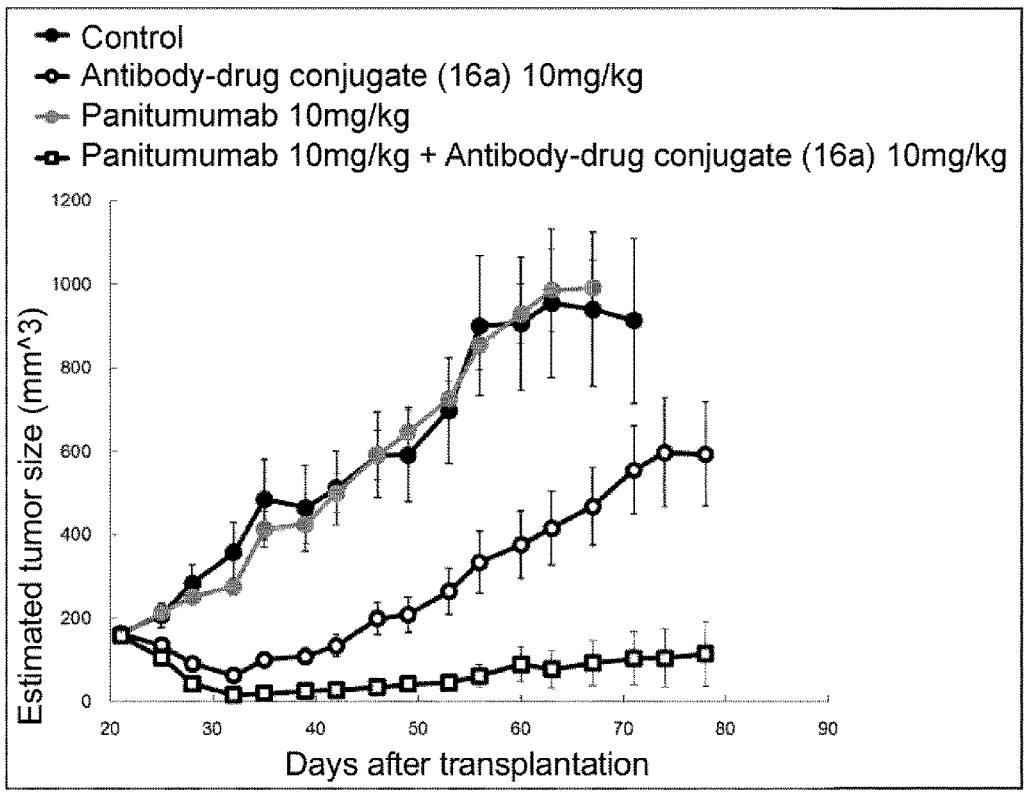

The results are shown in FIGS. 28A and 28B. The antitumor effect brought about by combined use on the human triple-negative breast cancer line was observed in the administration of cetuximab (FIG. 28A) or panitumumab (FIG. 28B) and the antibody-drug conjugate compared with the administration of each medicine alone. These results demonstrated that the pharmaceutical effect of the antibody-drug conjugate is potentiated by the combined use thereof with cetuximab or panitumumab. No weight loss was observed in the mice of the treated groups. The antitumor effect brought about by combined use on the other human triple-negative breast cancer line in MDA-MB-231 was also observed in the administration of cetuximab or panitumumab and the antibody-drug conjugate (16a) compared with the administration of each medicine alone.

Test Example 21 Antibody-Drug Conjugate (16a) Exhibited Antitumor Effect in Combined Use with Cetuximab or Panitumumab in In Vivo Antitumor Test Using Human Head and Neck Cancer Line An anti-EGFR antibody cetuximab has been approved against human head and neck cancer, while panitumumab is under clinical trial against this cancer. In this test, whether or not the combined use of cetuximab or panitumumab and the antibody-drug conjugate was effective was evaluated.

Five- to 6-week-old female CAnN.Cg-Foxn1[nu]/CrlCrlj 〔Foxn1nu/Foxn1nu〕nude mice (Charles River Laboratories Japan, Inc.) having a body weight of 15 to 20 g after acclimation were used. The mice were placed in individually ventilated cages (IVC, 4 mice at maximum per cage) which were kept at room temperature and a constant humidity. After randomization, the body weights of the mice were measured every other day, and the behaviors of the animals were recorded every day.

$4 \times 10^6$ cells of a human head and neck cancer cell line Fadu (HTB-43) from ATCC were suspended in 200 uL of PBS (PAA #10010-023) and subcutaneously transplanted to the right side area of the body of each nude mouse using a 29 G needle. The body weights were measured using a weight scale (Mettler Toledo PB602-L).

The major axis and minor axis of the tumor were measured using an electronic digital caliper (CD-15CX, Mitsutoyo Corp), and the tumor volume (mm$^3$) was calculated. The calculation was carried out according to the following expression.

$$\text{Tumor volume (mm}^3\text{)}=\frac{1}{2}\times\text{Major axis (mm)}\times[\text{Minor axis (mm)}]^2$$

At Day 6 when the tumor size reached about 330 mm$^3$, 30 animals were randomly divided into 6 groups on the basis of their tumor sizes. At the same day, the antibody-drug conjugate (16a), cetuximab or panitumumab, combined use of the conjugate and cetuximab or panitumumab, or PBS for a control group were administered at the following doses.

Administration group: PBS was administered at the same single dose as the antibody-drug conjugate.

Administration group: Cetuximab (Bristol-Myers Squibb Company) was administered at a single dose of 5 mg/kg.

Administration group: Panitumumab (Amgen Inc.) was administered at a single dose of 5 mg/kg.

Administration group: The antibody-drug conjugate (16a) was administered at a single dose of 10 mg/kg.

Administration group: 30 minutes after administration (administration at a single dose) of cetuximab (Bristol-Myers Squibb Company), the antibody-drug conjugate (16a) was administered at a single dose of 10 mg/kg.

Administration group: 30 minutes after administration (administration at a single dose) of panitumumab (Amgen Inc.), the antibody-drug conjugate (16a) was administered at a single dose of 10 mg/kg.

Figure 29A:
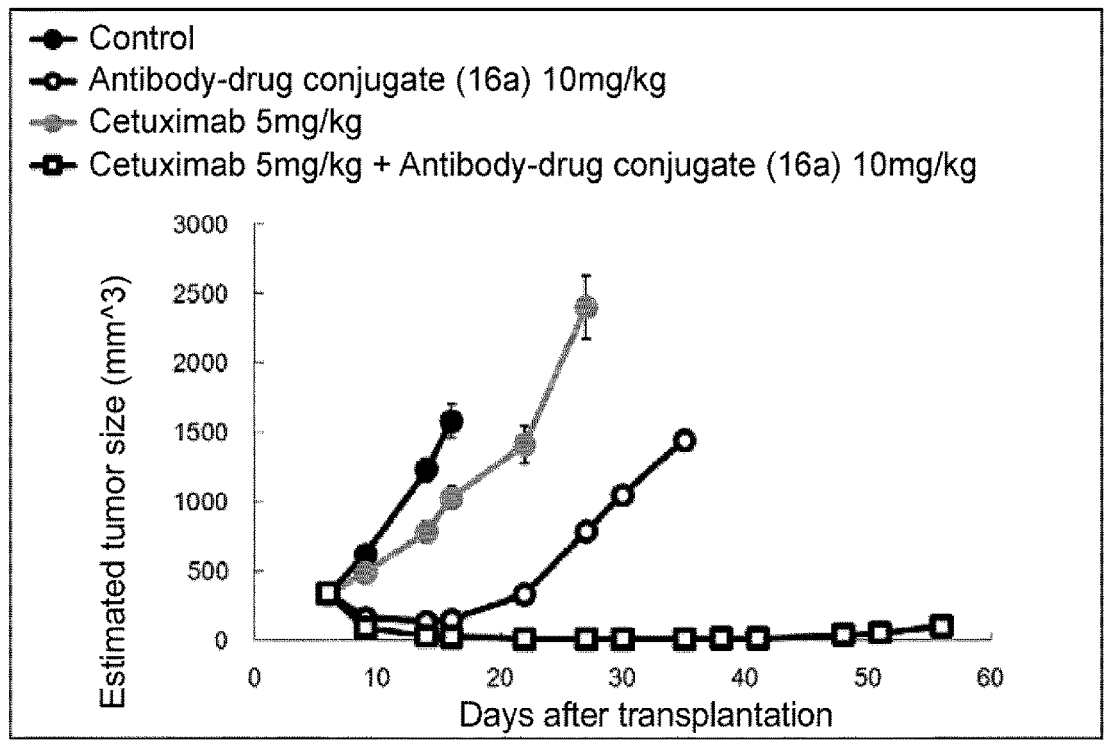
FIGS. 29A and 29B show results of a human head and neck cancer line (Fadu) antitumor test using the antibody-drug conjugate (16a). The ordinate depicts an average tumor volume. The abscissa depicts the number of days from cell transplantation. All values are indicated by mean+/−standard deviation. The initial tumor volume and the initial mouse weight were analyzed on the basis of descriptive data (mean and standard deviation) using Microsoft Excel 2009.
Figure 29B:
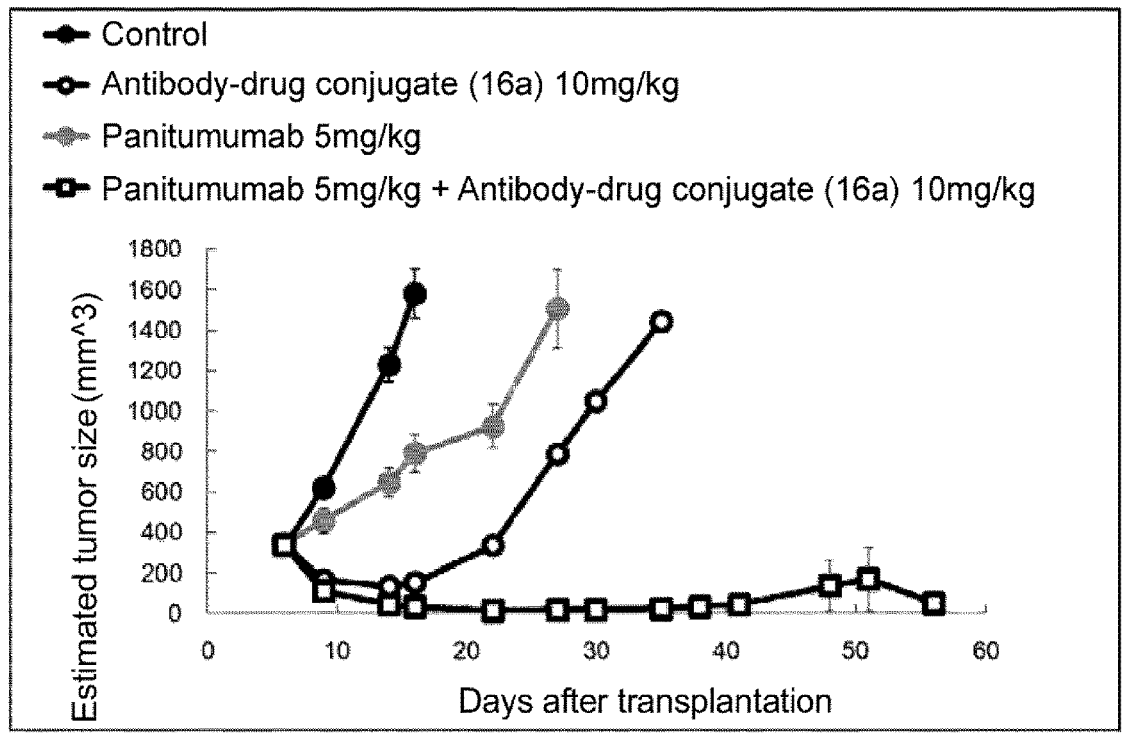

The results are shown in FIGS. 29A and 29B. The antitumor effect brought about by combined use on the human head and neck cancer line was observed in the administration of cetuximab (FIG. 29A) or panitumumab (FIG. 29B) and the antibody-drug conjugate compared with the administration of each medicine alone. These results demonstrated that the pharmaceutical effect of the antibody-drug conjugate is potentiated by the combined use thereof with cetuximab or panitumumab. No weight loss was observed in the mice of the treated groups.

Test Example 22 Antibody-Drug Conjugate (16a) Exhibited Antitumor Effect in Combined Use with Cetuximab or Pertuzumab in In Vivo Antitumor Test by Transplantation of Tumor from Stomach Cancer Patient An anti-EGFR antibody cetuximab and an anti-HER2 antibody pertuzumab are under clinical trial against human stomach cancer. In this test, whether or not the combined use of cetuximab or pertuzumab and the antibody-drug conjugate was effective was evaluated. The evaluation was carried out by conducting an antitumor test close to clinical condition involving the stroma of a patient using the patient-derived tumors transplanted in mice instead of the general evaluation system using a human cancer line.

Five- to 6-week-old female CAnN.Cg-Foxn1[nu]/CrlCrlj 〔Foxn1nu/Foxn1nu〕nude mice (Charles River Laboratories Japan, Inc.) having a body weight of 15 to 20 g after acclimation were used. The mice were placed in individually ventilated cages (IVC, 4 mice at maximum per cage) which were kept at room temperature and a constant humidity. After randomization, the body weights of the mice were measured every other day, and the behaviors of the animals were recorded every day.

A stomach cancer patient-derived tumor NIBIO-G016 from National Institute of Biomedical Innovation was subcutaneously transplanted to the right side area of the body of each nude mouse. The body weights were measured using a weight scale (Mettler Toledo PB602-L).

The major axis and minor axis of the tumor were measured using an electronic digital caliper (CD-15CX, Mitsutoyo Corp), and the tumor volume (mm$^3$) was calculated. The calculation was carried out according to the following expression.

$$\text{Tumor volume (mm}^3\text{)}=\frac{1}{2}\times\text{Major axis (mm)}\times[\text{Minor axis (mm)}]^2$$

At Day 56 when the tumor size reached about 220 mm$^3$, 30 animals were randomly divided into 6 groups on the basis of their tumor sizes. At the same day, the antibody-drug conjugate (16a), cetuximab or pertuzumab, combined use of the conjugate and cetuximab or pertuzumab, or PBS for a control group were administered at the following doses.

Administration group: PBS was administered at the same single dose as the antibody-drug conjugate.

Administration group: Cetuximab (Bristol-Myers Squibb Company) was administered at a single dose of 10 mg/kg.

Administration group: Pertuzumab (Roche Diagnostics, Inc.) was administered at a single dose of 10 mg/kg.

Administration group: The antibody-drug conjugate (16a) was administered at a single dose of 10 mg/kg.

Administration group: 30 minutes after administration (administration at a single dose) of cetuximab (Bristol-Myers Squibb Company), the antibody-drug conjugate (16a) was administered at a single dose of 10 mg/kg.

Administration group: 30 minutes after administration (administration at a single dose) of pertuzumab (Roche Diagnostics, Inc.), the antibody-drug conjugate (16a) was administered at a single dose of 10 mg/kg.

Figure 30A:
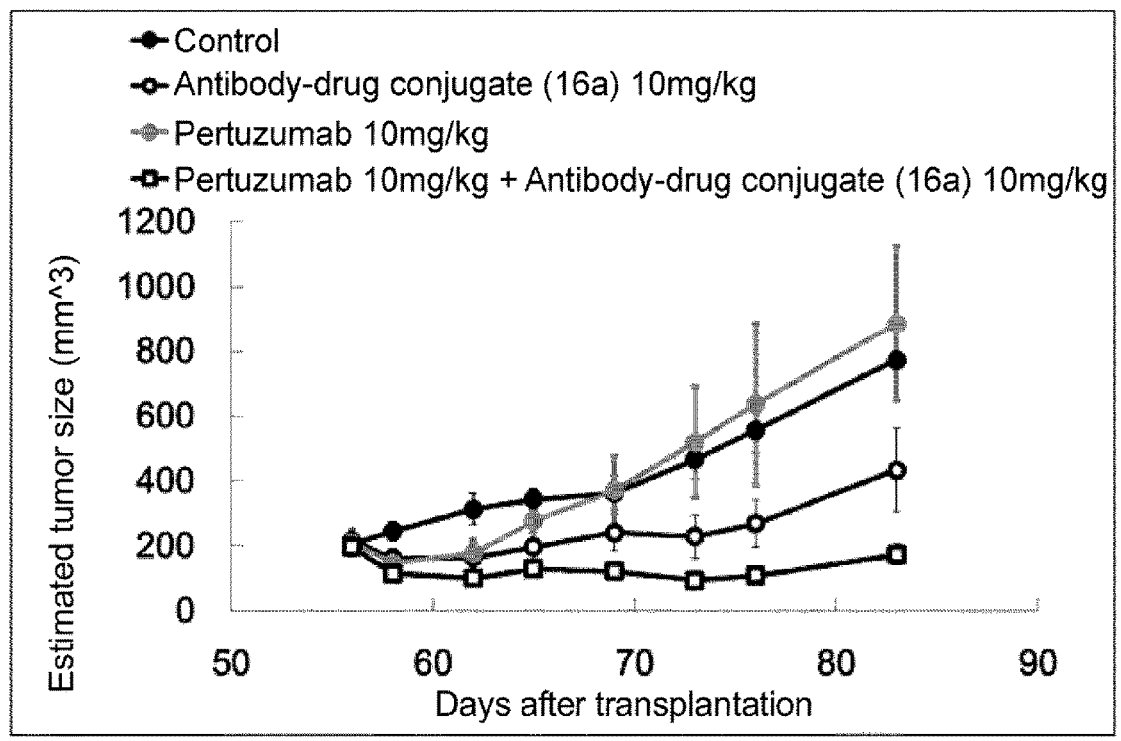
FIGS. 30A and 30B show results of an antitumor test using a human stomach cancer patient-derived tumor section (NIBIO-G016) and the antibody-drug conjugate (16a). The ordinate depicts an average tumor volume. The abscissa depicts the number of days from cell transplantation. All values are indicated by mean+/−standard deviation. The initial tumor volume and the initial mouse weight were analyzed on the basis of descriptive data (mean and standard deviation) using Microsoft Excel 2009.
Figure 30B:
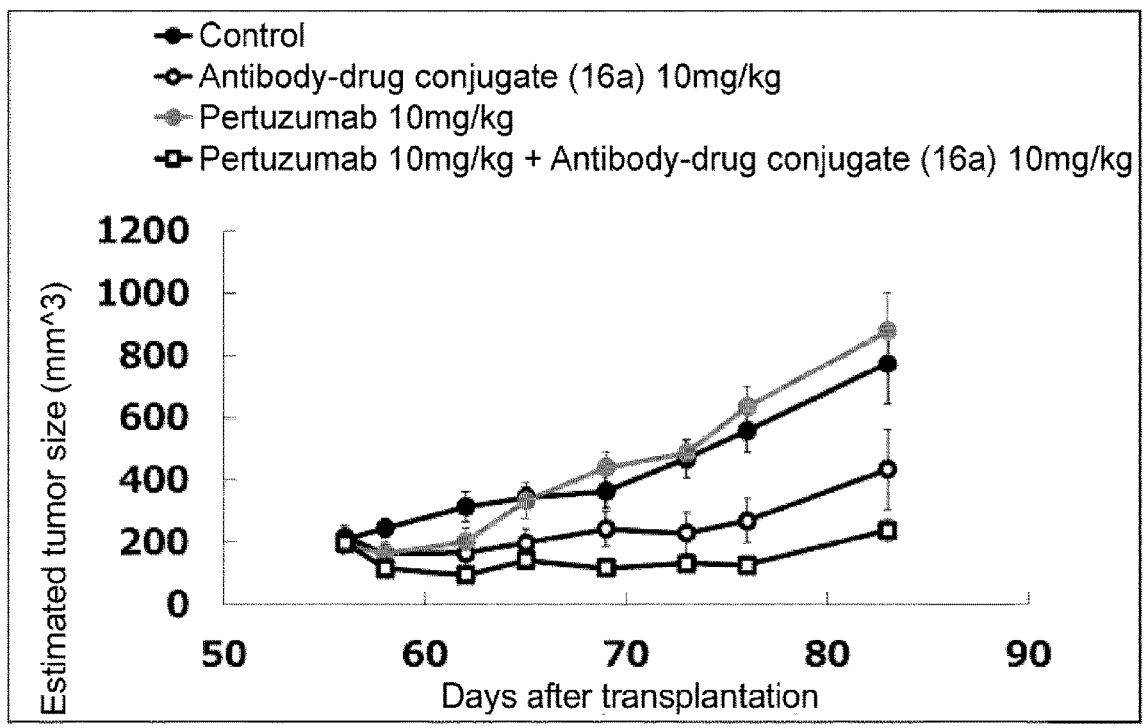

The results are shown in FIGS. 30A and 30B. The antitumor effect brought about by combined use on the stomach cancer patient-derived tumor model was observed in the administration of cetuximab (FIG. 30A) or pertuzumab (FIG. 30B) and the antibody-drug conjugate compared with the administration of each medicine alone. These results demonstrated that the pharmaceutical effect of the antibody-drug conjugate is potentiated by the combined use thereof with cetuximab or panitumumab in the cancer patient-derived tumor model. No weight loss was observed in the mice of the treated groups. Further, in an antitumor test using a human pancreatic cancer cell line BxPC3, the antibody-drug conjugate (13) exhibited a stronger antitumor effect as compared with the PBS administration group or the U1-59 administration group. The antibody-drug conjugate also exhibited a strong antitumor effect on in vivo antitumor model using a HER2-positive breast cancer cell line JIMT1 which had acquired resistance to combined use of trastuzumab and pertuzumab or to trastuzumab emtansine.

Test Example 23 Safety of Antibody-Drug Conjugate for Non-Human Animal

The anti-HER3 antibody-drug conjugate of the present invention and the pharmaceutical composition containing this anti-HER3 antibody-drug conjugate have excellent safety as a therapeutic or prophylactic agent for a disease. For example, when the antibody-drug conjugate (5), (10), or (13) was administered up to 30 mg/kg to a cross-breed rat, two times in total with an interval of once per week, no serious toxicity findings were observed from any of the antibody-drug conjugates as a result of observation until Day 7 after the final administration. Further, when the antibody-drug conjugate (5), (10), or (13) was administered up to 30 mg/kg to a cross-breed monkey, no remarkable toxicity findings were observed from any of the antibody-drug conjugates as a result of observation for 7 days.

Further, when antibody-drug conjugate (5), (10), or (13) was administered at a plurality of doses to a monkey (3-week intervals), no remarkable toxicity findings were observed from any of the antibody-drug conjugates as a result of observation. Accordingly, the antibody-drug conjugate of the present invention has excellent safety as a pharmaceutical composition for treatment or prevention of a disease.

SEQUENCE LISTING FREE TEXT

SEQ ID NO: 1—Nucleotide sequence encoding a heavy chain variable region amino acid sequence of the anti-HER3 human antibody U1-39
SEQ ID NO: 2—Heavy chain variable region amino acid sequence of the anti-HER3 human antibody U1-39
SEQ ID NO: 3—Nucleotide sequence encoding a light chain variable region amino acid sequence of the anti-HER3 human antibody U1-39
SEQ ID NO: 4—Light chain variable region amino acid sequence of the anti-HER3 human antibody U1-39
SEQ ID NO: 5—Nucleotide sequence encoding a heavy chain variable region amino acid sequence of the anti-HER3 human antibody U1-40
SEQ ID NO: 6—Heavy chain variable region amino acid sequence of the anti-HER3 human antibody U1-40
SEQ ID NO: 7—Nucleotide sequence encoding a light chain variable region amino acid sequence of the anti-HER3 human antibody U1-40
SEQ ID NO: 8—Light chain variable region amino acid sequence of the anti-HER3 human antibody U1-40
SEQ ID NO: 9—Nucleotide sequence encoding a heavy chain variable region amino acid sequence of the anti-HER3 human antibody U1-38
SEQ ID NO: 10—Heavy chain variable region amino acid sequence of the anti-HER3 human antibody U1-38
SEQ ID NO: 11—Nucleotide sequence encoding a light chain variable region amino acid sequence of the anti-HER3 human antibody U1-38
SEQ ID NO: 12—Light chain variable region amino acid sequence of the anti-HER3 human antibody U1-38
SEQ ID NO: 13—Nucleotide sequence encoding a heavy chain variable region amino acid sequence of the anti-HER3 human antibody U1-41
SEQ ID NO: 14—Heavy chain variable region amino acid sequence of the anti-HER3 human antibody U1-41
SEQ ID NO: 15—Nucleotide sequence encoding a light chain variable region amino acid sequence of the anti-HER3 human antibody U1-41
SEQ ID NO: 16—Light chain variable region amino acid sequence of the anti-HER3 human antibody U1-41
SEQ ID NO: 17—Nucleotide sequence encoding a heavy chain variable region amino acid sequence of the anti-HER3 human antibody U1-42
SEQ ID NO: 18—Heavy chain variable region amino acid sequence of the anti-HER3 human antibody U1-42
SEQ ID NO: 19—Nucleotide sequence encoding a light chain variable region amino acid sequence of the anti-HER3 human antibody U1-42
SEQ ID NO: 20—Light chain variable region amino acid sequence of the anti-HER3 human antibody U1-42
SEQ ID NO: 21—Nucleotide sequence encoding a heavy chain variable region amino acid sequence of the anti-HER3 human antibody U1-43
SEQ ID NO: 22—Heavy chain variable region amino acid sequence of the anti-HER3 human antibody U1-43
SEQ ID NO: 23—Nucleotide sequence encoding a light chain variable region amino acid sequence of the anti-HER3 human antibody U1-43
SEQ ID NO: 24—Light chain variable region amino acid sequence of the anti-HER3 human antibody U1-43
SEQ ID NO: 25—Nucleotide sequence encoding a heavy chain variable region amino acid sequence of the anti-HER3 human antibody U1-44
SEQ ID NO: 26—Heavy chain variable region amino acid sequence of the anti-HER3 human antibody U1-44
SEQ ID NO: 27—Nucleotide sequence encoding a light chain variable region amino acid sequence of the anti-HER3 human antibody U1-44
SEQ ID NO: 28—Light chain variable region amino acid sequence of the anti-HER3 human antibody U1-44

SEQ ID NO: 29—Nucleotide sequence encoding a heavy chain variable region amino acid sequence of the anti-HER3 human antibody U1-45
SEQ ID NO: 30—Heavy chain variable region amino acid sequence of the anti-HER3 human antibody U1-45
SEQ ID NO: 31—Nucleotide sequence encoding a light chain variable region amino acid sequence of the anti-HER3 human antibody U1-45
SEQ ID NO: 32—Light chain variable region amino acid sequence of the anti-HER3 human antibody U1-45
SEQ ID NO: 33—Nucleotide sequence encoding a heavy chain variable region amino acid sequence of the anti-HER3 human antibody U1-46
SEQ ID NO: 34—Heavy chain variable region amino acid sequence of the anti-HER3 human antibody U1-46
SEQ ID NO: 35—Nucleotide sequence encoding a heavy chain variable region amino acid sequence of the anti-HER3 human antibody U1-47
SEQ ID NO: 36—Heavy chain variable region amino acid sequence of the anti-HER3 human antibody U1-47
SEQ ID NO: 37—Nucleotide sequence encoding a light chain variable region amino acid sequence of the anti-HER3 human antibody U1-47
SEQ ID NO: 38—Light chain variable region amino acid sequence of the anti-HER3 human antibody U1-47
SEQ ID NO: 39—Nucleotide sequence encoding a heavy chain variable region amino acid sequence of the anti-HER3 human antibody U1-48
SEQ ID NO: 40—Heavy chain variable region amino acid sequence of the anti-HER3 human antibody U1-48
SEQ ID NO: 41—Nucleotide sequence encoding a heavy chain variable region amino acid sequence of the anti-HER3 human antibody U1-49
SEQ ID NO: 42—Heavy chain variable region amino acid sequence of the anti-HER3 human antibody U1-49
SEQ ID NO: 43—Nucleotide sequence encoding a light chain variable region amino acid sequence of the anti-HER3 human antibody U1-49
SEQ ID NO: 44—Light chain variable region amino acid sequence of the anti-HER3 human antibody U1-49
SEQ ID NO: 45—Nucleotide sequence encoding a heavy chain variable region amino acid sequence of the anti-HER3 human antibody U1-50
SEQ ID NO: 46—Heavy chain variable region amino acid sequence of the anti-HER3 human antibody U1-50
SEQ ID NO: 47—Nucleotide sequence encoding a light chain variable region amino acid sequence of the anti-HER3 human antibody U1-50
SEQ ID NO: 48—Light chain variable region amino acid sequence of the anti-HER3 human antibody U1-50
SEQ ID NO: 49—Nucleotide sequence encoding a heavy chain variable region amino acid sequence of the anti-HER3 human antibody U1-51
SEQ ID NO: 50—Heavy chain variable region amino acid sequence of the anti-HER3 human antibody U1-51
SEQ ID NO: 51—Nucleotide sequence encoding a light chain variable region amino acid sequence of the anti-HER3 human antibody U1-51
SEQ ID NO: 52—Light chain variable region amino acid sequence of the anti-HER3 human antibody U1-51
SEQ ID NO: 53—Nucleotide sequence encoding a heavy chain variable region amino acid sequence of the anti-HER3 human antibody U1-53
SEQ ID NO: 54—Heavy chain variable region amino acid sequence of the anti-HER3 human antibody U1-53
SEQ ID NO: 55—Nucleotide sequence encoding a light chain variable region amino acid sequence of the anti-HER3 human antibody U1-53
SEQ ID NO: 56—Light chain variable region amino acid sequence of the anti-HER3 human antibody U1-53
SEQ ID NO: 57—Nucleotide sequence encoding a light chain variable region amino acid sequence of the anti-HER3 human antibody U1-55
SEQ ID NO: 58—Light chain variable region amino acid sequence of the anti-HER3 human antibody U1-55
SEQ ID NO: 59—Nucleotide sequence encoding a heavy chain variable region amino acid sequence of the anti-HER3 human antibody U1-55.1
SEQ ID NO: 60—Heavy chain variable region amino acid sequence of the anti-HER3 human antibody U1-55.1
SEQ ID NO: 61—Nucleotide sequence encoding a heavy chain variable region amino acid sequence of the anti-HER3 human antibody U1-57
SEQ ID NO: 62—Heavy chain variable region amino acid sequence of the anti-HER3 human antibody U1-57
SEQ ID NO: 63—Nucleotide sequence encoding a light chain variable region amino acid sequence of the anti-HER3 human antibody U1-57.1
SEQ ID NO: 64—Light chain variable region amino acid sequence of the anti-HER3 human antibody U1-57.1
SEQ ID NO: 65—Nucleotide sequence encoding a heavy chain variable region amino acid sequence of the anti-HER3 human antibody U1-58
SEQ ID NO: 66—Heavy chain variable region amino acid sequence of the anti-HER3 human antibody U1-58
SEQ ID NO: 67—Nucleotide sequence encoding a light chain variable region amino acid sequence of the anti-HER3 human antibody U1-58
SEQ ID NO: 68—Light chain variable region amino acid sequence of the anti-HER3 human antibody U1-58
SEQ ID NO: 69—Nucleotide sequence encoding a heavy chain variable region amino acid sequence of the anti-HER3 human antibody U1-59
SEQ ID NO: 70—Heavy chain variable region amino acid sequence of the anti-HER3 human antibody U1-59
SEQ ID NO: 71—Nucleotide sequence encoding a light chain variable region amino acid sequence of the anti-HER3 human antibody U1-59
SEQ ID NO: 72—Light chain variable region amino acid sequence of the anti-HER3 human antibody U1-59
SEQ ID NO: 73—Nucleotide sequence encoding a heavy chain variable region amino acid sequence of the anti-HER3 human antibody U1-52
SEQ ID NO: 74—Heavy chain variable region amino acid sequence of the anti-HER3 human antibody U1-52
SEQ ID NO: 75—Nucleotide sequence encoding a light chain variable region amino acid sequence of the anti-HER3 human antibody U1-52
SEQ ID NO: 76—Light chain variable region amino acid sequence of the anti-HER3 human antibody U1-52
SEQ ID NO: 77—Nucleotide sequence encoding a heavy chain variable region amino acid sequence of the anti-HER3 human antibody U1-61
SEQ ID NO: 78—Heavy chain variable region amino acid sequence of the anti-HER3 human antibody U1-61
SEQ ID NO: 79—Nucleotide sequence encoding a heavy chain variable region amino acid sequence of the anti-HER3 human antibody U1-61.1
SEQ ID NO: 80—Heavy chain variable region amino acid sequence of the anti-HER3 human antibody U1-61.1

SEQ ID NO: 81—Nucleotide sequence encoding a light chain variable region amino acid sequence of the anti-HER3 human antibody U1-61.1

SEQ ID NO: 82—Light chain variable region amino acid sequence of the anti-HER3 human antibody U1-61.1

SEQ ID NO: 83—Nucleotide sequence encoding a heavy chain variable region amino acid sequence of the anti-HER3 human antibody U1-62

SEQ ID NO: 84—Heavy chain variable region amino acid sequence of the anti-HER3 human antibody U1-62

SEQ ID NO: 85—Nucleotide sequence encoding a light chain variable region amino acid sequence of the anti-HER3 human antibody U1-62

SEQ ID NO: 86—Light chain variable region amino acid sequence of the anti-HER3 human antibody U1-62

SEQ ID NO: 87—Nucleotide sequence encoding a heavy chain variable region amino acid sequence of the anti-HER3 human antibody U1-2

SEQ ID NO: 88—Heavy chain variable region amino acid sequence of the anti-HER3 human antibody U1-2

SEQ ID NO: 89—Nucleotide sequence encoding a light chain variable region amino acid sequence of the anti-HER3 human antibody U1-2

SEQ ID NO: 90—Light chain variable region amino acid sequence of the anti-HER3 human antibody U1-2

SEQ ID NO: 91—Nucleotide sequence encoding a heavy chain variable region amino acid sequence of the anti-HER3 human antibody U1-7

SEQ ID NO: 92—Heavy chain variable region amino acid sequence of the anti-HER3 human antibody U1-7

SEQ ID NO: 93—Nucleotide sequence encoding a light chain variable region amino acid sequence of the anti-HER3 human antibody U1-7

SEQ ID NO: 94—Light chain variable region amino acid sequence of the anti-HER3 human antibody U1-7

SEQ ID NO: 95—Nucleotide sequence encoding a heavy chain variable region amino acid sequence of the anti-HER3 human antibody U1-9

SEQ ID NO: 96—Heavy chain variable region amino acid sequence of the anti-HER3 human antibody U1-9

SEQ ID NO: 97—Nucleotide sequence encoding a light chain variable region amino acid sequence of the anti-HER3 human antibody U1-9

SEQ ID NO: 98—Light chain variable region amino acid sequence of the anti-HER3 human antibody U1-9

SEQ ID NO: 99—Nucleotide sequence encoding a heavy chain variable region amino acid sequence of the anti-HER3 human antibody U1-10

SEQ ID NO: 100—Heavy chain variable region amino acid sequence of the anti-HER3 human antibody U1-10

SEQ ID NO: 101—Nucleotide sequence encoding a light chain variable region amino acid sequence of the anti-HER3 human antibody U1-10

SEQ ID NO: 102—Light chain variable region amino acid sequence of the anti-HER3 human antibody U1-10

SEQ ID NO: 103—Nucleotide sequence encoding a heavy chain variable region amino acid sequence of the anti-HER3 human antibody U1-12

SEQ ID NO: 104—Heavy chain variable region amino acid sequence of the anti-HER3 human antibody U1-12

SEQ ID NO: 105—Nucleotide sequence encoding a light chain variable region amino acid sequence of the anti-HER3 human antibody U1-12

SEQ ID NO: 106—Light chain variable region amino acid sequence of the anti-HER3 human antibody U1-12

SEQ ID NO: 107—Nucleotide sequence encoding a heavy chain variable region amino acid sequence of the anti-HER3 human antibody U1-13

SEQ ID NO: 108—Heavy chain variable region amino acid sequence of the anti-HER3 human antibody U1-13

SEQ ID NO: 109—Nucleotide sequence encoding a light chain variable region amino acid sequence of the anti-HER3 human antibody U1-13

SEQ ID NO: 110—Light chain variable region amino acid sequence of the anti-HER3 human antibody U1-13

SEQ ID NO: 111—Nucleotide sequence encoding a heavy chain variable region amino acid sequence of the anti-HER3 human antibody U1-14

SEQ ID NO: 112—Heavy chain variable region amino acid sequence of the anti-HER3 human antibody U1-14

SEQ ID NO: 113—Nucleotide sequence encoding a light chain variable region amino acid sequence of the anti-HER3 human antibody U1-14

SEQ ID NO: 114—Light chain variable region amino acid sequence of the anti-HER3 human antibody U1-14

SEQ ID NO: 115—Nucleotide sequence encoding a heavy chain variable region amino acid sequence of the anti-HER3 human antibody U1-15

SEQ ID NO: 116—Heavy chain variable region amino acid sequence of the anti-HER3 human antibody U1-15

SEQ ID NO: 117—Nucleotide sequence encoding a light chain variable region amino acid sequence of the anti-HER3 human antibody U1-15

SEQ ID NO: 118—Light chain variable region amino acid sequence of the anti-HER3 human antibody U1-15

SEQ ID NO: 119—Nucleotide sequence encoding a heavy chain variable region amino acid sequence of the anti-HER3 human antibody U1-19

SEQ ID NO: 120—Heavy chain variable region amino acid sequence of the anti-HER3 human antibody U1-19

SEQ ID NO: 121—Nucleotide sequence encoding a heavy chain variable region amino acid sequence of the anti-HER3 human antibody U1-20

SEQ ID NO: 122—Heavy chain variable region amino acid sequence of the anti-HER3 human antibody U1-20

SEQ ID NO: 123—Nucleotide sequence encoding a light chain variable region amino acid sequence of the anti-HER3 human antibody U1-20

SEQ ID NO: 124—Light chain variable region amino acid sequence of the anti-HER3 human antibody U1-20

SEQ ID NO: 125—Nucleotide sequence encoding a heavy chain variable region amino acid sequence of the anti-HER3 human antibody U1-21

SEQ ID NO: 126—Heavy chain variable region amino acid sequence of the anti-HER3 human antibody U1-21

SEQ ID NO: 127—Nucleotide sequence encoding a light chain variable region amino acid sequence of the anti-HER3 human antibody U1-21

SEQ ID NO: 128—Light chain variable region amino acid sequence of the anti-HER3 human antibody U1-21

SEQ ID NO: 129—Nucleotide sequence encoding a heavy chain variable region amino acid sequence of the anti-HER3 human antibody U1-22

SEQ ID NO: 130—Heavy chain variable region amino acid sequence of the anti-HER3 human antibody U1-22

SEQ ID NO: 131—Nucleotide sequence encoding a light chain variable region amino acid sequence of the anti-HER3 human antibody U1-22

SEQ ID NO: 132—Light chain variable region amino acid sequence of the anti-HER3 human antibody U1-22

SEQ ID NO: 133—Nucleotide sequence encoding a heavy chain variable region amino acid sequence of the anti-HER3 human antibody U1-23
SEQ ID NO: 134—Heavy chain variable region amino acid sequence of the anti-HER3 human antibody U1-23
SEQ ID NO: 135—Nucleotide sequence encoding a light chain variable region amino acid sequence of the anti-HER3 human antibody U1-23
SEQ ID NO: 136—Light chain variable region amino acid sequence of the anti-HER3 human antibody U1-23
SEQ ID NO: 137—Nucleotide sequence encoding a heavy chain variable region amino acid sequence of the anti-HER3 human antibody U1-24
SEQ ID NO: 138—Heavy chain variable region amino acid sequence of the anti-HER3 human antibody U1-24
SEQ ID NO: 139—Nucleotide sequence encoding a light chain variable region amino acid sequence of the anti-HER3 human antibody U1-24
SEQ ID NO: 140—Light chain variable region amino acid sequence of the anti-HER3 human antibody U1-24
SEQ ID NO: 141—Nucleotide sequence encoding a heavy chain variable region amino acid sequence of the anti-HER3 human antibody U1-25
SEQ ID NO: 142—Heavy chain variable region amino acid sequence of the anti-HER3 human antibody U1-25
SEQ ID NO: 143—Nucleotide sequence encoding a light chain variable region amino acid sequence of the anti-HER3 human antibody U1-25
SEQ ID NO: 144—Light chain variable region amino acid sequence of the anti-HER3 human antibody U1-25
SEQ ID NO: 145—Nucleotide sequence encoding a heavy chain variable region amino acid sequence of the anti-HER3 human antibody U1-26
SEQ ID NO: 146—Heavy chain variable region amino acid sequence of the anti-HER3 human antibody U1-26
SEQ ID NO: 147—Nucleotide sequence encoding a light chain variable region amino acid sequence of the anti-HER3 human antibody U1-26
SEQ ID NO: 148—Light chain variable region amino acid sequence of the anti-HER3 human antibody U1-26
SEQ ID NO: 149—Nucleotide sequence encoding a heavy chain variable region amino acid sequence of the anti-HER3 human antibody U1-27
SEQ ID NO: 150—Heavy chain variable region amino acid sequence of the anti-HER3 human antibody U1-27
SEQ ID NO: 151—Nucleotide sequence encoding a light chain variable region amino acid sequence of the anti-HER3 human antibody U1-27
SEQ ID NO: 152—Light chain variable region amino acid sequence of the anti-HER3 human antibody U1-27
SEQ ID NO: 153—Nucleotide sequence encoding a heavy chain variable region amino acid sequence of the anti-HER3 human antibody U1-28
SEQ ID NO: 154—Heavy chain variable region amino acid sequence of the anti-HER3 human antibody U1-28
SEQ ID NO: 155—Nucleotide sequence encoding a light chain variable region amino acid sequence of the anti-HER3 human antibody U1-28
SEQ ID NO: 156—Light chain variable region amino acid sequence of the anti-HER3 human antibody U1-28
SEQ ID NO: 157—Nucleotide sequence encoding a heavy chain variable region amino acid sequence of the anti-HER3 human antibody U1-31
SEQ ID NO: 158—Heavy chain variable region amino acid sequence of the anti-HER3 human antibody U1-31
SEQ ID NO: 159—Nucleotide sequence encoding a light chain variable region amino acid sequence of the anti-HER3 human antibody U1-31
SEQ ID NO: 160—Light chain variable region amino acid sequence of the anti-HER3 human antibody U1-31
SEQ ID NO: 161—Nucleotide sequence encoding a heavy chain variable region amino acid sequence of the anti-HER3 human antibody U1-32
SEQ ID NO: 162—Heavy chain variable region amino acid sequence of the anti-HER3 human antibody U1-32
SEQ ID NO: 163—Nucleotide sequence encoding a light chain variable region amino acid sequence of the anti-HER3 human antibody U1-32
SEQ ID NO: 164—Light chain variable region amino acid sequence of the anti-HER3 human antibody U1-32
SEQ ID NO: 165—Nucleotide sequence encoding a heavy chain variable region amino acid sequence of the anti-HER3 human antibody U1-35
SEQ ID NO: 166—Heavy chain variable region amino acid sequence of the anti-HER3 human antibody U1-35
SEQ ID NO: 167—Nucleotide sequence encoding a light chain variable region amino acid sequence of the anti-HER3 human antibody U1-35
SEQ ID NO: 168—Light chain variable region amino acid sequence of the anti-HER3 human antibody U1-35
SEQ ID NO: 169—Nucleotide sequence encoding a heavy chain variable region amino acid sequence of the anti-HER3 human antibody U1-36
SEQ ID NO: 170—Heavy chain variable region amino acid sequence of the anti-HER3 human antibody U1-36
SEQ ID NO: 171—Nucleotide sequence encoding a light chain variable region amino acid sequence of the anti-HER3 human antibody U1-36
SEQ ID NO: 172—Light chain variable region amino acid sequence of the anti-HER3 human antibody U1-36
SEQ ID NO: 173—Nucleotide sequence encoding a heavy chain variable region amino acid sequence of the anti-HER3 human antibody U1-37
SEQ ID NO: 174—Heavy chain variable region amino acid sequence of the anti-HER3 human antibody U1-37
SEQ ID NO: 175—Nucleotide sequence encoding a light chain variable region amino acid sequence of the anti-HER3 human antibody U1-37
SEQ ID NO: 176—Light chain variable region amino acid sequence of the anti-HER3 human antibody U1-37
SEQ ID NO: 177—Nucleotide sequence encoding a heavy chain variable region amino acid sequence of the anti-HER3 human antibody U1-34
SEQ ID NO: 178—Heavy chain variable region amino acid sequence of the anti-HER3 human antibody U1-34
SEQ ID NO: 179—Nucleotide sequence encoding a light chain variable region amino acid sequence of the anti-HER3 human antibody U1-34
SEQ ID NO: 180—Light chain variable region amino acid sequence of the anti-HER3 human antibody U1-34
SEQ ID NO: 181—Nucleotide sequence encoding a heavy chain variable region amino acid sequence of the anti-HER3 human antibody U1-1
SEQ ID NO: 182—Heavy chain variable region amino acid sequence of the anti-HER3 human antibody U1-1
SEQ ID NO: 183—Nucleotide sequence encoding a light chain variable region amino acid sequence of the anti-HER3 human antibody U1-1
SEQ ID NO: 184—Light chain variable region amino acid sequence of the anti-HER3 human antibody UT-1

SEQ ID NO: 185—Nucleotide sequence encoding a heavy chain variable region amino acid sequence of the anti-HER3 human antibody U1-3
SEQ ID NO: 186—Heavy chain variable region amino acid sequence of the anti-HER3 human antibody U1-3
SEQ ID NO: 187—Nucleotide sequence encoding a light chain variable region amino acid sequence of the anti-HER3 human antibody U1-3
SEQ ID NO: 188—Light chain variable region amino acid sequence of the anti-HER3 human antibody U1-3
SEQ ID NO: 189—Nucleotide sequence encoding a heavy chain variable region amino acid sequence of the anti-HER3 human antibody U1-4
SEQ ID NO: 190—Heavy chain variable region amino acid sequence of the anti-HER3 human antibody U1-4
SEQ ID NO: 191—Nucleotide sequence encoding a light chain variable region amino acid sequence of the anti-HER3 human antibody U1-4
SEQ ID NO: 192—Light chain variable region amino acid sequence of the anti-HER3 human antibody U1-4
SEQ ID NO: 193—Nucleotide sequence encoding a heavy chain variable region amino acid sequence of the anti-HER3 human antibody U1-5
SEQ ID NO: 194—Heavy chain variable region amino acid sequence of the anti-HER3 human antibody U1-5
SEQ ID NO: 195—Nucleotide sequence encoding a light chain variable region amino acid sequence of the anti-HER3 human antibody U1-5
SEQ ID NO: 196—Light chain variable region amino acid sequence of the anti-HER3 human antibody U1-5
SEQ ID NO: 197—Nucleotide sequence encoding a heavy chain variable region amino acid sequence of the anti-HER3 human antibody U1-6
SEQ ID NO: 198—Heavy chain variable region amino acid sequence of the anti-HER3 human antibody U1-6
SEQ ID NO: 199—Nucleotide sequence encoding a light chain variable region amino acid sequence of the anti-HER3 human antibody U1-6
SEQ ID NO: 200—Light chain variable region amino acid sequence of the anti-HER3 human antibody U1-6
SEQ ID NO: 201—Nucleotide sequence encoding a heavy chain variable region amino acid sequence of the anti-HER3 human antibody U1-8
SEQ ID NO: 202—Heavy chain variable region amino acid sequence of the anti-HER3 human antibody U1-8
SEQ ID NO: 203—Nucleotide sequence encoding a light chain variable region amino acid sequence of the anti-HER3 human antibody U1-8
SEQ ID NO: 204—Light chain variable region amino acid sequence of the anti-HER3 human antibody U1-8
SEQ ID NO: 205—Nucleotide sequence encoding a heavy chain variable region amino acid sequence of the anti-HER3 human antibody U1-11
SEQ ID NO: 206—Heavy chain variable region amino acid sequence of the anti-HER3 human antibody U1-11
SEQ ID NO: 207—Nucleotide sequence encoding a light chain variable region amino acid sequence of the anti-HER3 human antibody U1-11
SEQ ID NO: 208—Light chain variable region amino acid sequence of the anti-HER3 human antibody U1-11
SEQ ID NO: 209—Nucleotide sequence encoding a heavy chain variable region amino acid sequence of the anti-HER3 human antibody U1-16
SEQ ID NO: 210—Heavy chain variable region amino acid sequence of the anti-HER3 human antibody U1-16
SEQ ID NO: 211—Nucleotide sequence encoding a light chain variable region amino acid sequence of the anti-HER3 human antibody U1-16
SEQ ID NO: 212—Light chain variable region amino acid sequence of the anti-HER3 human antibody U1-16
SEQ ID NO: 213—Nucleotide sequence encoding a heavy chain variable region amino acid sequence of the anti-HER3 human antibody U1-17
SEQ ID NO: 214—Heavy chain variable region amino acid sequence of the anti-HER3 human antibody U1-17
SEQ ID NO: 215—Nucleotide sequence encoding a light chain variable region amino acid sequence of the anti-HER3 human antibody U1-17
SEQ ID NO: 216—Light chain variable region amino acid sequence of the anti-HER3 human antibody U1-17
SEQ ID NO: 217—Nucleotide sequence encoding a heavy chain variable region amino acid sequence of the anti-HER3 human antibody U1-18
SEQ ID NO: 218—Heavy chain variable region amino acid sequence of the anti-HER3 human antibody U1-18
SEQ ID NO: 219—Nucleotide sequence encoding a light chain variable region amino acid sequence of the anti-HER3 human antibody U1-18
SEQ ID NO: 220—Light chain variable region amino acid sequence of the anti-HER3 human antibody U1-18
SEQ ID NO: 221—Nucleotide sequence encoding a heavy chain variable region amino acid sequence of the anti-HER3 human antibody U1-33
SEQ ID NO: 222—Heavy chain variable region amino acid sequence of the anti-HER3 human antibody U1-33
SEQ ID NO: 223—Nucleotide sequence encoding a light chain variable region amino acid sequence of the anti-HER3 human antibody U1-33
SEQ ID NO: 224—Light chain variable region amino acid sequence of the anti-HER3 human antibody U1-33
SEQ ID NO: 225—Nucleotide sequence encoding a heavy chain variable region amino acid sequence of the anti-HER3 human antibody U1-29
SEQ ID NO: 226—Heavy chain variable region amino acid sequence of the anti-HER3 human antibody U1-29
SEQ ID NO: 227—Nucleotide sequence encoding a light chain variable region amino acid sequence of the anti-HER3 human antibody U1-29
SEQ ID NO: 228—Light chain variable region amino acid sequence of the anti-HER3 human antibody U1-29
SEQ ID NO: 229—Nucleotide sequence encoding a heavy chain variable region amino acid sequence of the anti-HER3 human antibody U1-30
SEQ ID NO: 230—Heavy chain variable region amino acid sequence of the anti-HER3 human antibody U1-30
SEQ ID NO: 231—Nucleotide sequence encoding a light chain variable region amino acid sequence of the anti-HER3 human antibody U1-30
SEQ ID NO: 232—Light chain variable region amino acid sequence of the anti-HER3 human antibody U1-30
SEQ ID NO: 233—Primer
SEQ ID NO: 234—Primer
SEQ ID NO: 235—Heavy chain CDRH1 amino acid sequence of the anti-HER3 human antibody U1-1
SEQ ID NO: 236—Heavy chain CDRH2 amino acid sequence of the anti-HER3 human antibody U1-1
SEQ ID NO: 237—Heavy chain CDRH3 amino acid sequence of the anti-HER3 human antibody U1-1
SEQ ID NO: 238—Light chain CDRL1 amino acid sequence of the anti-HER3 human antibody U1-1
SEQ ID NO: 239—Light chain CDRL2 amino acid sequence of the anti-HER3 human antibody U1-1

SEQ ID NO: 240—Light chain CDRL3 amino acid sequence of the anti-HER3 human antibody U1-1
SEQ ID NO: 241—Heavy chain CDRH1 amino acid sequence of the anti-HER3 human antibody U1-2
SEQ ID NO: 242—Heavy chain CDRH2 amino acid sequence of the anti-HER3 human antibody U1-2
SEQ ID NO: 243—Heavy chain CDRH3 amino acid sequence of the anti-HER3 human antibody U1-2
SEQ ID NO: 244—Light chain CDRL1 amino acid sequence of the anti-HER3 human antibody U1-2
SEQ ID NO: 245—Light chain CDRL2 amino acid sequence of the anti-HER3 human antibody U1-2
SEQ ID NO: 246—Light chain CDRL3 amino acid sequence of the anti-HER3 human antibody U1-2
SEQ ID NO: 247—Heavy chain CDRH1 amino acid sequence of the anti-HER3 human antibody U1-3
SEQ ID NO: 248—Heavy chain CDRH2 amino acid sequence of the anti-HER3 human antibody U1-3
SEQ ID NO: 249—Heavy chain CDRH3 amino acid sequence of the anti-HER3 human antibody U1-3
SEQ ID NO: 250—Light chain CDRL1 amino acid sequence of the anti-HER3 human antibody U1-3
SEQ ID NO: 251—Light chain CDRL2 amino acid sequence of the anti-HER3 human antibody U1-3
SEQ ID NO: 252—Light chain CDRL3 amino acid sequence of the anti-HER3 human antibody U1-3
SEQ ID NO: 253—Heavy chain CDRH1 amino acid sequence of the anti-HER3 human antibody U1-4
SEQ ID NO: 254—Heavy chain CDRH2 amino acid sequence of the anti-HER3 human antibody U1-4
SEQ ID NO: 255—Heavy chain CDRH3 amino acid sequence of the anti-HER3 human antibody U1-4
SEQ ID NO: 256—Light chain CDRL1 amino acid sequence of the anti-HER3 human antibody U1-4
SEQ ID NO: 257—Light chain CDRL2 amino acid sequence of the anti-HER3 human antibody U1-4
SEQ ID NO: 258—Light chain CDRL3 amino acid sequence of the anti-HER3 human antibody U1-4
SEQ ID NO: 259—Heavy chain CDRH1 amino acid sequence of the anti-HER3 human antibody U1-5
SEQ ID NO: 260—Heavy chain CDRH2 amino acid sequence of the anti-HER3 human antibody U1-5
SEQ ID NO: 261—Heavy chain CDRH3 amino acid sequence of the anti-HER3 human antibody U1-5
SEQ ID NO: 262—Light chain CDRL1 amino acid sequence of the anti-HER3 human antibody U1-5
SEQ ID NO: 263—Light chain CDRL2 amino acid sequence of the anti-HER3 human antibody U1-5
SEQ ID NO: 264—Light chain CDRL3 amino acid sequence of the anti-HER3 human antibody U1-5
SEQ ID NO: 265—Heavy chain CDRH1 amino acid sequence of the anti-HER3 human antibody U1-6
SEQ ID NO: 266—Heavy chain CDRH2 amino acid sequence of the anti-HER3 human antibody U1-6
SEQ ID NO: 267—Heavy chain CDRH3 amino acid sequence of the anti-HER3 human antibody U1-6
SEQ ID NO: 268—Light chain CDRL1 amino acid sequence of the anti-HER3 human antibody U1-6
SEQ ID NO: 269—Light chain CDRL2 amino acid sequence of the anti-HER3 human antibody U1-6
SEQ ID NO: 270—Light chain CDRL3 amino acid sequence of the anti-HER3 human antibody U1-6
SEQ ID NO: 271—Heavy chain CDRH1 amino acid sequence of the anti-HER3 human antibody U1-7
SEQ ID NO: 272—Heavy chain CDRH2 amino acid sequence of the anti-HER3 human antibody U1-7
SEQ ID NO: 273—Heavy chain CDRH3 amino acid sequence of the anti-HER3 human antibody U1-7
SEQ ID NO: 274—Light chain CDRL1 amino acid sequence of the anti-HER3 human antibody U1-7
SEQ ID NO: 275—Light chain CDRL2 amino acid sequence of the anti-HER3 human antibody U1-7
SEQ ID NO: 276—Light chain CDRL3 amino acid sequence of the anti-HER3 human antibody U1-7
SEQ ID NO: 277—Heavy chain CDRH1 amino acid sequence of the anti-HER3 human antibody U1-8
SEQ ID NO: 278—Heavy chain CDRH2 amino acid sequence of the anti-HER3 human antibody U1-8
SEQ ID NO: 279—Heavy chain CDRH3 amino acid sequence of the anti-HER3 human antibody U1-8
SEQ ID NO: 280—Light chain CDRL1 amino acid sequence of the anti-HER3 human antibody U1-8
SEQ ID NO: 281—Light chain CDRL2 amino acid sequence of the anti-HER3 human antibody U1-8
SEQ ID NO: 282—Light chain CDRL3 amino acid sequence of the anti-HER3 human antibody U1-8
SEQ ID NO: 283—Heavy chain CDRH1 amino acid sequence of the anti-HER3 human antibody U1-9
SEQ ID NO: 284—Heavy chain CDRH2 amino acid sequence of the anti-HER3 human antibody U1-9
SEQ ID NO: 285—Heavy chain CDRH3 amino acid sequence of the anti-HER3 human antibody U1-9
SEQ ID NO: 286—Light chain CDRL1 amino acid sequence of the anti-HER3 human antibody U1-9
SEQ ID NO: 287—Light chain CDRL2 amino acid sequence of the anti-HER3 human antibody U1-9
SEQ ID NO: 288—Light chain CDRL3 amino acid sequence of the anti-HER3 human antibody U1-9
SEQ ID NO: 289—Heavy chain CDRH1 amino acid sequence of the anti-HER3 human antibody U1-10
SEQ ID NO: 290—Heavy chain CDRH2 amino acid sequence of the anti-HER3 human antibody U1-10
SEQ ID NO: 291—Heavy chain CDRH3 amino acid sequence of the anti-HER3 human antibody U1-10
SEQ ID NO: 292—Light chain CDRL1 amino acid sequence of the anti-HER3 human antibody U1-10
SEQ ID NO: 293—Light chain CDRL2 amino acid sequence of the anti-HER3 human antibody U1-10
SEQ ID NO: 294—Light chain CDRL3 amino acid sequence of the anti-HER3 human antibody U1-10
SEQ ID NO: 295—Heavy chain CDRH1 amino acid sequence of the anti-HER3 human antibody U1-11
SEQ ID NO: 296—Heavy chain CDRH2 amino acid sequence of the anti-HER3 human antibody U1-11
SEQ ID NO: 297—Heavy chain CDRH3 amino acid sequence of the anti-HER3 human antibody U1-11
SEQ ID NO: 298—Light chain CDRL1 amino acid sequence of the anti-HER3 human antibody U1-11
SEQ ID NO: 299—Light chain CDRL2 amino acid sequence of the anti-HER3 human antibody U1-11
SEQ ID NO: 300—Light chain CDRL3 amino acid sequence of the anti-HER3 human antibody U1-11
SEQ ID NO: 301—Heavy chain CDRH1 amino acid sequence of the anti-HER3 human antibody U1-12
SEQ ID NO: 302—Heavy chain CDRH2 amino acid sequence of the anti-HER3 human antibody U1-12
SEQ ID NO: 303—Heavy chain CDRH3 amino acid sequence of the anti-HER3 human antibody U1-12
SEQ ID NO: 304—Light chain CDRL1 amino acid sequence of the anti-HER3 human antibody U1-12
SEQ ID NO: 305—Light chain CDRL2 amino acid sequence of the anti-HER3 human antibody U1-12

SEQ ID NO: 306—Light chain CDRL3 amino acid sequence of the anti-HER3 human antibody U1-12
SEQ ID NO: 307—Heavy chain CDRH1 amino acid sequence of the anti-HER3 human antibody U1-13
SEQ ID NO: 308—Heavy chain CDRH2 amino acid sequence of the anti-HER3 human antibody U1-13
SEQ ID NO: 309—Heavy chain CDRH3 amino acid sequence of the anti-HER3 human antibody U1-13
SEQ ID NO: 310—Light chain CDRL1 amino acid sequence of the anti-HER3 human antibody U1-13
SEQ ID NO: 311—Light chain CDRL2 amino acid sequence of the anti-HER3 human antibody U1-13
SEQ ID NO: 312—Light chain CDRL3 amino acid sequence of the anti-HER3 human antibody U1-13
SEQ ID NO: 313—Heavy chain CDRH1 amino acid sequence of the anti-HER3 human antibody U1-14
SEQ ID NO: 314—Heavy chain CDRH2 amino acid sequence of the anti-HER3 human antibody U1-14
SEQ ID NO: 315—Heavy chain CDRH3 amino acid sequence of the anti-HER3 human antibody U1-14
SEQ ID NO: 316—Light chain CDRL1 amino acid sequence of the anti-HER3 human antibody U1-14
SEQ ID NO: 317—Light chain CDRL2 amino acid sequence of the anti-HER3 human antibody U1-14
SEQ ID NO: 318—Light chain CDRL3 amino acid sequence of the anti-HER3 human antibody U1-14
SEQ ID NO: 319—Heavy chain CDRH1 amino acid sequence of the anti-HER3 human antibody U1-15
SEQ ID NO: 320—Heavy chain CDRH2 amino acid sequence of the anti-HER3 human antibody U1-15
SEQ ID NO: 321—Heavy chain CDRH3 amino acid sequence of the anti-HER3 human antibody U1-15
SEQ ID NO: 322—Light chain CDRL1 amino acid sequence of the anti-HER3 human antibody U1-15
SEQ ID NO: 323—Light chain CDRL2 amino acid sequence of the anti-HER3 human antibody U1-15
SEQ ID NO: 324—Light chain CDRL3 amino acid sequence of the anti-HER3 human antibody U1-15
SEQ ID NO: 325—Heavy chain CDRH1 amino acid sequence of the anti-HER3 human antibody U1-16
SEQ ID NO: 326—Heavy chain CDRH2 amino acid sequence of the anti-HER3 human antibody U1-16
SEQ ID NO: 327—Heavy chain CDRH3 amino acid sequence of the anti-HER3 human antibody U1-16
SEQ ID NO: 328—Light chain CDRL1 amino acid sequence of the anti-HER3 human antibody U1-16
SEQ ID NO: 329—Light chain CDRL2 amino acid sequence of the anti-HER3 human antibody U1-16
SEQ ID NO: 330—Light chain CDRL3 amino acid sequence of the anti-HER3 human antibody U1-16
SEQ ID NO: 331—Heavy chain CDRH1 amino acid sequence of the anti-HER3 human antibody U1-17
SEQ ID NO: 332—Heavy chain CDRH2 amino acid sequence of the anti-HER3 human antibody U1-17
SEQ ID NO: 333—Heavy chain CDRH3 amino acid sequence of the anti-HER3 human antibody U1-17
SEQ ID NO: 334—Light chain CDRL1 amino acid sequence of the anti-HER3 human antibody U1-17
SEQ ID NO: 335—Light chain CDRL2 amino acid sequence of the anti-HER3 human antibody U1-17
SEQ ID NO: 336—Light chain CDRL3 amino acid sequence of the anti-HER3 human antibody U1-17
SEQ ID NO: 337—Heavy chain CDRH1 amino acid sequence of the anti-HER3 human antibody U1-18
SEQ ID NO: 338—Heavy chain CDRH2 amino acid sequence of the anti-HER3 human antibody U1-18
SEQ ID NO: 339—Heavy chain CDRH3 amino acid sequence of the anti-HER3 human antibody U1-18
SEQ ID NO: 340—Light chain CDRL1 amino acid sequence of the anti-HER3 human antibody U1-18
SEQ ID NO: 341—Light chain CDRL2 amino acid sequence of the anti-HER3 human antibody U1-18
SEQ ID NO: 342—Light chain CDRL3 amino acid sequence of the anti-HER3 human antibody U1-18
SEQ ID NO: 343—Heavy chain CDRH1 amino acid sequence of the anti-HER3 human antibody U1-19
SEQ ID NO: 344—Heavy chain CDRH2 amino acid sequence of the anti-HER3 human antibody U1-19
SEQ ID NO: 345—Heavy chain CDRH3 amino acid sequence of the anti-HER3 human antibody U1-19
SEQ ID NO: 346—Heavy chain CDRH1 amino acid sequence of the anti-HER3 human antibody U1-20
SEQ ID NO: 347—Heavy chain CDRH2 amino acid sequence of the anti-HER3 human antibody U1-20
SEQ ID NO: 348—Heavy chain CDRH3 amino acid sequence of the anti-HER3 human antibody U1-20
SEQ ID NO: 349—Light chain CDRL1 amino acid sequence of the anti-HER3 human antibody U1-20
SEQ ID NO: 350—Light chain CDRL2 amino acid sequence of the anti-HER3 human antibody U1-20
SEQ ID NO: 351—Light chain CDRL3 amino acid sequence of the anti-HER3 human antibody U1-20
SEQ ID NO: 352—Heavy chain CDRH1 amino acid sequence of the anti-HER3 human antibody U1-21
SEQ ID NO: 353—Heavy chain CDRH2 amino acid sequence of the anti-HER3 human antibody U1-21
SEQ ID NO: 354—Heavy chain CDRH3 amino acid sequence of the anti-HER3 human antibody U1-21
SEQ ID NO: 355—Light chain CDRL1 amino acid sequence of the anti-HER3 human antibody U1-21
SEQ ID NO: 356—Light chain CDRL2 amino acid sequence of the anti-HER3 human antibody U1-21
SEQ ID NO: 357—Light chain CDRL3 amino acid sequence of the anti-HER3 human antibody U1-21
SEQ ID NO: 358—Heavy chain CDRH1 amino acid sequence of the anti-HER3 human antibody U1-22
SEQ ID NO: 359—Heavy chain CDRH2 amino acid sequence of the anti-HER3 human antibody U1-22
SEQ ID NO: 360—Heavy chain CDRH3 amino acid sequence of the anti-HER3 human antibody U1-22
SEQ ID NO: 361—Light chain CDRL1 amino acid sequence of the anti-HER3 human antibody U1-22
SEQ ID NO: 362—Light chain CDRL2 amino acid sequence of the anti-HER3 human antibody U1-22
SEQ ID NO: 363—Light chain CDRL3 amino acid sequence of the anti-HER3 human antibody U1-22
SEQ ID NO: 364—Heavy chain CDRH1 amino acid sequence of the anti-HER3 human antibody U1-23
SEQ ID NO: 365—Heavy chain CDRH2 amino acid sequence of the anti-HER3 human antibody U1-23
SEQ ID NO: 366—Heavy chain CDRH3 amino acid sequence of the anti-HER3 human antibody U1-23
SEQ ID NO: 367—Light chain CDRL1 amino acid sequence of the anti-HER3 human antibody U1-23
SEQ ID NO: 368—Light chain CDRL2 amino acid sequence of the anti-HER3 human antibody U1-23
SEQ ID NO: 369—Light chain CDRL3 amino acid sequence of the anti-HER3 human antibody U1-23
SEQ ID NO: 370—Heavy chain CDRH1 amino acid sequence of the anti-HER3 human antibody U1-24
SEQ ID NO: 371—Heavy chain CDRH2 amino acid sequence of the anti-HER3 human antibody U1-24

SEQ ID NO: 372—Heavy chain CDRH3 amino acid sequence of the anti-HER3 human antibody U1-24
SEQ ID NO: 373—Light chain CDRL1 amino acid sequence of the anti-HER3 human antibody U1-24
SEQ ID NO: 374—Light chain CDRL2 amino acid sequence of the anti-HER3 human antibody U1-24
SEQ ID NO: 375—Light chain CDRL3 amino acid sequence of the anti-HER3 human antibody U1-24
SEQ ID NO: 376—Heavy chain CDRH1 amino acid sequence of the anti-HER3 human antibody U1-25
SEQ ID NO: 377—Heavy chain CDRH2 amino acid sequence of the anti-HER3 human antibody U1-25
SEQ ID NO: 378—Heavy chain CDRH3 amino acid sequence of the anti-HER3 human antibody U1-25
SEQ ID NO: 379—Light chain CDRL1 amino acid sequence of the anti-HER3 human antibody U1-25
SEQ ID NO: 380—Light chain CDRL2 amino acid sequence of the anti-HER3 human antibody U1-25
SEQ ID NO: 381—Light chain CDRL3 amino acid sequence of the anti-HER3 human antibody U1-25
SEQ ID NO: 382—Heavy chain CDRH1 amino acid sequence of the anti-HER3 human antibody U1-26
SEQ ID NO: 383—Heavy chain CDRH2 amino acid sequence of the anti-HER3 human antibody U1-26
SEQ ID NO: 384—Heavy chain CDRH3 amino acid sequence of the anti-HER3 human antibody U1-26
SEQ ID NO: 385—Light chain CDRL1 amino acid sequence of the anti-HER3 human antibody U1-26
SEQ ID NO: 386—Light chain CDRL2 amino acid sequence of the anti-HER3 human antibody U1-26
SEQ ID NO: 387—Light chain CDRL3 amino acid sequence of the anti-HER3 human antibody U1-26
SEQ ID NO: 388—Heavy chain CDRH1 amino acid sequence of the anti-HER3 human antibody U1-27
SEQ ID NO: 389—Heavy chain CDRH2 amino acid sequence of the anti-HER3 human antibody U1-27
SEQ ID NO: 390—Heavy chain CDRH3 amino acid sequence of the anti-HER3 human antibody U1-27
SEQ ID NO: 391—Light chain CDRL1 amino acid sequence of the anti-HER3 human antibody U1-27
SEQ ID NO: 392—Light chain CDRL2 amino acid sequence of the anti-HER3 human antibody U1-27
SEQ ID NO: 393—Light chain CDRL3 amino acid sequence of the anti-HER3 human antibody U1-27
SEQ ID NO: 394—Heavy chain CDRH1 amino acid sequence of the anti-HER3 human antibody U1-28
SEQ ID NO: 395—Heavy chain CDRH2 amino acid sequence of the anti-HER3 human antibody U1-28
SEQ ID NO: 396—Heavy chain CDRH3 amino acid sequence of the anti-HER3 human antibody U1-28
SEQ ID NO: 397—Light chain CDRL1 amino acid sequence of the anti-HER3 human antibody U1-28
SEQ ID NO: 398—Light chain CDRL2 amino acid sequence of the anti-HER3 human antibody U1-28
SEQ ID NO: 399—Light chain CDRL3 amino acid sequence of the anti-HER3 human antibody U1-28
SEQ ID NO: 400—Heavy chain CDRH1 amino acid sequence of the anti-HER3 human antibody U1-29
SEQ ID NO: 401—Heavy chain CDRH2 amino acid sequence of the anti-HER3 human antibody U1-29
SEQ ID NO: 402—Heavy chain CDRH3 amino acid sequence of the anti-HER3 human antibody U1-29
SEQ ID NO: 403—Light chain CDRL1 amino acid sequence of the anti-HER3 human antibody U1-29
SEQ ID NO: 404—Light chain CDRL2 amino acid sequence of the anti-HER3 human antibody U1-29
SEQ ID NO: 405—Light chain CDRL3 amino acid sequence of the anti-HER3 human antibody U1-29
SEQ ID NO: 406—Heavy chain CDRH1 amino acid sequence of the anti-HER3 human antibody U1-30
SEQ ID NO: 407—Heavy chain CDRH2 amino acid sequence of the anti-HER3 human antibody U1-30
SEQ ID NO: 408—Heavy chain CDRH3 amino acid sequence of the anti-HER3 human antibody U1-30
SEQ ID NO: 409—Light chain CDRL1 amino acid sequence of the anti-HER3 human antibody U1-30
SEQ ID NO: 410—Light chain CDRL2 amino acid sequence of the anti-HER3 human antibody U1-30
SEQ ID NO: 411—Light chain CDRL3 amino acid sequence of the anti-HER3 human antibody U1-30
SEQ ID NO: 412—Heavy chain CDRH1 amino acid sequence of the anti-HER3 human antibody U1-31
SEQ ID NO: 413—Heavy chain CDRH2 amino acid sequence of the anti-HER3 human antibody U1-31
SEQ ID NO: 414—Heavy chain CDRH3 amino acid sequence of the anti-HER3 human antibody U1-31
SEQ ID NO: 415—Light chain CDRL1 amino acid sequence of the anti-HER3 human antibody U1-31
SEQ ID NO: 416—Light chain CDRL2 amino acid sequence of the anti-HER3 human antibody U1-31
SEQ ID NO: 417—Light chain CDRL3 amino acid sequence of the anti-HER3 human antibody U1-31
SEQ ID NO: 418—Heavy chain CDRH1 amino acid sequence of the anti-HER3 human antibody U1-32
SEQ ID NO: 419—Heavy chain CDRH2 amino acid sequence of the anti-HER3 human antibody U1-32
SEQ ID NO: 420—Heavy chain CDRH3 amino acid sequence of the anti-HER3 human antibody U1-32
SEQ ID NO: 421—Light chain CDRL1 amino acid sequence of the anti-HER3 human antibody U1-32
SEQ ID NO: 422—Light chain CDRL2 amino acid sequence of the anti-HER3 human antibody U1-32
SEQ ID NO: 423—Light chain CDRL3 amino acid sequence of the anti-HER3 human antibody U1-32
SEQ ID NO: 424—Heavy chain CDRH1 amino acid sequence of the anti-HER3 human antibody U1-33
SEQ ID NO: 425—Heavy chain CDRH2 amino acid sequence of the anti-HER3 human antibody U1-33
SEQ ID NO: 426—Heavy chain CDRH3 amino acid sequence of the anti-HER3 human antibody U1-33
SEQ ID NO: 427—Light chain CDRL1 amino acid sequence of the anti-HER3 human antibody U1-33
SEQ ID NO: 428—Light chain CDRL2 amino acid sequence of the anti-HER3 human antibody U1-33
SEQ ID NO: 429—Light chain CDRL3 amino acid sequence of the anti-HER3 human antibody U1-33
SEQ ID NO: 430—Heavy chain CDRH1 amino acid sequence of the anti-HER3 human antibody U1-34
SEQ ID NO: 431—Heavy chain CDRH2 amino acid sequence of the anti-HER3 human antibody U1-34
SEQ ID NO: 432—Heavy chain CDRH3 amino acid sequence of the anti-HER3 human antibody U1-34
SEQ ID NO: 433—Light chain CDRL1 amino acid sequence of the anti-HER3 human antibody U1-34
SEQ ID NO: 434—Light chain CDRL2 amino acid sequence of the anti-HER3 human antibody U1-34
SEQ ID NO: 435—Light chain CDRL3 amino acid sequence of the anti-HER3 human antibody U1-34
SEQ ID NO: 436—Heavy chain CDRH1 amino acid sequence of the anti-HER3 human antibody U1-35
SEQ ID NO: 437—Heavy chain CDRH2 amino acid sequence of the anti-HER3 human antibody U1-35

SEQ ID NO: 438—Heavy chain CDRH3 amino acid sequence of the anti-HER3 human antibody U1-35
SEQ ID NO: 439—Light chain CDRL1 amino acid sequence of the anti-HER3 human antibody U1-35
SEQ ID NO: 440—Light chain CDRL2 amino acid sequence of the anti-HER3 human antibody U1-35
SEQ ID NO: 441—Light chain CDRL3 amino acid sequence of the anti-HER3 human antibody U1-35
SEQ ID NO: 442—Heavy chain CDRH1 amino acid sequence of the anti-HER3 human antibody U1-36
SEQ ID NO: 443—Heavy chain CDRH2 amino acid sequence of the anti-HER3 human antibody U1-36
SEQ ID NO: 444—Heavy chain CDRH3 amino acid sequence of the anti-HER3 human antibody U1-36
SEQ ID NO: 445—Light chain CDRL1 amino acid sequence of the anti-HER3 human antibody U1-36
SEQ ID NO: 446—Light chain CDRL2 amino acid sequence of the anti-HER3 human antibody U1-36
SEQ ID NO: 447—Light chain CDRL3 amino acid sequence of the anti-HER3 human antibody U1-36
SEQ ID NO: 448—Heavy chain CDRH1 amino acid sequence of the anti-HER3 human antibody U1-37
SEQ ID NO: 449—Heavy chain CDRH2 amino acid sequence of the anti-HER3 human antibody U1-37
SEQ ID NO: 450—Heavy chain CDRH3 amino acid sequence of the anti-HER3 human antibody U1-37
SEQ ID NO: 451—Light chain CDRL1 amino acid sequence of the anti-HER3 human antibody U1-37
SEQ ID NO: 452—Light chain CDRL2 amino acid sequence of the anti-HER3 human antibody U1-37
SEQ ID NO: 453—Light chain CDRL3 amino acid sequence of the anti-HER3 human antibody U1-37
SEQ ID NO: 454—Heavy chain CDRH1 amino acid sequence of the anti-HER3 human antibody U1-38
SEQ ID NO: 455—Heavy chain CDRH2 amino acid sequence of the anti-HER3 human antibody U1-38
SEQ ID NO: 456—Heavy chain CDRH3 amino acid sequence of the anti-HER3 human antibody U1-38
SEQ ID NO: 457—Light chain CDRL1 amino acid sequence of the anti-HER3 human antibody U1-38
SEQ ID NO: 458—Light chain CDRL2 amino acid sequence of the anti-HER3 human antibody U1-38
SEQ ID NO: 459—Light chain CDRL3 amino acid sequence of the anti-HER3 human antibody U1-38
SEQ ID NO: 460—Heavy chain CDRH1 amino acid sequence of the anti-HER3 human antibody U1-39
SEQ ID NO: 461—Heavy chain CDRH2 amino acid sequence of the anti-HER3 human antibody U1-39
SEQ ID NO: 462—Heavy chain CDRH3 amino acid sequence of the anti-HER3 human antibody U1-39
SEQ ID NO: 463—Light chain CDRL1 amino acid sequence of the anti-HER3 human antibody U1-39
SEQ ID NO: 464—Light chain CDRL2 amino acid sequence of the anti-HER3 human antibody U1-39
SEQ ID NO: 465—Light chain CDRL3 amino acid sequence of the anti-HER3 human antibody U1-39
SEQ ID NO: 466—Heavy chain CDRH1 amino acid sequence of the anti-HER3 human antibody U1-40
SEQ ID NO: 467—Heavy chain CDRH2 amino acid sequence of the anti-HER3 human antibody U1-40
SEQ ID NO: 468—Heavy chain CDRH3 amino acid sequence of the anti-HER3 human antibody U1-40
SEQ ID NO: 469—Light chain CDRL1 amino acid sequence of the anti-HER3 human antibody U1-40
SEQ ID NO: 470—Light chain CDRL2 amino acid sequence of the anti-HER3 human antibody U1-40
SEQ ID NO: 471—Light chain CDRL3 amino acid sequence of the anti-HER3 human antibody U1-40
SEQ ID NO: 472—Heavy chain CDRH1 amino acid sequence of the anti-HER3 human antibody U1-41
SEQ ID NO: 473—Heavy chain CDRH2 amino acid sequence of the anti-HER3 human antibody U1-41
SEQ ID NO: 474—Heavy chain CDRH3 amino acid sequence of the anti-HER3 human antibody U1-41
SEQ ID NO: 475—Light chain CDRL1 amino acid sequence of the anti-HER3 human antibody U1-41
SEQ ID NO: 476—Light chain CDRL2 amino acid sequence of the anti-HER3 human antibody U1-41
SEQ ID NO: 477—Light chain CDRL3 amino acid sequence of the anti-HER3 human antibody U1-41
SEQ ID NO: 478—Heavy chain CDRH1 amino acid sequence of the anti-HER3 human antibody U1-42
SEQ ID NO: 479—Heavy chain CDRH2 amino acid sequence of the anti-HER3 human antibody U1-42
SEQ ID NO: 480—Heavy chain CDRH3 amino acid sequence of the anti-HER3 human antibody U1-42
SEQ ID NO: 481—Light chain CDRL1 amino acid sequence of the anti-HER3 human antibody U1-42
SEQ ID NO: 482—Light chain CDRL2 amino acid sequence of the anti-HER3 human antibody U1-42
SEQ ID NO: 483—Light chain CDRL3 amino acid sequence of the anti-HER3 human antibody U1-42
SEQ ID NO: 484—Heavy chain CDRH1 amino acid sequence of the anti-HER3 human antibody U1-43
SEQ ID NO: 485—Heavy chain CDRH2 amino acid sequence of the anti-HER3 human antibody U1-43
SEQ ID NO: 486—Heavy chain CDRH3 amino acid sequence of the anti-HER3 human antibody U1-43
SEQ ID NO: 487—Light chain CDRL1 amino acid sequence of the anti-HER3 human antibody U1-43
SEQ ID NO: 488—Light chain CDRL2 amino acid sequence of the anti-HER3 human antibody U1-43
SEQ ID NO: 489—Light chain CDRL3 amino acid sequence of the anti-HER3 human antibody U1-43
SEQ ID NO: 490—Heavy chain CDRH1 amino acid sequence of the anti-HER3 human antibody U1-44
SEQ ID NO: 491—Heavy chain CDRH2 amino acid sequence of the anti-HER3 human antibody U1-44
SEQ ID NO: 492—Heavy chain CDRH3 amino acid sequence of the anti-HER3 human antibody U1-44
SEQ ID NO: 493—Light chain CDRL1 amino acid sequence of the anti-HER3 human antibody U1-44
SEQ ID NO: 494—Light chain CDRL2 amino acid sequence of the anti-HER3 human antibody U1-44
SEQ ID NO: 495—Light chain CDRL3 amino acid sequence of the anti-HER3 human antibody U1-44
SEQ ID NO: 496—Heavy chain CDRH1 amino acid sequence of the anti-HER3 human antibody U1-45
SEQ ID NO: 497—Heavy chain CDRH2 amino acid sequence of the anti-HER3 human antibody U1-45
SEQ ID NO: 498—Heavy chain CDRH3 amino acid sequence of the anti-HER3 human antibody U1-45
SEQ ID NO: 499—Light chain CDRL1 amino acid sequence of the anti-HER3 human antibody U1-45
SEQ ID NO: 500—Light chain CDRL2 amino acid sequence of the anti-HER3 human antibody U1-45
SEQ ID NO: 501—Light chain CDRL3 amino acid sequence of the anti-HER3 human antibody U1-45
SEQ ID NO: 502—Heavy chain CDRH1 amino acid sequence of the anti-HER3 human antibody U1-46
SEQ ID NO: 503—Heavy chain CDRH2 amino acid sequence of the anti-HER3 human antibody U1-46

SEQ ID NO: 504—Heavy chain CDRH3 amino acid sequence of the anti-HER3 human antibody U1-46
SEQ ID NO: 505—Heavy chain CDRH1 amino acid sequence of the anti-HER3 human antibody U1-47
SEQ ID NO: 506—Heavy chain CDRH2 amino acid sequence of the anti-HER3 human antibody U1-47
SEQ ID NO: 507—Heavy chain CDRH3 amino acid sequence of the anti-HER3 human antibody U1-47
SEQ ID NO: 508—Light chain CDRL1 amino acid sequence of the anti-HER3 human antibody U1-47
SEQ ID NO: 509—Light chain CDRL2 amino acid sequence of the anti-HER3 human antibody U1-47
SEQ ID NO: 510—Light chain CDRL3 amino acid sequence of the anti-HER3 human antibody U1-47
SEQ ID NO: 511—Heavy chain CDRH1 amino acid sequence of the anti-HER3 human antibody U1-48
SEQ ID NO: 512—Heavy chain CDRH2 amino acid sequence of the anti-HER3 human antibody U1-48
SEQ ID NO: 513—Heavy chain CDRH3 amino acid sequence of the anti-HER3 human antibody U1-48
SEQ ID NO: 514—Heavy chain CDRH1 amino acid sequence of the anti-HER3 human antibody U1-49
SEQ ID NO: 515—Heavy chain CDRH2 amino acid sequence of the anti-HER3 human antibody U1-49
SEQ ID NO: 516—Heavy chain CDRH3 amino acid sequence of the anti-HER3 human antibody U1-49
SEQ ID NO: 517—Light chain CDRL1 amino acid sequence of the anti-HER3 human antibody U1-49
SEQ ID NO: 518—Light chain CDRL2 amino acid sequence of the anti-HER3 human antibody U1-49
SEQ ID NO: 519—Light chain CDRL3 amino acid sequence of the anti-HER3 human antibody U1-49
SEQ ID NO: 520—Heavy chain CDRH1 amino acid sequence of the anti-HER3 human antibody U1-50
SEQ ID NO: 521—Heavy chain CDRH2 amino acid sequence of the anti-HER3 human antibody U1-50
SEQ ID NO: 522—Heavy chain CDRH3 amino acid sequence of the anti-HER3 human antibody U1-50
SEQ ID NO: 523—Light chain CDRL1 amino acid sequence of the anti-HER3 human antibody U1-50
SEQ ID NO: 524—Light chain CDRL2 amino acid sequence of the anti-HER3 human antibody U1-50
SEQ ID NO: 525—Light chain CDRL3 amino acid sequence of the anti-HER3 human antibody U1-50
SEQ ID NO: 526—Heavy chain CDRH1 amino acid sequence of the anti-HER3 human antibody U1-51
SEQ ID NO: 527—Heavy chain CDRH2 amino acid sequence of the anti-HER3 human antibody U1-51
SEQ ID NO: 528—Heavy chain CDRH3 amino acid sequence of the anti-HER3 human antibody U1-51
SEQ ID NO: 529—Light chain CDRL1 amino acid sequence of the anti-HER3 human antibody U1-51
SEQ ID NO: 530—Light chain CDRL2 amino acid sequence of the anti-HER3 human antibody U1-51
SEQ ID NO: 531—Light chain CDRL3 amino acid sequence of the anti-HER3 human antibody U1-51
SEQ ID NO: 532—Heavy chain CDRH1 amino acid sequence of the anti-HER3 human antibody U1-52
SEQ ID NO: 533—Heavy chain CDRH2 amino acid sequence of the anti-HER3 human antibody U1-52
SEQ ID NO: 534—Heavy chain CDRH3 amino acid sequence of the anti-HER3 human antibody U1-52
SEQ ID NO: 535—Light chain CDRL1 amino acid sequence of the anti-HER3 human antibody U1-52
SEQ ID NO: 536—Light chain CDRL2 amino acid sequence of the anti-HER3 human antibody U1-52
SEQ ID NO: 537—Light chain CDRL3 amino acid sequence of the anti-HER3 human antibody U1-52
SEQ ID NO: 538—Heavy chain CDRH1 amino acid sequence of the anti-HER3 human antibody U1-53
SEQ ID NO: 539—Heavy chain CDRH2 amino acid sequence of the anti-HER3 human antibody U1-53
SEQ ID NO: 540—Heavy chain CDRH3 amino acid sequence of the anti-HER3 human antibody U1-53
SEQ ID NO: 541—Light chain CDRL1 amino acid sequence of the anti-HER3 human antibody U1-53
SEQ ID NO: 542—Light chain CDRL2 amino acid sequence of the anti-HER3 human antibody U1-53
SEQ ID NO: 543—Light chain CDRL3 amino acid sequence of the anti-HER3 human antibody U1-53
SEQ ID NO: 544—Heavy chain CDRH1 amino acid sequence of the anti-HER3 human antibody U1-55.1
SEQ ID NO: 545—Heavy chain CDRH2 amino acid sequence of the anti-HER3 human antibody U1-55.1
SEQ ID NO: 546—Heavy chain CDRH3 amino acid sequence of the anti-HER3 human antibody U1-55.1
SEQ ID NO: 547—Light chain CDRL1 amino acid sequence of the anti-HER3 human antibody U1-55
SEQ ID NO: 548—Light chain CDRL2 amino acid sequence of the anti-HER3 human antibody U1-55
SEQ ID NO: 549—Light chain CDRL3 amino acid sequence of the anti-HER3 human antibody U1-55
SEQ ID NO: 550—Light chain CDRL1 amino acid sequence of the anti-HER3 human antibody U1-57.1
SEQ ID NO: 551—Light chain CDRL2 amino acid sequence of the anti-HER3 human antibody U1-57.1
SEQ ID NO: 552—Light chain CDRL3 amino acid sequence of the anti-HER3 human antibody U1-57.1
SEQ ID NO: 553—Heavy chain CDRH1 amino acid sequence of the anti-HER3 human antibody U1-57
SEQ ID NO: 554—Heavy chain CDRH2 amino acid sequence of the anti-HER3 human antibody U1-57
SEQ ID NO: 555—Heavy chain CDRH3 amino acid sequence of the anti-HER3 human antibody U1-57
SEQ ID NO: 556—Heavy chain CDRH1 amino acid sequence of the anti-HER3 human antibody U1-58
SEQ ID NO: 557—Heavy chain CDRH2 amino acid sequence of the anti-HER3 human antibody U1-58
SEQ ID NO: 558—Heavy chain CDRH3 amino acid sequence of the anti-HER3 human antibody U1-58
SEQ ID NO: 559—Light chain CDRL1 amino acid sequence of the anti-HER3 human antibody U1-58
SEQ ID NO: 560—Light chain CDRL2 amino acid sequence of the anti-HER3 human antibody U1-58
SEQ ID NO: 561—Light chain CDRL3 amino acid sequence of the anti-HER3 human antibody U1-58
SEQ ID NO: 562—Heavy chain CDRH1 amino acid sequence of the anti-HER3 human antibody U1-59
SEQ ID NO: 563—Heavy chain CDRH2 amino acid sequence of the anti-HER3 human antibody U1-59
SEQ ID NO: 564—Heavy chain CDRH3 amino acid sequence of the anti-HER3 human antibody U1-59
SEQ ID NO: 565—Light chain CDRL1 amino acid sequence of the anti-HER3 human antibody U1-59
SEQ ID NO: 566—Light chain CDRL2 amino acid sequence of the anti-HER3 human antibody U1-59
SEQ ID NO: 567—Light chain CDRL3 amino acid sequence of the anti-HER3 human antibody U1-59
SEQ ID NO: 568—Heavy chain CDRH1 amino acid sequence of the anti-HER3 human antibody U1-61.1
SEQ ID NO: 569—Heavy chain CDRH2 amino acid sequence of the anti-HER3 human antibody U1-61.1

SEQ ID NO: 570—Heavy chain CDRH3 amino acid sequence of the anti-HER3 human antibody U1-61.1
SEQ ID NO: 571—Light chain CDRL1 amino acid sequence of the anti-HER3 human antibody U1-61.1
SEQ ID NO: 572—Light chain CDRL2 amino acid sequence of the anti-HER3 human antibody U1-61.1
SEQ ID NO: 573—Light chain CDRL3 amino acid sequence of the anti-HER3 human antibody U1-61.1
SEQ ID NO: 574—Heavy chain CDRH1 amino acid sequence of the anti-HER3 human antibody U1-61
SEQ ID NO: 575—Heavy chain CDRH2 amino acid sequence of the anti-HER3 human antibody U1-61
SEQ ID NO: 576—Heavy chain CDRH3 amino acid sequence of the anti-HER3 human antibody U1-61
SEQ ID NO: 577—Heavy chain CDRH1 amino acid sequence of the anti-HER3 human antibody U1-62
SEQ ID NO: 578—Heavy chain CDRH2 amino acid sequence of the anti-HER3 human antibody U1-62
SEQ ID NO: 579—Heavy chain CDRH3 amino acid sequence of the anti-HER3 human antibody U1-62
SEQ ID NO: 580—Light chain CDRL1 amino acid sequence of the anti-HER3 human antibody U1-62
SEQ ID NO: 581—Light chain CDRL2 amino acid sequence of the anti-HER3 human antibody U1-62
SEQ ID NO: 582—Light chain CDRL3 amino acid sequence of the anti-HER3 human antibody U1-62
SEQ ID NO: 583—Full-length amino acid sequence of a heavy chain of anti-HER3 human antibody U1-59
SEQ ID NO: 584—Full-length amino acid sequence of a light chain of anti-HER3 human antibody U1-59

The invention claimed is:

1. An antibody-drug conjugate, wherein a linker and an antitumor compound represented by any one of the following formulae and anti-HER3 antibody are connected:

-(Succinimid-3-yl-N)—CH$_2$CH$_2$CH$_2$CH$_2$CH$_2$—C(=O)-GGFG (SEQ ID NO: 585)-NH—CH$_2$CH$_2$CH$_2$—C(=O)-(NH-DX), or -(Succinimid-3-yl-N)—CH$_2$CH$_2$CH$_2$CH$_2$CH$_2$—C(=O)-DGGFG (SEQ ID NO: 590)-NH—CH$_2$CH$_2$CH$_2$—C(=O)-(NH-DX);

wherein

-(Succinimid-3-yl-N)— has a structure represented by the following formula:

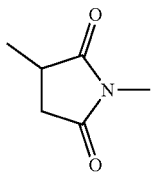

which is connected to the antibody at position 3 thereof and is connected to a methylene group in the linker structure containing this structure on the nitrogen atom at position 1, and (NH-DX) represents a group represented by the following formula:

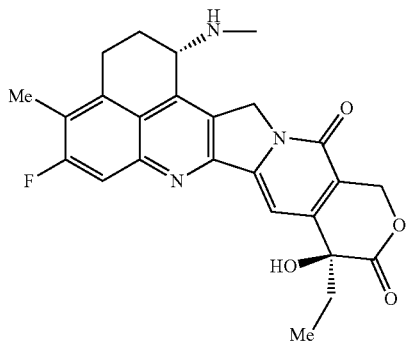

wherein the nitrogen atom of the amino group at position 1 is the connecting position.

2. The antibody-drug conjugate according to claim 1, wherein an average number of units of the drug-linker structure conjugated per antibody is in a range of from 2 to 8.

3. The antibody-drug conjugate according to claim 1, wherein an average number of units of the drug-linker structure conjugated per antibody is in a range of from 3 to 8.

4. A drug containing the antibody-drug conjugate according to claim 1 or a salt thereof.

5. A method of treating cancer in an individual comprising administering to an individual with cancer the drug according to claim 4.

6. The method of claim 5, wherein the cancer is lung cancer, kidney cancer, urothelial cancer, colorectal cancer, prostate cancer, glioblastoma multiforme, ovarian cancer, pancreatic cancer, breast cancer, melanoma, liver cancer, bladder cancer, gastric cancer, gastrointestinal stromal tumor, cervical cancer, head and neck cancer, esophageal cancer, epidermoid cancer, peritoneal cancer, adult glioblastoma multiforme, hepatic cancer, hepatocellular carcinoma, colon cancer, rectal cancer, colon and rectal cancer, endometrial cancer, uterus cancer, salivary cancer, renal cancer, vulval cancer, thyroid cancer, hepatic carcinoma, anus carcinoma, or penis cancer.

7. A pharmaceutical composition containing the antibody-drug conjugate according to claim 1 or a salt thereof as an active component, and a pharmaceutically acceptable formulation component.

8. A method of treating cancer in an individual comprising administering to an individual with cancer the pharmaceutical composition according to claim 7.

9. The method according to claim 8, wherein the cancer is lung cancer, kidney cancer, urothelial cancer, colorectal cancer, prostate cancer, glioblastoma multiforme, ovarian cancer, pancreatic cancer, breast cancer, melanoma, liver cancer, bladder cancer, gastric cancer, gastrointestinal stromal tumor, cervical cancer, head and neck cancer, esophageal cancer, epidermoid cancer, peritoneal cancer, adult glioblastoma multiforme, hepatic cancer, hepatocellular carcinoma, colon cancer, rectal cancer, colon and rectal cancer, endometrial cancer, uterus cancer, salivary cancer, renal cancer, vulval cancer, thyroid cancer, hepatic carcinoma, anus carcinoma, or penis cancer.

10. The antibody-drug conjugate according to claim 1, wherein the antibody comprises the CDRH1 to CDRH3 and CDRL1 to CDRL3 of U1-49, U1-53, U1-59, U1-7 or U1-9 in the heavy and light chains, respectively.

11. The antibody-drug conjugate according to claim 1, wherein the antibody comprises the heavy chain variable region and the light chain variable chain of U1-49, U1-53, U1-59, U1-7 or U1-9 on the heavy and light chains, respectively.

12. The antibody-drug conjugate according to claim 1, wherein the antibody comprises the amino acid sequences represented by SEQ ID Nos: 42 and 44, SEQ ID Nos: 54 and 56, SEQ ID Nos: 70 and 72, SEQ ID Nos: 92 and 94, or SEQ ID Nos: 96 and 98, in the heavy and light chains, respectively.

13. The antibody-drug conjugate according to claim 1, wherein the antibody comprises the amino acid sequences represented by SEQ ID Nos: 583 and 584 in the heavy and light chains, respectively.

14. A pharmaceutical composition comprising the antibody-drug conjugate according to claim 10, a salt thereof as an active ingredient, and a pharmaceutically acceptable formulation ingredient.

15. A method of treating cancer in an individual comprising administering to an individual with cancer the pharmaceutical composition according to claim 14.

16. The method of claim 15, wherein the cancer is lung cancer, kidney cancer, urothelial cancer, colorectal cancer, prostate cancer, glioblastoma multiforme, ovarian cancer, pancreatic cancer, breast cancer, melanoma, liver cancer, bladder cancer, gastric cancer, gastrointestinal stromal tumor, cervical cancer, head and neck cancer, esophageal cancer, epidermoid cancer, peritoneal cancer, adult glioblastoma multiforme, hepatic cancer, hepatocellular carcinoma, colon cancer, rectal cancer, colon and rectal cancer, endometrial cancer, uterus cancer, salivary cancer, renal cancer, vulval cancer, thyroid cancer, hepatic carcinoma, anus carcinoma, or penis cancer.

17. The antibody-drug conjugate according to claim 13, wherein the antibody lacks a lysine residue at the carboxyl terminus of the heavy chain.

* * * * *